(12) United States Patent
Polisetti et al.

(10) Patent No.: US 7,541,373 B2
(45) Date of Patent: Jun. 2, 2009

(54) ARYL CARBONYL DERIVATIVES AS THERAPEUTIC AGENTS

(75) Inventors: Dharma Rao Polisetti, Greensboro, NC (US); Janos Tibor Kodra, Copenhagen O (DK); Jesper Lau, Farum (DK); Paw Bloch, Taastrup (DK); Mustafa Guzel, Jamestown, NC (US); Kalpathy Chidambareswaran Santhosh, High Point, NC (US); Adnan M. M. Mjalli, Jamestown, NC (US); Robert Carl Andrews, Jamestown, NC (US); Govindan Subramanian, High Point, NC (US); Michael Ankersen, Stenlose (DK); Per Vedso, Frederiksberg (DK); Anthony Murray, Hellerup (DK); Lone Jeppesen, Virum (DK); Jesper Lau, Farum (DK)

(73) Assignee: Novo Nordisk A/S, Bagsvaerd (DK)

( * ) Notice: Subject to any disclaimer, the term of this patent is extended or adjusted under 35 U.S.C. 154(b) by 548 days.

(21) Appl. No.: 11/365,534

(22) Filed: Mar. 1, 2006

(65) Prior Publication Data
US 2006/0183783 A1    Aug. 17, 2006

Related U.S. Application Data

(63) Continuation of application No. PCT/DK03/00449, filed on Jun. 27, 2003.

(30) Foreign Application Priority Data

| Jun. 27, 2002 | (DK) | ................................ 2002 00999 |
| Feb. 25, 2003 | (DK) | ................................ 2003 00286 |

(51) Int. Cl.
*A61K 31/426* (2006.01)
*C07D 277/38* (2006.01)

(52) U.S. Cl. ...................................... 514/370; 548/189
(58) Field of Classification Search ................. 548/189; 514/370
See application file for complete search history.

(56) References Cited

U.S. PATENT DOCUMENTS 3,152,136 A   10/1964   Harris et al. ................. 260/295

| 3,317,534 A | 5/1967 | Nitta et al. ................. 260/256.4 |
| 7,196,104 B2* | 3/2007 | Askew et al. ................. 514/342 |

FOREIGN PATENT DOCUMENTS

| DE | 2117807 | 10/1971 |
| DE | 2712630 | 9/1978 |
| EP | 1211246 A1 | 6/2002 |
| WO | WO 97/24328 A1 | 7/1997 |
| WO | WO 99/24035 A1 | 5/1999 |
| WO | WO 99/32106 A1 | 7/1999 |
| WO | WO 99/32111 A1 | 7/1999 |
| WO | WO 00/58293 A2 | 10/2000 |
| WO | WO 00/58293 A3 | 10/2000 |
| WO | WO 01/00206 | 4/2001 |
| WO | WO 01/44216 A1 | 6/2001 |
| WO | WO 01/57008 A1 | 8/2001 |
| WO | WO 01/83465 A2 | 11/2001 |
| WO | WO 01/83478 A2 | 11/2001 |
| WO | WO 01/83478 A3 | 11/2001 |
| WO | WO 01/85706 A1 | 11/2001 |
| WO | WO 01/85707 A1 | 11/2001 |
| WO | WO 02/08209 A1 | 1/2002 |
| WO | WO 02/14311 A2 | 2/2002 |
| WO | WO 02/14311 A3 | 2/2002 |
| WO | WO 02/46173 A1 | 6/2002 |
| WO | WO 02/070494 A1 | 9/2002 |
| WO | WO 03/055482 A1 | 7/2003 |
| WO | WO 03/007027 A1 | 8/2003 |

OTHER PUBLICATIONS

Atwal et al., Journal of Medicinal Chemistry, vol. 39, No. 1, pp. 304-313.
Hirsch et al., NIH, Annals of Internal Medicine, vol. 103, pp. 147-151 (1985).
Mann, The New England Journal of Medicine, vol. 291, pp. 226-232 (1974).
Purchase et al., Bioorganic and Medicinal Chemistry Letters, vol. 6, No. 15, pp. 1753-1758 (1996).
Regel et al., Liebigs Annalen der Chemie, vol. 1, pp. 145-158 (1977).
White et al., Journal of Medicinal Chemistry, vol. 39, No. 22, pp. 4382-4395 (1996).

* cited by examiner

*Primary Examiner*—Kamal Saeed
*Assistant Examiner*—Janet L Coppins
(74) *Attorney, Agent, or Firm*—Rosemarie R. Wilk-Orescan

(57) ABSTRACT

This invention relates to aryl carbonyl derivatives which are activators of glucokinase which may be useful for the management, treatment, control, or adjunct treatment of diseases, where increasing glucokinase activity is beneficial.

22 Claims, No Drawings

ARYL CARBONYL DERIVATIVES AS THERAPEUTIC AGENTS

CROSS-REFERENCE TO RELATED APPLICATIONS

This application is a continuation of U.S. application Ser. No. 10/679,887, filed Oct. 6, 2003, which was a contiuation of the International Application No. PCT/DK03/00449, filed Jun. 27, 2003, which claimed priority under 35 U.S.C. 119 of Danish Application No. PA 2002 00999 filed Jun. 27, 2002, and Danish Application No. PA 2003 00286, filed Feb. 25, 2003, and U.S. Application No. 60/394,144, filed Jul. 3, 2002, and U.S. Application No. 60/452,228, filed Mar. 5, 2003, the contents of each of which are fully incorporated herein by reference.

FIELD OF THE INVENTION

This invention relates to compounds which are activators of glucokinase (GK), which may be useful for the management, treatment, control, or adjunct treatment of diseases, where increasing glucokinase activity is beneficial.

BACKGROUND OF THE INVENTION

Diabetes is characterised by an impaired glucose metabolism manifesting itself among other things by an elevated blood glucose level in the diabetic patients. Underlying defects lead to a classification of diabetes into two major groups: Type 1 diabetes, or insulin demanding diabetes mellitus (IDDM), which arises when patients lack β-cells producing insulin in their pancreatic glands, and type 2 diabetes, or non-insulin dependent diabetes mellitus (NIDDM), which ocurs in patients with an impaired β-cell function besides a range of other abnormalities.

Type 1 diabetic patients are currently treated with insulin, while the majority of type 2 diabetic patients are treated either with sulphonylureas that stimulate β-cell function or with agents that enhance the tissue sensitivity of the patients towards insulin or with insulin. Among the agents applied to enhance tissue sensitivity towards insulin metformin is a representative example.

Even though sulphonylureas are widely used in the treatment of NIDDM this therapy is, in most instances, not satisfactory: In a large number of NIDDM patients sulphonylureas do not suffice to normalise blood sugar levels and the patients are, therefore, at high risk for acquiring diabetic complications. Also, many patients gradually lose the ability to respond to treatment with sulphonylureas and are thus gradually forced into insulin treatment. This shift of patients from oral hypoglycaemic agents to insulin therapy is usually ascribed to exhaustion of the β-cells in NIDDM patients.

In normal subjects as well as in diabetic subjects, the liver produces glucose in order to avoid hypoglycaemia. This glucose production is derived either from the release of glucose from glycogen stores or from gluconeogenesis, which is a de novo intracellular synthesis of glucose. In type 2 diabetes, however, the regulation of hepatic glucose output is poorly controlled and is increased, and may be doubled after an overnight fast. Moreover, in these patients there exists a strong correlation between the increased fasting plasma glucose levels and the rate of hepatic glucose production. Similarly, hepatic glucose production will be increased in type 1 diabetes, if the disease is not properly controlled by insulin treatment.

Since existing forms of therapy of diabetes does not lead to sufficient glycaemic control and therefore are unsatisfactory, there is a great demand for novel therapeutic approaches.

Atherosclerosis, a disease of the arteries, is recognized to be the leading cause of death in the United States and Western Europe. The pathological sequence leading to atherosclerosis and oclusive heart disease is well known. The earliest stage in this sequence is the formation of "fatty streaks" in the carotid, coronary and cerebral arteries and in the aorta. These lesions are yellow in colour due to the presence of lipid deposits found principally within smooth-muscle cells and in macrophages of the intima layer of the arteries and aorta. Further, it is postulated that most of the cholesterol found within the fatty streaks, in turn, give rise to development of the "fibrous plaque", which consists of accumulated intimal smooth muscle cells laden with lipid and surrounded by extra-cellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particular high risk. Independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition, which ocurs in the human population as a secondary symptom to various other disorders such as renal artery stenosis, pheochromocytoma, or endocrine disorders. However, hypertension is also evidenced in many patients in whom the causative agent or disorder is unknown. While such "essential" hypertension is often associated with disorders such as obesity, diabetes, and hypertriglyceridemia, the relationship between these disorders has not been elucidated. Additionally, many patients display the symptoms of high blood pressure in the complete absence of any other signs of disease or disorder.

It is known that hypertension can directly lead to heart failure, renal failure, and stroke (brain haemorrhaging). These conditions are capable of causing short-term death in a patient. Hypertension can also contribute to the development of atherosclerosis and coronary disease. These conditions gradually weaken a patient and can lead to long-term death.

The exact cause of essential hypertension is unknown, though a number of factors are believed to contribute to the onset of the disease. Among such factors are stress, uncontrolled emotions, unregulated hormone release (the renin, angiotensin aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus a broad range of beta-blockers, vasoconstrictors, angiotensin converting enzyme inhibitors and the like have been developed and marketed as antihypertensives. The treatment of hypertension utilizing these compounds has proven beneficial in the prevention of short-interval deaths such as heart failure, renal failure, and brain haemorrhaging. However, the development of atherosclerosis or heart disease due to hypertension over a long period of time remains a problem. This implies that although high blood pressure is being reduced, the underlying cause of essential hypertension is not responding to this treatment.

Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries, while sodium retention increases blood volume. Thus, the lowering of insulin levels in hyperinsulinemics can prevent abnormal vascular growth and renal sodium retention caused by high insulin levels and thereby alleviates hypertension.

Cardiac hypertrophy is a significant risk factor in the development of sudden death, myocardial infarction, and congestive heart failure. Theses cardiac events are due, at least in part, to increased susceptibility to myocardial injury after ischemia and reperfusion, which can ocur in out-patient as well as perioperative settings. There is an unmet medical need to prevent or minimize adverse myocardial perioperative outcomes, particularly perioperative myocardial infarction. Both non-cardiac and cardiac surgery are associated with substantial risks for myocardial infarction or death. Some 7 million patients undergoing non-cardiac surgery are considered to be at risk, with incidences of perioperative death and serious cardiac complications as high as 20-25% in some series. In addition, of the 400,000 patients undergoing coronary bypass surgery annually, perioperative myocardial infarction is estimated to ocur in 5% and death in 1-2%. There is currently no drug therapy in this area, which reduces damage to cardiac tissue from perioperative myocardial ischemia or enhances cardiac resistance to ischemic episodes. Such a therapy is anticipated to be life-saving and reduce hospitalizations, enhance quality of life and reduce overall health care costs of high risk patients.

Obesity is a well-known risk factor for the development of many very common diseases such as atherosclerosis, hypertension, and diabetes. The incidence of obese people and thereby also these diseases is increasing throughout the entire industrialised world. Except for exercise, diet and food restriction no convincing pharmacological treatment for reducing body weight effectively and acceptably currently exist. However, due to its indirect but important effect as a risk factor in mortal and common diseases it will be important to find treatment for obesity and/or means of appetite regulation.

The term obesity implies an excess of adipose tissue. In this context obesity is best viewed as any degree of excess adiposity that imparts a health risk. The cut off between normal and obese individuals can only be approximated, but the health risk imparted by the obesity is probably a continuum with increasing adiposity. The Framingham study demonstrated that a 20% excess over desirable weight clearly imparted a health risk (Mann G V N. Engl. J. Med 291:226, 1974). In the United States a National Institutes of Health consensus panel on obesity agreed that a 20% increase in relative weight or a body mass index (BMI=body weight in kilograms divided by the square of the height in meters) above the 85 th percentile for young adults constitutes a health risk. By the use of these criteria 20 to 30 percent of adult men and 30 to 40 percent of adult women in the United States are obese. (NIH, Ann Intern Med 103:147, 1985).

Even mild obesity increases the risk for premature death, diabetes, hypertension, atherosclerosis, gallbladder disease, and certain types of cancer. In the industrialised western world the prevalence of obesity has increased significantly in the past few decades. Because of the high prevalence of obesity and its health consequences, its prevention and treatment should be a high public health priority.

When energy intake exceeds expenditure, the excess calories are stored in adipose tissue, and if this net positive balance is prolonged, obesity results, i.e. there are two components to weight balance, and an abnormality on either side (intake or expenditure) can lead to obesity.

The regulation of eating behaviour is incompletely understood. To some extent appetite is controlled by discrete areas in the hypothalamus: a feeding centre in the ventrolateral nucleus of the hypothalamus (VLH) and a satiety centre in the ventromedial hypothalamus (VMH). The cerebral cortex receives positive signals from the feeding centre that stimulate eating, and the satiety centre modulates this process by sending inhibitory impulses to the feeding centre. Several regulatory processes may influence these hypothalamic centres. The satiety centre may be activated by the increases in plasma glucose and/or insulin that follow a meal. Meal-induced gastric distension is another possible inhibitory factor. Additionally the hypothalamic centres are sensitive to catecholamines, and beta-adrenergic stimulation inhibits eating behaviour. Ultimately, the cerebral cortex controls eating behaviour, and impulses from the feeding centre to the cerebral cortex are only one input. Psychological, social, and genetic factors also influence food intake.

At present a variety of techniques are available to effect initial weight loss. Unfortunately, initial weight loss is not an optimal therapeutic goal. Rather, the problem is that most obese patients eventually regain their weight. An effective means to establish and/or sustain weight loss is the major challenge in the treatment of obesity today.

WO 00/58293, WO 01/44216, WO/0183465, WO/0183478, WO/0185706, WO 01/85707, and WO02/08209, to Hoffman-La Roche, discloses compounds as glucokinase activators.

SUMMARY OF THE INVENTION

This invention provides amide derivatives of the general formula (I), as described below, as activators of glucokinase. The compounds of the present invention are useful as activators of glucokinase and thus are useful for the management, treatment, control and adjunct treatment of diseases where increasing the activity of glucokinase is beneficial. Such diseases include type I diabetes and type II diabetes. The present invention provides compounds as described below, pharmaceutical compositions comprising the compounds, their use for increasing the activity of glucokinase, their use in preparation of a medicament for treating said diseases and conditions and the use of compounds or pharmaceutical preparations of the present invention for treating said diseases and conditions as well as methods for treating said diseases and conditions, which methods comprise administering to a subject in need thereof an effective amount of a compound according to the present invention.

The present invention also provides glucokinase activators, for instance of the general formula (I), which are glucose sensitive glucokinase activators, that is, glucokinase activators, the activity of which decreases with increasing glucose concentrations.

The present invention also provides glucokinase activators, for instance of the general formula (I), which are liver specific glucokinase activators, that is, glucokinase activators which increase glucose utilization in the liver (i.e. increase glycogen deposition) without inducing any increase in insulin secretion in response to glucose.

The present invention provides the use of a compound or a pharmaceutical preparation according to the present invention for treatment of metabolic disorders.

The present invention provides the use of a compound or a pharmaceutical preparation according to the present invention for blood glucose lowering.

The present invention provides the use of a compound or a pharmaceutical preparation according to the present invention for prevention of hyperglycemia.

The present invention provides the use of a compound or a pharmaceutical preparation according to the present invention for treatment of impaired glucose tolerance IGT.

The present invention provides the use of a compound or a pharmaceutical preparation according to the present invention for treatment of Syndrome X.

The present invention provides the use of a compound or a pharmaceutical preparation according to the present invention for the treatment of impaired fasting glucose (IFG).

The present invention provides the use of a compound or a pharmaceutical preparation according to the present invention for treatment of type 2 diabetes.

The present invention provides the use of a compound or a pharmaceutical preparation according to the present invention for treatment of type 1 diabetes.

The present invention provides the use of a compound or a pharmaceutical preparation according to the present invention for delaying the progression of impaired glucose tolerance (IGT) to type 2 diabetes.

The present invention provides the use of a compound or a pharmaceutical preparation according to the present invention for delaying the progression of non-insulin requiring type 2 diabetes to insulin requiring type 2 diabetes.

The present invention provides the use of a compound or a pharmaceutical preparation according to the present invention for treatment of dyslipidemia or hyper-lipidemia.

The present invention provides the use of a compound or a pharmaceutical preparation according to the present invention for treatment of hypertension.

The present invention provides the use of a compound or a pharmaceutical preparation according to the present invention for the treatment of obesity.

The present invention provides the use of a compound or a pharmaceutical preparation according to the present invention for lowering of food intake The present invention provides the use of a compound or a pharmaceutical preparation according to the present invention for appetite regulation.

The present invention provides the use of a compound or a pharmaceutical preparation according to the present invention for regulating feeding behaviour.

The present invention provides the use of a compound or a pharmaceutical preparation according to the present invention for enhancing the secretion of enteroincretins, such as GLP-1.

The present invention provides the use of a compound or a pharmaceutical preparation according to the present invention for the adjuvant treatment of type 1 diabetes for preventing the onset of diabetic complications.

The present invention provides the use of a compound or a pharmaceutical preparation according to the present invention for increasing the number and/or the size of beta cells in a mammalian subject.

The present invention provides the use of a compound or a pharmaceutical preparation according to the present invention for treatment of beta cell degeneration, in particular apoptosis of beta cells.

The present invention provides the use of a compound or a pharmaceutical preparation according to the present invention for treatment of functional dyspepsia, in particular irritable bowel syndrome.

The present invention provides the use of a compound according to the present invention for the preparation of a medicament for treatment of metabolic disorders.

The present invention provides the use of a compound according to the present invention for the preparation of a medicament for blood glucose lowering.

The present invention provides the use of a compound according to the present invention for the preparation of a medicament for the treatment of hyperglycemia.

The present invention provides the use of a compound according to the present invention for the preparation of a medicament for the treatment of IGT.

The present invention provides the use of a compound according to the present invention for the preparation of a medicament for the treatment of Syndrome X.

The present invention provides the use of a compound according to the present invention for the preparation of a medicament for the treatment of impaired fasting glucose (IFG).

The present invention provides the use of a compound according to the present invention for the preparation of a medicament for the treatment of type 2 diabetes.

The present invention provides the use of a compound according to the present invention for the preparation of a medicament for the treatment of type 1 diabetes.

The present invention provides the use of a compound according to the present invention for the preparation of a medicament for delaying the progression of impaired glucose tolerance (IGT) to type 2 diabetes.

The present invention provides the use of a compound according to the present invention for the preparation of a medicament for delaying the progression of non-insulin requiring type 2 diabetes to insulin requiring type 2 diabetes.

The present invention provides the use of a compound according to the present invention for the preparation of a medicament for the treatment of dyslipidemia.

The present invention provides the use of a compound according to the present invention for the preparation of a medicament for the treatment of hyperlipidemia.

The present invention provides the use of a compound according to the present invention for the preparation of a medicament for the treatment of hypertension.

The present invention provides the use of a compound according to the present invention for the preparation of a medicament for lowering of food intake.

The present invention provides the use of a compound according to the present invention for the preparation of a medicament for appetite regulation.

The present invention provides the use of a compound according to the present invention for the preparation of a medicament for the treatment of obesity.

The present invention provides the use of a compound according to the present invention for the preparation of a medicament for regulating feeding behaviour.

The present invention provides the use of a compound according to the present invention for the preparation of a medicament for enhancing the secretion of enteroincretins, such as GLP-1.

The present invention provides the use of a compound according to the present invention for the preparation of a medicament for the adjuvant treatment of type 1 diabetes for preventing the onset of diabetic complications.

The present invention provides the use of a compound according to the present invention for the preparation of a medicament for increasing the number and/or the size of beta cells in a mammalian subject.

The present invention provides the use of a compound according to the present invention for the preparation of a medicament for treatment of beta cell degeneration, in particular apoptosis of beta cells.

The present invention provides the use of a compound according to the present invention for the preparation of a medicament for treatment of functional dyspepsia, in particular irritable bowel syndrome.

The present invention provides a method of preventing hypoglycaemia comprising administration of a liver-specific glucokinas activator.

The present invention provides the use of a liver-specific glucokinas activator for the preparation of a medicament for the prevention of hypoglycaemia.

Other embodiments and aspects are as defined below and by the appended claims.

Definitions

In the structural formulas given herein and throughout the present specification, the following terms have the indicated meaning:

The term "optionally substituted" as used herein means that the group in question is either unsubstituted or substituted with one or more of the substituents specified. When the group in question are substituted with more than one substituent the substituent may be the same or different.

The term "adjacent" as used herein regards the relative postions of two atoms or variables, these two atoms or variables sharing a bond or one variable preceding or succeeding the other in a variable specification. By way of example, "atom A adjacent to atom B" means that the two atoms A and B share a bond.

The term "halogen" or "halo" means fluorine, chlorine, bromine or iodine.

The term "perhalomethyl" means trifluoromethyl, trichloromethyl, tribromomethyl, or triiodomethyl.

The use of prefixes of this structure: $C_{x-y}$-alkyl, $C_{x-y}$-alkenyl, $C_{x-y}$-alkynyl, $C_{x-y}$-cycloalyl or $C_{x-y}$-cycloalkyl-$C_{x-y}$-alkenyl- designates radical of the designated type having from x to y carbon atoms.

The term "alkyl" as used herein, alone or in combination, refers to a straight or branched chain saturated monovalent hydrocarbon radical having from one to ten carbon atoms, for example $C_{1-8}$-alkyl or $C_{1-6}$-alkyl. Typical $C_{1-8}$-alkyl groups and $C_{1-6}$-alkyl groups include, but are not limited to e.g. methyl, ethyl, n-propyl, isopropyl, n-butyl, sec-butyl, isobutyl, tert-butyl, n-pentyl, 2-methylbutyl, 3-methylbutyl, 4-methylpentyl, neopentyl, n-pentyl, n-hexyl, 1,2-dimethylpropyl, 2,2-dimethylpropyl, 1,2,2-trimethylpropyl and the like. The term "$C_{1-8}$-alkyl" as used herein also includes secondary $C_{3-8}$-alkyl and tertiary $C_{4-8}$-alkyl. The term "$C_{1-6}$-alkyl" as used herein also includes secondary $C_{3-6}$-alkyl and tertiary $C_{4-6}$-alkyl.

The term "alkylene" as used herein, alone or in combination, refers to a straight or branched chain saturated divalent hydrocarbon radical having from one to ten carbon atoms, for example $C_{1-8}$-alkylene or $C_{1-6}$-alkylene. Examples of "alkylene" as used herein include, but are not limited to, methylene, ethylene, and the like.

The term "alkenyl" as used herein, alone or in combination, refers to a straight or branched chain monovalent hydrocarbon radical containing from two to ten carbon atoms and at least one carbon-carbon double bond, for example $C_{2-8}$-alkenyl or $C_{2-6}$-alkenyl. Typical $C_{2-8}$-alkenyl groups and $C_{2-6}$-alkenyl groups include, but are not limited to, vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 2,4-hexadienyl, 5-hexenyl and the like.

The term "alkenylene" as used herein, alone or in combination, refers to a straight or branched chain divalent hydrocarbon radical having from two to ten carbon atoms and at least one carbon-carbon double bond, for example $C_{2-8}$-alkenylene or $C_{2-6}$-alkenylene. Typical $C_{2-8}$-alkenylene groups and $C_{2-6}$-alkenylene groups include, but are not limited to, ethene-1,2-diyl, propene-1,3-diyl, methylene-1,1-diyl, and the like.

The term "alkynyl" as used herein alone or in combination, refers to a straight or branched monovalent hydrocarbon radical containing from two to ten carbon atoms and at least one triple carbon-carbon bond, for example $C_{2-8}$-alkynyl or $C_{2-6}$-alkynyl. Typical $C_{2-8}$-alkynyl groups and $C_{2-6}$-alkynyl groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 5-hexynyl, 2,4-hexadiynyl and the like.

The term "alkynylene" as used herein alone or in combination, refers to a straight or branched chain divalent hydrocarbon radical having from two to ten carbon atoms and at least one carbon-carbon triple bond, for example $C_{2-8}$-alkynylene or $C_{2-6}$-alkynylene. Typical $C_{2-8}$-alkynylene groups and $C_{2-6}$-alkynylene groups include, but are not limited to, ethyne-1,2-diyl, propyne-1,3-diyl, and the like.

The term "cycloalkyl" as used herein, alone or in combination, refers to a non-aromatic monovalent hydrocarbon radical having from three to twelve carbon atoms, and optionally with one or more degrees of unsaturation, for example $C_{3-8}$-cycloalkyl. Such a ring may be optionally fused to one or more benzene rings or to one or more of other cycloalkyl ring(s). Typical $C_{3-8}$-cycloalkyl groups include, but are not limited to, cyclopropyl, cyclobutyl, cyclopentyl, cyclohexyl, cyclohexenyl, cycloheptyl, cycloheptenyl, cyclooctyl and the like.

The term "cycloalkylene" as used herein, alone or in combination, refers to a non-aromatic carbocyclic divalent hydrocarbon radical having from three to twelve carbon atoms and optionally possessing one or more degrees of unsaturation, for example $C_{3-8}$-cycloalkylene. Such a ring may be optionally fused to one or more benzene rings or to one or more of other cycloalkyl ring(s). Typical $C_{3-8}$-cycloalkylene groups include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

The term "heterocyclic" or the term "heterocyclyl" as used herein, alone or in combination, refers to a three to twelve membered heterocyclic ring having one or more degrees of unsaturation containing one or more heteroatomic substitutions selected from S, SO, $SO_2$, O, or N, for example $C_{3-8}$-heterocyclyl. Such a ring may be optionally fused to one or more of another "heterocyclic" ring(s) or cycloalkyl ring(s). Typical $C_{3-8}$-heterocyclyl groups include, but are not limited to, tetrahydrofuran, 1,4-dioxane, 1,3-dioxane, piperidine, pyrrolidine, morpholine, piperazine, and the like.

The term "heterocyclylene" as used herein, alone or in combination, refers to a three to twelve-membered heterocyclic ring diradical optionally having one or more degrees of unsaturation containing one or more heteroatoms selected from S, SO, $SO_2$, O, or N. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, piperazine-1,4-dyil, and the like.

The term "alkoxy" as used herein, alone or in combination, refers to the monovalent radical $R^aO$—, where $R^a$ is alkyl as defined above, for example $C_{1-8}$-alkyl giving $C_{1-8}$-alkoxy. Typical $C_{1-8}$-alkoxy groups include, but are not limited to, methoxy, ethoxy, n-propoxy, isopropoxy, butoxy, sec-butoxy, tert-butoxy, pentoxy, isopentoxy, hexoxy, isohexoxy and the like.

The term "alkylthio" as used herein, alone or in combination, refers to a straight or branched monovalent radical comprising an alkyl group as described above linked through a divalent sulphur atom having its free valence bond from the sulphur atom, for example $C_{1-8}$-alkylthio. Typical $C_{1-8}$-alkylthio groups include, but are not limited to, methylthio, ethylthio, propylthio, butylthio, pentylthio, hexylthio and the like.

The term "alkoxycarbonyl" as used herein refers to the monovalent radical $R^aOC(O)$—, where $R^a$ is alkyl as described above, for example $C_{1-8}$-alkoxycarbonyl. Typical $C_{1-8}$-alkoxycarbonyl groups include, but are not limited to, methoxycarbonyl, ethoxycarbonyl, propoxycarbonyl, isopropoxycarbonyl, n-butoxycarbonyl, sec-butoxycarbonyl, tertbutoxycarbonyl, 3-methylbutoxycarbonyl, n-hexoxycarbonyl and the like.

The term "carbamoyl" as used herein refers to $NH_2C(O)$—.

The term "aryl" as used herein refers to a carbocyclic aromatic ring radical or to a aromatic ring system radical. Aryl is also intended to include the partially hydrogenated derivatives of the carbocyclic systems.

The term "heteroaryl", as used herein, alone or in combination, refers to an aromatic ring radical with for instance 5 to 7 member atoms, or to a aromatic ring system radical with for instance from 7 to 18 member atoms, containing one or more heteroatoms selected from nitrogen, oxygen, or sulfur heteroatoms, wherein N-oxides and sulfur monoxides and sulfur dioxides are permissible heteroaromatic substitutions; such as e.g. furanyl, thienyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, and indazolyl, and the like. Heteroaryl is also intended to include the partially hydrogenated derivatives of the heterocyclic systems enumerated below.

Examples of "aryl" and "heteroaryl" includes, but are not limited to phenyl, biphenyl, indene, fluorene, naphthyl (1-naphthyl, 2-naphthyl), anthracene (1-anthracenyl, 2-anthracenyl, 3-anthracenyl), thiophene (2-thienyl, 3-thienyl), furyl (2-furyl, 3-furyl), indolyl, oxadiazolyl, isoxazolyl, thiadiazolyl, oxatriazolyl, thiatriazolyl, quinazolin, fluorenyl, xanthenyl, isoindanyl, benzhydryl, acridinyl, thiazolyl, pyrrolyl (1-pyrrolyl, 2-pyrrolyl, 3-pyrrolyl), pyrazolyl (1-pyrazolyl, 3-pyrazolyl, 4-pyrazolyl, 5-pyrazolyl), imidazolyl (1-imidazolyl, 2-imidazolyl, 4-imidazolyl, 5-imidazolyl), triazolyl (1,2,3-triazol-1-yl, 1,2,3-triazol-4-yl 1,2,3-triazol-5-yl, 1,2,4-triazol-3-yl, 1,2,4-triazol-5-yl), oxazolyl (2-oxazolyl, 4-oxazolyl, 5-oxazolyl), isooxazolyl (isooxazo-3-yl, isooxazo-4-yl, isooxaz-5-yl), isothiazolyl (isothiazo-3-yl, isothiazo-4-yl, isothiaz-5-yl) thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl)), benzo[b]thiophenyl (benzo[b]thiophen-2-yl, benzo[b]thiophen-3-yl, benzo[b]thiophen-4-yl, benzo[b]thiophen-5-yl, benzo[b]thiophen-6-yl, benzo[b]thiophen-7-yl), 2,3-dihydro-benzo[b]thiophenyl (2,3-dihydro-benzo[b]thiophen-2-yl, 2,3-dihydro-benzo[b]thiophen-3-yl, 2,3-dihydro-benzo[b]thiophen-4-yl, 2,3-dihydro-benzo[b]thiophen-5-yl, 2,3-dihydro-benzo[b]thiophen-6-yl, 2,3-dihydro-benzo[b]thiophen-7-yl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (2-benzoxazolyl, 3-benzoxazolyl, 4-benzoxazolyl, 5-benzoxazolyl, 6-benzoxazolyl, 7-benzoxazolyl), benzothiazolyl (2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), benzo[1,3]dioxole (2-benzo[1,3]dioxole, 4-benzo[1,3]dioxole, 5-benzo[1,3]dioxole, 6-benzo[1,3]dioxole, 7-benzo[1,3]dioxole), purinyl, and tetrazolyl (5-tetrazolyl, N-tetrazolyl).

The present invention also relates to partly or fully saturated analogues of the ring systems mentioned above.

When two such terms are used in combination, such as in aryl-alkyl-, heteroaryl-alkyl-, cycloalkyl-$C_{1-6}$alkyl- and the like, it is to be understood that the first mentioned radical is a substituent on the latter mentioned radical, where the point of substitution is on the latter of the radicals, for example aryl-alkyl-:

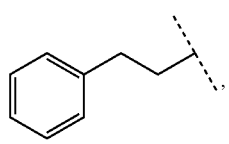

cycloalkyl-alkyl-:

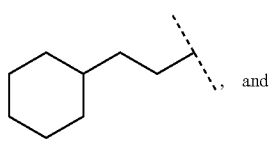, and aryl-alkoxy-:

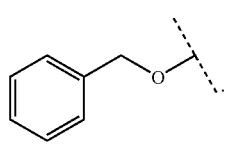.

The term "arylene", as used herein, alone or in combination, refers to carbocyclic aromatic ring diradical or to a aromatic ring system diradical. Examples of "arylene" include, but are not limited to, benzene-1,4-diyl, naphthalene-1,8-diyl, and the like. The term "arylene" alone or in combination also include other divalent radicals of the monovalent radicals mentioned in the definition of aryl.

The term "heteroarylene", as used herein, alone or in combination, refers to a five to seven membered aromatic ring diradical, or to a aromatic ring system diradical, containing one or more heteroatoms selected from nitrogen, oxygen, or sulfur heteroatoms, wherein N-oxides and sulfur monoxides and sulfur dioxides are permissible heteroaromatic substitutions. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like. The term "heteroarylene" alone or in combination also include other divalent radicals of the monovalent radicals mentioned in the definition of heteroaryl.

As used herein, the term "fused cycloalkylaryl" refers to a cycloalkyl group fused to an aryl group, the two having two atoms in common, and wherein the aryl group is the point of substitution. Examples of "fused cycloalkylaryl" used herein include 5-indanyl, 5,6,7,8-tetrahydro-2-naphthyl,

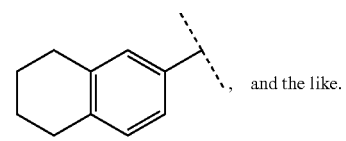, and the like.

As used herein, the term "fused cycloalkylarylene" refers to a fused cycloalkylaryl, wherein the aryl group is divalent. Examples include

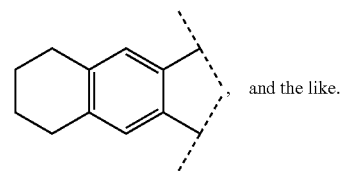, and the like.

As used herein, the term "fused arylcycloalkyl" refers to an aryl group fused to a cycloalkyl group, the two having two atoms in common, and wherein the cycloalkyl group is the point of substitution. Examples of "fused arylcycloalkyl" used herein include 1-indanyl, 2-indanyl, 1-(1,2,3,4-tetrahydronaphthyl),

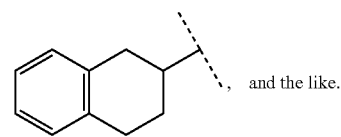, and the like.

As used herein, the term "fused arylcycloalkylene" refers to a fused arylcycloalkyl, wherein the cycloalkyl group is divalent. Examples include

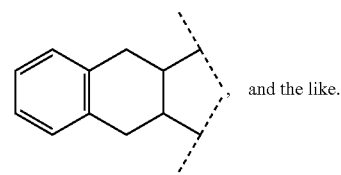, and the like.

As used herein, the term "fused heterocyclylaryl" refers to a heterocyclyl group fused to an aryl group, the two having two atoms in common, and wherein the aryl group is the point of substitution. Examples of "fused heterocyclylaryl" used herein include 3,4-methylenedioxy-1-phenyl,

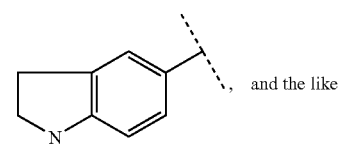, and the like

As used herein, the term "fused heterocyclylarylene" refers to a fused heterocyclylaryl, wherein the aryl group is divalent. Examples include

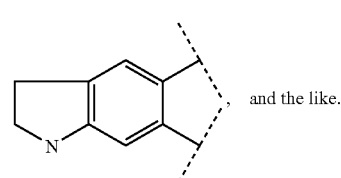, and the like.

As used herein, the term "fused arylheterocyclyl" refers to an aryl group fused to a heterocyclyl group, the two having two atoms in common, and wherein the heterocyclyl group is the point of substitution. Examples of "fused arylheterocyclyl" used herein include 2-(1,3-benzodioxolyl),

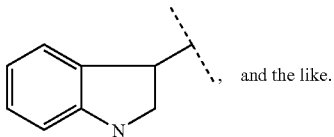, and the like.

As used herein, the term "fused arylheterocyclylene" refers to a fused arylheterocyclyl, wherein the heterocyclyl group is divalent. Examples include

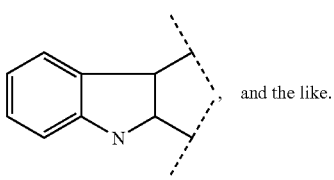, and the like.

As used herein, the term "fused cycloalkylheteroaryl" refers to a cycloalkyl group fused to a heteroaryl group, the two having two atoms in common, and wherein the heteroaryl group is the point of substitution. Examples of "fused cycloalkylheteroaryl" used herein include 5-aza-6-indanyl,

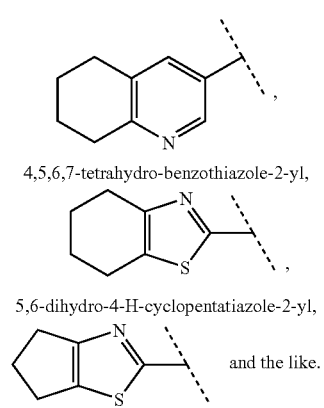

4,5,6,7-tetrahydro-benzothiazole-2-yl, 5,6-dihydro-4-H-cyclopentatiazole-2-yl, and the like.

As used herein, the term "fused heteroarylcycloalkylene" refers to a fused heteroarylcycloalkyl, wherein the cycloalkyl group is divalent. Examples include

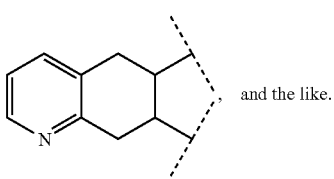, and the like.

As used herein, the term "fused heterocyclylheteroaryl" refers to a heterocyclyl group fused to a heteroaryl group, the two having two atoms in common, and wherein the heteroaryl group is the point of substitution. Examples of "fused heterocyclylheteroaryl" used herein include 1,2,3,4-tetrahydro-beta-carbolin-8-yl,

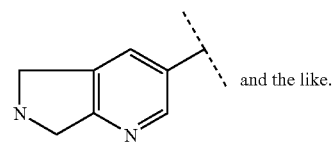, and the like.

As used herein, the term "fused heterocyclylheteroarylene" refers to a fused heterocyclylheteroaryl, wherein the heteroaryl group is divalent. Examples include

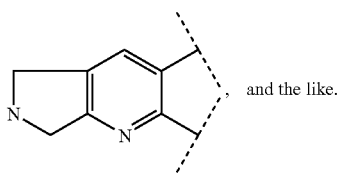, and the like.

As used herein, the term "fused heteroarylheterocyclyl" refers to a heteroaryl group fused to a heterocyclyl group, the two having two atoms in common, and wherein the heterocyclyl group is the point of substitution. Examples of "fused heteroarylheterocyclyl" used herein include 5-aza-2,3-dihydrobenzofuran-2-yl,

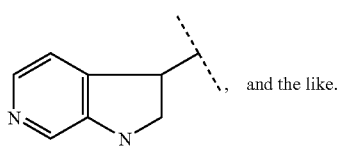, and the like.

As used herein, the term "fused heteroarylheterocyclylene" refers to a fused heteroarylheterocyclyl, wherein the heterocyclyl group is divalent. Examples include

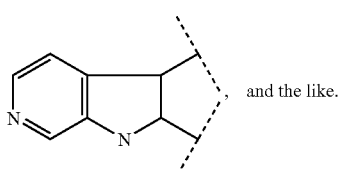, and the like.

The term "alkylsulfanyl", as used herein, refers to the group $R^aS-$, where $R^a$ is alkyl as described above.

The term "alkylsulfenyl", as used herein, refers to the group $R^aS(O)-$, where $R^a$ is alkyl as described above.

The term "alkylsulfonyl", as used herein, refers to the group $R^aSO_2-$, where $R^a$ is alkyl as described above.

The term "acyl", as used herein, refers to the group $R^aC(O)-$, where $R^a$ is alkyl, alkenyl, alkynyl, cycloalkyl, cycloalkenyl, or heterocyclyl as described above.

The term "aroyl", as used herein, refers to the group $R^aC(O)-$, where $R^a$ is aryl as described above.

The term "heteroaroyl", as used herein, refers to the group $R_aC(O)-$, where $R^a$ is heteroaryl as described above.

The term "aryloxycarbonyl", as used herein, refers to the group $R^a-O-C(O)-$, where $R^a$ is aryl as described above.

The term "acyloxy", as used herein, refers to the group $R^aC(O)O-$, where $R^a$ is alkyl, alkenyl, alkynyl, cycloalkyl, cycloalkenyl, or heterocyclyl as described above.

The term "aryloxy", as used herein refers to the group $R^a$—O—, where $R^a$ is aryl as described above.

The term "aroyloxy", as used herein, refers to the group $R^aC(O)O$—, where $R^a$ is aryl as described above.

The term "heteroaroyloxy", as used herein, refers to the group $R^aC(O)O$—, where $R^a$ is heteroaryl as described above.

Whenever the terms "alkyl", "cycloalkyl", "aryl", "heteroaryl" or the like or either of their prefix roots appear in a name of a substituent (e.g. arylalkoxyaryloxy) they shall be interpreted as including those limitations given above for "alkyl" and "aryl".

As used herein, the term "oxo" shall refer to the substituent =O.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent —$SO_2NH_2$.

As used herein, the term "sulfanyl" shall refer to the substituent —S—.

As used herein, the term "sulfenyl" shall refer to the substituent —S(O)—.

As used herein, the term "sulfonyl" shall refer to the substituent —$S(O)_2$—.

As used herein, the term "direct bond", where part of a structural variable specification, refers to the direct joining of the substituents flanking (preceding and succeeding) the variable taken as a "direct bond".

The term "lower", as used herein, refers to an group having between one and six carbons, and may be indicated with the prefix $C_{x-6}$-. Lower alkyl may thus be indicated as $C_{1-6}$-alkyl, while lower alkylene may be indicated as $C_{2-6}$-alkylene.

A radical such as $C_{x-y}$-cycloalkyl-$C_{a-b}$-alkenyl shall designate that the radical's point of attachment is in part of the radical mentioned last.

As used herein, the term "optionally" means that the subsequently described event(s) may or may not ocur, and includes both event(s) which ocur and events that do not ocur.

As used herein, the term "substituted" refers to substitution with the named substituent or substituents, multiple degrees of substitution being allowed unless otherwise stated.

As used herein, the terms "contain" or "containing" can refer to in-line substitutions at any position along the above defined alkyl, alkenyl, alkynyl or cycloalkyl substituents with one or more of any of O, S, SO, $SO_2$, N, or N-alkyl, including, for example, —$CH_2$—O—$CH_2$—, —$CH_2$—$SO_2$—$CH_2$—, —$CH_2$—NH—$CH_3$ and so forth.

Certain of the above defined terms may ocur more than once in the structural formulae, and upon such ocurrence each term shall be defined independently of the other.

As used herein, the term "solvate" is a complex of variable stoichiometry formed by a solute (in this invention, a compound of formula (I)) and a solvent. Such solvents for the purpose of the present invention may not interfere with the biological activity of the solute. Solvents may be, by way of example, water, ethanol, or acetic acid.

As used herein, the term "biohydrolyzable ester" is an ester of a drug substance (in this invention, a compound of formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to (I) in plasma. Many examples of such are known in the art and include by way of example lower alkyl esters (e.g., $C_{1-4}$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, α-amino acid amides, alkoxyacyl amides, and alkylaminoalkylcarbonyl amides.

As used herein, the term "prodrug" includes biohydrolyzable amides and biohydrolyzable esters and also encompasses a) compounds in which the biohydrolyzable functionality in such a prodrug is encompassed in the compound of formula (I) and b) compounds which may be oxidized or reduced biologically at a given functional group to yield drug substances of formula (I). Examples of these functional groups include, but are not limited to, 1,4-dihydropyridine, N-alkylcarbonyl-1,4-dihydropyridine, 1,4-cyclohexadiene, tert-butyl, and the like.

The term "pharmacologically effective amount" or shall mean that amount of a drug or pharmaceutical agent that will elicit the biological or medical response of a tissue, animal or human that is being sought by a researcher or clinician. This amount can be a therapeutically effective amount. The term "therapeutically effective amount" shall mean that amount of a drug or pharmaceutical agent that will elicit the therapeutic response of an animal or human that is being sought.

The term "treatment" and "treating" as used herein means the management and care of a patient for the purpose of combating a disease, disorder or condition. The term is intended to include the full spectrum of treatments for a given disorder from which the patient is suffering, such as the delaying of the progression of the disease, disorder or condition, the alleviation or relief of symptoms and complications, the prevention of the disease and/or the cure or elimination of the disease, disorder or condition. The patient to be treated is preferably a mammal, in particular a human being.

The term "human insulin" as used herein refers to naturally produced insulin or recombinantly produced insulin. Recombinant human insulin may be produced in any suitable host cell, for example the host cells may be bacterial, fungal (including yeast), insect, animal or plant cells.

The expression "insulin derivative" as used herein (and related expressions) refers to human insulin or an analogue thereof in which at least one organic substituent is bound to one or more of the amino acids.

By "analogue of human insulin" as used herein (and related expressions) is meant human insulin in which one or more amino acids have been deleted and/or replaced by other amino acids, including non-codeable amino acids, or human insulin comprising additional amino acids, i.e. more than 51 amino acids, such that the resulting analogue possesses insulin activity.

DETAILED DESCRIPTION OF THE INVENTION

Glucokinase (GK) plays an essential role in blood glucose homeostasis. GK catalyses glucose phosphorylation, and is the rate-limiting reaction for glycolysis in hepatocytes and pancreatic β-cells. In liver GK determine the rates of both glucose uptake and glycogen synthesis, and it is also thought to be essential for the regulation of various glucose-responsive genes (Girard, J. et al., Annu Rev Nutr 17, 325-352 (1997)). In the β-cells, GK determines glucose utilization and thus is necessary for glucose-stimulated insulin secretion. GK is also expressed in a population of neurones in the hypothalamus where it might be involved in feeding behaviour, and in the gut where it might contribute to the secretion of enteroincretins.

GK has two main distinctive characteristics: its expression, which is limited to tissues that require glucose-sensing (mainly liver and pancreatic β-cells), and its $S_{0.5}$ for glucose, which is much higher (8-12 mM) than that of the other members of the hexokinase family. Due to these kinetic characteristics, changes in serum glucose levels are paralleled by changes in glucose metabolism in liver which in turn regulate the balance between hepatic glucose output and glucose consumption.

Activators of glucokinase may thus be useful for treating diseases where increasing the activity of glucokinase is beneficial. Thus, there is a need for agents which activate glucokinase and increase glucokinase enzymatic activity. Such agents would be useful for the treatment of type I diabetes and type II diabetes.

Activators of glucokinase may also play a role in sensing low glucose levels and generating neurohumoral responses to hypoglycemia and may thus be useful for treating those patients with type 1 diabetes, which have a higher tendency to suffer from hypoglycemia.

Type I diabetes mellitus is a complex disease characterized by an elevated blood glucose concentration and polyuria. Secondary to the persistent elevation in blood glucose, patients develop devastating complications such as retinopathy, nephropathy, neuropathy, and cardiovascular disease. A major goal to improve the diabetic phenotype is to reduce fasting and postprandial hyperglycemia and, thus, avoid or delay the onset of diabetic complications. The Diabetes Control and Complications Trial has indicated that tight glycemic control through administration of daily multiple insulin injections delays the onset of complications. However, such intensive therapy is associated with an increase in body weight and higher risk for development of hypoglycaemic events. Alternative treatments to achieve glucose control without these side effects are, therefore, being developed. The combination of GK overexpression in the liver and subcutaneous insulin injections provides better glycemic control in type 1 diabetic animals than treatment with insulin alone (Morral, N., et al. Human Gene Therapy 13, 1561-1570 (2002)). Moreover, overexpression of hepatic GK can compensate, in part, for the metabolic disorders developed by insulin receptor-deficient mice (Jackerott, M. et al. Diabetologia 45, 1292-1297 (2002)).

The present invention also relates to the use of a GK activator for the combined treatment of diabetes and obesity. GK, the GK regulatory protein and the KATP channel are expressed in neurones of the hypothalamus, a region of the brain that is important in the regulation of energy balance and the control of food intake. These neurones have been shown to express orectic and anorectic neuropeptides and have been assumed to be the glucose-sensing neurones within the hypothalamus that are either inhibited or excited by changes in ambient glucose concentrations (Mobbs, C. V. et al, American Journal of Physiology, Endocrinology & Metabolism 281, E649-54 (2001)). The ability of these neurones to sense changes in glucose levels is defective in a variety of genetic and experimentally induced models of obesity (Spanswick, D. et al, Nature Neuroscience 3, 757-8 (2000), Levin, B. E. et al, Brain Research 808, 317-9 (1998)). Intracerebroventricular (icv) infusion of glucose analogues, which are competitive inhibitors of glucokinase, stimulate food intake in lean rats (Kurata, K. et al, Metabolism: Clinical & Experimental 38, 46-51 (1989)). In contrast, icv infusion of glucose suppresses feeding (Kurata, K. et al, Physiology & Behavior 37, 615-20 (1986)). Small molecule activators of GK may thus decrease food intake and weight gain through central effects on GK. Therefore, GK activators may be of therapeutic use in treating eating disorders, including obesity, in addition to diabetes. The hypothalamic effects will be additive or synergistic to the effects of the same compounds acting in the liver and/or pancreas in normalising glucose homeostasis, for the treatment of type 2 diabetes. Thus the GK/GK regulatory protein system can be described as a potential target of benefit in both diabetes and obesity.

The amplitude of glucose-induce insulin release is highly dependent on the action of the gastrointestinal hormones GLP-1 (glucogen-like peptide 1) and GIP. Unlike sulfonylureas, which stimulate insulin release at low as well as high glucose levels, the action of GLP-1 on β-cells is glucose dependent (Gromada, J. et al., Pflügers Arch 435, 583-594 (1998)). GLP-1 receptor agonist and drugs that slow the degradation of active GLP-1 are therefore under development as a novel treatments for type 2 diabetes. An alternative strategy would be to enhance endogenous GLP-1 levels. Of potential interest is the possibility that the release of GLP-1 and GIP might be regulated by glucokinase-expressing endocrine cells (Jetton, T. L. et al., J. Biol. Chem. 269, 3641-3654 (1994)) and glucose-responsive neurons (Liu, M. et al., J. Neurosci. 19, 10305-10317 (1999)). It has been reported that the release of GIP by intestinal K-cells is directly controlled by glucose (Kieffer, T. J. et al., Am J Physiol 267, E489-E496 (1994)), and GLP-1 secretion from GLUTag cells is triggered by glucose through a mechanism similar to that found in β-cells for insulin secretion (Reimann, F. et al, Diabetes 51, 2757-2763 (2002)). Small molecule activators of glucokinase may thus be used to increase GLP-1 and/or GIP secretion and thus for treatment, modulation, inhibition, decreasion, reduction, arrest or prevention of beta cell degeneration, such as necrosis or apoptosis of β-cells.

The present invention provides ortho-substituted heteroaryl and aryl ureas or carboxamide or sulfonamide activators of glucokinase.

In a first embodiment, the present invention provides compounds of the general formula (I).

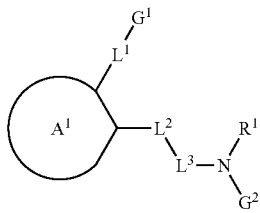

(I)

wherein
$A^1$ is selected from the group consisting of arylene, heteroarylene, fused cycloalkylarylene, fused heterocyclylarylene, fused cycloalkylheteroarylene, or fused heterocyclylheteroarylene; optionally substituted with one or more substitutents $R^{23}$, $R^{24}$, $R^{25}$, $R^{26}$, and $R^{27}$, wherein $R^{23}$, $R^{24}$, $R^{25}$, $R^{26}$, and $R^{27}$ independently of each other are selected from the group consisting of halogen, —C(O)OR$^2$, —CN, —CF$_3$, —OCF$_3$, —NO$_2$, —OR$^2$, —NR$^2$R$^3$, C$_{1-6}$alkyl-Z-, C$_{2-6}$-alkenyl-Z-, C$_{2-6}$-alkynyl-Z-, cycloalkyl-Z-, heterocyclyl-Z-, aryl-Z-, heteroaryl-Z-, aryl-C$_{1-6}$-alkylene-Z-, heteroaryl-C$_{1-6}$-alkylene-Z-, heterocyclyl-C$_{1-6}$-alkylene-Z-, cycloalkyl-C$_{1-6}$-alkylene-Z-, N(R$^4$R$^5$)—C$_{1-6}$-alkylene-Z-, R$^6$—W$^1$-Z-, R$^6$—W$^1$—N(R$^4$)-Z-, R$^6$—N(R$^4$)-Z, and R$^6$—W$^1$—C$_{1-6}$-alkylene-Z-, wherein $R^2$ and $R^3$ independently of each other are hydrogen, C$_{1-6}$alkyl, aryl-C$_{1-6}$-alkylene-, heteroaryl-C$_{1-6}$-alkylene-, C$_{1-6}$-alkyl-arylene-, C$_{1-6}$alkyl-heteroarylene-, heteroaryl, or aryl;

or $R^2$ and $R^3$, when attached to the same nitrogen atom, together with said nitrogen atom may form a 3 to 8 membered heterocyclic ring optionally containing one or two further heteroatoms selected from nitrogen, oxygen and sulfur, and optionally containing one or two double bonds;

Z and W$^1$ independently of each other are a direct bond, —O—, —N(R$^7$)—, —S—, —SO$_2$—, —C(O)N(R$^7$)—, —N(R$^7$)C(O)—, —N(R$^7$)CON(R$^8$)—, —N(R$^7$)SO$_2$—, —SO$_2$N(R$^7$)—, —C(O)—O—, —N(R$^7$)SO$_2$N(R$^8$)—, or —O—C(O)—, wherein $R^7$ and $R^8$ in each individual case independently of each other are hydrogen or alkyl; and $R^4$, $R^5$, and $R^6$ independently of each other are selected from the group consisting of hydrogen, aryl, alkyl, heteroaryl-alkylene-, and aryl-alkylene-;

or $R^4$ and $R^5$ may be taken together to form a ring having the formula —(CH$_2$)$_j$-Q-(CH$_2$)$_k$— bonded to the nitrogen atom to which $R^4$ and $R^5$ are attached, wherein j and k independently of each other is 1, 2, 3, or 4; and
Q is a direct bond, —CH$_2$—, —O—, —S—, —S(O$_2$)—, —C(O)—, —C(O)NH—, —NHC(O)—, —NHC(O)NH—, —NHSO$_2$—, —SO$_2$NH—, —C(O)—O—, —O—C(O)—, —NHSO$_2$NH—,

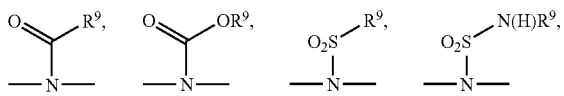

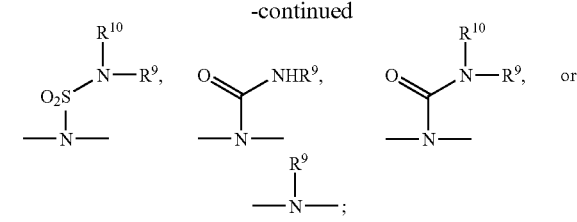

wherein
$R^9$ and $R^{10}$ independently of each other are selected from the group consisting of hydrogen, aryl, alkyl, and aryl-alkylene-;

$L^1$ is -D-alkylene-E-, -D-alkenylene-E-, -D-alkynylene-E-, -D-cycloalkylene-E-, -D-heterocyclylene-E-, —O—, —S—, —S(O)—, —S(O)$_2$—, —C(O)—, —N(R$^{11}$)—, or —C(=N—OR$^{12}$)—, wherein D and E independently of each other are a direct bond, —O— or —S—;

$R^{11}$ is selected from hydrogen, alkyl, aryl, carbamoyl, aryl-alkylene-, heteroaryl-alkylene-, alkyl-O—C(O)—, aryl-alkylene-O—C(O)—, heteroaryl-alkylene-O—C(O)—, alkyl-NH—C(O)—, aryl-alkylene-NH—C(O)—, heteroaryl-alkylene-NH—C(O)—, alkyl-SO$_2$—, aryl-alkylene-SO$_2$—, heteroaryl-alkylene-SO$_2$—, aryl-SO$_2$—, heteroaryl-SO$_2$—, alkyl-NH—SO$_2$—, aryl-alkylene-NH—SO$_2$—, heteroaryl-alkylene-NH—SO$_2$—, alkyl-C(O)—, aryl-alkylene-C(O)—, heteroaryl-alkylene-C(O)—, alkyl-Y—, aryl-Y—, heteroaryl-Y—, aryl-alkylene-Y—, heteroaryl-alkylene-Y—, N(R$^{13}$)(R$^{14}$)-alkylene-Y—, and R$^{15}$—W$^2$-alkylene-Y—, wherein Y and W$^2$ independently of each other are a direct bond, —CH$_2$—, —SO$_2$—, —N(H)CO—, —N(H)SO$_2$—, or —O—C(O)—;

$R^{13}$ and $R^{14}$ independently of each other are selected from hydrogen, aryl, heteroaryl, C$_{1-6}$-alkyl, C$_{1-6}$-alkoxy, aryl-C$_{1-6}$-alkylene-, heteroaryl-C$_{1-6}$-alkylene-, aryl-C$_{1-6}$-alkoxy-, heteroaryl-C$_{1-6}$-alkoxy-, C$_{1-6}$-alkyl-arylene-, C$_{1-6}$-alkyl-heteroarylene-, C$_{1-6}$alkoxy-heteroarylene-, or C$_{1-6}$-alkoxy-arylene-;

or $R_{13}$ and $R_{14}$ may be taken together to form a ring having the formula —(CH$_2$)$_o$—X—(CH$_2$)$_p$— bonded to the nitrogen atom to which $R_{13}$ and $R_{14}$ are attached, wherein o and p are independently of each other are 1, 2, 3, or 4; and X is a direct bond, —CH$_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

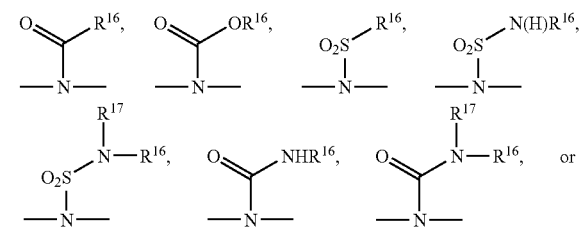

-continued

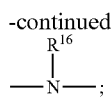

wherein
R$^{16}$ and R$^{17}$ are selected from hydrogen, aryl, heteroaryl, C$_{1-6}$-alkyl, C$_{1-6}$-alkoxy, aryl-C$_{1-6}$alkylene-, heteroaryl-C$_{1-6}$-alkylene-, C$_{1-6}$-alkyl-arylene-, C$_{1-6}$-alkyl-heteroarylene-, C$_{1-6}$-alkoxy-arylene-, C$_{1-6}$-alkoxy-heteroarylene-, heteroarylaryl-C$_{1-6}$-alkoxy-, or aryl-alkoxy-; and R$^{15}$ is selected from the group consisting of aryl, heteroaryl, cycloalkyl, heterocyclyl, alkyl, heteroaryl-alkylene-, or aryl-alkylene-; and R$^{12}$ is selected from hydrogen, aryl, heteroaryl, alkyl, aryl-alkylene-, heteroaryl-alkylene-, alkyl-arylene-, alkyl-heteroarylene-, alkoxy-heteroarylene-, or alkoxy-arylene-;

G$^1$ is alkyl, alkenyl, alkynyl, cycloalkyl or heterocyclyl, optionally substituted with one or more substituents selected from the group consisting of —CN, —CF$_3$, —OCF$_3$, —OR$^{18}$, —NR$^{18}$R$^{19}$, C$_{3-10}$-cycloalkyl and C$_{1-6}$-alkyl, wherein R$^{18}$ and R$^{19}$ independently of each other are hydrogen, C$_{1-6}$-alkyl, heteroaryl-C$_{1-6}$-alkylene-, aryl-C$_{1-6}$-alkylene-, C$_{1-6}$-alkyl-arylene-, C$_{1-6}$-alkyl-heteroarylene-, heteroaryl, or aryl;

or

R$^{18}$ and R$^{19}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds;

or

G$^1$ is aryl, heteroaryl, fused cycloalkylheteroaryl, fused heterocyclylaryl, or fused cycloalkylaryl, optionally substituted with one or more substituents R$^{40}$, R$^{41}$, and R$^{42}$;

L$^2$ is a direct bond, alkylene, alkenylene, alkynylene, —N(R$^{20}$)—, -alkylene-N(R$^{20}$)—, -alkenylene-N(R$^{20}$)—, -alkynylene-N(R$^{20}$)—, wherein R$^{20}$ is hydrogen, or R$^{20}$ is alkyl, alkenyl, alkynyl, cycloalkyl-W$^3$—, heterocyclyl-W$^3$—, aryl-W$^3$—, heteroaryl-W$^3$—, optionally substituted with one or more substituents R$^{30}$, R$^{31}$, and R$^{32}$, wherein W$^3$ is alkylene or a direct bond;

wherein L$^1$ and L$^2$ are attached to adjacent atoms in A$^1$;

L$^3$ is —C(O)—, or —S(O)$_2$—;

R$^1$ is hydrogen, or

R$^1$ is alkyl, alkenyl, alkynyl, cycloalkyl-W$^4$—, heterocyclyl-W$^4$—, aryl-W$^4$—, or heteroaryl-W$^4$—, optionally substituted with one or more substituents R$^{33}$, R$^{34}$, and R$^{35}$, wherein W$^4$ is alkylene or a direct bond;

G$^2$ is heteroaryl, fused heterocyclylheteroaryl, or fused cycloalkylheteroaryl, optionally substituted with one or more substituents R$^{43}$, R$^{44}$, and R$^{45}$, wherein said heteroaryl group posesses a nitrogen atom adjacent to the atom joining said heteroaryl group to —N(R$^1$)—;

or a group of the formula

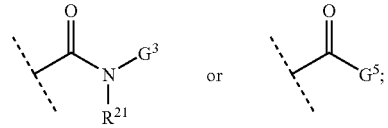

wherein
G$^3$ and G$^5$ independently of each other are alkyl, alkenyl, alkynyl, cycloalkyl-R$^{22}$—, heterocyclyl-R$^{22}$—, aryl-R$^{22}$—, heteroaryl-R$^{22}$-, optionally substituted with one or more substituents R$^{46}$, R$^{47}$, and R$^{48}$, wherein R$^{22}$ is alkylene or a direct bond; and R$^{21}$ is hydrogen, alkyl, alkenyl, alkynyl, cycloalkyl-W$^5$—, or heterocyclyl-W$^5$—, optionally substituted with one or more substituents R$^{36}$, R$^{37}$, and R$^{38}$, or R$^{21}$ is aryl-W$^5$—, or heteroaryl-W$^5$—, optionally substituted with one or more substituents R$^{49}$, R$^{50}$, and R$^{51}$, wherein W$^5$ is alkylene or a direct bond;

wherein

R$^{30}$, R$^{31}$, R$^{32}$, R$^{33}$, R$^{34}$, R$^{35}$, R$^{36}$, R$^{37}$, and R$^{38}$ independently of each other are selected from —CHF$_2$, —CF$_3$, —OCF$_3$, —OCHF$_2$, —OCH$_2$CF$_3$, —OCF$_2$CHF$_2$, —S(O)$_2$CF$_3$, —SCF$_3$, —OR$^{52}$, —NR$^{52}$R$^{53}$, —SR$_{52}$, —NR$^{52}$S(O)$_2$R$^{53}$, —S(O)$_2$NR$^{52}$R$^{53}$, —S(O)NR$^{52}$R$^{53}$, —S(O)R$^{52}$, —S(O)$_2$R$^{52}$, —C(O)NR$^{52}$R$^{53}$, —OC(O)NR$^{52}$R$^{53}$, —NR$^{52}$C(O)R$^{53}$, —CH$_2$C(O)NR$^{52}$R$^{53}$, —OCH$_2$C(O)NR$^{52}$R$^{53}$, —CH$_2$OR$^{52}$, —CH$_2$NR$^{52}$R$^{53}$, —OC(O)R$^{52}$, —C(O)R$^{52}$ and —C(O)OR$^{52}$; or C$_{2-6}$-alkenyl and C$_{2-6}$-alkynyl, which may optionally be substituted with one or more substituents selected from —CN, —CF$_3$, —OCF$_3$, —OR$^{52}$, —NR$^{52}$R$^{53}$ and C$_{1-6}$alkyl; or C$_{3-10}$-cycloalkyl, C$_{4-8}$-cycloalkenyl, heterocyclyl, C$_{3-10}$-cycloalkyl-C$_{1-6}$-alkylene-, C$_{3-10}$-cycloalkyl-C$_{1-6}$-alkoxy-, C$_{3-10}$-Cycloalkyloxy, C$_{3-10}$-cycloalkyl-C$_{1-6}$-alkylthio-, C$_{3-10}$-cycloalkylthio, C$_{3-10}$-cycloalkyl-C$_{2-6}$-alkenylene-, C$_{3-10}$-cycloalkyl-C$_{2-6}$-alkynylene-, C$_{4-8}$-cycloalkenyl-C$_{1-6}$-alkylene-, C$_{4-8}$-cycloalkenyl-C$_{2-6}$-alkenylene-, C$_{4-8}$-cycloalkenyl-C$_{2-6}$-alkynylene-, heterocyclyl-C$_{1-6}$-alkylene-, heterocyclyl-C$_{2-6}$-alkenylene-, heterocyclyl-C$_{2-6}$-alkynylene-, aryl, aryloxy, aryloxycarbonyl, aroyl, aryl-C$_{1-6}$-alkoxy-, aryl-C$_{1-6}$-alkylene-, aryl-C$_{2-6}$-alkenylene-, aryl-C$_{2-6}$-alkynylene-, heteroaryl, heteroaryl-C$_{1-6}$-alkylene-, heteroaryl-C$_{2-6}$-alkenylene- and heteroaryl-C$_{2-6}$-alkynylene-, of which the aryl and heteroaryl moieties optionally may be substituted with one or more substituents selected from halogen, —C(O)OR$^{52}$, —CN, —CF$_3$, —OCF$_3$, —NO$_2$, —OR$^{52}$, —NR$^{52}$R$^{53}$ and C$_{1-6}$alkyl, wherein R$^{52}$ and R$^{53}$ independently of each other are hydrogen, C$_{1-6}$-alkyl, aryl-C$_{1-6}$alkylene-heteroaryl-C$_{1-6}$-alkylene-heteroaryl, or aryl;

or

R$^{52}$ and R$^{53}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds;

R$^{40}$, R$^{41}$, R$^{42}$, R$^{43}$, R$^{44}$, R$^{45}$, R$^{46}$, R$^{47}$, R$^{48}$, R$^{49}$, R$^{50}$ and R$^{51}$ independently of each other are halogen, —CN, —NO$_2$, C$_{1-6}$-alkyl, —CHF$_2$, —CF$_3$, —OCF$_3$, —OCHF$_2$, —OCH$_2$CF$_3$, —OCF$_2$CHF$_2$, —S(O)$_2$CF$_3$, —SCF$_3$, —OR$^{54}$, —NR$^{54}$R$^{55}$, —SR$^{54}$, —NR$^{54}$S(O)$_2$R$^{55}$, —S(O)$_2$NR$^{54}$R$^{55}$, —S(O)NR$^{54}$R$^{55}$, —S(O)R$^{54}$, —S(O)$_2$R$^{54}$, —C(O)NR$^{54}$R$^{55}$, —OC(O)NR$^{54}$R$^{55}$, —NR$^{54}$C(O)R$^{55}$, —CH$_2$C(O)NR$^{54}$R$^{55}$, —CH$_2$C(O)OR$^{54}$, —OCH$_2$C(O)NR$^{54}$R$^{55}$, —CH$_2$OR$^{54}$, —CH$_2$NR$^{54}$R$^{55}$, —OC(O)R$^{54}$, —C(O)R$^{54}$ and —C(O)OR$^{54}$; or C$_{2-6}$-alkenyl and C$_{2-6}$-alkynyl, which may optionally be substituted with one or more substituents selected from —CN, —CF$_3$, —OCF$_3$, —R$^{54}$, —NR$^{54}$R$^{55}$ and C$_{1-6}$-alkyl; C$_{3-10}$-cycloalkyl, C$_{4-8}$-cycloalkenyl, heterocyclyl, C$_{3-10}$-cycloalkyl-C$_{1-6}$-alkylene-, C$_{3-10}$-cycloalkyl-C$_{1-6}$-alkoxy-, C$_{3-10}$-cycloalkyloxy, C$_{3-10}$-cycloalkyl-C$_{1-6}$-alkylthio-, C$_{3-10}$-cycloalkylthio, C$_{3-10}$-cycloalkyl-C$_{2-6}$-alkenylene-, C$_{3-10}$-cycloalkyl-C$_{2-6}$-alkynylene-, C$_{4-8}$-cycloalkenyl-C$_{1-6}$-alkylene-, C$_{4-8}$-cycloalkenyl-C$_{2-6}$-alkenylene-, C$_{4-8}$-cycloalkenyl-C$_{2-6}$-alkynylene-, heterocyclyl-C$_{1-6}$-alkylene-, heterocyclyl-C$_{2-6}$-alkenylene-, heterocyclyl-C$_{2-6}$-alkynylene-; or aryl, aryloxy, aryloxycarbonyl, aroyl, aryl-C$_{1-6}$-alkoxy-, aryl-C$_{1-6}$-alkylene-, aryl-C$_{2-6}$-alkenylene-, aryl-C$_{2-6}$-alkynylene-, heteroaryl, heteroaryl-C$_{1-6}$-alkylene-, heteroaryl-C$_{2-6}$-alkenylene- and heteroaryl-C$_{2-6}$-alkynylene-, of which the aryl and heteroaryl moieties optionally may be substituted with one or more substituents selected from halogen, —C(O)OR$^{54}$, —CN, —CF$_3$, —OCF$_3$, —NO$_2$, —OR$^{54}$, —NR$^5$R$^{55}$ or C$_{1-6}$-alkyl wherein R$^{54}$ and R$^{55}$ independently of each other are hydrogen, C$_{1-6}$alkyl, C$_{1-6}$-alkyl-arylene-, C$_{1-6}$-alkyl-heteroarylene-, aryl-C$_{1-6}$-alkylene-, heteroaryl-C$_{1-6}$-alkylene-, heteroaryl, or aryl;

or

R$^{54}$ and R$^{55}$ independently of each other are hydrogen or —(CHR$^{63}$)$_u$—(CHR$^{64}$)$_v$-Z, wherein u is 1 or 2;
v is 0, 1 or 2;
R$^{63}$ and R$^{64}$ independently of each other are hydrogen, C$_{1-6}$-alkyl, C$_{1-6}$alkyl-arylene- aryl, hydroxy, hydroxyalkyl, amino, or aminoalkyl;
Z is hydrogen, —O—R$^{65}$, —C(O)O—R$^{65}$— CONR$^{65}$R$^{66}$, alkylamino, or dialkylamino, wherein R$^{65}$ and R$^{66}$ independently of each other is hydrogen or C$_{1-6}$-alkyl;
or
Z is a five or six membered ring wherein at least one ring atom is nitrogen and the remaining ring atoms are either carbon or oxygen;

or

R$^{54}$ and R$^{55}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds, and optionally substituted with one or more C$_{1-6}$alkyl groups;

or a pharmaceutically acceptable salt, solvate, or prodrug thereof.

Other embodiments of the present invention are clear from the following list of embodiments.

Embodiment 2: A compound according to embodiment 1, wherein
A$^1$ is arylene or heteroarylene, optionally substituted with one or more substituents R$^{23}$, R$^{24}$, R$^{25}$, R$^{26}$, and R$^{27}$, wherein R$^{23}$, R$^{24}$, R$^{25}$, R$^{26}$, and R$^{27}$ independently of each other are selected from the group consisting of
halogen, —C(O)OR$^2$, —CN, —CF$_3$, —OCF$_3$, —NO$_2$, —OR$^2$, —NR$^2$R$^3$, C$_{1-6}$-alkyl-Z-, C$_{2-6}$-alkenyl-Z-, C$_{2-6}$-alkynyl-Z-, cycloalkyl-Z-, heterocyclyl-Z-, aryl-Z-, heteroaryl-Z-, aryl-C$_{1-6}$-alkylene-Z-, heteroaryl-C$_{1-6}$-alkylene-Z-, heterocyclyl-C$_{1-6}$-alkylene-Z-, cycloalkyl-C$_{1-6}$-alkylene-Z-, N(R$^4$R$^5$)—C$_{1-6}$-alkylene-Z-, R$^6$—W$^1$-Z-, R$^6$—W$^1$—N(R$^4$)-Z-, R$^6$—N(R$^4$)-Z, and R$^6$—W$^1$—C$_{1-6}$ alkylene-Z-, wherein
R$^2$, R$^3$, R$^4$, R$^5$, R$^6$, Z, and W$^1$ are as defined for embodiment 1.

Embodiment 3: A compound according to embodiment 2, wherein
A$^1$ is C$_{6-10}$-arylene or C$_{4-10}$-heteroarylene, optionally substituted with one or more substitutents R$^{23}$, R$^{24}$, R$^{25}$, R$^{26}$, and R$^{27}$, wherein R$^{23}$, R$^{24}$, R$^{25}$, R$^{26}$, and R$^{27}$ independently of each other are selected from the group consisting of
halogen, —C(O)OR$^2$, —CN, —CF$_3$, —OCF$_3$, —NO$_2$, —OR$^2$, —NR$^2$R$^3$, C$_{1-6}$-alkyl-Z-, C$_{2-6}$-alkenyl-Z-, C$_{2-6}$-alkynyl-Z-, cycloalkyl-Z-, heterocyclyl-Z-, aryl-Z-, heteroaryl-Z-, aryl-C$_{1-6}$-alkylene-Z-, heteroaryl-C$_{1-6}$-alkylene-Z-, heterocyclyl-C$_{1-6}$-alkylene-Z-, cycloalkyl-C$_{1-6}$-alkylene-Z-, N(R$^4$R$^5$)—C$_{1-6}$-alkylene-Z-, R$^6$—W$^1$-Z-, R$^6$—W$^1$—N(R$^4$)-Z-, R$^6$—N(R$^4$)-Z, and R$^6$—W$^1$—C$_{1-6}$-alkylene-Z-, wherein
R$^2$, R$^3$, R$^4$, R$^5$, R$^6$, Z, and W$^1$ are as defined for embodiment 1.

Embodiment 4: A compound according to any of embodiments 1 to 3, wherein
R$^{23}$, R$^{24}$, R$^{25}$, R$^{26}$, and R$^{27}$ independently of each other are selected from the group consisting of
halogen, —C(O)OR$^2$, —CN, —CF$_3$, —OCF$_3$, —NO$_2$, —OR$^2$, —NR$^2$R$^3$, C$_{1-6}$-alkyl-Z-cycloalkyl-Z-, heterocyclyl-Z-, aryl-Z-, or heteroaryl-Z-, N(R$^4$R$^5$)—C$_{1-6}$-alkylene-Z-, R$^6$—W$^1$-Z-, R$^6$—W$^1$—N(R$^4$)-Z-, R$^6$—N(R$^4$)-Z, and R$^6$—W$^1$—C$_{1-6}$-alkylene-Z-, wherein
R$^2$, R$^3$, R$^4$, R$^5$, R$^6$, Z, and W$^1$ are as defined for embodiment 1.

Embodiment 5: A compound according to any of embodiments 1 to 7, wherein
R$^4$, R$^5$, and R$^6$ independently of each other are selected from the group consisting of hydrogen, aryl, alkyl, heteroaryl-alkylene-, and aryl-alkylene-.

Embodiment 6: A compound according to embodiment 11, wherein
R$^4$, R$^5$, and R$^6$ independently of each other are hydrogen or alkyl.

Embodiment 7: A compound according to embodiment 12, wherein
R$^4$, R$^5$, and R$^6$ are hydrogen.

Embodiment 8: A compound according to any of embodiments 1 to 7, wherein
R$^4$ and R$^5$ is taken together to form a ring having the formula —(CH$_2$)$_j$-Q-(CH$_2$)$_k$-bonded to the nitrogen atom to which R$^4$ and R$^5$ are attached, wherein
j and k independently of each other is 1, 2, 3, or 4;
Q is a direct bond, —CH$_2$—, —O—, —S—, —S(O$_2$)—, —C(O)—, —C(O)NH—, —NHC(O)—, —NHC(O)NH—, —NHSO$_2$—, —SO$_2$NH—, —C(O)—O—, —O—C(O)—, —NHSO$_2$NH—,

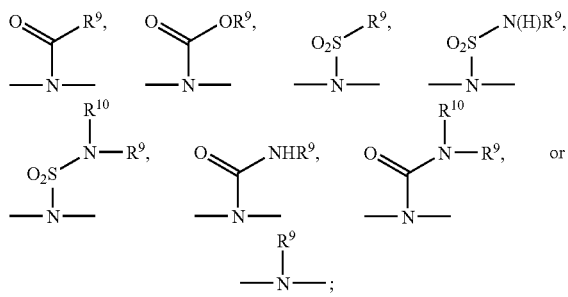

wherein
R⁹ and R¹⁰ independently of each other are selected from the group consisting of hydrogen, aryl, alkyl, and arylalkyl-.

Embodiment 9: A compound according to embodiment 14, wherein
Q is a direct bond, —CH$_2$—, —O—, —S—, —S(O$_2$)—, —C(O)—, —C(O)NH—, —NHC(O)—, —NHC(O)NH—, —NHSO$_2$—, —SO$_2$NH—, —C(O)—O—, —O—C(O)—, —NHSO$_2$NH—,

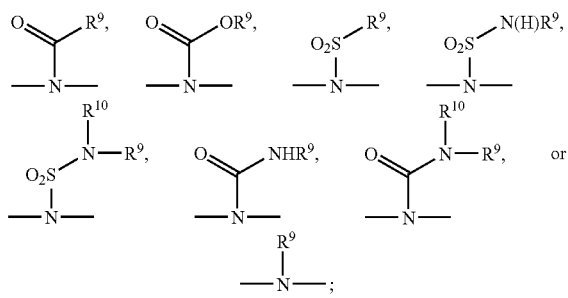

wherein
R⁹ and R¹⁰ independently of each other are hydrogen or alkyl.

Embodiment 10: A compound according to embodiment 15, wherein
Q is a direct bond, —CH$_2$—, —O—, —S—, —S(O$_2$)—, —C(O)—, —C(O)NH—, —NHC(O)—, —NHC(O)NH—, —NHSO$_2$—, —SO$_2$NH—, —C(O)—O—, —O—C(O)—, —NHSO$_2$NH—,

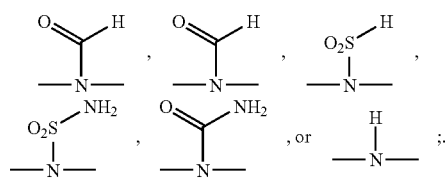

Embodiment 11: A compound according to embodiment 16, wherein Q is a direct bond.

Embodiment 12: A compound according to any of embodiments 1 to 17, wherein
W¹ is a direct bond, —O—, —NH—, —S—, —SO$_2$—, —C(O)NH—, —NHC(O)—, —N(H)CON(H)—, —N(H)SO$_2$—, —SO$_2$N(H)—, —C(O)—O—, —N(H)SO$_2$N(H)—, or —O—C(O)—.

Embodiment 13: A compound according to embodiment 18, wherein W¹ is a direct bond, —O—, —S—, or —SO$_2$—.

Embodiment 14: A compound according to embodiment 19, wherein W¹ is a direct bond.

Embodiment 15: A compound according to embodiment 7, wherein
at least one of R$^{23}$, R$^{24}$, R$^{25}$, R$^{26}$, and R$^{27}$ is halogen, —C(O)OR$^2$, —CN, —CF$_3$, —OCF$_3$, —NO$_2$, —OR$^2$, —NR$^2$R$^3$, C$_{1-6}$-alkyl-Z-, cycloalkyl-Z-, heterocyclyl-Z-, aryl-Z-, or heteroaryl-Z-, wherein
R$^2$, R$^3$, and Z are as defined for embodiment 1.

Embodiment 16: A compound according to embodiment 22, wherein
at least one of R$^{23}$, R$^{24}$, R$^{25}$, R$^{26}$, and R$^{27}$ is halogen, —C(O)OR$^2$, —CN, —CF$_3$—OCF$_3$, —NO$_2$, —OR$^2$, —NR$^2$R$^3$, C$_{1-6}$-alkyl-Z-, C$_{3-10}$-cycloalkyl-Z-, C$_{3-10}$-heterocyclyl-Z-, C$_{3-10}$-aryl-Z-, or C$_{3-10}$-heteroaryl-Z-, wherein
R$^2$, R$^3$, and Z are as defined for embodiment 1.

Embodiment 17: A compound according to embodiment 23, wherein
at least one of R$^{23}$, R$^{24}$, R$^{25}$, R$^{26}$, and R$^{27}$ is halogen, —C(O)OR$^2$, —CN, —NO$_2$, —OR$^2$, —NR$^2$R$^3$, C$_{1-6}$-alkyl-Z-, C$_{3-10}$-cycloalkyl-Z-, C$_{3-10}$-heterocyclyl-Z-, C$_{3-10}$-aryl-Z-, or C$_{3-10}$-heteroaryl-Z-, wherein
R$^2$, R$^3$, and Z are as defined for embodiment 1.

Embodiment 18: A compound according to embodiment 24, wherein
at least one of R$^{23}$, R$^{24}$, R$^{25}$, R$^{26}$, and R$^{27}$ is halogen, —C(O)OR$^2$, —CN, —NO$_2$, —OR$^2$, or —NR$^2$R$^3$, wherein
R$^2$, R$^3$, and Z are as defined for embodiment 1.

Embodiment 19: A compound according to any of embodiments 1 to 26, wherein
R$^2$ and R$^3$ independently of each other are hydrogen, C$_{1-6}$-alkyl, aryl-C$_{1-6}$-alkylene-, heteroaryl-C$_{1-6}$-alkylene-, C$_{1-6}$-alkyl-arylene-, C$_{1-6}$alkyl-heteroarylene-, heteroaryl, or aryl.

Embodiment 20: A compound according to embodiment 27, wherein
R$^2$ and R$^3$ independently of each other, are hydrogen, C$_{1-6}$alkyl, aryl-C$_{1-6}$-alkylene- or aryl.

Embodiment 21: A compound according to embodiment 28, wherein
R$^2$ is hydrogen or C$_{1-6}$-alkyl.

Embodiment 22: A compound according to embodiment 29, wherein
R$^2$ is hydrogen.

Embodiment 23: A compound according to any of embodiments 1 to 30, wherein
R$^3$ is hydrogen or C$_{1-6}$alkyl.

Embodiment 24: A compound according to embodiment 31, wherein
R$^3$ is hydrogen.

Embodiment 25: A compound according to any of embodiments 1 to 22, wherein
R$^2$ and R$^3$, when attached to the same nitrogen atom, together with said nitrogen atom may form a 3 to 8 membered heterocyclic ring optionally containing one or two further heteroatoms selected from nitrogen, oxygen and sulfur, and optionally containing one or two double bonds.

Embodiment 26: A compound according to any of embodiments 1 to 33, wherein
Z is a direct bond, —O—, —NH—, —S—, —SO$_2$—, —C(O)NH—, —NHC(O)—, —N(H)CON(H)—, —N(H)SO$_2$—, —SO$_2$N(H)—, —C(O)—O—, —N(H)SO$_2$N(H)—, or —O—C(O)—.

Embodiment 27: A compound according to embodiment 34, wherein
Z is a direct bond, —O—, —S—, or —SO$_2$—.

Embodiment 28: A compound according to embodiment 35, wherein
Z is a direct bond.

Embodiment 29: A compound according to embodiment 2, wherein
A$^1$ is

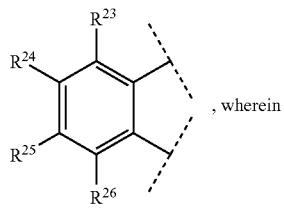, wherein

R$^{23}$, R$^{24}$, R$^{25}$, and R$^{26}$, independently of each other, are hydrogen or as defined for embodiment 1.

Embodiment 30: A compound according to embodiment 37, wherein
R$^{23}$, R$^{24}$, R$^{25}$, and R$^{26}$ independently of each other are selected from the group consisting of
halogen, —C(O)OR$^2$, —CN, —CF$_3$, —OCF$_3$, —NO$_2$, —OR$^2$, —NR$^2$R$^3$, C$_{1-6}$-alkyl-Z-, cycloalkyl-Z-, heterocyclyl-Z-, aryl-Z-, or heteroaryl-Z-, N(R$^4$R$^5$)—C$_{1-6}$-alkylene-Z-, R$^6$—W$^1$-Z-, R$^6$—W$^1$—N(R$^4$)-Z-, R$^6$—N(R$^4$)-Z, and R$^6$—W$^1$—C$_{1-6}$-alkylene-Z-, wherein R$^2$, R$^3$, R$^4$, R$^5$, R$^6$, Z, and W$^1$ are as defined for embodiment 1.

Embodiment 31: A compound according to embodiment 37 or 38, wherein
R$^4$, R$^5$, and R$^6$ independently of each other are selected from the group consisting of hydrogen, aryl, alkyl, heteroaryl-alkylene-, and aryl-alkylene-.

Embodiment 32: A compound according to embodiment 39, wherein
R$^4$, R$^5$, and R$^6$ independently of each other are hydrogen or alkyl.

Embodiment 33: A compound according to embodiment 40, wherein
R$^4$, R$^5$, and R$^6$ are hydrogen.

Embodiment 34: A compound according to embodiment 37 or 38, wherein
R$^4$ and R$^5$ is taken together to form a ring having the formula —(CH$_2$)$_j$-Q-(CH$_2$)$_k$— bonded to the nitrogen atom to which R$^4$ and R$^5$ are attached, wherein
j and k independently of each other is 1, 2, 3, or 4;

Q is a direct bond, —CH$_2$—, —O—, —S—, —S(O$_2$)—, —C(O)—, —C(O)NH—, —NHC(O)—, —NHC(O)NH—, —NHSO$_2$—, —SO$_2$NH—, —C(O)—O—, —O—C(O)—, —NHSO$_2$NH—,

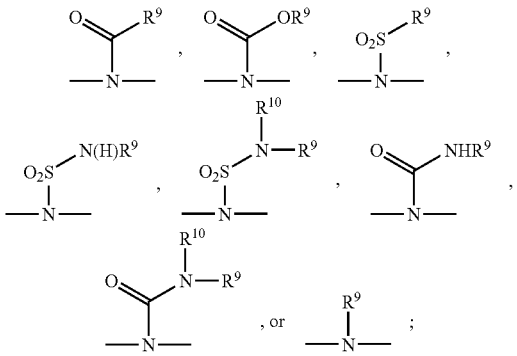

wherein
R$^9$ and R$^{10}$ independently of each other are selected from the group consisting of hydrogen, aryl, alkyl, and arylalkyl-.

Embodiment 35: A compound according to embodiment 42, wherein
Q is a direct bond, —CH$_2$—, —O—, —S—, —S(O$_2$)—, —C(O)—, —C(O)NH—, —NHC(O)—, —NHC(O)NH—, —NHSO$_2$—, —SO$_2$NH—, —C(O)—O—, —O—C(O)—, —NHSO$_2$NH—,

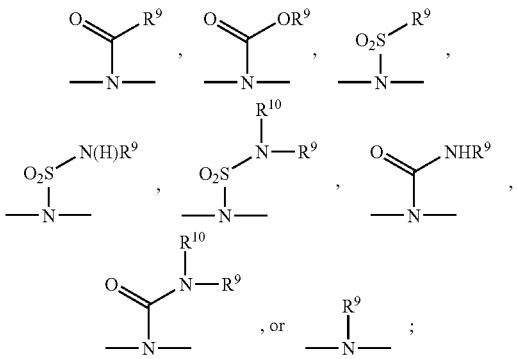

wherein
R$^9$ and R$^{10}$ independently of each other are hydrogen or alkyl.

Embodiment 36: A compound according to embodiment 43, wherein
Q is a direct bond, —CH$_2$—, —O—, —S—, —S(O$_2$)—, —C(O)—, —C(O)NH—, —NHC(O)—, —NHC(O)NH—, —NHSO$_2$—, —SO$_2$NH—, —C(O)—O—, —O—C(O)—, —NHSO$_2$NH—,

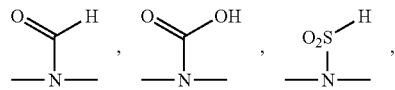

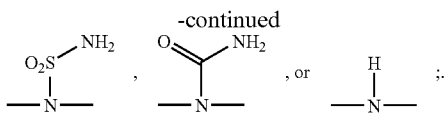

Embodiment 37: A compound according to embodiment 44, wherein
Q is a direct bond.

Embodiment 38: A compound according to any of embodiments 37 to 45, wherein
$W^1$ is a direct bond, —O—, —NH—, —S—, —SO$_2$—, —C(O)NH—, —NHC(O)—, —N(H)CON(H)—, —N(H)SO$_2$—, —SO$_2$N(H)—, —C(O)—O—, —N(H)SO$_2$N(H)—, or —O—C(O)—.

Embodiment 39: A compound according to embodiment 46, wherein
$W^1$ is a direct bond, —O—, —S—, or —SO$_2$—.

Embodiment 40: A compound according to embodiment 48, wherein
$W^1$ is a direct bond.

Embodiment 41: A compound according to embodiment 37, wherein
at least one of $R^{23}$, $R^{24}$, $R^{25}$, and $R^{26}$ is halogen, —C(O)OR$^2$, —CN, —CF$_3$, —OCF$_3$, —NO$_2$, —OR$^2$, —NR$^2$R$^3$, C$_{1-6}$-alkyl-Z-, cycloalkyl-Z-, heterocyclyl-Z-, aryl-Z-, or heteroaryl-Z-, wherein
$R^2$, $R^3$, and Z are as defined for embodiment 37.

Embodiment 42: A compound according to embodiment 50, wherein
at least one of $R^{23}$, $R^{24}$, $R^{25}$, and $R^{26}$ is halogen, —C(O)OR$^2$, —CN, —CF$_3$, —OCF$_3$, —NO$_2$, OR$^2$, —NR$^2$R$^3$, C$_{1-6}$-alkyl-Z-, C$_{3-10}$-cycloalkyl-Z-, C$_{3-10}$-heterocyclyl-Z-, C$_{3-10}$-aryl-Z-, or C$_{3-10}$-heteroaryl-Z-, wherein
$R^2$, $R^3$, and Z are as defined for embodiment 37.

Embodiment 43: A compound according to embodiment 51, wherein
at least one of $R^{23}$, $R^{24}$, $R^{25}$, and $R^{26}$ is halogen, —C(O)OR$^2$, —CN, —NO$_2$, —OR$^2$, —NR$^2$R$^3$, C$_{1-6}$-alkyl-Z-, C$_{3-10}$-cycloalkyl-Z-, C$_{3-10}$-heterocyclyl-Z-, C$_{3-10}$-aryl-Z-, or C$_{3-10}$-heteroaryl-Z-, wherein
$R^2$, $R^3$, and Z are as defined for embodiment 37.

Embodiment 44: A compound according to any of embodiments 37 to 52, wherein
Z is a direct bond, —O—, —NH—, —S—, —SO$_2$—, —C(O)NH—, —NHC(O)—, —N(H)CON(H)—, —N(H)SO$_2$—, —SO$_2$N(H)—, —C(O)—O—, —N(H)SO$_2$N(H)—, or —O—C(O)—.

Embodiment 45: A compound according to embodiment 53, wherein
Z is a direct bond, —O—, —S—, or —SO$_2$—.

Embodiment 46: A compound according to embodiment 54, wherein
Z is a direct bond.

Embodiment 47: A compound according to embodiment 52, wherein
at least one of $R^{23}$, $R^{24}$, $R^{25}$, and $R^{26}$ is halogen, —C(O)OR, —CN, —NO$_2$, —OR$^2$, —NR$^2$R$^3$, or C$_{1-6}$alkyl, wherein
$R^2$, and $R^3$ are as defined for embodiment 37.

Embodiment 48: A compound according to any of embodiments 37 to 56, wherein
$R^2$ and $R^3$ independently of each other are hydrogen, C$_{1-6}$alkyl, aryl-C$_{1-6}$alkylene-, heteroaryl-C$_{1-6}$-alkylene-, C$_{1-6}$-alkyl-arylene-, C$_{1-6}$-alkyl-heteroarylene-, heteroaryl, or aryl.

Embodiment 49: A compound according to embodiment 57, wherein
$R^2$ and $R^3$ independently of each other, are hydrogen, C$_{1-6}$alkyl, aryl-C$_{1-6}$-alkylene- or aryl.

Embodiment 50: A compound according to embodiment 58, wherein
$R^2$ is hydrogen or C$_{1-6}$-alkyl.

Embodiment 51: A compound according to embodiment 59, wherein
$R^2$ is hydrogen.

Embodiment 52: A compound according to any of embodiments 37 to 60, wherein
$R^3$ is hydrogen or C$_{1-6}$-alkyl.

Embodiment 53: A compound according to embodiment 61, wherein
$R^3$ is hydrogen.

Embodiment 54: A compound according to any of embodiments 37 to 50, wherein
$R^2$ and $R^3$, when attached to the same nitrogen atom, together with said nitrogen atom may form a 3 to 8 membered heterocyclic ring optionally containing one or two further heteroatoms selected from nitrogen, oxygen and sulfur, and optionally containing one or two double bonds.

Embodiment 55: A compound according to any of embodiments 37 to 55, wherein
at least one of $R^{23}$, $R^{24}$, $R^{25}$, and $R^{26}$ are hydrogen.

Embodiment 56: A compound according to embodiment 64, wherein
at least two of $R^{23}$, $R^{24}$, $R^{25}$, and $R^{26}$ are hydrogen.

Embodiment 57. A compound according to embodiment 65, wherein
$R^{23}$ and $R^{26}$ are hydrogen.

Embodiment 58: A compound according to embodiment 65 or embodiment 66, wherein
at least three of $R^{23}$, $R^{24}$, $R^{25}$, and $R^{26}$ are hydrogen.

Embodiment 59: A compound according to any of embodiments 37 to 67, wherein $R^{24}$ or $R^{25}$ is halogen.

Embodiment 60: A compound according to embodiment 68, wherein $R^{24}$ or $R^{25}$ is fluoro.

Embodiment 61: A compound according to any of embodiments 37 to 67, wherein $R^{24}$ or $R^{25}$ is C$_{1-6}$-alkyl.

Embodiment 62: A compound according to embodiment 68, wherein $R^{24}$ or $R^{25}$ is methyl.

Embodiment 63: A compound according to any of embodiments 37 to 67, wherein
$R^{24}$ is hydrogen.

Embodiment 64: A compound according to any of embodiments 37 to 72, wherein
$R^{25}$ is hydrogen.

Embodiment 65: A compound according to embodiment 37, wherein
$R^{23}$, $R^{24}$, $R^{25}$, and $R^{26}$ are hydrogen.

Embodiment 66: A compound according to any of embodiments 1 to 74, wherein
$L^1$ is -D-alkylene-E-, —O—, —S—, —S(O)—, —S(O)$_2$—, —C(O)—, —N($R^{11}$)—, or —C(=N—O$R^{12}$), wherein
D, E, $R^{11}$ and $R^{12}$ are as defined for embodiment 1.

Embodiment 67: A compound according to embodiment 75, wherein
$L^1$ is -D-alkylene-E-, —O—, —C(O)—, —N($R^{11}$)—, or —C(=N—O$R^{12}$)—, wherein
D, E, $R^{11}$ and $R^{12}$ are as defined for embodiment 1.

Embodiment 68: A compound according to embodiment 75, wherein
$L^1$ is —O—.

Embodiment 69: A compound according to embodiment 75, wherein
$L^1$ is —S—.

Embodiment 70: A compound according to embodiment 75, wherein
$L^1$ is —C(O)—.

Embodiment 71: A compound according to any of embodiments 1 to 76, wherein
D is a direct bond or —O—;
E is a direct bond or —O—; and
$R^{11}$ and $R^{12}$ are as defined for embodiment 1.

Embodiment 72: A compound according to embodiment 81, wherein
D is a direct bond.

Embodiment 73: A compound according to embodiment 81, wherein
D is —O—.

Embodiment 74: A compound according to any of embodiments 81 to 83, wherein
E is a direct bond.

Embodiment 75: A compound according to any of embodiments 81 to 83, wherein
E is —O—.

Embodiment 76: A compound according to any of embodiments 1 to 85, wherein
$R^{11}$ is selected from hydrogen, alkyl, aryl, carbamoyl, aryl-alkylene-, alkyl-NH—C(O)—, aryl-alkylene-NH—C(O)—, alkyl-SO$_2$—, aryl-alkylene-SO$_2$—, aryl-SO$_2$—, SO$_2$—, alkyl-C(O)—, aryl-alkylene-C(O)—, N($R^{13}$)($R^{14}$)-alkylene-Y—, and $R^{15}$—W$^2$-alkylene-Y—, wherein
Y and W$^2$ independently of each other are a direct bond, —CH$_2$—, —SO$_2$—, —N(H)CO—, —N(H)SO$_2$—, or —O—C(O)—;
$R^{13}$ and $R^{14}$ independently of each other are selected from hydrogen, aryl, $C_{1-6}$alkyl, or aryl-$C_{1-6}$alkylene-; or
$R^{13}$ and $R^{14}$ may be taken together to form a ring having the formula —(CH$_2$)$_o$—X—(CH$_2$)$_p$— bonded to the nitrogen atom to which $R^{13}$ and $R^{14}$ are attached, wherein
o and p are independently of each other are 1, 2, 3, or 4; and
X is a direct bond, —CH$_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

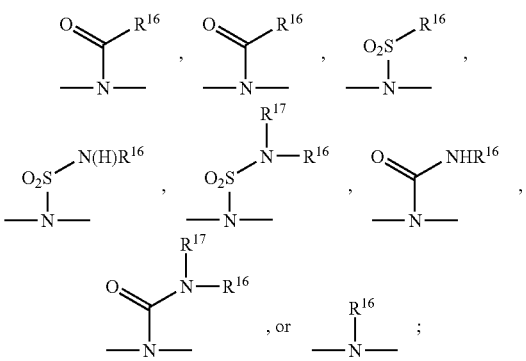

wherein
$R^{16}$ and $R^{17}$ are selected from hydrogen, aryl, heteroaryl, $C_{1-6}$alkyl, $C_{1-6}$-alkoxy, aryl-$C_{1-6}$alkylene-, heteroaryl-$C_{1-6}$-alkylene-, $C_{1-6}$-alkyl-arylene-, $C_{1-6}$-alkyl-heteroarylene-, $C_{1-6}$-alkoxy-arylene-, $C_{1-6}$-alkoxy-heteroarylene-, heteroarylaryl-$C_{1-6}$-alkoxy-, or aryl-$C_{1-6}$ alkoxy-; and
$R^{15}$ is selected from the group consisting of aryl, heteroaryl, cycloalkyl, heterocyclyl, alkyl, or aryl-alkylene-.

Embodiment 77: A compound according to embodiment 86, wherein
$R^{11}$ is selected from hydrogen, alkyl, aryl, carbamoyl, aryl-alkylene-, alkyl-NH—C(O)—, aryl-alkylene-NH—C(O)—, alkyl-SO$_2$—, aryl-alkylene-SO$_2$—, aryl-SO$_2$—, SO$_2$—, alkyl-C(O)—, aryl-alkylene-C(O)—, N($R^{13}$)($R^{14}$)-alkylene-Y—, and $R^{15}$—W$^2$-alkylene-Y—, wherein
Y and W$^2$ independently of each other are a direct bond, —CH$_2$—, —SO$_2$—, —N(H)CO—, —N(H)SO$_2$—, or —O—C(O)—;
$R^{13}$ and $R^{14}$ independently of each other are selected from hydrogen, aryl, $C_{1-6}$alkyl, or aryl-$C_{1-6}$-alkylene-;
or
$R^{13}$ and $R^{14}$ may be taken together to form a ring having the formula —(CH$_2$)$_o$—X—(CH$_2$)$_p$— bonded to the nitrogen atom to which $R^{13}$ and $R^{14}$ are attached, wherein
o and p are independently of each other are 1, 2, 3, or 4; and
X is a direct bond, —CH$_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

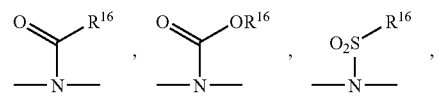

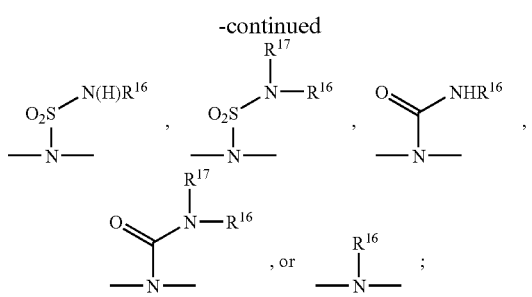

wherein
R$^{16}$ and R$^{17}$ are hydrogen; and
R$^{15}$ is selected from the group consisting of aryl, heteroaryl, cycloalkyl, heterocyclyl, alkyl, or aryl-alkylene-.

Embodiment 78: A compound according to embodiment 87, wherein
R$^{11}$ is selected from hydrogen, alkyl, aryl, carbamoyl, aryl-alkylene-, alkyl-NH—C(O)—, aryl-alkylene-NH—C(O)—, alkyl-SO$_2$—, aryl-alkylene-SO$_2$—, aryl-SO$_2$—, SO$_2$—, alkyl-C(O)—, aryl-alkylene-C(O)—, N(R$^{13}$)(R$^{14}$)-alkylene-Y—, and R$^{15}$—W$^2$-alkylene-Y—, wherein
Y and W$^2$ independently of each other are a direct bond, —CH$_2$—, —SO$_2$—, —N(H)CO—, —N(H)SO$_2$—, or —O—C(O)—;
R$^{13}$ and R$^{14}$ independently of each other are selected from hydrogen, aryl, C$_{1-6}$-alkyl, or aryl-C$_{1-6}$-alkylene-;
or
R$^{13}$ and R$^{14}$ may be taken together to form a ring having the formula —(CH$_2$)$_o$—X—(CH$_2$)$_p$— bonded to the nitrogen atom to which R$^{13}$ and R$^{14}$ are attached, wherein
o and p are independently of each other are 1, 2, 3, or 4;
X is a direct bond; and
R$^{15}$ is selected from the group consisting of aryl, heteroaryl, cycloalkyl, heterocyclyl, alkyl, or aryl-alkylene-.

Embodiment 79: A compound according to embodiment 88, wherein.
R$^{11}$ is selected from hydrogen, alkyl, aryl, carbamoyl, aryl-alkylene-, alkyl-NH—C(O)—, aryl-alkylene-NH—C(O)—, alkyl-SO$_2$—, aryl-alkylene-SO$_2$—, aryl-SO$_2$—, SO$_2$—, alkyl-C(O)—, aryl-alkylene-C(O)—, N(R$^{13}$)(R$^{14}$)-alkylene-Y—, and R$^{15}$—W$^2$-alkylene-Y—, wherein
Y and W$^2$ independently of each other are a direct bond, —CH$_2$—, —SO$_2$—, —N(H)CO—, —N(H)SO$_2$—, or —O—C(O)—;
R$^{13}$ and R$^{14}$ independently of each other are selected from hydrogen, aryl, C$_{1-6}$alkyl, or aryl-C$_{1-6}$-alkylene-; and
R$^{15}$ is selected from the group consisting of aryl, heteroaryl, cycloalkyl, heterocyclyl, alkyl, or aryl-alkylene-.

Embodiment 80: A compound according to embodiment 89, wherein
R$^{11}$ is selected from hydrogen, alkyl, aryl, carbamoyl, aryl-alkylene-, alkyl-NH—C(O)—, aryl-alkylene-NH—C(O)—, alkyl-SO$_2$—, aryl-alkylene-SO$_2$—, aryl-SO$_2$—, SO$_2$—, alkyl-C(O)—, aryl-alkylene-C(O)—, N(R$^{13}$)(R$^{14}$)-alkylene-Y—, and R$^{15}$—W$^2$-alkylene-Y—, wherein
Y and W$^2$ independently of each other are a direct bond, —CH$_2$—, —SO$_2$—, —N(H)CO—, —N(H)SO$_2$—, or —O—C(O)—;
R$^{13}$ and R$^{14}$ are hydrogen; and
R$^{15}$ is selected from the group consisting of aryl, heteroaryl, cycloalkyl, heterocyclyl, alkyl, or aryl-alkylene-.

Embodiment 81: A compound according to embodiment 90, wherein
R$^{11}$ is selected from hydrogen, alkyl, aryl, carbamoyl, aryl-alkylene-, alkyl-NH—C(O)—, aryl-alkylene-NH—C(O)—, alkyl-SO$_2$—, aryl-alkylene-SO$_2$—, aryl-SO$_2$—, SO$_2$—, alkyl-C(O)—, aryl-alkylene-C(O)—, N(R$^{13}$)(R$^{14}$)-alkylene-Y—, and R$^{15}$—W$^2$-alkylene-Y—, wherein
Y is a direct bond;
W$^2$ is a direct bond, —CH$_2$—, —SO$_2$—, —N(H)CO—, —N(H)SO$_2$—, or —O—C(O)—;
R$^{13}$ and R$^{14}$ are hydrogen; and
R$^{15}$ is selected from the group consisting of aryl, heteroaryl, cycloalkyl, heterocyclyl, alkyl, or aryl-alkylene-.

Embodiment 82: A compound according to embodiment 90, wherein
R$^{11}$ is selected from hydrogen, alkyl, aryl, carbamoyl, aryl-alkylene-, alkyl-NH—C(O)—, aryl-alkylene-NH—C(O)—, alkyl-SO$_2$—, aryl-alkylene-SO$_2$—, aryl-SO$_2$—, SO$_2$—, alkyl-C(O)—, aryl-alkylene-C(O)—, N(R$^{13}$)(R$^{14}$)-alkylene-Y—, and R$^{15}$—W$^2$-alkylene-Y—, wherein
Y is a direct bond, —CH$_2$—, —SO$_2$—, —N(H)CO—, —N(H)SO$_2$—, or —O—C(O)—;
W$^2$ is a direct bond;
R$^{13}$ and R$^{14}$ are hydrogen; and
R$^{15}$ is selected from the group consisting of aryl, heteroaryl, cycloalkyl, heterocyclyl, alkyl, or aryl-alkylene-.

Embodiment 83: A compound according to any of embodiments 90 to 92, wherein
R$^{11}$ is selected from hydrogen, alkyl, aryl, carbamoyl, aryl-alkylene-, alkyl-NH—C(O)—, aryl-alkylene-NH—C(O)—, alkyl-SO$_2$—, aryl-alkylene-SO$_2$—, aryl-SO$_2$—, SO$_2$—, alkyl-C(O)—, aryl-alkylene-C(O)—, NH$_2$-alkylene-, and R$^{15}$-alkylene-, wherein
R$^{15}$ is selected from the group consisting of aryl, heteroaryl, cycloalkyl, heterocyclyl, alkyl, or aryl-alkylene-.

Embodiment 84: A compound according to embodiment 93, wherein
R$^{11}$ is selected from hydrogen, alkyl, aryl, carbamoyl, aryl-alkylene-, alkyl-NH—C(O)—, aryl-alkylene-NH—C(O)—, alkyl-SO$_2$—, aryl-alkylene-SO$_2$—, aryl-SO$_2$—, SO$_2$—, alkyl-C(O)—, aryl-alkylene-C(O)—, and NH$_2$-alkylene-.

Embodiment 85: A compound according to embodiment 94, wherein
R$^{11}$ is hydrogen or alkyl.

Embodiment 86: A compound according to embodiment 95, wherein
R$^{11}$ is hydrogen.

Embodiment 87: A compound according to any of embodiments 1 to 96, wherein
$R^{12}$ is hydrogen or alkyl.

Embodiment 88: A compound according to embodiment 97, wherein
$R^{12}$ is hydrogen.

Embodiment 89: A compound according to any of embodiments 1 to 98, wherein
$G^1$ is alkyl, alkenyl, alkynyl, cycloalkyl or heterocyclyl, optionally substituted with one or more substituents selected from the group consisting of —CN, —CF$_3$, —OCF$_3$, —OR$^1$, —NR$^{18}$R$^{19}$, C$_{3-10}$-cycloalkyl and C$_{1-6}$alkyl, wherein
$R^{18}$ and $R^{19}$ are as defined for embodiment 1.

Embodiment 90: A compound according to embodiment 99, wherein
$G^1$ is alkyl, alkenyl, alkynyl, cycloalkyl or heterocyclyl, optionally substituted with one or more substituents selected from the group consisting of —CN, —CF$_3$, —OCF$_3$, —OR$^{18}$, —NR$^{18}$R$^{19}$ and C$_{1-6}$alkyl, wherein
$R^{18}$ and $R^{19}$ are as defined for embodiment 1.

Embodiment 91: A compound according to embodiment 99, wherein
$G^1$ is C$_{1-6}$-alkyl, C$_{2-6}$-alkenyl, C$_{2-6}$-alkynyl, C$_{3-10}$-cycloalkyl or C$_{3-10}$-heterocyclyl, optionally substituted with one or more substituents selected from the group consisting of —CN, —CF$_3$, —OCF$_3$, —OR$^{18}$, —NR$^{18}$R$^{19}$, C$_{3-10}$-cycloalkyl and C$_{1-6}$-alkyl, wherein
$R^{18}$ and $R^{19}$ are as defined for embodiment 1.

Embodiment 92: A compound according to embodiment 100 or embodiment 101, wherein
$G^1$ is C$_{1-6}$-alkyl, C$_{2-6}$-alkenyl, C$_{2-6}$-alkynyl, C$_{3-10}$-cycloalkyl or C$_{3-10}$-heterocyclyl, optionally substituted with one or more substituents selected from the group consisting of —CN, —CF$_3$, —OCF$_3$, —OR$^{18}$, —NR$^{18}$R$^{19}$ and C$_{1-4}$alkyl, wherein
$R^{18}$ and $R^{19}$ are as defined for embodiment 1.

Embodiment 93: A compound according to any of embodiments 99 to 102, wherein
$R^{18}$ and $R^{19}$, independently of each other, are hydrogen, C$_{1-6}$alkyl, heteroaryl-C$_{1-6}$-alkylene-, aryl-C$_{1-6}$alkylene-, C$_{1-6}$alkyl-arylene-, C$_{1-6}$-alkyl-heteroarylene-, heteroaryl, or aryl.

Embodiment 94: A compound according to embodiment 110, wherein
$R^{18}$ and $R^{19}$, independently of each other, are hydrogen, C$_{1-6}$alkyl, C$_{3-10}$-heteroaryl-C$_{1-6}$-alkylene-, C$_{3-10}$-aryl-C$_{1-6}$-alkylene-, C$_{1-6}$-alkyl-C$_{3-10}$-arylene-, C$_{1-6}$-alkyl-C$_{3-10}$-heteroarylene-, C$_{3-10}$-heteroaryl, or C$_{3-10}$-aryl.

Embodiment 95: A compound according to embodiment 111, wherein
$R^{18}$ and $R^{19}$, independently of each other, are hydrogen or C$_{1-6}$alkyl.

Embodiment 96: A compound according to embodiment 112, wherein
$R^{18}$ is hydrogen.

Embodiment 97: A compound according to embodiment 112 or 113, wherein
$R^{19}$ is hydrogen.

Embodiment 98: A compound according to embodiment 100 or embodiment 102, wherein $R^{18}$ and $R^{19}$, when attached to the same nitrogen atom, together with the said nitrogen atom forms a 3 to 8 membered heterocyclic ring optionally containing one or two further heteroatoms selected from nitrogen, oxygen and sulfur, and optionally containing one or two double bonds.

Embodiment 99: A compound according to any of embodiments 1 to 98, wherein
$G^1$ is alkyl or cycloalkyl, optionally substituted with one or more substituents selected from the group consisting of —CN, —CF$_3$, —OCF$_3$, —OR$^{18}$, —NR$^{18}$R$^{19}$ and C$_{1-6}$alkyl,
or $G^1$ is aryl optionally substituted with one or more substituents $R^{40}$, $R^{41}$, and $R^{42}$, wherein $R^{18}$, $R^{19}$, $R^{40}$, $R^{41}$, and $R^{42}$ are as defined for embodiment 1.

Embodiment 100: A compound according to embodiment 116, wherein
$G^1$ is C$_{1-6}$-alkyl or C$_{3-10}$-cycloalkyl, optionally substituted with one or more substituents selected from the group consisting of —CN, —CF$_3$, —OCF$_3$, —OR$^{18}$, —NR$^{18}$R$^{19}$ and C$_{1-6}$-alkyl,
or $G^1$ is C$_{3-10}$-aryl optionally substituted with one or more substituents $R^{40}$, $R^{41}$, and $R^{42}$, wherein $R^{18}$, $R^{19}$, $R^{40}$, $R^{41}$, and $R^{42}$ are as defined for embodiment 1.

Embodiment 101: A compound according to embodiment 116 or embodiment 117, wherein
$R^{18}$ and $R^{19}$, independently of each other, are hydrogen, C$_{1-6}$alkyl, heteroaryl-C$_{1-6}$-alkylene-, aryl-C$_{1-6}$-alkylene-, C$_{1-6}$-alkyl-arylene-, C$_{1-6}$-alkyl-heteroarylene-, heteroaryl, or aryl.

Embodiment 102: A compound according to embodiment 119, wherein
$R^{18}$ and $R^{19}$, independently of each other, are hydrogen, C$_{1-6}$alkyl, C$_{3-10}$-heteroaryl-C$_{1-6}$-alkylene-, C$_{3-10}$-aryl-C$_{1-6}$-alkylene-, C$_{1-6}$-alkyl-C$_{3-10}$-arylene-, C$_{1-6}$-alkyl-C$_{3-10}$-heteroarylene-, C$_{3-10}$-heteroaryl, or C$_{3-10}$-aryl.

Embodiment 103: A compound according to embodiment 120, wherein
$R^{18}$ and $R^{19}$, independently of each other, are hydrogen or C$_{1-6}$alkyl.

Embodiment 104: A compound according to embodiment 121, wherein
$R^{18}$ is hydrogen.

Embodiment 105: A compound according to embodiment 121 or 122, wherein
$R^{19}$ is hydrogen.

Embodiment 106: A compound according to embodiment 116 or embodiment 117, wherein
$R^{18}$ and $R^{19}$, when attached to the same nitrogen atom, together with the said nitrogen atom forms a 3 to 8 membered heterocyclic ring optionally containing one or two further heteroatoms selected from nitrogen, oxygen and sulfur, and optionally containing one or two double bonds.

Embodiment 107: A compound according to any of embodiments 116 to 124, wherein
$R^{40}$, $R^{41}$, and $R^{42}$ independently of each other are halogen, —CN, —NO$_2$, C$_{1-6}$-alkyl, —CHF$_2$, —CF$_3$, —OR$^{54}$, —NR$^{54}$R$^{55}$, —SR$^{54}$, —NR$^{54}$S(O)$_2$R$^{55}$, —S(O)$_2$NR$^{54}$R$^{55}$, —S(O)NR$^{54}$R$^{55}$—S(O)R$^{54}$, —S(O)$_2$ R$^{54}$, —C(O)NR$^{54}$R$^{55}$, —OC(O)NR$^{54}$R$^{55}$—NR$^{54}$C(O)R$^{55}$, —CH$_2$C(O)NR$^{54}$R$^{55}$, —CH$_2$C(O)

OR$^{54}$, —OCH$_2$C(O)NR$^{54}$R$^{55}$, —CH$_2$OR$^{54}$, —CH$_2$NR$^{54}$R$^{55}$, and —C(O)OR$^{54}$; or C$_{2-6}$-alkenyl and C$_{2-6}$-alkynyl, which may optionally be substituted with one or more substituents selected from —CN, —CF$_3$, —OCF$_3$, —OR$^{54}$, —NR$^{54}$R$^{55}$ and C$_{1-6}$-alkyl, wherein R$^{54}$ and R$^{55}$ independently of each other are hydrogen, C$_{1-6}$-alkyl, C$_{1-6}$-alkyl-arylene-, C$_{1-6}$alkyl-heteroarylene-, aryl-C$_{1-6}$-alkylene-, heteroaryl-C$_{1-6}$-alkylene-, heteroaryl, or aryl; or R$^{54}$ and R$^{55}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds.

Embodiment 108: A compound according to embodiment 125, wherein
R$^{54}$ and R$^{55}$ independently of each other are hydrogen, or C$_{1-6}$alkyl, C$_{1-6}$-alkyl-C$_{3-10}$-arylene-, C$_{1-6}$-alkyl-C$_{3-10}$-heteroarylene-, C$_{3-10}$-aryl-C$_{1-6}$alkylene-, C$_{3-10}$-heteroaryl-C$_{1-6}$-alkylene-, C$_{3-10}$-heteroaryl, or C$_{3-10}$-aryl.

Embodiment 109: A compound according to embodiment 128, wherein
R$^{54}$ and R$^{55}$ independently of each other are hydrogen or C$_{1-6}$alkyl.

Embodiment 110: A compound according to embodiment 129, wherein
R$^{54}$ is hydrogen.

Embodiment 111: A compound according to embodiment 129 or embodiment 130, wherein
R$^{55}$ is hydrogen.

Embodiment 112: A compound according to any of embodiments 1 to 98, wherein
G$^1$ is aryl or heteroaryl, optionally substituted with one or more substituents R$^{40}$, R$^{41}$, and R$^{42}$, wherein
R$^{40}$, R$^{41}$, and R$^{42}$ are as defined for embodiment 1.

Embodiment 113: A compound according to embodiment 133, wherein
G$^1$ is C$_{3-10}$-aryl or C$_{3-10}$-heteroaryl, optionally substituted with one or more substituents R$^{40}$, R$^{41}$, and R$^{42}$, wherein
R$^{40}$, R$^{41}$, and R$^{42}$ are as defined for embodiment 1.

Embodiment 114: A compound according to embodiment 133, wherein
G$^1$ is aryl, optionally substituted with one or more substituents R$^{40}$, R$^{41}$, and R$^{42}$, wherein
R$^{40}$, R$^{41}$, and R$^{42}$ are as defined for embodiment 1.

Embodiment 115: A compound according to embodiment 135, wherein
G$^1$ is C$_{3-10}$-aryl, optionally substituted with one or more substituents R$^{40}$, R$^{41}$, and R$^{42}$, wherein
R$^{40}$, R$^{41}$, and R$^{42}$ are as defined for embodiment 1.

Embodiment 116: A compound according to any of embodiments 133 to 136, wherein
R$^{40}$, R$^{41}$, and R$^{42}$ independently of each other are halogen, —CN, —NO$_2$, C$_{1-6}$alkyl, —CHF$_2$, —CF$_3$, —OR$^{54}$, —NR$^{54}$R$^{55}$, —SR$^{54}$, —NR$^{54}$S(O)$_2$R$^{55}$, —S(O)$_2$NR$^{54}$R$^{55}$, —S(O)NR$^{54}$R$^{55}$—S(O)$_2$R$^{54}$, —S(O)$_2$R$^{54}$—C(O)NR$^{54}$R$^{55}$, —OC(O)NR$^{54}$R$^{55}$—NR$^{54}$C(O)R$^{55}$, —CH$_2$C(O)NR$^{54}$R$^{55}$, —CH$_2$C(O)

OR$^{54}$, —OCH$_2$C(O)NR$^{54}$R$^{55}$, —CH$_2$OR$^{54}$, —CH$_2$NR$^{54}$R$^{55}$, and —C(O)OR$^{54}$; or C$_{2-6}$-alkenyl and C$_{2-6}$-alkynyl, which may optionally be substituted with one or more substituents selected from —CN, —CF$_3$, —OCF$_3$, —OR$^{54}$, —NR$^{54}$R$^{55}$ and C$_{1-6}$-alkyl, wherein R$^{54}$ and R$^{55}$ independently of each other are hydrogen, C$_{1-6}$alkyl, C$_{1-6}$-alkyl-arylene-, C$_{1-6}$alkyl-heteroarylene-, aryl-C$_{1-6}$-alkylene-, heteroaryl-C$_{1-6}$alkylene-, heteroaryl, or aryl; or R$^{54}$ and R$^{55}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds.

Embodiment 117: A compound according to embodiment 138, wherein
R$^{54}$ and R$^{55}$ independently of each other are hydrogen, or C$_{1-6}$-alkyl, C$_{1-6}$-alkyl-C$_{3-10}$-arylene-, C$_{1-6}$-alkyl-C$_{3-10}$-heteroarylene-, C$_{3-10}$-aryl-C$_{1-6}$-alkylene-, C$_{3-10}$-heteroaryl-C$_{1-6}$-alkylene-, C$_{3-10}$-heteroaryl, or C$_{3-10}$-aryl Embodiment 118: A compound according to embodiment 141, wherein
R$^{54}$ and R$^{55}$ independently of each other are hydrogen or C$_{1-6}$alkyl.

Embodiment 119: A compound according to embodiment 142, wherein
R$^{54}$ is hydrogen.

Embodiment 120: A compound according to embodiment 142 or embodiment 143, wherein
R$^{55}$ is hydrogen.

Embodiment 121: A compound according to embodiment 135, wherein
G$^1$ is

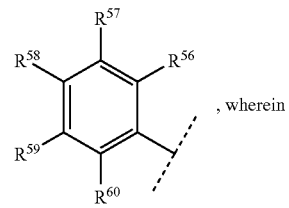

, wherein

R$^{56}$, R$^{57}$, R$^{58}$, R$^{59}$, and R$^{60}$, independently of each other, are hydrogen or halogen, —CN, —NO$_2$, C$_{1-6}$-alkyl, —CHF$_2$, —CF$_3$, —OCF$_3$, —OCHF$_2$, —OCH$_2$CF$_3$, —OCF$_2$CHF$_2$, —S(O)$_2$CF$_3$, —SCF$_3$, —OR$^{61}$, —NR$^{61}$R$^{62}$, —SR$^{61}$, —NR$^{61}$S(O)$_2$R$^{62}$, —S(O)$_2$NR$^{61}$R$^{62}$, —S(O)NR$^{61}$R$^{62}$, —S(O)R$^{61}$, —S(O)$_2$R$^{61}$—C(O)NR$^{61}$R$^{62}$, —OC(O)NR$^{61}$R$^{62}$, —NR$^{61}$C(O)R$^{62}$, —CH$_2$C(O)NR$^{61}$R$^{62}$, —CH$_2$C(O)OR$^{61}$, —OCH$_2$C(O)NR$^{61}$R$^{62}$—CH$_2$OR$^{61}$, —CH$_2$NR$^{61}$R$^{62}$—OC(O)R$^{61}$, —C(O)R$^{61}$ and —C(O)OR$^{61}$; or C$_{2-6}$-alkenyl and C$_{2-6}$-alkynyl, which may optionally be substituted with one or more substituents selected from —CN, —CF$_3$, —OCF$_3$, —OR$^{61}$, —NR$^{61}$R$^{62}$ and C$_1$ alkyl; C$_{3-10}$-cycloalkyl, C$_{4-8}$-cycloalkenyl, heterocyclyl, C$_{3-10}$-cycloalkyl-C$_{1-6}$-alkylene-, C$_{3-10}$-cycloalkyl-C$_{1-6}$-alkoxy-, C$_{3-10}$-cycloalkyloxy, C$_{3-10}$-cycloalkyl-C$_{1-6}$alkylthio-, C$_{3-10}$-cycloalkylthio, C$_{3-10}$-cycloalkyl-C$_{2-6}$-alkenylene-, C$_{3-10}$-cycloalkyl-C$_{2-6}$- alkynylene-, $C_{4-8}$-cycloalkenyl-$C_{1-6}$-alkylene-, $C_{4-8}$-cycloalkenyl-$C_{2-6}$-alkenylene-, $C_{4-8}$-cycloalkenyl-$C_{2-6}$-alkynylene-, heterocyclyl-$C_{1-6}$-alkylene-, heterocyclyl-$C_{2-6}$-alkenylene-, heterocyclyl-$C_{2-6}$-alkynylene-; or aryl, aryloxy, aryloxycarbonyl, aroyl, aryl-$C_{1-6}$-alkoxy-, aryl-$C_{1-6}$-alkylene-, aryl-$C_{2-6}$-alkenylene-, aryl-$C_{2-6}$-alkynylene-, heteroaryl, heteroaryl-$C_{1-6}$-alkylene-, heteroaryl-$C_{2-6}$-alkenylene- and heteroaryl-$C_{2-6}$-alkynylene-, of which the aryl and heteroaryl moieties optionally may be substituted with one or more substituents selected from halogen, —C(O)OR$^{61}$, —CN, —CF$_3$, —OCF$_3$, —NO$_2$, —OR$^{61}$, —NR$^{61}$R$^{62}$ or $C_{1-6}$-alkyl, wherein
  $R^{61}$ and $R^{62}$ independently of each other are hydrogen, $C_{1-6}$-alkyl, $C_{1-6}$-alkyl-arylene-, $C_{1-6}$-alkyl-heteroarylene-, aryl-$C_{1-6}$-alkylene-, heteroaryl-$C_{1-6}$-alkylene-, heteroaryl, or aryl;
or
  $R^{61}$ and $R^{62}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds.

Embodiment 122: A compound according to embodiment 146, wherein
  $R^{56}$, $R^{57}$, $R^{58}$, $R^{59}$, and $R^{60}$ independently of each other are halogen, —CN, —NO$_2$, $C_{1-6}$alkyl, —CHF$_2$, —CF$_3$, —OR$^{61}$, —NR$^{61}$R$^{62}$—SR$^{61}$, —NR$^{61}$S(O)$_2$R$^{62}$—S(O)$_2$NR$^{61}$R$^{62}$, —S(O)NR$^{61}$R$^{62}$, —S(O)R$^{61}$, —S(O)$_2$R$^{61}$, —C(O)NR$^{61}$R$^{62}$, —OC(O)NR$^{61}$R$^{62}$. —NR$^{61}$C(O)R$^{62}$, —CH$_2$C(O)NR$^{61}$R$^{62}$, —CH$_2$C(O)OR$^{61}$, —OCH$_2$C(O)NR$^{61}$R$^{62}$, —CH$_2$OR$^{61}$, —CH$_2$NR$^{61}$R$^{62}$, and —C(O)OR$^{61}$; or
  $C_{2-6}$-alkenyl and $C_{2-6}$-alkynyl, which may optionally be substituted with one or more substituents selected from —CN, —CF$_3$, —OCF$_3$, —OR$^{61}$, —NR$^{61}$R$^{62}$ and $C_{1-6}$-alkyl, wherein
    $R^{61}$ and $R^{62}$ independently of each other are hydrogen, $C_{1-6}$alkyl, $C_{1-6}$-alkyl-arylene-, $C_{1-6}$-alkyl-heteroarylene-, aryl-$C_{1-6}$-alkylene-, heteroaryl-$C_{1-6}$-alkylene-, heteroaryl, or aryl;
  or
    $R^{61}$ and $R^{62}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds.

Embodiment 123: A compound according to embodiment 146 or embodiment 147, wherein
$R^{24}$ or $R^{25}$ is —OR$^{61}$.

Embodiment 124: A compound according to embodiment 147, wherein
  $R^{61}$ and $R^{62}$ independently of each other are hydrogen, or $C_{1-6}$-alkyl, $C_{1-6}$-alkyl-$C_{3-10}$-arylene-, $C_{1-6}$-alkyl-$C_{3-10}$-heteroarylene-, $C_{3-10}$-aryl-$C_{1-6}$-alkylene-, $C_{3-10}$-heteroaryl-$C_{1-6}$-alkylene-, $C_{3-10}$-heteroaryl, or $C_{3-10}$-aryl.

Embodiment 125: A compound according to embodiment 150, wherein
  $R^{61}$ and $R^{62}$ independently of each other are hydrogen or $C_{1-5}$-alkyl.

Embodiment 126: A compound according to embodiment 151, wherein
  $R^{61}$ is hydrogen.

Embodiment 127: A compound according to embodiment 151 or embodiment 152, wherein
  $R^{62}$ is hydrogen.

Embodiment 128: A compound according to any of embodiments 146 to 153, wherein
  at least one of $R^{56}$, $R^{57}$, $R^{58}$, $R^{59}$, and $R^{60}$ are hydrogen.

Embodiment 129: A compound according to embodiment 154, wherein
  at least two of $R^{23}$, $R^{24}$, $R^{25}$, and $R^{26}$ are hydrogen.

Embodiment 130: A compound according to embodiment 155, wherein
  at least three of $R^{23}$, $R^{24}$, $R^{25}$, and $R^{26}$ are hydrogen.

Embodiment 131: A compound according to any of embodiments 1 to 156, wherein
  $L^2$ is a direct bond, $C_{1-6}$-alkylene, $C_{2-6}$-alkenylene, $C_{2-6}$-alkynylene, —N—R$^{20}$—, —C$_{1-6}$-alkylene-N(R$^{20}$)—, —C$_{2-6}$-alkenylene-N(R$^{20}$)—, or —C$_{2-6}$-alkynylene-N(R$^{20}$)—, wherein
  $R^{20}$ is as defined for embodiment 1.

Embodiment 132: A compound according to any of embodiments 1 to 153, wherein
  $L^2$ is —N—R$^{20}$—, -alkylene-N(R$^{20}$)—, -alkenylene-N(R$^{20}$)—, or -alkynylene-N(R$^{20}$)—, wherein
  $R^{20}$ is as defined for embodiment 1.

Embodiment 133: A compound according to embodiment 157 or embodiment 158, wherein
  $L^2$ is —N—R$^{20}$—, —C$_{1-6}$-alkylene-N(R$^{20}$)—, —C$_{2-6}$-alkenylene-N(R$^{20}$)—, or —C$_{2-6}$-alkynylene-N(R$^{20}$)—, wherein
  $R^{20}$ is as defined for embodiment 1.

Embodiment 134: A compound according to embodiment 159, wherein
  $L^2$ is —N—R$^{20}$—, wherein
  $R^{20}$ is as defined for embodiment 1.

Embodiment 135: A compound according to embodiment 157, wherein
  $L^2$ is a direct bond.

Embodiment 136: A compound according to any of embodiments 1 to 160, wherein
  $R^{20}$ is hydrogen, or
  $R^{20}$ is $C_{1-6}$-alkyl, $C_{2-6}$-alkenyl, $C_{2-6}$-alkynyl, $C_{3-10}$-cycloalkyl-W$^3$—, $C_{3-10}$-heterocyclyl-W$^3$—, $C_{3-10}$-aryl-W$^3$—, or $C_{4-10}$-heteroaryl-W$^3$—, optionally substituted with one or more substituents $R^{30}$, $R^{31}$, and $R^{32}$, wherein
  $W^3$, $R^{30}$, $R^{31}$, and $R^{32}$ are as defined for embodiment 1.

Embodiment 137: A compound according to embodiment 162, wherein
  $W^3$ is alkylene.

Embodiment 138: A compound according to embodiment 163, wherein
  $W^3$ is $C_{2-6}$-alkylene.

Embodiment 139: A compound according to embodiment 162, wherein
  $W^3$ is a direct bond.

Embodiment 140: A compound according to any of embodiments 1 to 160, wherein
  $R^{20}$ is hydrogen, alkyl, alkenyl, or alkynyl, optionally substituted with one or more substituents $R^{30}$, $R^{31}$, and $R^{32}$ wherein
  $R^{30}$, $R^{31}$, and $R^{32}$ are as defined for embodiment 1.

Embodiment 141: A compound according to any of embodiments 162 to 166, wherein
$R^{20}$ is hydrogen, or
$R^{20}$ is $C_{1-6}$-alkyl, $C_{1-6}$-alkenyl, or $C_{1-6}$-alkynyl, optionally substituted with one or more substituents $R^{30}$, $R^{31}$, and $R^{32}$, wherein
$R^{30}$, $R^{31}$, and $R^{32}$ are as defined for embodiment 1.

Embodiment 142: A compound according to any of embodiments 1 to 167, wherein
$R^{30}$, $R^{31}$, and $R^{32}$ independently of each other are selected from —$CHF_2$, —$CF_3$, —$OCF_3$, —$OCHF_2$, —$OCH_2CF_3$, —$OCF_2CHF_2$, —$S(O)_2CF_3$, —$SCF_3$, —$OR^{52}$, —$NR^{52}R^{53}$, —$SR_{52}$, —$NR^{52}S(O)_2R^{53}$, —$S(O)_2NR^{52}R^{53}$, —$S(O)NR^{52}R^{53}$, —$S(O)R^{52}$, —$S(O)_2R^{52}$, —$C(O)NR^{52}R^{53}$, —$OC(O)NR^{52}R^{53}$, —$NR^{52}C(O)R^{53}$, —$CH_2C(O)NR^{52}R^{53}$, —$OCH_2C(O)NR^{52}R^{53}$, —$CH_2OR^{52}$, —$CH_2NR^{52}R^{53}$, —$OC(O)R^{52}$, —$C(O)R^{52}$ and —$C(O)OR^{52}$, wherein
$R^{52}$ and $R^{53}$ are as defined for embodiment 1.

Embodiment 143: A compound according to embodiment 168, wherein
$R^{52}$ and $R^{53}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds.

Embodiment 144: A compound according to any of embodiments 1 to 168, wherein
$R^{52}$ and $R^{53}$ independently of each other are hydrogen, $C_{1-6}$-alkyl, aryl-$C_{1-6}$-alkylene-heteroaryl-$C_{1-6}$-alkylene- heteroaryl, or aryl.

Embodiment 145: A compound according to embodiment 170, wherein
$R^{52}$ and $R^{53}$ independently of each other are hydrogen, $C_{1-6}$-alkyl, aryl-$C_{1-6}$-alkylene-or aryl.

Embodiment 146: A compound according to embodiment 171, wherein
$R^{52}$ and $R^{53}$ independently of each other are hydrogen or $C_{1-6}$-alkyl.

Embodiment 147: A compound according to embodiment 172, wherein
$R^{52}$ is hydrogen.

Embodiment 148: A compound according to embodiment 172 or embodiment 173, wherein
$R^{53}$ is hydrogen.

Embodiment 149: A compound according to embodiment 167, wherein
$R^{20}$ is hydrogen.

Embodiment 150: A compound according to any of embodiments 1 to 175, wherein
$L^3$ is —$C(O)$—.

Embodiment 151: A compound according to any of embodiments 1 to 176, wherein
$R^1$ is hydrogen, or
$R^1$ is $C_{1-6}$-alkyl, $C_{2-6}$-alkenyl, $C_{2-6}$-alkynyl, $C_{3-10}$-cycloalkyl-$W^4$—, $C_{3-10}$-heterocyclyl-$W^4$—, $C_{3-10}$-aryl-$W^4$—, or $C_{4-10}$-heteroaryl-$W^4$—, optionally substituted with one or more substituents $R^{33}$, $R^{34}$, and $R^{35}$ wherein $W^4$, $R^{33}$, $R^{34}$, and $R^{35}$ are as defined for embodiment 1.

Embodiment 152: A compound according to embodiment 180, wherein
$W^4$ is alkylene.

Embodiment 153: A compound according to embodiment 181, wherein
$W^4$ is $C_{2-6}$-alkylene.

Embodiment 154: A compound according to embodiment 180, wherein
$W^4$ is a direct bond.

Embodiment 155: A compound according to any of embodiments 1 to 176, wherein
$R^1$ is hydrogen, alkyl, alkenyl, or alkynyl, optionally substituted with one or more substituents $R^{33}$, $R^{34}$, and $R^{35}$, wherein
$R^{33}$, $R^{34}$, and $R^{35}$ are as defined for embodiment 1.

Embodiment 156: A compound according to any of embodiments 180 to 184, wherein
$R^1$ is hydrogen, $C_{1-6}$alkyl, $C_{2-6}$-alkenyl, or $C_{2-6}$-alkynyl, optionally substituted with one or more substituents $R^{33}$, $R^{34}$, and $R^{35}$, wherein
$R^{33}$, $R^{34}$, and $R^{35}$ are as defined for embodiment 1.

Embodiment 157: A compound according to embodiment 185, wherein
$R^1$ is hydrogen or $C_{1-6}$-alkyl optionally substituted with one or more substituents $R^{33}$, $R^{34}$ and $R^{35}$, wherein
$R^{33}$, $R^{34}$, and $R^{35}$ are as defined for embodiment 1.

Embodiment 158: A compound according to any of embodiments 1 to 186, wherein
$R^{33}$, $R^{34}$, and $R^{35}$ independently of each other are selected from —$CHF_2$, —$CF_3$, —$OCF_3$, —$OCHF_2$, —$OCH_2CF_3$, —$OCF_2CHF_2$, —$S(O)_2CF_3$, —$SCF_3$, —$OR^{52}$, —$NR^{52}R^{53}$, —$SR_{52}$, —$NR^{52}S(O)_2R^{53}$, —$S(O)_2NR^{52}R^{53}$, —$S(O)NR^{52}R^{53}$, —$S(O)R^{52}$, —$S(O)_2R^{52}$, —$C(O)NR^{52}R^{53}$, —$OC(O)NR^{52}R^{53}$, —$NR^{52}C(O)R^{53}$, —$CH_2C(O)NR^{52}R^{53}$, —$OCH_2C(O)NR^{52}R^{53}$, —$CH_2OR^{52}$, —$CH_2NR^{52}R^{53}$, —$OC(O)R^{52}$, —$C(O)R^{52}$ and —$C(O)OR^{52}$, wherein
$R^{52}$ and $R^{53}$ are as defined for embodiment 1.

Embodiment 159: A compound according to embodiment 186, wherein
$R^{52}$ and $R^{53}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds.

Embodiment 160: A compound according to embodiment 186, wherein
$R^{52}$ and $R^{53}$ independently of each other are hydrogen, $C_{1-6}$-alkyl, aryl-$C_{1-6}$-alkylene-heteroaryl-$C_{1-6}$alkylene-heteroaryl, or aryl.

Embodiment 161: A compound according to embodiment 189, wherein
$R^{52}$ and $R^{53}$ independently of each other are hydrogen, $C_{1-6}$-alkyl, aryl-$C_{1-6}$-alkylene-or aryl.

Embodiment 162: A compound according to embodiment 190, wherein
$R^{52}$ and $R^{53}$ independently of each other are hydrogen or $C_{1-6}$-alkyl.

Embodiment 163: A compound according to embodiment 191, wherein
$R^{52}$ is hydrogen.

Embodiment 164: A compound according to embodiment 191 or embodiment 192, wherein
$R^{53}$ is hydrogen.

Embodiment 165: A compound according to embodiment 186, wherein
$R^1$ is hydrogen.

Embodiment 166: A compound according to any of embodiments 1 to 194, wherein
$G^2$ is heteroaryl, fused heterocyclylheteroaryl, or fused cycloalkylheteroaryl, optionally substituted with one or more substituents $R^{43}$, $R^{44}$, and $R^{45}$, wherein said heteroaryl group posesses a nitrogen atom adjacent to the atom joining $G^2$ with —N($R^1$)—, and wherein
$R^{43}$, $R^{44}$, and $R^{45}$ are as defined for embodiment 1.

Embodiment 167: A compound according to embodiment 195, wherein
$G^2$ is heteroaryl optionally substituted with one or more substituents $R^{43}$, $R^{44}$, and $R^{45}$, wherein said heteroaryl group posesses a nitrogen atom adjacent to the atom joining $G^2$ with —N($R^1$)—, and wherein
$R^{43}$, $R^{44}$, and $R^{45}$ are as defined for embodiment 1.

Embodiment 168: A compound according to embodiment 199, wherein
$G^2$ is furanyl, thienyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, or indazolyl, optionally substituted with one or more substituents $R^{43}$, $R^{44}$, and $R^{45}$ wherein
$R^{43}$, $R^{44}$, and $R^{45}$ are as defined for embodiment 1.

Embodiment 169: A compound according to any of embodiments 1 to 200, wherein
$R^{43}$, $R^{44}$, and $R^{45}$ independently of each other are selected from halogen, —CN, —NO$_2$, C$_{1-6}$-alkyl, —CHF$_2$, —CF$_3$, —OCF$_3$, —OCHF$_2$, —OCH$_2$CF$_3$, —OCF$_2$CHF$_2$, —S(O)$_2$CF$_3$, —SCF$_3$, —OR$^{54}$, —NR$^{54}$R$^{55}$, —SR$^{54}$, —NR$^{54}$S(O)$_2$R$^{55}$, —S(O)$_2$NR$^{54}$R$^{55}$, —S(O)NR$^{54}$R$^{55}$—S(O)R$^{54}$, —S(O)$_2$R$^{54}$, —C(O)NR$^{54}$R$^{55}$, —OC(O)NR$^{54}$R$^{55}$, —NR$^{54}$C(O)R$^{55}$, —CH$_2$C(O)NR$^{54}$R$^{55}$, —CH$_2$C(O)OR$^{54}$, —OCH$_2$C(O)NR$^{54}$R$^{55}$, —CH$_2$OR$^{54}$, —CH$_2$NR$^{54}$R$^{55}$, —OC(O)R$^{54}$, —C(O)R$^{54}$ and —C(O)OR$^{54}$, wherein
$R^{54}$ and $R^{55}$ are as defined for embodiment 1.

Embodiment 170: A compound according to embodiment 207, wherein
$R^{54}$ and $R^{55}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds, and optionally substituted with one or more C$_{1-6}$-alkyl groups.

Embodiment 171: A compound according to embodiment 208, wherein
$R^{54}$ and $R^{55}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds.

Embodiment 172: A compound according to embodiment 207, wherein
$R^{54}$ and $R^{55}$ independently of each other are hydrogen, C$_{1-6}$-alkyl, aryl-C$_{1-6}$alkylene- or aryl.

Embodiment 173: A compound according to embodiment Error! Reference source not found., wherein
$R^{54}$ and $R^{55}$ independently of each other are hydrogen, C$_{1-6}$-alkyl, C$_{3-10}$-aryl-C$_{1-6}$-alkylene- or C$_{3-10}$-aryl.

Embodiment 174: A compound according to embodiment Error! Reference source not found., wherein
$R^{54}$ and $R^{55}$ independently of each other are hydrogen or C$_{1-6}$-alkyl.

Embodiment 175: A compound according to embodiment Error! Reference source not found., wherein
$R^{54}$ is hydrogen.

Embodiment 176: A compound according to embodiment Error! Reference source not found. or embodiment Error! Reference source not found., wherein
$R^{55}$ is hydrogen.

Embodiment 177: A compound according to embodiment 207, wherein
$R^{54}$ and $R^{55}$ independently of each other are hydrogen or —(CHR$^{63}$)$_u$—(CHR$^{64}$)$_v$-Z, wherein
u is 1 or 2;
v is 0, 1 or 2;
$R^{63}$ and $R^{64}$ independently of each other are hydrogen, C$_{1-6}$alkyl, C$_{1-6}$-alkyl-C$_{3-10}$-arylene- C$_{3-10}$-aryl, hydroxy, hydroxy-C$_{1-6}$-alkyl, amino, or amino-C$_{1-6}$-alkyl;
Z is hydrogen, —C—O—R$^{65}$, —C(O)O—R$^{65}$— CONR$^{65}$R$^{66}$, C$_{1-6}$-alkylamino, or di(C$_{1-6}$alkyl)-amino, wherein
$R^{65}$ and $R^{66}$ independently of each other is hydrogen or C$_{1-6}$alkyl;
or
Z is a five or six membered ring wherein at least one ring atom is nitrogen and the remaining ring atoms are either carbon or oxygen.

Embodiment 178: A compound according to embodiment Error! Reference source not found., wherein
u is 1; and
v is 0, or 1.

Embodiment 179: A compound according to embodiment Error! Reference source not found. or embodiment Error! Reference source not found., wherein
$R^{63}$ and $R^{64}$ independently of each other are hydrogen, C$_{1-6}$alkyl, hydroxy, hydroxy-C$_{1-6}$-alkyl, amino, or amino-C$_{1-6}$-alkyl.

Embodiment 180: A compound according to any of embodiments Error! Reference source not found. to Error! Reference source not found., wherein
Z is —C—O—R$^{65}$, or —C(O)O—R$^{65}$, wherein
$R^{65}$ and $R^{66}$ independently of each other is hydrogen or C$_{1-6}$alkyl.

Embodiment 181: A compound according to any of embodiments Error! Reference source not found. to Error! Reference source not found., wherein Z is a five or six membered ring where at least one ring atom is nitrogen and the remaining ring atoms are either carbon or oxygen.

Embodiment 182: A compound according to embodiment Error! Reference source not found., wherein
Z is a five or six membered ring wherein at least one ring atom is nitrogen, one ring atom is oxygen and the remaining ring atoms are carbon.

Embodiment 183: A compound according to embodiment Error! Reference source not found., wherein
Z is a five or six membered ring wherein at least one ring atom is nitrogen, and the remaining ring atoms are carbon.

Embodiment 184: A compound according to any of embodiments Error! Reference source not found. to Error! Reference source not found., wherein
Z is a five or six membered ring wherein one ring atom is nitrogen.

Embodiment 185: A compound according to any of embodiments Error! Reference source not found. to Error! Reference source not found., wherein
a nitrogen atom is the point of attachment of the Z group to the —(CHR$^{63}$)$_u$—(CHR$^{64}$)$_v$— group.

Embodiment 186: A compound according to any of embodiments Error! Reference source not found. to Error! Reference source not found., wherein
R$^{55}$ is hydrogen.

Embodiment 187: A compound according to any of embodiments 195 to 207, wherein
G$^2$ is substituted with a substituent R$^{43}$, wherein
R$^{43}$ is halogen, —CN, —NO$_2$, C$_{1-6}$-alkyl, —CHF$_2$, —CF$_3$, —OCF$_3$, —OCHF$_2$, —OCH$_2$CF$_3$, —OCF$_2$CHF$_2$, —S(O)$_2$CF$_3$, —SCF$_3$, —OR$^{54}$, —NR$^{54}$R$^{55}$, —SR$^{54}$—NR$^{54}$S(O)$_2$R$^{55}$, —S(O)$_2$NR$^{54}$R$^{55}$, —S(O)NR$^{54}$R$^{55}$, —S(O)R$^{54}$, —S(O)$_2$R$^{54}$, —C(O)NR$^{54}$R$^{55}$, —OC(O)NR$^{54}$R$^{55}$, —NR$^{54}$C(O)R$^{55}$, —CH$_2$C(O)NR$^{54}$R$^{55}$, —CH$_2$C(O)OR$^{54}$, —OCH$_2$C(O)NR$^{54}$R$^{55}$, —CH$_2$OR$^{54}$, —CH$_2$NR$^{54}$R$^{55}$, —OC(O)R$^{54}$—C(O)R$^{54}$ or —C(O)OR$^{54}$, wherein
R$^{54}$ and R$^{55}$ are as defined for embodiment 1.

Embodiment 188: A compound according to embodiment Error! Reference source not found., wherein
R$^{54}$ and R$^{55}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds, and optionally substituted with one or more C$_{1-6}$alkyl groups.

Embodiment 189: A compound according to embodiment Error! Reference source not found., wherein
R$^{54}$ and R$^{55}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds.

Embodiment 190: A compound according to embodiment Error! Reference source not found., wherein
R$^{54}$ and R$^{55}$ independently of each other are hydrogen, C$_{1-6}$alkyl, aryl-C$_{1-6}$alkylene- or aryl.

Embodiment 191: A compound according to embodiment Error! Reference source not found., wherein
R$^{54}$ and R$^{55}$ independently of each other are hydrogen, C$_{1-6}$alkyl, C$_{3-10}$-aryl-C$_{1-6}$-alkylene- or C$_{3-10}$-aryl.

Embodiment 192: A compound according to embodiment Error! Reference source not found., wherein
R$^{54}$ and R$^{55}$ independently of each other are hydrogen or C$_{1-6}$-alkyl.

Embodiment 193: A compound according to embodiment Error! Reference source not found., wherein
R$^{54}$ is hydrogen.

Embodiment 194: A compound according to embodiment Error! Reference source not found. or embodiment Error! Reference source not found., wherein
R$^{55}$ is hydrogen.

Embodiment 195: A compound according to embodiment Error! Reference source not found., wherein
R$^{54}$ and R$^{55}$ independently of each other are hydrogen or —(CHR$^{63}$)$_u$—(CHR$^{64}$)$_v$-Z, wherein
u is 1 or 2;
v is 0, 1 or 2;
R$^{63}$ and R$^{64}$ independently of each other are hydrogen, C$_{1-6}$-alkyl, C$_{1-6}$-alkyl-C$_{3-10}$-arylene- C$_{3-10}$-aryl, hydroxy, hydroxy-C$_{1-6}$-alkyl, amino, or amino-C$_{1-6}$-alkyl;
Z is hydrogen, —C—O—R$^{65}$, —C(O)O—R$^{65}$, —CONR$^{65}$R$^{66}$, C$_{1-6}$-alkylamino or di(C$_{1-6}$-alkyl)-amino, wherein
R$^{65}$ and R$^{66}$ independently of each other is hydrogen or C$_{1-6}$alkyl;
or
Z is a five or six membered ring wherein at least one ring atom is nitrogen and the remaining ring atoms are either carbon or oxygen.

Embodiment 196: A compound according to embodiment Error! Reference source not found., wherein
u is 1; and
v is 0, or 1.

Embodiment 197: A compound according to embodiment Error! Reference source not found. or embodiment Error! Reference source not found., wherein
R$^{63}$ and R$^{64}$ independently of each other are hydrogen, C$_{1-6}$-alkyl, hydroxy, hydroxy-C$_{1-6}$-alkyl, amino, or amino-C$_{1-6}$alkyl.

Embodiment 198: A compound according to any of embodiments Error! Reference source not found. to Error! Reference source not found., wherein
Z is —C—O—R$^{65}$, or —C(O)O—R$^{65}$, wherein
R$^{65}$ and R$^{66}$ independently of each other is hydrogen or C$_{1-6}$-alkyl.

Embodiment 199: A compound according to any of embodiments Error! Reference source not found. to Error! Reference source not found., wherein
Z is a five or six membered ring where at least one ring atom is nitrogen and the remaining ring atoms are either carbon or oxygen.

Embodiment 200: A compound according to embodiment Error! Reference source not found., wherein
Z is a five or six membered ring wherein at least one ring atom is nitrogen, one ring atom is oxygen and the remaining ring atoms are carbon.

Embodiment 201: A compound according to embodiment Error! Reference source not found., wherein
Z is a five or six membered ring wherein at least one ring atom is nitrogen, and the remaining ring atoms are carbon.

Embodiment 202: A compound according to any of embodiments Error! Reference source not found. to Error! Reference source not found., wherein
Z is a five or six membered ring wherein one ring atom is nitrogen.

Embodiment 203: A compound according to any of embodiments Error! Reference source not found. to Error! Reference source not found., wherein
a nitrogen atom is the point of attachment of the Z group to the —(CHR$^{63}$)$_u$—(CHR$^{64}$)$_v$— group.

Embodiment 204: A compound according to any of embodiments Error! Reference source not found. to Error! Reference source not found., wherein
R$^{55}$ is hydrogen.

Embodiment 205: A compound according to embodiment Error! Reference source not found., wherein
R$^{43}$ is —CH$_2$C(O)OR$^{54}$, wherein
R$^{54}$ is as defined for embodiment 1.

Embodiment 206: A compound according to embodiment Error! Reference source not found., wherein
R$^{54}$ is hydrogen, C$_{1-6}$-alkyl, aryl-C$_{1-6}$-alkylene- or aryl.

Embodiment 207: A compound according to embodiment Error! Reference source not found., wherein
R$^{54}$ is hydrogen, C$_{1-6}$-alkyl, C$_{3-10}$-aryl-C$_{1-6}$-alkylene- or C$_{3-10}$-aryl.

Embodiment 208: A compound according to embodiment Error! Reference source not found., wherein
R$^{54}$ is hydrogen or C$_{1-6}$-alkyl.

Embodiment 209: A compound according to embodiment Error! Reference source not found., wherein
R$^{54}$ is hydrogen.

Embodiment 210: A compound according to any of embodiments Error! Reference source not found. to Error! Reference source not found., wherein
R$^{43}$ is attached to the atom adjacent to the nitrogen atom adjacent to the atom joining G$^2$ with —N(R$^1$)—.

Embodiment 211: A compound according to any of embodiments 195 to Error! Reference source not found., wherein
G$^2$ is

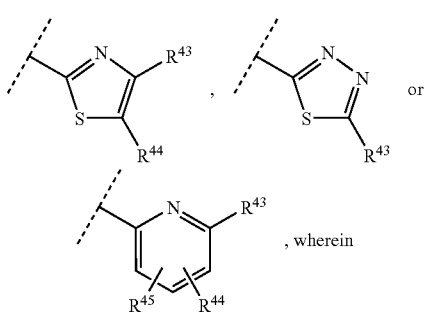

R$^{43}$, R$^{44}$, and R$^{45}$ independently of each other are hydrogen or as defined for embodiment 1.

Embodiment 212: A compound according to embodiment Error! Reference source not found., wherein
G$^2$ is

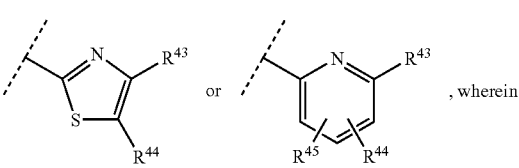

, wherein

R$^{43}$, R$^{44}$, and R$^{45}$ independently of each other are hydrogen or as defined for embodiment 1.

Embodiment 213: A compound according to embodiment Error! Reference source not found. or embodiment Error! Reference source not found., wherein
R$^{43}$, R$^{44}$, and R$^{45}$ independently of each other are selected from hydrogen, halogen, —CN, —NO$_2$, C$_{1-6}$-alkyl, —CHF$_2$, —CF$_3$, —OCF$_3$, —OCHF$_2$, —OCH$_2$CF$_3$, —OCF$_2$CHF$_2$, —S(O)$_2$CF$_3$, —SCF$_3$, —OR$^{54}$, —NR$^{54}$R$^{55}$, —SR$^{54}$, —NR$^{54}$S(O)$_2$R$^{55}$, —S(O)$_2$NR$^{54}$R$^{55}$, —S(O)NR$^{54}$R$^{55}$, —S(O)R$^{54}$, —S(O)$_2$R$^{54}$, —C(O)NR$^{54}$R$^{55}$, —OC(O)NR$^{54}$R$^{55}$, —NR$^{54}$C(O)R$^{55}$, —CH$_2$C(O)NR$^{54}$R$^{55}$, —CH$_2$C(O)OR$^{54}$, —OCH$_2$C(O)NR$^{54}$R$^{55}$, —CH$_2$OR$^{54}$, —CH$_2$NR$^{54}$R$^{55}$, —OC(O)R$^{54}$, —C(O)R$^{54}$ and —C(O)OR$^{54}$, wherein
R$^{54}$ and R$^{55}$ are as defined for embodiment 1.

Embodiment 214: A compound according to embodiment Error! Reference source not found., wherein
R$^{43}$ is halogen, —CN, —NO$_2$, C$_{1-6}$-alkyl, —CHF$_2$, —CF$_3$, —OCF$_3$, —OCHF$_2$, —OCH$_2$CF$_3$, —OCF$_2$CHF$_2$, —S(O)$_2$CF$_3$, —SCF$_3$, —OR$^{54}$, —NR$^{54}$R$^{55}$, —SR$^{54}$, —NR$^{54}$S(O)$_2$R$^{55}$, —S(O)$_2$NR$^{54}$R$^{55}$, —S(O)NR$^{54}$R$^{55}$, —S(O)R$^{54}$, —S(O)$_2$R$^{54}$, —C(O)NR$^{54}$R$^{55}$, —OC(O)NR$^{54}$R$^{55}$, —NR$^{54}$C(O)R$^{55}$, —CH$_2$C(O)NR$^{54}$R$^{55}$, —CH$_2$C(O)OR$^{54}$, —OCH$_2$C(O)NR$^{54}$R$^{55}$, —CH$_2$OR$^{54}$, —CH$_2$NR$^{54}$R$^{55}$, —OC(O)R$^{54}$, —C(O)R$^{54}$ or —C(O)OR$^{54}$, wherein
R$^{54}$ and R$^{55}$ are as defined for embodiment 1.

Embodiment 215: A compound according to embodiment Error! Reference source not found. or Error! Reference source not found., wherein
R$^{43}$ is —C(O)OR$^{54}$, —CH$_2$C(O)OR$^{54}$, —C(O)NR$^{54}$R$^{55}$, or —CH$_2$C(O)NR$^5$R$^{55}$, wherein
R$^{54}$ and R$^{55}$ are as defined for embodiment 1.

Embodiment 216: A compound according to embodiment Error! Reference source not found. or Error! Reference source not found., wherein
R$^{44}$ is alkyl or hydrogen.

Embodiment 217: A compound according to embodiment Error! Reference source not found., wherein
R$^{44}$ is C$_{1-6}$alkyl or hydrogen.

Embodiment 218: A compound according to embodiment Error! Reference source not found., wherein
R$^{44}$ is hydrogen.

Embodiment 219: A compound according to embodiment Error! Reference source not found., wherein
R$^{44}$ is halogen, —CN, —NO$_2$, C$_{1-6}$-alkyl, —CHF$_2$, —CF$_3$, —OCF$_3$, —OCHF$_2$, —OCH$_2$CF$_3$, —OCF$_2$CHF$_2$, —S(O)$_2$CF$_3$, —SCF$_3$, —OR$^{54}$, —NR$^{54}$R$^{55}$, —SR$^{54}$, —NR$^{54}$S(O)$_2$R$^{55}$, —S(O)$_2$NR$^{54}$R$^{55}$, —S(O)NR$^{54}$R$^{55}$, —S(O)R$^{54}$, —S(O)$_2$R$^{54}$, —C(O)NR$^{54}$R$^{55}$, —OC(O)

$NR^{54}R^{55}$, $-NR^{54}C(O)R^{55}$, $-CH_2C(O)NR^{54}R^{55}$, $-CH_2C(O)OR^{54}$, $-OCH_2C(O)NR^{54}R^{55}$, $-CH_2OR^{54}$, $-CH_2NR^{54}R^{55}$, $-OC(O)R^{54}$, $-C(O)R^{54}$ or $-C(O)OR^{54}$, wherein
$R^{54}$ and $R^{55}$ are as defined for embodiment 1.

Embodiment 220: A compound according to embodiment Error! Reference source not found. or embodiment Error! Reference source not found., wherein
$R^{44}$ is $-C(O)OR^{54}$, $-CH_2C(O)OR^{54}$, $-C(O)NR^{54}R^{55}$, or $-CH_2C(O)NR^{54}R^{55}$, wherein
$R^{54}$ and $R^{55}$ are as defined for embodiment 1.

Embodiment 221: A compound according to embodiment Error! Reference source not found. or Error! Reference source not found., wherein
$R^{43}$ is alkyl or hydrogen.

Embodiment 222: A compound according to embodiment Error! Reference source not found., wherein
$R^{43}$ is $C_{1-6}$-alkyl or hydrogen.

Embodiment 223: A compound according to embodiment Error! Reference source not found., wherein
$R^{43}$ is hydrogen.

Embodiment 224: A compound according to any of embodiments Error! Reference source not found. to Error! Reference source not found., wherein
$R^{45}$ is hydrogen.

Embodiment 225: A compound according to any of embodiments Error! Reference source not found. to Error! Reference source not found., wherein
$R^{54}$ and $R^{55}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds, and optionally substituted with one or more $C_{1-6}$alkyl groups.

Embodiment 226: A compound according to embodiment Error! Reference source not found., wherein
$R^{54}$ and $R^{55}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds.

Embodiment 227: A compound according to any of embodiments Error! Reference source not found. to Error! Reference source not found., wherein
$R^{54}$ and $R^{55}$ independently of each other are hydrogen, $C_{1-6}$alkyl, aryl-$C_{1-6}$-alkylene- or aryl.

Embodiment 228: A compound according to any of embodiments Error! Reference source not found. to Error! Reference source not found., wherein
$R^{54}$ and $R^{55}$ independently of each other are hydrogen, $C_{1-6}$alkyl, aryl-$C_{1-6}$-alkylene- or aryl.

Embodiment 229: A compound according to embodiment Error! Reference source not found., wherein
$R^{54}$ and $R^{55}$ independently of each other are hydrogen or $C_{1-6}$alkyl.

Embodiment 230: A compound according to embodiment Error! Reference source not found., wherein
$R^{54}$ is hydrogen.

Embodiment 231: A compound according to any of embodiments Error! Reference source not found. to Error! Reference source not found., wherein
$R^{55}$ is hydrogen.

Embodiment 232: A compound according to any of embodiments Error! Reference source not found. to Error! Reference source not found., wherein
$R^{54}$ and $R^{55}$ independently of each other are hydrogen or $-(CHR^{63})_u-(CHR^{64})_v-Z$, wherein
u is 1 or 2;
v is 0, 1 or 2;
$R^{63}$ and $R^{64}$ independently of each other are hydrogen, $C_{1-6}$alkyl, $C_{1-6}$-alkyl-$C_{3-10}$-arylene-$C_{3-10}$-aryl, hydroxy, hydroxy-$C_{1-6}$-alkyl, amino, or amino-$C_{1-6}$alkyl;
Z is hydrogen, $-C-O-R^{65}$, $-C(O)O-R^{65}$, $-CONR^{65}R^{66}$, $C_{1-6}$-alkylamino, or di($C_{1-6}$-alkyl)-amino, wherein
$R^{65}$ and $R^{66}$ independently of each other is hydrogen or $C_{1-6}$alkyl;
or
Z is a five or six membered ring wherein at least one ring atom is nitrogen and the remaining ring atoms are either carbon or oxygen.

Embodiment 233: A compound according to embodiment Error! Reference source not found., wherein
u is 1; and
v is 0, or 1.

Embodiment 234: A compound according to embodiment Error! Reference source not found. or embodiment Error! Reference source not found., wherein
$R^{63}$ and $R^{64}$ independently of each other are hydrogen, $C_{1-6}$alkyl, hydroxy, hydroxy-$C_{1-6}$alkyl, amino, or amino-$C_{1-6}$-alkyl.

Embodiment 235: A compound according to any of embodiments Error! Reference source not found. to Error! Reference source not found., wherein
Z is $-C-O-R^{65}$, or $-C(O)O-R^{65}$, wherein
$R^{65}$ and $R^{66}$ independently of each other is hydrogen or $C_{1-6}$-alkyl.

Embodiment 236: A compound according to any of embodiments Error! Reference source not found. to Error! Reference source not found., wherein
Z is a five or six membered ring where at least one ring atom is nitrogen and the remaining ring atoms are either carbon or oxygen.

Embodiment 237: A compound according to embodiment Error! Reference source not found., wherein
Z is a five or six membered ring wherein at least one ring atom is nitrogen, one ring atom is oxygen and the remaining ring atoms are carbon.

Embodiment 238: A compound according to embodiment Error! Reference source not found., wherein
Z is a five or six membered ring wherein at least one ring atom is nitrogen, and the remaining ring atoms are carbon.

Embodiment 239: A compound according to any of embodiments Error! Reference source not found. to Error! Reference source not found., wherein
Z is a five or six membered ring wherein one ring atom is nitrogen.

Embodiment 240: A compound according to any of embodiments Error! Reference source not found. to Error! Reference source not found., wherein
 a nitrogen atom is the point of attachment of the Z group to the —(CHR$^{63}$)$_u$—(CHR$^{64}$)$_v$— group.

Embodiment 241: A compound according to any of embodiments Error! Reference source not found. to Error! Reference source not found., wherein
 R$^{55}$ is hydrogen.

Embodiment 242: A compound according to embodiment Error! Reference source not found., wherein
 R$^{44}$ is hydrogen.

Embodiment 243: A compound according to embodiment Error! Reference source not found. or embodiment Error! Reference source not found., wherein
 R$^{43}$ is hydrogen.

Embodiment 244: A compound according to embodiment Error! Reference source not found. or embodiment Error! Reference source not found., wherein
 R$^{45}$ is hydrogen.

Embodiment 245: A compound according to embodiment 1, which is,
N-(2-phenoxyphenyl)-N'-(thiazol-2-yl)urea,
N-[2-(2,3-dimethoxyphenoxy)-5-fluorophenyl]-N'-(thizol-2-yl)sulfamide,
1-(2-phenoxyphenyl)-5-(thiazol-2-yl)biuret,
2-[([[(2-phenoxyanilino)sulfonyl]amino]carbonyl)amino] thiazole,
N-(2-phenylsulfanylphenyl)-N'-(thiazol-2-yl)urea,
N-(2-phenylsulfonylphenyl)-N'-(thiazol-2-yl)urea,
N-(2-benzylphenyl)-N'-(thiazol-2-yl)urea,
N-(2-benzoylphenyl)-N'-(thiazol-2-yl)urea,
N-[2-(phenylamino)phenyl]-N'-(thiazol-2-yl)urea,
N-[2-fluoro-6-(4-methoxyphenoxy)benzyl]-N'-(thiazol-2-yl)urea,
N-(2-benzyloxyphenyl)-N'-(thiazol-2-yl)urea,
N-[2-(2,3,4-trimethoxybenzyloxy)phenyl]-N'-(thiazol-2-yl) urea,
N-(2-ethoxyphenyl)-N'-(thiazol-2-yl)urea,
N-(2-phenoxyphenyl)-N'-(pyridin-2-yl)urea,
N-(2-phenoxyphenyl)-N'-[(4-methoxycarbonylmethyl)thiazol-2-yl]urea,
N-methyl-N-(2-phenoxyphenyl)-N'-(thiazol-2-yl)urea,
N-isopropyl-N-(2-phenoxyphenyl)-N'-(thiazol-2-yl)urea,
N-[2-(4-methoxyphenoxy)phenyl)-N'-(thiazol-2-yl)urea,
N-[2-(4-fluorophenoxy)phenyl]-N'-(thiazol-2-yl)urea,
N-[2-(4-chlorophenoxy)phenyl]-N'-(thiazol-2-yl)urea,
N-[2-(4-cyanophenoxy)phenyl]-N'-thiazolylurea,
N-[2-(4-methoxycarbonylphenoxy)phenyl]-N'-(thiazol-2-yl)urea,
N-[2-(4-isopropylphenoxy)phenyl]-N'-(thiazol-2-yl)urea,
N-[2-(3,4-difluorophenoxy)phenyl]-N'-(thiazol-2-yl)urea,
N-[2-(3,4-dichlorophenoxy)phenyl]-N'-(thiazol-2-yl)urea,
N-[2-(4-chloro-3-methylphenoxy)phenyl]-N'-(thiazol-2-yl)urea,
N-[2-(3,4-dimethoxyphenoxy)phenyl]-N'-(thiazol-2-yl) urea,
N-[2-(3,4-methylenedioxyphenoxy)phenyl]-N'-(thiazol-2-yl)urea,
N-[2-(2,4-dichlorophenoxy)phenyl]-N'-(thiazol-2-yl)urea,
N-[2-(2,4-difluorophenoxy)phenyl]-N'-(thiazol-2-yl)urea,
N-[2-(4-fluoro-2-methoxyphenoxy)phenyl]-N'-(thiazol-2-yl)urea,
N-[2-(4-methoxy-2-methoxycarbonylphenoxy)phenyl]-N'-(thiazol-2-yl)urea,
N-[2-(3-methoxyphenoxy)phenyl]-N'-(thiazol-2-yl)urea,
N-[2-(3-fluorophenoxy)phenyl]-N'-(thiazol-2-yl)urea,
N-[2-(3-trifluoromethylphenoxy)phenyl]-N'-(thiazol-2-yl) urea,
N-[2-(2-methylphenoxy)phenyl]-N'-(thiazol-2-yl)urea,
N-[2-2-methoxyphenoxy)phenyl]-N'-(thiazol-2-yl)urea,
N-[2-(2-isopropoxyphenoxy)phenyl]-N'-(thiazol-2-yl)urea,
N-[2-2-fluorophenoxy)phenyl]-N'-(thiazol-2-yl)urea,
N-[2-(2-methylsulfanylphenoxy)phenyl]-N'-(thiazol-2-yl) urea,
N-[2-(2-methylsulfonylphenoxy)phenyl]-N'-thiazolylurea,
N-[2-(2-trifluoromethylphenoxy)phenyl]-N'-(thiazol-2-yl) urea,
N-[2-(2,6-dimethoxyphenoxy)phenyl]-N'-(thiazol-2-yl) urea,
N-[2-(2,6-difluorophenoxy)phenyl]-N'-(thiazol-2-yl)urea,
N-[2-(2-fluoro-6-methoxyphenoxy)phenyl]-N'-(thiazol-2-yl)urea,
N-[2-2-methoxy-6-methoxycarbonylphenoxy)phenyl]-N'-(thiazol-2-yl)urea,
N-[(3-methoxy-2-methoxycarbonylphenoxy)phenyl]-N'-(thiazol-2-yl)urea,
N-[2-(2,3-dimethoxyphenoxy)phenyl]-N'-(thiazol-2-yl) urea,
N-[2-(2,3,4-trichlorophenoxy)phenyl]-N'-(thiazol-2-yl) urea,
N-[2-(2,4,6-trifluorophenoxy)phenyl]-N'-(thiazol-2-yl)urea,
N-[2-(2,4-dichloronaphth-1-oxy)phenyl]-N'-(thiazol-2-yl) urea,
N-[2-(2-methoxyphenoxy)-5-(methylsulfonyl)phenyl]-N'-(thiazol-2-yl)urea,
N-[5-cyano-2-(2-methoxyphenoxy)phenyl]-N'-(thiazol-2-yl)urea,
N-[5-fluoro-2-(2-methylsulfanylphenoxy)phenyl]-N'-thiazolylurea,
N-[5-fluoro-2-(2-fluoro-6-methoxyphenoxy)phenyl]-N'-(thiazol-2-yl)urea,
N-[2-(2,3-dimethoxyphenoxy)-5-fluorophenyl]-N'-(thiazol-2-yl)urea,
N-[2-(3,4-difluorophenoxy)-5-fluorophenyl]-N'-(thiazol-2-yl)urea,
N-[5-fluoro-2-(4-fluorophenoxy)phenyl]-N'-(thiazol-2-yl) urea,
N-[2-(2,4-dichlorophenoxy)-5-fluorophenyl]-N'-(thiazol-2-yl)urea,
N-[5-fluoro-2-(4-methoxyphenoxy)phenyl]-N'-(thiazol-2-yl)urea,
N-[5-fluoro-2-(2-methoxyphenoxy)phenyl]-N'-(thiazol-2-yl)urea,
N-[5-fluoro-2-(2-trifluoromethylphenoxy)phenyl]-N'-(thiazol-2-yl)urea,
N-[5-fluoro-2-(naphth-2-oxy)phenyl]-N'-(thiazol-2-yl)urea,
N-[2-(2,3-dimethoxyphenoxy)-6-fluorophenyl]-N'-(thiazol-2-yl)urea,
N-[2-(4-fluoro-2-methoxyphenoxy)phenyl]-N'-(thiazol-2-yl)urea,
N-[2-(2,3-dimethoxyphenoxy)-4-fluorophenyl]-N'-(thiazol-2-yl)urea,
N-[4-fluoro-2-(2-fluoro-6-methoxyphenoxy)phenyl]-N'-(thiazol-2-yl)urea,
N-[2-(2-fluoro-6-methoxyphenoxy)-4-methoxyphenyl]-N'-(thiazol-2-yl)urea,
N-[3-fluoro-2-(2-fluoro-6-methoxyphenoxy)phenyl]-N'-(thiazol-2-yl)urea, N-[2-2,3-dimethoxyphenoxy)-5-methoxyphenyl]-N'-thiazol-2-ylurea,
N-[2-(2,3-dimethoxyphenoxy)-4-methylphenyl]-N'-(thiazol-2-yl)urea,
N-[2-2,3-dimethoxyphenoxy)-3-methylphenyl]-N'-(thiazol-2-yl)urea,
N-[2-(2-chlorophenoxy)-5-chlorophenyl]-N'-(thiazol-2-yl)urea,
N-[5-chloro-2-(4-chloro-3-methylphenoxy)phenyl]-N'-(thiazol-2-yl)urea,
N-[2-(4-chlorophenoxy)-5-(trifluoromethyl)phenyl]-N'-(thiazol-2-yl)urea,
N-[4,5-difluoro-2-(2,3-dimethoxyphenoxy)phenyl]-N'-(thiazol-2-yl)urea,
N-[4,5-dichloro-2-(2,3-dimethoxyphenoxy)phenyl]-N'-(thiazol-2-yl)urea,
N-[5-chloro-2-(2,3-dimethoxyphenoxy)-4-dimethylaminophenyl]-N'-(thiazol-2-yl)urea,
N-[5-chloro-2-(2,3-dimethoxyphenoxy)-4-(4-morpholino)phenyl]-N'-(thiazol-2-yl)urea,
N-[2-(2,4-difluorophenoxy)pyridin-3-yl]-N'-(thiazol-2-yl)urea,
N-[2-(2-fluorophenoxy)pyridin-3-yl]-N'-[thiazol-2-yl]urea,
N-[2-(2-methoxyphenoxy)pyridin-3-yl]-N'-(thiazol-2-yl)urea,
N-[2-(2,3-dimethoxyphenoxy)pyridin-3-yl]-N-(thiazol-2-yl)urea,
N-[4-chloro-2-(2-chlorobenzoyl)phenyl]-N'-(thiazol-2-yl)urea,
N-[4-chloro-2-(2-fluorobenzoyl)phenyl]-N'-(thiazol-2-yl)urea,
N-[2-(2,4-difluorophenylsulfanyl)phenyl]-N'-(thiazol-2-yl)urea,
1-[2-(2-fluorophenylsulfanyl)phenyl]-3-(thiazol-2-yl)urea,
N-[2-(2-chloro-4-fluorophenylsulfanyl)phenyl]-N'-(thiazol-2-yl)urea,
N-[2-(2,3-dichlorophenylsulfanyl)phenyl]-N'-(thiazol-2-yl)urea,
N-[2-(3,5-dimethylphenylsulfanyl)phenyl]-N'-(thiazol-2-yl)urea,
N-[2-(2-methoxycarbonylphenylsulfanyl)phenyl]-N'-(thiazol-2-yl)urea,
N-[2-(2-methoxyphenylsulfanyl)phenyl]-N'-(thiazol-2-yl)urea,
N-[2-(2-pyridinylsulfanyl)phenyl]-N'-(thiazol-2-yl)urea,
N-(2-propyloxyphenyl)-N'-(thiazol-2-yl)urea,
N-(2-butyloxyphenyl)-N'-(thiazol-2-yl)urea,
N-(2-(cyclopentyloxyphenyl)-N'-(thiazol-2-yl)urea,
N-(2-isopropoxyphenyl)-N'-(thiazol-2-yl)urea,
N-[2-(2-methylpropoxy)phenyl]-N'-(thiazol-2-yl)urea,
N-(2-(cyclopentylmethoxy)phenyl]-N'-(thiazol-2-yl)urea,
N-[2-(3-pentoxy)phenyl]-N'-(thiazol-2-yl)urea,
N-[2-(2-pentoxy)phenyl]-N'-(thiazol-2-yl)urea,
N-[2-(2-methoxyethoxy)phenyl]-N'-(thiazol-2-yl)urea,
(2-[3-(2-benzylphenyl)ureido]thiazol-4-yl)acetic acid,
(2-[3-(2-benzoyl-4-chlorophenyl)ureido]thiazol-4-yl)acetic acid,
(2-[3-(2-(2-methylphenoxy)phenyl)ureido]thiazol-4-yl)acetic acid,
(2-[3-(2-(4-methoxyphenoxy)-5-(trifluoromethyl)phenyl)ureido]thiazol-4-yl)acetic acid,
{2-[3-(2-phenoxyphenyl)ureido]thiazol-4-y}acetic acid,
2-{3-[5-fluoro-2-(2-fluoro-6-methoxyphenoxy)phenyl]ureido}thiazole-4-carboxylic acid,
2-{3-[2-(2,3-dimethoxyphenoxy)-5-fluorophenyl]ureido}thiazole-4-carboxylic acid ethyl ester,
(2-{3-[2-(2,3-dimethoxyphenoxy)-5-fluorophenyl]ureido}thiazol-4-yl)acetic acid ethyl ester,
(2-{3-[5-fluoro-2-(2-fluoro-6-methoxyphenoxy)phenyl]ureido}thiazol-4-yl)acetic acid,
2-{3-[2-(2,3-dimethoxyphenoxy)-5-fluorophenyl]ureido}thiazole-4-carboxylic acid,
(2-{3-[2-(2,3-dimethoxyphenoxy)-5-fluorophenyl]ureido}thiazol-4-yl)acetic acid,
2-{3-[5-fluoro-2-(2-fluoro-6-methoxyphenoxy)phenyl]ureido}-4-methylthiazole-5-carboxylic acid ethyl ester,
2-{3-[5-fluoro-2-(2-fluoro-6-methoxyphenoxy)phenyl]ureido}-4-methylthiazole-5-carboxylic acid,
N-ethyl-2-(2-{3-[5-fluoro-2-(2-fluoro-6-methoxyphenoxy)phenyl]ureido}thiazol-4-yl)acetamide,
2-(2-{3-[5-fluoro-2-(2-fluoro-6-methoxyphenoxy)phenyl]ureido}thiazol-4-yl)-N-(2-methoxy-ethyl)acetamide,
2-(2-{3-[5-fluoro-2-(2-fluoro-6-methoxyphenoxy)phenyl]ureido}thiazol-4-yl)-N-(2-morpholin-4-ylethyl)acetamide,
[2-(2-{3-[5-fluoro-2-(2-fluoro-6-methoxyphenoxy)phenyl]ureido}thiazol-4-yl)acetylamino]acetic acid methyl ester,
2-{3-[2-(2,3-dimethoxyphenoxy)-5-fluorophenyl]ureido}thiazole-4-carboxylic acid (2-methoxyethyl)amide,
[2-(2-{3-[5-fluoro-2-(2-fluoro-6-methoxyphenoxy)phenyl]ureido}thiazol-4-yl)acetylamino]acetic acid,
2-{3-[2-(2,3-dimethoxyphenoxy)-5-fluorophenyl]ureido}thiazole-4-carboxylic acid ethylamide,
[(2-{3-[2-(2,3-dimethoxyphenoxy)-5-fluorophenyl]ureido}thiazole-4-carbonyl)amino]acetic acid methyl ester,
(5-{3-[5-fluoro-2-(2-fluoro-6-methoxyphenoxy)phenyl]ureido}-[1,3,4]thiadiazol-2-yl)acetic acid ethyl ester,
[(2-{3-[2-(2,3-dimethoxyphenoxy)-5-fluorophenyl]ureido}thiazole-4-carbonyl)amino]acetic acid,
(5-{3-[5-fluoro-2-(2-fluoro-6-methoxyphenoxy)phenyl]ureido}-[1,3,4]thiadiazol-2-yl)acetic acid,
5-{3-[2-(2,3-dimethoxyphenoxy)-5-fluorophenyl]ureido}-[1,3,4]thiadiazole-2-carboxylic acid ethyl ester,
(5-{3-[2-(2,3-dimethoxyphenoxy)-5-fluorophenyl]ureido}-[1,3,4]thiadiazol-2-yl) acetic acid ethyl ester,
3-[2-(2-{3-[2-(2,3-dimethoxyphenoxy)-5-fluorophenyl]ureido}thiazol-4-yl)acetylamino]propionic acid methyl ester,
2-(2-{3-[2-(2,3-dimethoxyphenoxy)-5-fluorophenyl]ureido}thiazol-4-yl)-N-(2-morpholin-4-ylethyl)acetamide,
[(2-{3-[5-fluoro-2-(2-fluoro-6-methoxyphenoxy)phenyl]ureido}thiazole-4-carbonyl)amino]acetic acid methyl ester,
3-[2-(2-{3-[2-(2,3-dimethoxyphenoxy)-5-fluorophenyl]ureido}thiazol-4-yl)acetylamino]propionic acid,
[(2-{3-[5-fluoro-2-(2-fluoro-6-methoxyphenoxy)phenyl]ureido}thiazole-4-carbonyl)amino]acetic acid,
(R) 3-[(2-{3-[5-fluoro-2-(2-fluoro-6-methoxyphenoxy)phenyl]ureido}thiazole-4-carbonyl)amino]-2-hydroxy-propionic acid,
2-[(2-{3-[5-fluoro-2-(2-fluoro-6-methoxyphenoxy)phenyl]ureido}thiazole-4-carbonyl)amino]-3-hydroxy-propionic acid,
1-(2-cyclopentanecarbonyl-4-methylphenyl)-3-thiazol-2-yl-urea,
1-(2-isobutyryl-4-methylphenyl)-3-thiazol-2-yl-urea,
1-[5-fluoro-2-(3-methylbutyryl)phenyl]-3-thiazol-2-yl-urea,
1-[5-methyl-2-(3-methylbutyryl)phenyl]-3-thiazol-2-yl-urea,

[3-cyclopentanecarbonyl-4-(3-thiazol-2-yl-ureido)phenyl] acetic acid ethyl ester,
[3-cyclopentanecarbonyl-4-(3-thiazol-2-yl-ureido)phenyl] acetic acid,
2-[3-cyclopentanecarbonyl-4-(3-thiazol-2-yl-ureido)phenyl]-N-methylacetamide,
{2-[3-(2-cyclopentanecarbonyl-4-methyl-phenyl)-ureido]-thiazol-4-yl}-acetic acid ethyl ester,
{2-[3-(2-cyclopentanecarbonyl-4-methyl-phenyl)-ureido]-thiazol-4-yl}acetic acid,
{3-cyclopentanecarbonyl-4-{3-(4-ethoxycarbonylmethylthiazol-2-yl)-ureido}phenyl}acetic acid ethyl ester,
1-(2-cyclopentanecarbonyl-4-methyl-phenyl)-3-(5-methanesulfonyl-thiazol-2-yl)-urea,
2-[3-(2-cyclopentanecarbonyl-4-methylphenyl)-ureido]-thiazole-4-carboxylic acid ethyl ester,
2-[3-(2-cyclopentanecarbonyl-4-methylphenyl)-ureido]-thiazole-4-carboxylic acid,
2-[3-(2-cyclopentanecarbonyl-4-methylphenyl)-ureido]-thiazole-4-carboxamide,
2-{2-[3-(2-cyclopentanecarbonyl-4-methylphenyl)-ureido]-thiazole-4-yl}-acetamide,
2-{2-[3-(2-cyclopentanecarbonyl-4-methylphenyl)-ureido]-thiazol-4-yl}-N-methyl-acetamide,
4-(2-{2-[3-(2-cyclopentanecarbonyl-4-methylphenyl)-ureido]-thiazol-4-yl}-acetyl)-1-methyl-piperazinium chloride,
1-[4-methyl-2-(2-methylpropoxy)phenyl]-3-thiazol-2-yl-urea,
{2-[3-(4-methyl-2-[2-methylpropoxy]phenyl)-ureido]-thiazol-4-yl}-acetic acid, or
{2-[3-(4-methyl-2-[2-methylpropoxy]phenyl)-ureido]-thiazol-4-yl)-N-methyl-acetamide.

Embodiment 246: A compound according to any of embodiments 1 to Error! Reference source not found., which compound is an activator of glucokinase, when tested in the Glucokinase Activation Assay (I) disclosed herein at a glucose concentration of 2 mM.

Embodiment 247: A compound according to any of embodiments 1 to 281, which compound is an activator of glucokinase, when tested in the Glucokinase Activation Assay (I) disclosed herein at a glucose concentration of from 10 to 15 mM.

Embodiment 248: A compound according to any of embodiments 1 to 282, which compound, at a concentration of 30 µM, is capable of providing an at least 1.5, such as at least 1.7, for instance at least 2.0 fold activation of glucokinase in the Glucokinase Activation Assay (I) disclosed herein at a glucose concentration of 2 mM.

Embodiment 249: A compound according to any of embodiments 1 to 283, which compound, at a concentration of 30 µM, is capable of providing an at least 1.5, such as at least 1.7, for instance at least 2.0 fold activation of glucokinase in the Glucokinase Activation Assay (I) disclosed herein at a glucose concentration of from 10 to 15 mM.

Embodiment 250: A compound according to any of embodiments 1 to 284, which at a concentration of 5 µM is capable of providing an at least 1.5, such as at least 1.7, for instance at least 2.0 fold activation of glucokinase in the Glucokinase Activation Assay (I) disclosed herein at a glucose concentration of 2 mM.

Embodiment 251: A compound according to any of embodiments 1 to 285, which at a concentration of 5 µM is capable of providing an at least 1.5, such as at least 1.7, for instance at least 2.0 fold activation of glucokinase in the Glucokinase Activation Assay (I) disclosed herein at a glucose concentration of from 10 to 15 mM.

Embodiment 252: A glucose kinase activator compound defined as a compound which at a compound concentration of at or below 30 µM at a glucose concentration of 2 mM in the Glucokinase Activation Assay (I) disclosed herein gives 1.5-fold higher glucokinase activity than measured at a glucose concentration of 2 mM in the Glucokinase Activation Assay (I) without compound, where the increase in glucokinase activity provided by the compound increases with decreasing concentrations of glucose.

Embodiment 253: A compound according to any of embodiments 1 to 286, which compound provides an increase in glucokinase activity, where the increase in glucokinase activity provided by the compound increases with decreasing concentrations of glucose.

Embodiment 254: A compound according to embodiment 287 or embodiment 288, which provides an increase in glucokinase activity in Glucokinase Activation Assay (I) disclosed herein at a glucose concentration of 5 mM, which increase is significantly higher than the increase in glucokinase activity provided by the compound in Glucokinase Activation Assay (I) disclosed herein at a glucose concentration of 15 mM.

Embodiment 255: A compound according to any of embodiments 287 to 289, which at a compound concentration of 10 µM provides an increase in glucokinase activity in Glucokinase Activation Assay (I) disclosed herein at a glucose concentration of 5 mM, which increase is significantly higher than the increase in glucokinase activity provided by the compound at a compound concentration of 10 µM in Glucokinase Activation Assay (I) disclosed herein at a glucose concentration of 15 mM.

Embodiment 256: A compound according to any of embodiments 287 to 290, which at a compound concentration of 10 µM provides an increase in glucokinase activity in Glucokinase Activation Assay (I) disclosed herein at a glucose concentration of 5 mM, which increase is at least 1.1 fold higher, such as at least 1.2 fold higher, for instance at least 1.3 fold higher, such as at least 1.4 fold higher, for instance 1.5 fold higher, such as at least 1.6 fold higher, for instance at least 1.7 fold higher, such as at least 1.8 fold higher, for instance at least 1.9 fold higher, such as at least 2.0 fold higher than the increase in glucokinase activity provided by the compound at a compound concentration of 10 µM in Glucokinase Activation Assay (I) disclosed herein at a glucose concentration of 15 mM.

Embodiment 257: A glucose kinase activator compound defined as a compound which at a compound concentration of at or below 30 µM at a glucose concentration of 2 mM in the Glucokinase Activation Assay (I) disclosed herein gives 1.5-fold higher glucokinase activity than measured at a glucose concentration of 2 mM in the Glucokinase Activation Assay (I) without compound, which glucose kinase activator compound increases glucose utilization in the liver without inducing any increase in insulin secretion in response to glucose.

Embodiment 258: A glucose kinase activator compound defined as a compound which at a compound concentration of at or below 30 µM at a glucose concentration of 2 mM in the Glucokinase Activation Assay (I) disclosed herein gives 1.5-fold higher glucokinase activity than measured at a glucose concentration of 2 mM in the Glucokinase Activation Assay (I) without compound, which glucokinase activator compound shows a significantly higher activity in isolated hepatocytes compared to the activity of the glucokinase compound in Ins-1 cells.

Embodiment 259: A compound according to any of embodiments 1 to 291, which compound increases glucose utilization in the liver without inducing any increase in insulin secretion in response to glucose.

Embodiment 260: A compound according to any of embodiments 1 to 291, which compound shows a significantly higher activity in isolated hepatocytes compared to the activity of the compound in Ins-1 cells.

Embodiment 261: A compound according to any of embodiments 292 to 295, which compound shows a significantly higher activity in isolated hepatocytes measured as described in the Glucokinase Activity Assay (II) compared to the activity of the compound in Ins-1 cells measured as described in the Glucokinase Activity Assay (III).

Embodiment 262: A compound according to embodiment 296, which compound shows an activity in isolated hepatocytes measured as described in the Glucokinase Activity Assay (II) which activity is at least 1.1 fold higher, such as at least 1.2 fold higher, for instance at least 1.3 fold higher, such as at least 1.4 fold higher, for instance 1.5 fold higher, such as at least 1.6 fold higher, for instance at least 1.7 fold higher, such as at least 1.8 fold higher, for instance at least 1.9 fold higher, such as at least 2.0 fold higher, for instance at least a 3.0 fold higher, such as at least a 4.0 fold higher, for instance at least 5.0 fold higher, such as at least 10 fold higher than the activity of the compound in Ins-1 cells measured as described in the Glucokinase Activity Assay (III).

Embodiment 263: A compound according to embodiment 296, which compound shows no activity in the Ins-1 cells measured as described in the Glucokinase Activity Assay (III).

Embodiment 264: A compound according to any one of embodiments 1 to 298, which is an agent useful for the treatment of an indication selected from the group consisting of hyperglycemia, IGT, insulin resistance syndrome, syndrome X, type 2 diabetes, type 1 diabetes, dyslipidemia, hypertension, and obesity.

Embodiment 265: A compound according to any one of embodiments 1 to 301 for use as a medicament.

Embodiment 266: A compound according to any one of embodiments 1 to 301 for treatment of hyperglycemia, for treatment of IGT, for treatment of Syndrome X, for treatment of type 2 diabetes, for treatment of type 1 diabetes, for treatment of dyslipidemia, for treatment of hyperlipidemia, for treatment of hypertension, for treatment of obesity, for lowering of food intake, for appetite regulation, for regulating feeding behaviour, or for enhancing the secretion of enteroincretins, such as GLP-1.

In a further aspect the invention provides in an Embodiment A1 a compound of the general formula (I)

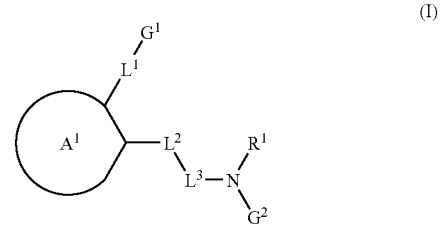

$A^1$ is selected from the group consisting of arylene, heteroarylene, fused cycloalkylarylene, fused heterocyclylarylene, fused cycloalkylheteroarylene, or fused heterocyclylheteroarylene; optionally substituted with one or more substitutents $R^{23}$, $R^{24}$, $R^{25}$, $R^{26}$, and $R^{27}$, wherein $R^{23}$, $R^{24}$, $R^{25}$, $R^{26}$, and $R^{27}$ independently of each other are selected from the group consisting of halogen, —C(O)OR$^2$, —C(O)R$^2$, —CN, —CF$_3$, —OCF$_3$, —NO$_2$, —OR$^2$, —NR$^2$R$^3$, $C_{1-6}$-alkyl-Z-, $C_{2-6}$-alkenyl-Z-, $C_{2-6}$-alkynyl-Z-, aryl-$C_{1-6}$-alkylene-Z-, heteroaryl-$C_{1-6}$alkylene-Z-, heterocyclyl-$C_{1-6}$-alkylene-Z-, cycloalkyl-$C_{1-6}$-alkylene-Z-, N(R$^4$R$^5$)—$C_{1-6}$-alkylene-Z-, R$^6$—W$^1$-Z-, R$^6$—W$^1$—$C_{1-6}$-alkylene-Z-, R$^6$—W$^1$—$C_{1-6}$-arylene-Z-, R$^6$—W$^1$-heteroarylene-Z-, R$^6$—W$^1$-heterocyclylene-Z-, R$^6$—W$^1$—N(R$^4$)-Z-, R$^6$—N(R$^4$)-Z, R$^6$—W$^1$—$C_{1-6}$-alkylene-Z-, heterocyclyl-Z-$C_{1-6}$-alkylene-, heterocyclyl-$C_{1-6}$-alkylene-Z-$C_{1-6}$-alkylene-, $C_{3-10}$-cycloalkyl-Z-$C_{1-6}$-alkylene-, $C_{3-10}$-cycloalkyl-$C_{1-6}$-alkylene-Z-$C_{1-6}$-alkylene-, $C_{3-10}$-cycloalkyl-arylene-Z-, heterocyclyl-arylene-Z-, $C_{3-10}$-cycloalkyl-heteroarylene-Z-, heterocyclyl-heteroarylene-Z-, aryl-$C_{3-10}$-cycloalkylene-Z-, aryl-heterocyclylene-Z-, heteroaryl-$C_{3-10}$-cycloalkylene-Z-, heteroaryl-heterocyclylene-Z-, heterocyclyl-$C_{3-10}$-cycloalkylene-Z-, aryl-heteroarylene-Z-, heteroaryl-arylene-Z-, aryl-arylene-Z-, heteroaryl-heteroarylene-Z-, wherein any mono- or divalent $C_{1-6}$-alkyl, $C_{3-10}$-cycloalkyl, heterocyclyl, aryl or heteroaryl moiety can optionally be substituted with one or more substituents independently selected from R$^2$, and wherein $R^2$ and $R^3$ independently of each other are hydrogen, halogen, hydroxy, —CN, —CF$_3$, —OCF$_3$, —NO$_2$, —C(O)OH, —NH$_2$, $C_{1-6}$-alkyl, $C_{1-6}$-alkoxy, aryloxy, R$^6$-Z-, aryl-$C_{1-6}$alkylene-, heteroaryl-$C_{1-6}$-alkylene-, $C_{1-6}$alkyl-arylene-, $C_{1-6}$-alkyl-heteroarylene-, heteroaryl, or aryl;

or $R^2$ and $R^3$, when attached to the same nitrogen atom, together with said nitrogen atom may form a 3 to 8 membered heterocyclic ring optionally containing one or two further heteroatoms selected from nitrogen, oxygen and sulfur, and optionally containing one or two double bonds;

Z and W$^1$ independently of each other are a direct bond, —O—, —N(R$^7$)—, —N(R$^7$)C(R$^7$R$^8$)—, —S—, —SO$_2$—, —C(O)N(R$^7$)—, —N(R$^7$)C(O)—, —N(R$^7$)C(O)C(R$^7$R$^8$)—, —N(R$^7$)CON(R$^8$)—, —N(R$^7$)SO$_2$—, —SO$_2$N(R$^7$)—, —C(O)—, —C(O)—O—, —N(R$^7$)SO$_2$N(R$^8$)—, or —O—C(O)—, wherein $R^7$ and $R^8$ in each individual case independently of each other are hydrogen or $C_{1-6}$-alkyl; and $R^4$, $R^5$, and $R^6$ independently of each other are selected from the group consisting of hydrogen, cyano, halogen, aryl, heteroaryl, heteroaryl-$C_{1-6}$alkylene-, aryl-$C_{1-6}$-alkylene-, $C_{3-10}$-cycloalkyl, heterocyclyl optionally substituted with one or more $C_{1-6}$-alkyl, or $C_{1-6}$alkyl optionally substituted with halogen, —S(O)$_2$CH$_3$ or COOH;

or $R^4$ and $R^5$ may be taken together to form a ring having the formula —(CH$_2$)$_j$-Q-(CH$_2$)$_k$-bonded to the nitrogen atom to which $R^4$ and $R^5$ are attached, wherein j and k independently of each other is 1, 2, 3, or 4; and Q is a direct bond, —CH$_2$—, —O—, —S—, —S(O$_2$)—, —C(O)—, —C(O)NH—, —NHC(O)—, —NHC(O)NH—, —NHSO$_2$—, —SO$_2$NH—, —C(O)—O—, —O—C(O)—, —NHSO$_2$NH—,

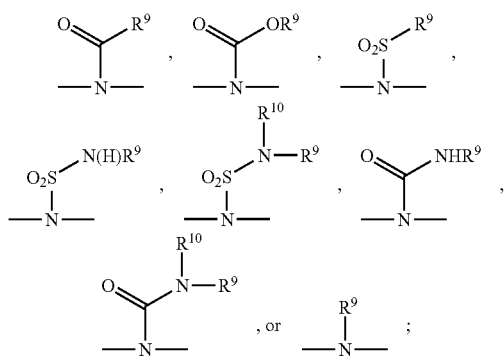

wherein $R^9$ and $R^{10}$ independently of each other are selected from the group consisting of hydrogen, aryl, $C_{1-6}$alkyl, and aryl-alkylene-;

$L^1$ is a bond, -D-$C_{1-6}$alkylene-E-, -D-$C_{2-6}$-alkenylene-E-, -D-$C_{2-6}$-alkynylene-E-, -D-cycloalkylene-E-, -D-heterocyclylene-E-, —O—, —S—, —S(O)—, —S(O)$_2$—, —C(O)—, —N(R$^{11}$)—, or —C(=N—OR$^{12}$)—, wherein D and E independently of each other are a direct bond, —O— or —S—;

$R^{11}$ is selected from hydrogen, $C_{1-6}$-alkyl, aryl, carbamoyl, aryl-$C_{1-6}$-alkylene-, heteroaryl-$C_{1-6}$alkylene-, $C_{1-6}$-alkyl-O—C(O)—, aryl-$C_{1-6}$alkylene-O—C(O)—, heteroaryl-$C_{1-6}$-alkylene-O—C(O)—, $C_{1-6}$-alkyl-NH—C(O)—, aryl-$C_{1-6}$-alkylene-NH—C(O)—, heteroaryl-$C_{1-6}$-alkylene-NH—C(O)—, $C_{1-6}$-alkyl-SO$_2$—, aryl-$C_{1-6}$-alkylene-SO$_2$—, heteroaryl-$C_{1-6}$-alkylene-SO$_2$—, aryl-SO$_2$—, heteroaryl-SO$_2$—, $C_{1-6}$alkyl-NH—SO$_2$—, aryl-$C_{1-6}$-alkylene-NH—SO$_2$—, heteroaryl-$C_{1-6}$-alkylene-NH—SO$_2$—, $C_{1-6}$-alkyl-C(O)—, aryl-$C_{1-6}$-alkylene-C(O)—, heteroaryl-$C_{1-6}$-alkylene-C(O)—, $C_{1-6}$-alkyl-Y—, aryl-Y—, heteroaryl-Y—, aryl-$C_{1-6}$-alkylene-Y—, heteroaryl-$C_{1-6}$-alkylene-Y—, N(R$^{13}$)(R$^{14}$)—$C_{1-6}$-alkylene-Y—, and R$^{15}$—W$^2$—$C_{1-6}$-alkylene-Y—, wherein Y and W$^2$ independently of each other are a direct bond, —CH$_2$—, —SO$_2$—, —N(H)CO—, —N(H)SO$_2$—, or —O—C(O)—;

$R^{13}$ and $R^{14}$ independently of each other are selected from hydrogen, aryl, heteroaryl, $C_{1-6}$-alkyl, $C_{1-6}$-alkoxy, aryl-$C_{1-6}$-alkylene-, heteroaryl-$C_{1-6}$-alkylene-, aryl-$C_{1-6}$-alkoxy-, heteroaryl-$C_{1-6}$-alkoxy-, $C_{1-6}$-alkyl-arylene-, $C_{1-6}$-alkyl-heteroarylene-, $C_{1-6}$-alkoxy-heteroarylene-, or $C_{1-6}$-alkoxy-arylene-;

or $R_{13}$ and $R_{14}$ may be taken together to form a ring having the formula —(CH$_2$)$_o$—X—(CH$_2$)$_p$— bonded to the nitrogen atom to which $R_{13}$ and $R_{14}$ are attached, wherein o and p are independently of each other are 1, 2, 3, or 4; and X is a direct bond, —CH$_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

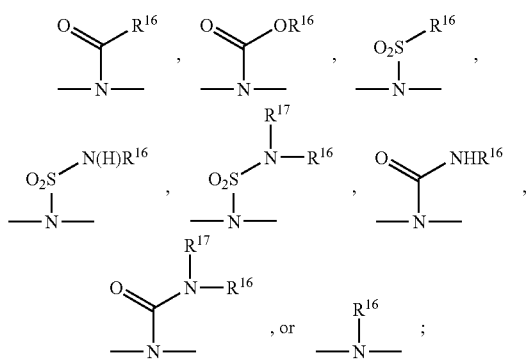

wherein $R^{16}$ and $R^{17}$ are selected from hydrogen, aryl, heteroaryl, $C_{1-6}$-alkyl, $C_{1-6}$alkoxy, aryl-$C_{1-6}$-alkylene-, heteroaroyl-$C_{1-6}$-alkylene-, $C_{1-6}$-alkyl-arylene-, $C_{1-6}$-alkyl-heteroarylene-, $C_{1-6}$-alkoxy-arylene-, $C_{1-6}$-alkoxy-heteroarylene-, heteroarylaryl-$C_{1-6}$-alkoxy-, or aryl-$C_{1-6}$ alkoxy-; and $R^{15}$ is selected from the group consisting of aryl, heteroaryl, cycloalkyl, heterocyclyl, $C_{1-6}$-alkyl, heteroaryl-$C_{1-6}$-alkylene-, or aryl-$C_{1-6}$-alkylene-; and $R^{12}$ is selected from hydrogen, aryl, heteroaryl, $C_{1-6}$alkyl, aryl-$C_{1-6}$-alkylene-, heteroaryl-$C_{1-6}$-alkylene-, $C_{1-6}$-alkyl-arylene-, $C_{1-6}$-alkyl-heteroarylene-, $C_{1-6}$-alkoxy-heteroarylene-, or $C_{1-6}$-alkoxy-arylene-;

$G^1$ is $C_{1-6}$-alkyl, $C_{3-10}$-cycloalkyl, $C_{3-10}$-cycloalkyl-$C_{1-6}$ alkylene-, $C_{2-6}$-alkenyl, or $C_{2-6}$-alkynyl, all of which may optionally be substituted with one or more substituents independently selected from the group consisting of —CN, —CF$_3$, —OCF$_3$, —OR$^{18}$, —NR$^{18}$R$^{19}$, $C_{3-10}$-cycloalkyl and $C_{1-6}$-alkyl, wherein $R^{18}$ and $R^{19}$ independently of each other are hydrogen, $C_{1-6}$-alkyl, heteroaryl-$C_{1-6}$-alkylene-, aryl-$C_{1-6}$-alkylene-, $C_{1-6}$-alkyl-arylene-, $C_{1-6}$-alkyl-heteroarylene-, heteroaryl, or aryl;

or $R^{18}$ and $R^{19}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds;

or $G^1$ is aryl, heteroaryl, heterocyclyl, fused cycloalkylheteroaryl, fused heterocyclylaryl, fused arylheterocyclyl, or fused cycloalkylaryl, all of which may optionally be substituted with one or more substituents selected from R$^{40}$, R$^{41}$, and R$^{42}$;

L² is a direct bond, $C_{1-6}$alkylene, $C_{2-6}$-alkenylene, $C_{2-6}$-alkynylene, —N(R²⁰)—, —$C_{1-6}$alkylene-N(R²⁰)—, —$C_{2-6}$-alkenylene-N(R²⁰)—, —$C_{2-6}$-alkynylene-N(R²⁰)—, wherein
  R²⁰ is hydrogen, or
  R²⁰ is $C_{1-6}$alkyl, $C_{2-6}$-alkenyl, $C_{2-6}$-alkynyl, cycloalkyl-W³—, heterocyclyl-W³—, aryl-W³—, heteroaryl-W³—, optionally substituted with one or more substituents R³⁰, R³¹, and R³² wherein
    W³ is $C_{1-6}$alkylene or a direct bond;
wherein L¹ and L² are attached to adjacent atoms in A¹;
L³ is —C(O)—, —C(O)—C(O)—, —C(O)CH₂C(O)— or —S(O)₂—;
R¹ is hydrogen, or
R¹ is $C_{1-6}$-alkyl, $C_{2-6}$-alkenyl, $C_{2-6}$-alkynyl, cycloalkyl-W⁴—, heterocyclyl-W⁴—, aryl-W⁴—, or heteroaryl-W⁴—,
optionally substituted with one or more substituents R³³, R³⁴, and R³⁵ wherein
  W⁴ is $C_{1-6}$alkylene or a direct bond;
G² is heteroaryl, fused heterocyclylheteroaryl, or fused cycloalkylheteroaryl,
optionally substituted with one or more substituents R⁴³, R⁴⁴, and R⁴⁵, wherein said heteroaryl group posesses a nitrogen atom adjacent to the atom joining said heteroaryl group to —N(R¹)—;

or a group of the formula

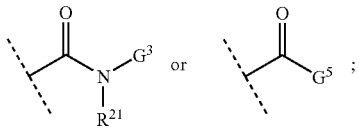

wherein
  G³ and G⁵ independently of each other are $C_{1-6}$alkyl, $C_{2-6}$-alkenyl, $C_{2-6}$-alkynyl, cycloalkyl-R²²—, heterocyclyl-R²²—, aryl-R²²—, heteroaryl-R²²-optionally substituted with one or more substituents R⁴⁶, R⁴⁷, and R⁴⁸, wherein
    R²² is alkylene or a direct bond; and
  R²¹ is hydrogen, $C_{1-6}$-alkyl, $C_{2-6}$-alkenyl, $C_{2-6}$-alkynyl, cycloalkyl-W⁵—, or heterocyclyl-W⁵—,
  optionally substituted with one or more substituents R³⁶, R³⁷, and R³⁸, or
  R²¹ is aryl-W⁵—, or heteroaryl-W⁵—, optionally substituted with one or more substituents R⁴⁹, R⁵⁰, and R⁵¹, wherein
    W⁵ is $C_{1-6}$alkylene or a direct bond;
wherein
R³⁰, R³¹, R³², R³³, R³⁴, R³⁵, R³⁶, R³⁷, and R³⁸ independently of each other are selected from —CHF₂, —CF₃, —OCF₃, —OCHF₂, —OCH₂CF₃, —OCF₂CHF₂, —S(O)₂CF₃, —SCF₃, —OR⁵², —NR⁵²R⁵³, —SR₅₂, —NR⁵²S(O)₂R⁵³, —S(O)₂NR⁵²R⁵³, —S(O)NR⁵²R⁵³, —S(O)R⁵², —S(O)₂R⁵², —C(O)NR⁵²R⁵³, —OC(O)NR⁵²R⁵³, —NR⁵²C(O)R⁵³, —CH₂C(O)NR⁵²R⁵³, —OCH₂C(O)NR⁵²R⁵³, —CH₂OR⁵², —CH₂NR⁵²R⁵³, —OC(O)R⁵², —C(O)R⁵² and —C(O)OR⁵²; or
$C_{2-6}$-alkenyl and $C_{2-6}$-alkynyl, which may optionally be substituted with one or more substituents selected from —CN, —CF₃, —OCF₃, —OR⁵², —NR⁵²R⁵³ and $C_{1-6}$-alkyl; or
$C_{3-10}$-cycloalkyl, $C_{4-8}$-cycloalkenyl, heterocyclyl, $C_{3-10}$-cycloalkyl-$C_{1-6}$-alkylene-, $C_{3-10}$-cycloalkyl-$C_{1-6}$-alkoxy-, $C_{3-10}$-Cycloalkyloxy, $C_{3-10}$-cycloalkyl-$C_{1-6}$-alkylthio-, $C_{3-10}$-cycloalkylthio, $C_{3-10}$-cycloalkyl-$C_{2-6}$-alkenylene-, $C_{3-10}$-cycloalkyl-$C_{2-6}$-alkynylene-, $C_{4-8}$-cycloalkenyl-$C_{1-6}$-alkylene-, $C_{4-8}$-cycloalkenyl-$C_{2-6}$-alkenylene-, $C_{4-8}$-cycloalkenyl-$C_{2-6}$-alkynylene-, heterocyclyl-$C_{1-6}$-alkylene-, heterocyclyl-$C_{2-6}$-alkenylene-, heterocyclyl-$C_{2-6}$-alkynylene-, aryl, aryloxy, aryloxycarbonyl, aroyl, aryl-$C_{1-6}$-alkoxy-, aryl-$C_{1-6}$-alkylene-, aryl-$C_{2-6}$-alkenylene-, aryl-$C_{2-6}$-alkynylene-, heteroaryl, heteroaryl-$C_{1-6}$-alkylene-, heteroaryl-$C_{2-6}$-alkenylene- and heteroaryl-$C_{2-6}$-alkynylene-, of which the aryl and heteroaryl moieties optionally may be substituted with one or more substituents selected from halogen, —C(O)OR⁵², —CN, —CF₃, —OCF₃, —NO₂, —OR⁵², —NR⁵²R⁵³ and $C_{1-6}$alkyl, wherein
  R⁵² and R⁵³ independently of each other are hydrogen, $C_{1-6}$alkyl, aryl-$C_{1-6}$-alkylene-heteroaryl-$C_{1-6}$-alkylene-heteroaryl, or aryl;
or
  R⁵² and R⁵³, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds;
R⁴⁰, R⁴¹, R⁴², R⁴³, R⁴⁴, R⁴⁵, R⁴⁶, R⁴⁷, R⁴⁸, R⁴⁹, R⁵⁰ and R⁵¹ independently of each other are —CN, —NO₂, —S(O)₂CF₃, —SCF₃, —OR⁵⁴, —NR⁵⁴R⁵⁵, —SR⁵⁴, —NR⁵⁴S(O)₂R⁵⁵, —S(O)₂NR⁵⁴R⁵⁵, —S(O)NR⁵⁴R⁵⁵, —S(O)R⁵⁴, —S(O)₂R⁵⁴, —C(O)NR⁵⁴R⁵⁵, —OC(O)NR⁵⁴R⁵⁵, —NR⁵⁴C(O)R⁵⁵, halogen, —S—$C_{1-6}$alkylene-OR⁵⁴, —S(O)₂—$C_{1-6}$alkylene-OR⁵⁴, —$C_{1-6}$-alkylene-S—R⁵, —$C_{1-6}$-alkylene-S(O)R⁵⁴, —$C_{1-6}$-alkylene-S(O)₂R⁵⁴, —$C_{1-6}$alkylene-N(R⁵⁴)S(O)₂R⁵⁵, —N(R⁵⁴)S(O)₂R⁵⁵, —$C_{1-1}$alkylene-CN, —$C_{1-6}$alkylene-C(O)NR⁵⁴R⁵⁵, —$C_{1-6}$ alkylene-N(R⁵⁴)C(O)R⁵⁵, —N(R⁵⁴)C(O)R⁵⁵, —$C_{1-6}$alkylene-N(R⁵⁴)C(O)NR⁵⁵R⁵⁶, —$C_{1-6}$-alkylene-NHC(=NR⁵⁴)NR⁵⁵R⁵⁶, —$C_{1-6}$alkylene-N(R⁵⁴)C(O)OR⁵⁵, —N(R⁵⁴)C(O)OR⁵⁵, —$C_{1-6}$-alkylene-C(O)OR⁵⁴, —$C_{1-6}$alkylene-N(R⁵⁴)S(O)₂R⁵⁵, —OCH₂C(O)NR⁵⁴R⁵⁵, —O(CH₂)$_{1-3}$OR⁵⁴, —$C_{1-6}$-alkylene-O—R⁵⁴, —$C_{1-6}$-alkylene-C(O)R⁵⁴, —$C_{1-6}$alkylene-NR⁵⁴R⁵⁵, —C(=NR⁵⁴)—O—R⁵⁵, —C(=N(OR⁵⁴))C(O)OR⁵⁵, —C(=N(OR⁵⁴))C(O)R⁵⁵, —$C_{1-6}$-alkylene-C(=N(OR⁵⁴))C(O)R⁵⁵, —$C_{1-6}$-alkylene=N—O—R⁵⁴, —$C_{1-6}$-alkylene-N(R⁵⁴)S(O)₂NR⁵⁵R⁵⁶, —N(R⁵⁴)S(O)₂NR⁵⁵R⁵⁶, —N(R⁵⁴)S(O)₂NR⁵⁵R⁵⁶, —OC(O)R⁵⁴, —$C_{1-6}$-alkylene-C(O)N(R⁵⁴)S(O)₂R⁵⁵, —C(O)N(R⁵⁴)S(O)₂R⁵⁵, —$C_{1-6}$alkylene-C(R⁵⁴)=N—OR⁵⁵, —NHC(=NR⁵⁴)NR⁵⁵R⁵⁶, —$C_{1-6}$-alkylene-NHC(=NR⁵⁴)NR⁵⁴R⁵⁵, —$C_{1-6}$alkylene-N=C(N(R⁵⁴R⁵⁵))₂, —N=C(N(R⁵⁴R⁵⁵))₂, —C(O)R⁵⁴ and —C(O)OR⁵⁴; or
$C_{1-6}$alkyl, $C_{2-6}$-alkenyl and $C_{2-6}$-alkynyl, each of which may optionally be substituted with one or more substituents independently selected from halogen, R⁵⁴, —CN, —CF₃, —OCF₃, —OR⁵⁴, —C(O)OR⁵⁴, —NR⁵⁴R⁵⁵ and $C_{1-6}$-alkyl; or
$C_{3-10}$-cycloalkyl, $C_{4-8}$-cycloalkenyl, heterocyclyl, $C_{3-10}$-cycloalkyl-$C_{1-6}$-alkylene-, $C_{3-10}$-cycloalkyl-$C_{1-6}$-alkoxy-, $C_{3-10}$-cycloalkyloxy, $C_{3-10}$-cycloalkyl-$C_{1-6}$alkylthio-, $C_{3-10}$-cycloalkylthio, $C_{3-10}$-cycloalkyl-$C_{2-6}$-alkenylene-, $C_{3-10}$-cycloalkyl-$C_{2-6}$-alkynylene-, $C_{4-8}$-cycloalkenyl-$C_{1-6}$-alkylene-, $C_{4-4}$-cycloalkenyl-$C_{2-6}$-alkenylene-, $C_{4-8}$-cycloalkenyl-$C_{2-6}$-alkynylene-, heterocyclyl-$C_{1-6}$-alkylene-, heterocyclyl-$C_{2-6}$-alkenylene-, heterocyclyl-$C_{2-6}$- alkynylene- of which the heterocyclyl moieties optionally may be substituted with one or more substituents independently selected from $R^{70}$; or aryl, aryloxy, aryloxycarbonyl, aroyl, aryl-$C_{1-6}$-alkoxy-, aryl-$C_{1-6}$-alkylene-, aryl-$C_{2-6}$-alkenylene-, aryl-$C_{2-6}$-alkynylene-, heteroaryl, heteroaryl-$C_{1-6}$-alkylene-, heteroaryl-S—$C_{1-6}$-alkylene-, heteroaryl-$C_{2-6}$-alkenylene- and heteroaryl-$C_{2-6}$-alkynylene-, of which the aryl and heteroaryl moieties optionally may be substituted with one or more substituents selected from halogen, —C(O)OR$^{54}$, —CN, —CF$_3$, —OCF$_3$, —NO$_2$, —OR$^{54}$, —NR$^{54}$R$^{55}$ or $C_{1-6}$-alkyl, wherein $R^{54}$, $R^{55}$ and $R^{56}$ independently of each other are hydrogen, $C_{1-6}$alkyl, —Si($C_{1-6}$-alkyl)$_3$, $C_{1-6}$alkyl-arylene-, $C_{1-6}$alkyl-heteroarylene-, aryl-$C_{1-6}$-alkylene-, heteroaryl-$C_{1-6}$-alkylene-, heterocyclyl, heterocyclyl-$C_{1-6}$ alkylene-, heteroaryl, or aryl, each of which is optionally substituted with one or more substituents independently selected from $R^{71}$;

or $R^{54}$ and $R^{55}$ independently of each other are hydrogen or —(CHR$^{72}$)$_u$—(CHR$^{73}$)$_v$—W$^6$, wherein u is 0, 1 or 2;

v is 0, 1 or 2;

$R^{72}$ and $R^{73}$ independently of each other are hydrogen, $C_{1-6}$alkyl, $C_{1-6}$-alkyl-arylene- aryl, hydroxy, hydroxyalkyl, —C(O)O—R$^{75}$, amino, or aminoalkyl;

W$^6$ is hydrogen, —O—R$^{75}$, —C(O)O—R$^{75}$, —C(O)—R$^{75}$, —CONR$^{75}$R$^{76}$, —NR$^{75}$R$^{76}$, —NHCH$_2$C(O)R$^{75}$, —NHC(O)R$^{75}$, —NHC(O)OR$^{75}$, —S(O)$_2$R$^{75}$, —NHS(O)$_2$R$^{75}$, alkylamino, or dialkylamino, or W$^6$ is a five or six membered ring wherein at least one ring atom is nitrogen and the remaining ring atoms are either carbon or oxygen or optionally substituted with $C_{1-6}$alkyl, —C(O)O—R$^{75}$, —(CH$_2$)$_{1-3}$C(O)O—R$^{75}$, =O;

or

W$^6$ is phathalimido or heterocyclyl.

or $R^{54}$ and $R^{55}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds, and optionally substituted with one or more $C_{1-6}$-alkyl groups;

$R^{70}$ is =O, —C(O)CH$_3$, —S(O)$_2$CH$_3$, —CF$_3$, —C(O)O—R$^{75}$, —(CH$_2$)$_{1-3}$C(O)O—R$^{75}$ or $C_{1-6}$-alkyl;

$R^{71}$ is =O, $C_{1-6}$alkyl, cycloalkyl, —C(O)O—R$^{75}$, —(CH$_2$)$_{1-3}$C(O)O—R$^{75}$, —(CH$_2$)$_{1-3}$NR$^{75}$R$^{76}$, —OH or amino;

$R^{75}$ and $R^{76}$ independently of each other is hydrogen, halogen, —OH, —CF$_3$, or $C_{1-6}$-alkyl optionally substituted with —NH$_2$;

or a pharmaceutically acceptable salt, solvate, or prodrug thereof.

Embodiment A2. A compound according to embodiment A1, wherein $A^1$ is arylene or heteroarylene, optionally substituted with one or more substitutents $R^{23}$, $R^{24}$, $R^{25}$, $R^{26}$, and $R^{27}$, wherein $R^{23}$, $R^{24}$, $R^{25}$, $R^{26}$, and $R^{27}$ independently of each other are selected from the group consisting of halogen, —C(O)OR$^2$, —CN, —CF$_3$, —OCF$_3$, —NO$_2$, —OR$^2$, —NR$^2$R$^3$, $C_{1-6}$alkyl-Z-, $C_{2-6}$-alkenyl-Z-, $C_{2-6}$-alkynyl-Z-, cycloalkyl-Z-, heterocyclyl-Z-, aryl-Z-, heteroaryl-Z-, aryl-$C_{1-6}$-alkylene-Z-, heteroaryl-$C_{1-6}$-alkylene-Z-, heterocyclyl-$C_{1-6}$-alkylene-Z-, cycloalkyl-$C_{1-6}$-alkylene-Z-, N(R$^4$R$^5$)—$C_{1-6}$-alkylene-Z-, R$^6$—W$^1$-Z-, R$^6$—W$^1$—N(R$^4$)-Z-, R$^6$—N(R$^4$)-Z, and R$^6$—W$^1$—$C_{1-6}$-alkylene-Z-, wherein $R^2$, $R^3$, $R^4$, $R^5$, $R^6$, Z, and W$^1$ are as defined in embodiment A1.

Embodiment A3. A compound according to embodiment A2, wherein $A^1$ is $C_{6-10}$-arylene or $C_{4-10}$-heteroarylene, optionally substitutted with one or more substitutents $R^{23}$, $R^{24}$, $R^{25}$, $R^{26}$, and $R^{27}$ wherein $R^{23}$, $R^{24}$, $R^{25}$, $R^{26}$, and $R^{27}$ independently of each other are selected from the group consisting of halogen, —C(O)OR$^2$, —CN, —CF$_3$, —OCF$_3$, —NO$_2$, —OR$^2$, —NR$^2$R$^3$, $C_{1-6}$-alkyl-Z-, $C_{2-6}$-alkenyl-Z-, $C_{2-6}$-alkynyl-Z-, cycloalkyl-Z-, heterocyclyl-Z-, aryl-Z-, heteroaryl-Z-, aryl-$C_{1-6}$-alkylene-Z-, heteroaryl-$C_{1-6}$-alkylene-Z-, heterocyclyl-$C_{1-6}$-alkylene-Z-, cycloalkyl-$C_{1-6}$-alkylene-Z-, N(R$^4$R$^5$)—$C_{1-6}$-alkylene-Z-, R$^6$—W$^1$-Z-, R$^6$—W$^1$—N(R$^4$)-Z-, R$^6$—N(R$^4$)-Z, and R$^6$—W$^1$—$C_{1-6}$ alkylene-Z-, wherein $R^2$, $R^3$, $R^4$, $R^5$, $R^6$, Z, and W$^1$ are as defined in embodiment A1.

Embodiment A4. A compound according to embodiment A3 wherein $A^1$ is phenylene optionally substituted with one or more substitutents $R^{23}$, $R^{24}$, $R^{25}$, $R^{26}$, and $R^{27}$, wherein $R^{23}$, $R^{24}$, $R^{25}$, $R^{26}$, and $R^{27}$ independently of each other are selected from the group consisting of halogen, —C(O)OR$^2$, —CN, —CF$_3$, —OCF$_3$, —NO$_2$, —OR$^2$, —NR$^2$R$^3$, $C_{1-6}$-alkyl-Z-, $C_{2-6}$-alkenyl-Z-, $C_{2-6}$-alkynyl-Z-, cycloalkyl-Z-, heterocyclyl-Z-, aryl-Z-, heteroaryl-Z-, aryl-$C_{1-6}$-alkylene-Z-, heteroaryl-$C_{1-6}$-alkylene-Z-, heterocyclyl-$C_{1-6}$-alkylene-Z-, cycloalkyl-$C_{1-6}$-alkylene-Z-, N(R$^4$R$^5$)—$C_{1-6}$-alkylene-Z-, R$^6$—W$^1$-Z-, R$^6$—W$^1$—N(R$^4$)-Z-, R$^6$—N(R$^4$)-Z, and R$^6$—W$^1$—$C_{1-6}$ -alkylene-Z-, wherein $R^2$, $R^3$, $R^4$, $R^5$, $R^6$, Z, and W$^1$ are as defined in embodiment A1.

Embodiment A5. A compound according to embodiment A4 of the formula (Ia)

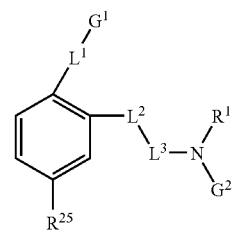

Formula (Ia)

wherein $L^1$, $G^1$, $L^2$, $L^3$, $R^1$, $G^2$ and $R^{25}$ are as defined in embodiment A1.

Embodiment A6. A compound according to embodiment A4 of the formula (Ib)

Formula (Ib)

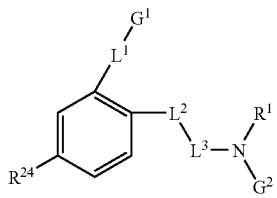

wherein $L^1$, $G^1$, $L^2$, $L^3$, $R^1$, $G^2$ and $R^{24}$ are as defined in embodiment A1.

Embodiment A7. A compound according to any one of the embodiments A1 to A6, wherein
$R^{23}$, $R^{24}$, $R^{25}$, $R^{26}$, and $R^{27}$ independently of each other are selected from the group consisting of
halogen, —C(O)OR$^2$, —CN, —CF$_3$, —OCF$_3$, —NO$_2$, —OR$^2$, —NR$^2$R$^3$, C$_{1-6}$alkyl-Z-, cycloalkyl-Z-, heterocyclyl-Z-, aryl-Z-, or heteroaryl-Z-, N(R$^4$R$^5$)—C$_{1-6}$-alkylene-Z-, R$^6$—W$^1$-Z-, R$^6$—W$^1$—N(R$^4$)-Z-, R$^6$—N(R$^4$)-Z, and R$^6$—W$^1$—C$_{1-6}$-alkylene-Z-, wherein
$R^2$, $R^3$, $R^4$, $R^5$, $R^6$, Z, and W$^1$ are as defined in embodiment A1.

Embodiment A8. A compound according to embodiment A7 wherein
$R^{23}$, $R^{24}$, $R^{25}$, $R^{26}$, and $R^{27}$ independently of each other are selected from the group consisting of
halogen, —CN, —CF$_3$, —OR$^2$, —NR$^2$R$^3$, C$_{1-6}$alkyl-Z-, cycloalkyl-Z-, heterocyclyl-Z-, aryl-Z-, or heteroaryl-Z-, R$^6$—W$^1$-Z-, R$^6$—W$^1$—N(R$^4$)-Z-, R$^6$—N(R$^4$)-Z, and R$^6$—W$^1$—C$_{1-6}$-alkylene-Z-, wherein
$R^2$, $R^3$, $R^4$, $R^5$, $R^6$, Z, and W$^1$ are as defined in embodiment A1.

Embodiment A9. a compound according to embodiment A8 wherein
$R^{23}$, $R^{24}$, $R^{25}$, $R^{26}$, and $R^{27}$ independently of each other are selected from the group consisting of
halogen, —OR$^2$, —NR$^2$R$^3$, C$_{1-6}$-alkyl-Z-, R$^6$—W$^1$-Z-, and R$^6$—W$^1$—C$_{1-6}$-alkylene-Z-, wherein
$R^2$, $R^3$, $R^4$, $R^5$, $R^6$, Z, and W$^1$ are as defined in embodiment A1.

Embodiment A10. A compound according to embodiment A9 wherein
$R^{23}$, $R^{24}$, $R^{25}$, $R^{26}$, and $R^{27}$ independently of each other are selected from the group consisting of
F, Cl, Br, and methyl.

Embodiment A11. A compound according to any one of the embodiments A1 to A10, wherein
$R^4$, $R^5$, and $R^6$ independently of each other are selected from the group consisting of hydrogen, aryl, C$_{1-6}$alkyl, heteroaryl-C$_{1-6}$-alkylene-, and aryl-C$_{1-6}$-alkylene-.

Embodiment A12. A compound according to embodiment A11, wherein
$R^4$, $R^5$, and $R^6$ independently of each other are hydrogen or C$_{1-6}$-alkyl.

Embodiment A13. A compound according to embodiment A12, wherein
$R^4$, $R^5$, and $R^6$ are hydrogen.

Embodiment A14. A compound according to any one of the embodiments A1 to A9, wherein $R^4$ and $R^5$ is taken together to form a ring having the formula —(CH$_2$)$_j$-Q-(CH$_2$)$_k$-bonded to the nitrogen atom to which $R^4$ and $R^5$ are attached, wherein
j and k independently of each other is 1, 2, 3, or 4;
Q is a direct bond, —CH$_2$—, —O—, —S—, —S(O$_2$)—, —C(O)—, —C(O)NH—, —NHC(O)—, —NHC(O)NH—, —NHSO$_2$—, —SO$_2$NH—, —C(O)—O—, —O—C(O)—, —NHSO$_2$NH—,

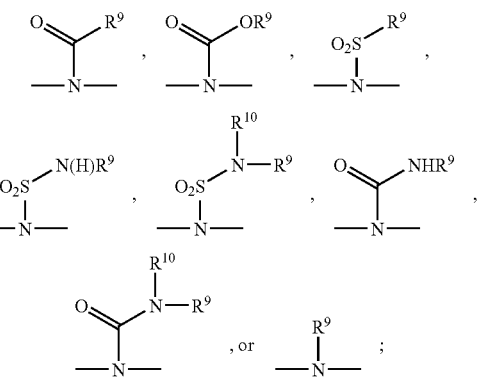

wherein
$R^9$ and $R^{10}$ independently of each other are selected from the group consisting of hydrogen, aryl, C$_{1-6}$-alkyl, and aryl-C$_{1-6}$alkyl-.

Embodiment A15. A compound according to embodiment A14, wherein
Q is a direct bond, —CH$_2$—, —O—, —S—, —S(O$_2$)—, —C(O)—, —C(O)NH—, —NHC(O)—, —NHC(O)NH—, —NHSO$_2$—, —SO$_2$NH—, —C(O)—O—, —O—C(O)—, —NHSO$_2$NH—,

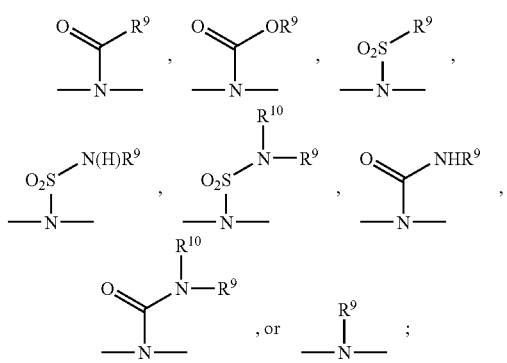

wherein
$R^9$ and $R^{10}$ independently of each other are hydrogen or C$_{1-6}$-alkyl.

Embodiment A16. A compound according to embodiment A15, wherein
Q is a direct bond, —CH$_2$—, —O—, —S—, —S(O$_2$)—, —C(O)—, —C(O)NH—, —NHC(O)—, —NHC(O)NH—, —NHSO$_2$—, —SO$_2$NH—, —C(O)—O—, —O—C(O)—, —NHSO$_2$NH—,

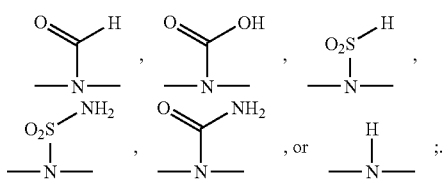

Embodiment A17. A compound according to embodiment A16, wherein Q is a direct bond.

Embodiment A18. A compound according to any one of the embodiments A1 to A17, wherein
$W^1$ is a direct bond, —O—, —C(O)—, —NH—, —S—, —SO$_2$—, —C(O)NH—, —NHC(O)—, —N(H)CON(H)—, —N(H)SO$_2$—, —SO$_2$N(H)—, —C(O)—O—, —N(H)SO$_2$N(H)—, or —O—C(O)—.

Embodiment A19. A compound according to embodiment A18, wherein
$W^1$ is a direct bond, —O—, —C(O)—, —SO$_2$—, —C(O)NH—, —NHC(O)—, —N(H)SO$_2$—, —C(O)—O—, or —O—C(O)—.

Embodiment A20. A compound according to embodiment A19, wherein $W^1$ is a direct bond or —C(O)—O—.

Embodiment A21. A compound according to embodiment A20, wherein $W^1$ is a direct bond.

Embodiment A22. A compound according to embodiment A7, wherein
at least one of $R^{23}$, $R^{24}$, $R^{25}$, $R^{26}$, and $R^{27}$ is halogen, —C(O)OR$^2$, —CN, —CF$_3$, —OCF$_3$, —NO$_2$, —OR$^2$, —NR$^2$R$^3$, C$_{1-6}$alkyl-Z-, cycloalkyl-Z-, heterocyclyl-Z-, aryl-Z-, or heteroaryl-Z-, wherein
$R^2$, $R^3$, and Z are as defined in embodiment A1.

Embodiment A23. A compound according to embodiment A22, wherein
at least one of $R^{23}$, $R^{24}$, $R^{25}$, $R^{26}$, and $R^{27}$ is halogen, —C(O)OR$^2$, —CN, —CF$_3$, —OCF$_3$, —NO$_2$, —OR$^2$, —NR$^2$R$^3$, C$_{1-6}$-alkyl-Z-, C$_{3-10}$-cycloalkyl-Z-, C$_{3-10}$-heterocyclyl-Z-, C$_{3-10}$-aryl-Z-, or C$_{3-10}$-heteroaryl-Z-, wherein
$R^2$, $R^3$, and Z are as defined in embodiment A1.

Embodiment A24. A compound according to embodiment A23, wherein
at least one of $R^{23}$, $R^{24}$, $R^{25}$, $R^{26}$, and $R^{27}$ is halogen, —C(O)OR$^2$, —CN, —NO$_2$, —OR$^2$, —NR$^2$R$^3$, C$_{1-6}$-alkyl-Z-, C$_{3-10}$-cycloalkyl-Z-, C$_{3-10}$-heterocyclyl-Z-, C$_{3-10}$-aryl-Z-, or C$_{3-10}$-heteroaryl-Z-, wherein
$R^2$, $R^3$, and Z are as defined in embodiment A1.

Embodiment A25. A compound according to embodiment A24, wherein
at least one of $R^{23}$, $R^{24}$, $R^{25}$, $R^{26}$, and $R^{27}$ is F, Cl, Br, or methyl.

Embodiment A26. A compound according to embodiment A24, wherein
at least one of $R^{23}$, $R^{24}$, $R^{25}$, $R^{26}$, and $R^{27}$ is halogen, —C(O)OR$^2$, —CN, —NO$_2$, —OR$^2$, or —NR$^2$R$^3$, wherein
$R^2$, $R^3$, and Z are as defined in embodiment A1.

Embodiment A27. A compound according to any one of the embodiments A1 to A26, wherein
$R^2$ and $R^3$ independently of each other are hydrogen, C$_{1-6}$-alkyl, aryl-C$_{1-6}$-alkylene-, heteroaryl-C$_{1-6}$-alkylene-, C$_{1-6}$-alkyl-arylene-, C$_{1-6}$-alkyl-heteroarylene-, heteroaryl, or aryl.

Embodiment A28. A compound according to embodiment A27, wherein
$R^2$ and $R^3$ independently of each other, are hydrogen, C$_{1-6}$alkyl, aryl-C$_{1-6}$alkylene- or aryl.

Embodiment A29. A compound according to embodiment A28, wherein
$R^2$ is hydrogen or C$_{1-6}$-alkyl.

Embodiment A30. A compound according to embodiment A29, wherein
$R^2$ is hydrogen.

Embodiment A31. A compound according to any one of the embodiments A1 to A30, wherein
$R^3$ is hydrogen or C$_{1-6}$-alkyl.

Embodiment A32. A compound according to embodiment A31, wherein
$R^3$ is hydrogen.

Embodiment A33. A compound according to any one of the embodiments A1 to A22, wherein
$R^2$ and $R^3$, when attached to the same nitrogen atom, together with said nitrogen atom may form a 3 to 8 membered heterocyclic ring optionally containing one or two further heteroatoms selected from nitrogen, oxygen and sulfur, and optionally containing one or two double bonds.

Embodiment A34. A compound according to any one of the embodiments A1 to A33, wherein
Z is a direct bond, —O—, —NH—, —NHCH$_2$—, —S—, —SO$_2$—, —C(O)NH—, —NHC(O)—, —N(H)CON(H)—, —N(CH$_3$)CONH—, —N(H)SO$_2$—, —SO$_2$N(H)—, —C(O)—O—, —N(H)SO$_2$N(H)—, or —O—C(O)—.

Embodiment A35. A compound according to embodiment A34, wherein
Z is a direct bond, —O—, —S—, —SO$_2$—, —C(O)NH—, —NHC(O)—, —N(H)SO$_2$—, —C(O)—O—, —N(H)SO$_2$N(H)—, or —O—C(O)—.

Embodiment A36. A compound according to embodiment A35, wherein
Z is a direct bond, —NHC(O)—, or —NHS(O)$_2$—.

Embodiment A37. A compound according to embodiment A2, wherein
$A^1$ is

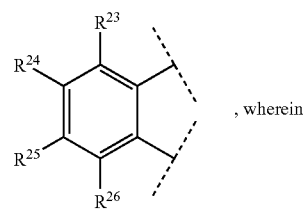
, wherein $R^{23}$, $R^{24}$, $R^{25}$, and $R^{26}$, independently of each other, are hydrogen or as defined in embodiment A1.

Embodiment A38. A compound according to embodiment A37, wherein $R^{23}$, $R^{24}$, $R^{25}$, and $R^{26}$ independently of each other are selected from the group consisting of halogen, —C(O)O$R^2$, —CN, —CF$_3$, —OCF$_3$, —NO$_2$, —O$R^2$, —N$R^2R^3$, C$_{1-6}$-alkyl-Z-, cycloalkyl-Z-, heterocyclyl-Z-, aryl-Z-, or heteroaryl-Z-, N($R^4R^5$)—C$_{1-6}$-alkylene-Z-, $R^6$—W$^1$-Z-, $R^6$—W$^1$—N($R^4$)-Z-, $R^6$—N($R^4$)-Z-, and $R^6$—W$^1$—C$_{1-6}$-alkylene-Z-, wherein $R^2$, $R^3$, $R^4$, $R^5$, $R^6$, Z, and W$^1$ are as defined in embodiment A1.

Embodiment A39. A compound according to embodiment A37 or A38, wherein
$R^4$, $R^5$, and $R^6$ independently of each other are selected from the group consisting of hydrogen, aryl, C$_{1-6}$alkyl, heteroaryl-C$_{1-6}$-alkylene-, and aryl-C$_{1-6}$-alkylene-.

Embodiment A40. A compound according to embodiment A39, wherein
$R^4$, $R^5$, and $R^6$ independently of each other are hydrogen or C$_{1-6}$alkyl.

Embodiment A41. A compound according to embodiment A40, wherein
$R^4$, $R^5$, and $R^6$ are hydrogen.

Embodiment A42. A compound according to embodiment A37 or A38, wherein
$R^4$ and $R^5$ is taken together to form a ring having the formula —(CH$_2$)$_j$-Q-(CH$_2$)$_k$-bonded to the nitrogen atom to which $R^4$ and $R^5$ are attached, wherein
j and k independently of each other is 1, 2, 3, or 4;
Q is a direct bond, —CH$_2$—, —O—, —S—, —S(O$_2$), —C(O)—, —C(O)NH—, —NHC(O)—, —NHC(O)NH—, —NHSO$_2$—, —SO$_2$NH—, —C(O)—O—, —O—C(O)—, —NHSO$_2$NH—,

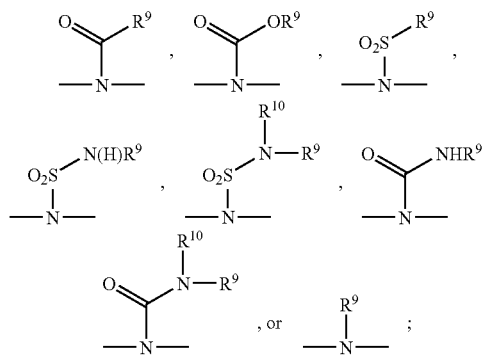

wherein
$R^9$ and $R^{10}$ independently of each other are selected from the group consisting of hydrogen, aryl, C$_{1-6}$-alkyl, and arylalkyl-.

Embodiment A43. A compound according to embodiment A42, wherein
Q is a direct bond, —CH$_2$—, —O—, —S—, —S(O$_2$)—, —C(O)—, —C(O)NH—, —NHC(O)—, —NHC(O)NH—, —NHSO$_2$—, —SO$_2$NH—, —C(O)—O—, —O—C(O)—, —NHSO$_2$NH—,

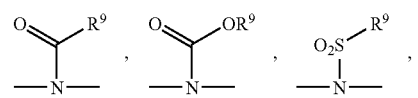

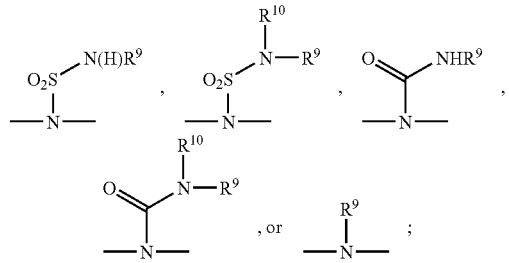

wherein
$R^9$ and $R^{10}$ independently of each other are hydrogen or alkyl.

Embodiment A44. A compound according to embodiment A43, wherein
Q is a direct bond, —CH$_2$—, —O—, —S—, —S(O$_2$)—, —C(O)—, —C(O)NH—, —NHC(O)—, —NHC(O)NH—, —NHSO$_2$—, —SO$_2$NH—, —C(O)—O—, —O—C(O)—, —NHSO$_2$NH—,

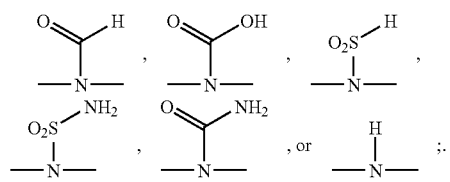

Embodiment A45. A compound according to embodiment A44, wherein
Q is a direct bond.

Embodiment A46. A compound according to any one of the embodiments A37 to A45, wherein
W$^1$ is a direct bond, —O—, —C(O)—, —NH—, —S—, —SO$_2$—, —C(O)NH—, —NHC(O)—, —N(H)CON(H)—, —N(H)SO$_2$—, —SO$_2$N(H)—, —C(O)—O—, —N(H)SO$_2$N(H)—, or —O—C(O)—.

Embodiment A47. A compound according to embodiment A46 wherein
W$^1$ is a direct bond, —O—, —C(O)—, —SO$_2$—, —C(O)NH—, —NHC(O)—, —N(H)SO$_2$—, —C(O)—O—, or —O—C(O)—.

Embodiment A48. A compound according to embodiment A47, wherein
W$^1$ is a direct bond, or —C(O)—O—.

Embodiment A49. A compound according to embodiment A48, wherein
W$^1$ is a direct bond.

Embodiment A50. A compound according to embodiment A37, wherein
at least one of $R^{23}$, $R^{24}$, $R^{25}$, and $R^{26}$ is halogen, —C(O)O$R^2$, —CN, —CF$_3$, —OCF$_3$—NO$_2$—O$R^2$, —N$R^2R^3$, C$_{1-6}$-alkyl-Z-, cycloalkyl-Z-, heterocyclyl-Z-, aryl-Z-, or heteroaryl-Z-, wherein
$R^2$, $R^3$, and Z are as defined in embodiment A37.

Embodiment A51. A compound according to embodiment A50, wherein at least one of $R^{23}$, $R^{24}$, $R^{25}$, and $R^{26}$ is halogen, —C(O)OR$^2$, —CN, —CF$_3$, —OCF$_3$, —NO$_2$, —OR$^2$, —NR$^2$R$^3$, C$_{1\text{-}6}$-alkyl-Z-, C$_{3\text{-}10}$-cycloalkyl-Z-, C$_{3\text{-}10}$-heterocyclyl-Z-, C$_{3\text{-}10}$-aryl-Z-, or C$_{3\text{-}10}$-heteroaryl-Z-, wherein
R$^2$, R$^3$, and Z are as defined in embodiment A37.

Embodiment A52. A compound according to embodiment A51, wherein
at least one of R$^{23}$, R$^{24}$, R$^{25}$ and R$^{26}$ is halogen, —C(O)OR$^2$, —CN, —NO$_2$, —OR$^2$, —NR$^2$R$^3$, C$_{1\text{-}6}$-alkyl-Z-, C$_{3\text{-}10}$-cycloalkyl-Z-, C$_{3\text{-}10}$-heterocyclyl-Z-, C$_{3\text{-}10}$-aryl-Z-, or C$_{3\text{-}10}$-heteroaryl-Z-, wherein
R$^2$, R$^3$, and Z are as defined in embodiment A37.

Embodiment A53. A compound according to any one of the embodiments A37 to A52, wherein
Z is a direct bond, —O—, —NH—, —NHCH$_2$—, —S—, —SO$_2$—, —C(O)NH—, —NHC(O)—, —N(H)CON(H)—, —N(CH$_3$)CON(H)—, —N(H)SO$_2$—, —SO$_2$N(H)—, —C(O)—O—, —N(H)SO$_2$N(H)—, or —O—C(O)—.

Embodiment A54. A compound according to embodiment A53, wherein
Z is a direct bond, —O—, —S—, —SO$_2$—, —C(O)NH—, —NHC(O)—, —N(H)SO$_2$—, —C(O)—O—, —N(H)SO$_2$N(H)—, or —O—C(O)—.

Embodiment A55. A compound according to embodiment A54, wherein
Z is a direct bond, —NHC(O)—, or —NHS(O)$_2$.

Embodiment A56. A compound according to embodiment A52, wherein
at least one of R$^{23}$, R$^{24}$, R$^{25}$, and R$^{26}$ is halogen, —C(O)OR$^2$, —CN, —NO$_2$, —OR$^2$, —NR$^2$R$^3$, or C$_{1\text{-}6}$alkyl, wherein
R$^2$, and R$^3$ are as defined in embodiment A37.

Embodiment A57. A compound according to any one of the embodiments A37 to A56, wherein
R$^2$ and R$^3$ independently of each other are hydrogen, C$_{1\text{-}6}$-alkyl, aryl-C$_{1\text{-}6}$-alkylene-, heteroaryl-C$_{1\text{-}6}$-alkylene-, C$_{1\text{-}6}$-alkyl-arylene-, C$_{1\text{-}6}$-alkyl-heteroarylene-, heteroaryl, or aryl.

Embodiment A58. A compound according to embodiment A57, wherein
R$^2$ and R$^3$ independently of each other, are hydrogen, C$_{1\text{-}6}$-alkyl, aryl-C$_{1\text{-}6}$alkylene- or aryl.

Embodiment A59. A compound according to embodiment A58, wherein
R$^2$ is hydrogen or C$_{1\text{-}6}$-alkyl.

Embodiment A60. A compound according to embodiment A59, wherein
R$^2$ is hydrogen.

Embodiment A61. A compound according to any one of the embodiments A37 to A60, wherein
R$^3$ is hydrogen or C$_{1\text{-}6}$-alkyl.

Embodiment A62. A compound according to embodiment A61, wherein
R$^3$ is hydrogen.

Embodiment A63. A compound according to any one of the embodiments A37 to A50, wherein
R$^2$ and R$^3$, when attached to the same nitrogen atom, together with said nitrogen atom may form a 3 to 8 membered heterocyclic ring optionally containing one or two further heteroatoms selected from nitrogen, oxygen and sulfur, and optionally containing one or two double bonds.

Embodiment A64. A compound according to any one of the embodiments A37 to A55, wherein
at least one of R$^{23}$, R$^{24}$, R$^{25}$, and R$^{26}$ are hydrogen.

Embodiment A65. A compound according to embodiment A64, wherein
at least two of R$^{23}$, R$^{24}$, R$^{25}$, and R$^{26}$ are hydrogen.

Embodiment A66. A compound according to embodiment A65, wherein
R$^{23}$ and R$^{26}$ are hydrogen.

Embodiment A67. A compound according to embodiment A65 or embodiment A66, wherein
at least three of R$^{23}$, R$^{24}$, R$^{25}$, and R$^{26}$ are hydrogen.

Embodiment A68. A compound according to any one of the embodiments A37 to A67, wherein R$^{24}$ or R$^{25}$ is halogen.

69. A compound according to embodiment A68, wherein R$^{24}$ or R$^{25}$ is fluoro.

Embodiment A70. A compound according to any one of the embodiments A37 to A67, wherein R$^{24}$ or R$^{25}$ is C$_{1\text{-}6}$-alkyl.

Embodiment A71. A compound according to embodiment A68, wherein R$^{24}$ or R$^{25}$ is methyl.

Embodiment A72. A compound according to any one of the embodiments A37 to A67, wherein
R$^{24}$ is hydrogen.

Embodiment A73. A compound according to any one of the embodiments A37 to A72, wherein
R$^{25}$ is hydrogen.

Embodiment A74. A compound according to embodiment A37, wherein
R$^{23}$, R$^{24}$, R$^{25}$, and R$^{26}$ are hydrogen.

Embodiment A75. A compound according to any one of the embodiments A1 to A74, wherein
L$^1$ is a bond, -D-alkylene-E-, —O—, —S—, —S(O)—, —S(O)$_2$—, —C(O)—, —N(R$^{11}$)—, or —C(=N—OR$^{12}$), wherein
D, E, R$^{11}$ and R$^{12}$ are as defined in embodiment A1.

Embodiment A76. A compound according to embodiment A75, wherein
L$^1$ is a bond, -D-alkylene-E-, —O—, —C(O)—, —N(R$^{11}$)—, or —C(=N—OR$^{12}$)—, wherein
D, E, R$^{11}$ and R$^{12}$ are as defined in embodiment A1.

Embodiment A77. A compound according to embodiment A75, wherein
L$^1$ is —O—.

Embodiment A78. A compound according to embodiment A75, wherein
L$^1$ is —S—.

Embodiment A79. A compound according to embodiment A75, wherein
L$^1$ is a bond.

80. A compound according to embodiment A75, wherein
L$^1$ is —C(O)—.

Embodiment A81. A compound according to any one of the embodiments A1 to A76, wherein D is a direct bond or —O—;
E is a direct bond or —O—; and
$R^{11}$ and $R^{12}$ are as defined in embodiment A1.

Embodiment A82. A compound according to embodiment A81, wherein
D is a direct bond.

Embodiment A83. A compound according to embodiment A81, wherein
D is —O—.

Embodiment A84. A compound according to any one of the embodiments A81 to A83, wherein
E is a direct bond.

Embodiment A85. A compound according to any one of the embodiments A81 to A83, wherein
E is —O—.

Embodiment A86. A compound according to any one of the embodiments A1 to A85, wherein
$R^{11}$ is selected from hydrogen, $C_{1-6}$alkyl, aryl, carbamoyl, aryl-$C_{1-6}$-alkylene-, $C_{1-6}$alkyl-NH—C(O)—, aryl-$C_{1-6}$-alkylene-NH—C(O)—, $C_{1-6}$-alkyl-SO$_2$—, aryl-$C_{1-6}$-alkylene-SO$_2$—, aryl-SO$_2$—, SO$_2$—, $C_{1-6}$alkyl-C(O)—, aryl-$C_{1-6}$-alkylene-C(O)—, N(R$^{13}$)(R$^{14}$)—$C_{1-6}$-alkylene-Y—, and $R^{15}$—$W^2$—$C_1$]-alkylene-Y—, wherein
Y and $W^2$ independently of each other are a direct bond, —CH$_2$—, —SO$_2$—, —N(H)CO—, —N(H)SO$_2$—, or —O—C(O)—;
$R^{13}$ and $R^{14}$ independently of each other are selected from hydrogen, aryl, $C_{1-6}$alkyl, or aryl-$C_{1-6}$-alkylene-; or
$R^{13}$ and $R^{14}$ may be taken together to form a ring having the formula —(CH$_2$)$_o$—X—(CH$_2$)$_p$— bonded to the nitrogen atom to which $R^{13}$ and $R^{14}$ are attached, wherein
o and p are independently of each other are 1, 2, 3, or 4; and
X is a direct bond, —CH$_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

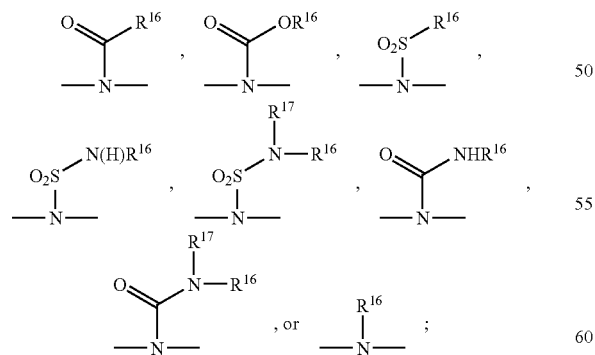

wherein
$R^{16}$ and $R^{17}$ are selected from hydrogen, aryl, heteroaryl, $C_{1-6}$-alkyl, $C_{1-6}$-alkoxy, aryl-$C_{1-6}$-alkylene-, heteroaryl-$C_{1-6}$-alkylene-, $C_{1-6}$-alkyl-arylene-, $C_{1-6}$-alkyl-heteroarylene-, $C_{1-6}$-alkoxy-arylene-, $C_{1-6}$-alkoxy-heteroarylene-, heteroarylaryl-$C_{1-6}$-alkoxy-, or aryl-$C_{1-6}$ alkoxy-; and
$R^{15}$ is selected from the group consisting of aryl, heteroaryl, cycloalkyl, heterocyclyl, $C_{1-6}$-alkyl, or aryl-$C_{1-6}$-alkylene-.

Embodiment A87. A compound according to embodiment A86, wherein
$R^{11}$ is selected from hydrogen, $C_{1-6}$alkyl, aryl, carbamoyl, aryl-$C_{1-6}$-alkylene-, $C_{1-6}$alkyl-NH—C(O)—, aryl-$C_{1-6}$-alkylene-NH—C(O)—, $C_{1-6}$-alkyl-SO$_2$—, aryl-$C_{1-6}$-alkylene-SO$_2$—, aryl-SO$_2$—, SO$_2$—, $C_{1-6}$alkyl-C(O)—, aryl-$C_{1-6}$-alkylene-C(O)—, N(R$^{13}$)(R$^{14}$)—$C_{1-6}$-alkylene-Y—, and $R^{15}$—$W^2$—$C_{1-6}$-alkylene-Y—, wherein
Y and $W^2$ independently of each other are a direct bond, —CH$_2$—, —SO$_2$—, —N(H)CO—, —N(H)SO$_2$—, or —O—C(O)—;
$R^{13}$ and $R^{14}$ independently of each other are selected from hydrogen, aryl, $C_{1-6}$alkyl, or aryl-$C_{1-6}$-alkylene-;
or
$R^{13}$ and $R^{14}$ may be taken together to form a ring having the formula —(CH$_2$)$_o$—X—(CH$_2$)$_p$— bonded to the nitrogen atom to which $R^{13}$ and $R^{14}$ are attached, wherein
o and p are independently of each other are 1, 2, 3, or 4; and
X is a direct bond, —CH$_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

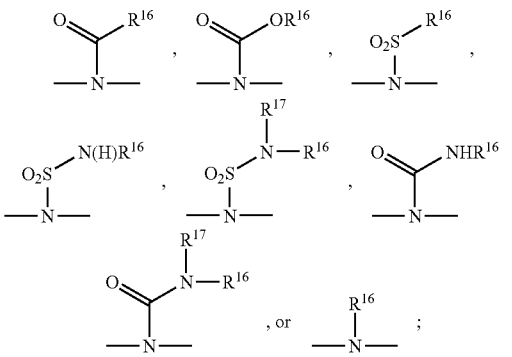

wherein
$R^{16}$ and $R^{17}$ are hydrogen; and
$R^{15}$ is selected from the group consisting of aryl, heteroaryl, cycloalkyl, heterocyclyl, $C_{1-6}$-alkyl, or aryl-$C_{1-6}$-alkylene-.

Embodiment A88. A compound according to embodiment A87, wherein
$R^{11}$ is selected from hydrogen, $C_{1-6}$alkyl, aryl, carbamoyl, aryl-$C_{1-6}$-alkylene-, $C_{1-6}$-alkyl-NH—C(O)—, aryl-$C_{1-6}$ alkylene-NH—C(O)—, $C_{1-6}$-alkyl-SO$_2$—, aryl-$C_{1-6}$-alkylene-SO$_2$—, aryl-SO$_2$—, SO$_2$—, $C_{1-6}$alkyl-C(O)—, aryl-$C_{1-6}$alkylene-C(O)—, N(R$^{13}$)(R$^{14}$)—$C_{1-6}$-alkylene-Y—, and $R^{15}$—$W^2$—$C_{1-6}$-alkylene-Y—, wherein Y and $W^2$ independently of each other are a direct bond, —$CH_2$—, —$SO_2$—, —N(H)CO—, —N(H)$SO_2$—, or —O—C(O)—;

$R^{13}$ and $R^{14}$ independently of each other are selected from hydrogen, aryl, $C_{1-6}$-alkyl, or aryl-$C_{1-6}$alkylene-;

or $R^{13}$ and $R^{14}$ may be taken together to form a ring having the formula —$(CH_2)_o$—X—$(CH_2)_p$— bonded to the nitrogen atom to which $R^{13}$ and $R^{14}$ are attached, wherein o and p are independently of each other are 1, 2, 3, or 4;

X is a direct bond; and $R^{15}$ is selected from the group consisting of aryl, heteroaryl, cycloalkyl, heterocyclyl, $C_{1-6}$-alkyl, or aryl-$C_{1-6}$-alkylene-.

Embodiment A89. A compound according to embodiment A88, wherein $R^{11}$ is selected from hydrogen, $C_{1-6}$alkyl, aryl, carbamoyl, aryl-$C_{1-6}$-alkylene-, $C_{1-6}$-alkyl-NH—C(O)—, aryl-$C_{1-6}$-alkylene-NH—C(O)—, $C_{1-6}$-alkyl-$SO_2$—, aryl-$C_{1-6}$-alkylene-$SO_2$—, aryl-$SO_2$—, $SO_2$—, $C_{1-6}$-alkyl-C(O)—, aryl-$C_{1-6}$-alkylene-C(O)—, N($R^{13}$)($R^{14}$)—$C_{1-6}$-alkylene-Y—, and $R^{15}$—$W^2$—$C_{1-6}$-alkylene-Y—, wherein Y and $W^2$ independently of each other are a direct bond, —$CH_2$—, —$SO_2$—, —N(H)CO—, —N(H)$SO_2$—, or —O—C(O)—;

$R^{13}$ and $R^{14}$ independently of each other are selected from hydrogen, aryl, $C_{1-6}$-alkyl, or aryl-$C_{1-6}$-alkylene-; and $R^{15}$ is selected from the group consisting of aryl, heteroaryl, cycloalkyl, heterocyclyl, $C_{1-6}$-alkyl, or aryl-$C_{1-6}$-alkylene-.

Embodiment A90. A compound according to embodiment A89, wherein $R^{11}$ is selected from hydrogen, $C_{1-6}$alkyl, aryl, carbamoyl, aryl-$C_{1-6}$-alkylene-, $C_{1-6}$-alkyl-NH—C(O)—, aryl-$C_{1-6}$-alkylene-NH—C(O)—, $C_{1-6}$-alkyl-$SO_2$—, aryl-$C_{1-6}$-alkylene-$SO_2$—, aryl-$SO_2$—, $SO_2$—, $C_{1-6}$-alkyl-C(O)—, aryl-$C_{1-6}$-alkylene-C(O)—, N($R^{13}$)($R^{14}$)—$C_{1-6}$-alkylene-Y—, and $R^{15}$—$W^2$—$C_{1-6}$-alkylene-Y—, wherein Y and $W^2$ independently of each other are a direct bond, —$CH_2$—, —$SO_2$—, —N(H)CO—, —N(H)$SO_2$—, or —O—C(O)—;

$R^{13}$ and $R^{14}$ are hydrogen; and $R^{15}$ is selected from the group consisting of aryl, heteroaryl, cycloalkyl, heterocyclyl, $C_{1-6}$-alkyl, or aryl-$C_{1-6}$-alkylene-.

Embodiment A91. A compound according to embodiment A90, wherein $R^{11}$ is selected from hydrogen, $C_{1-6}$alkyl, aryl, carbamoyl, aryl-$C_{1-6}$-alkylene-, $C_{1-6}$-alkyl-NH—C(O)—, aryl-$C_{1-6}$-alkylene-NH—C(O)—, $C_{1-6}$-alkyl-$SO_2$—, aryl-$C_{1-6}$-alkylene-$SO_2$—, aryl-$SO_2$—, $SO_2$—, $C_{1-6}$-alkyl-C(O)—, aryl-$C_{1-6}$-alkylene-C(O)—, N($R^{13}$)($R^{14}$)—$C_{1-6}$-alkylene-Y—, and $R^{15}$—$W^2$—$C_{1-6}$-alkylene-Y—, wherein Y is a direct bond;

$W^2$ is a direct bond, —$CH_2$—, —$SO_2$—, —N(H)CO—, —N(H)$SO_2$—, or —O—C(O)—;

$R^{13}$ and $R^{14}$ are hydrogen; and $R^{15}$ is selected from the group consisting of aryl, heteroaryl, cycloalkyl, heterocyclyl, $C_{1-6}$-alkyl, or aryl-$C_{1-6}$-alkylene-.

Embodiment A92. A compound according to embodiment A90, wherein $R^{11}$ is selected from hydrogen, $C_{1-6}$alkyl, aryl, carbamoyl, aryl-$C_{1-6}$-alkylene-, $C_{1-6}$-alkyl-NH—C(O)—, aryl-$C_{1-6}$-alkylene-NH—C(O)—, $C_{1-6}$-alkyl-$SO_2$—, aryl-$C_{1-6}$-alkylene-$SO_2$—, aryl-$SO_2$—, $SO_2$—, $C_{1-6}$alkyl-C(O)—, aryl-$C_{1-6}$-alkylene-C(O)—, N($R^{13}$)($R^{14}$)—$C_{1-6}$-alkylene-Y—, and $R^{15}$—$W^2$—$C_{1-6}$-alkylene-Y—, wherein Y is a direct bond, —$CH_2$—, —$SO_2$—, —N(H)CO—, —N(H)$SO_2$—, or —O—C(O)—;

$W^2$ is a direct bond;

$R^{13}$ and $R^{14}$ are hydrogen; and $R^{15}$ is selected from the group consisting of aryl, heteroaryl, cycloalkyl, heterocyclyl, $C_{1-6}$alkyl, or aryl-$C_{1-6}$-alkylene-.

Embodiment A93. A compound according to any one of the embodiments A90 to A92, wherein $R^{11}$ is selected from hydrogen, $C_{1-6}$-alkyl, aryl, carbamoyl, aryl-$C_{1-6}$-alkylene-, $C_{1-6}$-alkyl-NH—C(O)—, aryl-$C_{1-6}$-alkylene-NH—C(O)—, $C_{1-6}$-alkyl-$SO_2$—, aryl-$C_{1-6}$-alkylene-$SO_2$—, aryl-$SO_2$—, $SO_2$—, $C_{1-6}$-alkyl-C(O)—, aryl-$C_{1-6}$-alkylene-C(O)—, $NH_2$—$C_{1-6}$alkylene-, and $R^{15}$—$C_{1-6}$-alkylene-, wherein $R^{15}$ is selected from the group consisting of aryl, heteroaryl, cycloalkyl, heterocyclyl, $C_{1-6}$alkyl, or aryl-$C_{1-6}$-alkylene-.

Embodiment A94. A compound according to embodiment A93, wherein $R^{11}$ is selected from hydrogen, $C_{1-6}$alkyl, aryl, carbamoyl, aryl-$C_{1-6}$-alkylene-, $C_{1-6}$alkyl-NH—C(O)—, aryl-$C_{1-6}$-alkylene-NH—C(O)—, $C_{1-6}$-alkyl-$SO_2$—, aryl-$C_{1-6}$-alkylene-$SO_2$—, aryl-$SO_2$—, $SO_2$—, $C_{1-6}$-alkyl-C(O)—, aryl-$C_{1-6}$-alkylene-C(O)—, and $NH_2$—$C_{1-6}$ alkylene-.

Embodiment A95. A compound according to embodiment A94, wherein $R^{11}$ is hydrogen or $C_{1-6}$alkyl.

Embodiment A96. A compound according to embodiment A95, wherein $R^{11}$ is hydrogen.

Embodiment A97. A compound according to any one of the embodiments A1 to A96, wherein $R^{12}$ is hydrogen or $C_{1-6}$alkyl.

Embodiment A98. A compound according to embodiment A97, wherein $R^{12}$ is hydrogen.

Embodiment A99. A compound according to any one of the embodiments A1 to A98, wherein $G^1$ is $C_{1-6}$alkyl, $C_{2-6}$-alkenyl, $C_{2-6}$-alkynyl, cycloalkyl or heterocyclyl, optionally substituted with one or more substituents selected from the group consisting of —CN, —$CF_3$, —$OCF_3$, —$OR^{18}$, —$NR^{18}R^{19}$, $C_{3-10}$-cycloalkyl and $C_{1-6}$alkyl, wherein $R^{18}$ and $R^{19}$ are as defined in embodiment A1.

Embodiment A100. A compound according to embodiment A99, wherein $G^1$ is $C_{1-6}$-alkyl, $C_{2-6}$-alkenyl, $C_{2-6}$-alkynyl, cycloalkyl or heterocyclyl, optionally substituted with one or more substituents selected from the group consisting of —CN, —CF$_3$, —OCF$_3$, —OR$^{18}$, —NR$^{18}$R$^{19}$ and C$_{1-6}$alkyl, wherein
R$^{18}$ and R$^{19}$ are as defined in embodiment A1.

Embodiment A101. A compound according to embodiment A99, wherein
G$^1$ is C$_{1-6}$-alkyl, C$_{2-6}$-alkenyl, C$_{2-6}$-alkynyl, C$_{3-10}$-cycloalkyl or C$_{3-10}$-heterocyclyl, optionally substituted with one or more substituents selected from the group consisting of —CN, —CF$_3$, —OCF$_3$, —OR$^{18}$, —NR$^{18}$R$^{19}$, C$_{3-10}$-cycloalkyl and C$_{1-6}$-alkyl, wherein
R$^{18}$ and R$^{19}$ are as defined in embodiment A1.

Embodiment A102. A compound according to embodiment A100 or embodiment A101, wherein
G$^1$ is C$_{1-6}$-alkyl, C$_{2-6}$-alkenyl, C$_{2-6}$-alkynyl, C$_{3-10}$-cycloalkyl or C$_{3-10}$-heterocyclyl, optionally substituted with one or more substituents selected from the group consisting of —CN, —CF$_3$, —OCF$_3$, —OR$^{18}$, —NR$^{18}$R$^{19}$ and C$_{1-6}$alkyl, wherein
R$^{18}$ and R$^{19}$ are as defined in embodiment A1.

Embodiment A103. A compound according to any one of the embodiments A99 to A102, wherein
G$^1$ is selected from the group consisting of methyl, ethyl, propyl, butyl, isopropyl, isobutyl, sec-butyl, tert-butyl, 3-pentyl, 2-pentyl, 3-methyl-butyl, 2-propenyl, cyclopropyl, cyclobutyl, cyclopentyl, cyclohexyl, cycloheptyl, oxetanyl, tetrahydrofuranyl, tetrahydropyranyl, azetidyl, pyrrolidyl, piperidyl, hexahydroazepinyl, thiolanyl, tetrahydrothiopyranyl, thiepanyl, 1,4-oxathianyl, 1,3-dioxolanyl, 1,2-dithiolanyl, 1,3-dithiolanyl, hexahydro-pyridazinyl, imidazolidyl, 1,3-dioxanyl, morpholinyl, 1,3-dithianyl, 1,4-dioxanyl, 1,4-dithianyl, or thiomorpholinyl.

Embodiment A104. A compound according to embodiment A103 wherein
G$^1$ is selected from the group consisting of methyl, ethyl, propyl, butyl, isopropyl, isobutyl, sec-butyl, tert-butyl, cyclopropyl, cyclobutyl, cyclopentyl, cyclohexyl, cycloheptyl, tetrahydrofuranyl, tetrahydropyranyl, pyrrolidyl, piperidyl, hexahydroazepinyl, thiolanyl, tetrahydrothiopyranyl, or thiepanyl.

Embodiment A105. A compound according to embodiment A104 wherein
G$^1$ is selected from the group consisting of methyl, ethyl, propyl, butyl, isopropyl, isobutyl, cyclopentyl, cyclohexyl, tetrahydrofuranyl, tetrahydropyranyl, piperidyl, or hexahydroazepinyl.

Embodiment A106. A compound according to embodiment A105 wherein
G$^1$ is selected from the group consisting of isobutyl, cyclopentyl, and piperidyl.

Embodiment A107. A compound according to embodiment A105 wherein
G$^1$ is isobutyl.

Embodiment A108. A compound according to embodiment A105 wherein
G$^1$ is cyclopentyl.

Embodiment A109. A compound according to embodiment A105 wherein
G$^1$ is piperidyl.

Embodiment A110. A compound according to any one of the embodiments A99 to A1O$_2$, wherein
R$^{18}$ and R$^{19}$, independently of each other, are hydrogen, C$_{1-6}$alkyl, heteroaryl-C$_{1-6}$-alkylene-, aryl-C$_{1-6}$-alkylene-, C$_{1-6}$alkyl-arylene-, C$_{1-6}$alkyl-heteroarylene-, heteroaryl, or aryl.

Embodiment A111. A compound according to embodiment A110, wherein
R$^{18}$ and R$^{19}$, independently of each other, are hydrogen, C$_{1-6}$-alkyl, C$_{3-10}$-heteroaryl-C$_{1-6}$-alkylene-, C$_{3-10}$-aryl-C$_{1-6}$-alkylene-, C$_{1-6}$-alkyl-C$_{3-10}$-arylene-, C$_{1-6}$-alkyl-C$_{3-10}$-heteroarylene-, C$_{3-10}$-heteroaryl, or C$_{3-10}$-aryl.

Embodiment A112. A compound according to embodiment A111, wherein
R$^{18}$ and R$^{19}$, independently of each other, are hydrogen or C$_{1-6}$alkyl.

Embodiment A113. A compound according to embodiment A112, wherein
R$^{18}$ is hydrogen.

Embodiment A114. A compound according to embodiment A112 or A113, wherein
R$^{19}$ is hydrogen.

Embodiment A115. A compound according to embodiment A100 or embodiment A102, wherein
R$^{18}$ and R$^{19}$, when attached to the same nitrogen atom, together with the said nitrogen atom forms a 3 to 8 membered heterocyclic ring optionally containing one or two further heteroatoms selected from nitrogen, oxygen and sulfur, and optionally containing one or two double bonds.

Embodiment A116. A compound according to any one of the embodiments A1 to A98, wherein
G$^1$ is alkyl or cycloalkyl, optionally substituted with one or more substituents selected from the group consisting of —CN, —CF$_3$, —OCF$_3$, —OR$^{18}$, —NR$^{18}$R$^{19}$ and C$_{1-6}$alkyl,
or G$^1$ is aryl optionally substituted with one or more substituents R$^{40}$, R$^{41}$, and R$^{42}$, wherein R$^{18}$, R$^{19}$, R$^{40}$, R$^{41}$, and R$^{42}$ are as defined in embodiment A1.

Embodiment A117. A compound according to embodiment A116, wherein
G$^1$ is C$_{1-6}$alkyl or C$_{3-10}$-cycloalkyl, optionally substituted with one or more substituents selected from the group consisting of —CN, —CF$_3$, —OCF$_3$, —OR$^{18}$—NR$^{18}$R$^{19}$ and C$_{1-6}$-alkyl,
or G$^1$ is C$_{3-10}$-aryl optionally substituted with one or more substituents R$^{40}$, R$^{41}$, and R$^{42}$, wherein R$^{18}$, R$^{19}$, R$^{40}$, R$^{41}$, and R$^{42}$ are as defined in embodiment A1.

Embodiment A118. A compound according to embodiment A117, wherein
G$^1$ is C$_{1-6}$alkyl or C$_{3-10}$-cycloalkyl, optionally substituted with one or more substituents selected from the group consisting of —CN, —CF$_3$, —OCF$_3$, —OR$^{18}$, —NR$^{18}$R$^{19}$ and C$_{1-6}$alkyl,
or G$^1$ is phenyl optionally substituted with one or more substituents R$^{40}$, R$^{41}$, and R$^{42}$, wherein R$^{18}$, R$^{19}$, R$^{40}$, R$^{41}$, and R$^{42}$ are as defined in embodiment A1.

Embodiment A119. A compound according to embodiment A116, A117, or A118, wherein
R$^{18}$ and R$^{19}$, independently of each other, are hydrogen, C$_{1-6}$alkyl, heteroaryl-C$_{1-6}$-alkylene-, aryl-C$_{1-6}$-alkylene-, C$_{1-6}$-alkyl-arylene-, C$_{1-6}$-alkyl-heteroarylene-, heteroaryl, or aryl.

Embodiment A120. A compound according to embodiment A119, wherein
$R^{18}$ and $R^{19}$, independently of each other, are hydrogen, $C_{1-6}$alkyl, $C_{3-10}$-heteroaryl-$C_{1-6}$-alkylene-, $C_{3-10}$-aryl-$C_{1-6}$-alkylene-, $C_{1-6}$alkyl-$C_{3-10}$-arylene-, $C_{1-6}$-alkyl-$C_{3-10}$-heteroarylene-, $C_{3-10}$-heteroaryl, or $C_{3-10}$-aryl.

Embodiment A121. A compound according to embodiment A120, wherein
$R^{18}$ and $R^{19}$, independently of each other, are hydrogen or $C_{1-6}$alkyl.

Embodiment A122. A compound according to embodiment A121, wherein
$R^{18}$ is hydrogen.

Embodiment A123. A compound according to embodiment A121 or A122, wherein
$R^{19}$ is hydrogen.

Embodiment A124. A compound according to embodiment A116 or embodiment A117, wherein
$R^{18}$ and $R^{19}$, when attached to the same nitrogen atom, together with the said nitrogen atom forms a 3 to 8 membered heterocyclic ring optionally containing one or two further heteroatoms selected from nitrogen, oxygen and sulfur, and optionally containing one or two double bonds.

Embodiment A125. A compound according to any one of the embodiments A116 to A124, wherein
$R^{40}$, $R^{41}$, and $R^{42}$ independently of each other are halogen, —CN, —NO$_2$, $C_{1-6}$alkyl, —CHF$_2$, —CF$_3$, —OR$^{54}$, —NR$^{54}$R$^{55}$, —SR$^{54}$, —NR$^{54}$S(O)$_2$R$^{55}$, —S(O)$_2$NR$^{54}$R$^{55}$, —S(O)NR$^{54}$R$^{55}$, —S(O)R$^{54}$, —S(O)$_2$R$^{54}$, —C(O)NR$^{54}$R$^{55}$, —OC(O)NR$^{54}$R$^{55}$, —NR$^{54}$C(O)R$^{55}$, —CH$_2$C(O)NR$^{54}$R$^{55}$, —CH$_2$C(O)OR$^{54}$, —OCH$_2$C(O)NR$^{54}$R$^{55}$, —CH$_2$OR$^{54}$, —CH$_2$NR$^{54}$R$^{55}$, and —C(O)OR$^{54}$; or
$C_{2-6}$-alkenyl and $C_{2-6}$-alkynyl, which may optionally be substituted with one or more substituents selected from —CN, —CF$_3$, —OCF$_3$, —OR$^{54}$, —NR$^{54}$R$^{55}$ and $C_{1-6}$-alkyl,
wherein
$R^{54}$ and $R^{55}$ independently of each other are hydrogen, $C_{1-6}$-alkyl, $C_{1-6}$-alkyl-arylene-, $C_{1-6}$-alkyl-heteroarylene-, aryl-$C_{1-6}$-alkylene-, heteroaryl-$C_{1-6}$-alkylene-, heteroaryl, or aryl;
or
$R^{54}$ and $R^{55}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds.

Embodiment A126. A compound according to embodiment A125, wherein
$R^{40}$, $R^{41}$, and $R^{42}$ independently of each other are halogen, —CN, $C_{1-6}$-alkyl, —CF$_3$, —OR$^{54}$, —NR$^{54}$R$^{55}$, —SR$^{54}$, —NR$^{54}$S(O)$_2$R$^{55}$, —S(O)R$^{54}$, —S(O)$_2$R$^{54}$, —CH$_2$C(O)OR$^{54}$, —CH$_2$OR$^{54}$, —CH$_2$NR$^{54}$R$^{55}$, and —C(O)OR$^{54}$;
wherein
$R^{54}$ and $R^{55}$ independently of each other are hydrogen, $C_{1-6}$-alkyl, $C_{1-6}$-alkyl-arylene-, $C_{1-6}$-alkyl-heteroarylene-, aryl-$C_{1-6}$-alkylene-, heteroaryl-$C_{1-6}$-alkylene-, heteroaryl, or aryl;
or
$R^{54}$ and $R^{55}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds.

Embodiment A127. A compound according to embodiment A126 wherein
$R^{40}$, $R^{41}$, and $R^{42}$ independently of each other are halogen, or —OR$^{54}$
wherein
$R^{54}$ is hydrogen, $C_{1-6}$-alkyl, $C_{1-6}$-alkyl-arylene-, $C_{1-6}$-alkyl-heteroarylene-, aryl-$C_{1-6}$-alkylene-, heteroaryl-$C_{1-6}$-alkylene-, heteroaryl, or aryl.

Embodiment A128. A compound according to embodiment A126, wherein
$R^{54}$ and $R^{55}$ independently of each other are hydrogen, or $C_{1-6}$-alkyl, $C_{1-6}$-alkyl-$C_{3-10}$-arylene-, $C_{1-6}$-alkyl-$C_{3-10}$-heteroarylene-, $C_{3-10}$-aryl-$C_{1-6}$-alkylene-, $C_{3-10}$-heteroaryl-$C_{1-6}$-alkylene-, $C_{3-10}$-heteroaryl, or $C_{3-10}$-aryl.

Embodiment A129. A compound according to embodiment A128, wherein
$R^{54}$ and $R^{55}$ independently of each other are hydrogen or $C_{1-6}$-alkyl.

Embodiment A130. A compound according to embodiment A129, wherein
$R^{54}$ is hydrogen.

Embodiment A131. A compound according to embodiment A129 or embodiment A130, wherein
$R^{55}$ is hydrogen.

Embodiment A132. A compound according to embodiment A127 wherein
$R^{54}$ is methyl.

Embodiment A133. A compound according to any one of the embodiments A1 to A98, wherein
$G^1$ is aryl or heteroaryl, optionally substituted with one or more substituents $R^{40}$, $R^{41}$, and $R^{42}$, wherein
$R^{40}$, $R^{41}$, and $R^{42}$ are as defined in embodiment A1.

Embodiment A134. A compound according to embodiment A133, wherein
$G^1$ is $C_{3-10}$-aryl or $C_{3-10}$-heteroaryl, optionally substituted with one or more substituents $R^{40}$, $R^{41}$, and $R^{42}$, wherein
$R^{40}$, $R^{41}$, and $R^{42}$ are as defined in embodiment A1.

Embodiment A135. A compound according to embodiment A133, wherein
$G^1$ is aryl, optionally substituted with one or more substituents $R^{40}$, $R^{41}$, and $R^{42}$, wherein
$R^{40}$, $R^{41}$, and $R^{42}$ are as defined in embodiment A1.

Embodiment A136. A compound according to embodiment A135, wherein
$G^1$ is $C_{3-10}$-aryl, optionally substituted with one or more substituents $R^{40}$, $R^{41}$, and $R^{42}$, wherein
$R^{40}$, $R^{41}$, and $R^{42}$ are as defined in embodiment A1.

Embodiment A137. A compound according to embodiment A136, wherein
$G^1$ is phenyl, optionally substituted with one or more substituents $R^{40}$, $R^{41}$, and $R^{42}$, wherein
$R^{40}$, $R^{41}$, and $R^{42}$ are as defined in embodiment A1.

Embodiment A138. A compound according to any one of the embodiments A133 to A137, wherein $R^{40}$, $R^{41}$, and $R^{42}$ independently of each other are halogen, —CN, —NO$_2$, C$_{1-6}$-alkyl, —CHF$_2$, —CF$_3$, —OR$^{54}$, —NR$^{54}$R$^{55}$, —SR$^{54}$, —NR$^{54}$S(O)$_2$R$^{55}$, —S(O)$_2$NR$^{54}$R$^{55}$, —S(O)NR$^{54}$R$^{55}$, —S(O)R$^{54}$, —S(O)$_2$R$^{54}$, —C(O)NR$^{54}$R$^{55}$, —OC(O)NR$^{54}$R$^{55}$, —NR$^{54}$C(O)R$^{55}$, —CH$_2$C(O)NR$^{54}$R$^{55}$, —CH$_2$C(O)OR$^{54}$, —OCH$_2$C(O)NR$^{54}$R$^{55}$, —CH$_2$OR$^{54}$, —CH$_2$NR$^{54}$R$^{55}$, and —C(O)OR$^{54}$; or C$_{2-6}$-alkenyl and C$_{2-6}$-alkynyl, which may optionally be substituted with one or more substituents selected from —CN, —CF$_3$, —OCF$_3$, —R$^{54}$, —NR$^{54}$R$^{55}$ and C$_{1-6}$-alkyl, wherein $R^{54}$ and $R^{55}$ independently of each other are hydrogen, C$_{1-6}$-alkyl, C$_{1-6}$-alkyl-arylene-, C$_{1-6}$-alkyl-heteroarylene-, aryl-C$_{1-6}$-alkylene-, heteroaryl-C$_{1-6}$-alkylene-, heteroaryl, or aryl;

or $R^{54}$ and $R^{55}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds.

Embodiment A139. A compound according to embodiment A138, wherein $R^{40}$, $R^{41}$, and $R^{42}$ independently of each other are halogen, —CN, C$_{1-6}$-alkyl, —CF$_3$, —OR$^{54}$, —NR$^{54}$R$^{55}$, —SR$^{54}$, —NR$^{54}$S(O)$_2$R$^{55}$, —S(O)R$^{54}$, —S(O)$_2$R$^{54}$, —CH$_2$C(O)OR$^{54}$, —CH$_2$OR$^{54}$, —CH$_2$NR$^{54}$R$^{55}$, and —C(O)OR$^{54}$;

wherein $R^{54}$ and $R^{55}$ independently of each other are hydrogen, C$_{1-6}$-alkyl, C$_{1-6}$-alkyl-arylene-, C$_{1-6}$-alkyl-heteroarylene-, aryl-C$_{1-6}$-alkylene-, heteroaryl-C$_{1-6}$-alkylene-, heteroaryl, or aryl;

or $R^{54}$ and $R^{55}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds.

Embodiment A140. A compound according to embodiment A139 wherein $R^{40}$, $R^{41}$, and $R^{42}$ independently of each other are halogen, or —OR$^{54}$ wherein $R^{54}$ is hydrogen, C$_{1-6}$-alkyl, C$_{1-6}$-alkyl-arylene-, C$_{1-6}$-alkyl-heteroarylene-, aryl-C$_{1-6}$-alkylene-, heteroaryl-C$_{1-6}$-alkylene-, heteroaryl, or aryl.

Embodiment A141. A compound according to any one of the embodiments A138 to A139, wherein $R^{54}$ and $R^{55}$ independently of each other are hydrogen, or C$_{1-6}$-alkyl, C$_{1-6}$-alkyl-C$_{3-10}$-arylene-, C$_{1-6}$-alkyl-C$_{3-10}$-heteroarylene-, C$_{3-10}$-aryl-C$_{1-6}$-alkylene-, C$_{3-10}$-heteroaryl-C$_{1-6}$-alkylene-, C$_{3-10}$-heteroaryl, or C$_{3-10}$-aryl.

Embodiment A142. A compound according to embodiment A141, wherein $R^{54}$ and $R^{55}$ independently of each other are hydrogen or C$_{1-6}$-alkyl.

Embodiment A143. A compound according to embodiment A142, wherein $R^{54}$ is hydrogen.

Embodiment A144. A compound according to embodiment A142 or embodiment A143, wherein $R^{55}$ is hydrogen.

Embodiment A145. A compound according to embodiment A140 wherein $R^{54}$ is methyl.

Embodiment A146. A compound according to embodiment A135, wherein

G$^1$ is

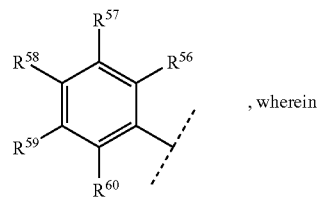, wherein $R^{56}$, $R^{57}$, $R^{58}$, $R^{59}$, and $R^{60}$, independently of each other, are hydrogen or halogen, —CN, —NO$_2$, C$_{1-6}$-alkyl, —CHF$_2$, —CF$_3$, —OCF$_3$, —OCHF$_2$, —OCH$_2$CF$_3$, —OCF$_2$CHF$_2$, —S(O)$_2$CF$_3$, —SCF$_3$, —OR$^{61}$, —NR$^{61}$R$^{62}$, —SR$^{61}$, —NR$^{61}$S(O)$_2$R$^{62}$, —S(O)$_2$NR$^{61}$R$^{62}$, —S(O)NR$^{61}$R$^{62}$, —S(O)R$^{61}$, —S(O)$_2$R$^{61}$, —C(O)NR$^{61}$R$^{62}$, —OC(O)NR$^{61}$R$^{62}$, —NR$^{61}$C(O)R$^{62}$, —CH$_2$C(O)NR$^{61}$R$^{62}$, —CH$_2$C(O)OR$^{61}$, —OCH$_2$C(O)NR$^{61}$R$^{62}$, —CH$_2$OR$^{61}$, —CH$_2$NR$^{61}$R$^{62}$, —OC(O)R$^{61}$, —C(O)R$^{61}$ and —C(O)OR$^{61}$; or C$_{2-6}$-alkenyl and C$_{2-6}$-alkynyl, which may optionally be substituted with one or more substituents selected from —CN, —CF$_3$, —OCF$_3$, —OR$^{61}$, —NR$^{61}$R$^{62}$ and C$_{1-6}$-alkyl;

C$_{3-10}$-cycloalkyl, C$_{4-8}$-cycloalkenyl, heterocyclyl, C$_{3-10}$-cycloalkyl-C$_{1-6}$-alkylene-, C$_{3-10}$-cycloalkyl-C$_{1-6}$-alkoxy-, C$_{3-10}$-cycloalkyloxy, C$_{3-10}$-cycloalkyl-C$_{1-6}$-alkylthio-, C$_{3-10}$-cycloalkylthio, C$_{3-10}$-cycloalkyl-C$_{2-6}$-alkenylene-, C$_{3-10}$-cycloalkyl-C$_{2-6}$-alkynylene-, C$_{4-8}$-cycloalkenyl-C$_{1-6}$-alkylene-, C$_{4-8}$-cycloalkenyl-C$_{2-6}$-alkenylene-, C$_{4-8}$-cycloalkenyl-C$_{2-6}$-alkynylene-, heterocyclyl-C$_{1-6}$-alkylene-, heterocyclyl-C$_{2-6}$-alkenylene-, heterocyclyl-C$_{2-6}$-alkynylene-; or aryl, aryloxy, aryloxycarbonyl, aroyl, aryl-C$_{1-6}$-alkoxy-, aryl-C$_{1-6}$-alkylene-, aryl-C$_{2-6}$-alkenylene-, aryl-C$_{2-6}$-alkynylene-, heteroaryl, heteroaryl-C$_{1-6}$-alkylene-, heteroaryl-C$_{2-6}$-alkenylene- and heteroaryl-C$_{2-6}$-alkynylene-, of which the aryl and heteroaryl moieties optionally may be substituted with one or more substituents selected from halogen, —C(O)OR$^{61}$, —CN, —CF$_3$, —OCF$_3$, —NO$_2$, —OR$^{61}$, —NR$^{61}$R$^{62}$ or C$_{1-6}$-alkyl, wherein $R^{61}$ and $R^{62}$ independently of each other are hydrogen, C$_{1-6}$-alkyl, C$_{1-6}$-alkyl-arylene-, C$_{1-6}$-alkyl-heteroarylene-, aryl-C$_{1-6}$-alkylene-, heteroaryl-C$_{1-6}$-alkylene-, heteroaryl, or aryl;

or $R^{61}$ and $R^{62}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds.

Embodiment A147. A compound according to embodiment A146, wherein $R^{56}$, $R^{57}$, $R^{58}$, $R^{59}$, and $R^{60}$ independently of each other are halogen, —CN, —NO$_2$, C$_{1-6}$-alkyl, —CHF$_2$, —CF$_3$, —OR$^{61}$, —NR$^{61}$R$^{62}$, —SR$^{61}$, —NR$^{61}$S(O)$_2$R$^{62}$, —S(O)$_2$NR$^{61}$R$^{62}$, —S(O)NR$^{61}$R$^{62}$, —S(O)R$^{61}$, —S(O)$_2$R$^{61}$, —C(O)NR$^{61}$R$^{62}$, —OC(O)NR$^{61}$R$^{62}$, —NR$^{61}$C(O)R$^{62}$, —CH$_2$C(O)NR$^{61}$R$^{62}$, —CH$_2$C(O)OR$^{61}$, —OCH$_2$C(O)NR$^{61}$R$^{62}$, —CH$_2$OR$^{61}$, —CH$_2$NR$^{61}$R$^{62}$, and —C(O)OR$^{61}$; or C$_{2-6}$-alkenyl and C$_{2-6}$-alkynyl, which may optionally be substituted with one or more substituents selected from —CN, —CF$_3$, —OCF$_3$, —OR$^{61}$, —NR$^{61}$R$^{62}$ and C$_{1-6}$-alkyl, wherein
R$^{61}$ and R$^{62}$ independently of each other are hydrogen, C$_{1-6}$-alkyl, C$_{1-6}$-alkyl-arylene-, C$_{1-6}$-alkyl-heteroarylene-, aryl-C$_{1-6}$-alkylene-, heteroaryl-C$_{1-6}$-alkylene-, heteroaryl, or aryl;

or
R$^{61}$ and R$^{62}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds.

Embodiment A148. A compound according to embodiment A146 or embodiment A147, wherein R$^{56}$ or R$^{57}$ is —OR$^{61}$.

Embodiment A149. A compound according to embodiment A148 wherein R$^{61}$ is methyl.

Embodiment A150. A compound according to embodiment A147, wherein
R$^{61}$ and R$^{62}$ independently of each other are hydrogen, or C$_{1-6}$-alkyl, C$_{1-6}$-alkyl-C$_{3-10}$-arylene-, C$_{1-6}$-alkyl-C$_{3-10}$-heteroarylene-, C$_{3-10}$-aryl-C$_{1-6}$-alkylene-, C$_{3-10}$-heteroaryl-C$_{1-6}$-alkylene-, C$_{3-10}$-heteroaryl, or C$_{3-10}$-aryl.

Embodiment A151. A compound according to embodiment A150, wherein
R$^{61}$ and R$^{62}$ independently of each other are hydrogen or C$_{1-6}$-alkyl.

Embodiment A152. A compound according to embodiment A151, wherein
R$^{61}$ is hydrogen.

Embodiment A153. A compound according to embodiment A151 or embodiment A152, wherein
R$^{62}$ is hydrogen.

Embodiment A154. A compound according to any one of the embodiments A146 to A153, wherein
at least one of R$^{56}$, R$^{57}$, R$^{58}$, R$^{59}$, and R$^{60}$ are hydrogen.

Embodiment A155. A compound according to embodiment A154, wherein
at least two of R$^{23}$, R$^{24}$, R$^{25}$, and R$^{26}$ are hydrogen.

Embodiment A156. A compound according to embodiment A155, wherein
at least three of R$^{23}$, R$^{24}$, R$^{25}$, and R$^{26}$ are hydrogen.

Embodiment A157. A compound according to any one of the embodiments A1 to A156, wherein
L$^2$ is a direct bond, C$_{1-6}$-alkylene, C$_{2-6}$-alkenylene, C$_{2-6}$-alkynylene, —N—R$^{20}$—, —C$_{1-6}$-alkylene-N(R$^{20}$)—, —C$_{2-6}$-alkenylene-N(R$^{20}$)—, or —C$_{2-6}$-alkynylene-N(R$^{20}$)—, wherein
R$^{20}$ is as defined in embodiment A1.

Embodiment A158. A compound according to any one of the embodiments A1 to A153, wherein L$^2$ is —N—R$^{20}$—, -alkylene-N(R$^{20}$)—, -alkenylene-N(R$^{20}$)—, or -alkynylene-N(R$^{20}$)—, wherein
R$^{20}$ is as defined in embodiment A1.

Embodiment A159. A compound according to embodiment A157 or embodiment A158, wherein
L$^2$ is —N—R$^{20}$—, —C$_{1-6}$-alkylene-N(R$^{20}$)—, —C$_{2-6}$-alkenylene-N(R$^{20}$)—, or —C$_{2-6}$-alkynylene-N(R$^{20}$)—, wherein
R$^{20}$ is as defined in embodiment A1.

Embodiment A160. A compound according to embodiment A159, wherein
L$^2$ is —N—R$^{20}$—, wherein
R$^{20}$ is as defined in embodiment A1.

Embodiment A161. A compound according to embodiment A157, wherein
L$^2$ is a direct bond.

Embodiment A162. A compound according to any one of the embodiments A1 to A160, wherein
R$^{20}$ is hydrogen, or
R$^{20}$ is C$_{1-6}$-alkyl, C$_{2-6}$-alkenyl, C$_{2-6}$-alkynyl, C$_{3-10}$-cycloalkyl-W$^3$—, C$_{3-10}$-heterocyclyl-W$^3$—, C$_{3-10}$-aryl-W$^3$—, or C$_{4-10}$-heteroaryl-W$^3$—, optionally substituted with one or more substituents R$^{30}$, R$^{31}$, and R$^{32}$, wherein
W$^3$, R$^{30}$, R$^{31}$, and R$^{32}$ are as defined in embodiment A1.

Embodiment A163. A compound according to embodiment A162, wherein
W$^3$ is alkylene.

Embodiment A164. A compound according to embodiment A163, wherein
W$^3$ is C$_{2-6}$-alkylene.

Embodiment A165. A compound according to embodiment A162, wherein
W$^3$ is a direct bond.

Embodiment A166. A compound according to any one of the embodiments A1 to A160, wherein
R$^{20}$ is hydrogen, C$_{1-6}$-alkyl, C$_{2-6}$-alkenyl, or C$_{2-6}$-alkynyl, optionally substituted with one or more substituents R$^{30}$, R$^{31}$, and R$^{32}$, wherein
R$^{30}$, R$^{31}$, and R$^{32}$ are as defined in embodiment A1.

Embodiment A167. A compound according to any one of the embodiments A162 to A166, wherein
R$^{20}$ is hydrogen, or
R$^{20}$ is C$_{1-6}$-alkyl, C$_{1-6}$-alkenyl, or C$_{1-6}$-alkynyl, optionally substituted with one or more substituents R$^{30}$, R$^{31}$, and R$^{32}$ wherein
R$^{30}$, R$^{31}$, and R$^{32}$ are as defined in embodiment A1.

Embodiment A168. A compound according to any one of the embodiments A1 to A167, wherein
R$^{30}$, R$^{31}$, and R$^{32}$ independently of each other are selected from —CHF$_2$, —CF$_3$, —OCF$_3$, —OCHF$_2$, —OCH$_2$CF$_3$, —OCF$_2$CHF$_2$, —S(O)$_2$CF$_3$, —SCF$_3$, —OR$^{52}$, —NR$^{52}$R$^{53}$, —SR$_{52}$, —NR$^{52}$S(O)$_2$R$^{53}$, —S(O)$_2$NR$^{52}$R$^{53}$, —S(O)NR$^{52}$R$^{53}$, —S(O)R$^{52}$, —S(O)$_2$R$^{52}$, —C(O)NR$^{52}$R$^{53}$, —OC(O)NR$^{52}$R$^{53}$, —NR$^{52}$C(O)R$^{53}$, —CH$_2$C(O)NR$^{52}$R$^{53}$, —OCH$_2$C(O)NR$^{52}$R$^{53}$, —CH$_2$OR$^{52}$, —CH$_2$NR$^{52}$R$^{53}$, —OC(O)R$^{52}$, —C(O)R$^{52}$ and —C(O)OR$^{52}$, wherein
R$^{52}$ and R$^{53}$ are as defined in embodiment A1.

Embodiment A169. A compound according to embodiment A168, wherein

Embodiment A170. A compound according to any one of the embodiments A1 to A168, wherein
$R^{52}$ and $R^{53}$ independently of each other are hydrogen, $C_{1-6}$-alkyl, aryl-$C_{1-6}$-alkylene-heteroaryl-$C_{1-6}$-alkylene-heteroaryl, or aryl.

Embodiment A171. A compound according to embodiment A170, wherein
$R^{52}$ and $R^{53}$ independently of each other are hydrogen, $C_{1-6}$-alkyl, aryl-$C_{1-6}$-alkylene-or aryl.

Embodiment A172. A compound according to embodiment A171, wherein
$R^{52}$ and $R^{53}$ independently of each other are hydrogen or $C_{1-6}$-alkyl.

Embodiment A173. A compound according to embodiment A172, wherein
$R^{52}$ is hydrogen.

Embodiment A174. A compound according to embodiment A172 or embodiment A173, wherein
$R^{53}$ is hydrogen.

Embodiment A175. A compound according to embodiment A167, wherein
$R^{20}$ is hydrogen.

Embodiment A176. A compound according to any one of the embodiments A1 to A175, wherein
$L^3$ is —C(O)—, —C(O)—C(O)— or —C(O)CH$_2$C(O)—.

Embodiment A177. A compound according to embodiment A176 wherein
$L^3$ is —C(O)—.

Embodiment A178. A compound according to embodiment A176 wherein
$L^3$ is —C(O)—C(O)—.

Embodiment A179. A compound according to embodiment A176 wherein
$L^3$ is —C(O)CH$_2$C(O)—.

Embodiment A180. A compound according to any one of the embodiments A1 to A179, wherein
$R^1$ is hydrogen, or
$R^1$ is $C_{1-6}$-alkyl, $C_{2-6}$-alkenyl, $C_{2-6}$-alkynyl, $C_{3-10}$-cycloalkyl-$W^4$—, $C_{3-10}$-heterocyclyl-$W^4$—, $C_{3-10}$-aryl-$W^4$—, or $C_{4-10}$-heteroaryl-$W^4$—, optionally substituted with one or more substituents $R^{33}$, $R^{34}$, and $R^{35}$, wherein $W^4$, $R^{33}$, $R^{34}$, and $R^{35}$ are as defined in embodiment A1.

Embodiment A181. A compound according to embodiment A180, wherein
$W^4$ is alkylene.

Embodiment A182. A compound according to embodiment A181, wherein
$W^4$ is $C_{2-6}$-alkylene.

Embodiment A183. A compound according to embodiment A180, wherein
$W^4$ is a direct bond.

Embodiment A184. A compound according to any one of the embodiments A1 to A176, wherein
$R^1$ is hydrogen, $C_{1-6}$-alkyl, $C_{2-6}$-alkenyl, or $C_{2-6}$-alkynyl, optionally substituted with one or more substituents $R^{33}$, $R^{34}$, and $R^{35}$, wherein
$R^{33}$, $R^{34}$, and $R^{35}$ are as defined in embodiment A1.

Embodiment A185. A compound according to any one of the embodiments A180 to A184, wherein
$R^1$ is hydrogen, $C_{1-6}$-alkyl, $C_{2-6}$-alkenyl, or $C_{2-6}$-alkynyl, optionally substituted with one or more substituents $R^{33}$, $R^{34}$, and $R^{35}$, wherein
$R^{33}$, $R^{34}$, and $R^{35}$ are as defined in embodiment A1.

Embodiment A186. A compound according to embodiment A185, wherein
$R^1$ is hydrogen or $C_{1-6}$-alkyl optionally substituted with one or more substituents $R^{33}$, $R^{34}$, and $R^{35}$, wherein
$R^{33}$, $R^{34}$, and $R^{35}$ are as defined in embodiment A1.

Embodiment A187. A compound according to any one of the embodiments A1 to A186, wherein
$R^{33}$, $R^{34}$, and $R^{35}$ independently of each other are selected from —CHF$_2$, —CF$_3$, —OCF$_3$, —OCHF$_2$, —OCH$_2$CF$_3$, —OCF$_2$CHF$_2$, —S(O)$_2$CF$_3$, —SCF$_3$, —OR$^{52}$, —NR$^{52}$R$^{53}$, —SR$_{52}$—NR$^{52}$S(O)$_2$R$^{53}$, —S(O)$_2$ NR$^{52}$R$^{53}$, —S(O)NR$^{52}$R$^{53}$, —S(O)R$^{52}$, —S(O)$_2$R$^{52}$, —C(O)NR$^{52}$R$^{53}$, —OC(O)NR$^{52}$R$^{53}$, —NR$^{52}$C(O)R$^{53}$, —CH$_2$C(O)NR$^{52}$R$^{53}$, —OCH$_2$C(O) NR$^{52}$R$^{53}$, —CH$_2$OR$^{52}$, —CH$_2$NR$^{52}$R$^{53}$, —OC(O)R$^{52}$, —C(O)R$^{52}$ and —C(O)OR$^{52}$, wherein
$R^{52}$ and $R^{53}$ are as defined in embodiment A1.

Embodiment A188. A compound according to embodiment A186, wherein
$R^{52}$ and $R^{53}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds.

Embodiment A189. A compound according to embodiment A186, wherein
$R^{52}$ and $R^{53}$ independently of each other are hydrogen, $C_{1-6}$-alkyl, aryl-$C_{1-6}$-alkylene-heteroaryl-$C_{1-6}$-alkylene-heteroaryl, or aryl.

Embodiment A190. A compound according to embodiment A189, wherein
$R^{52}$ and $R^{53}$ independently of each other are hydrogen, $C_{1-6}$-alkyl, aryl-$C_{1-6}$-alkylene-or aryl.

Embodiment A191. A compound according to embodiment A190, wherein
$R^{52}$ and $R^{53}$ independently of each other are hydrogen or $C_{1-6}$-alkyl.

Embodiment A192. A compound according to embodiment A191, wherein
$R^{52}$ is hydrogen.

Embodiment A193. A compound according to embodiment A191 or embodiment A192, wherein
$R^{53}$ is hydrogen.

Embodiment A194. A compound according to embodiment A186, wherein
$R^1$ is hydrogen.

Embodiment A195. A compound according to any one of the embodiments A1 to A194, wherein $R^{52}$ and $R^{53}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds.

G² is heteroaryl, fused heterocyclylheteroaryl, or fused cycloalkylheteroaryl, optionally substituted with one or more substituents $R^{43}$, $R^{44}$, and $R^{45}$, wherein said heteroaryl group posesses a nitrogen atom adjacent to the atom joining G² with —N(R¹)—, and wherein $R^{43}$, $R^{44}$, and $R^{45}$ are as defined in embodiment A1.

Embodiment A196. A compound according to embodiment A195, wherein
G² is fused cycloalkylheteroaryl optionally substituted with one or more substituents $R^{43}$, $R^{44}$, and $R^{45}$, wherein said heteroaryl group posesses a nitrogen atom adjacent to the atom joining G² with —N(R¹)—, and wherein $R^{43}$, $R^{44}$, and $R^{45}$ are as defined in embodiment A1.

Embodiment A197. A compound according to embodiment A196 wherein
G² is fused cycloalkylthiazolyl optionally substituted with one or more substituents $R^{43}$, $R^{44}$, and $R^{45}$ and wherein $R^{43}$, $R^{44}$, and $R^{45}$ are as defined in embodiment A1.

Embodiment A198. A compound according to embodiment A197, wherein
G² is fused cycloalkylthiazolyl optionally substituted with —COOH Embodiment A199. A compound according to embodiment A195, wherein
G² is heteroaryl optionally substituted with one or more substituents $R^{43}$, $R^{44}$, and $R^{45}$, wherein said heteroaryl group posesses a nitrogen atom adjacent to the atom joining G² with —N(R¹)—, and wherein $R^{43}$, $R^{44}$, and $R^{45}$ are as defined in embodiment A1.

Embodiment A200. A compound according to embodiment A199, wherein
G² is furanyl, thienyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, or indazolyl, optionally substituted with one or more substituents $R^{43}$, $R^{44}$, and $R^{45}$, wherein $R^{43}$, $R^{44}$, and $R^{45}$ are as defined in embodiment A1.

Embodiment A201. A compound according to embodiment A200 wherein G² is thiazolyl, optionally substituted with one or more substituents $R^{43}$, $R^{44}$, and $R^{45}$, wherein $R^{43}$, $R^{44}$, and $R^{45}$ are as defined in embodiment A1.

Embodiment A202. A compound according to embodiment A201 wherein G² is

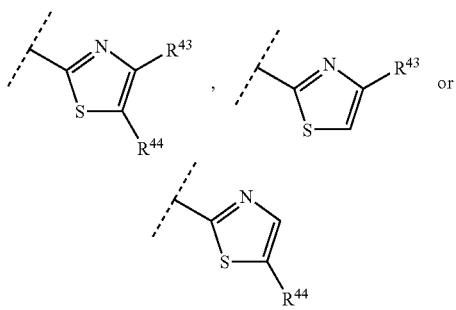

wherein
$R^{43}$ and $R^{44}$ are as defined in embodiment A1.

Embodiment A203. A compound according to embodiment A202 wherein G² is

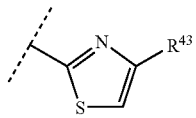

wherein
$R^{43}$ is as defined in embodiment A1.

Embodiment A204. A compound according to embodiment A202 wherein G² is

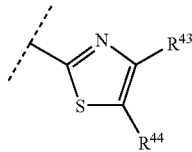

wherein
$R^{43}$ and $R^{44}$ are as defined in embodiment A1.

Embodiment A205. A compound according to embodiment A200 wherein G² is

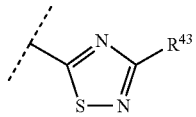

wherein
$R^{43}$ is as defined in embodiment A1.

Embodiment A206. A compound according to embodiment A202 wherein G² is

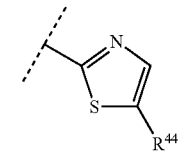

wherein
$R^{44}$ is as defined in embodiment A1.

Embodiment A207. A compound according to any one of the embodiments A1 to A206, wherein
$R^{43}$, $R^{44}$, and $R^{45}$ independently of each other are selected from
—CN, —NO₂, —SCF₃, —OR⁵⁴, —NR⁵⁴R⁵⁵, —SR⁵⁴, —S(O)₂NR⁵⁴R⁵⁵, —S(O)NR⁵⁴R⁵⁵, —S(O)R⁵⁴, —S(O)₂R⁵⁴, —C(O)NR⁵⁴R⁵⁵, —OC(O)NR⁵⁴R⁵⁵, —NR⁵⁴C(O)R⁵⁵, halogen, —S—C₁₋₆-alkylene-OR⁵⁴, —S(O)₂—C₁₋₆-alkylene-OR⁵⁴, —C₁₋₆-alkylene-S—R⁵⁴, —C₁₋₆-alkylene-S(O)R⁵⁴, —C₁₋₆-alkylene-S(O)₂R⁵⁴, —C₁₋₆-alkylene-N(R⁵⁴)S(O)₂R⁵⁵, —N(R⁵⁴)S(O)₂R⁵⁵, —C₁₋₆-alkylene-C(O)NR⁵⁴R⁵⁵, —C₁₋₆-alkylene-N(R⁵⁴)C(O)R⁵⁵, —N(R⁵⁴)C(O)R⁵⁵, —C₁₋₆-alkylene-N(R⁵⁴)C(O)NR⁵⁵R⁵⁶, C₁₋₆-alkylene-NHC(=NR⁵⁴)NR⁵⁵R⁵⁶, —C₁₋₆-alkylene-N(R⁵⁴)C(O)OR⁵⁵, —N($R^{54}$)C(O)O$R^{55}$, —$C_{1-6}$-alkylene-C(O)O$R^{54}$, —OCH$_2$C(O)N$R^{54}R^{55}$, —O(CH$_2$)$_{1-3}$O$R^{54}$, —$C_{1-6}$-alkylene-O—$R^{54}$, —$C_{1-6}$-alkylene-C(O)$R^{54}$, —$C_{1-6}$-alkylene-N$R^{54}R^{55}$, —$C_{1-6}$-alkylene=N—O—$R^{54}$, —$C_{1-6}$-alkylene-N($R^{54}$)S(O)$_2$N$R^{55}R^{56}$, —N($R^{54}$)S(O)$_2$ N$R^{55}R^{56}$, —N($R^{54}$)S(O)$_2$N$R^{55}R^{56}$, —OC(O)$R^{54}$, —C(O)N($R^{54}$)S(O)$_2R^{55}$, —$C_{1-6}$-alkylene-C($R^{54}$)=N—O$R^{55}$, —NHC(=N$R^{54}$)N$R^{55}R^{56}$, —$C_{1-6}$-alkylene-N=C(N($R^{54}R^{55}$))$_2$, —N=C(N($R^{54}R^{55}$))$_2$, —C(O)$R^{54}$ and —C(O)O$R^{54}$; or $C_{1-6}$-alkyl or $C_{2-6}$-alkenyl, each of which may optionally be substituted with one or more substituents independently selected from halogen, $R^{54}$, —CN, —CF$_3$, —OCF$_3$, —O$R^{54}$, —C(O)O$R^{54}$, —N$R^{54}R^{55}$ and $C_{1-6}$-alkyl; or $C_{3-10}$-cycloalkyl, heterocyclyl, $C_{3-10}$-cycloalkyl-$C_{1-6}$-alkylene-, $C_{3-10}$-cycloalkyl-$C_{1-6}$-alkoxy-, $C_{3-10}$-Cycloalkyloxy, heterocyclyl-$C_{1-6}$-alkylene-, of which the heterocyclyl moieties optionally may be substituted with one or more substituents independently selected from $R^{70}$; or aryl, aryloxy, aryl-$C_{1-6}$-alkoxy-, aryl-$C_{1-6}$-alkylene-, heteroaryl, heteroaryl-$C_{1-6}$-alkylene-, of which the aryl and heteroaryl moieties optionally may be substituted with one or more substituents selected from halogen, —C(O)O$R^{54}$, —CN, —CF$_3$, —OCF$_3$, —NO$_2$, —O$R^{54}$, —N$R^{54}R^{55}$ or $C_{1-6}$-alkyl, wherein $R^{54}$, $R^{55}$ and $R^{56}$ are as defined in embodiment A1.

Embodiment A208. A compound according to embodiment A207, wherein $R^{43}$, $R^{44}$, and $R^{45}$ independently of each other are selected from —O$R^{54}$, —N$R^{54}R^{55}$, —S$R^{54}$, —S(O)$R^{54}$, —S(O)$_2$ $R^{54}$, —C(O)N$R^{54}R^{55}$, halogen, —S—$C_{1-6}$-alkylene-O$R^{54}$, —$C_{1-6}$-alkylene-S—$R^{54}$, —$C_{1-6}$-alkylene-S(O)$R^{54}$, —$C_{1-6}$-alkylene-S(O)$_2R^{54}$, —$C_{1-6}$-alkylene-N($R^{54}$)S(O)$_2R^{55}$, —$C_{1-6}$-alkylene-C(O)N$R^{54}R^{55}$, —$C_{1-6}$-alkylene-N($R^{54}$)C(O)$R^{55}$, —$C_{1-6}$-alkylene-N($R^{54}$)C(O)N$R^{55}R^{56}$, $C_{1-6}$-alkylene-NHC(=N$R^{54}$)N$R^{55}R^{56}$, —$C_{1-6}$-alkylene-N($R^{54}$)C(O)O$R^{55}$, —$C_{1-6}$-alkylene-C(O)O$R^{54}$, —$C_{1-6}$-alkylene-O—$R^{54}$, —$C_{1-6}$-alkylene-C(O)$R^{54}$, —$C_{1-6}$-alkylene-N$R^{54}R^{55}$, —$C_{1-6}$-alkylene=N—O—$R^{54}$, —$C_{1-6}$-alkylene-N=C(N($R^{54}R^{55}$))$_2$, —N=C(N($R^{54}R^{55}$))$_2$, —C(O)$R^{54}$ and —C(O)O$R^{54}$; or $C_{1-6}$-alkyl optionally substituted with one or more substituents independently selected from halogen, $R^{54}$, —CN, —CF$_3$, —OCF$_3$, —O$R^{54}$, —C(O)O$R^{54}$, —N$R^{54}R^{55}$ and $C_{1-6}$-alkyl; or Heterocyclyl or heterocyclyl-$C_{1-6}$-alkylene-, of which the heterocyclyl moieties optionally may be substituted with one or more substituents independently selected from $R^{70}$; or aryl, aryl-$C_{1-6}$-alkylene-, heteroaryl, heteroaryl-$C_{1-6}$-alkylene-, of which the aryl and heteroaryl moieties optionally may be substituted with one or more substituents selected from halogen, —C(O)O$R^{54}$, —CN, —CF$_3$, —OCF$_3$, —NO$_2$, —O$R^{54}$, —N$R^{54}R^{55}$ or $C_{1-6}$-alkyl, wherein $R^{54}$, $R^{55}$, $R^{56}$, and $R^{70}$ are as defined in embodiment A1.

Embodiment A209. A compound according to embodiment A208, wherein $R^{43}$, $R^{44}$, and $R^{45}$ independently of each other are selected from
—S$R^{54}$, —S(O)$R^{54}$, —S(O)$_2R^{54}$, halogen, —$C_{1-6}$-alkylene-S—$R^{54}$, —$C_{1-6}$-alkylene-S(O)$R^{54}$, —$C_{1-6}$-alkylene-S(O)$_2R^{54}$, —$C_{1-6}$-alkylene-N($R^{54}$)C(O)O$R^{55}$, —$C_{1-6}$-alkylene-C(O)O$R^{54}$, —$C_{1-6}$-alkylene-O—$R^{54}$, —$C_{1-6}$-alkylene-N$R^{54}R^{55}$, —$C_{1-6}$-alkylene-C(O)$R^{54}$, —C(O)$R^{54}$ and —C(O)O$R^{54}$; or $C_{1-6}$-alkyl optionally substituted with one or more substituents independently selected from halogen, $R^{54}$, —CN, —CF$_3$, —OCF$_3$, —O$R^{54}$, —C(O)O$R^{54}$, —N$R^{54}R^{55}$ and $C_{1-6}$-alkyl; or Heterocyclyl or heterocyclyl-$C_{1-6}$-alkylene-, of which the heterocyclyl moieties optionally may be substituted with one or more substituents independently selected from $R^{70}$; or heteroaryl or heteroaryl-$C_{1-6}$-alkylene-, of which the aryl and heteroaryl moieties optionally may be substituted with one or more substituents selected from halogen, —C(O)O$R^{54}$, —CN, —CF$_3$, —OCF$_3$, —NO$_2$, —O$R^{54}$, —N$R^{54}R^{55}$ or $C_{1-6}$-alkyl, wherein $R^{54}$, $R^{55}$, $R^{56}$, and $R^{70}$ are as defined in embodiment A1.

Embodiment A210. A compound according to embodiment A209, wherein $R^{43}$, $R^{44}$, and $R^{45}$ independently of each other are selected from —S$R^{54}$, —S(O)$_2R^{54}$, halogen, —$C_{1-6}$-alkylene-C(O)O$R^{54}$, and —C(O)O$R^{54}$; or Heterocyclyl or heterocyclyl-$C_{1-6}$-alkylene-, of which the heterocyclyl moieties optionally may be substituted with one or more substituents independently selected from $R^{70}$; or heteroaryl or heteroaryl-$C_{1-6}$-alkylene-, of which the heteroaryl moieties optionally may be substituted with one or more substituents selected from halogen, —C(O)O$R^{54}$, —CN, —CF$_3$, —OCF$_3$, —NO$_2$, —O$R^{54}$, —N$R^{54}R^{55}$ or $C_{1-6}$-alkyl, wherein $R^{54}$, $R^{55}$, $R^{56}$, and $R^{70}$ are as defined in embodiment A1.

Embodiment A211. A compound according to embodiment A210, wherein $R^{43}$, $R^{44}$, and $R^{45}$ independently of each other are selected from —S$R^{54}$, —S(O)$_2R^{54}$, halogen, —$C_{1-6}$-alkylene-C(O)O$R^{54}$, and —C(O)O$R^{54}$; or heterocyclyl-$C_{1-6}$-alkylene-, wherein heterocyclyl is selected from imidazolyl, piperidyl, piperazinyl, and morpholinyl, and of which the heterocyclyl moieties optionally may be substituted with one or more substituents independently selected from $R^{70}$; or heteroaryl or heteroaryl-$C_{1-6}$-alkylene-, wherein heteroaryl is selected from thiazolyl, triazolyl, or tetrazolyl, and of which the heteroaryl moieties optionally may be substituted with one or more substituents selected from halogen, —C(O)O$R^{54}$, —CN, —CF$_3$, —OCF$_3$, —NO$_2$, —O$R^{54}$, —N$R^{54}R^{55}$ or $C_{1-6}$-alkyl, wherein $R^{54}$, $R^{55}$, $R^{56}$, and $R^{70}$ are as defined in embodiment A1.

Embodiment A212. A compound according to embodiment A209, wherein $R^{43}$, $R^{44}$, and $R^{45}$ independently of each other are selected from —$C_{1-6}$-alkylene-S—$R^{54}$, —$C_{1-6}$-alkylene-O—$R^{54}$, —$C_{1-6}$-alkylene-S(O)$_2R^{54}$ or —$C_{1-6}$-alkylene-N$R^{54}R^{55}$, wherein $R^{54}$ and $R^{55}$ are as defined in embodiment A1.

Embodiment A213. A compound according to embodiment A209, wherein $R^{43}$ is —$C_{1-6}$-alkylene-S—$R^{54}$, wherein $R^{54}$ is as defined in embodiment A1.

Embodiment A214. $R^{43}$ is —$C_{1-6}$-alkylene-O—$R^{54}$, wherein $R^{54}$ is as defined in embodiment A1.

Embodiment A215. $R^{43}$ is —$C_{1-6}$-alkylene-$NR^{54}R^{55}$, wherein
$R^{54}$ and $R^{55}$ are as defined in embodiment A1.

Embodiment A216. $R^{43}$ is —$C_{1-6}$-alkylene-$S(O)_2R^{54}$, wherein
$R^{54}$ is as defined in embodiment A1.

Embodiment A217. A compound according to any one of the embodiments A207 to A210 wherein $R^{43}$ is heteroaryl or heteroaryl-$C_{1-6}$-alkylene-optionally substituted with one or more substituents selected from halogen, —$C(O)OR^{54}$, —CN, —$CF_3$, —$OCF_3$, —$NO_2$, —$OR^{54}$, —$NR^{54}R^{55}$ or $C_{1-6}$-alkyl, wherein $R^{54}$ and $R^{55}$ are as defined in embodiment A1.

Embodiment A218. A compound according to embodiment A217 wherein $R^{43}$ is heteroaryl optionally substituted with one or more substituents selected from halogen, —$C(O)OR^{54}$, —CN, —$CF_3$, —$OCF_3$, —$NO_2$, —$OR^{54}$, —$NR^{54}R^{55}$ or $C_{1-6}$-alkyl, wherein $R^{54}$ and $R^{55}$ are as defined in embodiment A1.

Embodiment A219. A compound according to embodiment A217 wherein $R^{43}$ is heteroaryl-$C_{1-6}$-alkylene-optionally substituted with one or more substituents selected from halogen, —$C(O)OR^{54}$, —CN, —$CF_3$, —$OCF_3$, —$NO_2$, —$OR^{54}$, —$NR^{54}R^{55}$ or $C_{1-6}$-alkyl, wherein $R^{54}$ and $R^{55}$ are as defined in embodiment A1.

Embodiment A220. A compound according to any one of the embodiments A207 to A211 wherein $R^{70}$ is =O, methyl or $C(O)OR^{75}$.

Embodiment A221. A compound according to any one of the embodiments A207 to A211 wherein $R^{70}$ is —C(O)OH Embodiment A222. A compound according to any one of the embodiments A207 to A211 wherein $R^{70}$ is —$(CH_2)_{1-3}C(O)$OH.

Embodiment A223. A compound according to any one of the embodiments A207 to A211 wherein $R^{70}$ is —$S(O)_2CH_3$.

Embodiment A224. A compound according to embodiment A211 wherein $R^{43}$ is —$C_{1-6}$-alkylene-$C(O)OR^{54}$.

Embodiment A225. A compound according to embodiment A224 wherein $R^{43}$ is —$CH_2$—$C(O)OR^{54}$.

Embodiment A226. A compound according to embodiment A211 wherein $R^{44}$ is —$SR^{54}$.

Embodiment A227. A compound according to embodiment A211 wherein $R^{44}$ is —$S(O)_2R^{54}$.

Embodiment A228. A compound according to embodiment A211 wherein $R^{44}$ is halogen.

Embodiment A229. A compound according to any one of the embodiments A1 to A228 wherein
$R^{54}$, $R^{55}$ and $R^{56}$ independently of each other are hydrogen, $C_{1-6}$-alkyl, aryl-$C_{1-6}$-alkylene-, heteroaryl-$C_{1-6}$-alkylene-, heterocyclyl, heterocyclyl-$C_{1-6}$-alkylene-, heteroaryl, or aryl, each of which is optionally substituted with one or more substituents independently selected from $R^{71}$;
or
$R^{54}$ and $R^{55}$ independently of each other are hydrogen or —$(CHR^{72})_u$—$(CHR^{73})_v$—$W^6$,
or
$R^{54}$ and $R^{55}$, when attached to the same nitrogen atom, together with the said nitrogen atom may form a 3 to 8 membered heterocyclic ring optionally containing one or two further heteroatoms selected from nitrogen, oxygen and sulfur, and optionally containing one or two double bonds, and optionally substituted with one or more $C_{1-6}$-alkyl groups,
wherein $R^{71}$, $R^{72}$, $R^{73}$, u, v, and $W^6$ are as defined in embodiment A1.

Embodiment A230. A compound according to embodiment A229 wherein
$R^{54}$, $R^{55}$ and $R^{56}$ independently of each other are hydrogen, $C_{1-6}$-alkyl, heterocyclyl, heterocyclyl-$C_{1-6}$-alkylene-, heteroaryl, or aryl, each of which is optionally substituted with one or more substituents independently selected from $R^{71}$;
or
$R^{54}$ and $R^{55}$ independently of each other are hydrogen or —$(CHR^{72})_u$—$(CHR^{73})_v$—$W^6$,
wherein $R^{71}$, $R^{72}$, $R^{73}$, u, v, and $W^6$ are as defined in embodiment A1.

Embodiment A231. A compound according to any one of the embodiments A1 to A230 wherein
$R^{54}$, $R^{55}$ and $R^{56}$ independently of each other are hydrogen, methyl, ethyl, propyl, butyl, isopropyl, isobutyl, sec-butyl, tert-butyl, 3-pentyl, 2-pentyl, or 3-methyl-butyl.

Embodiment A232. A compound according to embodiment A231 wherein
$R^{54}$, $R^{55}$ and $R^{56}$ independently of each other are hydrogen, methyl, ethyl, propyl, butyl, isopropyl, isobutyl, sec-butyl, or tert-butyl.

Embodiment A233. A compound according to embodiment A232 wherein
$R^{54}$, $R^{55}$ and $R^{56}$ independently of each other are hydrogen, methyl, ethyl, propyl, butyl, isopropyl, isobutyl, sec-butyl, or tert-butyl.

Embodiment A234. A compound according to embodiment A233 wherein
$R^{54}$, $R^{55}$ and $R^{56}$ independently of each other are hydrogen, methyl or ethyl.

Embodiment A235. A compound according to embodiment A234 wherein
$R^{54}$ is hydrogen.

Embodiment A236. A compound according to any one of the embodiments A1 to A230 wherein
$R^{54}$, $R^{55}$ and $R^{56}$ independently of each other are oxetanyl, tetrahydrofuranyl, tetrahydropyranyl, oxepanyl, azetidyl, pyrrolidyl, piperidyl, hexahydroazepinyl, thietanyl, thiolanyl, tetrahydrothiopyranyl, thiepanyl, 1,4-oxathianyl, 1,3-dioxolanyl, 1,2-dithiolanyl, 1,3-dithiolanyl, hexahydro-pyridazinyl, imidazolidyl, 1,3-dioxanyl, morpholinyl, 1,3-dithianyl, 1,4-dioxanyl, 1,4-dithianyl, or thiomorpholinyl, each of which is optionally substituted with one or more substituents independently selected from $R^{71}$, wherein $R^{71}$ is as defined in embodiment A1.

Embodiment A237. A compound according to embodiment A236 wherein
$R^{54}$, $R^{55}$ and $R^{56}$ independently of each other are tetrahydropyranyl, oxepanyl, piperidyl, hexahydroazepinyl, tetrahydrothiopyranyl, thiepanyl, 1,4-oxathianyl, 1,3-dithiolanyl, hexahydro-pyridazinyl, 1,3-dioxanyl, morpholinyl, 1,3-dithianyl, 1,4-dioxanyl, 1,4-dithianyl, or thiomorpholinyl, each of which is optionally substituted with one or more substituents independently selected from $R^{71}$, wherein $R^{71}$ is as defined in embodiment A1.

Embodiment A238. A compound according to embodiment A237 wherein
$R^{54}$, $R^{55}$ and $R^{56}$ independently of each other are tetrahydropyranyl, piperidyl, tetrahydrothiopyranyl, 1,4-oxathianyl, hexahydro-pyridazinyl, morpholinyl, 1,4-dioxanyl, 1,4-dithianyl, or thiomorpholinyl, each of which is optionally substituted with one or more substituents independently selected from $R^{71}$, wherein $R^{71}$ is as defined in embodiment A1.

Embodiment A239. A compound according to embodiment A238 wherein
$R^{54}$, $R^{55}$ and $R^{56}$ independently of each other are tetrahydropyranyl, piperidyl, tetrahydrothiopyranyl, or morpholinyl, each of which is optionally substituted with one or more substituents independently selected from $R^{71}$, wherein $R^{71}$ is as defined in embodiment A1.

Embodiment A240. A compound according to embodiment A239 wherein
$R^{54}$, $R^{55}$ and $R^{56}$ independently of each other are piperidyl or morpholinyl, each of which is optionally substituted with one or more substituents independently selected from $R^{71}$, wherein $R^{71}$ is as defined in embodiment A1.

Embodiment A241. A compound according to embodiment A240 wherein
$R^{54}$, $R^{55}$ and $R^{56}$ independently of each other are piperidyl or morpholinyl.
242.

Embodiment A243. A compound according to any one of the embodiments A1 to A230 wherein
$R^{54}$, $R^{55}$ and $R^{56}$ independently of each other are furanyl, thienyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, purinyl, or indazolyl, each of which is optionally substituted with one or more substituents independently selected from $R^{71}$, wherein $R^{71}$ is as defined in embodiment A1.

Embodiment A244. A compound according to embodiment A243 wherein
$R^{54}$, $R^{55}$ and $R^{56}$ independently of each other are furanyl, thienyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, benzofuranyl, indolyl, or purinyl, each of which is optionally substituted with one or more substituents independently selected from $R^{71}$, wherein $R^{71}$ is as defined in embodiment A1.

Embodiment A245. A compound according to embodiment A244 wherein
$R^{54}$, $R^{55}$ and $R^{56}$ independently of each other are imidazolyl, triazolyl, tetrazolyl, thiazolyl, pyridinyl, pyrimidinyl, benzofuranyl, indolyl, or purinyl, each of which is optionally substituted with one or more substituents independently selected from $R^{71}$, wherein $R^{71}$ is as defined in embodiment A1.

Embodiment A246. A compound according to embodiment A245 wherein
$R^{54}$, $R^{55}$ and $R^{56}$ independently of each other are imidazolyl, triazolyl, tetrazolyl, thiazolyl, pyridinyl, pyrimidinyl, or purinyl, each of which is optionally substituted with one or more substituents independently selected from $R^{71}$, wherein $R^{71}$ is as defined in embodiment A1.

Embodiment A247. A compound according to embodiment A246 wherein
$R^{54}$, $R^{55}$ and $R^{56}$ independently of each other are imidazolyl, triazolyl, tetrazolyl, thiazolyl, pyridinyl, pyrimidinyl, each of which is optionally substituted with one or more substituents independently selected from $R^{71}$, wherein $R^{71}$ is as defined in embodiment A1.

Embodiment A248. A compound according to embodiment A247 wherein $R^{54}$ is imidazolyl optionally substituted with one or more substituents independently selected from $R^{71}$, wherein $R^{71}$ is as defined in embodiment A1.

Embodiment A249. A compound according to embodiment A247 wherein $R^{54}$ is triazolyl optionally substituted with one or more substituents independently selected from $R^{71}$, wherein $R^{71}$ is as defined in embodiment A1.

Embodiment A250. A compound according to embodiment A247 wherein $R^{54}$ is tetrazolyl optionally substituted with one or more substituents independently selected from $R^{71}$, wherein $R^{71}$ is as defined in embodiment A1.

Embodiment A251. A compound according to embodiment A247 wherein $R^{54}$ is thiazolyl optionally substituted with one or more substituents independently selected from $R^{71}$, wherein $R^{71}$ is as defined in embodiment A1.

Embodiment A252. A compound according to embodiment A247 wherein $R^{54}$ is pyridinyl optionally substituted with one or more substituents independently selected from $R^{71}$, wherein $R^{71}$ is as defined in embodiment A1.

Embodiment A253. A compound according to embodiment A247 wherein $R^{54}$ is pyrimidinyl optionally substituted with one or more substituents independently selected from $R^{71}$, wherein $R^{71}$ is as defined in embodiment A1.

Embodiment A254. A compound according to embodiment A246 wherein $R^{54}$ is purinyl optionally substituted with one or more substituents independently selected from $R^{71}$, wherein $R^{71}$ is as defined in embodiment A1.

Embodiment A255. A compound according to any one of the embodiments A1 to A254 wherein $R^{71}$ is methyl or =O.

Embodiment A256. A compound according to any one of the embodiments A1 to A254 wherein $R^{71}$ is —C(O)OH Embodiment A257. A compound according to any one of the embodiments A1 to A254 wherein $R^{71}$ is —(CH$_2$)$_{1-3}$C(O)OH.

Embodiment A258. A compound according to any one of the embodiments A1 to A254 wherein $R^{70}$ is —(CH$_2$)$_{1-3}$NR$^{75}$R$^{76}$.

Embodiment A259. A compound according to any one of the embodiments A1 to A230 wherein u is 0 or 1.

Embodiment A260. A compound according to embodiment A259 wherein u is 0.

Embodiment A261. A compound according to embodiment A259 wherein u is 1.

Embodiment A262. A compound according to any one of the embodiments A1 to A230 wherein v is 0 or 1.

Embodiment A263. A compound according to embodiment A262 wherein v is 0.

Embodiment A264. A compound according to embodiment A262 wherein v is 1.

Embodiment A265. A compound according to any one of the embodiments A1 to A230 wherein u is 0 and v is 1.

Embodiment A266. A compound according to any one of the embodiments A1 to A230 wherein u and v are both 0.

Embodiment A267. A compound according to any one of the embodiments A1 to A230 or A259 to A266 wherein $R^{72}$ and $R^{73}$ are independently selected from hydrogen, hydroxy or —C(O)OR$^{75}$.

Embodiment A268. A compound according to embodiment A267 wherein $R^{72}$ and $R^{73}$ are independently selected from hydrogen or —C(O)OR$^{75}$, wherein $R^{75}$ is as defined in embodiment A1.

Embodiment A269. A compound according to embodiment A267 wherein $R^{72}$ and $R^{73}$ are hydrogen.

Embodiment A270. A compound according to any one of the embodiments A1 to A230 or A259 to A269 wherein
- $W^6$ is —O—R$^{75}$, —C(O)O—R$^{75}$, —C(O)—R$^{75}$, —NR$^{75}$R$^{76}$, —NHCH$_2$C(O)R$^{75}$, —NHC(O)R$^{75}$, —S(O)$_2$R$^{75}$, —NHS(O)$_2$R$^{75}$, or
- $W^6$ is heterocyclyl, wherein $R^{75}$ and $R^{76}$ are as defined in embodiment A1.

Embodiment A271. A compound according to embodiment A270 wherein
- $W^6$ is —O—R$^{75}$, —C(O)O—R$^{75}$, —C(O)—R$^{75}$, —NR$^{75}$R$^{76}$, —NHCH$_2$C(O)R$^{75}$, —NHC(O)R$^{75}$, —S(O)$_2$R$^{75}$, —NHS(O)$_2$R$^{75}$, or
- $W^6$ is oxetanyl, tetrahydrofuranyl, tetrahydropyranyl, oxepanyl, azetidyl, pyrrolidyl, piperidyl, hexahydroazepinyl, thietanyl, thiolanyl, tetrahydrothiopyranyl, thiepanyl, 1,4-oxathianyl, 1,3-dioxolanyl, 1,2-dithiolanyl, 1,3-dithiolanyl, hexahydro-pyridazinyl, imidazolidyl, 1,3-dioxanyl, morpholinyl, 1,3-dithianyl, 1,4-dioxanyl, 1,4-dithianyl, or thiomorpholinyl, wherein $R^{75}$ and $R^{76}$ are as defined in embodiment A1.

Embodiment A272. A compound according to embodiment A270 wherein
- $W^6$ is —O—R$^{75}$, —C(O)O—R$^{75}$, —C(O)—R$^{75}$, —NR$^{75}$R$^{76}$, —NHCH$_2$C(O)R$^{75}$, —NHC(O)R$^{75}$, —S(O)$_2$R$^{75}$, —NHS(O)$_2$R$^{75}$, or
- $W^6$ is tetrahydropyranyl, oxepanyl, piperidyl, hexahydroazepinyl, tetrahydrothiopyranyl, thiepanyl, 1,4-oxathianyl, morpholinyl, 1,4-dioxanyl, 1,4-dithianyl, or thiomorpholinyl, wherein $R^{75}$ and $R^{76}$ are as defined in embodiment A1.

Embodiment A273. A compound according to embodiment A272 wherein
- $W^6$ is —O—R$^{75}$, —C(O)O—R$^{75}$, —C(O)—R$^{75}$, —NR$^{75}$R$^{76}$, —NHCH$_2$C(O)R$^{75}$, —NHC(O)R$^{75}$, —S(O)$_2$R$^{75}$, —NHS(O)$_2$R$^{75}$, or
- $W^6$ is tetrahydropyranyl, piperidyl, tetrahydrothiopyranyl, or morpholinyl, wherein $R^{75}$ and $R^{76}$ are as defined in embodiment A1.

Embodiment A274. A compound according to embodiment A273 wherein
- $W^6$ is —O—R$^{75}$, —C(O)O—R$^{75}$, —NR$^{75}$R$^{76}$, —NHC(O)R$^{75}$, —S(O)$_2$R$^{75}$, or
- $W^6$ is tetrahydropyranyl, piperidyl, tetrahydrothiopyranyl, or morpholinyl, wherein $R^{75}$ and $R^{76}$ are as defined in embodiment A1.

Embodiment A275. A compound according to embodiment A274 wherein
- $W^6$ is —O—R$^{75}$, or —C(O)O—R$^{75}$, wherein $R^{75}$ is as defined in embodiment A1.

Embodiment A276. A compound according to embodiment A275 wherein $W^6$ is —C(O)O—R$^{75}$, wherein $R^{75}$ is as defined in embodiment A1.

Embodiment A277. A compound according to any one of the embodiments A1 to A230 or A259 to A276 wherein $R^{75}$ and $R^{76}$ are independently selected from hydrogen, —OH, or $C_{1-6}$-alkyl optionally substituted with —NH$_2$.

Embodiment A278. A compound according to embodiment A277 wherein $R^{75}$ and $R^{76}$ are independently selected from hydrogen, —OH, or methyl.

Embodiment A279. A compound according to embodiment A278 wherein $R^{75}$ and $R^{76}$ are independently selected from hydrogen or —OH.

Embodiment A280. A compound according to embodiment A279 wherein $R^{75}$ is hydrogen.

Embodiment A281. A compound according to any one of the embodiments A1 to A280, which compound is an activator of glucokinase, when tested in the Glucokinase Activation Assay (I) disclosed herein at a glucose concentration of 2 mM.

Embodiment A282. A compound according to any one of the embodiments A1 to A281, which compound is an activator of glucokinase, when tested in the Glucokinase Activation Assay (I) disclosed herein at a glucose concentration of from 10 to 15 mM.

Embodiment A283. A compound according to any one of the embodiments A1 to A282, which compound, at a concentration of 30 μM, is capable of providing an at least 1.5, such as at least 1.7, for instance at least 2.0 fold activation of glucokinase in the Glucokinase Activation Assay (I) disclosed herein at a glucose concentration of 2 mM.

Embodiment A284. A compound according to any one of the embodiments A1 to A283, which compound, at a concentration of 30 μM, is capable of providing an at least 1.5, such as at least 1.7, for instance at least 2.0 fold activation of glucokinase in the Glucokinase Activation Assay (I) disclosed herein at a glucose concentration of from 10 to 15 mM.

Embodiment A285. A compound according to any one of the embodiments A1 to A284, which at a concentration of 5 μM is capable of providing an at least 1.5, such as at least 1.7, for instance at least 2.0 fold activation of glucokinase in the Glucokinase Activation Assay (I) disclosed herein at a glucose concentration of 2 mM.

Embodiment A286. A compound according to any one of the embodiments A1 to A285, which at a concentration of 5 μM is capable of providing an at least 1.5, such as at least 1.7, for instance at least 2.0 fold activation of glucokinase in the Glucokinase Activation Assay (I) disclosed herein at a glucose concentration of from 10 to 15 mM.

Embodiment A287. A glucose kinase activator compound defined as a compound which at a compound concentration of at or below 30 μM at a glucose concentration of 2 mM in the Glucokinase Activation Assay (I) disclosed herein gives 1.5-fold higher glucokinase activity than measured at a glucose concentration of 2 mM in the Glucokinase Activation Assay (I) without compound, where the increase in glucokinase activity provided by the compound increases with increasing concentrations of glucose.

Embodiment A288. A compound according to any one of the embodiments A1 to A286, which compound provides an increase in glucokinase activity, where the increase in glucokinase activity provided by the compound increases with increasing concentrations of glucose.

Embodiment A289. A compound according to embodiment A287 or embodiment A288, which provides an increase in glucokinase activity in Glucokinase Activation Assay (I) disclosed herein at a glucose concentration of 15 mM, which increase is significantly higher than the increase in glucokinase activity provided by the compound in Glucokinase Activation Assay (I) disclosed herein at a glucose concentration of 5 mM.

Embodiment A290. A compound according to any one of the embodiments A287 to A289, which at a compound concentration of 10 µM provides an increase in glucokinase activity in Glucokinase Activation Assay (I) disclosed herein at a glucose concentration of 15 mM, which increase is significantly higher than the increase in glucokinase activity provided by the compound at a compound concentration of 10 µM in Glucokinase Activation Assay (I) disclosed herein at a glucose concentration of 5 mM.

Embodiment A291. A compound according to any one of the embodiments A287 to A290, which at a compound concentration of 10 µM provides an increase in glucokinase activity in Glucokinase Activation Assay (I) disclosed herein at a glucose concentration of 15 mM, which increase is at least 1.1 fold higher, such as at least 1.2 fold higher, for instance at least 1.3 fold higher, such as at least 1.4 fold higher, for instance 1.5 fold higher, such as at least 1.6 fold higher, for instance at least 1.7 fold higher, such as at least 1.8 fold higher, for instance at least 1.9 fold higher, such as at least 2.0 fold higher than the increase in glucokinase activity provided by the compound at a compound concentration of 10 µM in Glucokinase Activation Assay (I) disclosed herein at a glucose concentration of 5 mM.

Embodiment A292. A glucose kinase activator compound defined as a compound which at a compound concentration of at or below 30 µM at a glucose concentration of 2 mM in the Glucokinase Activation Assay (I) disclosed herein gives 1.5-fold higher glucokinase activity than measured at a glucose concentration of 2 mM in the Glucokinase Activation Assay (I) without compound, which glucose kinase activator compound increases glucose utilization in the liver without inducing any increase in insulin secretion in response to glucose.

Embodiment A293. A glucose kinase activator compound defined as a compound which at a compound concentration of at or below 30 µM at a glucose concentration of 2 mM in the Glucokinase Activation Assay (I) disclosed herein gives 1.5-fold higher glucokinase activity than measured at a glucose concentration of 2 mM in the Glucokinase Activation Assay (I) without compound, which glucose kinase activator compound shows a significantly higher activity in isolated hepatocytes compared to the activity of the glucokinase compound in Ins-1 cells.

Embodiment A294. A compound according to any one of the embodiments A1 to A291, which compound increases glucose utilization in the liver without inducing any increase in insulin secretion in response to glucose.

Embodiment A295. A compound according to any one of the embodiments A1 to A291, which compound shows a significantly higher activity in isolated hepatocytes compared to the activity of the compound in Ins-1 cells.

Embodiment A296. A compound according to any one of the embodiments A292 to A295, which compound shows a significantly higher activity in isolated hepatocytes measured as described in the Glucokinase Activity Assay (II) compared to the activity of the compound in Ins-1 cells measured as described in the Glucokinase Activity Assay (III).

Embodiment A297. A compound according to embodiment A296, which compound shows an activity in isolated hepatocytes measured as described in the Glucokinase Activity Assay (II) which activity is at least 1.1 fold higher, such as at least 1.2 fold higher, for instance at least 1.3 fold higher, such as at least 1.4 fold higher, for instance 1.5 fold higher, such as at least 1.6 fold higher, for instance at least 1.7 fold higher, such as at least 1.8 fold higher, for instance at least 1.9 fold higher, such as at least 2.0 fold higher, for instance at least a 3.0 fold higher, such as at least a 4.0 fold higher, for instance at least 5.0 fold higher, such as at least 10 fold higher than the activity of the compound in Ins-1 cells measured as described in the Glucokinase Activity Assay (III).

Embodiment A298. A compound according to embodiment A296, which compound shows no activity in the Ins-1 cells measured as described in the Glucokinase Activity Assay (III).

Embodiment A299. A method of preventing hypoglycaemia comprising administration of a compound according to any one of the embodiments A1 to A298.

Embodiment A300. The use of a compound according to any one of the embodiments A1 to Embodiment A298 for the preparation of a medicament for the prevention of hypoglycaemia.

Embodiment A301. A compound according to any one of embodiments A1 to A298, which is an agent useful for the treatment of an indication selected from the group consisting of hyperglycemia, IGT, insulin resistance syndrome, syndrome X, type 2 diabetes, type 1 diabetes, dyslipidemia, hypertension, and obesity.

Embodiment A302. A compound according to any one of embodiments A1 to A301 for use as a medicament.

Embodiment A303. A compound according to any one of embodiments A1 to A301 for treatment of hyperglycemia, for treatment of IGT, for treatment of Syndrome X, for treatment of type 2 diabetes, for treatment of type 1 diabetes, for treatment of dyslipidemia, for treatment of hyperlipidemia, for treatment of hypertension, for treatment of obesity, for lowering of food intake, for appetite regulation, for regulating feeding behaviour, or for enhancing the secretion of enteroincretins, such as GLP-1.

Embodiment A304. A pharmaceutical composition comprising, as an active ingredient, at least one compound according to any one of embodiments A1 to 303 together with one or more pharmaceutically acceptable carriers or excipients.

Embodiment A305. A pharmaceutical composition according to embodiment A304 in unit dosage form, comprising from about 0.05 mg to about 1000 mg, preferably from about 0.1 mg to about 500 mg and especially preferred from about 0.5 mg to about 200 mg of the compound according to any one of embodiments A1 to 303.

Embodiment A306. Use of a compound according to any one of the embodiments A1 to 303 for increasing the activity of glucokinase.

Embodiment A307. Use of a compound according to any one of embodiments A1 to A303 for the preparation of a medicament for the treatment of metabolic disorders, for blood glucose lowering, for the treatment of hyperglycemia, for the treatment of IGT, for the treatment of Syndrome X, for the treatment of impaired fasting glucose (IFG), for the treatment of type 2 diabetes, for the treatment of type 1 diabetes, for delaying the progression of impaired glucose tolerance (IGT) to type 2 diabetes, for delaying the progression of non-insulin requiring type 2 diabetes to insulin requiring type 2 diabetes, for the treatment of dyslipidemia, for the treatment of hyperlipidemia, for the treatment of hypertension, for lowering of food intake, for appetite regulation, for the treatment of obesity, for regulating feeding behaviour, or for enhancing the secretion of enteroincretins.

Embodiment A308. Use of a compound according to any one of embodiments A1 to A303 for the preparation of a medicament for the adjuvant treatment of type 1 diabetes for preventing the onset of diabetic complications.

Embodiment A309. Use of a compound according to any one of embodiments A1 to A303 for the preparation of a medicament for increasing the number and/or the size of beta cells in a mammalian subject, for treatment of beta cell degeneration, in particular apoptosis of beta cells, or for treatment of functional dyspepsia, in particular irritable bowel syndrome.

Embodiment A310. Use according to any one of the embodiments A307 to A309 in a regimen which comprises treatment with a further antidiabetic agent.

Embodiment A311. Use according to any one of the embodiments A307 to A310 in a regimen which comprises treatment with a further antihyperlipidemic agent.

Embodiment A312. Use according to any one of embodiments A307 to A311 in a regimen which comprises treatment with a further antiobesity agent.

Embodiment A313. Use according to any one of embodiments A307 to A312 in a regimen which comprises treatment with a further antihypertensive agent.

Embodiment A314. Use of a compound according to any one of the embodiments A1 to A303 or a pharmaceutical composition according to embodiment A304 or embodiment A305 for the treatment of metabolic disorders, for blood glucose lowering, for the treatment of hyperglycemia, for treatment of IGT, for treatment of Syndrome X, for the treatment of impaired fasting glucose (IFG), for treatment of type 2 diabetes, for treatment of type 1 diabetes, for delaying the progression of impaired glucose tolerance (IGT) to type 2 diabetes, for delaying the progression of non-insulin requiring type 2 diabetes to insulin requiring type 2 diabetes, for treatment of dyslipidemia, for treatment of hyperlipidemia, for treatment of hypertension, for the treatment or prophylaxis of obesity, for lowering of food intake, for appetite regulation, for regulating feeding behaviour, or for enhancing the secretion of enteroincretins.

Embodiment A315. Use of a compound according to any one of the embodiments A1 to A303 or a pharmaceutical composition according to embodiment A304 or embodiment A305 for the adjuvant treatment of type 1 diabetes for preventing the onset of diabetic complications.

Embodiment A316. Use of a compound according to any one of the embodiments A1 to A303 or a pharmaceutical composition according to embodiment A304 or embodiment A305 for increasing the number and/or the size of beta cells in a mammalian subject, for treatment of beta cell degeneration, in particular apoptosis of beta cells, or for treatment of functional dyspepsia, in particular irritable bowel syndrome.

Further embodiments are clear from the appended claims.

Included within the scope of the present invention are the individual enantiomers of the compounds represented by formula (I) above as well as any wholly or partially racemic mixtures thereof. The present invention also covers the individual enantiomers of the compounds represented by formula (I) above as mixtures with diastereoisomers thereof in which one or more stereocenters are inverted.

The present invention provides glucose sensitive glucokinase activators, that is glucokinase activators, for instance of the general formula (I), which provides a higher increase in glucokinase activity at lower concentrations of glucose. This should be taken to mean that when the glucose concentration is low, then the glucose sensitive glucokinase activator provides an increase in the glucokinase activity, which increase is higher than the increase in glucokinase activity provided by the compound when glucose concentration is high. The compound may for instance provide a 4.0 fold increase in glucokinase activity at a glucose concentration of 5 mM and a 2.0 fold increase in glucokinase activity at a glucose concentration of 15 mM, thus providing an increase in glucokinase activity at a glucose concentration of 5 mM, which increase is 2.0 fold higher than the increase in glucokinase activity provided by the compound at a glucose concentration of 15 mM. For the purpose of describing the present invention, the glucose sensitivity may be assayed by use of Glucokinase Activity Assay (I) where the activity of the glucokinase activator is measured at different concentrations of glucose.

The glucose sensitivity of a glucokinase activator may for instance be measured at a glucose concentration of 5 mM and at a glucose concentration of 15 mM using the same concentration of glucokinase activator, such as a concentration of 10 µM. The two measurements may then be compared and if the fold activity at a glucose concentration of 5 mM (the lower glucose concentration)—in the above example 4.0 fold—is significantly higher than the fold activity at a glucose concentration of 15 mM (the higher glucose concentration—in the above example 2.0 fold—then the glucokinase activator is deemed to be a glucose sensitive glucokinase activator. In the above example, the increase in glucokinase activity at a glucose concentration of 5 mM is 2.0 fold higher than the increase in glucokinase activity at a glucose concentration of 15 mM. The increase in glucokinase activity provided by the glucokinase activator at 5 mM glucose may for instance be at least 1.1 fold higher, such as at least 1.2 fold higher, for instance at least 1.3 fold higher, such as at least 1.4 fold higher, for instance 1.5 fold higher, such as at least 1.6 fold higher, for instance at least 1.7 fold higher, such as at least 1.8 fold higher, for instance at least 1.9 fold higher, such as at least 2.0 fold higher than the activity of the glucokinase activator at 15 mM glucose.

The present invention provides liver specific glucokinase activators, that is, glucokinase activators, for instance of the general formula (I), which increase glucose utilization in the liver (i.e. increase glycogen deposition) without inducing any increase in insulin secretion in response to glucose. For the purpose of describing this invention, the potential liver selectivity of a glucokinase activator may be assayed by comparison of the results obtained in response to the glucokinase activator in isolated hepatocytes and the results obtained in response to the glucokinase activator in Ins-1 cells. Glucokinase activators, which show a significantly higher activity in isolated hepatocytes measured as described in the Glucokinase Activity Assay (II) compared to the activity in Ins-1 cells measured as described in the Glucokinase Activity Assay (III), are deemed to be liver specific glucokinase activators. The activity of the glucokinase activator in Glucokinase Activity Assay (II) (hepatocytes) may for instance be at least 1.1 fold higher, such as at least 1.2 fold higher, for instance at least 1.3 fold higher, such as at least 1.4 fold higher, for instance 1.5 fold higher, such as at least 1.6 fold higher, for instance at least 1.7 fold higher, such as at least 1.8 fold higher, for instance at least 1.9 fold higher, such as at least 2.0 fold higher, for instance at least a 3.0 fold higher, such as at least a 4.0 fold higher, for instance at least 5.0 fold higher, such as at least 10 fold higher than the activity of the glucokinase activator in Glucokinase Activity Assay (III) (Ins-1 cells). Alternatively, the glucokinase activator may show no activity in the Ins-1 cells measured as described in the Glucokinase Activity Assay (III), while showing a significant activity in hepatocytes measured as described in the Glucokinase Activity Assay (II).

Such liver-specific glucokinase activators may be particularly useful in patients that are at risk of experiencing hypoglycaemia. Since liver glucokinase is highly sensitive to the serum concentration of glucose, the blood glucose-decreasing effect of the GK in the liver will only occur when the serum concentration of glucose is relatively high. When the serum concentration of glucose is relatively low, the effect of the GK in the liver decreases, and thus does not further lower the glucose concentration in the blood. This mechanism remains even when the liver GK is affected by a GK activator. The effect of GK on the pancreatic beta cells is not similarly glucose-sensitive. Therefore a GK activator which affects both liver and beta cells may have a glucose-lowering effect even at low serum glucose concentration, resulting in a risk of hypoglycaemia. A GK activator which affects only, or which primarily effects, the liver GK will thus provide a treatment with a lower risk of hypoglycaemia. Thus the invention provides a method of preventing hypoglycaemia comprising administration of a liver-specific glucokinase activator, as well as the use of a liver-specific glucokinase activator for the preparation of a medicament for the prevention of hypoglycaemia.

Examples of liver specific glucokinase activators are

2-{3-[2-(2,3-dimethoxyphenoxy)-5-fluorophenyl]ureido}thiazole-4-carboxylic acid ethyl ester, (2-{3-[2-(2,3-dimethoxyphenoxy)-5-fluorophenyl]ureido}thiazol-4-yl)acetic acid ethyl ester, (2-{3-[5-fluoro-2-(2-fluoro-6-methoxyphenoxy)phenyl]ureido}thiazol-4-yl)acetic acid, 2-{3-[2-(2,3-dimethoxyphenoxy)-5-fluorophenyl]ureido}thiazole-4-carboxylic acid, 2-(2-{3-[5-fluoro-2-(2-fluoro-6-methoxyphenoxy)phenyl]ureido}thiazol-4-yl)-N-(2-morpholin-4-ylethyl)acetamide,

[2-(2-{3-[5-fluoro-2-(2-fluoro-6-methoxyphenoxy)phenyl]ureido}thiazol-4-yl)acetylamino]acetic acid, {2-[3-(2-cyclopentanecarbonyl-4-methyl-phenyl)-ureido]-thiazol-4-yl}acetic acid, and {2-[3-(4-methyl-2-[2-methylpropoxy]phenyl)-ureido]-thiazol-4-yl}-acetic acid.

In one embodiment, a compound according to the present invention is for use as a medicament in the treatment of hyperglycemia.

In one embodiment, a compound according to the present invention is for use as a medicament in the treatment of IGT.

In one embodiment, a compound according to the present invention is for use as a medicament in the treatment of Syndrome X.

In one embodiment, a compound according to the present invention is for use as a medicament in the treatment of type 2 diabetes.

In one embodiment, a compound according to the present invention is for use as a medicament in the treatment of type 1 diabetes.

In one embodiment, a compound according to the present invention is for use as a medicament in the treatment of hyperlipidemia.

In one embodiment, a compound according to the present invention is for use as a medicament in the treatment of dyslipidemia.

In one embodiment, a compound according to the present invention is for use as a medicament in the treatment of hypertension.

In one embodiment, a compound according to the present invention is for use as a medicament in the treatment of obesity.

In one embodiment, a compound according to the present invention is for use as a medicament for lowering of food intake.

In one embodiment, a compound according to the present invention is for use as a medicament for appetite regulation.

In one embodiment, a compound according to the present invention is for use as a medicament for regulating feeding behaviour.

In one embodiment, a compound according to the present invention is for use as a medicament for enhancing the secretion of enteroincretins, such as GLP-1.

The present compounds are activators of glucokinase and are as such useful for the activation of glucokinase.

Accordingly, the present invention provides a method for activating glucokinase in a patient in need thereof, which method comprises administering to a subject in need thereof a compound according to the present invention, preferably in a pharmacologically effective amount, more preferably in a therapeutically effective amount. The present invention also provides a method for lowering blood glucose in a patient in need thereof, which method comprises administering to a subject in need thereof a compound according to the present invention, preferably in a pharmacologically effective amount, more preferably in a therapeutically effective amount. The present invention also provides a method for prevention and/or treatment of glucokinase deficiency-mediated human diseases, the method comprising administration to a human in need thereof a therapeutically effective amount of a compound according to the present invention. As used herein, the phrase "a subject in need thereof" includes mammalian subjects, preferably humans, who either suffer from one or more of the aforesaid diseases or disease states or are at risk for such. Accordingly, in the context of the therapeutic method of the present invention, this method also is comprised of a method for treating a mammalian subject prophylactically, or prior to the onset of diagnosis such disease(s) or disease state(s).

In one embodiment, the present invention provides a method for the treatment of hyperglycemia, the method comprising administering to a subject in need thereof an effective amount of a compound or a pharmaceutical composition according to the present invention.

In one embodiment, the present invention provides a method for the treatment of IGT, the method comprising administering to a subject in need thereof an effective amount of a compound or a pharmaceutical composition according to the present invention.

In one embodiment, the present invention provides a method for the treatment of Syndrome X, the method comprising administering to a subject in need thereof an effective amount of a compound or a pharmaceutical composition according to the present invention.

In one embodiment, the present invention provides a method for the treatment of type 2 diabetes, the method comprising administering to a subject in need thereof an effective amount of a compound or a pharmaceutical composition according to the present invention.

In one embodiment, the present invention provides a method for the treatment of type 1 diabetes, the method comprising administering to a subject in need thereof an effective amount of a compound or a pharmaceutical composition according to the present invention.

In one embodiment, the present invention provides a method for the treatment of dyslipidemia or hyperlipidemia, the method comprising administering to a subject in need thereof an effective amount of a compound or a pharmaceutical composition according to the present invention.

In one embodiment, the present invention provides a method for the treatment of obesity, the method comprising administering to a subject in need thereof an effective amount of a compound or a pharmaceutical composition according to the present invention.

In one embodiment, the effective amount of the compound is in the range of from about 0.05 mg to about 2000 mg, preferably from about 0.1 mg to about 1000 mg and especially preferred from about 0.5 mg to about 500 mg per day.

In one embodiment, the method according to the present invention is part of a regimen, which comprises treatment with a further antidiabetic agent, for example an antidiabetic agent such as insulin or an insulin analogue, a sulphonylurea, a biguanide, a meglitinide, an insulin sensitizer, a thiazolidinedione insulin sensitizer, an α-glucosidase inhibitor, a glycogen phosphorylase inhibitor, or an agent acting on the ATP-dependent potassium channel of the pancreatic β-cells.

In one embodiment, the method according to the present invention is part of a regimen, which comprises treatment with a further antihyperlipidemic agent, for example an antihyperlipidemic agent such as cholestyramine, colestipol, clofibrate, gemfibrozil, lovastatin, pravastatin, simvastatin, probucol or dextrothyroxine.

In one embodiment, the method according to the present invention is part of a regimen, which comprises treatment with a further antihypertensive agent.

In one embodiment, the method according to the present invention is part of a regimen, which comprises treatment with a further antiobesity or appetite regulating agent.

In one embodiment, the method according to the present invention is part of a regimen, which comprises treatment with a further antihypertensive agent.

Other embodiments of such methods will be clear from the following description.

Compounds according to the present invention are useful for the treatment of disorders, diseases and conditions, wherein the activation of glucokinase is beneficial.

Accordingly, the present compounds are useful for the treatment of hyperglycemia, IGT (impaired glucose tolerance), insulin resistance syndrome, syndrome X, type 1 diabetes, type 2 diabetes, dyslipidemia, dyslipoproteinemia (abnormal lipoproteins in the blood) including diabetic dyslipidemia, hyperlipidemia, hyperlipoproteinemia (excess of lipoproteins in the blood) including type I, II-a (hypercholesterolemia), II-b, III, IV (hypertriglyceridemia) and V (hypertriglyceridemia) hyperlipoproteinemias, and obesity. Furthermore, they may be useful for the treatment of albuminuria, cardiovascular diseases such as cardiac hypertrophy, hypertension and arteriosclerosis including atherosclerosis; gastrointestinal disorders; acute pancreatitis; and appetite regulation or energy expenditure disorders.

Accordingly, in a further aspect the invention relates to a compound according to the present invention for use as a medicament.

The invention also relates to pharmaceutical compositions comprising, as an active ingredient, at least one compound according to the present invention together with one or more pharmaceutically acceptable carriers or excipients.

The pharmaceutical composition is preferably in unit dosage form, comprising from about 0.05 mg to about 1000 mg, preferably from about 0.1 mg to about 500 mg and especially preferred from about 0.5 mg to about 200 mg of the compound according to the present invention.

In one embodiment, the pharmaceutical composition according to the present invention comprises a further antidiabetic agent, for example an antidiabetic agent such as insulin, an insulin derivative or an insulin analogue, a sulphonylurea, a biguanide, a meglitinide, an insulin sensitizer, a thiazolidinedione insulin sensitizer, an α-glucosidase inhibitor, a glycogen phosphorylase inhibitor, or an agent acting on the ATP-dependent potassium channel of the pancreatic β-cells.

In one embodiment, the pharmaceutical composition according to the present invention comprises a further antihyperlipidemic agent, for example an antihyperlipidemic agent such as cholestyramine, colestipol, clofibrate, gemfibrozil, lovastatin, pravastatin, simvastatin, probucol or dextrothyroxine.

In one embodiment, the pharmaceutical composition according to the present invention comprises a further antiobesity or appetite regulating agent.

In one embodiment, the pharmaceutical composition according to the present invention comprises a further antihypertensive agent.

In one embodiment of the present invention, the pharmaceutical composition according to the present invention comprises a compound according to the present invention in combination with one or more of the agents mentioned above e.g. in combination with metformin and a sulphonylurea such as glyburide; a sulphonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

In one embodiment of the present invention, the present compounds are used for the preparation of a medicament for the treatment of hyperglycemia. As used herein hyperglycemia is to be taken as generally understood in the art, with reference for example to the Report of the Expert Committee of the Diagnosis and Classification of Diabetes Mellitus, published in Diabetes Care 20, 1183-1197, (1997), but is usually taken to mean an elevated plasma glucose level exceeding about 110 mg/dl. The present compounds are effective in lowering the blood glucose both in the fasting and postprandial stage.

In one embodiment of the present invention, the present compounds are used for the preparation of a pharmaceutical composition for the treatment of IGT.

In one embodiment of the present invention, the present compounds are used for the preparation of a pharmaceutical composition for the treatment of Syndrome X.

In one embodiment of the present invention, the present compounds are used for the preparation of a pharmaceutical composition for the treatment of type 2 diabetes. Such treatment includes ia treatment for the purpose of the delaying of the progression from IGT to type 2 diabetes as well as delaying the progression from non-insulin requiring type 2 diabetes to insulin requiring type 2 diabetes.

In one embodiment of the present invention the present compounds are used for the preparation of a pharmaceutical composition for the treatment of type 1 diabetes. Such therapy is normally accompanied by insulin administration.

In one embodiment of the present invention the present compounds are used for the preparation of a pharmaceutical composition for the treatment of dyslipidemia and hyperlipidemia.

In one embodiment of the present invention the present compounds are used for the preparation of a pharmaceutical composition for the treatment of obesity.

In another aspect of the present invention treatment of a patient with the present compounds are combined with diet and/or exercise.

The present invention provides methods of activating glucokinase activity in a mammal, which methods comprise administering, to a mammal in need of activation of glucokinase activity, a therapeutically defined amount of a compound according to the present invention defined above, as a single or polymorphic crystalline form or forms, an amorphous form, a single enantiomer, a racemic mixture, a single stereoisomer, a mixture of stereoisomers, a single diastereoisomer, a mixture of diastereoisomers, a solvate, a pharmaceutically acceptable salt, a solvate, a prodrug, a biohydrolyzable ester, or a biohydrolyzable amide thereof.

The present invention provides a method of activating glucokinase, comprising the step of administering to a mammal in need thereof a pharmacologically effective amount of a compound according to the present invention. The invention further provides a pharmaceutical composition comprising a pharmaceutically acceptable carrier and a pharmacologically effective amount of a compound according to the present invention sufficient to activate glucokinase. A glucokinase—activating amount can be an amount that reduces or inhibits a PTPase activity in the subject.

Additionally provided by the present invention is a pharmaceutical composition comprising a pharmaceutically acceptable carrier and a pharmacologically effective amount of a compound according to the present invention sufficient to treat type I diabetes.

Also provided by the present invention is a pharmaceutical composition comprising a pharmaceutically acceptable carrier and a pharmacologically effective amount of a compound according to the present invention sufficient to treat type II diabetes.

The compounds of the present invention can be administered to any mammal in need of activation of glucokinase activity. Such mammals can include, for example, horses, cows, sheep, pigs, mice, dogs, cats, primates such as chimpanzees, gorillas, rhesus monkeys, and, most preferably humans.

In a further aspect of the present invention the present compounds are administered in combination with one or more further active substances in any suitable ratios. Such further active agents may be selected from antidiabetic agents, antihyperlipidemic agents, antiobesity agents, antihypertensive agents and agents for the treatment of complications resulting from or associated with diabetes.

Suitable antidiabetic agents include insulin, GLP-1 (glucagon like peptide-1) derivatives such as those disclosed in WO 98/08871 (Novo Nordisk A/S), which is incorporated herein by reference, as well as orally active hypoglycemic agents.

Suitable orally active hypoglycemic agents preferably include imidazolines, sulfonylureas, biguanides, meglitinides, oxadiazolidinediones, thiazolidinediones, insulin sensitizers, α-glucosidase inhibitors, agents acting on the ATP-dependent potassium channel of the pancreatic β-cells e.g. potassium channel openers such as those disclosed in WO 97/26265, WO 99/03861 and WO 00/37474 (Novo Nordisk A/S) which are incorporated herein by reference, potassium channel openers, such as ormitiglinide, potassium channel blockers such as nateglinide or BTS-67582, glucagon antagonists such as those disclosed in WO 99/01423 and WO 00/39088 (Novo Nordisk A/S and Agouron Pharmaceuticals, Inc.), all of which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antihyperlipidemic agents and antilipidemic agents, compounds lowering food intake, and PPAR (peroxisome proliferator-activated receptor) and RXR (retinoid X receptor) agonists such as ALRT-268, LG-1268 or LG-1069.

In one embodiment of the present invention, the present compounds are administered in combination with insulin, insulin derivatives or insulin analogues.

In one embodiment of the present invention, the present compounds are administered in combination with a sulphonylurea e.g. tolbutamide, chlorpropamide, tolazamide, glibenclamide, glipizide, glimepiride, glicazide or glyburide.

In one embodiment of the present invention, the present compounds are administered in combination with a biguanide e.g. metformin.

In one embodiment of the present invention, the present compounds are administered in combination with a meglitinide e.g. repaglinide or senaglinide/nateglinide.

In one embodiment of the present invention, the present compounds are administered in combination with a thiazolidinedione insulin sensitizer e.g. troglitazone, ciglitazone, pioglitazone, rosiglitazone, isaglitazone, darglitazone, englitazone, CS-011/CI-1037 or T 174 or the compounds disclosed in WO 97/41097 (DRF-2344), WO 97/41119, WO 97/41120, WO 00/41121 and WO 98/45292 (Dr. Reddy's Research Foundation), which are incorporated herein by reference.

In one embodiment of the present invention the present compounds may be administered in combination with an insulin sensitizer e.g. such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313 (NN622/DRF-2725), WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

In one embodiment of the present invention the present compounds are administered in combination with an α-glucosidase inhibitor e.g. voglibose, emiglitate, miglitol or acarbose.

In one embodiment of the present invention the present compounds are administered in combination with a glycogen phosphorylase inhibitor e.g. the compounds described in WO 97/09040 (Novo Nordisk A/S).

In one embodiment of the present invention the present compounds are administered in combination with an agent acting on the ATP-dependent potassium channel of the pancreatic β-cells e.g. tolbutamide, glibenclamide, glipizide, glicazide, BTS-67582 or repaglinide.

In one embodiment of the present invention the present compounds are administered in combination with nateglinide.

In one embodiment of the present invention the present compounds are administered in combination with an antihyperlipidemic agent or a antilipidemic agent e.g. cholestyramine, colestipol, clofibrate, gemfibrozil, lovastatin, pravastatin, simvastatin, probucol or dextrothyroxine.

In another aspect of the present invention, the present compounds are administered in combination with more than one of the above-mentioned compounds e.g. in combination with metformin and a sulphonylurea such as glyburide; a sulphonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Furthermore, the compounds according to the invention may be administered in combination with one or more anti-obesity agents or appetite regulating agents.

Such agents may be selected from the group consisting of CART (cocaine amphetamine regulated transcript) agonists, NPY (neuropeptide Y) antagonists, MC3 (melanocortin 3) agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin reuptake inhibitors (fluoxetine, seroxat or citalopram), serotonin and norepinephrine reuptake inhibitors, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA (dopamine) agonists (bromocriptin, doprexin), lipase/amylase inhibitors, PPAR modulators, RXR modulators, TR β agonists, adrenergic CNS stimulating agents, AGRP (agouti related protein) inhibitors, H3 histamine antagonists such as those disclosed in WO 00/42023, WO 00/63208 and WO 00/64884, which are incorporated herein by reference, exendin-4, GLP-1 agonists and ciliary neurotrophic factor. Further antiobesity agents are bupropion (antidepressant), topiramate (anticonvulsant), ecopipam (dopamine D1/D5 antagonist) and naltrexone (opioid antagonist).

In one embodiment of the present invention the antiobesity agent is leptin.

In one embodiment of the present invention the antiobesity agent is a serotonin and norepinephrine reuptake inhibitor e.g. sibutramine.

In one embodiment of the present invention the antiobesity agent is a lipase inhibitor e.g. orlistat.

In one embodiment of the present invention the antiobesity agent is an adrenergic CNS stimulating agent e.g. dexamphetamine, amphetamine, phentermine, mazindol phendimetrazine, diethylpropion, fenfluramine or dexfenfluramine.

Furthermore, the present compounds may be administered in combination with one or more antihypertensive agents.

Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19th Edition, Gennaro, Ed., Mack Publishing Co., Easton, Pa., 1995.

In a further aspect the invention provides a pharmaceutical preparation comprising an activator of glucokinase and an insulin derivative.

In one embodiment of the invention the insulin derivative is selected from the group consisting of B29-N$^\epsilon$-myristoyl-des(B30) human insulin, B29-N$^\epsilon$-palmitoyl-des(B30) human insulin, B29-N$^\epsilon$-myristoyl human insulin, B29-N$^\epsilon$-palmitoyl human insulin, B28-N$^\epsilon$-myristoyl Lys$^{B28}$Pro$^{B29}$ human insulin, B28-N$^\epsilon$-palmitoyl Lys$^{B28}$ Pro$^{B29}$ human insulin, B30-N$^\epsilon$-myristoyl-Thr$^{B29}$Lys$^{B30}$ human insulin, B30-N$^\epsilon$-palmitoyl-Thr$^{B29}$Lys$^{B30}$ human insulin, B29-N$^\epsilon$-(N-palmitoyl-γ-glutamyl)-des(B30) human insulin, B29-N$^\epsilon$-(N-lithocholyl-γ-glutamyl)-des(B30) human insulin, B29-N$^\epsilon$-(ω-carboxyheptadecanoyl)-des(B30) human insulin and B29-N$^\epsilon$-(ω-carboxyheptadecanoyl) human insulin.

In another embodiment of the invention the insulin derivative is B29-N$^\epsilon$-myristoyl-des(B30) human insulin.

It should be understood that any suitable combination of the compounds according to the invention with diet and/or exercise, one or more of the above-mentioned compounds and optionally one or more other active substances are considered to be within the scope of the present invention.

Pharmaceutical Compositions

The compounds of the present invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, aqueous or oily suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 1000 mg, preferably from about 0.1 to about 500 mg, and more preferred from about 0.5 mg to about 200 mg.

For parenteral routes such as intravenous, intrathecal, intramuscular and similar administration, typically doses are in the order of about half the dose employed for oral administration.

The compounds of this invention are generally utilized as the free substance or as a pharmaceutically acceptable salt thereof. Examples are an acid addition salt of a compound having the utility of a free base and a base addition salt of a compound having the utility of a free acid. The term "pharmaceutically acceptable salts" refers to non-toxic salts of the compounds of this invention which are generally prepared by reacting the free base with a suitable organic or inorganic acid or by reacting the acid with a suitable organic or inorganic base. When a compound according to the present invention contains a free base such salts are prepared in a conventional manner by treating a solution or suspension of the compound with a chemical equivalent of a pharmaceutically acceptable acid. When a compound according to the present invention contains a free acid such salts are prepared in a conventional manner by treating a solution or suspension of the compound with a chemical equivalent of a pharmaceutically acceptable base. Physiologically acceptable salts of a compound with a hydroxy group include the anion of said compound in combination with a suitable cation such as sodium or ammonium ion. Other salts which are not pharmaceutically acceptable may be useful in the preparation of compounds of the present invention and these form a further aspect of the present invention.

For parenteral administration, solutions of the novel compounds of the formula (I) in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the novel compounds of the present invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alchol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectible aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the present invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the present invention are contemplated. For the purpose of this application, topical applications shall include mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some of the compounds of the present invention may form solvates with water or common organic solvents. Such solvates are also encompassed within the scope of the present invention.

Thus, in a further embodiment, there is provided a pharmaceutical composition comprising a compound according to the present invention, or a pharmaceutically acceptable salt, solvate, or prodrug therof, and one or more pharmaceutically acceptable carriers, excipients, or diluents.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet that may be prepared by conventional tabletting techniques may contain:

| Core: | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ® IRP88* | 1.0 mg |
| Magnesii stearas Ph. Eur. | q.s. |
| Coating: | |
| Hydroxypropyl methylcellulose | approx. 9 mg |
| Mywacett 9-40 T** | approx. 0.9 mg |

*Polacrillin potassium NF, tablet disintegrant, Rohm and Haas.
**Acylated monoglyceride used as plasticizer for film coating.

If desired, the pharmaceutical composition of the present invention may comprise a compound according to the present invention in combination with further active substances such as those described in the foregoing.

The present invention also provides a method for the synthesis of compounds useful as intermediates in the preparation of compounds of formula (I) along with methods for the preparation of compounds of formula (I). The compounds can be prepared readily according to the following reaction Schemes (in which all variables are as defined before, unless so specified) using readily available starting materials, reagents and conventional synthesis procedures. In these reactions, it is also possible to make use of variants which are themselves known to those of ordinary skill in this art, but are not mentioned in greater detail.

Abbreviations

| | |
|---|---|
| d = | days |
| g = | grams |
| h = | hours |
| Hz = | hertz |
| kD = | kiloDalton |
| L = | liters |
| M = | molar |
| mbar = | millibar |
| mg = | milligrams |
| min = | minutes |
| ml = | milliliters |
| mM = | millimolar |

| | |
|---|---|
| mmol = | millimoles |
| mol = | moles |
| N = | normal |
| ppm = | parts per million |
| psi = | pounds per square inch |
| APCI = | atmospheric pressure chemical ionization |
| ESI = | electrospray ionization |
| i.v. = | intravenous |
| m/z = | mass to charge ratio |
| mp = | melting point |
| MS = | mass spectrometry |
| NMR = | nuclear magnetic resonance spectroscopy |
| p.o. = | per oral |
| $R_f$ = | relative TLC mobility |
| rt = | room temperature |
| s.c. = | subcutaneous |
| TLC = | thin layer chromatography |
| $t_r$ = | retention time |
| BOP = | (1-benzotriazolyloxy)tris(dimethylamino)phosphonium hexafluorophosphate |
| DCM = | dichloromethane |
| DIEA = | diisopropylethylamine |
| DMF = | N,N-dimethylformamide |
| DMPU = | 1,3-dimethypropylene urea |
| DMSO = | dimethylsulfoxide |
| EDC = | 1-ethyl-3-(3-dimethylaminopropyl)-carbodiimide hydrochloride |
| ether = | diethyl ether |
| EtOAc = | ethyl acetate |
| HMPA = | hexamethylphosphoric triamide |
| HOBt = | 1-hydroxybenzotriazole |
| LAH = | lithium aluminum hydride |
| LDA = | lithium diisopropylamide |
| MeOH = | methanol |
| NMM = | N-methylmorpholine, 4-methylmorpholine |
| TEA = | triethylamine |
| TFA = | trifluoroacetic acid |
| THF = | tetrahydrofuran |
| THP = | tetrahydropyranyl |
| TTF = | Fluoro-N,N,N'-tetramethylformamidinium hexafluorophosphate |

Reaction Schemes

Unless otherwise specified, the variables in the Schemes are as defined for formula (I).

Scheme 1 describes the preparation of compounds of formula (74).

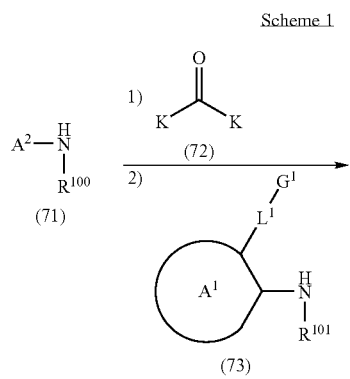

Scheme 1

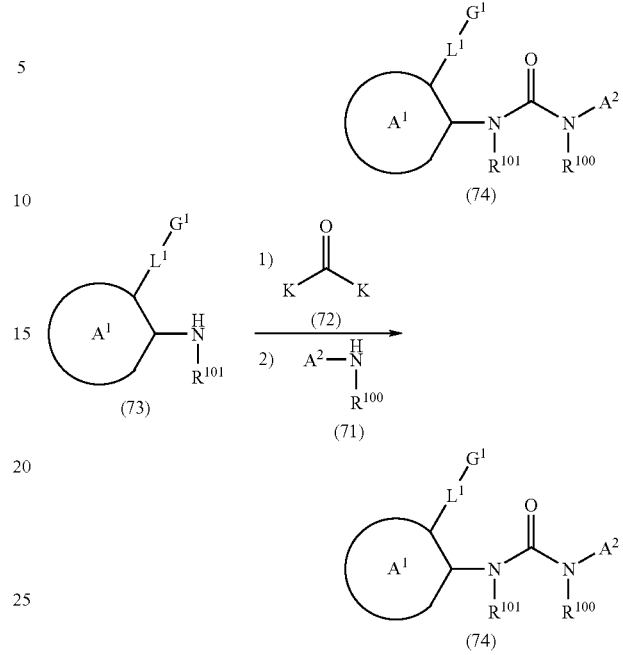

$A^2$ is heteroaryl, fused heterocyclylheteroaryl, or fused cycloalkylheteroaryl.

$R^{100}$ and $R^{101}$, independently of each other, are substituents such as, but not limited to, H, alkyl, alkenyl, alkynyl, -alkylene-aryl, alkylene-cycloalkyl, and the like.

K is halogen or 1-imidazolyl.

The amine (71) may be treated with carbonyldiimidazole, 4-nitrophenyl chloroformate, phosgene or a derivative of phosgene such as diphosgene or triphosgene, in a solvent such as DCM or DCE. DMAP may be used as a catalyst in this reaction. The reaction may be conducted at a temperature of from 0° C. to 100° C. The reaction mixture may be then be treated with the compound (73) and the whole may be incubated at a temperature of from 25° C. to 100° C. to afford the urea (75). It is also understood that (73) may be treated with the reagent (72) under similar conditions, followed by treatment with the amine (71), to afford (74).

Scheme 2 describes the preparation of a compound of formula (79).

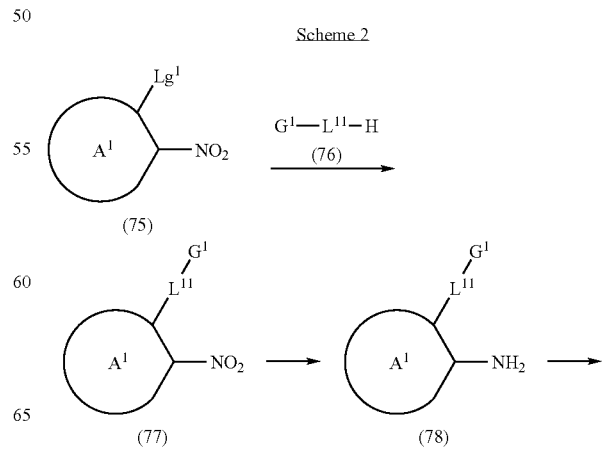

-continued

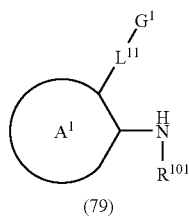

(79)

$L^{11}$ has the meaning of $L^1$ in formula (I), with the provisio that when $L^{11}$ is -D-alkylene-E-, -D-alkenylene-E-, -D-alkynylene-E-, -D-cycloalkylene-E-, or -D-heterocyclylene-E-, then D is selected from —O— or —S—, and that $L^{11}$ is not —S(O)—, —S(O)$_2$—, —C(O)—, or —C(=N—OR$^{12}$)—.

$Lg^1$ is a leaving group such as F, Cl, Br, or I.

$R^{101}$ is a substituent such as but not limited to H, alkyl, alkenyl, alkynyl, -alkylene-aryl, alkylene-cycloalkyl, and the like.

A nitro-substitued aryl or heteroaryl ring compound such as (75) may be treated with (76) in the presence of a base such as NaH or potassium tert-butoxide, in a solvent such as THF, DMF, or NMP at a temperature of from 0° C. to 100° C., to afford (77). The resulting adduct (77) may be treated with tin(II) chloride in ethanol or other alcoholic solvent, at a temerature of from 25° C. to 100° C., in the presence of aqueous HCl, to afford the amine (78). The amine (78) may, is desired, be treated with an alkyl halide $R^{101}$-$Lg^2$, wherein $Lg^2$ is a leaving group such as Br, I, or p-toluenesulfonate, and a base such as DBU or sodium hydride, to afford (79). Alternatively, (78) may be treated with a reagent $R^{102}$—C(O)—$R^{103}$, wherein $R^{102}$ and $R^{103}$ independently of each other are substituents such as, but not limited to, H, alkyl, alkenyl, alkynyl, -alkylene-aryl, alkylene-cycloalkyl, and the like, in the presence of a reducing agent such as sodium cyanoborohydrode or sodium triacetoxyborohydride, to afford (79) wherein $R^{101}$ should be understood as $R^{102}$—C(H)(R$^{103}$)—.

Alternatively, (78) may be treated with a reagent $R^{102}$C(O)—OH in the presence of a dehydrating agent such as EDC, to afford an intermediate amide, which may be reduced with a reagent such as DIBAL or LAH, in a solvent such as THF, at a temperature of from 0° C. to 80° C., to afford (71) wherein $R^{102}$ should be understood as —CH$_2$—R$^{102}$. Alternatively, (79) wherein $R^{101}$ is —CH$_3$ may be prepared by treatment of (78) with a reagent $R^{102}$—O—CO—Cl, or $R^{102}$O—CO—O—CO—O—$R^{102}$, in the presence of a base such as TEA or aqueous alkali, to afford an intermediate which may be reduced as above employing DIBAL or LAH giving (79). Compound (79) may be employed in the same manner as is compound (73) according to the chemistry in Scheme (1).

Scheme 3 describes the synthesis of a compound of formula (71).

Scheme 3

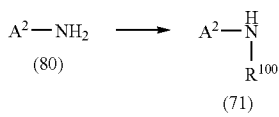

(80) → (71)

$A^2$ is (un)substituted heteroaryl, (un)substituted fused heterocyclylheteroaryl, or (un)substituted fused cycloalkylheteroaryl.

$R^{100}$ is a substituent such as, but not limited to, H, (un)substituted alkyl, (un)substituted alkenyl, (un)substituted alkynyl, (un)substituted -alkylene-aryl, (un)substituted -alkylene-cycloalkyl, and the like.

The amine (80) may, if desired, be treated with an alkyl halide $R^{100}$-Lg$^2$, wherein Lg$^2$ is a leaving group such as Br, I, or p-toluenesulfonate, and a base such as DBU or sodium hydride, to afford (71). Alternatively, (80) may be treated with a reagent $R^{102}$—C(O)—$R^{103}$ wherein $R^{102}$ and $R^{103}$, independently of each other, are substituents such as, but not limited to, H, alkyl, alkenyl, alkynyl, -alkylene-aryl, -alkylene-cycloalkyl, and the like, in the presence of a reducing agent such as sodium cyanoborohydrode or sodium triacetoxyborohydride, to afford (71) wherein $R^{100}$ should be understood as $R^{102}$—C(H)(R$^{103}$)—.

Alternatively, (78) may be treated with a reagent such as $R^{102}$C(O)—Cl and a base such as TEA, or $R^{102}$C(O)—OH in the presence of a dehydrating agent such as EDC, to afford an intermediate amide, which may be reduced with a reagent such as DIBAL or LAH, in a solvent such as THF, at a temperature of from 0° C. to 80° C., to afford (71) wherein $R^{100}$ should be understood as —CH$_2$—R$^{102}$. Alternatively, (71) wherein $R^{100}$ is —CH$_3$ may be prepared by treatment of (78) with a reagent $R^{102}$—O—C(O)—Cl, or $R^{102}$O—C(O)—O—C(O)—O—$R^{102}$, in the presence of a base such as TEA or aqueous alkali, to afford an intermediate which may be reduced as above employing DIBAL or LAH giving (71).

Scheme 4 describes the synthesis of a compound of formula (81).

Scheme 4

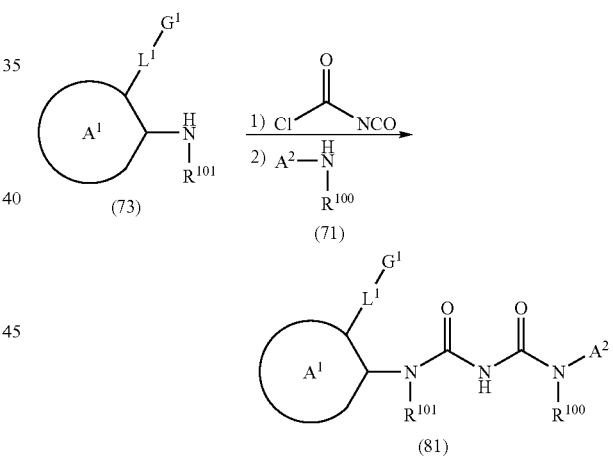

$A^2$ is (un)substituted heteroaryl, (un)substituted fused heterocyclylheteroaryl, or (un)substituted fused cycloalkylheteroaryl.

$R^{100}$ and $R^{101}$ are, independently of each other, substituents such as but not limited to H, (un)substituted alkyl, (un)substituted alkenyl, (un)substituted alkynyl, (un)substituted -alkylene-aryl, (un)substituted -alkylene-cycloalkyl, and the like.

The amine (73) may be treated with the reagent chlorocarbonyl isocyanate in the presence of a base such as DIEA, in a solvent such as THF, DCE, or dioxane, at a temperature of from −60° C. to 25° C. The intermediate thus formed may be treated at a temperature of from 0° C. to 80° C. with (71) to afford (81).

Scheme 5 describes the preparation of an intermediate of formula (87).

Scheme 5

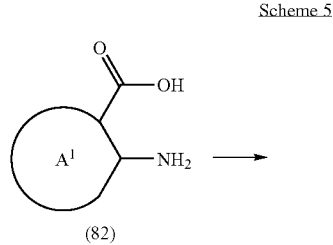

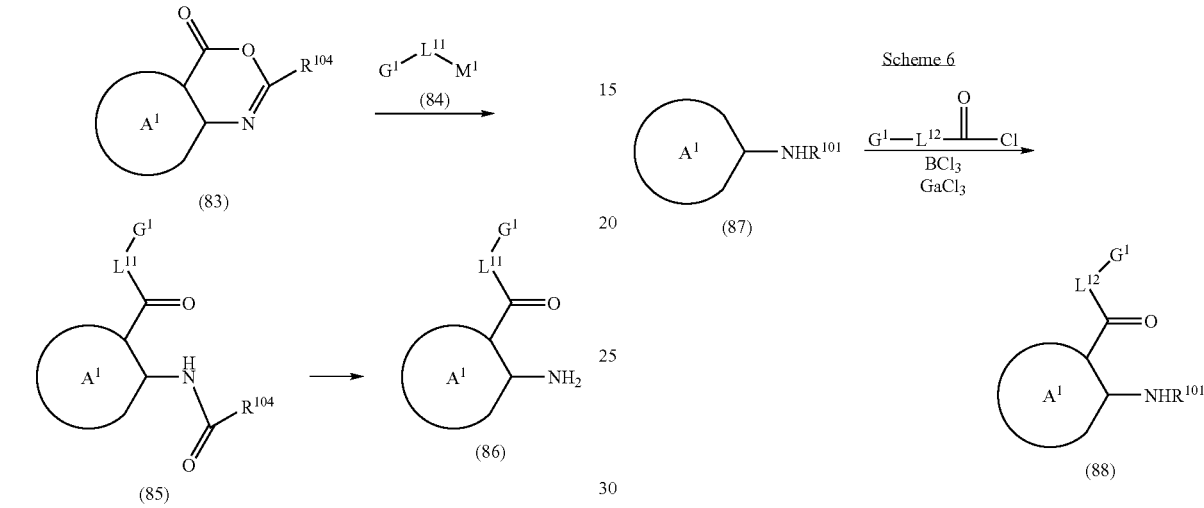

where $G^1$ is aryl and $L^{11}$ is a direct bond, $G^1$-$L^{11}$—Br may be treated with n-butyllithium in a solvent such as ether, at a temperature of from −78° C. to 0° C., to afford the reagent (84) where $M^1$ is Li. (84) may be treated with (83) in a solvent such as THF, at a temperature of from −78° C. to 50° C., to afford (85). The amide (85) may be treated with aqueous alkali in a solvent such as ethanol, at a temperature of from 25° C. to 100° C., to afford (86).

Scheme 6 describes an alternate synthesis of a compound of formula (88).

Scheme 6

$L^{11}$ is, in this instance, a group such as (un)substituted alkylene or a direct bond.

$R^{104}$ is a substituent such as but not limited to (un)substituted alkyl, (un)substituted aryl, (un)substituted alkenyl, (un)substituted alkynyl, (un)substituted -alkylene-aryl, (un)substituted -alkylene-cycloalkyl, and the like.

The anthranilic acid (82) may be treated with an acid chloride $R^{104}$—CO—Cl in the presence of a base such as TEA or aqueous alkali to afford an amide intermediate, which may be treated with a dehydrating agent such as $POCl_3$ or $SOCl_2$ in a solvent such as DCE, at a temperature of from 0° C. to 80° C., to afford (83). A reagent (84) derived from an active metallating agent such as lithium or magnesium metal and $G^1$-$L^{11}$—Br or $G^1$-$L^{11}$-I may be prepared. For example, $L^{12}$ is, in this instance, a group such as but not limited to (un)substituted alkylene, (un)substituted cycloalkylene, or a direct bond.

An amine compound (87) may be treated with an acid chloride, or other acid halide, in the presence of boron trichloride at a temperature of from −40° C. to 25° C., followed by treatment with gallium (III) chloride and chlorobenzene and heating at a temperature of from 50° C. to 150° C., to afford (88).

Scheme 7 describes synthesis of intermediates of formulae (91), (92), (93), (94), and (95).

Scheme 7

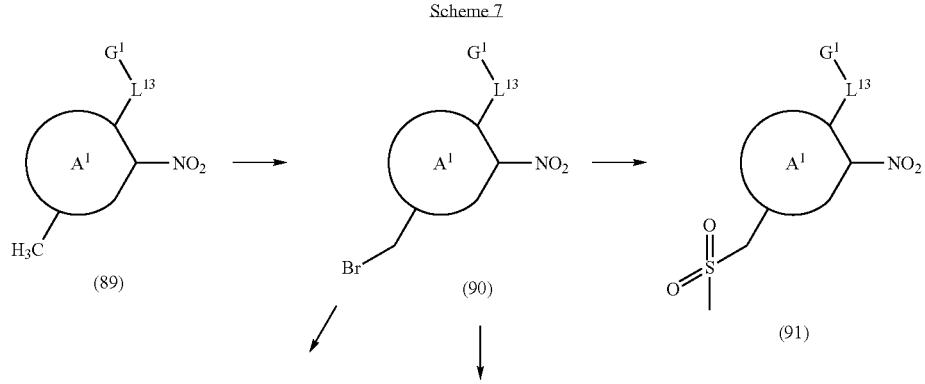

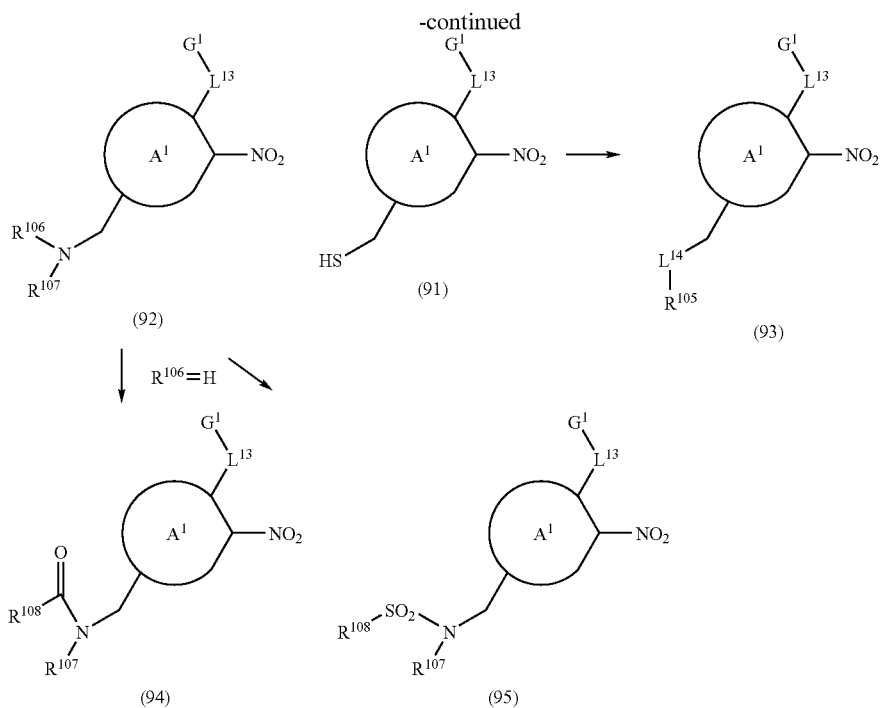

$L^{13}$ is a group such as oxygen, or may be a group broadly defined as for $L^{12}$ and $L^{11}$. R106, R107 and R108 are groups such as but not limited to (un)substituted alkyl, (un)substituted -alkylene-aryl, or H.

The nitrotoluene (89) can be brominated with a reagent such as N-bromosuccinimide in carbon tetrachloride to get the bromide intermediate (90). The methyl group in (89) may also be a more elaborate alkyl broup with hydrogen(s) on the carbon adjacent to $A^1$. The bromide (90) may be treated with sodium methanesulfinate to afford intermediate (91) and with secondary or primary amines to obtain the intermediate (92). Alternately, the $R^{106}$ and $R^{107}$ groups in the compound $R^{106}R^{107}NH$ may be taken together for constitute an heteroaryl or heterocyclic group, and treatment of (90) with such a compound in the presence of a base such as potassium tert-butoxide affords (92) where the $R^{106}$ and $R^{107}$ groups are taken together for constitute a heteroaryl or heterocyclic group. Alternately, (90) may be treated with sodium thiolacetate, followed by hydrolysis with aqueous alkali, to afford the thiol (91). From (91), various compounds may be prepared. For example, treatment of (91) with an alkylating agent such as an alkyl bromide in the presence of base such as sodium hydride affords (93) where $L^{14}$ is S and $R^{105}$ is alkyl. Oxidation of this species with a reagent such as m-chloroperbenzoic acid may afford the compound where $L_{14}$ is —$SO_2$—. Compound (92) where $R^{106}$ is H may be treated with a compound $R^{108}SO_2Cl$ in the presence of a base such as pyridine to form (95). Alternately, (92) where $R^{106}$ is H may be treated with a carboxylic acid $R^{108}COOH$ in the presence of a peptide coupling agent such as dicyclohexylcarbodiimide to form (94).

Scheme 8 describes synthesis of compounds of formula (97).

Scheme 8

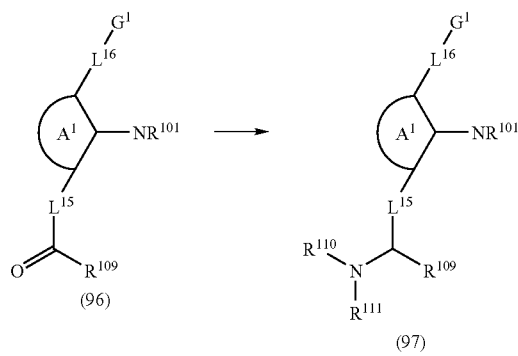

$L^{16}$ is oxygen. $G^1$ and $L^{16}$, in this instance, preferably contain no ketone, aldehyde, or primary or secondary amine groups.

$R^{109}$, $R^{110}$, and $R^{111}$ are groups such as but not limited to (un)substituted alkyl, H, or (un)substituted alkylene-aryl. $R^{110}$ and $R^{111}$ may optionally be taken together to constitute a heterocyclic ring.

Ureas of formula (91) can be reductively aminated using amines $R^{110}NHR^{111}$ and a reagend such as sodium triacetoxyborohydride in a solvent such as 1,2-dichloroethane in the presence or absence of acetic acid to obtain compounds of formula (92).

Scheme (9) describes synthesis of compounds of formulae (100) and (101).

Scheme 9

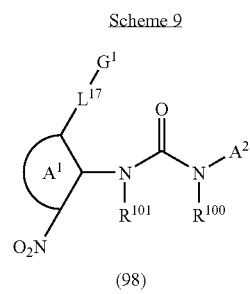
(98)

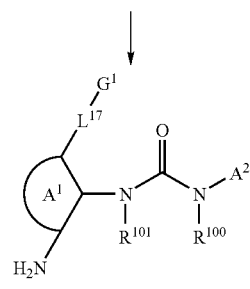
(99)

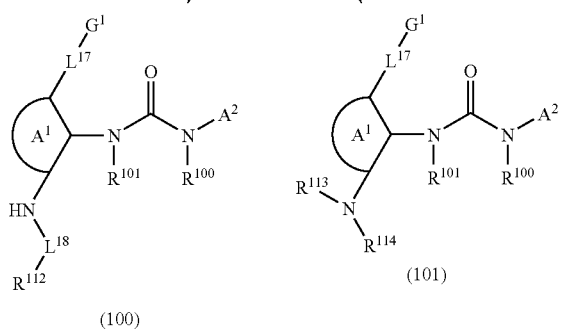
(100)                                 (101)

$L^{17}$ is carbonyl or sulfonyl group.

Nitrophenylureas (98) can be reduced to aniline derivatives of formula (99). Treatment of intermediate (99) with acid chlorides or sulfonyl chlorides can yield compounds of formula (100). Alkylation of intermediate (99) using aldehydes or ketones in the presense of sodium triacetoxyborohydride affords (101). Alternately, (99) may be treated with a dialkyl halide and a base such as DIEA to afford (101) where $R^{113}$ and $R^{114}$ and the nitrogen to which they are attached constitute a ring.

Scheme 10

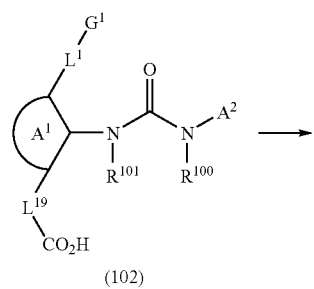
(102)

-continued

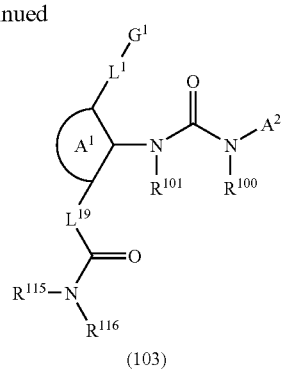
(103)

$L^{19}$ in this instance is a group such as (un)substituted alkylene. $R^{115}$ and $R^{116}$ are independently, groups such as (un)substituted alkyl, (un)substituted alkylene-aryl, or H. Alternately, $R^{115}$ and $R^{116}$ may be taken together to constitute a heterocyclic ring.

The acid (102) may be coupled with an amine $R^{115}NHR^{116}$ in the presence of a coupling agent such as dicyclohexylcarbodiimide in a solvent such as THF or dichloromethane to afford (103).

Scheme 11

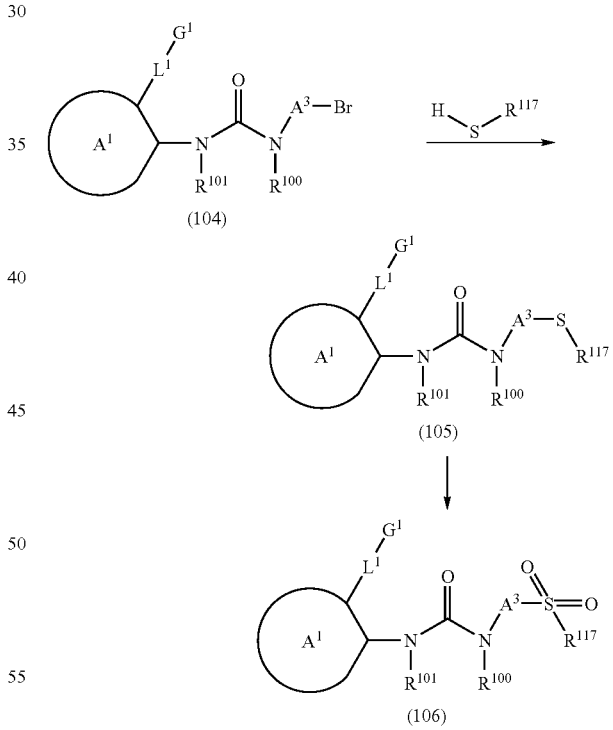

$A^3$ is a group such as (un)substituted heteroarylene, (un)substituted fused heterocyclylheteroarylene, or (un)substituted fused cycloalkylheteroarylene.

$R^{117}$ is a group such as (un)substituted alkyl, (un)substituted alkylene-aryl, (un)substituted aryl, or (un)substituted heteroaryl.

The compound (104) may be treated with a thiol reagent in the presence of a base such as DIEA at temperatures of from 50° C. to 150° C. to afford the thioether (105). (105) may be oxidized with a oxidizing reagent such as m-chloroperbenzoic acid in a solvent such as dichloromethane to afford the sulfone (106). Where only one equivalent of the oxidant is employed, the sulfoxide may be obtained. Where 2 or more equivalents of oxidant are employed, the sulfone is obtained.

Scheme 12 describes the synthesis of compounds of formula (109).

Scheme 12

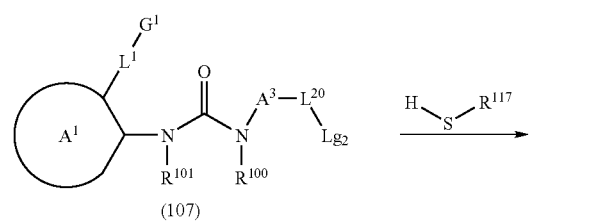

(107)

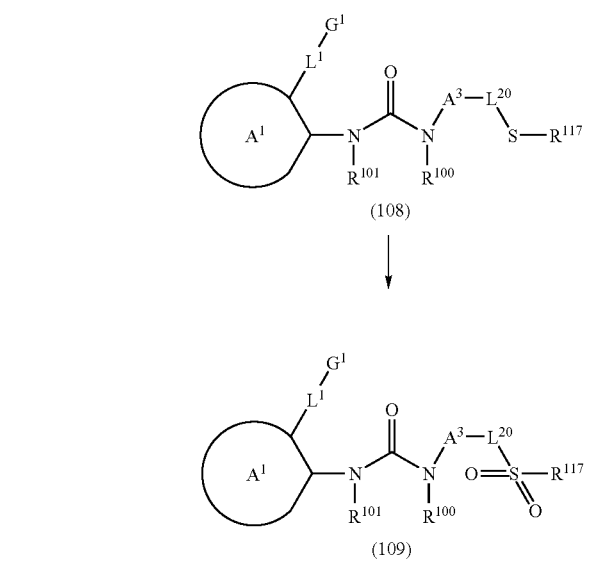

$A^3$ is a group such as (un)substituted heteroarylene, (un)substituted fused heterocyclylheteroarylene, or (un)substituted fused cycloalkylheteroarylene.

$L^{20}$ in this instance is a group such as (un)substituted alkylene. $R^{117}$ is a group such as (un)substituted alkyl, (un)substituted alkylene-aryl, (un)substituted aryl, or (un)substituted heteroaryl. $Lg_2$ is a leaving group such as chloride, methanesulfonate, or p-toluenesulfonate.

The compound (107) where $Lg_2$ is methanesulfonate may be synthesized from the precursor where $Lg_2$ is hydroxyl by treatment with methanesulfonyl chloride in the presence of pyridine. (107) then may be treated with a thiol reagent in the presence of a base such as DIEA, potassium tert-butoxide, or sodium hydride, to afford the displacement product (108). The thioether product (108) may be oxidized to the sulfoxide or sulfone (109) as described in Scheme 11.

Scheme 13 describes the synthesis of compounds of formula (111).

Scheme 13

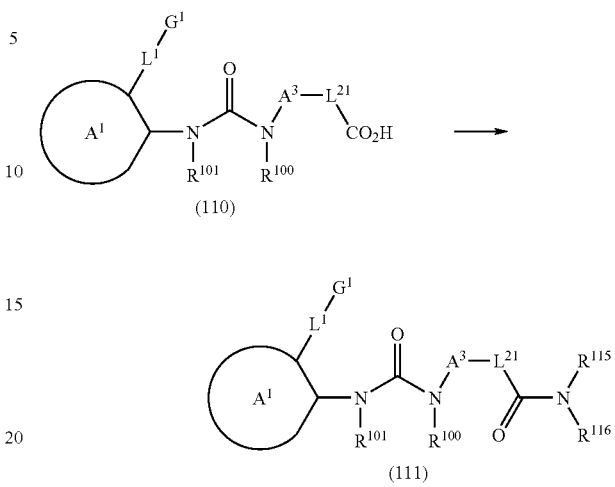

$L^{21}$ in this instance is a group such as alkylene. $R^{115}$ and $R^{116}$ may have the meaning denoted previously, or may be, independently, groups such as (un)substituted alkyl, (un)substituted alkylene-aryl, (un)substituted aryl, H, or (un)substituted heteroaryl. $A^3$ is a group such as (un)substituted heteroarylene, (un)substituted fused heterocyclylheteroarylene, or (un)substituted fused cycloalkylheteroarylene.

The acid (110) may be coupled with an amine $R^{115}NHR^{116}$ in the presence of a coupling agent such as dicyclohexylcarbodiimide to afford (111).

Scheme 14 describes a synthesis of intermediates of formula (113).

Scheme 14

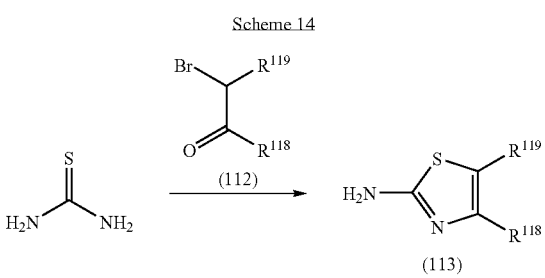

$R^{118}$ and $R^{119}$ may be, independently, groups such as (un)substituted alkyl, (un)substituted alkylene-aryl, (un)substituted aryl, H, or (un)substituted heteroaryl.

Thiourea may be condensed with the bromo carbonyl compound (112) in the presence or absence of a mild base such as potassium carbonate or triethylamine, in a solvent such as ethanol, at a temperature of from 25° C. to 120° C., to afford (113). The bromo compound (112) may be accessed by a variety of methods known in art. For example, bromination of the ketone with pyrrolidinium hydrotribromide in THF or N-bromosuccinimide in THF in the presence of a mild base such as potassium carbonate affords (112).

Scheme 15 describes synthesis of intermediates of formula (117)

Scheme 15

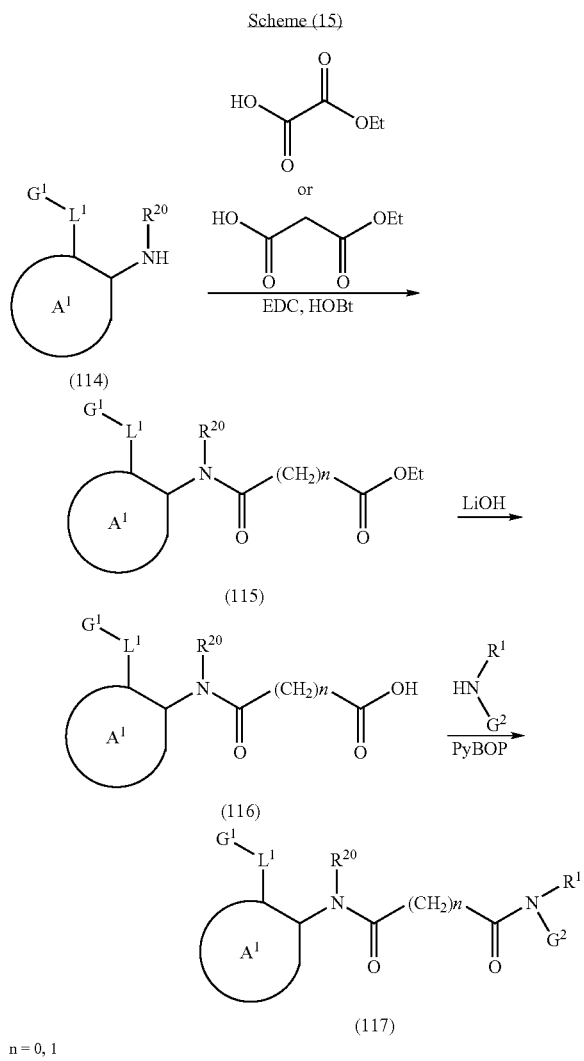

n = 0, 1

Scheme 15 shows the synthetic route to diamides of the type (117), where $A^1$, $L^1$, $R^{20}$, $R^1$, $G^1$, $G^2$ are as defined in Formula (I). Amine (114) can be coupled with an activated oxalic or malonic esters using EDC/HOBt to give amide (115). Deprotection of the t-butyl ester of B is done with lithium hydroxide to give the carboxylic acid (116), which can be coupled using standard amide coupling reagents (e.g. PyBOP) to give diamides of the type (115).

The intermediates in the above Schemes may be substituted with amino, hydroxyl, or carboxyl groups which may require protection and deprotection during the course of preparation of Example compounds.

"Amino protection" refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)iso-propoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl) ethoxycarbonyl, 2(methylsulfonyl)ethoxycarbonyl, 2-(triphenylphosphino)ethoxycarbonyl, 9-fluorenylmethoxycarbonyl ("FMOC"), t-butoxycarbonyl ("BOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the condition of subsequent reaction(s) on other positions of the compound of Formula (I) and can be removed at the desired point without disrupting the remainder of the molecule. Preferred amino-protecting groups are the allyloxycarbonyl, the t-butoxycarbonyl, 9-fluorenylmethoxycarbonyl, and the trityl groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981. The related term "protected amino" defines an amino group substituted with an amino-protecting group discussed above.

"Hydroxyl protection" refers to substituents of the alcohol group commonly employed to block or protect the alcohol functionality while reacting other functional groups on the compound. Examples of such alcohol-protecting groups include the 2-tetrahydropyranyl group, 2-ethoxyethyl group, the trityl group, the trichloroacetyl group, urethane-type blocking groups such as benzyloxycarbonyl, and the trialkylsilyl group, examples of such being trimethylsilyl, tert-butyldimethylsilyl, phenyldimethylsilyl, triiospropylsilyl and thexyldimethylsilyl. The choice of of alcohol-protecting group employed is not critical so long as the derivatized alcohol group is stable to the condition of subsequent reaction(s) on other positions of the compound of the formulae and can be removed at the desired point without disrupting the remainder of the molecule. Further examples of groups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981. The related term "protected hydroxyl" or "protected alcohol" defines a hydroxyl group substituted with a hydroxyl-protecting group as discussed above.

"Carboxyl protection" refers to substituents of the carboxyl group commonly employed to block or protect the —OH functionality while reacting other functional groups on the compound. Examples of such alcohol-protecting groups include the 2-tetrahydropyranyl group, 2-ethoxyethyl group, the trityl group, the allyl group, the trimethylsilylethoxymethyl group, the 2,2,2-trichloroethyl group, the benzyl group, and the trialkylsilyl group, examples of such being trimethylsilyl, tert-butyldimethylsilyl, phenyldimethylsilyl, triiospropylsilyl and thexyldimethylsilyl. The choice of carboxyl protecting group employed is not critical so long as the derivatized alcohol group is stable to the condition of subsequent reaction(s) on other positions of the compound of the formulae and can be removed at the desired point without disrupting the remainder of the molecule. Further examples of groups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981. The related term "protected carboxyl" defines a carboxyl group substituted with a carboxyl-protecting group as discussed above.

EXAMPLES

General Procedure A: Preparation of
1-Aryloxy-2-nitrobenzenes,
1-Arylsulfanyl-2-nitrobenzenes and
2-Aryloxy-3-nitropyridines To a solution of potassium t-butoxide (0.62 g, 5.5 mmol) in anhydrous DMF (10 ml) was added a phenol, arylmercaptan or 2-mercaptopyridine (5.5 mmol) at room temperature and the mixture was stirred for 30 min. A 1-fluoro-2-nitrobenzene derivative or 2-bromo-3-nitropyridine (5.0 mmol) was added and the contents were heated at 80° C. for 12 h. The contents were poured into water and extracted with ethyl acetate. The organic layer was washed (dil. NaOH, water, brine), dried ($Na_2SO_4$) and concentrated. In general, the desired products were of >90% pure and were used as such for further manipulations.

General Procedure B: Preparation of
2-Aryloxyanilines, 2-Arylsulfanylanilines and
3-amino-2-aryloxypyridines The crude 2-substituted-1-nitrobenzene from procedure A was dissolved in ethanol (10 ml). To this solution were added anhydrous tin(II) chloride (3.8 g, 20 mmol) and conc HCl (0.2 ml). The resulting mixture was heated at 80° C. for 10 h, cooled and concentrated. The residue was diluted with water (100 ml), neutralized to pH 8-9. To the suspension, ethyl acetate (40 ml) was added, stirred for 5 min and filtered through celite. The layers were separated and the aqueous layer was extracted with ethyl acetate (2×10 ml). The combined organic layer was washed with brine, dried ($Na_2SO_4$) and concentrated under reduced pressure to obtain the desired aniline in 60-70% yield. In general, the desired anilines were of >85% pure (LC-MS) and were used as such for further manipulations.

General Procedure C for Preparation of
2-Aryloxyanilines and 2-Arylsulfanylanilines The crude 2-substituted-1-nitrobenzene (~5 mmol) was dissolved in methanol (10 ml) in a 100 ml round-bottom flask. To this solution was added 10% palladium on charcoal (300 mg) and the flask was evacuated. The flask was filled with hydrogen with the aid of a balloon and the contents were stirred overnight. The mixture was filtered through celite and concentrated to obtain desired aniline (>90% purity by LC-MS).

General Procedure D: Preparation of Urea

A mixture of 1,1'-carbonyldiimidazole (98 mg, 0.6 mmol), 2-aminoheteroarene (0.6 mmol) and 4-(N,N-dimethylamino)pyridine (5 mg) in dichloroethane (5 ml) was heated at 80° C. for 2 h. The reaction mixture was cooled to room temperature and was added solution of a substituted aniline (0.5 mmol) in dichloroethane (2 ml). The resulting suspension was heated at 80° C. for 10 h and concentrated. The residue was purified by column chromatography (silica, $CH_2Cl_2$ then 10-30% ethyl acetate in $CH_2Cl_2$) to afford the desired urea in 60-80% yield.

General Procedure E: Preparation of Urea

A mixture of isocyanate (0.5 mmol) and 2-aminoheteroarene (0.5 mmol) in dichloroethane (4 ml) was heated at 80° C. for 12 h. The reaction mixture was concentrated under reduced pressure. The residue was purified by column chromatography (silica, $CH_2Cl_2$ then 10-30% ethyl acetate in $CH_2Cl_2$) to afford the desired urea in 60-80% yield.

General Procedure F: for Preparation of
2-Aryloxy-1-nitrobenzenes

To a solution of potassium t-butoxide (0.62 g, 5.5 mmol) in anhydrous THF (20 ml) was added a phenol (5.5 mmol) at −10° C. and the mixture was stirred for 30 min. A fluoro-1-nitrobenzene derivative (5.0 mmol) was added at −10° C. and stirred for 12 h at room temperature. The contents were poured into water (25 ml) and extracted with ethyl acetate (3×20 ml). The organic layer was washed (dil. NaOH, water, brine), dried ($Na_2SO_4$) and concentrated to give the desired products with >90% purity by LC-MS and were used as such in the next step.

General Procedure G: for Preparation of
1-Alkoxy-2-nitrobenzenes

To a suspension of NaH (60%, 0.20 g, 5.0 mmol) in anhydrous THF (10 ml) was added an alcohol (5.0 mmol) dropwise at room temperature and the mixture was stirred for 30 min. 1-Fluoro-2-nitrobenzene (5.0 mmol) was added and the contents were heated at 60° C. for 12 h. The contents were poured into water and extracted with ethyl acetate. The organic layer was washed (dil. NaOH, water, brine), dried ($Na_2SO_4$) and concentrated. In general, the desired products were of >90% pure and were used as such in the further manipulations.

General Procedure H: General Procedure for
Preparation of Compounds of General Formula I that
Contain a Urea Moiety in the Central Core.

One equivalent of a mono- di- or tri.substituted aniline is dissolved in an organic solvent such as ethyl acetate, toluene, or dichloromethane and hydrochloride dissolved in an organic solvent such as ethyl acetate, toluene or dichloromethane is added. The mixture is concentrated in vacuo to give the hydrochloride of the aniline. The residue is dissolved or suspended in a non protic organic solvent such as toluene or dichloromethane and excess (e.g. 2 to 5 equivalents) of diphosgene or another phosgene equivalent is added. The mixture is either run at room temperature or heated (up to reflux temperature of the solvent) for 5 to 20 hours. The reaction mixture is concentrated in vacuo and the intermediate residue used in the next step without further purification.

The crude intermediate isocyanate is dissolved in an organic solvent such as ethyl acetate, toluene, dichloromethane, dioxane, DMSO or DMF and one equivalent of a heterocyclic amine is added. The reaction mixture is run at either room temperature or heated until the reaction is taking place. The reaction temperature will depend on the reactivity of the isocyanate and the nucleophilicity of the amine and can be followed either using HPLC or TLC. The reaction mixture is diluted with an organic solvent such as ethyl acetate, toluene or dicloromethane and the mixture extracted with water. The product is purified using standard procedures as described in the art or as exemplified below.

General Procedure H1: Preparation of Amides from Carboxylic Acids Prepared Using Procedure H:

One equivalent of a N-substituted aminothiazol-4-ylcarboxylic acid or N-substituted aminothiazol-4-ylacetic acid prepared by using general procedure H is dissolved in an organic solvent such as 1,2-dichloropropane, dimethylformamide or a mixture of two organic solvents such as a mixture of 1,2-dichloropropane and dimethylformamide. One equivalent of PyBOP (benzotriazole-1-yl-oxy-tris-pyrrolidino-phosphonium hexafluorophosphate) is added, the reaction mixture is left standing for 20 minutes followed by addition of two equivalents of an appropriate amine and DIPEA (diisopropylethylamine), and the mixture is left overnight.

The reaction mixture is diluted with ethylacetate and extracted using a general washing procedure such as washing twice with water, twice with 4N HCl, once with water, twice with 50% saturated sodiumhydrogencarbonate, and three times with water. The organic solvent is evaporated in vacuo giving an amorphous product. The product is purified by either recrystalization in an organic solvent such as diethylether or by HPLC (e.g. a Waters Deltprep 4000).

In case the isolated product contains a carboxylic acid ester functionality, the ester group can be hydrolysed to the corresponding acid by dissolving the compound in ethanol 96% and adding 2N NaOH. The mixture is left standing for some time (e.g. 2 hours) whereafter the ethanol is evaporated in vacuo, water is added, and pH is adjusted to acidic with 2N HCl. The mixture is extracted with an organic solvent such as ethylacetate and the combined organic phases are evaporated in vacuo giving an amorphous product.

General Procedure H2: Preparation of Intermediate Isocyanates:

2-Benzylphenyl isocyanate

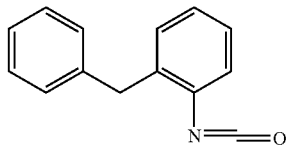

2-Benzylaniline (2.0 g, 11 mmol) was dissolved in ethylacetate (5 ml) and hydrochloride in ethylacetate (3N, 5 ml) was added. After 2 hrs the organic solvent was removed in vacuo giving a solid residue. Toluene (50 ml) was added, then diphosgene (2.2 g, 33 mmol) and the reaction-mixture was heated at 110° C. for 16 hours. The solvent and excess diphosgene was removed in vacuo giving an residual oil that was used for the next step without further purification.

The following isocyanates were prepared using the same procedure used for preparation of benzylphenyl isocyanate:

(5-Chloro-2-isocyanatophenyl)phenyl methanone

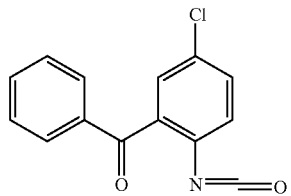

2-(2-Methylphenoxy)phenyl isocyanate

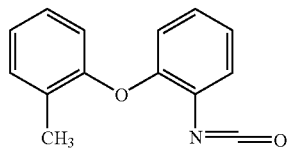

2-(4-Methoxyphenoxy)-5-(trifluoromethyl)phenyl isocyanate

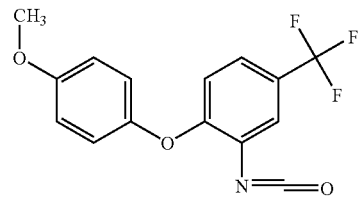

2-(Phenylsulfonyl)phenyl isocyanate

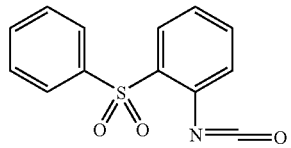

General Procedure I: Preparation of 2-acyl Anilines

A solution of 1 M borontrichloride in dichloromethane (110 mL, 0.11 mol) was cooled to −20° C. To this solution was added a solution of aniline (0.1 mol) in dichloromethane (100 mL). The mixture was warmed to room temperature and was stirred for 3 h. The mixture was re-cooled to −20° C. Alkyl nitrile (0.1 mol) was added over 5 min, followed by 1 M solution of (anhydrous) GaCl$_3$ (100 mL, 0.1 mol) in dichloromethane. To this solution was added chlorobenzene (300 mL) and the mixture was heated to reflux for 24 h. After being cooled to room temperature, the mixture was poured into ice water (1 L) and the mixture was stirred for 3 h. The organic layer was separated and the aqueous layer was extracted with dichloromethane (4×400 mL). The combined organic layer was washed with water (4×500 mL), brine (2×500 mL), dried over anhydrous $Na_2SO_4$. The aqueous layer was then basified to pH 7.5 with $Na_2CO_3$ and the mixture was extracted with dichloromethane (2×400 mL). The organic layer was washed with water (4×500 mL), brine (2×500 mL), dried over anhydrous $Na_2SO_4$. Both organic layers were combined and concentrated in vacuo. The crude mixture was purified by column chromatography with hexanes-ethyl acetate (9:1) as eluent to give the 2-amino-alkylphenones in 10-50% yield.

General Procedure J: Preparation of Acids from Esters

The ester (1 mmol) was dissolved in 1:1 mixture of THF and methanol (5 mL). To this solution was added 2 M solution of LiOH (2 mL, 4 mmol). The mixture was stirred for 1 h and was concentrated. The residue was diluted with water (10 mL) and the aqueous layer was washed with ether (2×10 mL). The water layer was acidified with HCl to pH 6.0 and precipitated acid was extracted with ethyl acetate (2×50 mL). The organic layer was washed with water (2×20 mL), dried ($Na_2SO_4$) and concentrated in vacuo to furnish the desired acid in almost quantitative yield.

General Procedure K: Preparation of Amides

A mixture of acid (0.5 mmol) and HBTU (0.5 mmol) was dissolved in anhydrous DMF (2 mL). To this solution was added DIEA (0.6 mmol) and stirred for 2-3 minutes. A solution of alkyl amine (0.5 mmol) in DMF (1 mL) was added and the mixture was stirred at room temperature for 30 min. The mixture was poured into water (20 mL) and was extracted with ethyl acetate (2×20 mL). The organic layer was washed with saturated solution of citric acid (5 mL), NaHCO3 (2×10 mL) water (2×0 mL), brine (2×10 mL), dried ($Na_2SO_4$) and concentrated in vacuo to give the desired amide. The crude mixture was purified by column chromatography (silica, $CH_2Cl_2$ then 10-50% ethyl acetate in $CH_2Cl_2$) to furnish amide in 50-75% yield.

General Procedure L: Preparation of Sulfonamides/Amides

To a solution of acid (1.0 mmol) and DIEA (1.5 mmol) in anhydrous THF (20 mL) was added diphenylphosphoroyl azide (1.5 mmol) and was heated to reflux for 8-12 hours. The reaction mixture was then concentrated in vacuo to give crude isocyanate. To this crude product was added dilute HCl (1.2 M, 20 mL) and the mixture was heated to reflux for 2 hours. The reaction mixture was neutralized with $Na_2CO_3$ and the aqueous layer was extracted with ethyl acetate (3×30 mL). The organic layer was washed with water (2×30 mL), brine (1×30 mL) and dried (anhydrous $Na_2SO_4$) and concentrated in vacuo to give the desired amine. This crude amine (1.0 mmol) was reacted with aryl/alkylsulfonyl chloride (1 mmol) and $Et_3N$ (2 mmol) to give the desired sulfonamides. The amides were prepared as described in procedure K. The crude product was purified by silica gel chromatography [hexanes: EtOAc/MeOH (70:30:0 to 5:90:5)] to furnish the desired sulfonamides in 20-30% yield.

General Procedure M: Preparation of Bis-ureas or Carbamates

A mixture of acid (1.0 mmol) and DIEA (1.5 mmol) was dissolved in anhydrous THF or $CH_3CN$ (30 mL). Then dipenylphosphoroyl azide (1.5 mmol) added to the reaction mixture. Reaction mixture was refluxed for 8-12 hours. The reaction mixture was then concentrated in vacuo to give crude isocyanate. To this crude product desired amines or alcohols (2.0 mmol) were added and stirred at rt for 2 h. The reaction mixture was then concentrated in vacuo. The crude reaction mixture was then purified by silica gel chromatography (hexanes:EtOAc 70:30 to 10:90) to furnish the desired bis-ureas or carbamates in 30-45% yield.

General Procedure N: Preparation of Alcohols

To a solution of ethyl-2-amino-4-thiazolyl acetate or ethyl-2-amino-4thiazoyl carboxylate (100 mmol) in anhydrous THF (100 mL) was added lithiumborohydride (200 mmol, 2.0 M solution in THF) at −10° C., and the mixture was allowed to warm up to ambient temperature and stirred for 8-10 h. The mixture was then concentrated in vacuo. Methanol (200 mL) was added to quench excess lithiumborohydride and filtered through with a plug of silica gel to afford the amino alcohol.

To this crude amino alcohol (100 mmol) and imidazole (500 mmol) in anhydrous DMF (50 ml) was added tert-butyldimethylsilyl chloride (500 mmol) and stirred at rt for 6 h. The reaction mixture was then washed with water (5×100 mL) and brine (2×100 mL) and extracted with ethylacetate (3×200 mL), dried over $Na_2SO_4$, and concentrated in vacuo to give TBS-protected amino alcohol.

TBS-protected amino alcohol (50 mmol) was subjected to urea formation following general procedure D to give desired urea. This crude urea (25 mmol) was then treated with TBAF (50 mmol, 1.0 M solution in THF) and stirred at rt for 4 h. The reaction mixture was poured in to water and extracted with ethyl acetate. The organic extracts were combined, washed (water), dried ($Na_2SO_4$) and concentrated in vacuo The crude mixture was purified by silica gel chromatography [hexanes: EtOAc (70:30 to 10:90)] to afford the desired alcohol in 70-80% yield.

General Procedure O: Preparation of Amines by Reductive Amination

To the aldehyde (0.11 mmol) in dichloroethane or THF (5 mL) was added the respective amine (0.11 mmol) and stirred at room temperature for 15 min. To this solution was added sodium triacetoxyborohydride (0.16 mmol). After stirring at room temperature overnight, the mixture was concentrated in vacuo and purified by column chromatography (silica, 2-8% MeOH in DCM) to obtain the desired product in 30-50% yield.

General Procedure P: Preparation of Arylethers by Mitsunobu Reaction

To a solution of 1-[2-(cyclopentanecarbonyl-4-methylphenyl]-3-[4-(2-hydroxy-ethyl)-thiazol-2-yl]-urea (0.268 mmol), phenol (0.536 mmol) and triphenylphosphine (0.268 mmol) in THF (2 mL) was added diisopropyl azodicarboxylate (0.268 mmol) at 0° C. The resulting solution was stirred at rt overnight, The mixture was concentrated and purified by flash chromatography on silica gel (10-50% EtOAc/hexane) to give the desired product in 28-40% yield.

General procedure Q: Synthesis of 1-(2-cyclopentanoyl-4-methyl-phenyl)-3-(5-alkylthio-2-thiazolyl) ureas A mixture of 1-(2-cyclopentanoyl-4-methyl-phenyl)-3-(5-bromol-2-thiazolyl)urea (1 mmol), alkylthiol (2 mmol) and DIEA (2 mmol) in DMF (5 mL) was heated at 80° C. for 3 h. The mixture was poured into water (20 mL) and was extracted with ethyl acetate (3×25 mL). The organic layer was washed with water (2×30 mL), brine (1×30 mL), dried (anhydrous $Na_2SO_4$) and concentrated in vacuo to furnish a residue containing 1-(2-cyclopentanoyl-4-methyl-phenyl)-3-(5-alkythio-2-thiazolyl)urea along with 1-(2-cyclopentanoyl-4-methyl-phenyl)-3-(thiazol-2-yl)urea. The crude product was purified by column chromatography (silica, $CH_2Cl_2$ then 5-20% ethyl acetate in $CH_2Cl_2$) to afford the desired product in 25-35% yield Same procedure was adopted for the synthesis of 1-(2-cyclopentanoyl-4-methyl-phenyl)-3-(5-arylthio-2-thiazolyl) ureas. The crude products were purified by column chromatography (silica, $CH_2Cl_2$ then 5-20% ethyl acetate in $CH_2Cl_2$ and 2% MeOH in $CH_2Cl_2$) to afford the desired product in 25-35% yield.

General Procedure R: Oxidation of Alkyl and Arylthio Substituted Thiazolyl Ureas Alkyl or arylthio substituted thiazolyl urea (0.5 mmol) was dissolved in $CH_2Cl_2$ (5 mL) and was cooled to 0° C. in an ice bath. To this solution was added m-cpba (133 mg, 0.75 mmol) in $CH_2Cl_2$ (3 mL). The mixture was stirred at 0° C. for 4 h and was diluted with $CH_2Cl_2$ (30 mL). The organic layer was washed with saturated solution of $NaHCO_3$ (2×20 mL), water (3×20 mL), brine (1×20 mL), dried (anhydrous $Na_2SO_4$) and concentrated in vacuo. The crude mixture was purified by column chromatography (silica, $CH_2Cl_2$ then 5-20% ethyl acetate in $CH_2Cl_2$ and 2% MeOH in $CH_2Cl_2$) to give the desired alkyl or aryl sulfone in 60-80% yield.

General Procedure S: Preparation of 2-Amino Arylphenones

To a solution of 2-amino benzoic acid (10 mmol) in THF was added benzoyl chloride (2.8 g, 20 mmol) followed by pyridine (1.58 g, 20 mmol). The mixture was stirred for 1 h at room temperature. The 2-phenyl-benzo[d][1,3]oxazin-4-one formed was filtered and the residue was washed with water and dried in vaccuum desiccator.

To a solution of 2-phenyl-benzo[d][1,3]oxazin-4-one (5 mmol) in dry $CH_2Cl_2$ (20 mL) was added 1N solution of aryl magnesium bromide in THF (5 mL) at 0° C. The mixture was stirred at room temperature for 2 h and poured into water (30 mL). The aqueous layer was extracted with ethyl acetate (3×30 mL) and was washed with water (3×50 mL), brine (1×50 mL), dried (anhydrous $Na_2SO_4$) and concentrated in vacuo to afford N-(2-benzoyl-phenyl)-benzamide in 60-70% yield.

To a solution of the crude N-(2-benzoyl-phenyl)-benzamide (2 mmol) in THF (10 mL) was added 10 N solution of NaOH (5 mL) and was heated to reflux for 18 h. The mixture was poured into water (50 mL) and was extracted with ethyl acetate (3×30 mL). The organic layer was washed with water (3×50 mL), brine (1×50 mL), dried (anhydrous $Na_2SO_4$) and concentrated in vacuo to afford 2-amino arylphenone. The crude product was purified by column chromatography (silica, hexanes then 5-20% ethyl acetate) to furnish the desired product in 28-40% yield.

General Procedure T: Preparation of Amides/Sulfonamides

To a solution of amine (0.5 mmol) in DCM (5 mL) was added triethylamine (1 mmol) and cooled the reaction mixture to 0° C. Acid chloride or sulfonyl chloride (0.5 mmol) was added drop-wise and stirred for overnight. The reaction mixture was concentrated in vacuo and the residue was purified by column chromatography [silica, DCM:ethyl acetate (80:20 to 20:80)] to yield desired amides or sulfonamides respectively.

General Procedure U: Preparation of Hydantoins from Amino Acids:

To a solution of Boc-Gly-Merrifield resin (1.2 g, 0.96 mmol) was added trifluoroacetic acid (5 ml, 20% in DCM), then the resin was washed with three cycles of DMF, methanol, and DCM. To this resin in DCM (20 mL) was slowly added phosgene (10 mL, 20% in toluene, 2.0 mmol)) and triethylamine (0.56 ml, 4.0 mmol) at −20° C. The reaction mixture was allowed to warm up to room temperature. The excess phosgene was washed away with there cycles of DCM. To this resin in DCM (20 mL) was added 1-(4-aminomethyl-thiazol-2-yl)-3-(2-cyclopentanecarbonyl-4-methyl-phenyl)-urea (0.9 g, 2.5 mmol) in DCM (10 mL) and the reaction mixture was placed in a shaker and reacted for 4 h to give the corresponding urea. The resin was then washed with three cycles of DMF, methanol and DCM and dried over 2 h. To the resin was added triethylamine (10 mL, 20% solution in THF) and the reaction mixture was heated for 16 h. The mixture was filtered and the filtrate was concentrated in vacuo to afford hydantoins in 60-75% overall yields.

General Procedure V: Preparation of Specific 2-Aminothiazole Analogs:

To a solution of 1,3-dichloroacetone, 1,3-dibromoacetone, 1-acetoxy-3-chloroacetone, bromomalonaldehyde or 1,4-dibromobutan-2,3-dione (100 mmol) in methanol (100 ml) was added thiourea (7.6 g, 100 mmol) and the mixture was stirred at rt. for 3 h. The reaction mixture was concentrated in vacuo to give the desired products in almost quantitative yields.

4-Chloromethyl-thiazole-2-ylamine (172 mg, 1.0 mmol) was reacted with arylthiols (2 mmol) and DIEA (2 mmol) in THF (5 mL) following the general procedure Z. These intermediates were coupled with CDI and 2-amino-5-methyl-phenyl)-cyclopentyl-methanone (203 mg, 1.0 mmol) following the general procedure D.

General Procedure W: Preparation of Alkylamino Nitrobenzenes

1-Fluoro-2-nitrobenzene derivative (5.0 mmol) and an amine (10 mmol) in THF (25 mL) were heated at 60° C. for 12 h. The contents were poured into water and extracted with ethyl acetate. The organic layer was washed (water, brine), dried ($Na_2SO_4$) and concentrated. The residue was dissolved in methanol (25 mL) and subjected reduction following the general procedure C. In general, the desired products were of >90% pure and were used as such in the further manipulations.

General Procedure X: Preparation of Alkenes by Wittig Reaction

The aldehyde (0.10 g, 0.28 mmol) and (carbethoxymethylene)-triphenylphosphorane (0.12 g, 0.34 mmol) were stirred at room temperature in benzene overnight. The reaction mixture was concentrated under vacuum and purified by column chromatography (silica, 15% EtOAc/hexanes) to obtain the product in 80% yield.

General procedure Y: Synthesis of 1-(2-cyclopentanoyl-4-methyl-phenyl)-3-(5-arylthio-2-thiazolyl) ureas A mixture of 1-(2-cyclopentanoyl-4-methyl-phenyl)-3-(5-bromol-2-thiazolyl)urea (1 mmol), arylthiol (2 mmol) and tert. BuOK (2 mmol; 4 equivalent of tert.BuOK was used for arylthio carboxylic acids) in DMF (5 mL) was heated at 80° C. for 3 h. The mixture was poured into water (20 mL). Urea containing arylthio carboxylic acid was neutralized with saturated $NaHCO_3$ solution. The aqueous layer was extracted with ethyl acetate (3×25 mL). The organic layer was washed with water (2×30 mL), brine (1×30 mL), dried (anhydrous $Na_2SO_4$) and concentrated in vacuo to furnish a residue containing 1-(2-cyclopentanoyl-4-methyl-phenyl)-3-(5-arylthio-2-thiazolyl)urea along with 1-(2-cyclopentanoyl-4-methyl-phenyl)-3-(2-thiazolyl)urea. The crude product was purified by column chromatography (silica, $CH_2Cl_2$ then 5-20% ethyl acetate in $CH_2Cl_2$ and 2% MeOH in $CH_2Cl_2$) to afford the desired product in 25-35% yield.

General procedure Z: Synthesis of 1-(2-cyclopentanecarbonyl-4-methyl-phenyl)-3-[4-(aryl-sulfanylmethyl)-thiazol-2-yl]-ureas and 1-(2-cyclopentanecarbonyl-4-methyl-phenyl)-3-{4-[arylsulfanyl)-ethyl]-thiazol-2-yl}-ureas A mixture of 1-(4-chloromethyl-thiazol-2-yl)-3-(2-cyclopentanecarbonyl-4-methyl-phenyl)-urea (1 mmol), arylthiol (2 mmol) and DIEA (2 mmol) in THF (5 mL) was heated at 80° C. for 3 h. The mixture was poured into water (20 mL) and was extracted with ethyl acetate (3×25 mL). The organic layer was washed with water (2×30 mL), brine (1×30 mL), dried (anhydrous $Na_2SO_4$) and concentrated in vacuo to furnish a residue containing 1-(2-cyclopentanecarbonyl-4-methyl-phenyl)-3-[4-(arylsulfanylmethyl)-thiazol-2-yl]-urea. The crude product was purified by column chromatography (silica, $CH_2Cl_2$ then 5-20% ethyl acetate in $CH_2Cl_2$ and 2% MeOH in $CH_2Cl_2$) to afford the desired product in 79-85% yield Similarly, synthesis of 1-(2-cyclopentanecarbonyl-4-methyl-phenyl)-3-{4-[arylsulfanyl)-ethyl]-thiazol-2-yl}-urea was carried out by reacting methanesulfonic acid 2-{2-[3-(2-cyclopentanecarbonyl-4-methyl-phenyl)-ureido]-thiazol-4-yl}-ethyl ester with arylthiol and $Et_3N$. This afforded the desired product in 60-80% yield.

General procedure M: Preparation of Urea.

A mixture of 1,1'-carbonyldiimidazole (98 mg, 0.6 mmol), (2-aminothiazol-4-yl)acetic acid ethyl ester (0.6 mmol) and 4-(N,N-dimethylamino)pyridine (2 mg) in dichloromethane (5 ml) was stirred at room temperature for 2 h. A solution of a substituted aniline derivative (0.6 mmol) in dichloromethane (1 ml) was added and stirring was continued at room temperature for 24 h. The reaction mixture was concentrated and the residue was purified by column chromatography (silica, $CH_2Cl_2$ then 10-30% ethyl acetate in $CH_2Cl_2$) to afford the desired urea.

HPLC-MS (Method A)

The following instrumentation is used:

Hewlett Packard series 1100 G1312A Bin Pump

Hewlett Packard series 1100 Column compartment

Hewlett Packard series 1100 G1315A DAD diode array detector

Hewlett Packard series 1100 MSD

Sedere 75 Evaporative Light Scattering detector

The instrument is controlled by HP Chemstation software.

The HPLC pump is connected to two eluent reservoirs containing:

A: 0.01% TFA in water

B: 0.01% TFA in acetonitrile

The analysis is performed at 40° C. by injecting an appropriate volume of the sample (preferably 1 μl) onto the column which is eluted with a gradient of acetonitrile.

The HPLC conditions, detector settings and mass spectrometer settings used are giving in the following table.

Column: Waters Xterra MS C-18×3 mm id 5 □m

Gradient: 5%-100% acetonitrile linear during 7.5 min at 1.5 ml/min

Detection: 210 nm (analogue output from DAD (diode array detector))

ELS (analogue output from ELS)

MS ionisation mode API-ES

Scan 100-1000 amu step 0.1 amu

After the DAD the flow is divided yielding approx 1 ml/min to the ELS and 0.5 ml/min to the MS.

Example 1

N-(2-Phenoxyphenyl)-N'-(thiazol-2-yl)urea

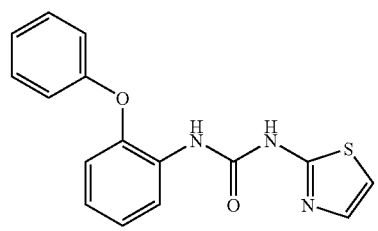

N-(2-Phenoxyphenyl)-N'-(thiazol-2-yl)urea (0.59 g, 94.9%) was prepared from 2-phenoxyaniline (0.37 g, 2.00 mmol) and 2-aminothiazole (0.20 g, 2.00 mmol) following the general procedure D.

LC-MS (m/z): 313 (M+1)$^+$. $^1$H NMR (400 MHz, acetone-$d_6$): δ 6.76 (d, J=13.8 Hz, 1H), 6.98-7.04 (m, 4H), 7.11 (t, J=4.8 Hz, 2H), 7.32 (t, J=8.0 Hz, 2H), and 8.35 (dd, J=1.6, 8.0 Hz, 1H), 10.2 (br, 2H).

Example 2

N-[2-(2,3-Dimethoxyphenoxy)-5-Fluorophenyl]-N'-(thizol-2-yl)sulfamide

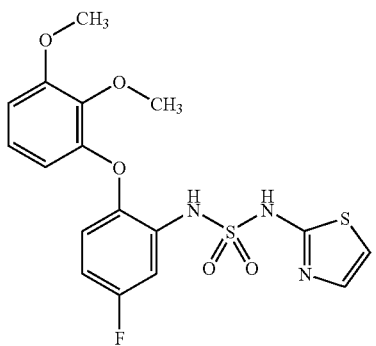

To a solution of sulfuryl chloride (2.0 ml, 2.0 mmol, 1.0 M solution in dichloro-methane) were added p-nitrophenol (0.55 g, 4.0 mmol) in dichloromethane and N,N-diisopropylethylamine (0.71 ml, 4.0 mmol) at −78° C. The reaction mixture was stirred for 1 hour at −78° C. and 2-(2,3-dimethoxyphenoxy)-5-fluoroaniline (0.52 g, 2.0 mmol) in dichloromethane (5 ml) was added. The reaction mixture was stirred for 10 min and 2-aminothiazole (0.2 g, 2.0 mmol) was added. The reaction mixture was allowed to warm up slowly to ambient temperature. The mixture was concentrated under reduced pressure. The residue was dissolved in ethyl acetate and was washed (dil. NaOH, water, brine), dried ($Na_2SO_4$) and concentrated under reduced pressure. The crude product was treated with Dowex-50 acidic resin in ethyl acetate-methanol (1:1) to remove unreacted 2-aminothiazole. The filtrate was concentrated and the residue was purified by silica gel column chromatography (ethylacetate:hexanes, from 50:50 to 90:10 as eluent system) to afford the title compound (0.42 g, 49%).

LC-MS (m/z): 427 (M+1)$^+$. $^1$H NMR (400 MHz, acetone-$d_6$): δ 3.12 (br, 2H), 3.71 (s, 3H), 3.86 (s, 3H), 6.56 (dd, J=7.6, 1.6 Hz, 1H), 6.66 (m, 1 H), 6.77-6.87 (m, 3H), 6.99 (t, J=3.6 Hz, 1H), 7.26 (d, J=4.8 Hz, 1H), and 7.38 (dd, J=10.8, 3.2 Hz, 1H)

Example 3

1-(2-phenoxyphenyl)-5-(thiazol-2-yl)biuret

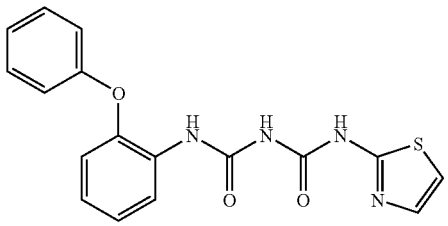

To a solution of 2-phenoxyaniline (0.46 g, 2.50 mmol) in tetrahydrofuran (20 ml) was added diisopropylethylamine (0.89 ml, 5.00 mmol) and the solution was cooled to −30° C., then N-(chlorocarbonyl)isocyanate (0.3 ml, 3.75 mmol) was slowly added. The mixture was then allowed to warm up to the room temperature during 30 min. 2-Aminothiazole (0.375 g, 3.75 mmol) was added to the reaction mixture and stirred at room temperature for 6 hours. The reaction mixture was concentrated under reduced pressure to afford crude product, which was purified by silica gel chromatography (hexanes: ethyl acetate from 80:20 to 30:70) to afford title compound (0.49 g, 55%) as pale yellow solid.

LC-MS (m/z): 356 (M+1). $^1$H NMR (400 MHz, acetone-$d_6$): δ 6.92 (dd, J=1.6, 7.6 Hz, 1H), 7.06 (m, 5H), 7.40 (m, 3H), 8.32 (d, J=4.8 Hz, 1H), 8.45 (d, J=5.6 Hz, 1H), 9.02 (br, 1H), 9.78 (br, 1H), and 10.46 (br, 1H).

Example 4

2-[([[(2-Phenoxyanilino)sulfonyl]amino]carbonyl)amino]thiazole

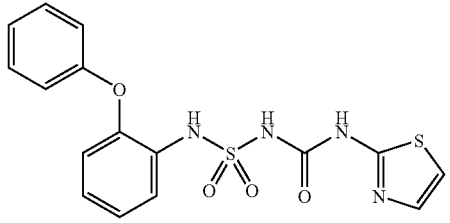

To a solution of chlorosulfonyl isocyanate (0.22 ml, 2.5 mmol) in tetrahydrofuran (25 ml) were added 2-phenoxyaniline (0.37 g, 2.0 mmol) and DIEA (0.89 ml, 5.0 mmol) at −78° C. The solution was stirred and slowly allowed to warmed up to 0° C. To this reaction mixture, was added 2-amino thiazole (0.20 g, 2.0 mmol) and continued stirring at room temperature for 3 h. The reaction mixture was concentrated under reduced pressure and the crude product was purified by column chromatography (ethylacetate:hexanes, from 50:50 to 90:10 as eluent system) to afford the title compound (0.52 g, 66%).

LC-MS (m/z): 392 (M+1)$^+$. $^1$H NMR (400 MHz, acetone-$d_6$): δ 6.85 (dd, J=8.8, 1.6 Hz, 1H), 6.88 (dd, J=1.6, 8.8 Hz, 1H), 7.00-7.16 (m, 5H), 7.29-7.39 (m, 4H), 10.33 (br, 1H), 10.88 (br, 2H).

Example 5

N-(2-Phenylsulfanylphenyl)-N'-(thiazol-2-yl)urea

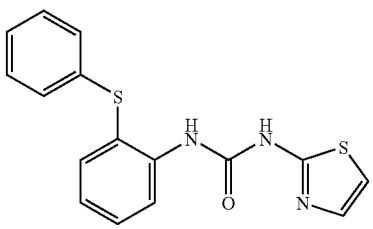

N-(2-Phenylsulfanylphenyl)-N'-(thiazol-2-yl)urea (116 mg, 71%) was prepared from 2-phenylsulfanylaniline (100 mg, 0.5 mmol) and 2-aminothiazole (60 mg, 0.6 mmol) following the general procedure D.

LC-MS (m/z): 329 (M+1)$^+$. $^1$H NMR (400 MHz, acetone-$d_6$): δ 7.03 (d, J=3.6 Hz, 1H), 7.10-7.18 (m, 4H), 7.25-7.31 (m, 3H), 7.48 (m, 1H), 7.59 (dd, J=3.6, 1.6 Hz, 1H), 8.44 (dd, J=8.4, 1.2 Hz, 1H), 9.00 (br, 1H), 10.44 (br, 1H).

Example 6

N-(2-Phenylsulfonylphenyl)-N'-(thiazol-2-yl)urea

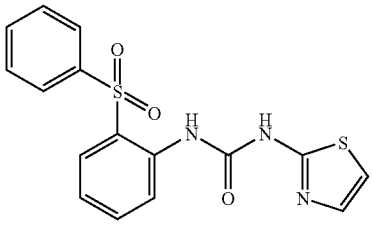

N-(2-Phenylsulfonylphenyl)-N'-(thiazol-2-yl)urea (98 mg, 55%) was prepared from 2-phenylsulfonylaniline (116 mg, 0.5 mmol) and 2-aminothiazole (60 mg, 0.6 mmol) following the general procedure D.

LC-MS (m/z): 361 (M+1)$^+$. $^1$H NMR (400 MHz, acetone-d$_6$): δ 7.07 (d, J=3.6 Hz, 1H), 7.33-7.37 (m, 1H), 7.40 (d, J=3.6 Hz, 1H), 7.55-7.60 (m, 2H), 7.63-7.71 (m, 2H), 7.98-8.01 (m, 2H), 8.12 (d, J=8.0 Hz, 1H), 8.22-8.25 (m, 1H), 9.26 (br, 1H), 10.99 (br, 1H).

Example 7

N-(2-Benzylphenyl)-N'-(thiazol-2-yl)urea

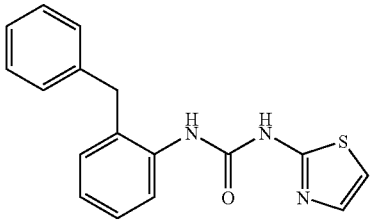

N-(2-Benzylphenyl)-N'-(thiazol-2-yl) urea (111 mg, 72%) was prepared from commercially available 2-benzylaniline (91 mg, 0.5 mmol) and 2-aminothiazole (60 mg, 0.6 mmol) following the general procedure D.

LC-MS (m/z): 311 (M+1)$^+$. $^1$H NMR (400 MHz, acetone-d$_6$): δ 4.08 (s, 2H), 7.02 (d, J=3.2 Hz, 1H), 7.06-7.14 (m, 2H), 7.14-7.19 (m, 4H), 7.23-7.29 (m, 4H), 7.96 (d, J=8.4 Hz, 1H), 8.75 (br, 1H), 10.01 (br, 1H).

Example 8

N-(2-Benzoylphenyl)-N'-(thiazol-2-yl)urea

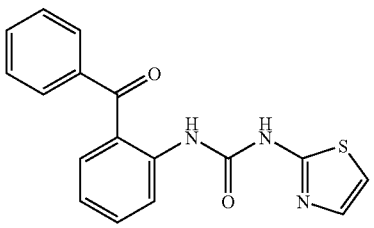

N-(2-Benzoylphenyl)-N'-(thiazol-2-yl)urea (100 mg, 63%) was prepared from 2-aminobenzophenone (97 mg, 0.5 mmol) and 2-aminothiazole (60 mg, 0.6 mmol) following the general procedure D.

LC-MS (m/z): 325 (M+1)$^+$. $^1$H NMR (400 MHz, acetone-d$_6$): δ 7.05 (s, 1H), 7.16 (s, 1H), 7.35 (d, J=3.6 Hz, 1H), 7.54 (d, J=7.2 Hz, 2H), 7.65 (s, 1H), 7.75 (s, 1H), 8.45 (s, 1H), 10.18 (br, 1H), 10.85 (br, 1H).

Example 9

N-[2-(Phenylamino)phenyl]-N'-(thiazol-2-yl)urea

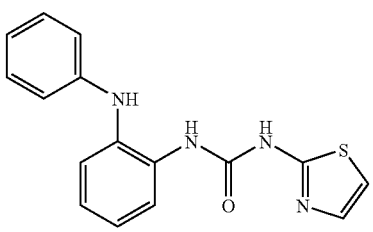

N-[2-(Phenylamino)phenyl]-N'-(thiazol-2-yl)urea (75 mg, 49%) was prepared from 2-(N-Phenylamino)aniline (92 mg, 0.5 mmol) and 2-aminothiazole (60 mg, 0.6 mmol) following the general procedure D.

LC-MS (m/z): 312 (M+1)$^+$. $^1$H NMR (400 MHz, acetone-d$_6$): δ 6.75-6.79 (m, 3H), 6.86 (br, 1H), 7.01 (d, J=3.6 Hz, 1H), 7.05-7.09 (m, 1H), 7.15-7.19 (m, 3H), 7.24-7.28 (m, 2H), 8.16 (d, J=8.0, 1.2 Hz, 1H), 8.65 (br, 1H), 10.15 (br, 1H).

Example 10

N-[2-Fluoro-6-(4-methoxyphenoxy)benzyl]-N'-(thiazol-2-yl)urea

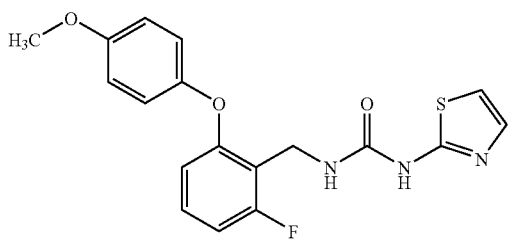

N-[2-Fluoro-6-(4-methoxyphenoxy)benzyl]-N'-(thiazol-2-yl)urea (0.61 g, 81%) was prepared from 2-fluoro-6-(4-methoxyphenoxy)benzylamine (0.494 g, 2.00 mmol) and 2-aminothiazole (0.20 g, 2.00 mmol) following general procedure D.

LC-MS (m/z): 327 (M+1)$^+$. $^1$H NMR (400 MHz, acetone-d$_6$): δ 3.06 (br, 1H), 3.78 (s, 3H), 4.67 (d, J=4.8 Hz, 2H), 6.52 (d, J=8.4 Hz, 1H), 6.85 (t, J=9.6 Hz, 1H), 6.95 (m, 3H), 7.05 (m, 2H), 7.24 (m, 2H), 10.06 (br, 1H).

Example 11

N-(2-Benzyloxyphenyl)-N'-(thiazol-2-yl)urea

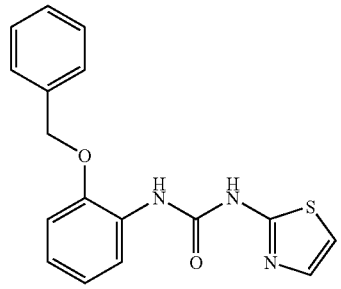

N-(2-Benzyloxyphenyl)-N'-(thiazol-2-yl)urea (0.56 g, 86%) was prepared from 2-benzyloxyaniline (0.40 g, 2.00 mmol) and 2-aminothiazole (0.20 g, 2.00 mmol) following the general procedure D.

LC-MS (m/z): 327 (M+1). $^1$H NMR (400 MHz, CDCl$_3$): δ 4.00 (br, 2H), 5.15 (s, 2H), 6.85 (dd, J=1.6, 8.8 Hz, 2H), 6.97 (dd, J=1.6, 7.2 Hz, 1H), 6.98 (dd, J=2.0, 6.0 Hz, 1H), 7.37 (m, 2H), 7.46 (t, J=7.2 Hz, 1H), 7.52 (d, J=5.6 Hz, 2H), and 7.56 (d, J=6.8 Hz, 2H)

Example 12

N-[2-(2,3,4-Trimethoxybenzyloxy)phenyl]-N'-(thiazol-2-yl)urea

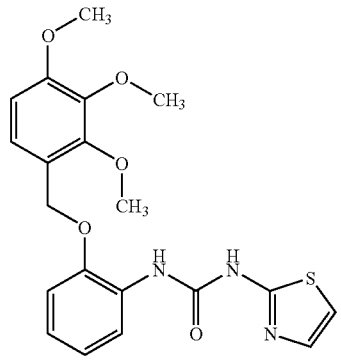

2-(2,3,4-Trimethoxybenzyloxy)-1-nitrobenzene (0.46 g, 72%) was prepared from 2,3,4-trimethoxybenzyl alcohol (0.35 ml, 2.0 mmol) and 1-fluoro-2-nitrobenzene (0.21 ml, 2.0 mmol) following the general procedure G. This was reduced to 2-(2,3,4-trimethoxybenzyl-oxy)aniline (0.26 g, 65%) following the general procedure B. N-[2-(2,3,4-trimethoxybenzyl-oxy)phenyl]-N'-(thiazol-2-yl)urea (240 mg, 65%) was prepared from 2-(2,3,4-trimethoxybenzyloxy) aniline (0.26 g, 0.9 mmol) and 2-aminothiazole (140 mg, 1.4 mmol) following the general procedure D.

LC-MS (m/z): 417 (M+1)$^+$. $^1$H NMR (400 MHz, acetone-d$_6$): δ 3.72 (s, 3H), 3.73 (s, 3H), 3.81 (s, 3H), 3.88 (s, 2H), 6.73-7.36 (m, 7H), 8.15 (t, J=8.4 Hz, 1H), 8.90 (br, 1H), 10.10 (br, 1H).

Example 13

N-(2-Ethoxyphenyl)-N'-(thiazol-2-yl)urea

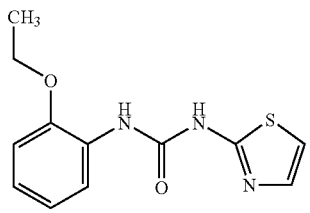

N-(2-Ethoxyphenyl)-N'-(thiazol-2-yl)urea (95 mg, 72%) was prepared from commercially available 2-ethoxyaniline (68 mg, 0.5 mmol) and 2-aminothiazole (60 mg, 0.6 mmol) following the general procedure D.

LC-MS (m/z): 265 (M+1)$^+$. $^1$H NMR (400 MHz, acetone-d$_6$): δ 1.29 (t, J=7.0 Hz, 3H), 3.94-3.98 (q, J=7.0 Hz, 2H), 6.74-6.88 (m, 4H), 7.27 (d, J=5.2 Hz, 1H), 8.17 (dd, J=1.6, 8.0 Hz, 1H), 8.42 (br, 1H), 10.92 (br, 1H).

Example 14

N-(2-Phenoxyphenyl)-N'-(pyridin-2-yl)urea

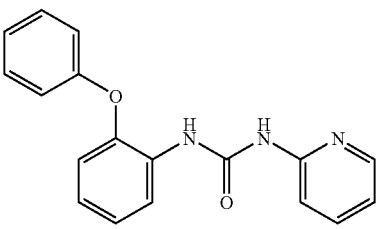

N-(2-Phenoxyphenyl)-N'-(pyridin-2-yl)urea (109 mg, 72%) was prepared from 2-phenoxyphenylisocyanate (106 mg, 0.5 mmol) and 2-aminopyridine (60 mg, 0.6 mmol) following the general procedure E.

LC-MS (m/z): 307 (M+1)$^+$. $^1$H NMR (400 MHz, DMSO-d$_6$): δ 6.88-6.91 (m, 1H), 6.96-7.08 (m, 4H), 7.15-7.19 (m, 2H), 7.32-7.36 (m, 2H), 7.65-7.69 (m, 1H), 7.88 (d, J=4.0 Hz, 1H), 8.36 (d, J=8.0 Hz, 1H), 9.84 (s, 1H), 11.5 (br, 1H).

Example 15

N-(2-Phenoxyphenyl)-N'-[(4-methoxycarbonylmethyl)thiazol-2-yl]urea

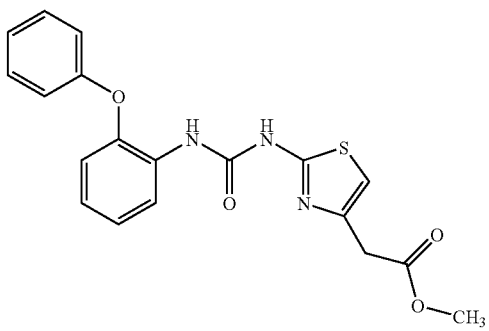

N-(2-Phenoxyphenyl)-N'-[(4-methoxycarbonylmethyl)thiazol-2-yl]urea (130 mg, 65%) was prepared from 2-phenoxyphenylisocyanate (106 mg, 0.5 mmol) and methyl 2-aminothiazole-4-acetate (104 mg, 0.6 mmol) following the general procedure E.

LC-MS (m/z): 401 (M+1)$^+$. $^1$H NMR (400 MHz, acetone-$d_6$): δ 3.58 (s, 2H), 3.61 (s, 3H), 6.84-6.89 (m, 2H), 7.01-7.05 (m, 3H), 7.13-7.18 (m, 2H), 7.38-8.42 (m, 2H), 8.40 (d, J=8.0 Hz, 1H), 8.91 (br, 1H), 10.12 (br, 1H).

Example 16

N-Methyl-N-(2-phenoxyphenyl)-N'-(thiazol-2-yl)urea

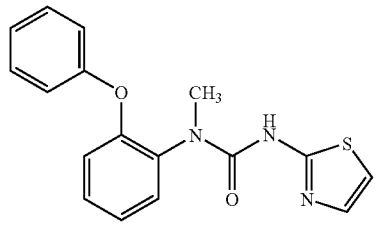

2-Phenoxyaniline (0.93 g, 5.00 mmol) and di-tert-butyl dicarbonate (2.18 g, 10.0 mmol) were dissolved in anhydrous dioxane (50 ml), then the reaction mixture was refluxed for 3 h. The mixture was concentrated under reduced pressure to quantitatively give 2-phenoxy-N-(t-butoxycarbonyl)aniline (1.43 g). The product was confirmed by LC-MS and subjected to next reaction without further purification.

To a solution of 2-phenoxy-N-(t-butoxycarbonyl)aniline (1.43 g, 5.0 mmol) in anhydrous tetrahydrofuran (50 ml) was added lithium aluminumhydride (10 ml, 10.0 mmol, 1.0 M solution in tetrahydrofuran) at –10° C. The mixture was then refluxed at 65° C. overnight. The reaction mixture was quenched with slow addition of MeOH (10 ml) and concentrated under reduced pressure. The reaction mixture was then poured into water (50 ml) and extracted with ethyl acetate (3×100 ml). Organic extracts were combined and washed with brine (2×100 ml) and dried over (Na$_2$SO$_4$), concentrated under reduced pressure to give N-methyl-2-phenoxyaniline (0.94 g, 94.0%) as a pale yellow oil. The product was confirmed by LC-MS and subjected to next reaction without further purification.

To a solution of 2-aminothiazole (0.20 g, 2.00 mmol) in dichloroethane (20 ml) was added 1,1'-carbonyldiimidazole (0.40 g, 2.5 mmol) and N,N-dimethylaminopyridine (0.05 g, 0.4 mmol) then the solution was refluxed at 80° C. for 1 h. N-Methyl-2-phenoxyaniline (0.40 g, 2.00 mmol) was added to the solution. The reaction mixture was then stirred overnight at 80° C. The reaction was monitored by LC-MS and TLC, then concentrated under reduced pressure to afford crude product which subsequently was subjected to silica gel chromatography (hexanes:ethyl acetate from 80:20 to 50:50 as eluent system) to afford title product (0.48 g, 73%) as orange solid.

LC-MS (m/z): 327 (M+1)$^+$. $^1$H NMR (400 MHz, CDCl$_3$): δ 3.30 (s, 3H), 6.84 (d, J=4.8 Hz, 1H), 6.97 (m, 3H), 7.16 (m, 2H), 7.29 (m, 5H), and 7.74 (br, 1H).

Example 17

N-isopropyl-N-(2-phenoxyphenyl)-N'-(thiazol-2-yl)urea

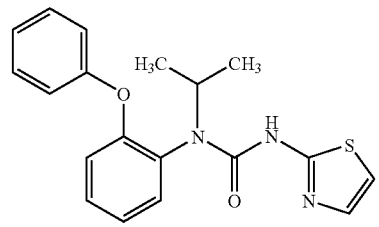

To a solution of 2-phenoxyaniline (0.93 g, 5.0 mmol) in dichloroethane (50 ml) was added anhydrous acetone (0.73 ml, 10.0 mmol) and acetic acid (0.1 ml, 2.0 mmol). The mixture was stirred for 30 min, and sodium triacetoxyborohydride (3.18 g, 15.0 mmol) was added in one portion. The reaction mixture was stirred overnight at ambient temperature. The reaction mixture was quenched by slow addition of MeOH (10 ml) and concentrated under reduced pressure. The residue was poured into water (50 ml) and extracted with ethyl acetate (3×100 ml). Organic extracts were combined and washed with brine (2×100 ml) and dried (Na$_2$SO$_4$), concentrated under reduced pressure to give N-isopropyl-2-phenoxyaniline (1.05 g, 91%) as colorless oil.

To a solution of 2-aminothiazole (0.20 g, 2.00 mmol) in dichloroethane (20 ml) was added 1,1'-carbonyldiimidazole (0.40 g, 2.5 mmol) and N,N-dimethylaminopyridine (0.05 g, 0.4 mmol) then the solution was refluxed at 80° C. for 1 h. N-Isopropyl-2-phenoxyaniline (0.46 g, 2.0 mmol) was added and the reaction mixture was then stirred overnight at 80° C. The reaction mixture was concentrated under reduced pressure to afford crude product, which was purified by silica gel chromatography (hexanes:ethyl acetate from 80:20 to 50:50 as eluent system) to afford title product (0.56 g, 79%).

LC-MS (m/z): 355 (M+1)$^+$. $^1$H NMR (400 MHz, acetone-$d_6$): δ 1.22 (d, J=6.4 Hz, 6H), 4.81 (m, 1H), 6.91 (m, 2H), 7.10-7.24 (m, 5H), 7.39 (m, 4H), and 9.00 (br, 1H).

Example 18

N-[2-(4-Methoxyphenoxy)phenyl)-N'-(thiazol-2-yl) urea

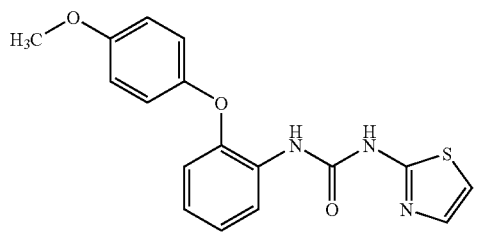

2-(4-Methoxyphenoxy)-1-nitrobenzene (0.98 g, 80%) was prepared from 4-methoxyphenol (0.62 g, 5.0 mmol) and 1-fluoro-2-nitrobenzene (0.71 g, 5.0 mmol) following the general procedure A. This was reduced to 2-(4-methoxyphenoxy)aniline (0.32 g, 60%, 2.5 mmol scale) following the general procedure B. N-[2-(4-Methoxyphenoxy)phenyl)-N'-(thiazol-2-yl)urea (256 mg, 75%) was prepared from 2-(4-methoxyphenoxy)aniline (215 mg, 1.0 mmol) and 2-aminothiazole (100 mg, 1.0 mmol) following the general procedure D.

LC-MS (m/z): 343 (M+1)$^+$. $^1$H NMR (400 MHz, acetone-$d_6$): δ 3.80 (s, 3H), 6.80 (d, J=8.0 Hz, 1H), 6.98-7.05 (m, 6H), 7.10 (m, 1H), 7.32 (d, J=3.6 Hz, 1H), 8.40 (d, J=8.0 Hz, 1H), 8.90 (br, 1H), 10.23 (br, 1H).

Example 19

N-[2-(4-Fluorophenoxy)phenyl]-N'-(thiazol-2-yl) urea

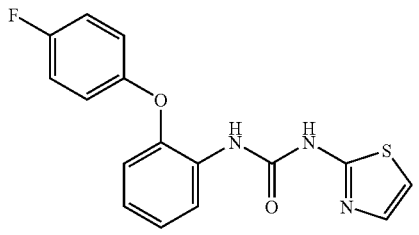

2-(4-Fluorophenoxy)-1-nitrobenzene (0.87 g, 75%) was prepared from 4-fluoro-phenol (0.62 g, 5.5 mmol) and 1-fluoro-2-nitrobenzene (0.71 g, 5.0 mmol) following the general procedure A. This was reduced to 2-(4-fluorophenoxy)aniline (0.51 g, 68%) following general procedure B. N-[2-(4-Fluorophenoxy)phenyl]-N'-(thiazol-2-yl)urea (118 mg, 72%) was prepared from 2-(4-fluorophenoxy)aniline (102 mg, 0.5 mmol) and 2-aminothiazole (60 mg, 0.6 mmol) following the general procedure D.

LC-MS (m/z): 331 (M+1)$^+$. $^1$H NMR (400 MHz, acetone-$d_6$): δ 6.89 (dd, J=8.4, 1.2 Hz, 1H), 7.01-7.11 (m, 4H), 7.14-7.29 (m, 3H), 7.31 (d, J=3.6 Hz, 1H), 8.42 (dd, J=8.0, 1.6 Hz, 1H), 9.12 (br, 1H), 10.19 (br, 1H).

Example 20

N-[2-(4-Chlorophenoxy)phenyl]-N'-(thiazol-2-yl) urea

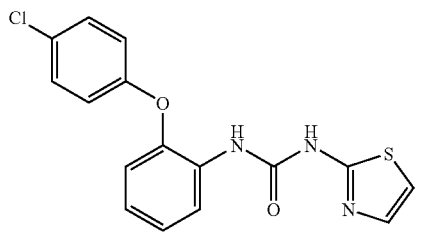

2-(4-Chlorophenoxy)-1-nitrobenzene (0.88 g, 71%) was prepared from 4-chlorophenol (0.70 g, 5.5 mmol) and 1-fluoro-2-nitrobenzene (0.71 g, 5.0 mmol) following the general procedure A. This was reduced to 2-(4-chlorophenoxy)aniline (0.50 g, 65%) following general procedure B. N-[2-(4-Chlorophenoxy)phenyl]-N'-(thiazol-2-yl)urea (106 mg, 62%) was prepared from 2-(4-chlorophenoxy)aniline (109 mg, 0.5 mmol) and 2-aminothiazole (60 mg, 0.6 mmol) following the general procedure D.

LC-MS (m/z): 347 (M+1)$^+$. $^1$H NMR (400 MHz, acetone-$d_6$): δ 6.98 (d, J=7.6 Hz, 1H), 7.04-7.09 (m, 4H), 7.19-7.23 (m, 1H), 7.31 (d, J=3.6 Hz, 1H), 7.39-7.43 (m, 2H), 8.44 (dd, J=8.4, 1.6 Hz, 1H), 8.90 (br, 1H), 10.13 (br, 1H).

Example 21

N-[2-(4-Cyanophenoxy)phenyl]-N'-thiazolylurea

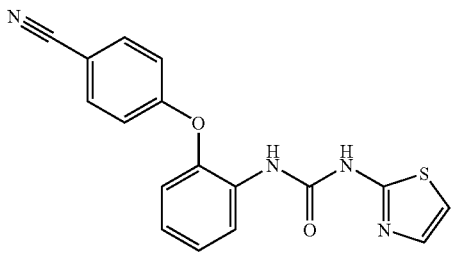

2-(4-Cyanophenoxy)-1-nitrobenzene (0.82 g, 69%) was prepared from 4-cyano-phenol (0.66 g, 5.5 mmol) and 1-fluoro-2-nitrobenzene (0.71 g, 5.0 mmol) following the general procedure A. This was reduced to 2-(4-cyanophenoxy)aniline (0.47 g, 65%) following general procedure B. N-[2-(4-Cyanophenoxy)phenyl]-N'-thiazolylurea (110 mg, 65%) was prepared from 2-(4-cyanophenoxy)aniline (105 mg, 0.5 mmol) and 2-aminothiazole (60 mg, 0.6 mmol) following the general procedure D.

LC-MS (m/z): 338 (M+1)$^+$. $^1$H NMR (400 MHz, acetone-$d_6$): δ 6.04 (d, J=8.0 Hz, 1H), 7.13-7.18 (m, 4H), 7.28-7.33 (m, 2H), 7.78-7.81 (m, 2H), 8.47 (d, J=8.0 Hz, 1H), 8.95 (br, 1H), 10.43 (br, 1H).

Example 22

N-[2-(4-Methoxycarbonylphenoxy)phenyl]-N'-(thiazol-2-yl)urea

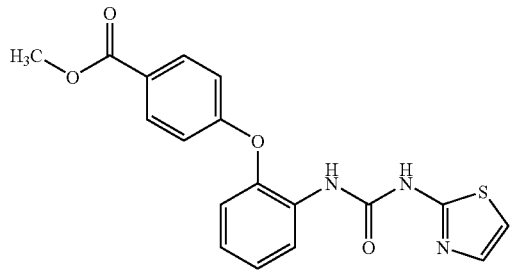

2-(4-Methoxycarbonylphenoxy)-1-nitrobenzene (0.79 g, 58%) was prepared from methyl 4-hydroxybenzoate (0.84 g, 5.5 mmol) and 1-fluoro-2-nitrobenzene (0.71 g, 5.0 mmol) following the general procedure A. This was reduced to 2-(4-methoxycarbonylphenoxy)-aniline (0.46 g, 66%) following general procedure B. N-[2-(4-Methoxycarbonylphenoxy)-phenyl]-N'-(thiazol-2-yl)urea (100 mg, 55%) was prepared from 2-(4-methoxycarbonyl-phenoxy)aniline (122 mg, 0.5 mmol) and 2-aminothiazole (60 mg, 0.6 mmol) following the general procedure D.

LC-MS (m/z): 371 (M+1)$^+$. $^1$H NMR (400 MHz, acetone-$d_6$): δ 3.85 (s, 3H), 7.03 (d, J=3.6 Hz, 1H), 7.07-7.14 (m, 4H), 7.25-7.29 (m, 2H), 8.01-4.04 (m, 2H), 8.46 (dd, J=8.1, 1.2 Hz, 1H), 8.76 (br, 1H), 10.07 (br, 1H).

Example 23

N-[2-(4-Isopropylphenoxy)phenyl]-N'-(thiazol-2-yl)urea

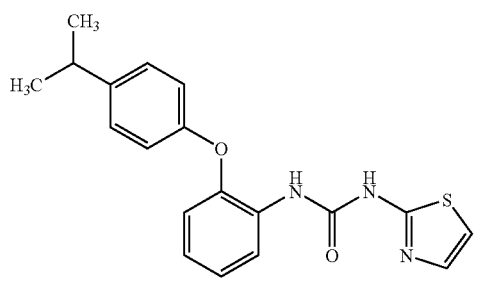

2-(4-Isopropylphenoxy)-1-nitrobenzene (0.95 g, 75%) was prepared from 4-isopropylphenol (0.68 g, 5.0 mmol) and 1-fluoro-2-nitrobenzene (0.71 g, 5.0 mmol) following the general procedure A. This was reduced to 2-(4-isopropylphenoxy)aniline (0.34 g, 60%, 2.5 mmol scale) following general procedure B. N-[2-(4-Isopropylphenoxy)phenyl]-N'-(thiazol-2-yl)urea (247 mg, 70%) was prepared from 2-(4-isopropylphenoxy)aniline (227 mg, 1.0 mmol) and 2-aminothiazole (100 mg, 1.0 mmol) following the general procedure D.

LC-MS (m/z): 355 (M+1)$^+$. $^1$H NMR (400 MHz, acetone-$d_6$): δ 1.17 (d, J=7.2 Hz, 3H), 1.22 (d, J=6.8 Hz, 3H), 2.88 (m, 1H), 6.74 (d, J=6.6 Hz, 1H), 6.88 (d, J=8.0 Hz, 1H), 6.94-7.15 (m, 4H), 7.28 (m, 2H), 8.43 (d, J=8.2 Hz, 1H), 10.15 (br, 2H).

Example 24

N-[2-(3,4-Difluorophenoxy)phenyl]-N'-(thiazol-2-yl)urea

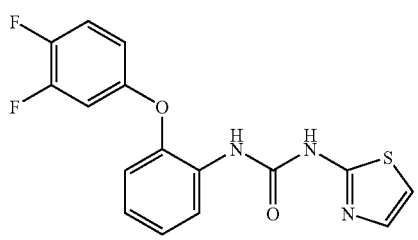

2-(3,4-Difluorophenoxy)-1-nitrobenzene (0.76 g, 60%) was prepared from 3,4-difluorophenol (0.65 g, 5.5 mmol) and 1-fluoro-2-nitrobenzene (0.71 g, 5.0 mmol) following the general procedure A. This was reduced to 2-(3,4-difluorophenoxy)aniline (0.33 g, 60%, 2.5 mmol scale) following general procedure B. N-[2-(3,4-Difluorophenoxy)phenyl]-N'-(thiazol-2-yl)urea (312 mg, 60%) was prepared from 2-(3,4-difluorophenoxy)aniline (330 mg, 1.5 mmol) and 2-aminothiazole (150 mg, 1.5 mmol) following the general procedure D.

LC-MS (m/z): 349 (M+1)$^+$. $^1$H NMR (400 MHz, acetone-$d_6$): δ 6.88 (m, 1H), 7.01 (d, J=8.0 Hz, 1H), 7.04-7.12 (m, 4H), 7.22 (m, 1H), 7.30-7.42 (m, 2H), 8.43 (d, J=8.2 Hz, 1H), 10.16 (br, 2H).

Example 25

N-[2-(3,4-Dichlorophenoxy)phenyl]-N'-(thiazol-2-yl)urea

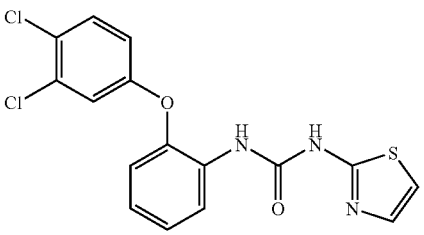

2-(3,4-Dichlorophenoxy)-1-nitrobenzene (1.15 g, 81%) was prepared from 3,4-dichlorophenol (0.9 g, 5.5 mmol) and 1-fluoro-2-nitrobenzene (0.71 g, 5.0 mmol) following the general procedure A. This was reduced to 2-(3,4-dichlorophenoxy)aniline (0.69 g, 68%) following general procedure B. N-[2-(3,4-Dichlorophenoxy)phenyl]-N'-(thiazol-2-yl)urea (129 mg, 68%) was prepared from 2-(3,4-dichlorophenoxy)aniline (127 mg, 0.5 mmol) and 2-aminothiazole (60 mg, 0.6 mmol) following the general procedure D.

LC-MS (m/z): 382 (M+1)+. $^1$H NMR (400 MHz, acetone-$d_6$): δ 6.99-7.13 (m, 4H), 7.24-7.28 (m, 2H), 7.30 (d, J=3.6 Hz, 1H), 7.57 (d, J=9.2 Hz, 1H), 8.44 (dd, J=8.4, 1.2 Hz, 1H), 9.20 (br, 1H), 10.09 (br, 1H).

Example 26

N-[2-(4-Chloro-3-methylphenoxy)phenyl]-N'-(thiazol-2-yl)urea

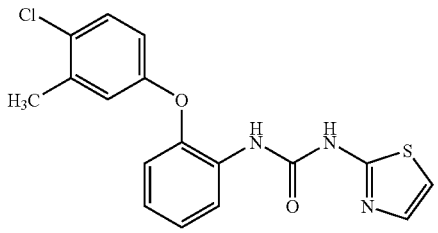

N-[2-(4-Chloro-3-methylphenoxy)phenyl]-N'-(thiazol-2-yl)urea (233 mg, 65%) was prepared from 2-(4-chloro-3-methylphenoxy)aniline (233 mg, 1.0 mmol) and 2-aminothiazole (100 mg, 1.0 mmol) following the general procedure D.

LC-MS (m/z): 361 (M+1)+. $^1$H NMR (400 MHz, acetone-$d_6$): δ 2.36 (s, 3H), 6.94-6.98 (m, 2H), 7.05 (m, 4H), 7.19 (m, 1H), 7.31 (d, J=4.0 Hz, 1H), 7.37 (d, J=8.4 Hz, 1H), 8.43 (d, J=8.4 Hz, 1H), 10.23 (br, 2H).

Example 27

N-[2-(3,4-Dimethoxyphenoxy)phenyl]-N'-(thiazol-2-yl)urea

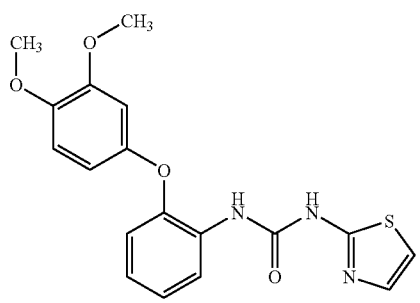

2-(3,4-Dimethoxyphenoxy)-1-nitrobenzene (0.93 g, 68%) was prepared from 3,4-dimethoxyphenol (0.85 g, 5.5 mmol) and 1-fluoro-2-nitrobenzene (0.71 g, 5.0 mmol) following the general procedure A. This was reduced to 2-(3,4-dimethoxyphenoxy)aniline (0.51 g, 62%) following general procedure B. N-[2-(3,4-Dimethoxyphenoxy)phenyl]-N'-(thiazol-2-yl)urea (128 mg, 69%) was prepared from 2-(3,4-dimethoxyphenoxy)aniline (123 mg, 0.5 mmol) and 2-aminothiazole (60 mg, 0.6 mmol) following the general procedure D.

LC-MS (m/z): 373 (M+1)+. $^1$H NMR (400 MHz, acetone-$d_6$): δ 3.80 (s, 6H), 6.54 (dd, J=8.4, 2.4 Hz, 1H), 6.78 (d, J=2.4 Hz, 1H), 6.82 (d, J=8.0 Hz, 1H), 6.97 (d, J=8.0 Hz, 1H), 6.99-7.01 (m, 1H), 7.04 (d, J=3.6 Hz, 1H), 7.07-7.12 (m, 1H), 7.33-7.34 (d, J=3.6 Hz, 1H), 8.39 (dd, J=8.0, 1.2 Hz, 1H), 8.90 (br, 1H), 10.23 (br, 1H).

Example 28

N-[2-(3,4-Methylenedioxyphenoxy)phenyl]-N'-(thiazol-2-yl)urea

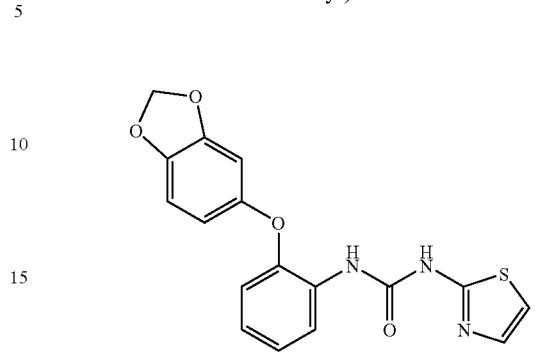

2-(3,4-Methylenedioxyphenoxy)-1-nitrobenzene (0.75 g, 58%) was prepared from 3,4-methylenedioxyphenol (0.76 g, 5.5 mmol) and 1-fluoro-2-nitrobenzene (0.71 g, 5.0 mmol) following the general procedure A. This was reduced to 2-(3,4-methylenedioxyphenoxy)-aniline (0.47 g, 71%) following general procedure B. N-[2-(3,4-Methylenedioxyphenoxy)-phenyl]-N'-(thiazol-2-yl)urea (120 mg, 68%) was prepared from 2-(3,4-methylenedioxy-phenoxy)aniline (115 mg, 0.5 mmol) and 2-aminothiazole (60 mg, 0.6 mmol) following the general procedure D.

LC-MS (m/z): 357 (M+1)+. $^1$H NMR (400 MHz, acetone-$d_6$): δ 6.06 (s, 2H), 6.51 (dd, J=8.4, 2.4 Hz, 1H), 6.67 (d, J=2.4 Hz, 1H), 6.84-6.87 (m, 2H), 6.99-7.05 (m, 2H), 7.10-7.14 (m, 1H), 7.32-7.33 (d, J=3.6 Hz, 1H), 8.39 (dd, J=8.0, 1.2 Hz, 1H), 8.95 (br, 1H), 10.22 (br, 1H).

Example 29

N-[2-(2,4-Dichlorophenoxy)phenyl]-N'-(thiazol-2-yl)urea

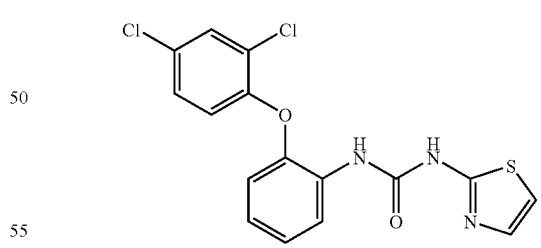

N-[2-(2,4-Dichlorophenoxy)phenyl]-N'-(thiazol-2-yl)urea (125 mg, 67%) was prepared from 2-(2,4-dichlorophenoxy)aniline (127 mg, 0.5 mmol) and 2-aminothiazole (60 mg, 0.6 mmol) following the general procedure D.

LC-MS (m/z): 382 (M+1)+. $^1$H NMR (400 MHz, acetone-$d_6$): δ 6.86 (d, J=8.0 Hz, 1H) 7.03-7.08 (m, 3H), 7.19-7.23 (m, 1H), 7.30 (d, J=4.0 Hz, 1H), 7.38 (dd, J=8.8, 2.8 Hz, 1H), 7.65 (d, J=2.4 Hz, 1H), 8.43 (dd, J=8.0, 1.2 Hz, 1H), 8.87 (br, 1H), 10.16 (br, 1H).

Example 30

N-[2-(2,4-Difluorophenoxy)phenyl]-N'-(thiazol-2-yl)urea

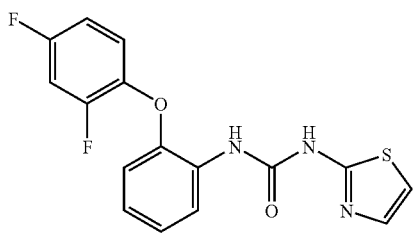

2-(2,4-Difluorophenoxy)-1-nitrobenzene (0.95 g, 76%) was prepared from 2,4-difluorophenol (0.72 g, 5.5 mmol) and 1-fluoro-2-nitrobenzene (0.71 g, 5.0 mmol) following the general procedure A. This was reduced to 2-(2,4-difluorophenoxy)aniline (0.53 g, 63%) following general procedure B. N-[2-(2,4-Difluorophenoxy)phenyl]-N'-(thiazol-2-yl)urea (120 mg, 69%) was prepared from 2-(2,4-difluorophenoxy)aniline (110 mg, 0.5 mmol) and 2-aminothiazole (60 mg, 0.6 mmol) following the general procedure D.

LC-MS (m/z): 349 (M+1)$^+$. $^1$H NMR (400 MHz, acetone-$d_6$): δ 6.83 (m, 1H), 7.00-7.30 (m, 6H), 7.32 (d, J=3.6 Hz, 1H), 8.42 (dd, J=8.0, 2.0 Hz, 1H), 9.00 (br, 1H), 10.19 (br, 1H).

Example 31

N-[2-(4-Fluoro-2-methoxyphenoxy)phenyl]-N'-(thiazol-2-yl)urea

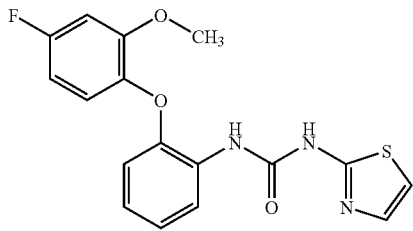

2-(4-Fluoro-2-methoxyphenoxy)-1-nitrobenzene (0.88 g, 67%) was prepared from 4-fluoro-2-methoxyphenol (0.78 g, 5.5 mmol) and 1-fluoro-2-nitrobenzene (0.71 g, 5.0 mmol) following the general procedure A. This was reduced to 2-(4-fluoro-2-methoxyphenoxy)-aniline (0.60 g, 78%) following general procedure C. N-[2-(4-Fluoro-2-methoxyphenoxy)phenyl]-N'-(thiazol-2-yl)urea (127 mg, 71%) was prepared from 2-(4-fluoro-2-methoxyphenoxy)aniline (116 mg, 0.5 mmol) and 2-aminothiazole (60 mg, 0.6 mmol) following the general procedure D.

LC-MS (m/z): 361 (M+1)$^+$. $^1$H NMR (400 MHz, acetone-$d_6$): δ 3.82 (s, 3H), 6.61 (dd, J=8.0, 2.8 Hz, 1H), 6.74-6.79 (m, 1H), 6.89-6.94 (m, 1H), 7.00-7.06 (m, 3H), 7.16 (dd, J=8.8, 5.6 Hz, 1H), 7.33 (d, J=3.6 Hz, 1H), 8.43 (dd, J=8.4, 1.6 Hz, 1H), 8.85 (br, 1H), 10.29 (br, 1H).

Example 32

N-[2-(4-Methoxy-2-methoxycarbonylphenoxy)phenyl]-N'-(thiazol-2-yl)urea

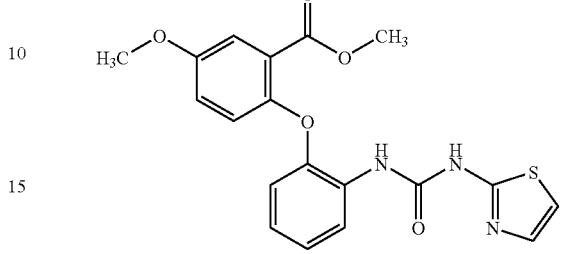

2-[4-Methoxy-2-methoxycarbonylphenoxy]-1-nitrobenzene (0.78 g, 52%) was prepared from methyl 5-methoxysalicylate (1.0 g, 5.5 mmol) and 1-fluoro-2-nitrobenzene (0.71 g, 5.0 mmol) following the general procedure A. This was reduced to 2-[4-methoxy-2-(methoxycarbonyl)phenoxy]aniline (0.47 g, 68%) following general procedure B. N-[2-(4-Methoxy-2-methoxycarbonylphenoxy)phenyl]-N'-(thiazol-2-yl)urea (130 mg, 66%) was prepared from 2-[4-methoxy-2-(methoxycarbonyl)phenoxy]aniline (136 mg, 0.5 mmol) and 2-aminothiazole (60 mg, 0.6 mmol) following the general procedure D.

LC-MS (m/z): 401 (M+1)$^+$. $^1$H NMR (400 MHz, acetone-$d_6$): δ 3.69 (s, 3H), 3.84 (s, 3H), 6.61 (dd, J=8.0, 1.6 Hz, 1H), 6.90-6.95 (m, 1H), 7.03-7.09 (m, 2H), 7.16-7.25 (m, 2H), 7.25-7.39 (m, 1H), 7.43-7.44 (m, 1H), 8.37 (dd, J=8.4, 1.6 Hz, 1H), 8.96 (br, 1H), 10.26 (br, 1H).

Example 33

N-[2-(3-Methoxyphenoxy)phenyl]-N'-(thiazol-2-yl)urea

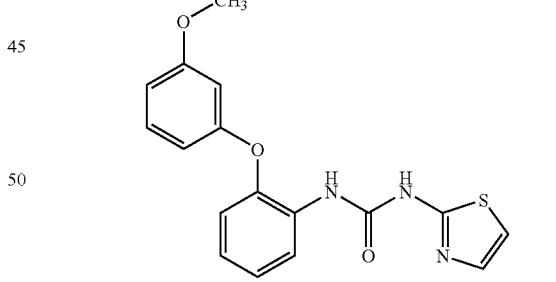

2-(3-Methoxyphenoxy)-1-nitrobenzene (0.84 g, 69%) was prepared from 3-methoxyphenol (0.68 g, 5.5 mmol) and 1-fluoro-2-nitrobenzene (0.71 g, 5.0 mmol) following the general procedure A. This was reduced to 2-(3-methoxyphenoxy)aniline (0.51 g, 70%) following general procedure B. N-[2-(3-Methoxyphenoxy)phenyl]-N'-(thiazol-2-yl)urea (136 mg, 68%) was prepared from 2-(3-methoxyphenoxy)aniline (108 mg, 0.5 mmol) and 2-amino-thiazole (60 mg, 0.6 mmol) following the general procedure D.

LC-MS (m/z): 343 (M+1)$^+$. $^1$H NMR (400 MHz, acetone-$d_6$): δ 3.78 (s, 3H), 6.55-6.62 (m, 2H), 6.71-6.73 (m, 1H), 6.95 (dd, J=8.0, 1.6 Hz, 1H), 7.03-7.07 (m, 2H), 7.16-7.20 (m, 1H), 7.27 (d, J=8.4 Hz, 1H), 7.31 (d, J=4.0 Hz, 1H), 8.43 (dd, J=8.4, 1.6 Hz, 1H), 8.84 (br, 1H), 10.37 (br, 1H).

Example 34

N-[2-(3-Fluorophenoxy)phenyl]-N'-(thiazol-2-yl) urea

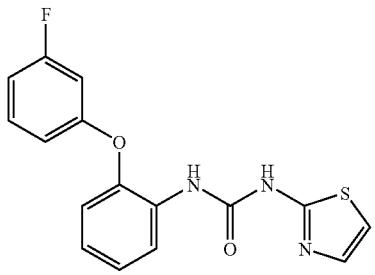

2-(3-Fluorophenoxy)-1-nitrobenzene (0.85 g, 73%) was prepared from 3-fluorophenol (0.62 g, 5.5 mmol) and 1-fluoro-2-nitrobenzene (0.71 g, 5.0 mmol) following the general procedure A. This was reduced to 2-(3-fluorophenoxy)aniline (0.50 g, 68%) following general procedure B. N-[2-(3-Fluorophenoxy)phenyl]-N'-(thiazol-2-yl)urea (110 mg, 68%) was prepared from 2-(3-fluorophenoxy)aniline (102 mg, 0.5 mmol) and 2-aminothiazole (60 mg, 0.6 mmol) following the general procedure D.

LC-MS (m/z): 331 (M+1)$^+$. $^1$H NMR (400 MHz, acetone-$d_6$): δ 6.80-6.84 (m, 2H), 6.85-6.93 (m, 1H), 7.03-7.07 (m, 2H), 7.08-7.13 (m, 1H), 7.30 (d, J=3.6 Hz, 1H), 7.38-7.45 (m, 1H), 8.45 (dd, J=8.0, 1.2 Hz, 1H), 9.06 (br, 1H), 10.1 (br 1H).

Example 35

N-[2-(3-Trifluoromethylphenoxy)phenyl]-N'-(thiazol-2-yl)urea

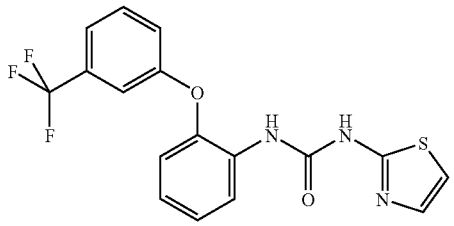

2-[3-(Trifluoromethyl)phenoxy]-1-nitrobenzene (0.92 g, 65%) was prepared from 3-hydroxybenzotrifluoride (0.89 g, 5.5 mmol) and 1-fluoro-2-nitrobenzene (0.71 g, 5.0 mmol) following the general procedure A. This was reduced to 2-[3-(trifluoromethyl)phenoxy]aniline (0.56 g, 68%) following general procedure B. N-[2-(3-Trifluoromethylphenoxy)phenyl]-N'-(thiazol-2-yl)urea (120 mg, 62%) was prepared from 2-[3-(trifluoromethyl)phenoxy]aniline (127 mg, 0.5 mmol) and 2-aminothiazole (60 mg, 0.6 mmol) following the general procedure D.

LC-MS (m/z): 381 (M+1)$^+$. $^1$H NMR (400 MHz, acetone-$d_6$): δ 7.04-7.13 (m, 3H), 7.24-7.29 (m, 3H), 7.36 (s, 1H), 7.47 (d, J=7.6 Hz, 1H), 7.63 (t, J=8.0 Hz, 1H), 8.46 (dd, J=8.0, 1.2 Hz, 1H), 8.95 (br, 1H), 10.08 (br, 1H).

Example 36

N-[2-(2-Methylphenoxy)phenyl]-N'-(thiazol-2-yl) urea

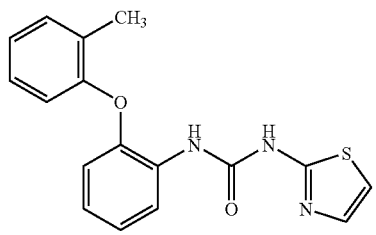

N-[2-(2-Methylphenoxy)phenyl]-N'-(thiazol-2-yl)urea (110 mg, 68%) was prepared from 2-(2-methylphenoxy) aniline (100 mg, 0.5 mmol) and 2-aminothiazole (60 mg, 0.6 mmol) following the general procedure D.

LC-MS (m/z): 327 (M+1)$^+$. $^1$H NMR (400 MHz, acetone-$d_6$): δ 2.25 (s, 3H), 6.68 (d, J=8.4 Hz, 1H), 6.89 (d, J=8.0 Hz, 1H), 6.96-7.00 (m, 1H), 7.04-7.13 (m, 3H), 7.20-7.34 (m, 3H), 8.42 (dd, J=8.0, 1.6 Hz, 1H), 8.95 (br, 1H), 10.25 (br, 1H).

Example 37

N-[2-(2-Methoxyphenoxy)phenyl]-N'-(thiazol-2-yl) urea

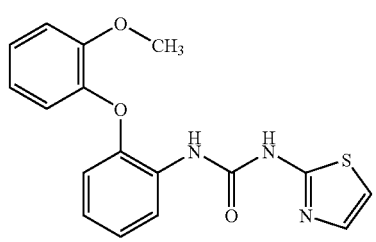

2-(2-Methoxyphenoxy)-1-nitrobenzene (0.99 g, 81%) was prepared from 2-methoxyphenol (0.68 g, 5.5 mmol) and 1-fluoro-2-nitrobenzene (0.71 g, 5.0 mmol) following the general procedure A. This was reduced to 2-(2-methoxyphenoxy)aniline (0.63 g, 73%) following general procedure B. N-2-(2-Methoxyphenoxy)phenyl-N'-(thiazol-2-yl)urea (110 g, 65%) was prepared from 2-(2-methoxyphenoxy)aniline (108 mg, 0.5 mmol) and 2-aminothiazole (60 mg, 0.6 mmol) following the general procedure D.

LC-MS (m/z): 343 (M+1)$^+$. $^1$H NMR (400 MHz, acetone-$d_6$): δ 3.78 (s, 3H), 6.61 (d, J=8.0 Hz, 1H), 6.91-7.33 (m, 8H), 8.37 (d, J=8.0 Hz, 1H), 9.13 (br, 1H), 10.31 (br, 1H).

Example 38

N-[2-(2-Isopropoxyphenoxy)phenyl]-N'-(thiazol-2-yl)urea

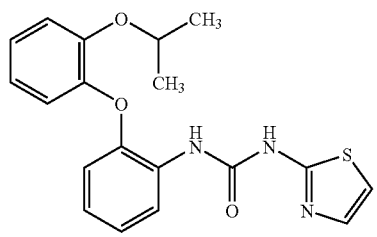

2-(2-Isopropoxyphenoxy)-1-nitrobenzene (0.90 g, 69%) was prepared from 2-isopropoxyphenol (0.84 g, 5.5 mmol) and 1-fluoro-2-nitrobenzene (0.71 g, 5.0 mmol) following the general procedure A. This was reduced to 2-(2-methoxyphenoxy)aniline (0.65 g, 81%) following general procedure B. N-[2-(2-Isopropoxyphenoxy)phenyl]-N'-(thiazol-2-yl)urea (120 mg, 65%) was prepared from 2-(2-isopropoxyphenoxy)aniline (122 mg, 0.5 mmol) and 2-aminothiazole (60 mg, 0.6 mmol) following the general procedure D.

LC-MS (m/z): 371 (M+1')+. $^1$H NMR (400 MHz, acetone-$d_6$): δ 1.07 (d, J=6.0 Hz, 6H), 4.54-4.59 (m, 1H), 6.64 (dd, J=8.0, 1.6 Hz, 1H), 6.88-6.92 (m, 1H), 6.97-7.06 (m, 3H), 7.12-7.22 (m, 3H), 7.33 (d, J=3.6 Hz, 1H), 8.38 (dd, J=8.0, 1.6 Hz, 1H), 8.86 (br, 1H), 10.3 (br, 1 H).

Example 39

N-[2-(2-Fluorophenoxy)phenyl]-N'-(thiazol-2-yl)urea

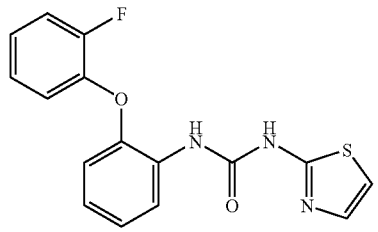

2-(2-Fluorophenoxy)-1-nitrobenzene (0.94 g, 81%) was prepared from 2-fluorophenol (0.62 g, 5.5 mmol) and 1-fluoro-2-nitrobenzene (0.71 g, 5.0 mmol) following the general procedure A. This was reduced to 2-(2-fluorophenoxy)aniline (0.59 g, 72%) following general procedure B. N-[2-(2-Fluorophenoxy)phenyl]-N'-(thiazol-2-yl)urea (110 mg, 68%) was prepared from 2-(2-fluorophenoxy)aniline (102 mg, 0.5 mmol) and 2-aminothiazole (60 mg, 0.6 mmol) following the general procedure D.

LC-MS: 331 (M+1)+. $^1$H NMR (400 MHz, acetone-$d_6$): δ 6.84 (d, J=8.0 Hz, 1H) 7.05-7.08 (m, 1H), 7.01-7.06 (m, 2H), 7.12-7.17 (m, 2H), 7.22-7.25 (m, 2H), 7.29-7.36 (m, 2H), 8.43 (dd, J=8.0, 1.6 Hz, 1H), 8.95 (br, 1H), 10.17 (br, 1H).

Example 40

N-[2-(2-Methylsulfanylphenoxy)phenyl]-N'-(thiazol-2-yl)urea

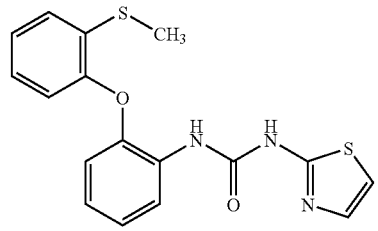

2-(2-Methylsulfanylphenoxy)-1-nitrobenzene (0.88 g, 68%) was prepared from 2-hydroxythioanisole (0.77 g, 5.5 mmol) and 1-fluoro-2-nitrobenzene (0.71 g, 5.0 mmol) following the general procedure A. This was reduced to 2-(2-methylsulfanylphenoxy)aniline (0.53 g, 68%) following general procedure B. N-[2-(2-Methylsulfanylphenoxy)phenyl]-N'-(thiazol-2-yl)urea (115 mg, 65%) was prepared from 2-(2-methylsulfanylphenoxy)aniline (115 mg, 0.5 mmol) and 2-aminothiazole (60 mg, 0.6 mmol) following the general procedure D.

LC-MS (m/z): 359 (M+1)+. $^1$H NMR (400 MHz, acetone-$d_6$): δ 2.42 (s, 3H), 6.68 (dd, J=8.0, 1.2 Hz, 1H), 6.92 (d, J=8.0 Hz, 1H), 6.95-6.99 (m, 1H), 7.04 (d, J=3.6 Hz, 1H), 7.09-7.14 (m, 1H), 7.17-7.26 (m, 2H), 7.31 (d, J=3.6 Hz, 1H), 7.38 (dd, J=7.6, 1.6 Hz, 1H), 8.42 (dd, J=8.0, 1.6 Hz, 1H), 8.95 (br, 1H), 10.26 (br, 1H).

Example 41

N-[2-(2-Methylsulfonylphenoxy)phenyl]-N'-thiazolylurea

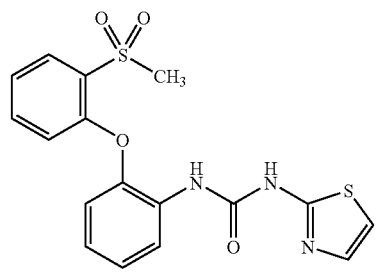

To a solution of 2-(2-methylsulfanylphenoxy)-1-nitrobenzene (1.3 g, 5.0 mmol) in dichloromethane (30 ml) at 0° C. was added mCPBA (70%, 3.68 g, 15 mmol), in portions during 10 min. The contents were stirred for 2 h at room temperature. The precipitate was filtered off and the mother liquor was washed thrice with 10% aq $Na_2S_2O_7$. The organic layer was washed (dil NaOH, water, brine), dried and concentrated to obtain 2-(2-methylsulfonylphenoxy)-1-nitrobenzene (1.0 g, 68%). This was reduced to 2-(2-methylsulfonylphenoxy)-aniline (0.68 g, 76%) following general procedure B. N-[2-(2-Methylsulfonylphenoxy)phenyl]-N'-(thiazol-2-yl)urea (105 mg, 55%) was prepared from 2-(2-methylsulfonylphenoxy)aniline (132 mg, 0.5 mmol) and 2-aminothiazole (60 mg, 0.6 mmol) following the general procedure D.

LC-MS (m/z): 391 (M+1)+. 1H NMR (400 MHz, acetone-$d_6$): δ 3.44 (s, 3H), 7.02 (d, J=3.6 Hz, 1H), 7.06 (d, J=8.4 Hz, 1H), 7.12-7.20 (m, 2H), 7.27-7.36 (m, 2H), 7.38-7.40 (m, 1H), 7.67-7.71 (m, 1H), 8.02 (dd, J=8.0, 1.6 Hz, 1H), 8.42 (dd, J=8.4, 1.2 Hz, 1H), 9.20 (br, 1H), 9.78 (br, 1H).

Example 42

N-[2-2-Trifluoromethylphenoxy)phenyl]-N'-(thiazol-2-yl)urea

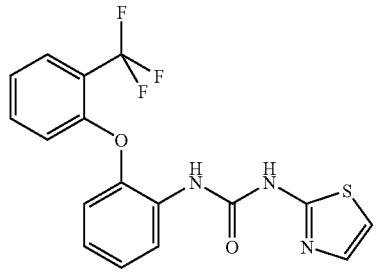

2-[2-(Trifluoromethyl)phenoxy]-1-nitrobenzene (0.92 g, 65%) was prepared from 2-hydroxybenzotrifluoride (0.89 g, 5.5 mmol) and 1-fluoro-2-nitrobenzene (0.71 g, 5.0 mmol) following the general procedure A. This was reduced to 2-[2-(trifluoromethyl)phenoxy]aniline (0.56 g, 68%) following general procedure B. N-[2-(2-Trifluoromethylphenoxy)phenyl]-N'-(thiazol-2-yl)urea (115 mg, 61%) was prepared from 2-[2-(trifluoromethyl)phenoxy]aniline (127 mg, 0.5 mmol) and 2-aminothiazole (60 mg, 0.6 mmol) following the general procedure D.

LC-MS (m/z): 381 (M+1)+. 1H NMR (400 MHz, acetone-$d_6$): δ 6.91 (dd, J=8.0, 1.6 Hz, 1H), 7.01-7.06 (m, 2H), 7.08-7.11 (m, 1H), 7.22-7.26 (m, 2H), 7.34 (t, J=7.6 Hz, 1H), 7.65 (t, J=7.6 Hz, 1H), 7.81 (dd, J=8.0, 1.2 Hz, 1H), 8.45 (dd, J=8.4, 1.6 Hz, 1H), 9.00 (br, 1H), 10.2 (br, 1H).

Example 43

N-[2-(2,6-Dimethoxyphenoxy)phenyl]-N'-(thiazol-2-yl)urea

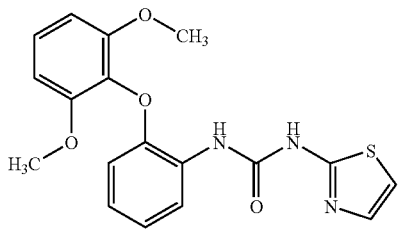

2-(2,6-Dimethoxyphenoxy)-1-nitrobenzene (0.85 g, 63%) was prepared from 2,6-dimethoxyphenol (0.85 g, 5.5 mmol) and 1-fluoro-2-nitrobenzene (0.71 g, 5.0 mmol) following the general procedure A. This was reduced to 2-(2,6-dimethoxyphenoxy)aniline (0.51 g, 68%) following general procedure C. N-[2-(2,6-Dimethoxyphenoxy)phenyl]-N'-(thiazol-2-yl)urea (117 g, 63%) was prepared from 2-(2,6-dimethoxyphenoxy)aniline (123 mg, 0.5 mmol) and 2-aminothiazole (60 mg, 0.6 mmol) following the general procedure D.

LC-MS (m/z): 373 (M+1)+. 1H NMR (400 MHz, acetone-$d_6$): δ 3.76 (s, 3H), 6.49 (dd, J=8.4, 1.2 Hz, 1H), 6.80 (d, J=8.4 Hz, 2H), 6.84-6.88 (m, 1H), 6.95-6.99 (m, 1H), 7.04 (d, J=3.2 Hz, 1H), 7.22 (t, J=8.4 Hz, 1H), 7.35 (d, J=3.6 Hz, 1H), 8.33 (dd, J=8.0, 1.6 Hz, 1H), 8.85 (br, 1H), 10.40 (br, 1H).

Example 44

N-[2-(2,6-difluorophenoxy)phenyl]-N'-(thiazol-2-yl)urea

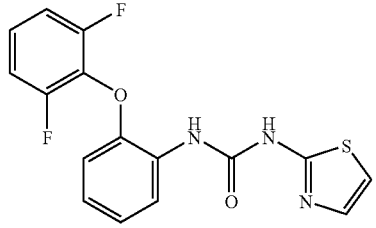

2-(2,6-difluorophenoxy)-1-nitrobenzene (0.44 g, 70%) was prepared from 2,6-difluorophenol (0.32 g, 2.5 mmol) and 1-fluoro-2-nitrobenzene (0.36 g, 2.5 mmol) following the general procedure A. This was reduced to 2-(2,6-difluorophenoxy)aniline (0.24 g, 60%) following general procedure B. N-[2-(2,6-difluorophenoxy)phenyl]-N'-(thiazol-2-yl)urea (133 mg, 60%) was prepared from 2-(2,6-difluorophenoxy)aniline (206 mg, 0.9 mmol) and 2-aminothiazole (405 mg, 2.5 mmol) following the general procedure D.

LC-MS (m/z): 349 (M+1)+. 1H NMR (400 MHz, acetone-$d_6$): δ 6.73 (d, J=8 Hz, 1H), 6.98 (m, 1H), 7.06 (d, J=3.2 Hz, 1H), 7.12 (m, 1H), 7.20-7.28 (m, 2H), 7.25 (d, J=3.6 Hz, 1H), 7.40 (m, 1H), 8.43 (d, J=8.2 Hz, 1H), 9.05 (br, 1H), 10.12 (br, 1H).

Example 45

N-[2-(2-Fluoro-6-methoxyphenoxy)phenyl]-N'-(thiazol-2-yl)urea

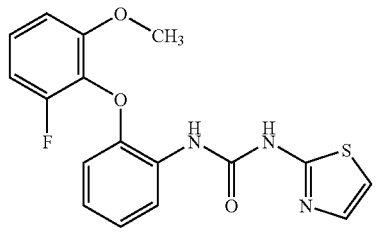

2-(2-Fluoro-6-methoxyphenoxy)-1-nitrobenzene (0.84 g, 64%) was prepared from 2-fluoro-6-methoxyphenol (0.78 g, 5.5 mmol) and 1-fluoro-2-nitrobenzene (0.71 g, 5.0 mmol) following the general procedure A. This was reduced to 2-(2-fluoro-6-methoxyphenoxy)-aniline (0.63 g, 85%) following general procedure C. N-2-(2-Fluoro-6-methoxyphenoxy)-phenyl)-N'-(thiazol-2-yl)urea (114 mg, 63%) was prepared from 2-(2-fluoro-6-methoxyphenoxy)aniline (117 mg, 0.5 mmol) and 2-aminothiazole (60 mg, 0.6 mmol) following the general procedure D.

LC-MS (m/z): 361 (M+1)+. 1H NMR (400 MHz, acetone-$d_6$): δ 3.82 (s, 3H), 6.59 (m, 1H), 6.89-6.96 (m, 2H), 7.02-7.07

(m, 3H), 7.27-7.33 (m, 1H), 7.34 (d, J=3.6 Hz, 1H), 8.38 (dd, J=8.4, 1.6 Hz, 1H), 8.85 (br, 1H), 10.31 (br, 1H).

Example 46

N-[2-(2-Methoxy-6-methoxycarbonylphenoxy)phenyl]-N'-(thiazol-2-yl)urea

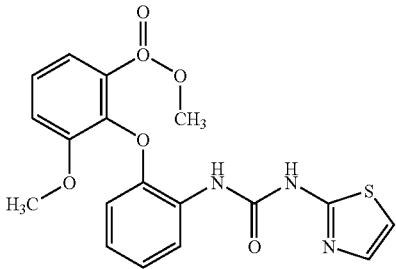

2-(2-Methoxy-6-methoxycarbonylphenoxy)-1-nitrobenzene (1.24 g, 82%) was prepared from methyl 3-methoxysalicylate (1.0 g, 5.5 mmol) and 1-fluoro-2-nitrobenzene (0.71 g, 5.0 mmol) following the general procedure A. This compound was reduced to 2-(2-methoxy-6-methoxycarbonylphenoxy)aniline (0.89 g, 80%) following the general procedure C. N-[2-(2-Methoxy-6-methoxycarbonylphenoxy)phenyl]-N'-(thiazol-2-yl)urea (143 mg, 72%) was prepared from 2-(2-methoxy-6-methoxycarbonylphenoxy)aniline (136 mg, 0.5 mmol) and 2-aminothiazole (60 mg, 0.6 mmol) following the general procedure D.

LC-MS (m/z): 401 (M+1)$^+$. $^1$H NMR (400 MHz, acetone-d$_6$): δ 3.78 (s, 3H), 3.87 (s, 3H), 6.89-6.97 (m, 1H), 7.04-7.23 (m, 3H), 7.36-7.47 (m, 2H), 7.67-7.76 (m, 2H), 8.17 (dd, J=1.6, 10.8 Hz, 1H), 8.78 (br, 1H), 10.64 (br, 1H).

Example 47

N-[(3-methoxy-2-methoxycarbonylphenoxy)phenyl]-N'-(thiazol-2-yl)urea

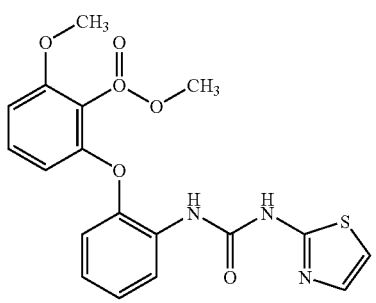

2-(3-Methoxy-2-methoxycarbonylphenoxy)-1-nitrobenzene (1.21 g, 80%) was prepared from methyl 6-methoxysalicylate (1.09 g, 5.5 mmol) and 1-fluoro-2-nitrobenzene (0.71 g, 5.0 mmol) following the general procedure A. This compound was reduced to 2-(3-methoxy-2-methoxycarbonylphenoxy)aniline (0.82 g, 75%) following the general procedure C. N-[(3-methoxy-2-methoxycarbonylphenoxy)phenyl]-N'-(thiazol-2-yl)urea (130 mg, 65%) was prepared from 2-(3-methoxy-2-methoxycarbonylphenoxy)aniline (136 mg, 0.5 mmol) and 2-aminothiazole (60 mg, 0.6 mmol) following the general procedure D.

LC-MS (m/z): 401 (M+1)$^+$. $^1$H NMR (400 MHz, acetone-d$_6$): δ 3.66 (s, 3H), 3.80 (s, 3H), 6.44-6.46 (m, 1H), 6.83-6.87 (m, 1H), 6.96-6.99 (m, 1H), 7.03 (d, J=3.6 Hz, 1H), 7.33 (d, J=4 Hz, 1H), 7.37-7.46 (m, 2H), 7.46-7.48 (m, 1H), 8.32-8.35 (dd, J=1.6, 8.0 Hz, 1H), 8.80 (br, 1H), 10.32 (br, 1H).

Example 48

N-[2-(2,3-Dimethoxyphenoxy)phenyl]-N'-(thiazol-2-yl)urea

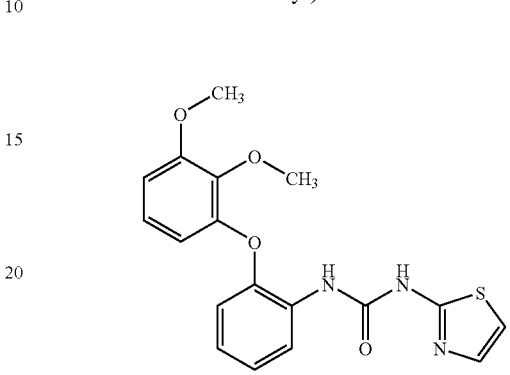

2-(2,3-Dimethoxyphenoxy)-1-nitrobenzene (0.88 g, 64%) was prepared from 2,3-dimethoxyphenol (0.85 g, 5.5 mmol) and 1-fluoro-2-nitrobenzene (0.71 g, 5.0 mmol) following the general procedure A. This was reduced to 2-(2,3-dimethoxyphenoxy)aniline (0.57 g, 73%) following general procedure B. N-[2-(2,3-Dimethoxyphenoxy)phenyl]-N'-(thiazol-2-yl)urea (131 g, 71%) was prepared from 2-(2,3-dimethoxyphenoxy)aniline (123 mg, 0.5 mmol) and 2-aminothiazole (60 mg, 0.6 mmol) following the general procedure D.

LC-MS (m/z): 373 (M+1)$^+$. $^1$H NMR (400 MHz, acetone-d$_6$): δ 3.66 (s, 3H), 3.88 (s, 3H), 6.66-6.74 (m, 2H), 6.91-6.98 (m, 2H), 7.04-7.16 (m, 3H), 7.32 (d, J=3.6 Hz, 1H), 8.39 (dd, J=8.0, 1.6 Hz, 1H), 8.90 (br, 1H), 10.26 (br, 1H).

Example 49

N-[2-(2,3,4-Trichlorophenoxy)phenyl]-N'-(thiazol-2-yl)urea

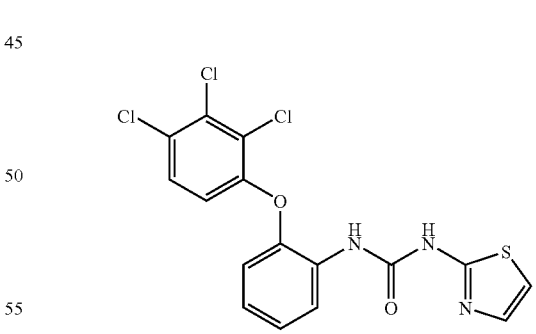

2-(2,3,4-Trichlorophenoxy)-1-nitrobenzene (1.04 g, 65%) was prepared from 2,3,4-trichlorophenol (0.98 g, 5.0 mmol) and 1-fluoro-2-nitrobenzene (0.71 g, 5.0 mmol) following the general procedure A. This was reduced to 2-(2,3,4-trichlorophenoxy)aniline (0.42 g, 60%, 2.5 mmol scale) following general procedure B. N-[2-(2,3,4-Trichlorophenoxy)phenyl]-N'-(thiazol-2-yl)urea (343 mg, 55%) was prepared from 2-(2,3,4-trichlorophenoxy)aniline (420 mg, 1.5 mmol) and 2-aminothiazole (150 mg, 1.5 mmol) following the general procedure D.

LC-MS (m/z): 415 (M+1)+. 1H NMR (400 MHz, acetone-d6): δ 9.97-7.12 (m, 4H), 7.23-7.28 (m, 2H), 7.58 (d, J=8.8 Hz, 1H), 8.45 (d, J=8.0 Hz, 1H), 10.13 (br, 1H).

Example 50

N-[2-(2,4,6-Trifluorophenoxy)phenyl]-N'-(thiazol-2-yl)urea

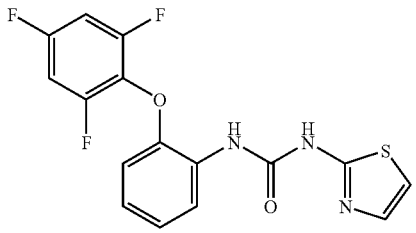

2-(2,4,6-Trifluorophenoxy)-1-nitrobenzene (1.14 g, 85%) was prepared from 2,4,6-trifluorophenol (0.74 g, 5.0 mmol) and 1-fluoro-2-nitrobenzene (0.71 g, 5.0 mmol) following the general procedure A. This was reduced to 2-(2,4,6-trifluorophenoxy)aniline (0.42 g, 70%, 2.5 mmol scale) following general procedure B. N-[2-(2,4,6-Trifluorophenoxy)phenyl]-N'-(thiazol-2-yl)urea (219 mg, 60%) was prepared from 2-(2,4,6-trifluorophenoxy)aniline (237 mg, 1.0 mmol) and 2-aminothiazole (100 mg, 1.0 mmol) following the general procedure D.

LC-MS (m/z): 367 (M+1)+. 1H NMR (400 MHz, acetone-d6): δ 6.78 (d, J=8.4 Hz, 1H), 7.00-7.21 (m, 5H), 7.36 (d, J=3.6 Hz, 1H), 8.42 (d, J=8.4 Hz, 1H), 9.05 (br, 1H), 10.36 (br, 1H).

Example 51

N-[2-(2,4-dichloronaphth-1-oxy)phenyl]-N'-(thiazol-2-yl)urea

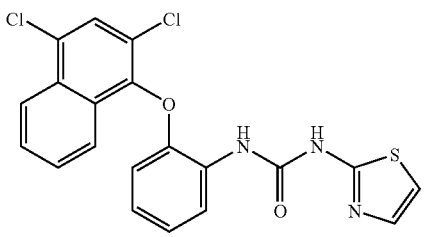

2-(2,4-Dichloronaphth-1-oxy)-1-nitrobenzene (1.17 g, 60%) was prepared from 2,4-dichloronaphth-1-ol (1.06 g, 5.0 mmol) and 1-fluoro-2-nitrobenzene (0.71 g, 5.0 mmol) following the general procedure A. This was reduced to 2-2,4-dichloronaphth-1-oxy)aniline (0.45 g, 60%, 2.5 mmol scale) following general procedure B. N-[2-(2,4-Dichloronaphth-1-oxy)phenyl]-N'-thiazolylurea (172 g, 40%) was prepared from 2-(2,4-dichloronaphth-1-oxy)aniline (303 mg, 1.0 mmol) and 2-aminothiazole (100 mg, 1.0 mmol) following the general procedure D.

LC-MS (m/z): 431 (M+1)+. 1H NMR (400 MHz, acetone-d6): δ 6.39 (d, J=8.2 Hz, 1H), 6.86 (m, 1H), 7.07 (m, 2H), 7.34 (d, J=3.6 Hz, 1H), 7.71-7.88 (m, 3H), 8.00 (d, J=8.0 Hz, 1H), 8.32 (d, J=8.0 Hz, 1H), 8.48 (d, J=8.0 Hz, 1H), 9.15 (br, 1H), 10.35 (br, 1H).

Example 52

N-[2-(2-Methoxyphenoxy)-5-(methylsulfonyl)phenyl]-N'-(thiazol-2-yl)urea

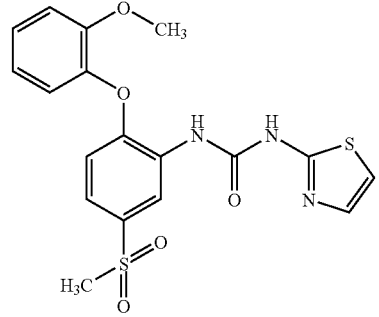

2-(2-Methoxyphenoxy)-5-(methylsulfonyl)-1-nitrobenzene (1.21 g, 75%) was prepared from 2-methoxyphenol (0.68 g, 5.5 mmol) and 1-fluoro-4-methylsulfonyl-2-nitrobenzene (1.09 g, 5.0 mmol) following the general procedure A. This was reduced to 2-(2-methoxyphenoxy)-5-(methylsulfonyl)aniline (0.68 g, 62%) following general procedure B. N-[2-(2-Methoxyphenoxy)-5-(methylsulfonyl)phenyl]-N'-(thiazol-2-yl)urea (136 mg, 65%) was prepared from 2-(2-methoxyphenoxy)-5-(methylsulfonyl)aniline (146 mg, 0.5 mmol) and 2-aminothiazole (60 mg, 0.6 mmol) following the general procedure D.

LC-MS (m/z): 421 (M+1)+. 1H NMR (400 MHz, acetone-d6): δ 2.82 (s, 3H), 3.77 (s, 3H), 6.73 (d, J=8.4 Hz, 1H) 7.05-7.11 (m, 2H), 7.23-7.28 (m, 2H), 7.32-7.37 (m, 2H), 7.50 (dd, J=8.4, 3.6 Hz, 1H), 9.02 (d, J=2.4 Hz, 1H), 9.12 (br, 1H), 10.42 (br, 1H).

Example 53

N-[5-Cyano-2-(2-methoxyphenoxy)phenyl]-N'-(thiazol-2-yl)urea

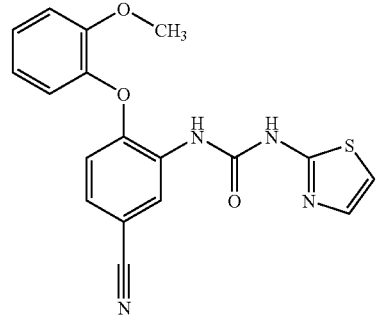

4-(2-Methoxyphenoxy)-3-nitrobenzonitrile (1.10 g, 81%) was prepared from 2-methoxyphenol (0.68 g, 5.5 mmol) and 4-fluoro-3-nitrobenzonitrile (1.33 g, 5.0 mmol) following general procedure A. This was reduced to 4-(2-methoxyphenoxy)-3-aminobenzonitrile (0.62 g, 63%) following general procedure B. N-[5-Cyano-2-(2-methoxyphenoxy)-phenyl]-N'-(thiazol-2-yl)urea (130 mg, 71%) was prepared from 4-(2- methoxyphenoxy)-3-aminobenzonitrile (120 mg, 0.5 mmol) and 2-aminothiazole (60 mg, 0.6 mmol) following general procedure D.

LC-MS (m/z): 368 (M+1)⁺. ¹H NMR (400 MHz, acetone-d₆): δ 3.79 (s, 3H), 6.69 (d, J=8.4 Hz, 1H) 7.05-7.09 (m, 1H), 7.10 (d, J=3.6 Hz, 1H), 7.22-7.27 (m, 2H), 7.32-7.36 (m, 3H), 8.75 (d, J=2.0 Hz, 1H), 9.12 (br, 1H), 10.38 (br, 1H).

Example 54

N-[5-Fluoro-2-(2-methylsulfanylphenoxy)phenyl]-N'-thiazolylurea

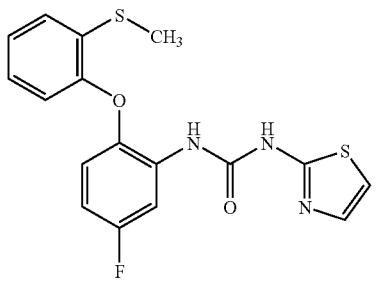

5-Fluoro-2-(2-methylsulfanylphenoxy)-1-nitrobenzene (0.95 g, 68%) was prepared from 2-hydroxythioanisole (0.77 g, 5.5 mmol) and 2,5-difluoro-1-nitrobenzene (0.80 g, 5.0 mmol) following the general procedure A. This was reduced to 5-fluoro-2-(2-methylsulfanyl-phenoxy)aniline (0.52 g, 62%) following general procedure B. N-[5-Fluoro-2-(2-methylsulfanylphenoxy)phenyl]-N'-(thiazol-2-yl)urea (120 mg, 65%) was prepared from 5-fluoro-2-(2-methylsulfanylphenoxy)aniline (125 mg, 0.5 mmol) and 2-aminothiazole (60 mg, 0.6 mmol) following the general procedure D.

LC-MS (m/z): 377 (M+1)⁺. ¹H NMR (400 MHz, acetone-d₆): δ 2.48 (s, 3H), 6.61 (m, 2H), 6.92 (d, J=7.6 Hz, 1H), 7.06 (d, J=3.6 Hz, 1H), 7.16-7.25 (m, 2H), 7.31 (d, J=3.6 Hz, 1H), 7.39 (dd, J=7.6, 2.0 Hz, 1H), 8.26-8.29 (m, 1H), 9.00 (br, 1H), 10.32 (br, 1H).

Example 55

N-[5-Fluoro-2-(2-fluoro-6-methoxyphenoxy)phenyl]-N'-(thiazol-2-yl)urea

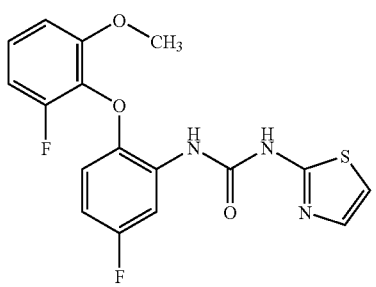

5-Fluoro-2-(2-fluoro-6-methoxyphenoxy)-1-nitrobenzene (0.91 g, 65%) was prepared from 2-fluoro-6-methoxyphenol (0.78 g, 5.5 mmol) and 2,5-difluoro-1-nitrobenzene (0.80 g, 5.0 mmol) following the general procedure A. This was reduced to 5-fluoro-2-(2-fluoro-6-methoxyphenoxy)aniline (0.66 g, 81%) following general procedure C. N-[5-Fluoro-2-(2-fluoro-6-methoxyphenoxy)phenyl]-N'-(thiazol-2-yl) urea (130 g, 69%) was prepared from 5-fluoro-2-(2-fluoro-6-methoxyphenoxy)aniline (126 mg, 0.5 mmol) and 2-aminothiazole (60 mg, 0.6 mmol) following the general procedure D.

LC-MS (m/z): 379 (M+1)⁺. ¹H NMR (400 MHz, acetone-d₆): δ 3.83 (s, 3H), 6.60-6.70 (m, 2H), 6.92-6.97 (m, 1H), 7.03-7.05 (m, 1H), 7.09 (d, J=4.0 Hz, 1H), 7.27-7.33 (m, 1H), 7.36 (d, J=3.6 Hz, 1H), 8.23 (dd, J=10.8, 3.2 Hz, 1H), 9.05 (br, 1H), 10.39 (br, 1H).

Example 56

N-[2-2,3-Dimethoxyphenoxy)-5-fluorophenyl]-N' (thiazol-2-yl)urea

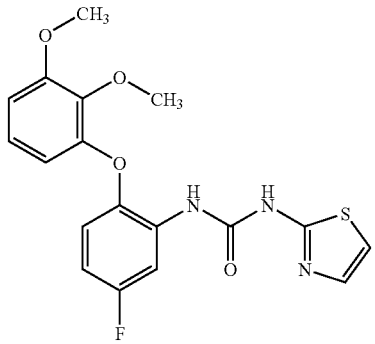

2-(2,3-Dimethoxyphenoxy)-5-fluoro-1-nitrobenzene (1.0 g, 68%) was prepared from 2,3-dimethoxyphenol (0.85 g, 5.5 mmol) and 2,5-difluoro-1-nitrobenzene (0.80 g, 5.0 mmol) following the general procedure A. This was reduced to 2-(2, 3-dimethoxyphenoxy)-5-fluoroaniline (0.67 g, 75%) following general procedure C. N-[2-(2,3-Dimethoxyphenoxy)-5-fluorophenyl]-N'-(thiazol-2-yl)urea (126 g, 65%) was prepared from 2-(2,3-dimethoxyphenoxy)-5-fluoroaniline (132 mg, 0.5 mmol) and 2-aminothiazole (60 mg, 0.6 mmol) following the general procedure D.

LC-MS (m/z): 391 (M+1)⁺. ¹H NMR (400 MHz, acetone-d₆): δ 3.68 (s, 3H), 3.88 (s, 3H), 6.67 (dd, J=9.2, 1.2 Hz, 1H), 6.70-6.79 (m, 2H), 6.92 (dd, J=8.0, 1.6 Hz, 1H), 7.05-7.09 (m, 2H), 7.32 (d, J=3.6 Hz, 1H), 8.25 (dd, J=11.2, 2.8 Hz, 1H), 9.03 (br, 1H), 10.33 (br, 1H).

Example 57

N-[2-(3,4-Difluorophenoxy)-5-fluorophenyl]-N'-(thiazol-2-yl)urea

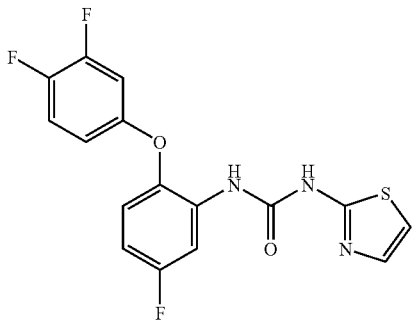

2-(3,4-Difluorophenoxy)-5-fluoro-1-nitrobenzene (1.05 g, 78%) was prepared from 3,4-difluorophenol (0.72 g, 5.5 mmol) and 2,5-difluoro-1-nitrobenzene (0.8 g, 5.0 mmol) following the general procedure A. This compound was reduced to 2-(3,4-difluorophenoxy)-5-fluoroaniline (0.63 g, 68%) following the general procedure B. N-[2-(3,4-Difluorophenoxy)-5-fluorophenyl]-N'-(thiazol-2-yl)urea (132 mg, 72%) was prepared from 2-(3,4-difluorophenoxy)-5-fluoroaniline (120 mg, 0.5 mmol) and 2-aminothiazole (60 mg, 0.6 mmol) following the general procedure D.

LC-MS (m/z): 367 (M+1)$^+$. $^1$H NMR (400 MHz, acetone-$d_6$): δ 6.81-6.89 (m, 2H), 7.05-7.11 (m, 3H), 7.31-7.38 (m, 2H), 8.28 (dd, J=2.8, 10.8 Hz, 1H), 9.10 (br, 1H), 10.34 (br, 1H).

Example 58

N-[5-Fluoro-2-(4-fluorophenoxy)phenyl]-N'-(thiazol-2-yl)urea

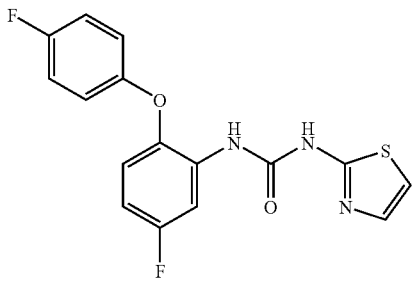

5-Fluoro-2-(4-fluorophenoxy)-1-nitrobenzene (0.94 g, 75%) was prepared from 4-fluorophenol (0.62 g, 5.5 mmol) and 2,5-difluoro-1-nitrobenzene (0.71 g, 5.0 mmol) following the general procedure A. This compound was reduced to 2-(4-fluorophenoxy)-5-fluoroaniline (0.53 g, 64%) following the general procedure B. N-[5-Fluoro-2-(4-fluorophenoxy)phenyl]-N'-(thiazol-2-yl)urea (130 mg, 75%) was prepared from 5-fluoro-2-(4-fluorophenoxy)aniline (110 mg, 0.5 mmol) and 2-aminothiazole (60 mg, 0.6 mmol) following the general procedure D.

LC-MS (m/z): 349 (M+1)$^+$. $^1$H NMR (400 MHz, acetone-$d_6$): δ 6.78-6.82 (m, 1H), 6.93-6.97 (m, 1H), 7.06-7.10 (m, 3H), 7.14-7.18 (m, 2H), 7.3 (d, J=3.2 Hz, 1H), 8.27 (dd, J=2.8, 10.8 Hz, 1H), 8.82 (br, 1H), 10.28 (br, 1H).

Example 59

N-[2-(2,4-Dichlorophenoxy)-5-fluorophenyl]-N'-(thiazol-2-yl)urea

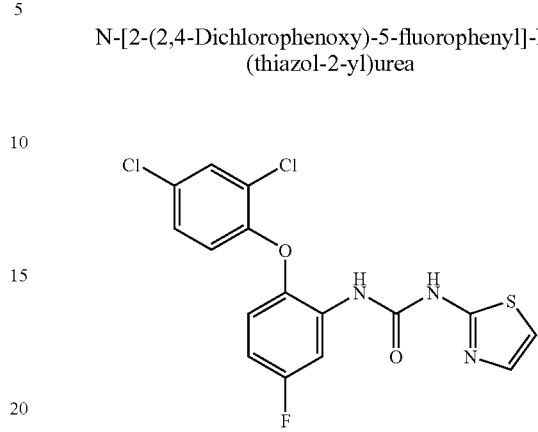

2-(2,4-Dichlorophenoxy)-5-fluoro-1-nitrobenzene (1.17 g, 78%) was prepared from 2,4-dichlorophenol (0.89 g, 5.5 mmol) and 2,5-difluoro-1-nitrobenzene (0.8 g, 5.0 mmol) following the general procedure A. This compound was reduced to 2-(2,4-dichlorophenoxy)-5-fluoroaniline (0.68 g, 64%) following the general procedure B. N-[2-(2,4-Dichlorophenoxy)-5-fluorophenyl]-N'-(thiazol-2-yl)urea (150 mg, 76%) was prepared from 2-(2,4-dichlorophenoxy)-5-fluoroaniline (135 mg, 0.5 mmol) and 2-aminothiazole (60 mg, 0.6 mmol) following the general procedure D.

LC-MS (m/z): 399 (M+1)$^+$. $^1$H NMR (400 MHz, acetone-$d_6$): δ 6.79-6.84 (m, 1H), 6.93 (m, 1H), 7.03-7.07 (m, 2H), 7.30 (d, J=3.2 Hz, 1H), 7.38 (dd, 2.4, 8.8 Hz 1H), 7.64 (d, J=2.4 Hz, 1H), 8.29 (dd, J=2.4, 11.2 Hz 1H), 9.00 (br, 1H), 10.24 (bs, 1H).

Example 60

N-[5-Fluoro-2-(4-methoxyphenoxy)phenyl]-N'-(thiazol-2-yl)urea

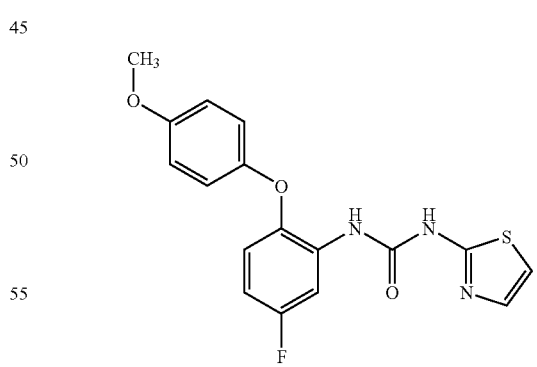

5-Fluoro-2-(4-methoxyphenoxy)-1-nitrobenzene (1.05 g, 80%) was prepared from 4-methoxyphenol (0.68 g, 5.5 mmol) and 2,5-difluoro-1-nitrobenzene (0.8 g, 5.0 mmol) following the general procedure A. This compound was reduced to 5-fluoro-2-(4-methoxy-phenoxy)aniline (0.62 g, 66%) following the general procedure B. N-[5-Fluoro-2-(4-methoxyphenoxy)phenyl]-N'-(thiazol-2-yl)urea (133 mg, 74%) was prepared from 2-(4-methoxyphenoxy)-5-fluoroaniline (117 mg, 0.5 mmol) and 2-aminothiazole (60 mg, 0.6 mmol) following the general procedure D.

LC-MS (m/z): 361 (M+1)$^+$. $^1$H NMR (400 MHz, acetone-$d_6$): δ 3.79 (s, 3H), 6.75-6.77 (m, 1H), 6.82-6.87 (m, 1H), 6.94-7.01 (m, 3H), 7.07 (d, J=2.1 Hz, 1H), 7.32 (d, J=3.6 Hz, 1H), 8.26 (dd, J=3.2, 11.2 Hz, 1H), 9.05 (br, 1H), 10.32 (br, 1H).

Example 61

N-[5-Fluoro-2-(2-methoxyphenoxy)phenyl]-N'-(thiazol-2-yl)urea

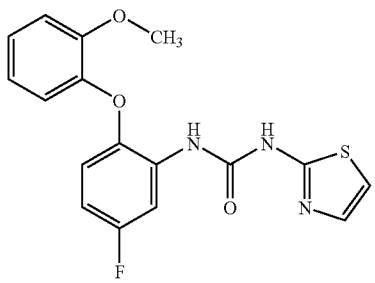

5-Fluoro-2-(2-methoxyphenoxy)-1-nitrobenzene (1.07 g, 81%) was prepared from 2-methoxyphenol (0.62 g, 5.5 mmol) and 2,5-difluoro-1-nitrobenzene (0.8 g, 5.0 mmol) following the general procedure A. This compound was reduced to 2-(2-methoxyphenoxy)-5-fluoroaniline (0.58 g, 66%) following the general procedure B. 1-[5-Fluoro-2-(2-methoxyphenoxy)phenyl]-3-(thiazol-2-yl)urea (129 mg, 72%) was prepared from 5-fluoro-2-(2-methoxyphenoxy) aniline (117 mg, 0.5 mmol) and 2-aminothiazole (60 mg, 0.6 mmol) following the general procedure D.

LC-MS (m/z): 361 (M+1)$^+$. $^1$H NMR (400 MHz, acetone-$d_6$): δ 3.79 (s, 3H), 6.65-6.7 (m, 2H), 6.98-7.01 (m, 1H), 7.05-7.22 (m, 4H), 7.32 (d, J=3.6 Hz, 1H), 8.22 (dd, J=2.8, 10.8 Hz, 1H), 9.12 (br, 1H), 10.42 (br, 1H).

Example 62

N-[5-Fluoro-2-(2-trifluoromethylphenoxy)phenyl]-N'-(thiazol-2-yl)urea

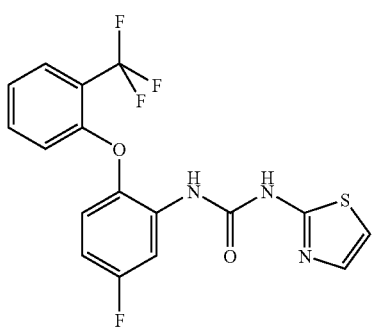

5-Fluoro-2-(2-triflurometylphenoxy)-1-nitrobenzene (1.17 g, 78%) was prepared from 2-hydroxybenzotrifluoride (0.89 g, 5.5 mmol) and 2,5-difluoro-1-nitrobenzene (0.8 g, 5.0 mmol) following the general procedure A. This compound was reduced to 5-fluoro-2-(2-trifluoromethylphenoxy)-aniline (0.65 g, 62%) following the general procedure B. N-[5-Fluoro-2-(2-trifluoromethylphenoxy)phenyl]-N'-(thiazol-2-yl)urea (146 mg, 74%) was prepared from 2-(2-trifluoromethylphenoxy)-5-fluoroaniline (135 mg, 0.5 mmol) and 2-aminothiazole (60 mg, 0.6 mmol) following the general procedure D.

LC-MS (m/z): 399 (M+1)$^+$. $^1$H NMR (400 MHz, acetone-$d_6$): δ 6.81-6.87 (m, 1H), 6.95-7.05 (m, 3H), 7.21 (m, 1H), 7.31-7.36 (m, 1H), 7.6-7.65 (m, 1H), 7.79 (d, J=7.6 Hz, 1H), 8.30 (dd, J=3.2,11.2 Hz, 1H), 8.72 (br, 1H), 10.24 (br, 1H).

Example 63

N-[5-Fluoro-2-(naphth-2-oxy)phenyl]-N'-(thiazol-2-yl)urea

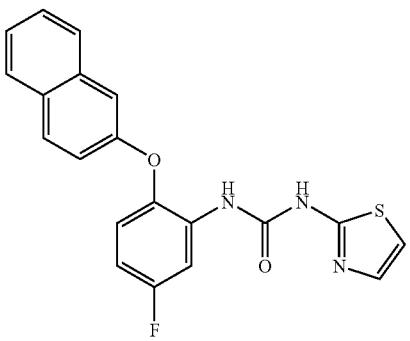

5-Fluoro-2-(naphth-2-oxy)-1-nitrobenzene (1.13 g, 80%) was prepared from 2-naphthol (0.79 g, 5.5 mmol) and 2,5-difluoro-1-nitrobenzene (0.8 g, 5.0 mmol) following the general procedure A. This compound was reduced to 2-(2-naphth-2-oxy)-5-fluoroaniline (0.64 g, 64%) following the general procedure B. N-[5-Fluoro-2-(naphth-2-oxy)phenyl]-N'-(thiazol-2-yl)urea (123 mg, 65%) was prepared from 5-Fluoro-2-(naphth-2-oxy)-aniline (127 mg, 0.5 mmol) and 2-aminothiazole (60 mg, 0.6 mmol) following the general procedure D.

LC-MS (m/z): 381 (M+1)$^+$. $^1$H NMR (400 MHz, acetone-$d_6$): δ 6.83-6.87 (m, 1H), 7.01(bs, 1H), 7.08 (m, 1H), 7.33 (bs, 1H), 7.42-7.49 (m, 3H), 7.80 (d, J=7.6 Hz, 1H), 7.90(d, J=7.6 Hz, 1H), 7.97 (d, J=8.8 Hz, 1H), 8.32 (d, J=8.4 Hz, 1H), 8.62 (br, 1H), 10.22 (br, 1H)

Example 64

N-[2-(2,3-Dimethoxyphenoxy)-6-fluorophenyl]-N'-(thiazol-2-yl)urea

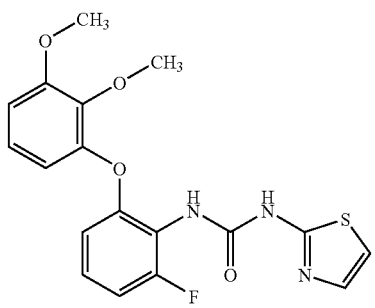

2-(2,3-Dimethoxyphenoxy)-6-fluoro-nitrobenzene (1.05 g, 72%) was prepared from 2,3-dimethoxyphenol (0.85 g, 5.5 mmol) and 2,6-difluoronitrobenzene (0.80 g, 5.0 mmol) following the general procedure A. This compound was reduced to 2-(2,3-dimethoxyphenoxy)-6-fluoroaniline (0.66 g, 70%) following the general procedure C N-[2-(2,3-Dimethoxyphenoxy)-6-fluorophenyl]-N'-(thiazol-2-yl)urea (136 mg, 70%) was prepared from 2-(2,3-dimethoxyphenoxy)-6-fluoroaniline (131 mg, 0.5 mmol) and 2-aminothiazole (60 mg, 0.6 mmol) following the general procedure D.

LC-MS (m/z): 391 (M+1)$^+$. $^1$H NMR (400 MHz, acetone-d$_6$): δ 3.64 (s, 3H), 3.85 (s, 3H), 6.59 (d, J=8.0 Hz, 1H), 6.68-6.69 (d, J=8.0 Hz, 1H), 6.88-7.06 (m, 4H), 7.22-7.22 (m 1H), 7.30-7.31 (d, J=3.2 Hz, 1H), 8.18 (br, 1H), 10.26 (br, 1H).

Example 65

N-[2-(4-Fluoro-2-methoxyphenoxy)phenyl]-N'-(thiazol-2-yl)urea

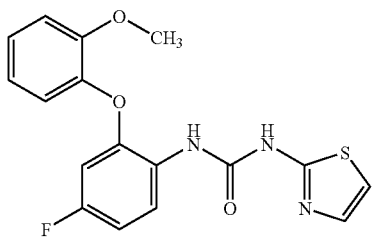

4-Fluoro-2-(2-methoxyphenoxy)-1-nitrobenzene (1.2 g, 91.6%) was prepared from 2-methoxyphenol (0.68 g, 5.5 mmol) and 2,4-difluoro-1-nitrobenzene (0.80 g, 5.0 mmol) following the general procedure F. The product was then reduced to 4-fluoro-2-(2-methoxyphenoxy)aniline (0.96 g, 73%) following general procedure B. N-[4-Fluoro-2-(2-methoxyphenoxy)phenyl]-N'-(thiazol-2-yl)urea (0.32 g, 86%) was prepared from 4-fluoro-2-(2-methoxyphenoxy)aniline (0.117 g, 0.5 mmol) and 2-aminothiazole (0.060 g, 0.6 mmol) following the general procedure D.

LC-MS (m/z): 361 (M+1)$^+$. $^1$H NMR (400 MHz, CDCl$_3$): δ 3.78 (s, 3H), 6.32 (dd, J=4.0, 14.0 Hz, 1H), 6.35 (dd, J=2.8, 10.4 Hz, 1H), 6.61 (t, J=4.0 Hz, 1H), 6.80 (m, 2H), 7.05 (m, 2H), 7.18 (m, 2H), 11.46 (br, 2H).

Example 66

N-[2-(2,3-Dimethoxyphenoxy)-4-fluorophenyl]-N'-(thiazol-2-yl)urea

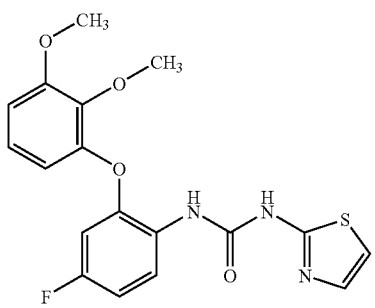

2-(2,3-Dimethoxyphenoxy)-4-fluoro-1-nitrobenzene (0.88 g, 60%) was prepared from 2,3-dimethoxyphenol (0.85 g, 5.5 mmol) and 2,4-difluoro-1-nitrobenzene (0.8 g, 5.0 mmol) following the general procedure F. This compound was reduced to 2-(2,3-dimethoxyphenoxy)-4-fluoroaniline (0.52 g, 66%) following the general procedure C. N-[2-(2,3-dimethoxyphenoxy)-4-fluorophenyl]-N'-(thiazol-2-yl)urea (116 mg, 60%) was prepared from 2-(2,3-dimethoxyphenoxy)-4-fluoroaniline (132 mg, 0.5 mmol) and 2-aminothiazole (60 mg, 0.6 mmol) following the general procedure D.

LC-MS (m/z): 391 (M+1)$^+$. $^1$H NMR (400 MHz, acetone-d$_6$): δ 3.68 (s, 3H), 3.89 (s, 3H), 6.46 (dd, J=2.4, 9.2 Hz, 1H), 6.76 (dd, J=1.6, 8.0 Hz, 1H), 6.82-6.87 (m, 1H), 6.98 (dd, J=2.3, 6.8 Hz, 1H), 7.04 (d, J=3.6 Hz, 1H), 7.1-7.13 (t, J=8.4 Hz, 1H), 7.31(d, J=4.0 Hz, 1H), 8.33-8.37 (dd, J=6.4, 9.6 Hz, 1H), 8.42 (br, 1H), 10.23 (br, 1H).

Example 67

N-[4-Fluoro-2-(2-fluoro-6-methoxyphenoxy)phenyl]-N'-(thiazol-2-yl)urea

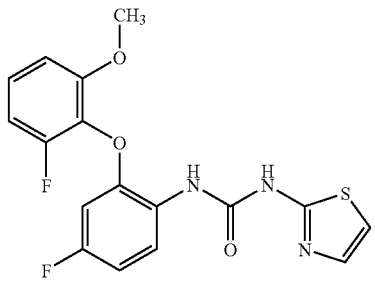

4-Fluoro-2-(2-fluoro-6-methoxyphenoxy)-1-nitrobenzene (0.91 g, 65%) was prepared from 2-fluoro-6-methoxyphenol (0.78 g, 5.5 mmol) and 2,4-difluoro-1-nitrobenzene (0.8 g, 5.0 mmol) following the general procedure F. This compound was reduced to 4-fluoro-2-(2-fluoro-6-methoxyphenoxy)aniline (0.61 g, 75%) following the general procedure C. N-[4-Fluoro-2-(2-fluoro-6-methoxyphenoxy)phenyl]-N'-(thiazol-2-yl)urea (122 mg, 65%) was prepared from 4-fluoro-2-(2-fluoro-6-methoxyphenoxy)aniline (126 mg, 0.5 mmol) and 2-aminothiazole (60 mg, 0.6 mmol) following the general procedure D.

LC-MS (m/z): 379 (M+1)$^+$. $^1$H NMR (400 MHz, acetone-d$_6$): δ 3.84 (s, 3H), 6.39 (dd, 2.8, 9.6 Hz 1H), 6.81-6.85 (m, 1H), 6.95-6.98 (m, 1H), 7.05-7.07 (m, 2 H) 7.29-7.35 (m, 2H), 8.32-8.36 (m, 1H), 8.85 (br, 1H), 10.26 (br, 1H)

Example 68

N-[2-(2-Fluoro-6-methoxyphenoxy)-4-methoxyphenyl]-N'-(thiazol-2-yl)urea

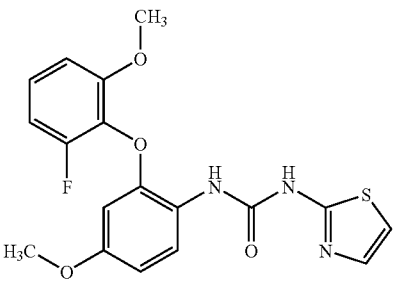

A mixture of 4-fluoro-2-(2-fluoro-6-methoxyphenoxy)-1-nitrobenzene (1.33 g, 5 mmol) and sodium methoxide (035 g, 6 mmol) in DMF (10 ml) was heated at 80° C. for 2 h. The mixture was poured into water and was extracted with ethyl acetate (3×20 ml). The combined organic layer was washed with water, brine and dried (Na$_2$SO$_4$). The solution was concentrated under reduced pressure to obtain 2-(2-fluoro-6-methoxyphenoxy)-4-methoxy-1-nitrobenzene (1.02 g, 70%). This compound was reduced to 2-(2-fluoro-6-methoxyphenoxy)-4-methoxyaniline (0.62 g, 73%) following the general procedure C. N-[2-(2-Fluoro-6-methoxyphenoxy)-4-methoxyphenyl]-N'-(thiazol-2-yl)urea (136 mg, 70%) was prepared from 2-(2-methoxy-6-fluorophenoxy)-4-methoxyaniline (132 mg, 0.5 mmol) and 2-aminothiazole (60 mg, 0.6 mmol) following the general procedure D.

LC-MS (m/z): 391 (M+1)$^+$. $^1$H NMR (400 MHz, CDCl$_3$): δ 3.74 (s, 3H), 6.19 (bs, 1H), 6.46 (dd, J=2.4, 7.6 Hz, 1H), 6.61-6.84 (m, 3H), 7.04-7.19 (m, 1H), 7.32-7.44 (bs, 1H), 8.04-8.12 (m, 1 H), 8.20 (br, 1H), 10.22 (br, 1H).

Example 69

N-[3-Fluoro-2-(2-fluoro-6-methoxyphenoxy)phenyl]-N'-(thiazol-2-yl)urea

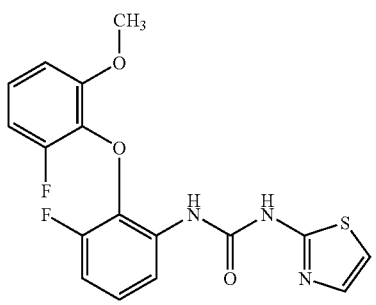

Methyl 3-fluoro-2-(2-fluoro-6-methoxyphenoxy)benzoate (0.88 g, 60%) was prepared from methyl 2,3-difluorobenzoate (0.86 g, 5 mmol) and 2-fluoro-6-methoxyphenol (0.78 g, 5.5 mmol) as described in procedure A. Hydrolysis of this ester with LiOH in aqueous methanol furnished 2-(2-methoxy-6-fluorophenoxy)-3-fluorobenzoic acid (0.86 g, 90%). To a solution of 3-fluoro-2-(2-fluoro-6-methoxyphenoxy) benzoic acid (0.56 g, 2.0 mmol) in 1,2-dichloroethane (10 ml) was added oxalyl chloride (0.18 ml, 2.2 mmol). The solution was stirred at room temperature for 45 min. To this solution was added NaN$_3$ (390 mg, 6 mmol) and the mixture was heated to reflux for 3 h. 2-Aminothiazole (200 mg, 2 mmol) was then added to this mixture and was further refluxed for 3 h. The mixture was concentrated and the residue was purified by column chromatography (silica, CH$_2$Cl$_2$ then 10% ethyl acetate in CH$_2$Cl$_2$) to afford 1-[3-fluoro-2-(2-fluoro-6-methoxyphenoxy)phenyl]-3-(thiazol-2-yl)urea in (414 mg, 55%).

LC-MS (m/z): 379 (M+1)$^+$. $^1$H NMR (400 MHz, acetone-d$_6$): δ 3.72 (s, 3H), 6.44 (d, J=8.4 Hz, 1H), 6.69-6.84 (m, 4H), 7.01-7.12 (m, 2H), 7.35-7.36 (d, J=4.0 Hz, 1H), 8.28 (br, 1H), 10.28 (br, 1H).

Example 70

N-[2-(2,3-Dimethoxyphenoxy)-5-methoxyphenyl]-N'-thiazol-2-ylurea

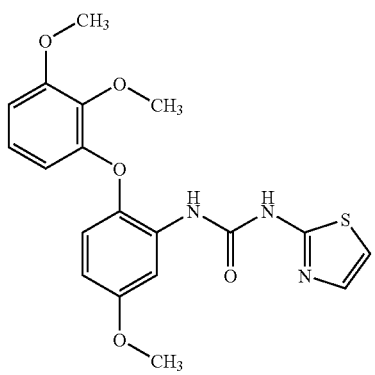

2-(2,3-Dimethoxyphenoxy)-5-methoxy-1-nitrobenzene (0.85 g, 56%) was prepared from 2,3-dimethoxyphenol (0.85 g, 5.5 mmol) and 4-chloro-3-nitroanisole (0.94 g, 5.0 mmol) following the general procedure A. This was reduced to 2-(2,3-dimethoxyphenoxy)-5-methoxyaniline (0.65 g, 85%) following general procedure C. N-[2-(2,3-Dimethoxyphenoxy)-5-methoxyphenyl]-N'-(thiazol-2-yl)urea (124 g, 62%) was prepared from 2-(2,3-dimethoxyphenoxy)-5-methoxyaniline (133 mg, 0.5 mmol) and 2-aminothiazole (60 mg, 0.6 mmol) following the general procedure D.

LC-MS (m/z): 403 (M+1)$^+$. $^1$H NMR (400 MHz, acetone-d$_6$): δ 3.70 (s, 3H), 3.79 (s, 3H), 3.87 (s, 3H), 6.53-6.57 (m, 2H), 6.75 (d, J=8.8 Hz, 1H), 6.85 (dd, J=8.4, 1.2 Hz, 1H), 7.00 (d, J=8.4 Hz, 1H), 7.04 (d, J=3.6 Hz, 1H), 7.30 (d, J=3.6 Hz, 1H), 8.10 (d, J=3.6 Hz, 1H), 10.26 (br, 1H).

Example 71

N-[2-(2,3-Dimethoxyphenoxy)-4-methylphenyl]-N'-(thiazol-2-yl)urea

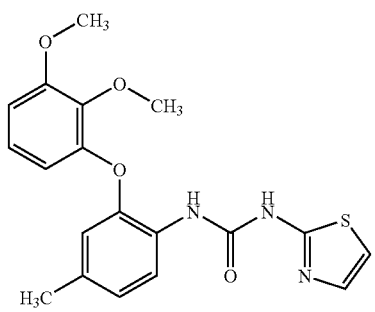

3-(2,3-Dimethoxyphenoxy)-4-nitrotoluene (0.92 g, 64%) was prepared from 2,3-dimethoxyphenol (0.85 g, 5.5 mmol) and 3-fluoro-4-nitrotoluene (0.78 g, 5.0 mmol) following the general procedure A. This was reduced to 2-(2,3-dimethoxyphenoxy)-4-methylaniline (0.65 g, 79%) following general procedure C. N-[2-(2,3-Dimethoxyphenoxy)-4-methylphenyl]-N'-(thiazol-2-yl)urea (120 mg, 63%) was prepared from 2-(2,3-dimethoxyphenoxy)-4-methylaniline (130 mg, 0.5 mmol) and 2-aminothiazole (60 mg, 0.6 mmol) following the general procedure D.

LC-MS (m/z): 387 (M+1)+. $^1$H NMR (400 MHz, acetone-$d_6$): δ 2.20 (s, 3H), 3.67 (s, 3H), 3.88 (s, 3H) 6.57 (d, J=1.2 Hz, 1H), 6.64 (dd, J=8.4, 1.6 Hz, 1H), 6.89-6.92 (m, 2H), 7.01-7.08 (m, 2H), 7.31 (d, J=3.6 Hz, 1H), 8.24 (d, J=8.4 Hz, 1H), 8.60 (br, 1H), 10.23 (br, 1H).

Example 72

N-[2-2,3-Dimethoxyphenoxy)-3-methylphenyl]-N'-(thiazol-2-yl)urea

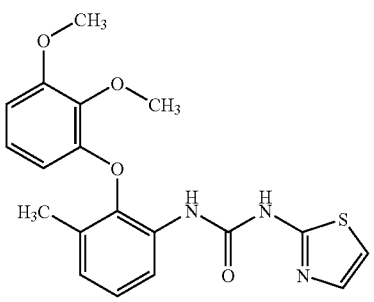

2-(2,3-Dimethoxyphenoxy)-3-nitrotoluene (0.80 g, 56%) was prepared from 2,3-dimethoxyphenol (0.85 g, 5.5 mmol) and 2-chloro-3-nitrotoluene (0.85 g, 5.0 mmol) following the general procedure A. This was reduced to 2-(2,3-dimethoxyphenoxy)-3-methylaniline (0.54 g, 76%) following general procedure C. N-[2-(2,3-Dimethoxyphenoxy)-3-methylphenyl]-N'-(thiazol-2-yl)urea (116 mg, 61%) was prepared from 2-(2,3-dimethoxyphenoxy)-3-methylaniline (130 mg, 0.5 mmol) and 2-aminothiazole (60 mg, 0.6 mmol) following the general procedure D.

LC-MS (m/z): 387 (M+1)+. $^1$H NMR (400 MHz, acetone-$d_6$): δ 2.09 (s, 3H), 3.88 (s, 6H), 6.07 (dd, J=8.4, 1.2 Hz, 1H), 6.73 (dd, J=8.4, 1.2 Hz, 1H), 6.85-6.89 (m, 1H), 6.98-7.00 (m, 2H), 7.16-7.20 (m, 1H), 7.24 (d, J=3.6 Hz, 1H), 8.27 (d, J=8.0 Hz, 1H), 8.95 (br, 1H), 10.09 (br, 1H).

Example 73

N-[2-(2-Chlorophenoxy)-5-chlorophenyl]-N'-(thiazol-2-yl)urea

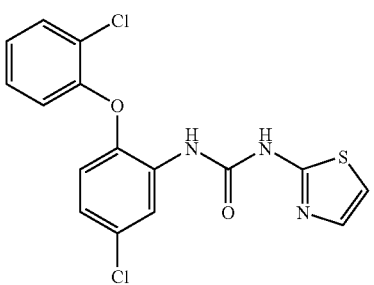

N-[2-(2-Chlorophenoxy)-5-chlorophenyl]-N'-(thiazol-2-yl)urea (119 mg, 63%) was prepared from 2-(2-chlorophenoxy)-5-chloroaniline (127 mg, 0.5 mmol) and 2-aminothiazole (60 mg, 0.6 mmol) following the general procedure D.

LC-MS (m/z): 381 (M+1)+. $^1$H NMR (400 MHz, acetone-$d_6$): δ 6.76 (d, J=8.4 Hz, 1H), 7.04 (dd, J=8.4, 2.4 Hz, 1H), 7.07 (d, J=3.6 Hz, 1H), 7.17 (d, J=8.4 Hz, 1H), 7.24-7.42 (m, 3H), 7.59 (dd, J=8.0, 1.6 Hz, 1H), 8.55 (d, J=2.4 Hz, 1H), 9.01 (br, 1H), 10.28 (br, 1H).

Example 74

N-[5-Chloro-2-(4-chloro-3-methylphenoxy)phenyl]-N'-(thiazol-2-yl)urea

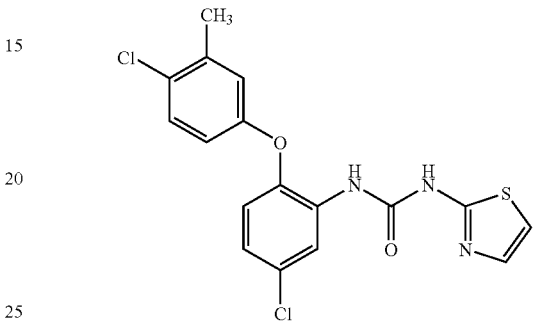

N-[5-Chloro-2-(4-chloro-3-methylphenoxy)phenyl]-N'-(thiazol-2-yl)urea (236 mg, 60%) was prepared from 2-(2-methyl-3-chlorophenoxy)-5-chloroaniline (commercially available, 268 mg, 1.0 mmol) and 2-aminothiazole (100 mg, 1.0 mmol) following the general procedure D.

LC-MS (m/z): 397 (M+1)+. $^1$H NMR (400 MHz, acetone-$d_6$): δ 2.35 (s, 3H), 6.90-7.02 (m, 2H), 7.06-7.10 (m, 3H), 7.32 (d, J=3.6 Hz, 1H), 7.40 (d, J=8.8 Hz, 1H), 8.54 (d, J=2.4 Hz, 1H), 10.22 (br, 2H).

Example 75

N-[2-(4-Chlorophenoxy)-5-(trifluoromethyl)phenyl]-N'-(thiazol-2-yl)urea

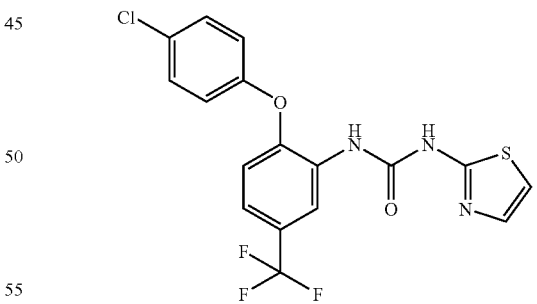

N-[2-(4-Chlorophenoxy)-5-(trifluoromethyl)phenyl]-N'-(thiazol-2-yl)urea (136 mg, 66%) was prepared from 2-(4-Chlorophenoxy)-5-(trifluoromethyl)aniline (144 mg, 0.5 mmol) and 2-aminothiazole (60 mg, 0.6 mmol) following the general procedure D.

LC-MS (m/z): 415 (M+1)+. $^1$H NMR (400 MHz, acetone-$d_6$): δ 5.12 (br, 1H); 7.02 (d, J=9 Hz, 1H), 7.09 (d, J=3.6 Hz, 1H), 7.21 (d, J=8.8 Hz, 2H), 7.34 (d, J=3.6 Hz, 1H), 7.39 (d, J=8.8 Hz, 1H), 7.49 (d, J=8.8 Hz, 2H), 8.85 (d, J=1.5 Hz, 1H), 8.95 (br, 1H), 10.29 (br, 1H).

Example 76

N-[4,5-difluoro-2-(2,3-dimethoxyphenoxy)phenyl]-N'-(thiazol-2-yl)urea

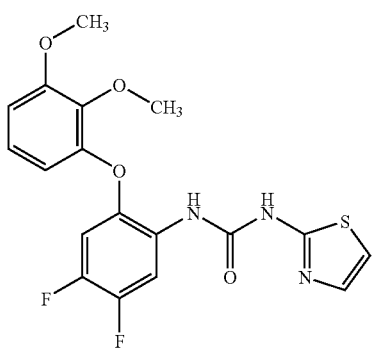

4,5-Difluoro-2-(2,3-dimethoxyphenoxy)-1-nitrobenzene (1.4 g, 90.3%) was prepared from 2,3-dimethoxyphenol (0.85 g, 5.5 mmol) and 1,3,4-trifluoronitrobenzene (0.885 g, 5.0 mmol) following the general procedure F. The product was then reduced to 2-(2-methoxyphenoxy)-4,5-difluoroaniline (1.35 g, 96.1%) following general procedure B. N-[4,5-Difluoro-2-(2,3-dimethoxyphenoxy)phenyl]-N'-(thiazol-2-yl) urea (0.181 g, 89%) was prepared from 2-(2,3-dimethoxyphenoxy)-4,5-difluoroaniline (0.140 g, 0.5 mmol) and 2-aminothiazole (0.060 g, 0.6 mmol) following the general procedure D.

LC-MS (m/z): 361 (M+1)$^+$. $^1$H NMR (400 MHz, acetone-$d_6$): δ 3.71 (s, 3H), 3.88 (s, 3H), 6.63 (dd, J=1.6, 8.4 Hz, 1H), 6.89 (dd, J=1.2, 6.4 Hz, 1H), 7.03-7.11 (m, 2H), 7.38 (d, J=3.6 Hz, 1H), 8.26 (dd, J=1.6 Hz, 7.6 Hz, 1H), 8.42 (dd, J=1.2 Hz, 7.2 Hz, 1H), 9.13 (br, 1H), 10.22 (br, 1H).

Example 77

N-[4,5-Dichloro-2-(2,3-dimethoxyphenoxy)phenyl]-N'-(thiazol-2-yl)urea

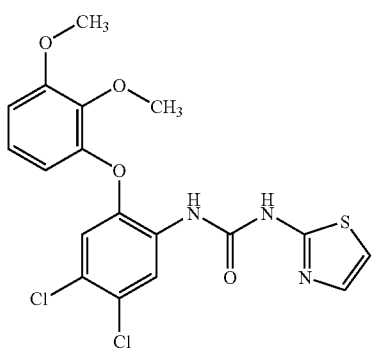

4,5-Dichloro-2-(2,3-dimethoxyphenoxy)-1-nitrobenzene (1.12 g, 65%) was prepared from 2,3-dimethoxyphenol (0.85 g, 5.5 mmol) and 4,5-dichloro-2-fluoro-1-nitrobenzene (1.05 g, 5.0 mmol) following the general procedure A. This was reduced to 4,5-dichloro-2-(2,3-dimethoxyphenoxy)aniline (0.68 g, 67%) following general procedure B. N-[4,5-Dichloro-2-(2,3-dimethoxyphenoxy)phenyl]-N'-(thiazol-2-yl)urea (136 mg, 62%) was prepared from 4,5-dichloro-2-(2,3-dimethoxyphenoxy)aniline (157 mg, 0.5 mmol) and 2-aminothiazole (60 mg, 0.6 mmol) following the general procedure D.

LC-MS (m/z): 441 (M+1)$^+$. $^1$H NMR (400 MHz, acetone-$d_6$): δ 3.70 (s, 3H), 3.91 (s, 3H), 6.81-6.83 (m, 2H), 7.01 (dd, J=8.4, 1.2 Hz, 1H), 7.09 (d, J=3.6 Hz, 1H), 7.15 (t, J=8.4 Hz, 1H), 7.34 (d, J=3.6 Hz, 1H), 8.65 (s, 1H), 8.95 (br, 1H), 10.36 (br, 1H).

Example 78

N-[5-Chloro-2-(2,3-dimethoxyphenoxy)-4-dimethylaminophenyl]-N'-(thiazol-2-yl)urea

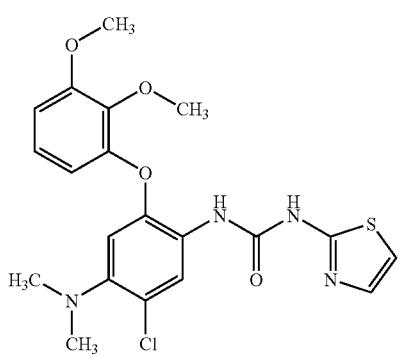

4,5-Dichloro-2-(2,3-dimethoxyphenoxy)-1-nitrobenzene (0.35 g, 1.0 mmol) was heated with dimethylamine in tetrahydofuran (4 ml, 2 M) in a sealed vial at 80° C. for 48 h. The reaction mixture was cooled to room temperature and dissolved in ethyl acetate (15 ml). The solution was washed (water, brine) and concentrated to obtain the desired nitrobenzene, which was reduced to 5-chloro-2-(2,3-dimethoxyphenoxy)-4-(dimethylamino)aniline (0.23 g, 73%) following general procedure B. N-[5-Chloro-2-(2,3-dimethoxyphenoxy)-4-dimethylaminophenyl]-N'-(thiazol-2-yl)urea (136 mg, 61%) was prepared from 5-chloro-2-(2,3-dimethoxyphenoxy)-4-(dimethylamino)aniline (161 mg, 0.5 mmol) and 2-aminothiazole (60 mg, 0.6 mmol) following the general procedure D.

LC-MS (m/z): 450 (M+1)$^+$. $^1$H NMR (400 MHz, acetone-$d_6$): δ 2.61 (s, 3H), 2.66 (s, 3H), 3.70 (s, 3H), 3.89 (s, 3H), 6.58 (s, 1H), 6.68 (dd, J=8.4, 1.2 Hz, 1H), 6.92 (dd, J=8.4, 1.6 Hz, 1H), 7.04-7.10 (m, 2H), 8.44 (s, 1H), 9.20 (br, 1H), 10.26 (br, 1H).

Example 79

N-[5-Chloro-2-(2,3-dimethoxyphenoxy)-4-(4-morpholino)phenyl]-N'-(thiazol-2-yl)urea

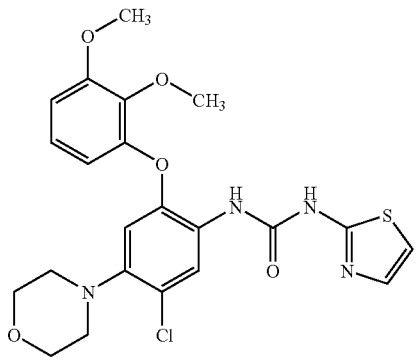

4,5-Dichloro-2-(2,3-dimethoxyphenoxy)-1-nitrobenzene (0.35 g, 1.0 mmol) was heated with morpholine (4 ml) in a sealed vial at 100° C. for 48 h. The reaction mixture was cooled to rt and dissolved in ethyl acetate (15 ml). The solution was washed (water, brine) and concentrated to obtain the desired nitrobenzene, which was reduced to 5-chloro-2-(2,3-dimethoxyphenoxy)-4-(4-morpholino)aniline (0.22 g, 61%) following general procedure B. N-[5-Chloro-2-(2,3-dimethoxyphenoxy)-4-(4-morpholino)phenyl]-N'-(thiazol-2-yl)urea (127 mg, 52%) was prepared from 5-chloro-2-(2,3-dimethoxyphenoxy)-4-(4-morpholino)aniline (182 mg, 0.5 mmol) and 2-aminothiazole (60 mg, 0.6 mmol) following the general procedure D.

LC-MS (m/z): 492 (M+1)$^+$. $^1$H NMR (400 MHz, acetone-d$_6$): δ 2.83 (m, 4H), 3.69-3.72 (m, 7H), 3.89 (s, 3H), 6.58 (s, 1H), 6.69 (dd, J=8.4, 1.6 Hz, 1H), 6.93 (dd, J=8.4, 1.6 Hz, 1H), 7.05-7.10 (m, 2H), 7.31 (d, J=3.2 Hz, 1H), 8.48 (s, 1H), 9.02 (br, 1H), 10.25 (s, 1H).

Example 80

N-[2-(2,4-Difluorophenoxy)pyridin-3-yl]-N'-(thiazol-2-yl)urea

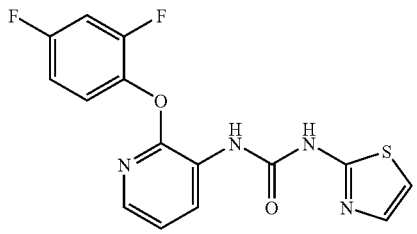

N-2-(2,4-Difluorophenoxy)pyridin-3-yl-N'-(thiazol-2-yl) urea (112 mg, 65%) was prepared from 3-amino-2-(2,4-difluorophenoxy)pyridine (111 mg, 0.5 mmol) and 2-aminothiazole (60 mg, 0.6 mmol) following the general procedure D.

LC-MS (m/z): 350 (M+1)$^+$. $^1$H NMR (400 MHz, acetone-d$_6$): δ 7.08-7.16 (m, 3H), 7.20-7.26 (m, 1H), 7.36 (d, J=3.2 Hz, 1H), 7.40-7.46 (m, 1H), 7.71 (dd, J=4.8, 1.6 Hz, 1H), 8.69 (dd, J=8.0, 1.6 Hz, 1H), 9.00 (br, 1H), 10.31 (br, 1H).

Example 81

N-[2-(2-Fluorophenoxy)pyridin-3-yl]-N'-[thiazol-2-yl]urea

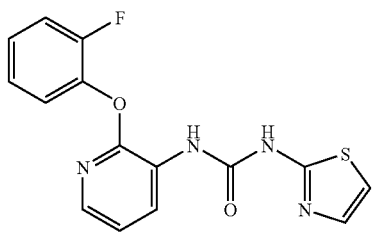

N-2-(2-Fluorophenoxy)pyridin-3-yl-N'-(thiazol-2-yl)urea (112 mg, 68%) was prepared from 3-amino-2-(2-fluorophenoxy)pyridine (102 mg, 0.5 mmol) and 2-aminothiazole (60 mg, 0.6 mmol) following the general procedure D.

LC-MS (m/z): 332 (M+1)$^+$. $^1$H NMR (400 MHz, acetone-d$_6$): δ 7.09 (d, J=3.6 Hz, 1H) 7.13 (dd, J=8.0, 4.8 Hz, 1H), 7.25-7.39 (m, 5H), 7.71 (dd, J=4.8, 1.6 Hz, 1H), 8.69 (dd, J=8.4, 1.6 Hz, 1H), 9.00 (br, 1H), 10.31 (br, 1H).

Example 82

N-[2-(2-Methoxyphenoxy)pyridin-3-yl]-N'-(thiazol-2-yl)urea

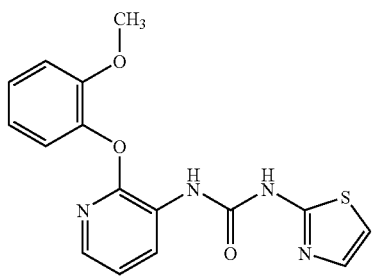

2-(2-Methoxy)phenoxy-3-nitropyridine (0.86 g, 70%) was prepared from 2-methoxyphenol (0.68 g, 5.5 mmol) and 2-bromo-3-nitropyridine (1.05 g, 5.0 mmol) following the general procedure A. This compound was reduced to 2-(2-methoxyphenoxy)-3-aminopyridine (0.49 g, 65%) following general procedure B. N-[2-(2-Methoxyphenoxy)pyridin-3-yl]-N'-(thiazol-2-yl)urea (126 g, 74%) was prepared from 2-(2-methoxyphenoxy)-3-aminopyridine (108 mg, 0.5 mmol) and 2-aminothiazole (60 mg, 0.6 mmol) following the general procedure D.

LC-MS (m/z): 344 (M+1)$^+$. $^1$H NMR (400 MHz, acetone-d$_6$): δ 3.69 (s, 3H), 6.74 (d, J=3.6 Hz, 1H), 6.99-7.01 (m, 2H), 7.16-7.21 (m, 3H), 7.45 (d, J=2.8 Hz, 1H), 7.71 (d, J=4.0 Hz, 1H), 8.57-8.59 (d, J=8.0 Hz, 1H), 8.89 (br, 1H), 10.44 (br, 1H).

Example 83

N-[2-(2,3-Dimethoxyphenoxy)pyridin-3-yl]-N-(thiazol-2-yl)urea

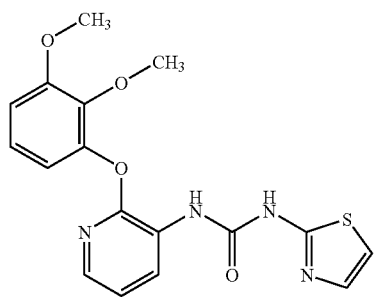

2-(2,3-Dimethoxy)phenoxy-3-nitropyridine (1.03 g, 75%) was prepared from 2,3-dimethoxyphenol (0.85 g, 5.5 mmol) and 2-bromo-3-nitropyridine (1.05 g, 5.0 mmol) following the general procedure A. This compound was reduced to 2-(2,3-dimethoxyphenoxy)-3-aminopyridine (0.57 g, 62%) following the general procedure B. N-[2-(2,3-Dimethoxyphenoxy)pyridin-3-yl]-N'-(thiazol-2-yl)urea (131 mg, 70%) was prepared from 2-(2,3-dimethoxyphenoxy)-3-aminopyridine (123 mg, 0.5 mmol) and 2-aminothiazole (60 mg, 0.6 mmol) following the general procedure D.

LC-MS (m/z): 374 (M+1)$^+$. $^1$H NMR (400 MHz, acetone-d$_6$): δ 3.58 (s, 3H), 3.87 (s, 3H), 6.81 (dd, J=1.6, 8.0 Hz, 1H), 6.95 (dd, J=1.6, 8.4 Hz, 1H), 7.05-7.07 (m, 3H), 7.35 (d, J=3.2 Hz, 1H), 7.67-7.79 (m, 1H), 8.64-8.86 (dd, J=2.4, 8.0 Hz, 1H), 8.89 (br, 1H), 10.26 (br, 1H).

Example 84

N-[4-Chloro-2-(2-chlorobenzoyl)phenyl]-N'-(thiazol-2-yl)urea

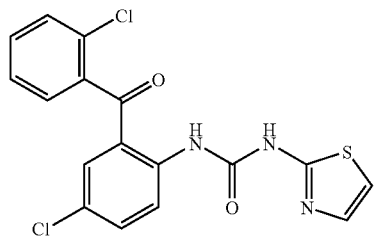

N-[4-Chloro-2-(2-chlorobenzoyl)phenyl]-N'-(thiazol-2-yl)urea (0.51 g, 86%) was prepared from 2-amino-2',5-dichlorobenzophenone (0.4 g, 1.50 mmol) and 2-aminothiazole (150 mg, 1.5 mmol) following the general procedure D.

LC-MS (m/z): 394 (M+1), $^1$H NMR (400 MHz, CDCl$_3$): δ 6.45 (br, 1H), 6.79 (dd, J=1.2, 7.6 Hz, 2H), 7.11 (d, J=7.2 Hz, 1H), 7.25-7.49 (m, 1H), 6.91-7.33 (m, 3H), 8.65 (d, J=8.8 Hz, 1H), 8.68 (d, J=9.6 Hz, 1H), 8.93 (br, 1H).

Example 85

N-[4-Chloro-2-(2-fluorobenzoyl)phenyl]-N'-(thiazol-2-yl)urea

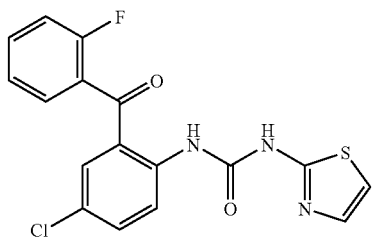

N-[4-Chloro-2-(2-fluorobenzoyl)phenyl]-N'-(thiazol-2-yl)urea (116 mg, 62%) was prepared from 2-amino-5-chloro-2'-fluorobenzophenone (125 mg, 0.5 mmol) and 2-aminothiazole (60 mg, 0.6 mmol) following the general procedure D.

LC-MS (m/z): 377 (M+1)$^+$.

Example 86

N-[2-2,4-Difluorophenylsulfanyl)phenyl]-N'-(thiazol-2-yl)urea

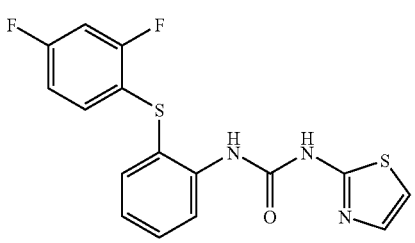

2-(2,4-Difluorophenylsulfanyl)-1-nitrobenzene (1.04 g, 78%) was prepared from 2,4-difluorothiophenol (0.73 g, 5.5 mmol) and 2-fluoronitrobenzene (0.71 g, 5.0 mmol) following the general procedure A. This compound was reduced to 2-(2,4-difluorophenylsulfanyl)-aniline (0.64 g, 70%) following the general procedure B. 1-[2-(2,4-Difluorophenylsulfanyl)-phenyl]-3-(thiazol-2-yl)urea (130 g, 72%) was prepared from 2-(2,4-difluorophenylsulfanyl)-aniline (118 mg, 0.5 mmol) and 2-aminothiazole (60 mg, 0.6 mmol) following the general procedure D.

LC-MS (m/z): 365 (M+1)$^+$. $^1$H NMR (400 MHz, acetone-d$_6$): δ 6.69-6.79 (m, 3H), 6.85 (d, J=3.6 Hz, 1H), 7.04-7.09 (m, 1H), 7.36-7.40 (m 2H), 7.51-7.53 (dd, J=1.6, 8.0 Hz, 1H), 8.42 (d, J=8.0 Hz, 1 H), 8.88 (br, 1H), 10.2 (br, 1H).

Example 87

1-[2-(2-Fluorophenylsulfanyl)phenyl]-3-(thiazol-2-yl)urea

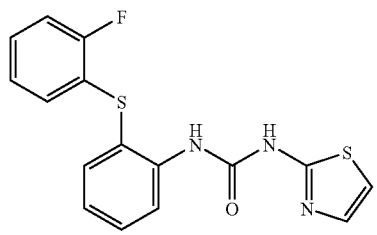

2-(2-Fluorophenylsulfanyl)nitrobenzene (1.03 g, 83%) was prepared from 2-fluorothiophenol (0.70 g, 5.5 mmol) and 2-fluoronitrobenzene (0.71 g, 5.0 mmol) following the general procedure A. This compound was reduced to 2-(2-fluorophenylsulfanyl)aniline (0.65 g, 72%) following general procedure B. N-[2-(2-Fluorophenylsulfanyl)phenyl]-N'-(thiazol-2-yl)-urea (129 mg, 75%) was prepared from 2-(2-fluorophenylsulfanyl)aniline (107 mg, 0.5 mmol) and 2-aminothiazole (60 mg, 0.6 mmol) following the general procedure D.

LC-MS (m/z): 347 (M+1)$^+$. $^1$H NMR (400 MHz, acetone-$d_6$): δ 6.74-6.82 (m, 1H), 7.02-7.07 (m, 2H), 7.14-7.23 (m, 3H), 7.29 (d, J=3.6 Hz, 1H), 7.51-7.58 (m, 1H), 7.60 (dd, J=1.2, 7.6 Hz, 1H), 8.43-8.46 (d, J=8.8 Hz, 1H), 9.08 (br, 1H), 10.39 (br, 1H).

Example 88

N-[2-(2-Chloro-4-fluorophenylsulfanyl)phenyl]-N'-(thiazol-2-yl)urea

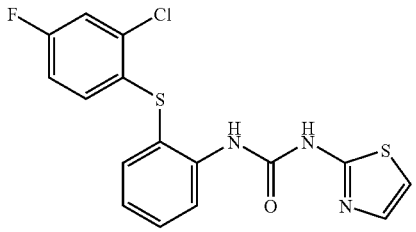

2-(2-Chloro-4-fluorophenylsulfanyl)nitrobenzene (1.13 g, 80%) was prepared from 2-chloro-4-fluorothiophenol (0.89 g, 5.5 mmol) and 2-fluoronitrobenzene (0.71 g, 5.0 mmol) following the general procedure A. This compound was reduced to 2-(2-chloro-4-fluorophenylsulfanyl)aniline (0.76 g, 75%) following the general procedure B. N-[2-(2-Chloro-4-fluorophenylsulfanyl)phenyl]-N'-(thiazol-2-yl)urea (144 mg, 76%) was prepared from 2-(2-chloro-4-fluorophenylsulfanyl)aniline (126 mg, 0.5 mmol) and 2-aminothiazole (60 mg, 0.6 mmol) following the general procedure D.

LC-MS (m/z): 381 (M+1)$^+$. $^1$H NMR (400 MHz, acetone-$d_6$): δ 6.59-6.68 (m, 1H), 6.96-7.04 (m, 2H), 7.16-7.22 (m, 1H), 7.26 (d, J=4.0 Hz, 1H), 7.32-7.38 (m, 1H), 7.50-7.61 (m, 2H), 8.47 (d, J=8.0 Hz, 1H), 9.00 (br, 1H), 10.23 (br, 1H).

Example 89

N-[2-(2,3-Dichlorophenylsulfanyl)phenyl]-N'-(thiazol-2-yl)urea

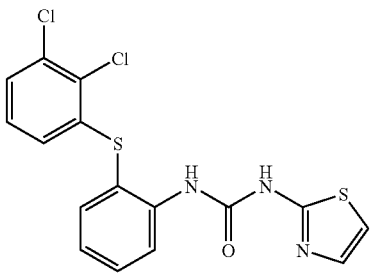

2-(2,3-Dichlorophenylsulfanyl)nitrobenzene (1.25 g, 84%) was prepared from 2,3-dichlorothiophenol (0.97 g, 5.5 mmol) and 2-fluoronitrobenzene (0.71 g, 5.0 mmol) following the general procedure A. This compound was reduced to 2-(2,4-dichlorophenylsulfanyl)-aniline (0.81 g, 72%) following the general procedure B. N-[2-(2,3-Dichlorophenylsulfanyl)-phenyl]-N'-(thiazol-2-yl)urea (154 mg, 78%) was prepared from 2-(2,3-chlorophenylsulfanyl)-aniline (135 mg, 0.5 mmol) and 2-aminothiazole (60 mg, 0.6 mmol) following the general procedure D.

LC-MS (m/z): 397 (M+1)$^+$. $^1$H NMR (400 MHz, CDCl$_3$): δ 6.34-6.44 (m, 1H), 6.72-6.78 (m, 1H), 6.88-6.96 (m, 1H), 7.11-7.22 (m, 3H), 7.50-7.57 (m, 2H), 8.51-8.53 (d, J=6.0 Hz, 1H), 9.08 (br, 1H), 10.32 (br, 1H).

Example 90

N-[2-(3,5-Dimethylphenylsulfanyl)phenyl]-N'-(thiazol-2-yl)urea

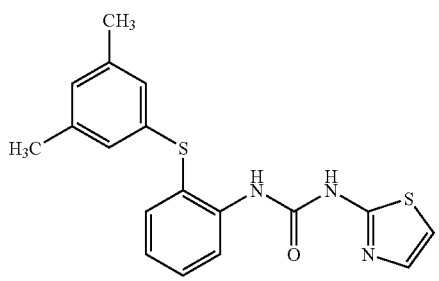

2-(3,5-Dimethylphenylsulfanyl)nitrobenzene (1.01 g, 78%) was prepared from 3,5-dimethylthiophenol (0.76 g, 5.5 mmol) and 2-fluoronitrobenzene (0.71 g, 5.0 mmol) following the general procedure A. This compound was reduced to 2-(3,5-dimethylphenylsulfanyl)-aniline (0.64 g, 72%) following the general procedure B. N-[2-3,5-Dimethylphenylsulfanyl)-phenyl]-N'-(thiazol-2-yl)urea (131 mg; 74%) was prepared from 2-(3,5-dimethylphenyl-sulfanyl)aniline (115 mg, 0.5 mmol) and 2-aminothiazole (60 mg, 0.6 mmol) following the general procedure D.

LC-MS (m/z): 357 (M+1)$^+$. $^1$H NMR (400 MHz, CDCl$_3$): δ 2.09 (s, 6 H), 6.54-6.86 (m, 4H), 7.04-7.10 (m, 1H), 7.27-

7.34 (m, 1H), 7.41-7.46 (m, 1H), 7.48-7.56 (bs, 1H), 8.41 (d, J=8.4 Hz, 1 H), 8.20 (br, 1H), 11.8 (br, 1H).

Example 91

N-[2-(2-Methoxycarbonylphenylsulfanyl)phenyl]-N'-(thiazol-2-yl)urea

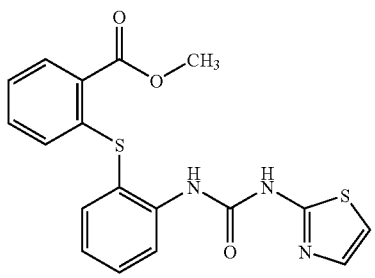

2-(2-Methoxycarbonylphenylsulfanyl)nitrobenzene (1.15 g, 80%) was prepared from methyl thiosalicylate (0.92 g, 5.5 mmol) and 2-fluoronitrobenzene (0.71 g, 5.0 mmol) following the general procedure A. This compound was reduced to 2-(2-methoxycarbonyl-phenylsulfanyl)aniline (0.75 g, 73%) following the general procedure B. N-[2-(2-Methoxycarbonylphenylsulfanyl)phenyl]-N'-(thiazol-2-yl)urea (142 mg, 74%) was prepared from 2-(2-methoxycarbonylphenylsulfanyl)aniline (130 mg, 0.5 mmol) and 2-aminothiazole (60 mg, 0.6 mmol) following the general procedure D.

LC-MS (m/z): 387 (M+1)$^+$. $^1$H NMR (400 MHz, acetone-d$_6$): δ 3.88 (s, 3H), 6.62-6.82 (m, 2H), 7.02-7.24 (m, 4H), 7.44-7.50 (m, 1H), 7.55-7.64 (bs, 1H), 7.87 (d, J=6.4, 1H), 8.42 (d, J=8.0 Hz, 1H), 8.82 (br, 1H), 10.9 (br. 1H).

Example 92

N-[2-(2-Methoxyphenylsulfanyl)phenyl]-N'-(thiazol-2-yl)urea

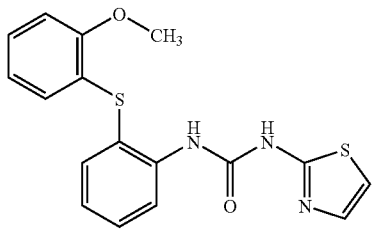

2-(2-Methoxyphenylsulfanyl)nitrobenzene (1.07 g, 82%) was prepared from 2-methoxy thiophenol (0.76 g, 5.5 mmol) and 2-fluoronitrobenzene (0.71 g, 5.0 mmol) following the general procedure A. This compound was reduced to 2-(2-methoxyphenylsulfanyl)aniline (0.66 g, 70%) following general procedure B. N-[2-(2-Methoxyphenylsulfanyl)phenyl]-N'-(thiazol-2-yl)urea (110 mg, 62%) was prepared from 2-(2-methoxyphenylsulfanyl)aniline (115 mg, 0.5 mmol) and 2-aminothiazole (60 mg, 0.6 mmol) following the general procedure D.

LC-MS (m/z): 359 (M+1)$^+$. $^1$H NMR (400 MHz, acetone-d$_6$): δ 3.48 (s, 3H), 6.77-6.89 (m, 2H), 6.90-7.00 (m, 2H), 7.05-7.24 (m, 2H), 7.29 (d, J=3.6 Hz, 1H), 7.38-7.42 (m, 1 H), 7.55 (dd, J=1.6, 8.0 Hz, 1H), 8.41-8.43 (d, J=8.4 Hz, 1H), 8.89 (br, 1H), 10.22 (br, 1H).

Example 93

N-[2-(2-Pyridinylsulfanyl)phenyl]-N'-(thiazol-2-yl)urea

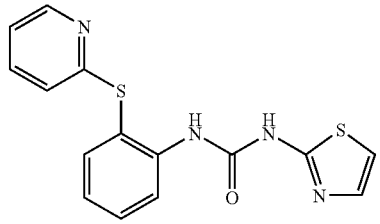

2-(2-Pyridylsulfanyl)nitrobenzene (0.70 g, 60%) was prepared from 2-mercaptopyridine (0.61 g, 5.5 mmol) and 2-fluoronitrobenzene (0.71 g, 5.0 mmol) following the general procedure A. This compound was reduced to 2-(2-pyridylsulfanyl)aniline (0.37 g, 62%) following general procedure B. N-[2-(2-Pyridylsulfanyl)phenyl]-N'-(thiazol-2-yl)urea (98 mg, 60%) was prepared from 2-(2-pyridylsulfanyl)aniline (101 mg, 0.5 mmol) and 2-aminothiazole (60 mg, 0.6 mmol) following the general procedure D.

LC-MS (m/z): 330 (M+1)$^+$. $^1$H NMR (400 MHz, CDCl$_3$): δ 6.78-6.80 (d, J=8.0 Hz, 1H), 6.96 (d, J=3.6 Hz, 1H), 7.03-7.07 (m, 1H), 7.13-7.18 (m, 1H), 7.23 (d, J=2.8 Hz, 1H), 7.51-7.57 (m, 2H), 7.64 (d, J=1.6, 7.6 Hz, 1H), 8.35 (d, J=4.0 Hz, 1H), 8.45 (d, J=8.4 Hz, 1H), 8.13 (br, 1H), 10.44 (br, 1H).

Example 94

N-(2-Propyloxyphenyl)-N'-(thiazol-2-yl)urea

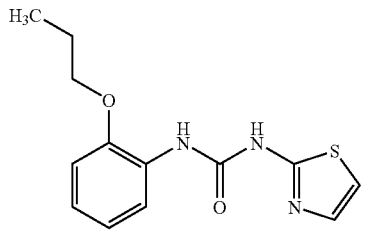

N-(2-Propyloxyphenyl)-N'-(thiazol-2-yl)urea (97 mg, 70%) was prepared from 2-propyloxyaniline (76 mg, 0.5 mmol) and 2-aminothiazole (60 mg, 0.6 mmol) following the general procedure D.

LC-MS (m/z): 279 (M+1)$^+$. $^1$H NMR (400 MHz, acetone-d$_6$): δ 1.07 (t, J=7.6 Hz, 3H), 1.88 (m, 2H), 4.05 (q, J=7.6 Hz), 6.90-7.01 (m, 3H), 7.05 (d, J=3.6 Hz), 7.36 (d, J=3.6 Hz), 8.30 (dd, J=7.6, 1.6 Hz, 1H), 8.80 (br, 1H), 10.24 (br, 1H).

Example 95

N-(2-Butyloxyphenyl)-N'-(thiazol-2-yl)urea

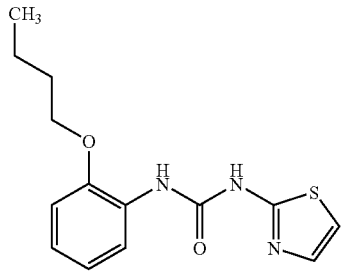

N-(2-Butyloxyphenyl)-N'-(thiazol-2-yl)urea (94 mg, 65%) was prepared from 2-butylyloxyaniline (82 mg, 0.5 mmol) and 2-aminothiazole (60 mg, 0.6 mmol) following the general procedure D.

LC-MS (m/z): 293 (M+1)$^+$. $^1$H NMR (400 MHz, acetone-$d_6$): δ 0.98 (t, J=7.2 Hz, 3H), 1.54 (m, 2H), 1.84 (quint, J=6.4 Hz, 2H), 4.10 (t, J=6.4 Hz, 2H), 6.90-7.03 (m, 3H), 7.05 (d, J=3.6 Hz, 1H), 7.25 (d, J=3.6 Hz, 1H), 8.30 (dd, J=8.0, 1.2 Hz, 1H), 9.00 (br, 1H), 10.20 (br, 1H).

Example 96

N-(2-(Cyclopentyloxyphenyl)-N'-(thiazol-2-yl)urea

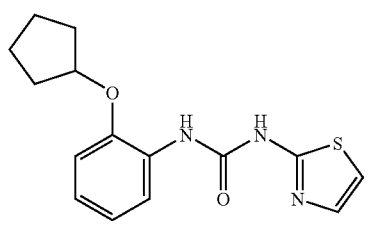

2-(Cyclopentyloxy)-1-nitrobenzene (1.04 g, 80%) was prepared from cyclopentanol (0.46 ml, 5.0 mmol) and 1-fluoro-2-nitrobenzene (0.71 g, 5.0 mmol) following the general procedure G. This was reduced to 2-(cyclopentyloxy)aniline (0.30 g, 68%, 2.5 mmol scale) following general procedure B. N-(2-Cyclopentyloxyphenyl)-N'-(thiazol-2-yl)urea (212 mg, 70%) was prepared from 2-(cyclopentyloxy)aniline (177 mg, 1.0 mmol) and 2-aminothiazole (100 mg, 1.0 mmol) following the general procedure D.

LC-MS (m/z): 305 (M+1)$^+$. $^1$H NMR (400 MHz, acetone-$d_6$): δ 1.60-2.05 (m, 8H), 4.94 (m, 1H), 6.90-7.05 (m, 4H), 7.35 (d, J=4.0 Hz, 1H), 8.30 (d, J=8.8 Hz, 1H), 10.20 (br, 2H).

Example 97

N-(2-Isopropoxyphenyl)-N'-(thiazol-2-yl)urea

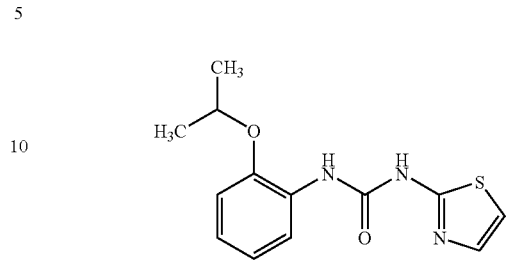

2-(Isopropoxy)-1-nitrobenzene (317 mg, 70%) was prepared from isopropyl alcohol (0.24 ml, 3.0 mmol) and 1-fluoro-2-nitrobenzene (0.36 g, 2.5 mmol) following the general procedure G. This was reduced to 2-(isopropoxy)aniline (198 mg, 75%) following general procedure B. N-(2-Isopropoxyphenyl)-N'-thiazolylurea (218 mg, 60%) was prepared from 2-(isopropoxy)aniline (198 mg, 01.3 mmol) and 2-aminothiazole (150 mg, 1.5 mmol) following the general procedure D.

LC-MS (m/z): 279 (M+1)$^+$. $^1$H NMR (400 MHz, acetone-$d_6$): δ 1.36 (d, J=6.4 Hz, 6H), 4.71 (m, 1H), 6.90-7.07 (m, 4H), 7.36 (d, J=3.6 Hz, 1H), 8.30 (d, J=8.0 Hz, 1H), 10.22 (br, 2H)

Example 98

N-[2-(2-Methylpropoxy)phenyl]-N'-(thiazol-2-yl)urea

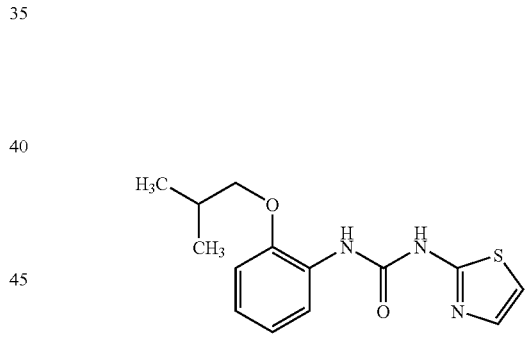

2-(2-Methylpropoxy)-1-nitrobenzene (0.73 g, 75%) was prepared from 2-methylpropanol (0.46 ml, 5.0 mmol) and 1-fluoro-2-nitrobenzene (0.71 g, 5.0 mmol) following the general procedure G. This was reduced to 2-(2-methylpropoxy)aniline (0.29 g, 70%, 2.5 mmol scale) following general procedure B. N-[2-(2-Methylpropoxy)phenyl]-N'-(thiazol-2-yl)-urea (189 mg, 65%) was prepared from 2-(2-methylpropoxy)aniline (165 mg, 1.0 mmol) and 2-aminothiazole (100 mg, 1.0 mmol) following the general procedure D.

LC-MS (m/z): 293 (M+1)$^+$. $^1$H NMR (400 MHz, acetone-$d_6$): δ 1.09 (d, 6H), 2.13 (m, 1H), 3.86 (d, J=6.8 Hz, 1H), 6.90-7.10 (m, 4H), 7.38 (d, J=3.6 Hz, 1H), 8.29 (d, J=7.2 Hz, 1H), 10.05 (br, 2H).

Example 99

N-[2-(Cyclopentylmethoxy)phenyl]-N'-(thiazol-2-yl)urea

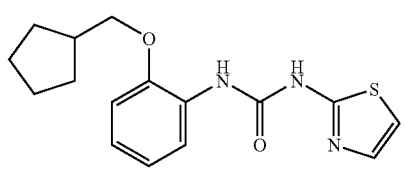

2-(Cyclopentylmethoxy)-1-nitrobenzene (443 mg, 80%) was prepared from cyclopentanemethanol (0.32 ml, 3.0 mmol) and 1-fluoro-2-nitrobenzene (0.36 g, 2.5 mmol) following the general procedure G. This was reduced to 2-(cyclopentylmethoxy)aniline (268 mg, 70%) following general procedure B. N-[2-(Cyclopentylmethoxy)phenyl]-N'-(thiazol-2-yl)-urea (286 mg, 60%) was prepared from 2-(cyclopentylmethoxy)aniline (0.25 g, 1.5 mmol) and 2-aminothiazole (150 mg, 1.5 mmol) following the general procedure D.

LC-MS (m/z): 319 (M+1)$^+$. $^1$H NMR (400 MHz, acetone-$d_6$): δ 1.40 (m, 2H), 1.65 (m, 4H), 1.91 (m, 2H), 2.45 (m, 1H), 3.98 (d, J=7.6 Hz, 1H), 6.88-7.06 (m, 4H), 7.35 (d, J=3.6 Hz, 1H), 8.29 (d, J=7.6 Hz, 1H), 10.14, (br, 2H).

Example 100

N-[2-(3-pentoxy)phenyl]-N'-(thiazol-2-yl)urea

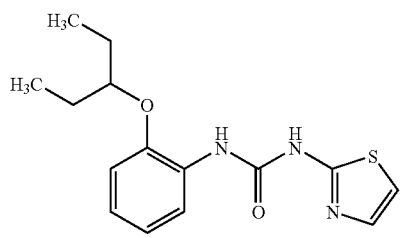

2-(3-Pentoxy)-1-nitrobenzene (366 mg, 70%) was prepared from 3-pentanol (0.27 ml, 2.5 mmol) and 1-fluoro-2-nitrobenzene (0.36 g, 2.5 mmol) following the general procedure G. This was reduced to 2-(3-pentoxy)aniline (0.25 g, 80%) following general procedure B. N-[2-(3-pentoxy)phenyl]-N'-(thiazol-2-yl)urea (0.26 g, 57%) was prepared from 2-(3-pentoxy)-aniline (0.25 g, 1.5 mmol) and 2-aminothiazole (150 mg, 1.5 mmol) following the general procedure D.

LC-MS (m/z): 307 (M+1)$^+$. $^1$H NMR (400 MHz, acetone-$d_6$): δ 0.92 (t, J=7.2 Hz, 6H), 1.75 (m, 4H), 4.38 (m, 1H), 6.89-7.06 (m, 4H), 7.36 (d, J=3.6 Hz, 1H), 8.32 (d, J=8.0 Hz, 1H).

Example 101

N-[2-(2-pentoxy)phenyl]-N'-(thiazol-2-yl)urea

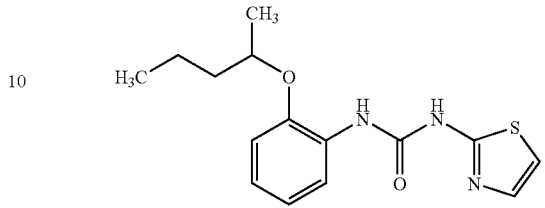

2-(2-Pentoxy)-1-nitrobenzene (387 mg, 74%) was prepared from 2-pentanol (0.27 ml, 2.5 mmol) and 1-fluoro-2-nitrobenzene (0.36 g, 2.5 mmol) following the general procedure G. This was reduced to 2-(2-pentoxy)aniline (0.26 g, 79%) following general procedure B. N-[2-(2-pentoxy)phenyl]-N'-(thiazol-2-yl)urea (280 mg, 62%) was prepared from 2-(2-pentoxy)aniline (0.25 g, 1.5 mmol) and 2-aminothiazole (150 mg, 1.5 mmol) following the general procedure D.

LC-MS (m/z): 307 (M+1)$^+$. $^1$H NMR (400 MHz, acetone-$d_6$): δ 0.93 (t, J=7.2 Hz, 3H), 1.32 (d, J=6.0 Hz, 3H), 1.40-1.90 (m, 4H), 4.55 (m, 1H), 6.85-7.07 (m, 4H), 7.36 (d, J=3.6 Hz, 1H), 8.31 (d, J=8.0 Hz, 1H), 10.15 (br, 1H).

Example 102

N-[2-(2-Methoxyethoxy)phenyl]-N'-(thiazol-2-yl)urea

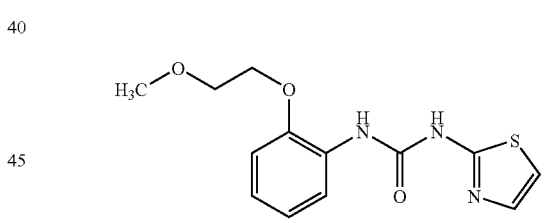

2-(2-Methoxyethoxy)-1-nitrobenzene (0.25 g, 64%) was prepared from 2-methoxyethanol (0.16 ml, 2.0 mmol) and 1-fluoro-2-nitrobenzene (0.21 ml, 2.0 mmol) following the general procedure G. This was reduced to 2-(2-methoxyethoxy)aniline (0.13 g, 60%) following general procedure B. N-[2-(2-Methoxyethoxy)phenyl]-N'-(thiazol-2-yl)urea (115 mg, 55%) was prepared from 2-(2-methoxyethoxy)aniline (115 mg, 0.7 mmol) and 2-aminothiazole (140 mg, 1.4 mmol) following the general procedure D.

LC-MS (m/z): 295 (M+1)$^+$. $^1$H NMR (400 MHz, acetone-$d_6$): δ 3.37 (s, 3H), 3.78 (t, J=4.8 Hz, 2H), 4.25 (t, J=4.8 Hz, 2H), 6.95-7.06 (m, 4H), 7.37 (d, J=3.6 Hz, 1H), 8.29 (d, J=8.0 Hz, 1H), 8.80 (br, 1H), 10.20 (br, 1H).

Example 103

General procedure (H)

(2-[3-(2-Benzylphenyl)ureido]thiazol-4-yl)acetic acid

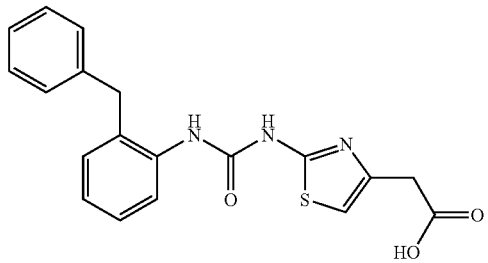

The intermediate 2-benzylphenyl isocyanate (0.26 g, 1.2 mmol) (general procedure H2) was dissolved in DMF(5 ml) and 2-amino-4-thiazole acetic acid (0.20 g, 1.2 mmol) was added. After 16 hours at 20° C. ethylacetate (60 ml) was added and the mixture was extracted with water (5×20 ml). The solvent was removed in vacuo and the remaining oil was purified on Waters Deltprep 4000 giving 150 mg of the title compound.

Preparative system: (gradient 20-90% $CH_3CN$ 40 min., 20 ml/min., Rt=35 min Solvent A=water, solvent B=$CH_3CN$, solvent C=0.5% TFA/water).

$^1$H-NMR (DMSO-$d_6$): δ 10.90 (broad, 1H); 8.45 (s, 1H); 7.80 (s, 1H); 7.20 (multi, 9H); 6.85 (s, 1H); 3.98 (s, 2H); 3.53 (s, 2H). HPLC-MS (Method A): m/z=368 (M+1); $R_t$=4.10 min $^1$H NMR (CDCl$_3$): δ 7.98 (br d, 2H), 7.88-7.70 (m, 4H), 7.50 (t, 3H), 7.18 (d, 1H), 6.84 (br s, 1H), 3.71 (br s, 2H), 2.70 (br s, 2H), 2.52 (m, 1H), 1.90-1.70 (m, 5H), 1.45-1.15 (m, 5H).

Example 104

General Procedure (H)

(2-[3-(2-Benzoyl-4-chlorophenyl)ureido]thiazol-4-yl)acetic acid

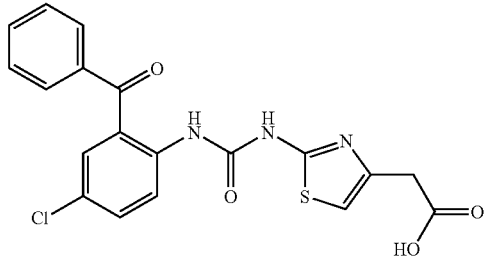

The title compound was prepared as in example 103 using (5-chloro-2-isocyanatophenyl)phenyl methanone (general procedure H2) as intermediate isocyanate.

$^1$H-NMR (DMSO-$d_6$): Selected data: δ 9.48 (broad, 1H); 8.12 (broad, 1H); (multi, 9H); 6.87 (s, 1H); 3.57 (s, 2H). HPLC-MS (method A): m/z=415 (M+1); $R_t$=3.79 min

Example 105

General Procedure (H)

(2-[3-(2-(2-Methylphenoxy)phenyl)ureido]thiazol-4-yl)acetic acid

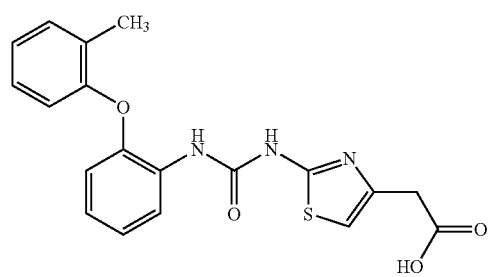

The title compound was prepared as in example 103 using 2-(2-methylphenoxy)-phenyl isocyanat (general procedure H2) as intermediate isocyanate.

$^1$H-NMR (DMSO-$d_6$): δ 11.09 (broad, 1H); 8.88 (broad, 1H); 8.25 (d, 1H); 7.37 (d, 1H); 7.22 (t, 1H); 7.11 (multi, 2H); 6.97 (t, 1H); 6.89 (d, 1H); 6.87 (s, 1H); 6.67 (d, 1H); 3.53 (s, 2H); 2.23 (s, 3H). HPLC-MS (method A): m/z=384 (M+1); $R_t$=4.67 min

Example 106

General Procedure (H)

(2-[3-(2-(4-Methoxyphenoxy)-5-(trifluoromethyl)phenyl)ureido]thiazol-4-yl)acetic acid

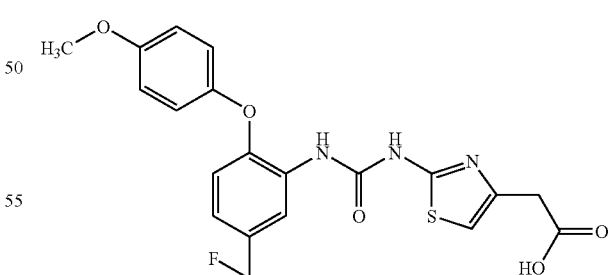

The title compound was prepared as in example 103 using 2-(4-methoxyphenoxy)-5-(trifluoromethyl)phenyl isocyanate (general procedure H2) as intermediate isocyanate.

¹H-NMR (DMSO-d₆): δ 12.32 (broad, 1H); 11.20 (broad, 1H); 9.30 (d, 1H); 8.62 (d, 1H); 7.32 (d, 1H); 7.17 (d, 2H); 7.05 (d, 2H); 6.90 (s, 1H); 6.83 (d, 1H); 3.78 (s, 3H); 3.53 (s, 2H).

Example 107

General Procedure (H)

{2-[3-(2-phenoxyphenyl)ureido]thiazol-4-y}acetic acid

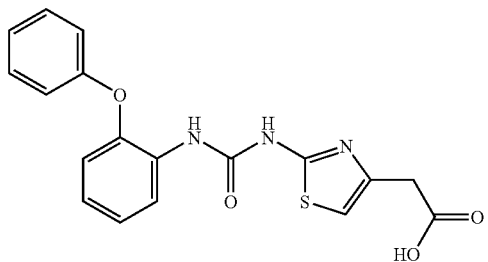

The title compound was prepared as in example 103 using 2-phenoxyphenyl isocyanate (general procedure H2) as intermediate isocyanate.

¹H NMR (CDCl₃) selected data: δ 3.47 (2H, s), 6.78 (1H, s), 6.90 (1H, d), 6.97-7.08 (3H, m), 7.09-7.19 (2H, m), 7.38 (2H, t), 8.16 (1H, br s), HPLC-MS (Method A): m/z=370 (M+1); R$_t$=3.50 min.

Example 108

General Procedure (H)

2-{3-[5-Fluoro-2-(2-fluoro-6-methoxyphenoxy)phenyl]ureido}thiazole-4-carboxylic acid

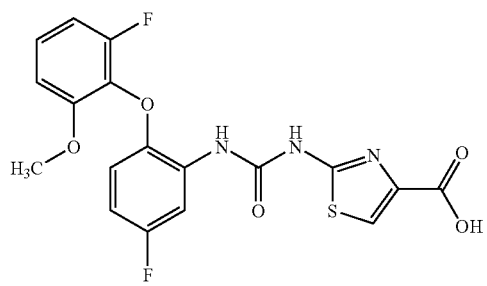

The title compound was prepared accorrding to general procedure H.

¹H NMR (DMSO): δ 12.76 (br, 1H), 11.21 (br 1H), 9.23 (s, 1H), 8.06 (dd, 1H), 7.94 (s, 1H), 7.33 (d, 1H), 7.10-7.01 (m, 2H), 6.74 (t, 1H), 6.55 (dd, 1H), 3.80 (s, 3H). HPLC-MS (Method B): m/z=422 (M+1); R$_t$=3.90 min.

Example 109

General Procedure (H)

2-{3-[2-(2,3-Dimethoxyphenoxy)-5-fluorophenyl]ureido}thiazole-4-carboxylic acid ethyl ester

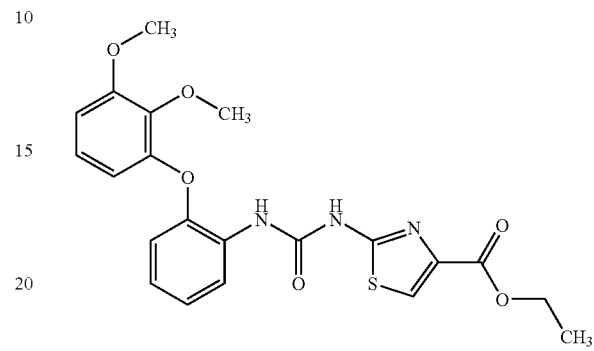

¹H NMR (DMSO): δ 11.44 (s, 1H), 8.99 (s 1H), 8.06 (dd, 1H), 7.99 (s, 1H), 7.09 (t, 1H), 6.94 (d, 1H), 6.80 (t, 1H), 6.72 (dd, 1H), 6.67 (d, 1H), 4.25 (q, 2H), 3.84 (s, 3H), 3.67 (s, 3H), 1.28 (t, 3H). HPLC-MS (Method B): m/z=462 (M+1); R$_t$=4.53 min.

Example 110

General Procedure (H)

(2-{3-[2-(2,3-Dimethoxyphenoxy)-5-fluorophenyl]ureido}thiazol-4-yl)acetic acid ethyl ester

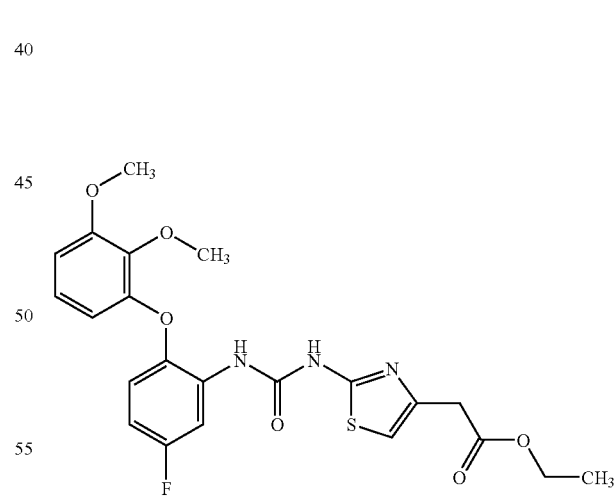

¹H NMR (DMSO): δ 11.16 (br, 1H), 9.09 (br 1H), 8.08 (dd, 1H), 7.09 (t, 1H), 6.94 (d, 1H), 6.92 (s, 1H), 6.78 (t, 1H), 6.70 (dd, 1H), 6.65 (d, 1H), 4.06 (q, 2H), 3.84 (s, 3H), 3.66 (s, 2H), 3.62 (s, 3H), 1.18 (t, 3H). HPLC-MS (Method B): m/z=476 (M+1); R$_t$=4.43 min.

Example 111

General Procedure (H)

(2-{3-[5-Fluoro-2-(2-fluoro-6-methoxyphenoxy)phenyl]ureido}thiazol-4-yl)acetic acid

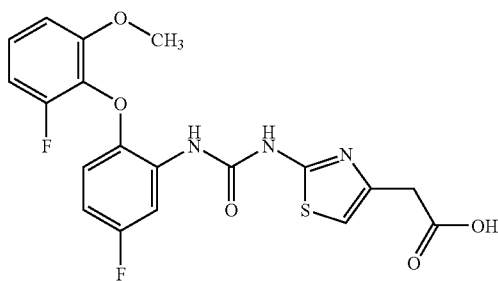

$^1$H NMR (DMSO): δ 12.27 (br, 1H), 11.06 (br, 1H), 9.22 (br, 1H), 8.06 (dd, 1H), 7.32 (dd, 1H), 7.08 (d, 1H), 7.03 (t, 1H), 6.90 (s, 1H), 6.75-6.70 (m, 2H), 6.53 (dd, 1H), 3.79 (s, 3H), 3.55 (s, 2H). HPLC-MS (Method B): m/z=436 (M+1); R$_t$=3.85 min.

Example 112

General Procedure (H)

2-{3-[2-(2,3-Dimethoxyphenoxy)-5-fluorophenyl]ureido}thiazole-4-carboxylic acid

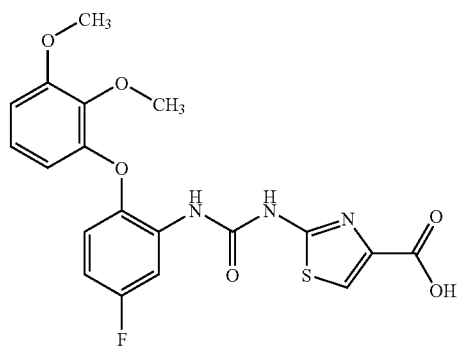

$^1$H NMR (DMSO): δ 12.77 (br, 1H), 11.33 (s, 1H), 9.06 (s, 1H), 8.07 (dd, 1H), 7.93 (s, 1H), 7.08 (d, 1H), 7.09 (t, 1H), 6.95 (dd, 1H), 6.80 (t, 1H), 6.73-6.63 (m, 2H), 3.84 (s, 3H), 3.66 (s, 3H). HPLC-MS (Method B): m/z=434 (M+1); R$_t$=3.92 min.

Example 113

General Procedure (H)

(2-{3-[2-(2,3-Dimethoxyphenoxy)-5-fluorophenyl]ureido}thiazol-4-yl)acetic acid

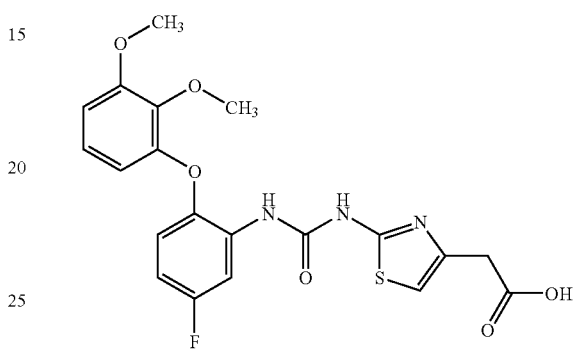

$^1$H NMR (DMSO): δ 12.30 (br, 1H), 11.14 (br, 1H), 9.08 (br 1H), 8.08 (dd, 1H), 7.08 (t, 1H), 6.94 (d, 1H), 6.89 (s, 1H), 6.78 (t, 1H), 6.70 (dd, 1H), 6.66(dd, 1H), 3.84 (s, 3H), 3.66 (s, 3H), 3.54 (s, 2H). HPLC-MS (Method B): m/z=448 (M+1); R$_t$=3.76 min.

Example 114

General Procedure (H)

2-{3-[5-Fluoro-2-(2-fluoro-6-methoxyphenoxy)phenyl]ureido}-4-methylthiazole-5-carboxylic acid ethyl ester

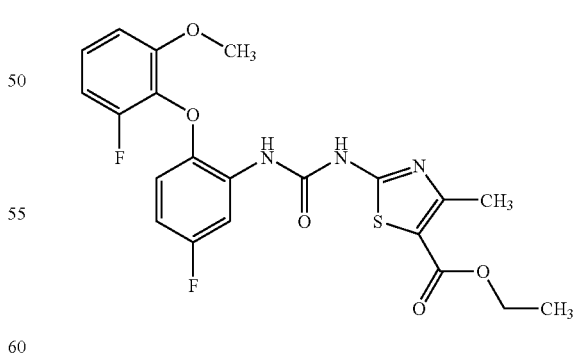

$^1$H NMR (DMSO): δ 11.35 (s, 1H), 9.38 (br 1H), 8.05 (dd, 1H), 7.32 (dd, 1H), 7.10-7.02 (m, 2H), 6.76 (t, 1H), 6.56(dd, 1H), 4.24 (q, 2H), 3.79 (s, 3H), 2.52 (s, 3H), 1.29 (t, 3H). HPLC-MS (Method B): m/z=464 (M+1); R$_t$=4.91 min.

Example 115

General Procedure (H)

2-{3-[5-Fluoro-2-(2-fluoro-6-methoxyphenoxy)phenyl]ureido}-4-methylthiazole-5-carboxylic acid

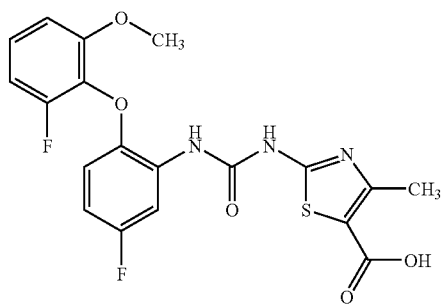

$^1$H NMR (DMSO): δ 12.79 (br, 1H), 11.29 (br, 1H), 9.38 (br 1H), 8.05 (dd, 1H), 7.32 (dd, 1H), 7.10-7.01 (m, 2H), 6.75 (t, 1H), 6.54 (dd, 1H), 3.79 (s, 3H), 2.51 (s, 2H). HPLC-MS (Method B): m/z=436 (M+1); $R_t$=4.19 min.

Example 116

General Procedure (H1)

N-Ethyl-2-(2-{3-[5-fluoro-2-(2-fluoro-6-methoxyphenoxy)phenyl]ureido}thiazol-4-yl)acetamide

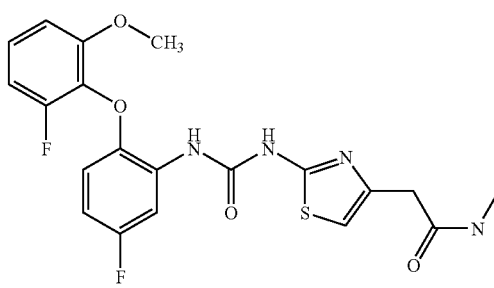

$^1$H NMR (DMSO): δ 11.03 (s, 1H), 9.22 (br 1H), 8.06 (dd, 1H), 7.89 (t, 1H), 7.32 (dd, 1H), 7.10-7.00 (m, 2H), 6.82 (s, 1H), 6.72 (t, 1H), 6.53 (dd, 1H), 3.79 (s, 3H), 3.39 (s, 2H), 3.07 (q, 2H), 1.01 (t, 3H). HPLC-MS (Method B): m/z=463 (M+1); $R_t$=4.06 min.

Example 117

General Procedure (H1)

2-(2-{3-[5-Fluoro-2-(2-fluoro-6-methoxyphenoxy)phenyl]ureido}thiazol-4-yl)-N-(2-methoxyethyl)acetamide

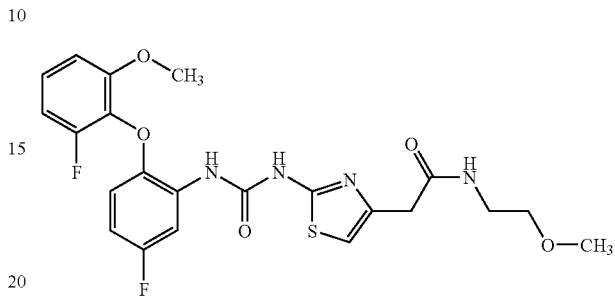

$^1$H NMR (DMSO): δ 11.03 (br, 1H), 9.22 (br 1H), 8.06 (dd, 1H), 7.99 (t, 1H), 7.32 (dd, 1H), 7.10-7.00 (m, 2H), 6.82 (s, 1H), 6.72 (t, 1H), 6.53 (dd, 1H), 3.79 (s, 3H), 3.43 (s, 2H), 3.34 (t, 2H), 3.24 (s, 3H), 3.23 (t, 2H). HPLC-MS (Method B): m/z=493 (M+1); $R_t$=4.01 min.

Example 118

General Procedure (H1)

2-(2-{3-[5-Fluoro-2-(2-fluoro-6-methoxyphenoxy)phenyl]ureido}thiazol-4-yl)-N-(2-morpholin-4-yl-ethyl)acetamide

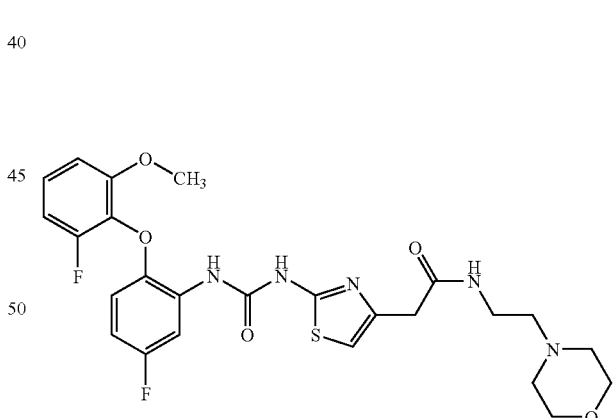

$^1$H NMR (DMSO): selected data: δ 11.01 (br, 1H), 9.77 (br, 1H), 9.23 (br 1H), 8.19 (br, 1H), 8.06 (dd, 1H), 7.32 (dd, 1H), 7.10-7.00 (m, 2H), 6.88 (s, 1H), 6.72 (t, 1H), 6.53 (dd, 1H), 3.97 (m, 2H), 3.79 (s, 3H), 3.64 (m, 2H), 3.47 (s, 2H). HPLC-MS (Method B): m/z=548 (M+1); $R_t$=3.24 min.

Example 119

General Procedure (H1)

[2-(2-{3-[5-Fluoro-2-(2-fluoro-6-methoxyphenoxy)phenyl]ureido}thiazol-4-yl)acetylamino]acetic acid methyl ester

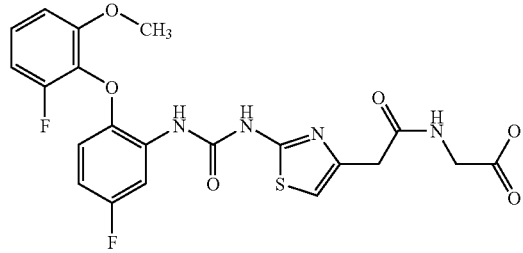

¹H NMR (DMSO): Selected data δ 11.06 (br, 1H), 9.25 (br 1H), 8.34 (t, 1H), 8.06 (dd, 1H), 7.31 (dd, 1H), 7.10-7.00 (m, 2H), 6.88 (s, 1H), 6.73 (t, 1H), 6.53(dd, 1H), 3.85 (d, 2H), 3.79 (s, 3H), 3.63 (s, 2H), 3.49 (s, 2H). HPLC-MS (Method B): m/z=507 (M+1); R$_t$=3.74 min.

Example 120

General Procedure (H1)

2-{3-[2-(2,3-Dimethoxyphenoxy)-5-fluorophenyl]ureido}thiazole-4-carboxylic acid (2-methoxyethyl)amide

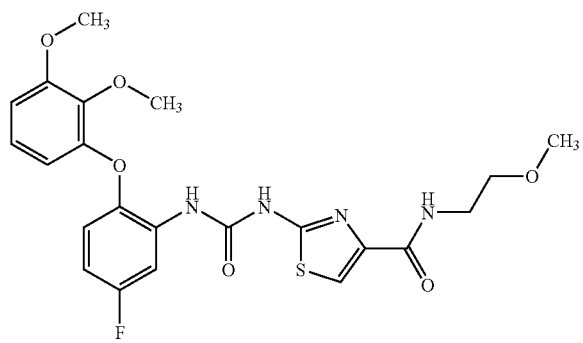

¹H NMR (DMSO): Selected data δ 11.29 (s, 1H), 9.13 (s 1H), 8.08 (dd, 1H), 7.78 (t, 1H), 7.73 (s, 1H), 7.09 (t, 1H), 6.95 (dd, 1H), 6.80 (t, 1H), 6.71(dd, 1H), 6.67 (dd, 1H), 3.84 (s, 3H), 3.67 (s, 3H), 3.26 (s, 3H). HPLC-MS (Method B): m/z=491 (M+1); R$_t$=3.86 min.

Example 121

General Procedure (H1)

[2-(2-{3-[5-Fluoro-2-(2-fluoro-6-methoxyphenoxy)phenyl]ureido}thiazol-4-yl)acetylamino]acetic acid

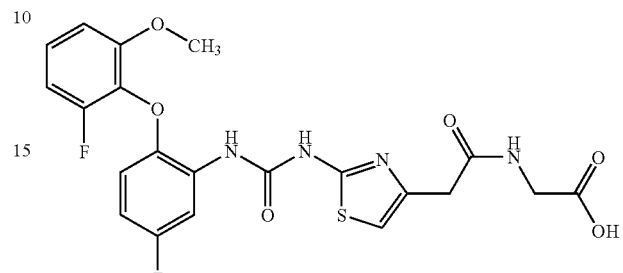

¹H NMR (DMSO): δ 12.54 (br, 1H), 11.06 (br, 1H), 9.23 (br 1H), 8.21 (t, 1H), 8.06 (dd, 1H), 7.31 (dd, 1H), 7.09-7.01 (m, 2H), 6.88 (s, 1H), 6.72 (t, 1H), 6.53(dd, 1H), 3.79 (s, 3H), 3.76 (s, 2H), 3.49 (s, 2H). HPLC-MS (Method B): m/z=493 (M+1); R$_t$=3.47 min.

Example 122

General Procedure (H)

2-{3-[2-(2,3-Dimethoxyphenoxy)-5-fluorophenyl]ureido}thiazole-4-carboxylic acid ethylamide

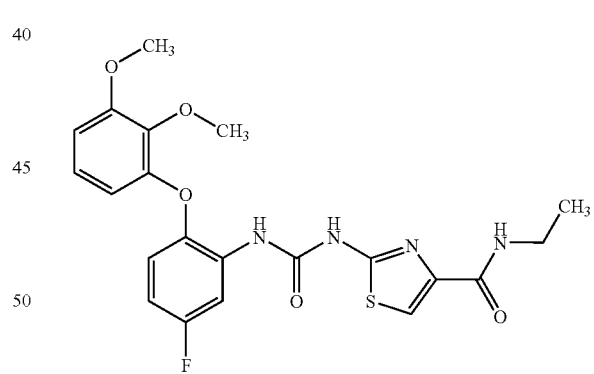

¹H NMR (DMSO): δ 11.21 (s, 1H), 9.19 (s 1H), 8.08 (dd, 1H), 7.89 (t, 1H), 7.69 (s, 1H), 7.10 (t, 1H), 6.95 (dd, 1H), 6.79 (t, 1H), 6.73-6.66 (m, 2H), 3.84 (s, 3H), 3.66 (s, 3H), 3.25 (q, 2H), 1.08 (t, 3H). HPLC-MS (Method B): m/z=461 (M+1); R$_t$=3.96 min.

Microanalysis:

Calculated for: C, 55.09%; H, 4.88%; N, 111.88%. Found: C, 55.18%; H, 4.67%; N, 12.21%.

Example 123

General Procedure (H1)

[(2-{3-[2-(2,3-Dimethoxyphenoxy)-5-fluorophenyl]ureido}thiazole-4-carbonyl)amino]acetic acid methyl ester

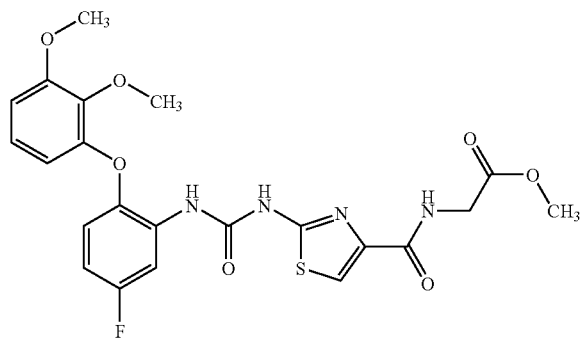

$^1$H NMR (DMSO): δ 11.26 (s, 1H), 9.20 (s 1H), 8.26 (t, 1H), 8.09 (dd, 1H), 7.77 (s, 1H), 7.10 (t, 1H), 6.95 (dd, 1H), 6.79 (t, 1H), 6.72-6.67 (m, 2H), 4.01 (d, 2H), 3.84 (s, 3H), 3.66 (s, 3H), 3.65 (s, 3H).

Example 124

General Procedure (H)

(5-{3-[5-Fluoro-2-(2-fluoro-6-methoxyphenoxy)phenyl]ureido}-[1,3,4]thiadiazol-2-yl)acetic acid ethyl ester

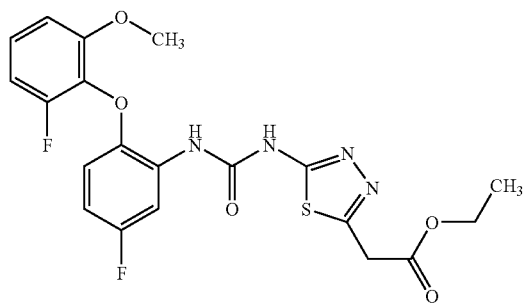

$^1$H NMR (DMSO): δ 11.35 (s, 1H), 9.31 (s 1H), 8.03 (t, 1H), 8.04 (dd, 1H), 7.31 (dd, 1H), 7.10-7.02 (m, 2H), 6.75 (t, 1H), 6.55(dd, 1H), 4.19-4.14(m, 4H), 3.80 (s, 3H), 1.23 (t, 3H). HPLC-MS (Method B): m/z=465 (M+1); $R_t$=4.14 min.

Example 125

General Procedure (H1)

[(2-{3-[2-(2,3-Dimethoxyphenoxy)-5-fluorophenyl]ureido}thiazole-4-carbonyl)amino]acetic acid

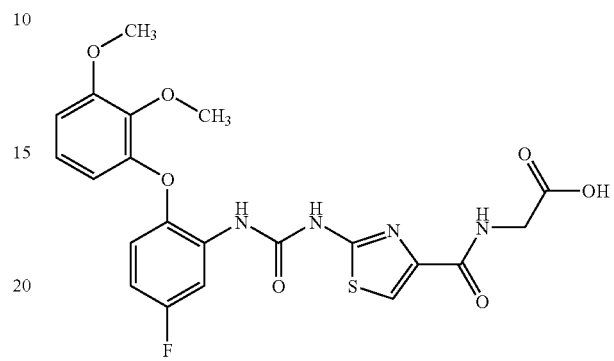

$^1$H NMR (DMSO): δ 12.67 (br, 1H), 11.36 (s, 1H), 9.24 (s 1H), 8.08 (dd, 1H), 7.78 (s, 1H), 7.10 (t, 1H), 6.95 (dd, 1H), 6.79 (t, 1H), 6.72-6.67 (m, 2H), 3.93 (d, 2H), 3.84 (s, 3H), 3.67 (s, 3H). HPLC-MS (Method B): m/z=491 (M+1); $R_t$=3.58 min.

Example 126

General Procedure (H)

(5-{3-[5-Fluoro-2-(2-fluoro-6-methoxyphenoxy)phenyl]ureido}-[1,3,4]thiadiazol-2-yl)acetic acid

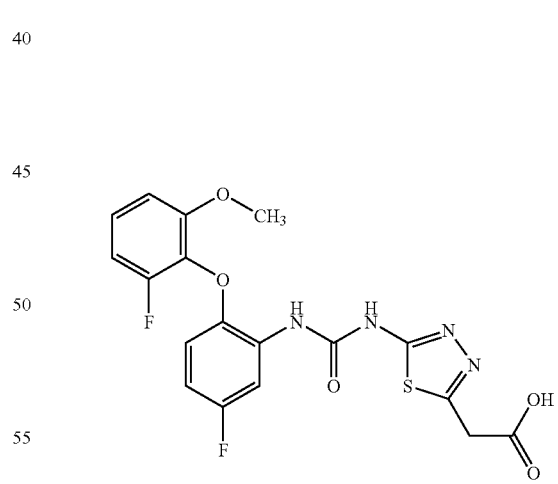

$^1$H NMR (DMSO): δ 12.96 (br, 1H), 11.33 (br, 1H), 9.31 (s 1H), 8.04 (dd, 1H), 7.33 (dd, 1H), 7.11-7.01 (m, 2H), 6.75 (t, 1H), 6.55 (dd, 1H), 4.10 (s, 2H), 3.80 (s, 3H). HPLC-MS (Method B): m/z=337 (M+1); $R_t$=3.47 min.

Example 127

General Procedure (H)

5-{3-[2-(2,3-Dimethoxyphenoxy)-5-fluorophenyl]ureido}-[1,3,4]thiadiazole-2-carboxylic acid ethyl ester

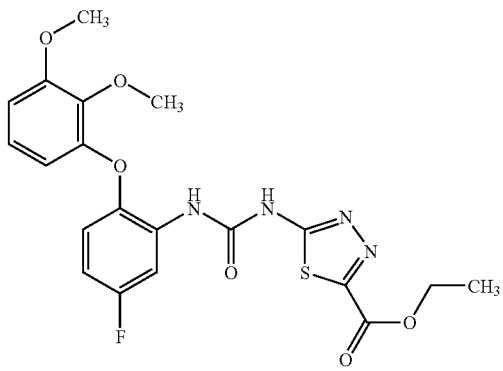

$^1$H NMR (DMSO): δ 11.91 (s, 1H), 9.26 (s 1H), 8.05 (dd, 1H), 7.10 (t, H), 6.95 (dd, 1H), 6.83 (t, 1H), 6.75-6.67 (m, 2H), 4.40 (q, 2H), 3.84 (s, 3H), 3.66 (s, 3H), 1.35 (t, 3H). HPLC-MS (Method B): m/z=463 (M+1); R$_t$=4.34 min.

Example 128

General Procedure (H)

(5-{3-[2-(2,3-Dimethoxyphenoxy)-5-fluorophenyl]ureido}-[1,3,4]thiadiazol-2-yl) acetic acid ethyl ester

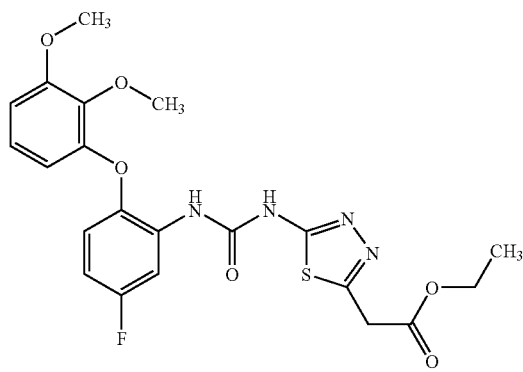

$^1$H NMR (DMSO): δ 11.42 (s, 1H), 9.17 (s 1H), 8.05 (dd, 1H), 7.09 (t, 1H), 6.95 (dd, 1H), 6.81 (t, 1H), 6.72 (dd, 1H), 6.67 (dd, 1H), 4.19-4.13 (m, 4H), 3.84 (s, 3H), 3.66 (s, 3H), 1.22 (t, 3H). HPLC-MS (Method B): m/z=477 (M+1); R$_t$=4.10 min.

Example 129

General Procedure (H1)

3-[2-(2-{3-[2-(2,3-Dimethoxyphenoxy)-5-fluorophenyl]ureido}thiazol-4-yl)acetylamino]propionic acid methyl ester

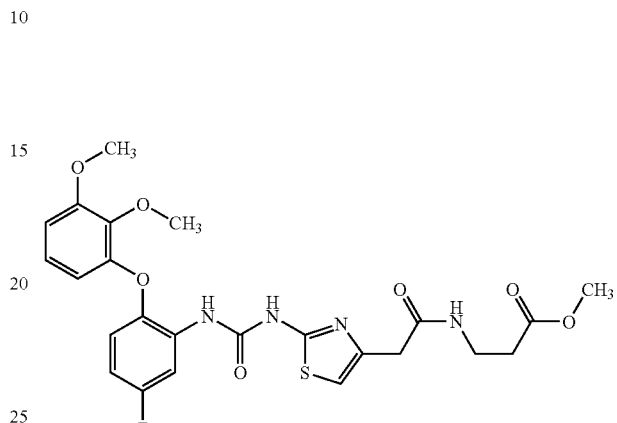

$^1$H NMR (DMSO): δ 11.11 (s, 1H), 9.07 (br 1H), 8.08 (dd, 1H), 7.98 (t, 1H), 7.08 (d, 1H), 6.94 (dd, 1H), 6.81 (s, 1H), 6.77 (dd, 1H), 6.70 (dd, 1H), 6.65 (dd, 1H), 3.84 (s, 3H), 3.66 (s, 3H), 3.58 (s, 3H), 3.39 (s, 2H), 3.27 (q, 2H), 2.46 (t, 2H). HPLC-MS (Method B): m/z=533 (M+1); R$_t$=3.71 min.

Example 130

General Procedure (H1)

2-(2-{3-[2-(2,3-Dimethoxyphenoxy)-5-fluorophenyl]ureido}thiazol-4-yl)-N-(2-morpholin-4-ylethyl)acetamide

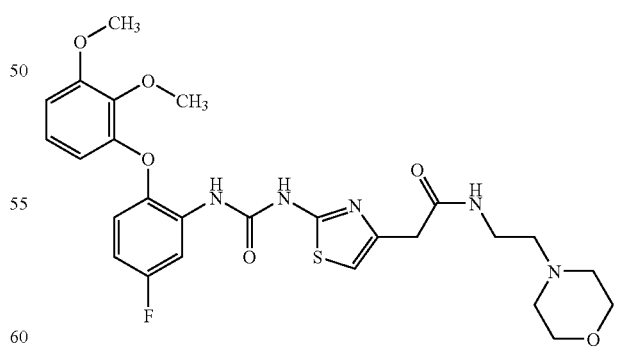

$^1$H NMR (DMSO): Selected data δ 11.11 (br, 1H), 9.08 (br 1H), 8.07 (dd, 1H), 7.09 (t, 1H), 6.94 (dd, 1H), 6.86 (s, 1H), 6.77 (t, 1H), 6.70 (dd, 1H), 6.66 (dd, 1H), 3.84 (s, 3H), 3.66 (s, 3H), 3.43 (s, 2H), 3.03-2.99 (m, 4H), 1.74-1.71 (m, 4H). HPLC-MS (Method B): m/z=560 (M+1); R$_t$=2.75 min.

Example 131

General Procedure (H1)

[(2-{3-[5-Fluoro-2-(2-fluoro-6-methoxyphenoxy)phenyl]ureido}thiazole-4-carbonyl)amino]acetic acid methyl ester

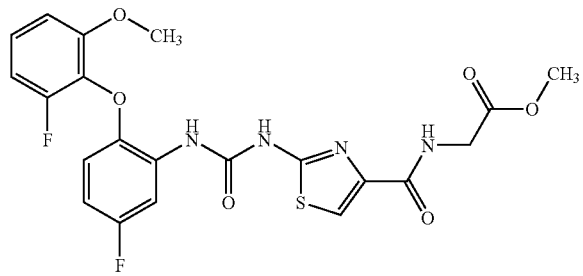

$^1$H NMR (DMSO): δ 11.27 (s, 1H), 9.36 (s 1H), 8.32 (t, 1H), 8.07 (dd, 1H), 7.79 (s, 1H), 7.33 (dd, 1H), 7.11-7.02 (m, 2H), 6.75 (t, 1H), 6.55 (dd, 1H), 4.03 (d, 2H), 3.80 (s, 3H), 3.66 (s, 3H). HPLC-MS (Method B): m/z=493 (M+1); $R_t$=3.91 ml.

Example 132

General Procedure (H1)

3-[2-(2-{3-[2-(2,3-Dimethoxyphenoxy)-5-fluorophenyl]ureido}thiazol-4-yl)acetylamino]propionic acid

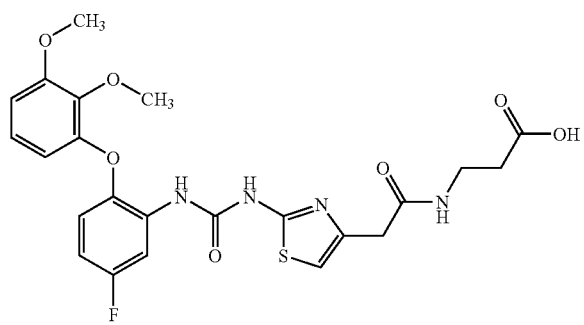

$^1$H NMR (DMSO): δ 12.21 (br, 1H), 11.09 (br, 1H), 9.06 (br 1H), 8.07 (dd, 1H), 7.98 (t, 1H), 7.09 (t, 1H), 6.94 (dd, 1H), 6.81 (s, 1H), 6.76 (t, 1H), 6.71 (t, 1H), 6.66 (dd, 1H), 3.84 (s, 3H), 3.66 (s, 3H), 3.39 (s, 2H), 3.24 (q, 2H), 2.38 (t, 2H).

Example 133

General Procedure (H1)

[(2-{3-[5-Fluoro-2-(2-fluoro-6-methoxyphenoxy)phenyl]ureido}thiazole-4-carbonyl)amino]acetic acid

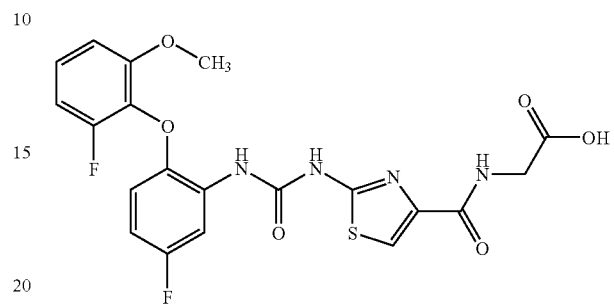

1H NMR (DMSO): δ 12.74 (br, 1H), 11.23 (s, 1H), 9.31 (s 1H), 8.17 (t, 1H), 8.07 (dd, 1H), 7.78 (s, 1H), 7.33 (dd, 1H), 7.11-7.01 (m, 2H), 6.75 (t, 1H), 6.54 (dd, 1H), 3.92 (d, 2H), 3.80 (s, 3H).

Example 134

General Procedure (H1)

(R) 3-[(2-{3-[5-Fluoro-2-(2-fluoro-6-methoxyphenoxy)phenyl]ureido}thiazole-4-carbonyl)amino]-2-hydroxy-propionic acid

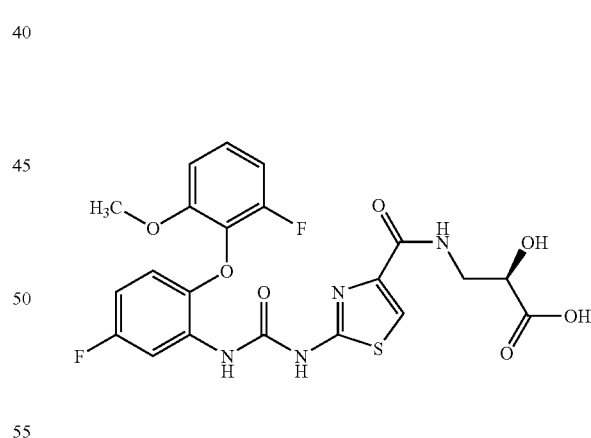

$^1$H NMR (DMSO): δ 12.62 (br, 1H), 11.32 (s, 1H), 9.23 (s 1H), 8.06 (dd, 1H), 7.79-7.76 (m, 2H), 7.33 (dd, 1H), 7.11-7.02 (m, 2H), 7.06 (dd, 1H), 6.75 (t, 1H), 6.54 (dd, 1H), 5.62 (br, 1H), 4.16 (t, 1H), 3.80 (s, 3H), 3.64-3.52 (m, 1H), 3.49-3.40 (m, 1H). HPLC-MS (Method B): m/z=509 (M+1); $R_t$=3.49 min.

Example 135

General Procedure (H1)

2-[(2-{3-[5-Fluoro-2-(2-fluoro-6-methoxyphenoxy)phenyl]ureido}thiazole-4-carbonyl)amino]-3-hydroxy-propionic acid

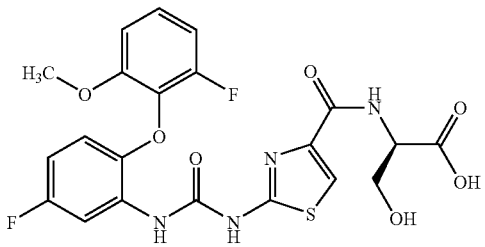

$^1$H NMR (DMSO): δ 12.88 (br, 1H), 11.42 (s, 1H), 9.17 (s 1H), 8.06 (dd, 1H), 7.92 (d, 1H), 7.80 (s, 1H), 7.32 (dd, 1H), 7.11-7.01 (m, 2H), 6.75 (t, 1H), 6.54 (dd, 1H), 5.10 (br, 1H), 4.46-4.43 (m, 1H), 3.89 (m, 4H).

Example 136

1-(2-Cyclopentanecarbonyl-4-methylphenyl)-3-thiazol-2-yl-urea

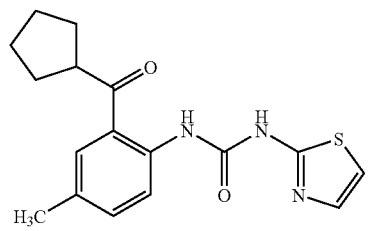

2-Cyclopentanecarbonyl-4-methylaniline (10.2 g) is prepared from p-toluidine (10.7 g, 0.1 mol) and cyclopentanecarbonitrile (9.5 g, 0.1 mol) following the general procedure I. 1-(2-Cyclopentanecarbonyl-4-methyl-phenyl)-3-thiazol-2-yl-urea (132 mg) is prepared from 2-cyclopentanecarbonyl-4-methylaniline (102 mg, 0.5 mmol) and 2-aminothiazole (0.060 g, 0.6 mmol) following the general procedure D.

LC-MS (m/z): 330 (M+1)$^+$ $^1$H NMR (400 MHz, CDCl$_3$): δ 1.69 (m, 2H), 1.91 (m, 2H), 2.37 (s, 3H), 3.76 (m, 1H), 6.89 (d, 1H), 7.35 (d, 1H), 7.71 (s, 2H), 8.42 (d, 1H), 11.57 (br, 1H) ppm.

Example 137

1-(2-Isobutyryl-4-methylphenyl)-3-thiazol-2-yl-urea

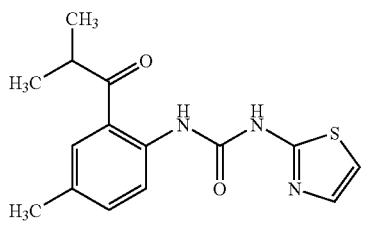

2-Isopropylcarbonyl-4-methylaniline (7.0 g) is prepared from p-toluidine (10.7 g, 0.1 mol) and isobutyronitrile (6.9 g, 0.1 mol) following the general procedure I. 1-(2-Isobutyryl-4-methylphenyl)-3-thiazol-2-yl-urea (113 mg) is prepared from 2-isopropylcarbonyl-4-methylaniline (88 mg, 0.5 mmol) and 2-aminothiazole (0.060 g, 0.6 mmol) following the general procedure D.

LC-MS (m/z): 304 (M+1)$^+$ $^1$H NMR (400 MHz, CDCl$_3$): δ 1.97 (d, 6H), 2.37 (s, 3H), 3.72 (m, 1H), 6.90 (d, 1H), 7.36 (d, 1H), 7.69 (s, 2H), 8.44 (s, 1H), 11.51 (br, 1H), 11.72 (br, 1H) ppm.

Example 138

1-[5-Fluoro-2-(3-methylbutyryl)phenyl]-3-thiazol-2-yl-urea

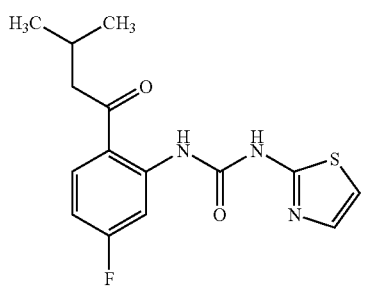

2-[(2-Methyl)-propylcarbonyl]-5-fluoroaniline (6.82 g) is prepared from m-fluoro aniline (11.1 g, 0.1 mol) and 3-methylbutyronitrile (8.3 g, 0.1 mol) following the general procedure I. 1-[5-Fluoro-2-(3-methyl-butyryl)-phenyl]-3-thiazol-2-yl-urea (128 mg) is prepared from 2-[(2-methyl)-propylcarbonyl]-5-fluoroaniline (97 mg, 0.5 mmol) and 2-aminothiazole (0.060 g, 0.6 mmol) following the general procedure D.

LC-MS (m/z): 322 (M+1)$^+$ $^1$H NMR (400 MHz, CDCl$_3$): δ 0.99 (d, 6H), 2.23 (m, 1H), 2.83 (d, 2H), 6.75 (m, 1H), 6.93 (d, 1H), 7.62 (d, 1H), 7.92 (dd, 1H), 8.43 (dd, 1H), 11.60 (br, 1H), 12.04 (br, 1H) ppm.

Example 139

1-[5-Methyl-2-(3-methylbutyryl)phenyl]-3-thiazol-2-yl-urea

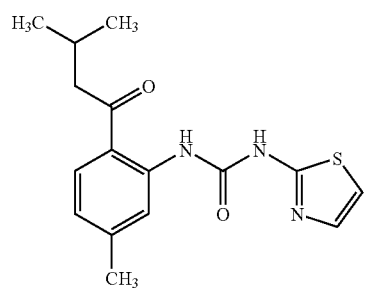

2-[2-Methylpropylcarbonyl]-5-methylaniline (6.8 g) is prepared from m-toluidine (10.2 g, 0.1 mol) and isobutyronitrile (8.3 g, 0.1 mol) following the general procedure I. 1-[5-Methyl-2-(3-methylbutyryl)phenyl]-3-thiazol-2-yl-urea (114 mg) is prepared from 2-[2-methylpropylcarbonyl]-5-methylaniline (95 mg, 0.5 mmol) and 2-aminothiazole (0.060 g, 0.6 mmol) following the general procedure D.

LC-MS (m/z): 318 (M+1)$^+$ $^1$H NMR (400 MHz, CDCl$_3$): δ 0.98 (d, 6H), 2.31 (m, 1H), 2.37 (s, 3H), 2.44 (d, 2H), 6.91 (m, 1H), 7.27 (m, 1H), 7.51 (d, 1H), 7.68 (dd, 1H), 8.45 (d, 1H), 11.58 (br, 1H), 11.60 (br, 1H) ppm.

Example 140

[3-Cyclopentanecarbonyl-4-(3-thiazol-2-yl-ureido)phenyl]acetic acid ethyl ester

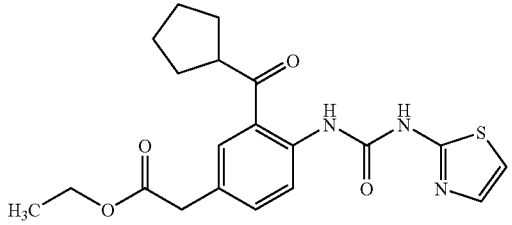

(4-Amino-3-cyclopentanecarbonylphenyl)acetic acid ethyl ester (2.7 g) is prepared from (4-aminophenyl)acetic acid ethyl ester (18.0 g, 0.1 mol) and cyclopentanecarbonitrile (9.5 g, 0.1 mol) following the general procedure I. [3-Cyclopentanecarbonyl-4-(3-thiazol-2-yl-ureido)phenyl]acetic acid ethyl ester (140 mg) is prepared from (4-amino-3-cyclopentanecarbonylphenyl)acetic acid ethyl ester (138 mg, 0.5 mmol) and 2-aminothiazole (0.060 g, 0.6 mmol) following the general procedure D.

LC-MS (m/z): 402 (M+1)$^+$ $^1$H NMR (400 MHz, CDCl$_3$): δ 1.12 (t, 3H), 1.73 (m, 2H), 1.82 (m, 2H), 3.27 (m, 1H), 3.62 (s, 2H), 4.15 (q, 2H), 6.89 (d, 1H), 7.44 (dd, 1H), 7.62 (d, 1H), 7.86 (s, 1H), 8.51 (s, 1H), 11.62 (br, 1H) ppm.

Example 141

[3-Cyclopentanecarbonyl-4-(3-thiazol-2-yl-ureido)phenyl]acetic acid

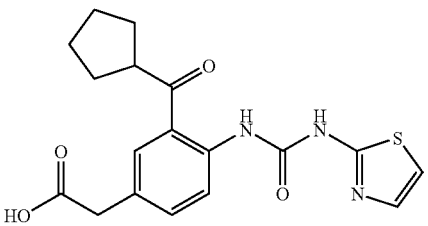

[3-Cyclopentanecarbonyl-4-(3-thiazol-2-yl-ureido)phenyl]acetic acid (168 mg) is prepared from [3-cyclopentanecarbonyl-4-(3-thiazol-2-yl-ureido)phenyl]acetic acid ethyl ester (201 mg, 0.5 mmol) following the general procedure J.

LC-MS (m/z): 374 (M+1)$^+$ $^1$H NMR (400 MHz, DMSO-d$_6$): δ 1.66 (m, 2H), 1.96 (m, 2H), 3.71 (s, 2H), 3.92 (m, 1H), 7.05 (d, 1H), 7.38 (d, 1H), 7.56 (dd, 1H), 8.08 (s, 1H), 8.55 (s, 1H), 11.26 (br, 1H) ppm.

Example 142

2-[3-Cyclopentanecarbonyl-4-(3-thiazol-2-yl-ureido)phenyl]-N-methylacetamide

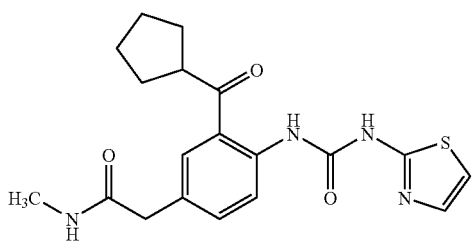

2-[3-Cyclopentanecarbonyl-4-(3-thiazol-2-yl-ureido)-phenyl]-N-methylacetamide (154 mg) is prepared from [3-cyclopentanecarbonyl-4-(3-thiazol-2-yl-ureido)phenyl]acetic acid (186 mg, 0.5 mmol) and 1 M solution of methylamine in THF (0.5 ml, 0.5 mmol) following the general procedure K.

LC-MS (m/z): 387 (M+1)$^+$ $^1$H NMR (400 MHz, CDCl$_3$/DMSO-d$_6$): δ 1.51 (m, 2H), 1.73 (m, 2H), 2.58 (s, 3H), 3.36 (s, 2H), 3.59 (m, 1H), 6.67 (m, 1H), 7.21 (m, 2H), 7.71 (s, 1H), 8.26 (bs, 1H), 10.95 (br, 1H) ppm.

Example 143

{2-[3-(2-Cyclopentanecarbonyl-4-methyl-phenyl)-ureido]-thiazol-4-yl}-acetic acid ethyl ester

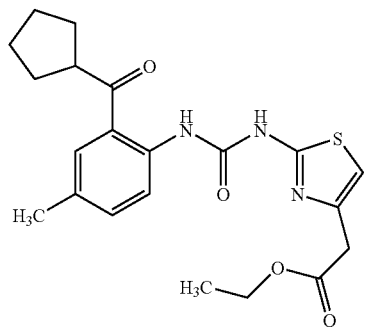

{2-[3-(2-Cyclopentanecarbonyl-4-methyl-phenyl)-ureido]-thiazol-4-yl}-acetic acid ethyl ester (154 mg) is prepared from (2-amino-5-methylphenyl)(cyclopentyl)methanone (102 mg, 0.5 mmol) and ethyl-2-amino-4-thiazolyl acetate (93 mg, 0.5 mmol) following the general procedure D.

LC-MS (m/z): 416 (M+1)$^+$ $^1$H NMR (400 MHz, CDCl$_3$): δ 1.23 (t, 3H), 1.67 (m, 2H), 1.87 (m, 2H), 2.34 (s, 3H), 3.70 (s, 2H), 4.18 (m, 3H), 6.68 (s, 1H), 7.25 (s, 2H), 7.32 (d, 1H), 7.67 (s, 1H), 8.45 (s, 1H), 9.75 (br, 1H), 11.51 (br, 1H) ppm.

Example 144

{2-[3-(2-Cyclopentanecarbonyl-4-methyl-phenyl)-ureido]-thiazol-4-yl}acetic acid

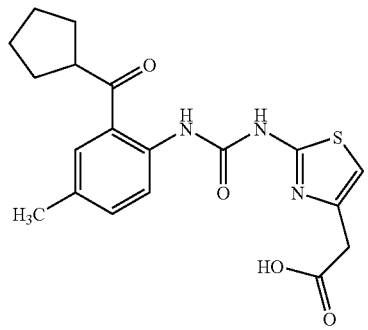

{2-[3-(2-Cyclopentanecarbonyl-4-methylphenyl)-ureido]-thiazol-4-yl}-acetic acid (198 mg) is prepared from {2-[3-(2-cyclopentanecarbonyl-4-methylphenyl)-ureido]-thiazol-4-yl}-acetic acid ethyl ester (208 mg, 0.5 mmol) following the general procedure J.

LC-MS (m/z): 388 (M+1)$^+$ $^1$H NMR (400 MHz, DMSO-d$_6$): δ 1.73 (m, 2H), 1.86 (m, 2H), 2.32 (s, 3H), 3.55 (s, 2H), 3.86 (m 1H), 6.84 (s, 1H), 7.36 (d, 1H), 7.84 (d, 1H), 8.15 (d, 1H), 10.62 (br, 1H), 11.92 (br, 1H), 12.24 (br, 1H) ppm.

Example 145

{3-Cyclopentanecarbonyl-4-{3-(4-ethoxycarbonylmethylthiazol-2-yl)-ureido}phenyl}acetic acid ethyl ester

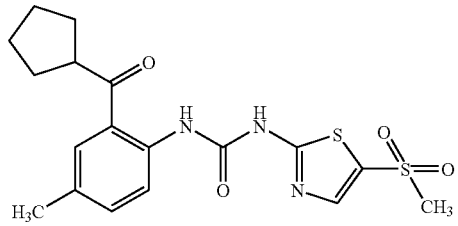

{3-Cyclopentanecarbonyl-4-{3-(4-ethoxycarbonylmethyl-thiazol-2-yl)-ureido}-phenyl}-acetic acid ethyl ester (205 mg) is prepared from (4-amino-3-cyclopentanecarbonylphenyl)acetic acid ethyl ester (138 mg, 0.5 mmol) and ethyl-2-amino-4-thiazolyl acetate (93 mg, 0.5 mmol) following the general procedure D.

LC-MS (m/z): 488 (M+1)$^+$ $^1$H NMR (400 MHz, CDCl$_3$): δ 1.24 (t, 6H), 1.67 (m, 2H), 1.88 (m, 2H), 2.34 (s, 3H), 3.61(s, 2H), 3.71 (s, 2H), 3.73 (m, 1H), 4.17(m, 4H), 4.18 (m, 3H), 6.69 (s, 1H), 7.42 (d, 2H), 7.85 (s, 1H), 8.53 (s, 1 H), 11.64 (br, 1H) ppm.

Example 146

1-(2-Cyclopentanecarbonyl-4-methyl-phenyl)-3-(5-methanesulfonyl-thiazol-2-yl)-urea 1-(2-Cyclopentanecarbonyl-4-methyl-phenyl)-3-(5-methanesulfonyl-thiazol-2-yl)-urea (149 mg) is prepared from 2-cyclopentanecarbonyl-4-methylaniline (102 mg, 0.5 mmol) and 5-methanesulfonyl-thiazol-2-yl-amine (106 mg, 0.6 mmol) following the general procedure D.

LC-MS (m/z): 408 (M+1)$^+$ $^1$H NMR (400 MHz, CDCl$_3$): δ 1.65-1.77 (m, 4H), 1.88-1.97 (m, 4H), 2.40 (s, 3H), 3.21 (s, 3H), 3.81 (p, 1H), 7.41 (dd, 1H), 7.78 (s, 1H), 8.31 (d, 1H), 8.43 (d, 1H), 11.57 (br, 1H), 11.95 (br, 1H) ppm.

Example 147

2-[3-(2-Cyclopentanecarbonyl-4-methylphenyl)-ureido]-thiazole-4-carboxylic acid ethyl ester

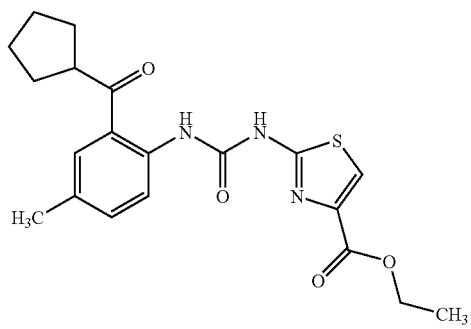

2-[3-(2-Cyclopentanecarbonyl-4-methylphenyl)-ureido]-thiazole-4-carboxylic acid ethyl ester (3.6 g) is prepared from 2-cyclopentanecarbonyl-4-methyl aniline (2.04 g, 10 mmol) and ethyl-2-amino-4-thiazole acetate (1.72 g, 10 mmol) following the general procedure D.

LC-MS (m/z): 402 (M+1)+ $^1$H NMR (400 MHz, CDCl$_3$): δ 1.35 (t, 3H), 1.62-1.78 (m, 4H), 1.83-1.96 (m, 4H), 2.37 (s, 3H), 3.74 (p, 1H), 4.33 (q, 2H), 7.36 (d, 1H), 7.72 (s, 1H), 7.81 (s, 1H), 8.44 (d, 1H), 9.25 (br, 1H), 11.84 (br, 1H) ppm.

Example 148

2-[3-(2-Cyclopentanecarbonyl-4-methylphenyl)-ureido]-thiazole-4-carboxylic acid

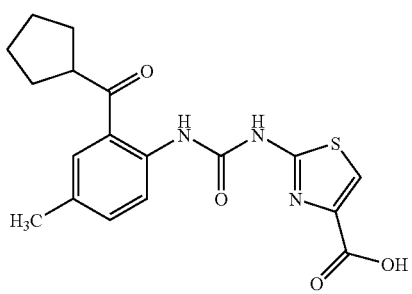

2-[3-(2-Cyclopentanecarbonyl-4-methylphenyl)-ureido]-thiazole-4-carboxylic acid (3.2 g) is prepared from 2-[3-(2-cyclopentanecarbonyl-4-methyl-phenyl)-ureido]-thiazole-4-carboxylic acid ethyl ester (3.6 g, 8.95 mmol) following the general procedure J.

LC-MS (m/z): 374 (M+1)+ $^1$H NMR (400 MHz, DMSO-d$_6$): δ 1.58 (m, 4H), 1.73 (m, 4H), 2.29 (s, 3H), 3.72 (m, 1H), 7.13 (s, 1H), 7.28 (d, 1H), 7.63 (d, 1H), 7.72 (br, 1H), 7.94 (s, 1H), 8.22 (br, 1H), 10.92 (br, 1H) ppm.

Example 149

2-[3-(2-Cyclopentanecarbonyl-4-methylphenyl)-ureido]-thiazole-4-carboxamide

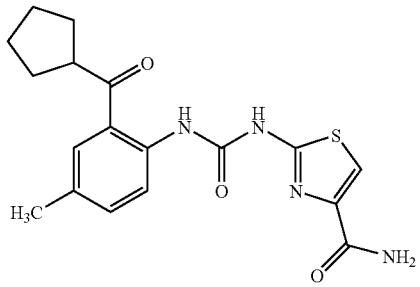

2-[3-(2-Cyclopentanecarbonyl-4-methylphenyl)-ureido]-thiazole-4-carboxamide (145 mg) is prepared from 2-[3-(2-cyclopentanecarbonyl-4-methylphenyl)-ureido]-thiazole-4-carboxylic acid (187 mg, 0.5 mmol) following the general procedure K.

LC-MS (m/z): 373 (M+1)+ $^1$H NMR (400 MHz, DMSO-d$_6$): δ 1.61 (m, 4H), 1.73 (m, 2H), 1.88 (m, 2H), 2.32 (s, 3H), 3.86 (m, 1H), 7.38 (d, 1H), 7.56 (s, 1H), 7.68 (s, 1H), 7.84 (s, 1H), 7.93 (s, 1H), 8.14 (d, 1H), 10.73 (br, 1H), 11.86 (br, 1H) ppm.

Example 150

2-{2-[3-(2-Cyclopentanecarbonyl-4-methylphenyl)-ureido]-thiazole-4-yl}-acetamide

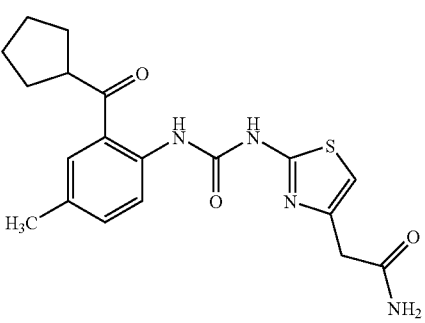

2-{2-[3-(2-Cyclopentanecarbonyl-4-methylphenyl)-ureido]-thiazole-4-yl}-acetamide (325 mg) is prepared from 2-[3-(2-cyclopentanecarbonyl-4-methylphenyl)-ureido]-thiazol-4-yl acetic acid (386 mg, 1.0 mmol) following the general procedure K.

LC-MS (m/z): 387 (M+1)+ $^1$H NMR (400 MHz, DMSO-d$_6$): δ 1.60 (m, 4H), 1.73 (m, 2H), 1.87 (m, 2H), 2.31 (s, 3H), 3.38 (s, 2H), 3.88 (m, 1H), 6.77 (s, 1H), 6.97 (s, 1H), 7.38 (d, 2H), 7.83 (s, 1H), 8.15 (d, 1H), 10.63 (br, 1H), 11.81 (br, 1H) ppm.

Example 151

2-{2-[3-(2-Cyclopentanecarbonyl-4-methylphenyl)-ureido]-thiazol-4-yl}-N-methyl-acetamide

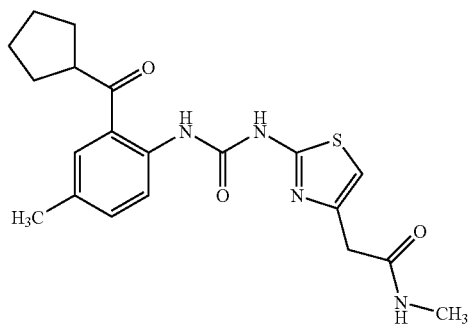

2-{2-[3-(2-Cyclopentanecarbonyl-4-methylphenyl)-ureido]-thiazol-4-yl}-N-methylacetamide (346 mg) is prepared from 2-[3-(2-cyclopentanecarbonyl-4-methyl-phenyl)-ureido]-thiazol-4-yl acetic acid (386 mg, 1.0 mmol) following the general procedure K.

LC-MS (m/z): 401 (M+1)$^+$ $^1$H NMR (400 MHz, DMSO-d$_6$): δ 1.70 (m, 4H), 1.88 (m, 2H), 1.94 (m, 2H), 2.63 (s, 3H), 2.79 (d, 3H), 3.62 (s, 2H), 3.77 (p, 1H), 6.65 (s, 1H), 6.77 (br, 1H), 7.35 (dd, 1H), 7.71 (s, 1H), 8.43 (d, 1H), 9.15 (br, 1H), 11.70 (br, 1H) ppm.

Example 152

4-(2-{2-[3-(2-Cyclopentanecarbonyl-4-methylphenyl)-ureido]-thiazol-4-yl}-acetyl)-1-methyl-piperazinium chloride

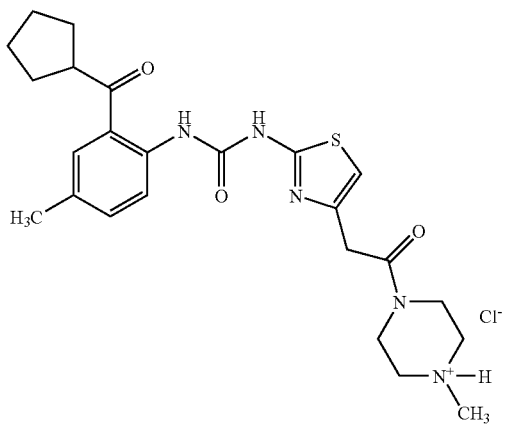

4-(2-{2-[3-(2-Cyclopentanecarbonyl-4-methylphenyl)-ureido]-thiazol-4-yl}-acetyl)-1-methyl-piperazine (337 mg) is prepared from 2-[3-(2-cyclopentanecarbonyl-4-methyl-phenyl)-ureido]-thiazol-4-ylacetic acid (386 mg, 1.0 mmol) and N-methylpiperazine following the general procedure K.

4-(2-{2-[3-(2-Cyclopentanecarbonyl-4-methylphenyl)-ureido]-thiazol-4-yl}-acetyl)-1-methyl-piperazinium chloride (392 mg) is prepared from 4-(2-{2-[3-(2-cyclopentanecarbonyl-4-methylphenyl)-ureido]-thiazol-4-yl}-acetyl)-1-methyl-piperazine (386 mg, 1.0 mmol) by treatment with anhydrous hydrogen chloride (5 ml, 4.0 M solution in dioxane) followed by collection of the solid product.

LC-MS (m/z): 471 (M+1)$^+$ $^1$H NMR (400 MHz, DMSO-d$_6$): δ 1.60 (m, 4H), 1.72 (m, 2H), 1.87 (m, 2H), 2.32 (s, 3H), 2.47 (s, 3H), 2.76 (d, 2H), 2.94 (m, 2H), 3.37 (m, 2H), 3.73 (d, 2H), 3.84 (m, 2H), 4.22 (d, 1H), 4.44 (d, 1H), 6.83 (s, 1H), 7.36 (d, 1H), 7.82 (s, 1H), 8.11 (d, 1H), 10.63 (br, 1H), 10.82 (br, 1H) ppm.

Example 153

1-[4-Methyl-2-(2-methylpropoxy)phenyl]-3-thiazol-2-yl-urea

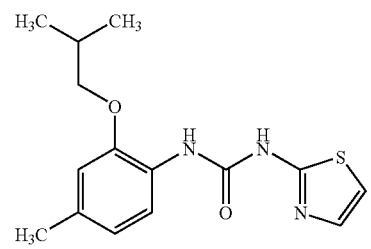

3-(2-Methylpropoxy)-4-nitrotoluene (0.78 g) is prepared from 2-methylpropanol (0.46 ml, 5.0 mmol) and 3-fluoro-4-nitrotoluene (0.77 g, 5.0 mmol) following the general procedure G. This is reduced to afford 4-methyl-2-(2-methylpropoxy)aniline (0.47 g) following general procedure C. N-[4-Methyl-2-(2-methylpropoxy)phenyl]-N'-(thiazol-2-yl)urea (210 mg) is prepared from 4-methyl-2-(2-methylpropoxy)aniline (179 mg, 1.0 mmol) and 2-aminothiazole (100 mg, 1.0 mmol) following the general procedure D.

LC-MS (m/z): 306 (M+1)$^+$ $^1$H NMR (400 MHz, CDCl$_3$): δ 1.01 (d, 6H), 2.16 (m, 1H), 2.32 (s, 3H), 3.78 (d, 2H), 6.70 (s, 1H), 6.75 (d, 1H), 6.86 (d, 1H), 7.40 (d, 1H), 8.07 (d, 1H), 9.30 (br, 1H), 10.72 (br, 1H) ppm.

Example 154

{2-[3-(4-Methyl-2-[2-methylpropoxy]phenyl)-ureido]-thiazol-4-yl}-acetic acid

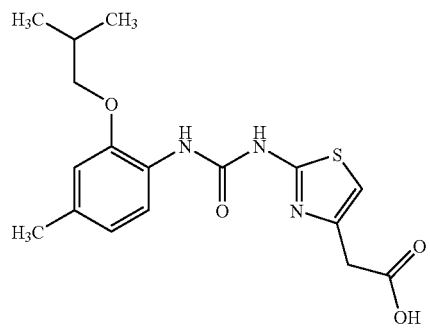

{2-[3-(4-Methyl-2-[2-methypropoxy]phenyl)-ureido]-thiazol-4-yl}-acetic acid ethyl ester (485 mg) is prepared from 4-methyl-2-(2-methylpropoxy)aniline (360 mg, 2.0 mmol) and ethyl 2-amino-4-thiazolylacetate (372 mg, 2.0 mmol) following the general procedure D. Hydrolysis of this ester following general procedure J gave {2-[3-(4-methyl-2-[2-methylpropoxy]phenyl)-ureido]-thiazol-4-yl}-acetic acid (400 mg).

LC-MS (m/z): 464 (M+1)+ 1H NMR (400 MHz, DMSO-d6): δ 1.01 (d, 6H), 2.07 (m, 1H), 2.23 (s, 3H), 3.53 (s, 2H), 3.77 (d, 2H), 6.67 (d, 1H), 6.81 (s, 2H), 7.91 (d, 1H), 8.01 (br, 1H), 11.45 (br, 1H), 12.35 (br, 1H) ppm.

Example 155

{2-[3-(4-Methyl-2-[2-methylpropoxy]phenyl)-ureido]-thiazol-4-yl}-N-methyl-acetamide

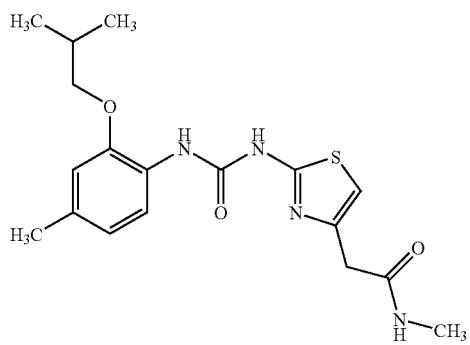

{2-[3-(4-Methyl-2-[2-methylpropoxy]phenyl)-ureido]-thiazol-4-yl}-N-methyl-acetamide (150 mg) is prepared from {2-[3-(4-methyl-2-[2-methylpropoxy]phenyl)-ureido]-thiazol-4-yl}-acetic acid (182 mg, 0.5 mmol) following the general procedure K.

LC-MS (m/z): 477 (M+1)+1H NMR (400 MHz, DMSO-d6): δ 1.00 (d, 6H), 2.06 (m, 1H), 2.19 (s, 3H), 2.48 (s, 3H), 3.40 (s, 2H), 3.68 (d, 2H), 6.54 (s, 1H), 6.59 (d, 2H), 7.40 (br, 1H), 7.91 (d, 1H), 8.08 (br, 1H), 11.27 (br, 1H) ppm.

Example 157

1-(2-Cyclopentanecarbonyl-4-methyl-phenyl)-3-(4-methyl-thiazol-2-yl)-urea

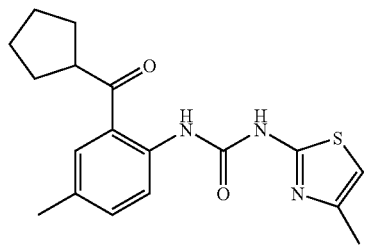

1-(2-Cyclopentanecarbonyl-4-methyl-phenyl)-3-(4-methyl-thiazol-2-yl)-urea (66 mg, 77%) was prepared from (2-amino-5-methyl-phenyl)-cyclopentyl-methanone (51 mg, 0.25 mmol) following the general procedure D.

LC-MS (m/z): 344 (M+1)+; 1H NMR (400 MHz, CDCl3): δ 1.60-175 (m, 4H), 1.80-194 (m, 4H), 2.32 (s, 3H), 2.36 (s, 3H), 3.73 (p, 1H), 6.44 (s, 1H), 7.28 (d, 1H), 7.35 (d, 1H), 7.67 (s, 1H), 8.44 (br, 1H), and 11.66 (br, 1H).

Example 158

1-(2-Cyclopentanecarbonyl-4-methyl-phenyl)-3-(4-methoxymethyl-thiazol-2-yl)-urea

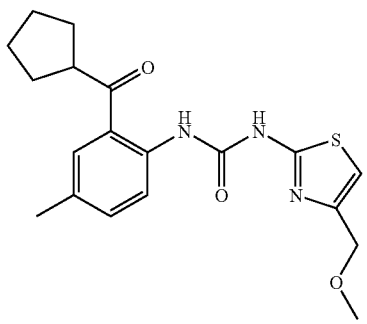

1-(2-Cyclopentanecarbonyl-4-methyl-phenyl)-3-(4-methoxymethyl-thiazol-2-yl)-urea (64 mg, 69%) was prepared from (2-amino-5-methyl-phenyl)-cyclopentyl-methanone (50 mg, 0.25 mmol) and 4-methoxymethyl-thiazol-2-ylamine (54 mg, 0.375 mmol) following the general procedure D to give title compound.

LC-MS (m/z): 373 (M+1)+; 1H NMR (400 MHz, CDCl3): δ 1.70 (m, 4H), 1.88 (m, 4H), 2.36 (s, 3H), 3.41 (s, 2H), 3.72 (m, 1H), 4.44 (s, 3H), 6.78 (dd, 1H), 7.32 (d, 1H), 7.70 (s, 1H), 8.42 (d, 1H), 10.52 (br, 1H), and 11.64 (br, 1H).

Example 159

1-(2-Cyclopentanecarbonyl-4-methyl-phenyl)-3-(4-formyl-thiazol-2-yl)-urea

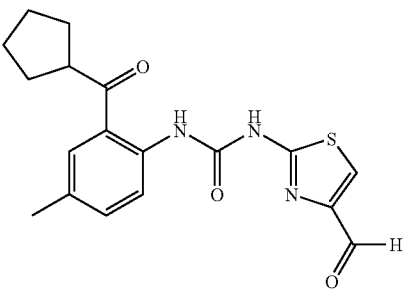

To 1-(2-cyclopentanecarbonyl-4-methyl-phenyl)-3-[4-hydroxymethyl-thiazol-2-yl]-urea (1.8 g, 5 mmol) in CH2Cl2 (40 mL) at 0° C. was added Et3N (2.88 mL, 20 mmol), dimethyl sulfoxide (10 mL) followed by sulfur trioxide-pyridine (2.38 g, 15.0 mmol). The reaction mixture was stirred for 1 h and then poured into water (30 mL). The mixture was extracted with CH2Cl2 and the organic layers was washed with 1.0 N ammonium chloride (2×20 mL), water (2×20 mL), brine (1×20 mL), dried (Na2SO4) and concentrated to give a solid. The solid was purified by column chromatography (silica, Hexanes/EtOAc, 20-50%) to obtain 1-(2-cyclopentanecarbonyl-4-methyl-phenyl)-3-(4-formyl-thiazol-2-yl)-urea (1.59 g, 86%) as a white solid.

LC-MS (m/z): 358 (M+1)+; $^1$H NMR (400 MHz, DMSO-$d_6$): δ 1.64 (m, 4H), 1.74 (m, 2H), 1.90 (m, 2H), 2.35 (s, 3H), 3.89 (p, 1H), 7.41 (d, 1H), 7.88 (s, 1H), 8.17 (d, 1H), 8.24 (s, 1H), 9.76 (s, 1H), 10.75 (s, 1H), and 12.20 (br, 1H).

Example 160

1-(2-Cyclopentanecarbonyl-4-methyl-phenyl)-3-(4-hydroxymethyl-thiazol-2-yl)-urea

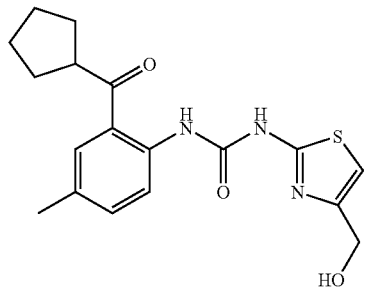

1-(2-Cyclopentanecarbonyl-4-methyl-phenyl)-3-(4-hydroxymethyl-thiazol-2-yl)-urea (2.66 g, 92%) was prepared from acetic acid 2-[3-(2-cyclopentanecarbonyl-4-methyl-phenyl)-ureido]-thiazol-4-ylmethyl ester (3.2 g, 8.0 mmol) following the general procedure J to give title compound.

LC-MS (m/z): 360 (M+1)+; $^1$H NMR (400 MHz, DMSO-$d_6$): δ 1.75 (m, 4H), 1.89 (m, 4H), 2.34 (s, 3H), 3.88 (m, 1H), 4.43 (d, 2H), 5.20 (t, 1H), 6.82 (s, 1H), 7.39 (d, 1H), 7.85 (s, 1H), 8.18 (d, 1H), 10.66 (br, 1H), and 11.72 (br, 1H).

Example 161

1-(4-Chloromethyl-thiazol-2-yl)-3-(2-cyclopentanecarbonyl-4-methyl-phenyl)-urea

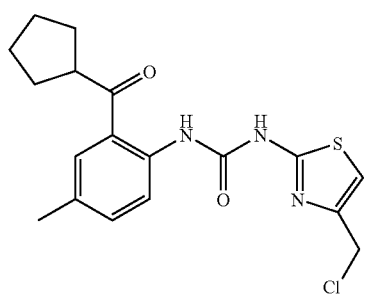

1-(4-Chloromethyl-thiazol-2-yl)-3-(2-cyclopentanecarbonyl-4-methyl-phenyl)-urea (2.16 g, 57.1%) was prepared from (2-amino-5-methyl-phenyl)-cyclopentyl-methanone (2.03 g, 10.0 mmol) and 4-chloromethyl-thiazol-2-ylamine (1.72 g, 10.0 mmol) following the general procedure D.

LC-MS (m/z): 378 (M+1)+, $^1$H NMR (400 MHz, CDCl$_3$): δ 1.68 (m, 4H), 1.88 (m, 4H), 2.36 (s, 3H), 3.76 (m, 1H), 4.52 (s, 2H), 6.88 (s, 1H), 7.34 (d, 1H), 7.73 (s, 1H), 8.42 (d, 1H), 11.36 (br, 1H), and 11.75 (br, 1H).

Example 162

1-(4-Aminomethyl-thiazol-2-yl)-3-(2-cyclopentanecarbonyl-4-methyl-phenyl)-urea

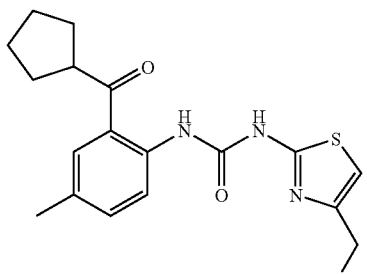

To a solution of thiourea (7.6 g, 100 mmol) in methanol (150 mL) was added 1,3-dicholoroacetone (12.7 g, 100 mmol) and the reaction mixture stirred at rt. for 3-4 hours. The mixture was concentrated in vacuo to give the crude product as hydrochloride salt. This salt was then washed with Et$_2$O (3×200 mL) and concentrated in vacuo to afford 4-chloromethyl-thiazol-2-ylamine in 95-100% yield.

To a solution of 4-chloromethyl-thiazol-2-ylamine (7.45 g, 50.0 mmol) in dioxane:water mixture (8:2) was added sodium azide (4.87 g, 75.0 mmol) and the reaction mixture was refluxed for 2-3 h. The mixture was concentrated in vacuo to remove all dioxane and the residue was dissolved in EtOAc (200 mL). The organic layer was washed with water (2×200 mL), brine (2×200 mL), dried over (Na$_2$SO$_4$) and concentrated in vacuo to give 4-azidomethyl-thiazol-2-ylamine in 70-90% yield.

(4-Azidomethyl-thiazol-2-ylamine) was subjected to urea formation by following general procedure D to give the desired urea (1-(4-azidomethyl-thiazol-2-yl)-3-(2-cyclopentanecarbonyl-4-methyl-phenyl)-urea) in 65-85% yield.

To a solution of (1-(4-azidomethyl-thiazol-2-yl)-3-(2-cyclopentanecarbonyl-4-methylphenyl)-urea) (7.7 g, 20 mmol) in EtOH (100 mL) was added catalytic amount of palladium on charcoal (200 mg) and the reaction mixture was hydrogenated (1 atmos) for 3-4 hours to give 1-(4-aminomethyl-thiazol-2-yl)-3-(2-cyclopentanecarbonyl-4-methyl-phenyl)-urea. This crude product was then purified by flash column chromatography with DCM:EtOAc (80:20 to 50:50) as eluent to give the desired amine (5.7 g, 80%).

LC-MS (m/z): 359 (M+1)+; $^1$H NMR (400 MHz, CDCl$_3$): δ 1.48 (m, 2H), 1.64 (m, 4H), 1.82 (m, 2H), 2.30 (s, 3H), 3.46 (d, 2H), 3.54 (p, 1H), 3.76 (t, 2H), 6.84 (s, 1H), 7.07 (s, 1H), 7.76 (d, 1H), 8.32 (d, 1H), 9.64 (br, 1H), and 11.18 (br, 1H).

Example 163

1-(2-Cyclopentanecarbonyl-4-methyl-phenyl)-3-(4-dimethylaminomethyl-thiazol-2-yl)-urea

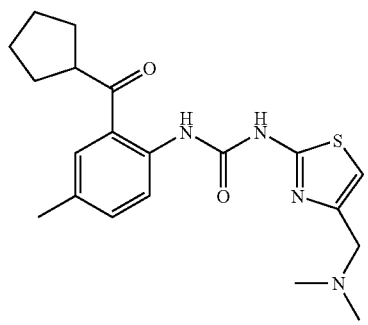

1-(2-Cyclopentanecarbonyl-4-methyl-phenyl)-3-(4-dimethylaminomethyl-thiazol-2-yl)-urea (79 mg, 82%) was prepared from 2-[3-(2-1-(2-cyclopentanecarbonyl-4-methyl-phenyl)-3-(4-formyl-thiazol-2-yl)-urea (89 mg, 0.25 mmol) and (30 mg, 0.3 mmol) and dimethylamine (0.1 mL, 2.0 M. solution in THF) following the general procedure O to give title compound.

LC-MS (m/z): 387 (M+1)$^+$; $^1$H NMR (400 MHz, CDCl$_3$): δ 1.62-1.72 (m, 4H), 1.78-1.88 (m, 4H), 2.23 (s, 6H), 2.34 (s, 3H), 3.53 (s, 2H), 3.70 (p, 1H), 6.64 (s, 1H), 7.30 (d, 1H), 7.64 (s, 1H), 8.32 (d, 1H), 10.25 (br, 1H), and 11.35 (br, 1H).

Example 164

N-{2-[3-(2-Cyclopentanecarbonyl-4-methyl-phenyl)-ureido]-thiazol-4-ylmethyl}-acetamide

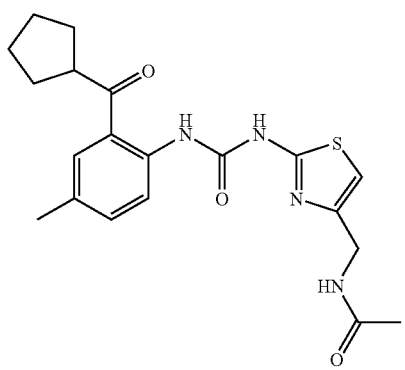

N-{2-[3-(2-Cyclopentanecarbonyl-4-methyl-phenyl)-ureido]-thiazol-4-ylmethyl}-acetamide (88 mg, 88%) was prepared from 1-(4-aminomethyl-thiazol-2-yl)-3-(2-cyclopentanecarbonyl-4-methyl-phenyl)-urea (90 mg, 0.25 mmol) and acetyl chloride (0.02 mL, 0.25 mmol) following the general procedure T.

LC-MS (m/z): 401 (M+1)$^+$; $^1$H NMR (400 MHz, CDCl$_3$): δ 1.56 (m, 4H), 1.72 (m, 2H), 1.78 (m, 2H), 2.22 (s, 3H), 2.82 (s, 3H), 3.18 (t, 1H), 3.64 (m, 1H), 4.07 (s, 2H), 6.55 (s, 1H), 7.22 (d, 1H), 7.53 (s, 1H), 8.18 (d, 1H), 10.18 (br, 1H), and 11.58 (br, 1H).

Example 165

1-{4-[2-(tert-Butyl-dimethyl-silanyloxy)-ethyl]-thiazol-2-yl}-3-(2-cyclopentanecarbonyl-4-methyl-phenyl)-urea

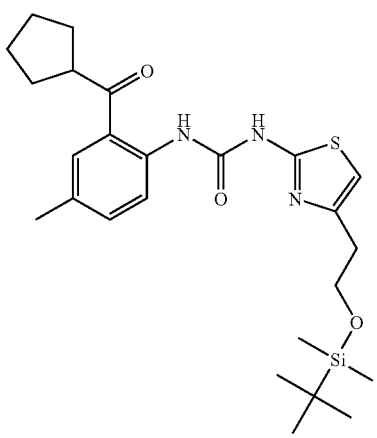

1-{4-[2-(tert-Butyl-dimethyl-silanyloxy)-ethyl]-thiazol-2-yl}-3-(2-cyclopentanecarbonyl-4-methyl-phenyl)-urea (425 mg, 87%) was prepared from (2-amino-5-methyl-phenyl)-cyclopentyl-methanone (203 mg, 1.00 mmol) and 4-[2-(tert-butyl-dimethyl-silanyloxy)-ethyl]-thiazol-2-ylamine (310 mg, 1.20 mmol) following the general procedure D.

LC-MS (m/z): 488 (M+1)$^+$; $^1$H NMR (400 MHz, CDCl$_3$): δ 0.10 (s, 9H), 0.85 (s, 6H), 1.70-1.78 (m, 4H), 1.82-194 (m, 4H), 2.35 (s, 3H), 2.84 (t, 2H), 3.73 (p, 1H), 3.87 (t, 2H), 6.52 (s, 1H), 6.60 (d, 1H), 7.32 (d, 1H), 7.72 (s, 1H), 8.48 (br, 1H), 11.68 (br, 1H).

Example 166

Acetic acid 2-[3-(2-cyclopentanecarbonyl-4-methyl-phenyl)-ureido]-thiazol-4-ylmethyl ester

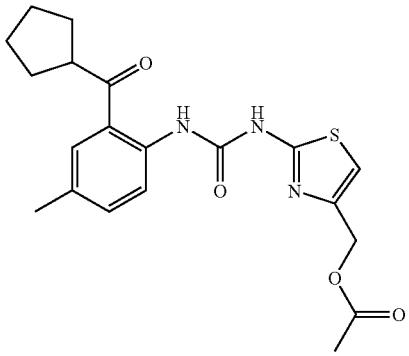

Acetic acid 2-[3-(2-cyclopentanecarbonyl-4-methyl-phenyl)-ureido]-thiazol-4-ylmethyl ester (3.66 g, 91%) was prepared from (2-amino-5-methyl-phenyl)-cyclopentyl-methanone (2.03 g, 10.0 mmol) and acetic acid 2-amino-thiazol-4-ylmethyl ester (2.05 g, 12.0 mmol) following the general procedure D.

LC-MS (m/z): 402 (M+1)+; 1H NMR (400 MHz, CDCl3): δ 1.70 (m, 4H), 1.86 (m, 4H), 2.10 (s, 3H), 2.37 (s, 3H), 3.75 (m, 1H), 5.09 (s, 2H), 6.87 (s, 1H), 7.35 (d, 1H), 7.71 (s, 1H), 8.45 (d, 1H), 9.20 (br, 1H), and 11.75 (br, 1H).

Example 167

1-(2-Cyclopentanecarbonyl-4-methyl-phenyl)-1-methyl-3-thiazol-2-yl-urea

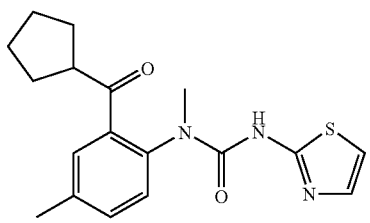

1-(2-Cyclopentanecarbonyl-4-methyl-phenyl)-1-methyl-3-thiazol-2-yl-urea (287 mg, 83%) was prepared from cyclopentyl-(5-methyl-2-methylamino-phenyl)-methanone (217 mg, 1.00 mmol) following the general procedure D.

LC-MS (m/z): 344 (M+1)+; 1H NMR (400 MHz, CDCl3): δ 1.72 (m, 4H), 1.88 (m, 4H), 2.37 (s, 3H), 3.42 (s, 3H), 3.84 (p, 1H), 6.85 (d, 1H), 6.94 (d, 1H), 7.17 (d, 1H), 7.43 (d, 1H), 7.46 (s, 1H), and 9.62 (br, 1H).

Example 168

1-(5-Chloro-thiazol-2-yl)-3-(2-cyclopentanecarbonyl-4-methyl-phenyl)-urea

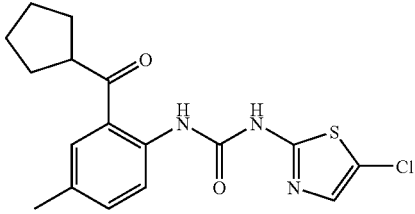

1-(5-Chloro-thiazol-2-yl)-3-(2-cyclopentanecarbonyl-4-methyl-phenyl)-urea (109 mg, 60%) was prepared from (2-amino-5-methyl-phenyl)-cyclopentyl-methanone (102 mg, 0.5 mmol) and 5-chloro-thiazol-2-ylamine (0.06 mg, 0.6 mmol) following the general procedure D.

LC-MS (m/z): 364 (M+1)+; 1H NMR (400 MHz, CDCl3): δ 1.72 (m, 4H), 1.93 (m, 4H), 2.38 (s, 3H), 3.80 (m, 1H), 7.37 (d, 1H), 7.64 (s, 1H), 7.74 (s, 1H), 8.44 (d, 1H), 11.69 (br, 1H).

Example 169

1-(5-Bromo-thiazol-2-yl)-3-(2-cyclopentanecarbonyl-4-methyl-phenyl)-urea

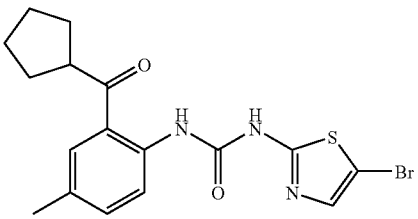

1-(5-Bromo-thiazol-2-yl)-3-(2-cyclopentanecarbonyl-4-methyl-phenyl)-urea (127 mg, 62%) was prepared from (2-amino-5-methyl-phenyl)-cyclopentyl-methanone (102 mg, 0.5 mmol) and 5-bromo-thiazol-2-ylamine (108 mg, 0.6 mmol) following the general procedure D.

LC-MS (m/z): 409 (M+1)+; 1H NMR (400 MHz, CDCl3): δ 1.72 (m, 4H), 1.93 (m, 4H), 2.38 (s, 3H), 3.78 (m, 1H), 7.38 (d, 1H), 7.66 (s, 1H), 7.74 (s, 1H), 8.44 (d, 1H), 11.67 (br, 1H).

Example 170

1-(5-Bromo-thiazol-2-yl)-3-(2-cyclopentanecarbonyl-5-fluoro-phenyl)-urea

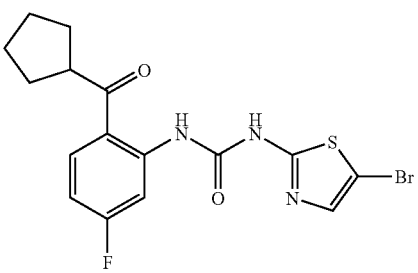

1-(5-Bromo-thiazol-2-yl)-3-(2-cyclopentanecarbonyl-5-fluoro-phenyl)-urea (132 mg, 64%) was prepared from (2-amino-4-fluoro-phenyl)-cyclopentyl-methanone (104 mg, 0.5 mmol) and 5-bromo-thiazol-2-ylamine (108 mg, 0.6 mmol) following the general procedure D.

LC-MS (m/z): 413 (M+1)+; 1H NMR (400 MHz, CDCl3): δ 1.72 (m, 4H), 1.93 (m, 4H), 2.38 (s, 3H), 3.74 (m, 1H), 6.81 (m, 1H), 7.61 (s, 1H), 8.01 (dd, 1H), 8.42 (dd, 1H), 11.02 (br, 1H), 12.16 (br, 1H).

Example 171

2-[3-(2-Cyclopentanecarbonyl-4-methyl-phenyl)-ureido]-4-methyl-thiazole-5-carboxylic acid ethyl ester

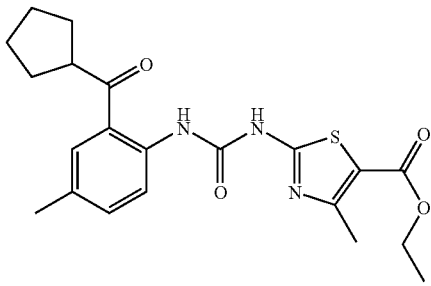

2-[3-(2-Cyclopentanecarbonyl-4-methyl-phenyl)-ureido]-4-methyl-thiazole-5-carboxylic acid ethyl ester (154 mg, 80%) was prepared from (2-amino-5-methyl-phenyl)-cyclopentyl-methanone (102 mg, 0.5 mmol) and 2-amino-4-methyl-thiazole-5-carboxylic acid ethyl ester (112 mg, 0.6 mmol) following the general procedure D.

LC-MS (m/z): 416 (M+1)$^+$; $^1$H NMR (400 MHz, CDCl$_3$): δ 1.33 (t, 3H), 1.66 (m, 4H), 1.87 (m, 4H), 2.37 (s, 3H), 2.59 (s, 3H), 3.72 (m, 1H), 4.28 (q, 2H), 7.37 (s, 1H), 7.70 (s, 1H), 8.48 (s, 1H), 10.35 (br, 1H), 11.81 (br, 1H).

Example 172

2-[3-(2-Cyclopentanecarbonyl-4-methyl-phenyl)-ureido]-4-methyl-thiazole-5-carboxylic acid

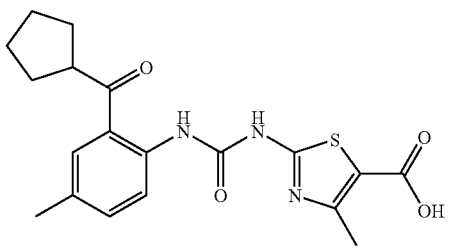

2-[3-(2-Cyclopentanecarbonyl-4-methyl-phenyl)-ureido]-4-methyl-thiazole-5-carboxylic acid (198 mg, 95%) was prepared from 2-[3-(2-cyclopentanecarbonyl-4-methylphenyl)-ureido]-4-methyl-thiazole-5-carboxylic acid ethyl ester (208 mg, 0.5 mmol) following the general procedure J.

LC-MS (m/z): 388 (M+1)$^+$; $^1$H NMR (400 MHz, CDCl$_3$): δ 1.66 (m, 4H), 1.74 (m, 2H), 1.94 (m, 2H), 2.61 (s, 3H), 2.65 (s, 3H), 3.88 (m, 1H), 7.42 (d, 1H), 7.88 (s, 1H), 8.20 (d, 1H), 10.25 (br, 1H), 12.22 (br, 2H).

Example 173

1-(2'-Amino-[4,4']bithiazolyl-2-yl)-3-(2-cyclopentanecarbonyl-4-methylphenyl)-urea

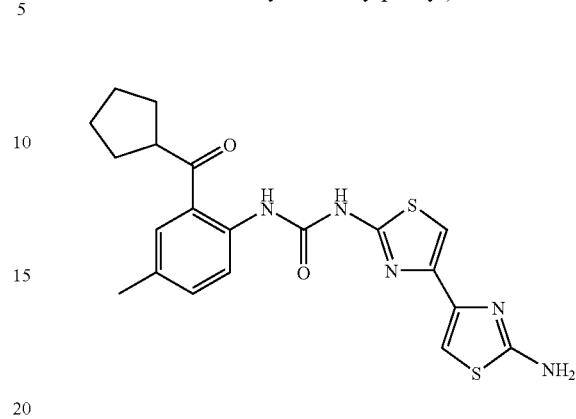

1-(2'-Amino-[4,4']bithiazolyl-2-yl)-3-(2-cyclopentanecarbonyl-4-methylphenyl)-urea (85 mg, 79%) was prepared from (2-Amino-5-methyl-phenyl)-cyclopentyl-methanone (51 mg, 0.25 mmol) following the general procedure D.

LC-MS (m/z): 428 (M+1)$^+$; $^1$H NMR (400 MHz, CDCl$_3$): δ 1.25 (m, 4H), 1.73 (m, 4H), 2.37 (s, 3H), 3.77 (p, 1H), 5.24 (br, 2H), 6.99 (s, 1H), 7.02 (s, 1H), 7.53 (dd, 1H), 7.58 (s, 1H), 7.72 (s, 1H), 8.42 (br, 1H), and 11.78 (br, 1H).

Example 174

2-{2-[3-(2-Cyclopentanecarbonyl-4-methyl-phenyl)-ureido]-thiazol-4-yl}-N-methoxy-N-methyl-acetamide

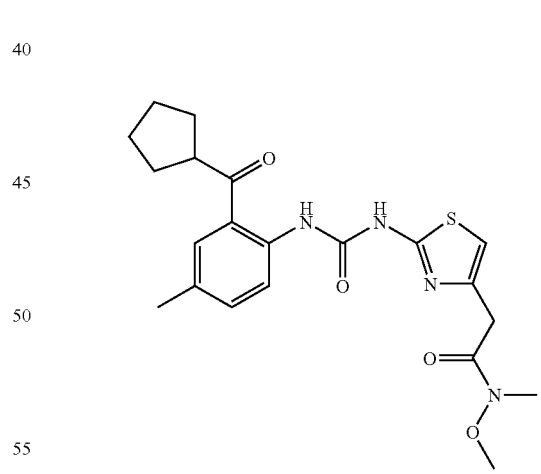

2-{2-[3-(2-Cyclopentanecarbonyl-4-methyl-phenyl)-ureido]-thiazol-4-yl}-N-methoxy-N-methyl-acetamide (88 mg, 82. %) was prepared from 2-[3-(2-cyclopentanecarbonyl-4-methyl-phenyl)-ureido]-thizol-4-yl acetic acid (97 mg, 0.25 mmol) following the general procedure K.

LC-MS (m/z): 431 (M+1)$^+$; $^1$H NMR (400 MHz, CDCl$_3$): δ 1.72 (m, 4H), 1.93 (m, 4H), 2.35 (s, 3H), 2.80 (s, 2H), 3.70 (s, 3H), 3.85 (s, 3H), 4.21 (p, 1H), 6.67 (s, 1H), 6.91 (d, 1H), 7.54 (dd, 1H), 7.70 (d, 1H), 8.40 (br, 1H), and 11.52 (br, 1H).

Example 175

1-(2-Cyclopentanecarbonyl-4-methyl-phenyl)-3-[4-(2-morpholin-4-yl-2-oxo-ethyl)-thiazol-2-yl]-urea

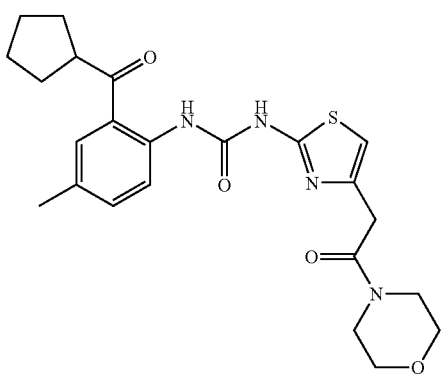

1-(2-Cyclopentanecarbonyl-4-methyl-phenyl)-3-[4-(2-morpholin-4-yl-2-oxo-ethyl)-thiazol-2-yl]-urea (92 mg, 80%) was prepared from 2-[3-(2-cyclopentanecarbonyl-4-methylphenyl)-ureido]-thizol-4-yl acetic acid (97 mg, 0.25 mmol) following the general procedure K.

LC-MS (m/z): 457 (M+1)$^+$; $^1$H NMR (400 MHz, CDCl$_3$): δ 1.64 (m, 4H), 1.82 (m, 2H), 1.88 (m, 2H), 2.34 (s, 3H), 2.96-3.14 (dd, 2H), 3.49 (t 2H), 3.60 (m, 4H), 3.72 (p, 1H), 3.76 (s, 2H), 6.60 (s, 1H), 7.33 (d, 1H), 7.67 (s, 1H), 8.42 (d, 1H), 8.70 (br, 1H), and 11.28 (br, 1H).

Example 176

2-{2-[3-(2-Cyclopentanecarbonyl-4-methyl-phenyl)-ureido]-thiazol-4-yl}-N-(4-methylpiperazin-1-yl)-acetamide

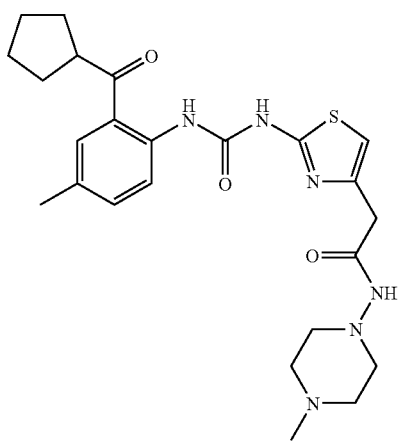

2-{2-[3-(2-Cyclopentanecarbonyl-4-methyl-phenyl)-ureido]-thiazol-4-yl}-N-(4-methylpiperazin-1-yl)-acetamide (105 mg, 87%) was prepared from 2-[3-(2-cyclopentanecarbonyl-4-methyl-phenyl)-ureido]-thizol-4-yl acetic acid (97 mg, 0.25 mmol) following the general procedure K.

LC-MS (m/z): 485 (M+1)$^+$; $^1$H NMR (400 MHz, CDCl$_3$): δ 1.66 (m, 4H), 1.82 (m, 2H), 1.94 (m, 2H), 2.35 (s, 3H), 3.02 (m, 2H), 3.46 (s, 3H), 3.53 (t (2H), 3.64 (m, 4H), 3.76 (p, 1H), 3.80 (s, 2H), 5.36 (br, 1H), 6.56 (s, 1H), 7.34 (d, 1H), 7.69 (s, 1H), 8.46 (d, 1H), 8.82 (br, 1H), and 11.46 (br, 1H).

Example 177

2-{2-[3-(2-Cyclopentanecarbonyl-4-methyl-phenyl)-ureido]-thiazol-4-yl}-N-(2-morpholin-4-yl-ethyl)-acetamide

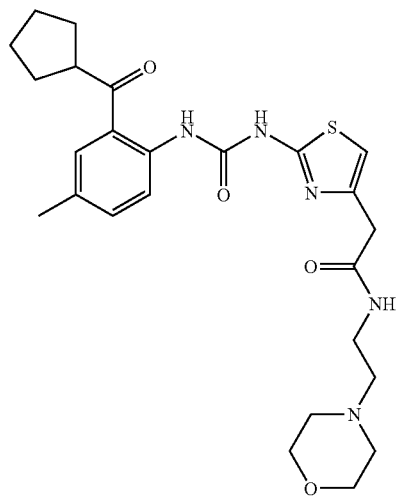

2-{2-[3-(2-Cyclopentanecarbonyl-4-methyl-phenyl)-ureido]-thiazol-4-yl}-N-(2-morpholin-4-yl-ethyl)-acetamide (108 mg, 86%) was prepared from 2-[3-(2-cyclopentanecarbonyl-4-methyl-phenyl)-ureido]-thizol-4-yl acetic acid (97 mg, 0.25 mmol) following the general procedure K.

LC-MS (m/z): 500 (M+1)$^+$; $^1$H NMR (400 MHz, CDCl$_3$): δ 1.22 (t, 2H), 1.35 (t, 4H), 1.70 (m, 2H), 1.86 (m, 2H), 1.94 (m, 2H), 2.32 (s, 3H), 2.88 (s, 2H), 2.96 (m, 4H), 3.22 (t, 4H), 3.77 (p, 1H), 5.30 (br, 1H), 6.58 (s, 1H), 7.34 (d, 1H), 7.90 (s, 1H), 8.38 (d, 1H), 9.14 (br, 1H), and 11.32 (br, 1H).

Example 178

2-[3-(2-Cyclopentanecarbonyl-4-methyl-phenyl)-ureido]-thiazole-4-carboxylic acid methylamide

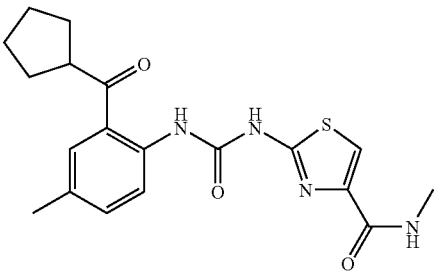

2-[3-(2-Cyclopentanecarbonyl-4-methyl-phenyl)-ureido]-thiazole-4-carboxylic acid methylamide (77 mg, 80%) was prepared from 2-[3-(2-cyclopentanecarbonyl-4-methylphenyl)-ureido]-thizol-4-yl acetic acid (97 mg, 0.25 mmol) following the general procedure K.

LC-MS (m/z): 387 (M+1)$^+$; $^1$H NMR (400 MHz, CDCl$_3$): δ 1.74 (m, 4H), 1.82 (m, 2H), 1.94 (m, 2H), 2.38 (s, 3H), 3.00

(d, 3H), 3.13 (m, 1H), 3.78 (p, 1H), 6.94 (s, 1H), 7.34 (d, 1H), 7.51 (br, 1H), 7.72 (d, 1H), 8.40 (d, 1H), and 11.88 (br, 1H).

Example 179

1-(2-Cyclopentanecarbonyl-4-methyl-phenyl)-3-[4-(morpholine-4-carbonyl)-thiazol-2-yl]-urea

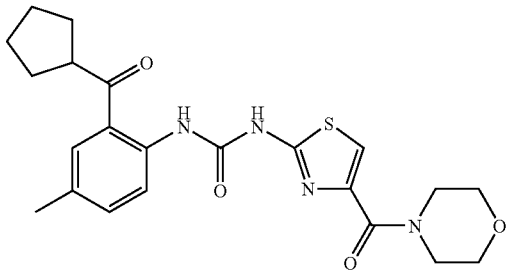

1-(2-Cyclopentanecarbonyl-4-methyl-phenyl)-3-[4-(morpholine-4-carbonyl)-thiazol-2-yl]-urea (92 mg, 80%) was prepared from 2-[3-(2-cyclopentanecarbonyl-4-methyl-phenyl)-ureido]-thizol-4-yl acetic acid (97 mg, 0.25 mmol) following the general procedure K.

LC-MS (m/z): 443 (M+1)$^+$; $^1$H NMR (400 MHz, CDCl$_3$): δ 1.70 (m, 4H), 1.90 (m, 4H), 2.36 (s, 3H), 3.12 (m, 2H), 3.76 (m, 4H), 3.82 (m, 1H), 6.69 (s, 1H), 7.34 (d, 1H), 7.69 (s, 1H), 8.38 (d, 1H), 9.83 (br, 1H), and 11.86 (br, 1H).

Example 180

N-(2-{2-[3-(2-Cyclopentanecarbonyl-4-methyl-phenyl)-ureido]-thiazol-4-yl}-acetyl)-methanesulfonamide

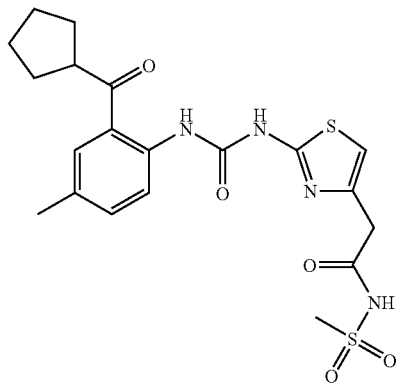

N-(2-{2-[3-(2-Cyclopentanecarbonyl-4-methyl-phenyl)-ureido]-thiazol-4-yl}-acetyl)-methanesulfonamide (88 mg, 76%) was prepared from 2-[3-(2-cyclopentanecarbonyl-4-methyl-phenyl)-ureido]-thizol-4-yl acetic acid (97 mg, 0.25 mmol) following the general procedure K.

LC-MS (m/z): 465 (M+1)$^+$; $^1$H NMR (400 MHz, CDCl$_3$): δ 1.72 (m, 4H), 1.92 (m, 4H), 2.37 (s, 3H), 3.13 (s, 3H), 3.30 (s, 2H), 3.81 (p, 1H), 4.88 (br, 1H), 6.66 (s, 1H), 7.36 (d, 1H), 7.72 (d, 1H), 8.46 (d, 1H), 10.70 (br, 1H), and 11.72 (br, 1H).

Example 181

N-{2-[3-(2-Cyclopentanecarbonyl-4-methyl-phenyl)-ureido]-thiazole-4-carbonyl}-methanesulfonamide

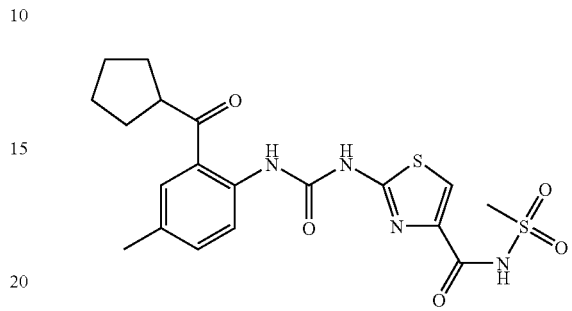

N-{2-[3-(2-Cyclopentanecarbonyl-4-methyl-phenyl)-ureido]-thiazole-4-carbonyl}-methanesulfonamide (103 mg, 91%) was prepared from 2-[3-(2-cyclopentanecarbonyl-4-methyl-phenyl)-ureido]-thizol-4-yl acetic acid (97 mg, 0.25 mmol) following the general procedure K.

LC-MS (m/z): 451 (M+1)$^+$; $^1$H NMR (400 MHz, CDCl$_3$): δ 1.74 (m, 4H), 1.94 (m, 4H), 2.32 (s, 3H), 3.11 (s, 3H), 3.32 (p, 1H), 4.66 (br, 1H), 6.62 (s, 1H), 7.32 (d, 1H), 7.62 (d, 1H), 8.22 (br, 1H), 8.40 (d, 1H), and 11.68 (br, 1H).

Example 182

1-(2-Cyclopentanecarbonyl-4-methyl-phenyl)-3-{4-[3-(2-dimethylamino-ethyl)-ureidomethyl]-thiazol-2-yl}-urea

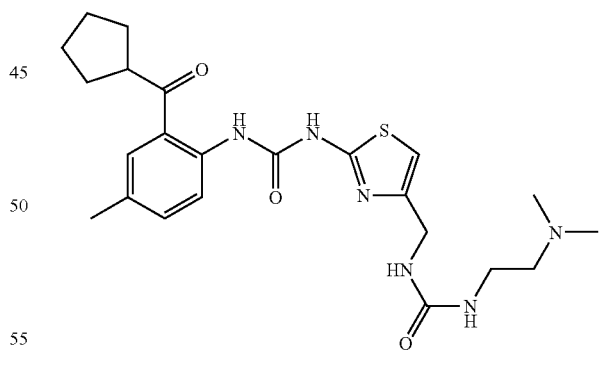

1-(2-Cyclopentanecarbonyl-4-methyl-phenyl)-3-{4-[3-(2-dimethylamino-ethyl)-ureidomethyl]-thiazol-2-yl}-urea (86 mg, 73%) was prepared from 2-[3-(2-cyclopentanecarbonyl-4-methyl-phenyl)-ureido]-thizol-4-yl acetic acid (97 mg, 0.25 mmol) following the general procedure M.

LC-MS (m/z): 473 (M+1)$^+$; $^1$H NMR (400 MHz, CDCl$_3$): δ 1.40 (t, 2H), 1.72 (m, 4H), 1.92 (m, 4H), 2.16 (s, 6H), 2.35 (s, 3H), 2.88 (m, 2H), 3.13 (s, 2H), 3.70 (p, 1H), 6.90 (s, 1H), 7.36 (d, 1H), 7.67 (s, 1H), 8.20 (d, 1H), 8.44 (br, 1H), 8.92 (br, 1H), 10.26 (br, 1H), and 11.90 (br, 1H).

Example 183

(3-{2-[3-(2-Cyclopentanecarbonyl-4-methyl-phenyl)-ureido]-thiazol-4-ylmethyl}-ureido)-acetic acid

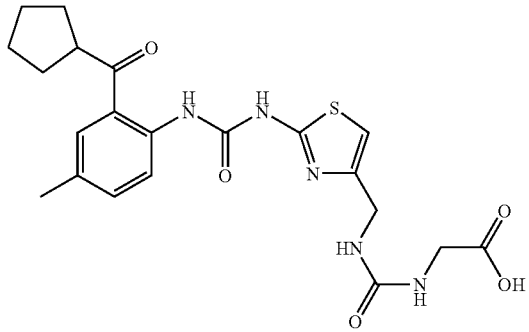

(3-{2-[3-(2-Cyclopentanecarbonyl-4-methyl-phenyl)-ureido]-thiazol-4-ylmethyl}-ureido)-acetic acid (96 mg, 83%) was prepared from 2-[3-(2-cyclopentanecarbonyl-4-methylphenyl)-ureido]-thizol-4-yl acetic acid (97 mg, 0.25 mmol) and glycine methyl ester (48 mg, 0.5 mmol) following the general procedure M followed by hydrolysis using the general procedure J.

LC-MS (m/z): 460 (M+1)$^+$; $^1$H NMR (400 MHz, CDCl$_3$): δ 1.70 (m, 4H), 1.90 (m, 4H), 2.38 (s, 3H), 3.49 (s, 2H), 3.71 (s, 2H), 3.84 (p, 1H), 6.78 (s, 1H), 7.34 (d, 1H), 7.73 (s, 1H), 8.36 (d, 1H), 8.42 (br, 1H), 8.94 (br, 1H), 9.86 (br, 1H), 10.26 (br, 1H), and 11.64 (br, 1H).

Example 184

{2-[3-(2-Cyclopentanecarbonyl-4-methyl-phenyl)-ureido]-thiazol-4-ylmethyl}-carbamic acid 2-dimethylamino-ethyl ester hydrochloride salt

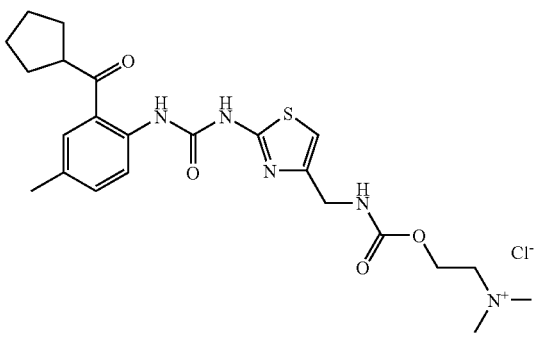

{2-[3-(2-Cyclopentanecarbonyl-4-methyl-phenyl)-ureido]-thiazol-4-ylmethyl}-carbamic acid 2-dimethylamino-ethyl ester hydrochloride salt (103 mg, 87%) was prepared from 2-[3-(2-cyclopentanecarbonyl-4-methyl-phenyl)-ureido]-thizol-4-yl acetic acid (97 mg, 0.25 mmol) and 2-N,N-dimethylethanol (0.05 mL, 0.5 mmol) following the general procedure M followed by treatment with HCl in ether.

LC-MS (m/z): 474 (M+1)$^+$; $^1$H NMR (400 MHz, CDCl$_3$): δ 1.42 (t, 2H), 1.74 (m, 4H), 1.92 (m, 4H), 2.28 (s, 6H), 2.39 (s, 3H), 2.96 (m, 2H), 3.24 (s, 2H), 3.74 (p, 1H), 6.86 (s, 1H), 7.34 (d, 1H), 7.72 (s, 1H), 8.44 (d, 1H), 9.12 (br, 1H), 10.34 (br, 1H), and 11.22 (br, 1H).

Example 185

N-{2-[3-(2-Cyclopentanecarbonyl-4-methyl-phenyl)-ureido]-thiazol-4-ylmethyl}-N',N'-dimethylsulfamide

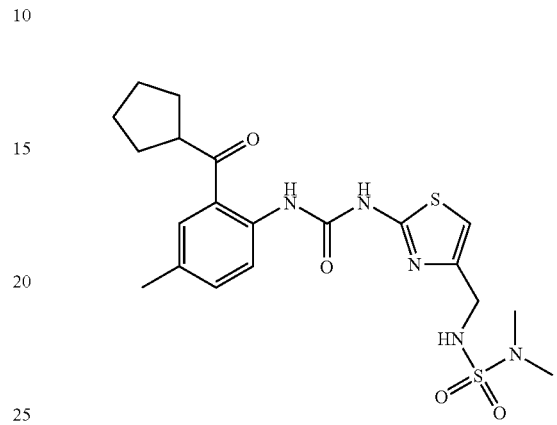

N-{2-[3-(2-Cyclopentanecarbonyl-4-methyl-phenyl)-ureido]-thiazol-4-ylmethyl}-N',N'-dimethylsulfamide (104 mg, 89%) was prepared from 1-(4-aminomethyl-thiazol-2-yl)-3-(2-cyclopentanecarbonyl-4-methyl-phenyl)-urea (90 mg, 0.25 mmol) and dimethylsulfamoyl chloride (0.06 mL, 0.5 mmol) following the general procedure T.

LC-MS (m/z): 466 (M+1)$^+$; $^1$H NMR (400 MHz, CDCl$_3$): δ 1.72 (m, 4H), 1.88 (m, 4H), 2.36 (s, 3H), 2.75 (s, 6H), 3.72 (p, 1H), 4.22 (d, 2H), 6.74 (s, 1H), 7.03 (br, 1H), 7.34 (d, 1H), 7.70 (s, 1H), 8.42 (d, 1H), 9.72 (br, 1H), and 11.66 (br, 1H).

Example 186

3-[{2-[3-(2-Cyclopentanecarbonyl-4-methyl-phenyl)-ureido]-thiazol-4-ylmethyl}-(2-methoxycarbonyl-ethyl)-amino]-propionic acid methyl ester

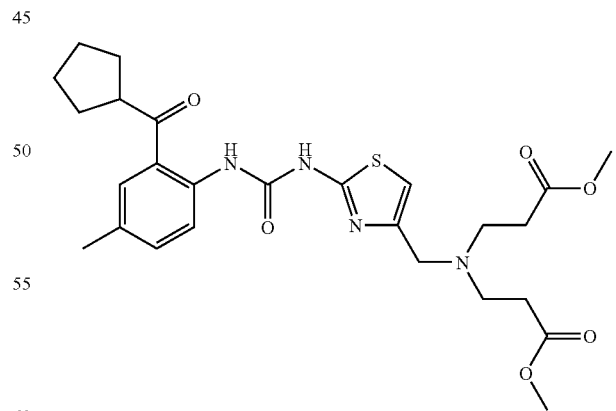

3-[{2-[3-(2-Cyclopentanecarbonyl-4-methyl-phenyl)-ureido]-thiazol-4-ylmethyl}-(2-methoxycarbonyl-ethyl)-amino]-propionic acid methyl ester (114 mg, 86%) was prepared by heating 1-(4-aminomethyl-thiazol-2-yl)-3-(2-cyclopentanecarbonyl-4-methyl-phenyl)-urea (90 mg, 0.25 mmol) with methyl acrylate (0.1 mL, 1.1 mmol) and Cs$_2$CO$_3$ (325 mg, 1.0 mmol) in THF (5 mL) at 60° C. for 2 h followed by column purification [silica, DCM:ethyl acetate (80:20 to 20:80)].

LC-MS (m/z): 531 (M+1)+; 1H NMR (400 MHz, CDCl3): δ 1.68 (m, 4H), 1.84 (m, 2H), 2.04 (m, 2H), 2.16 (s, 6H), 2.36 (s, 3H), 2.45 (t, 4H), 3.66 (m, 4H), 3.72 (p, 1H), 4.48 (s, 2H), 6.78 (s, 1H), 7.34 (d, 1H), 7.66 (s, 1H), 8.44 (d, 1H), 10.54 (br, 1H), and 11.62 (br, 1H).

Example 187

({2-[3-2-Cyclopentanecarbonyl-4-methyl-phenyl)-ureido]-thiazol-4-ylmethyl}-methoxycarbonylm-ethyl-amino)-acetic acid methyl ester

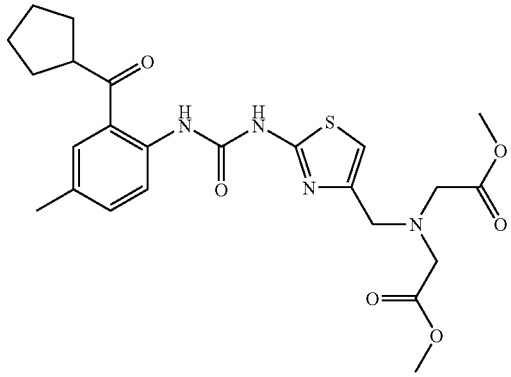

({2-[3-(2-Cyclopentanecarbonyl-4-methyl-phenyl)-ureido]-thiazol-4-ylmethyl}-methoxycarbonylmethyl-amino)-acetic acid methyl ester (99 mg, 79%) was prepared by treating 1-(4-aminomethyl-thiazol-2-yl)-3-(2-cyclopentanecarbonyl-4-methyl-phenyl)-urea (90 mg, 0.25 mmol) with methyl bromoacetate (0.04 mL, 0.5 mmol) and pyridine (0.082 mL) in DCM (5 mL) at 60° C. for 2 h followed by column purification [silica, DCM:ethyl acetate (80:20 to 20:80)].

LC-MS (m/z): 503 (M+1)+; 1H NMR (400 MHz, CDCl3): δ 1.53 (m, 4H), 1.76 (m, 4H), 2.18 (s, 3H), 2.59-2.74, (m, 6H), 3.50 (s, 6H), 3.62 (m, 1H), 6.69 (s, 1H), 7.18 (d, 1H), 7.54 (s, 1H), 8.18 (d, 1H), 10.58 (br, 1H), and 11.28 (br, 1H).

Example 188

(Carboxymethyl-{2-[3-(2-cyclopentanecarbonyl-4-methyl-phenyl)-ureido]-thiazol-4-ylmethyl}-amino)-acetic acid

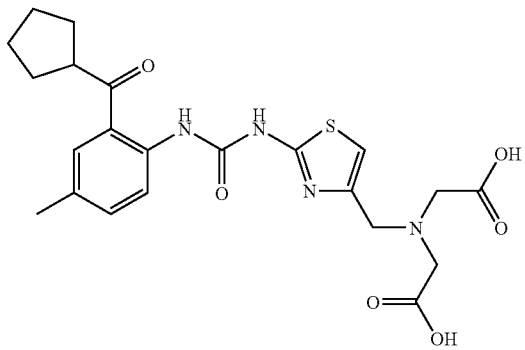

(Carboxymethyl-{2-[3-(2-cyclopentanecarbonyl-4-methyl-phenyl)-ureido]-thiazol-4-ylmethyl}-amino)-acetic acid (44 mg, 88%) was prepared from ({2-[3-(2-cyclopentanecarbonyl-4-methyl-phenyl)-ureido]-thiazol-4-ylmethyl}-methoxycarbonylmethylamino)-acetic acid methyl ester (50 mg, 0.1 mmol) following the general procedure J.

LC-MS (m/z): 474 (M+1)+; 1H NMR (400 MHz, CD3OD): δ 1.53 (m, 4H), 1.76 (m, 4H), 2.32 (s, 3H), 2.63 (s, 2H), 2.74 (s, 4H), 3.72 (m, 1H), 6.76 (s, 1H), 7.28 (d, 1H), 7.66 (s, 1H), 8.38 (d, 1H), 9.66 (br, 1H), 10.08 (br, 2H), and 11.46 (br, 1H).

Example 189

N-{2-[3-(2-Cyclopentanecarbonyl-4-methyl-phenyl)-ureido]-thiazol-4-ylmethyl}-2-dimethylamino-acetamide

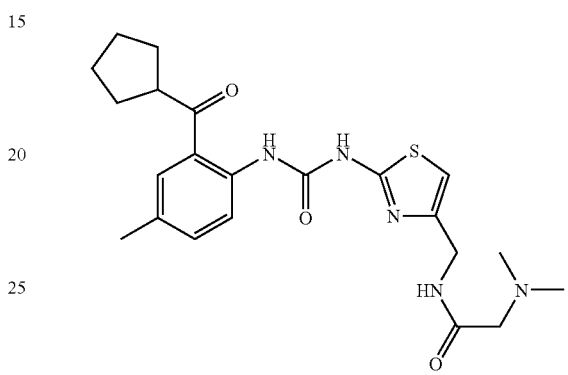

N-{2-[3-(2-Cyclopentanecarbonyl-4-methyl-phenyl)-ureido]-thiazol-4-ylmethyl}-2-dimethylamino-acetamide (86 mg, 78%) was prepared from 1-(4-aminomethyl-thiazol-2-yl)-3-(2-cyclopentanecarbonyl-4-methyl-phenyl)-urea (90 mg, 0.25 m mol) and N, —N-dimethyl glycine (0.30 mg, 0.30 mmol) following the general procedure K.

LC-MS (m/z): 444 (M+1)+; 1H NMR (400 MHz, CDCl3): δ 1.70 (m, 4H), 1.92 (m, 4H), 2.30 (s, 3H), 2.82 (s, 3H), 2.96 (s, 3H), 3.75 (s, 2H), 3.82 (m, 1H), 4.28 (d, 2H), 6.98 (s, 1H), 7.38 (d, 1H), 7.67 (s, 1H), 8.02 (d, 1H), 8.44 (br, 1H), 9.22 (br, 1H), and 11.44 (br, 1H).

Example 190

1-(2-Cyclopentanecarbonyl-4-methyl-phenyl)-3-(4-guanidinomethyl-thiazol-2-yl)-urea

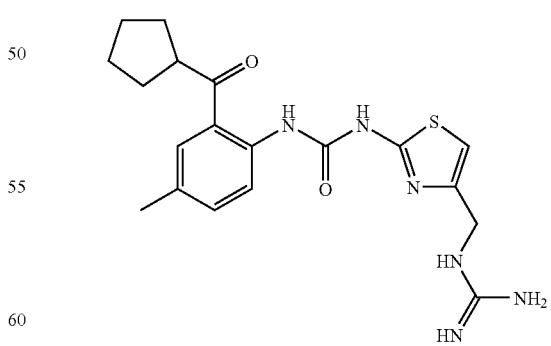

To a solution of 1-(4-aminomethyl-thiazol-2-yl)-3-(2-cyclopentanecarbonyl-4-methylphenyl)-urea (90 mg, 0.25 mmol) in THF (10 mL) was added pyrrole-1-carboxamidine (54 mg, 0.50 mmol) and DIEA (90 μL). The reaction mixture was heated 60° C. for 3 h and concentrated. The crude product was purified by flash chromatography [silica, DCM:ethyl acetate (50:50 to 10:90)] to yield 1-(2-cyclopentanecarbonyl-4-methyl-phenyl)-3-(4-guanidinomethyl-thiazol-2-yl)-urea (88 mg, 88%).

LC-MS (m/z): 401 (M+1)+; 1H NMR (400 MHz, CDCl3): δ 1.50 (m, 4H), 1.72 (m, 4H), 2.23 (s, 3H), 3.08 (q, 1H), 3.62 (p, 1H), 4.26 (br, 2H), 4.32 (t, 2H), 6.71 (s, 1H), 7.16 (d, 1H), 7.48 (s, 1H), 7.96 (br, 1H), 8.12 (d, 1H), 8.70 (br, 1H), and 10.92 (br, 1H).

Example 191

1-(2-Cyclopentanecarbonyl-4-methyl-phenyl)-3-[4-(4-S-methyl-2,5-dioxoimidazolidin-1-ylmethyl)-thiazol-2-yl]-urea

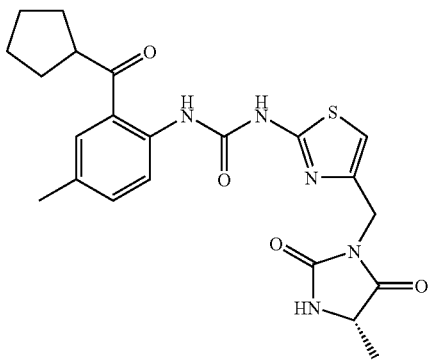

1-(2-Cyclopentanecarbonyl-4-methyl-phenyl)-3-[4-(4-S-methyl-2,5-dioxoimidazolidin-1-ylmethyl)-thiazol-2-yl]-urea (78 mg, 69%) was prepared from 1-(4-aminomethyl-thiazol-2-yl)-3-(2-cyclopentanecarbonyl-4-methyl-phenyl)-urea (358 mg, 1.0 mmol) and t-Boc-L-alanine (100 mg, 0.80 mmol) following the general procedure U.

LC-MS (m/z): 456 (M+1)+; 1H NMR (400 MHz, CDCl3): δ 1.43 (d, 3H), 1.64 (m, 4H), 1.88 (m, 4H), 2.35 (s, 3H), 3.56 (q, 1H), 3.74 (p, 1H), 4.73 (s, 2H), 5.52 (br, 1H), 6.84 (s, 1H), 7.32 (d, 1H), 7.68 (s, 1H), 8.40 (d, 1H), 9.84 (br, 1H), and 11.44 (br, 1H).

Example 192

1-(4-{[Bis-(3H-imidazol-4-ylmethyl)-amino]-methyl}-thiazol-2-yl)-3-(2-cyclopentanecarbonyl-4-methyl-phenyl)-urea

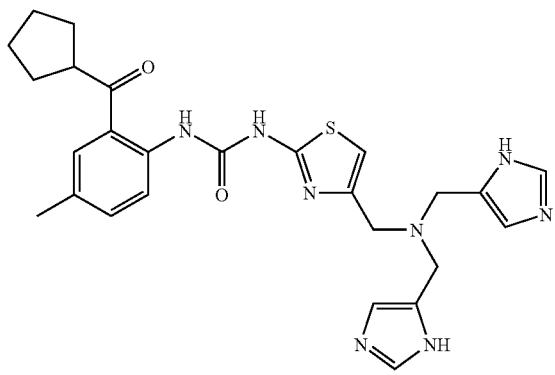

1-(4-{[Bis-(3H-imidazol-4-ylmethyl)-amino]-methyl}-thiazol-2-yl)-3-(2-cyclopentanecarbonyl-4-methyl-phenyl)-urea (110 mg, 85%) was prepared from 1-(4-aminomethyl-thiazol-2-yl)-3-(2-cyclopentanecarbonyl-4-methyl-phenyl)-urea (90 mg, 0.25 mmol) and imidazole-2-carboxyaldehyde (48 mg, 0.50 mmol) following the general procedure O.

LC-MS (m/z): 519 (M+1)+; 1H NMR (400 MHz, CDCl3): δ 1.58 (m, 4H), 1.84 (m, 4H), 2.34 (s, 3H), 3.10 (s, 2H), 3.51 (s, 4H), 3.64 (p, 1H), 6.62 (s, 1H), 6.84 (s, 1H), 7.08 (s, 1H), 7.11 (d, 1H), 7.66 (d, 1H), 7.70 (s, 1H), 7.83 (d, 1H), 8.36 (d, 1H), 8.70 (br, 2H), 9.74 (br, 1H), and 11.30 (br, 1H).

Example 193

1-(2-Cyclopentanecarbonyl-4-methyl-phenyl)-3-[4-(N',N', N'', N''-tetramethyl-guanidinomethyl)-thiazol-2-yl]-urea

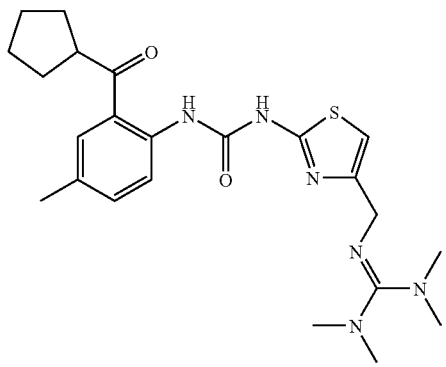

1-(4-Aminomethyl-thiazol-2-yl)-3-(2-cyclopentanecarbonyl-4-methyl-phenyl)-urea (90 mg, 0.25 mmol) in DMF were added HBTU (94 mg, 0.25 mmol) and DIEA (90 µL). The reaction mixture was stirred at rt for 2 h. The reaction mixture was poured into water (30 mL) and extracted with ethyl acetate (3×25 mL). The organic layer was washed (water, brine), dried (Na2SO4) and concentrated in vacuo. The crude product was purified by flash chromatography [silica, DCM:ethyl acetate (50:50 to 10:90)] to yield 1-(2-cyclopentanecarbonyl-4-methyl-phenyl)-3-[4-(N',N',N'',N''-tetramethyl-guanidinomethyl)-thiazol-2-yl]-urea (92 mg, 81%).

LC-MS (m/z): 457 (M+1)+; 1H NMR (400 MHz, CDCl3): δ 1.66 (m, 4H), 1.82 (m, 2H), 1.94 (m, 2H), 2.37 (s, 3H), 2.96 (s, 12H), 3.76 (p, 1H), 4.32 (s, 2H), 6.80 (s, 1H), 7.38 (d, 1H), 7.70 (s, 1H), 8.38 (d, 1H), 10.54 (br, 1H), and 11.58 (br, 1H).

Example 194

2-Amino-ethanesulfonic acid {2-[3-(2-cyclopentanecarbonyl-4-methyl-phenyl)-ureido]-thiazol-4-ylmethyl}-amide

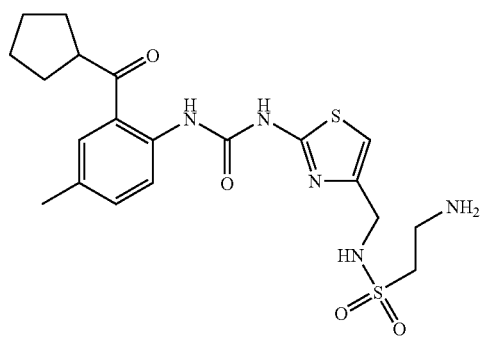

2-Amino-ethanesulfonic acid {2-[3-(2-cyclopentanecarbonyl-4-methyl-phenyl)-ureido]-thiazol-4-ylmethyl}-amide (104 mg, 83%) was prepared from 1-(4-aminomethyl-thiazol-2-yl)-3-(2-cyclopentanecarbonyl-4-methyl-phenyl)-urea (90 mg, 0.25 mmol) and 2-(1,3-Dioxo-1,3-dihydro-isoindol-2-yl)-ethanesulfonyl chloride (70 mg, 0.25 mmol) following the general procedure T. This intermediate was deprotected by heating with excess of hydrazine (0.2 mL, 1.0 M. in THF).

LC-MS (m/z): 466 (M+1)+; 1H NMR (400 MHz, CD3OD): δ 1.68 (m, 4H), 1.92 (m, 4H), 2.38 (s, 3H), 3.22 (t, 2H), 3.68 (m, 2H), 3.76 (p, 1H), 4.08 (s, 2H), 4.84 (br, 1H), 5.38 (br, 2H), 6.76 (s, 1H), 7.36 (d, 1H), 7.74 (s, 1H), 8.48 (d, 1H), 10.22 (br, 1H), and 11.36 (br, 1H).

Example 195

N-{2-[3-(2-Cyclopentanecarbonyl-4-methyl-phenyl)-ureido]-thiazol-4-ylmethyl}-2-methanesulfonylamino-acetamide

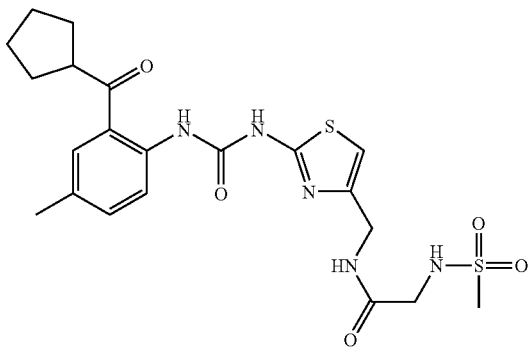

N-{2-[3-(2-Cyclopentanecarbonyl-4-methyl-phenyl)-ureido]-thiazol-4-ylmethyl}-2-methanesulfonylamino-acetamide (103 mg, 84%) was prepared from 2-amino-N-{2-[3-(2-cyclopentanecarbonyl-4-methyl-phenyl)-ureido]-thiazol-4-ylmethyl}-acetamide (104 mg, 0.25 mmol) and methanesulfonyl chloride (0.04 mL, 0.5 mmol) following the general procedure L.

LC-MS (m/z): 494 (M+1)+; 1H NMR (400 MHz, CDCl3): δ 1.70 (m, 4H), 1.88 (m, 4H), 2.36 (s, 3H), 3.28 (t, 2H), 3.38 (s, 3H), 3.74 (p, 1H), 4.16 (d, 2H), 6.84 (s, 1H), 6.96 (br, 1H), 7.38 (d, 1H), 7.44 (br, 1H), 7.69 (s, 1H), 8.36 (d, 1H), 10.58 (br, 1H), and 11.28 (br, 1H).

Example 196

{[({2-[3-(2-Cyclopentanecarbonyl-4-methyl-phenyl)-ureido]-thiazol-4-ylmethyl}-carbamoyl)-methyl]-amino}-acetic acid

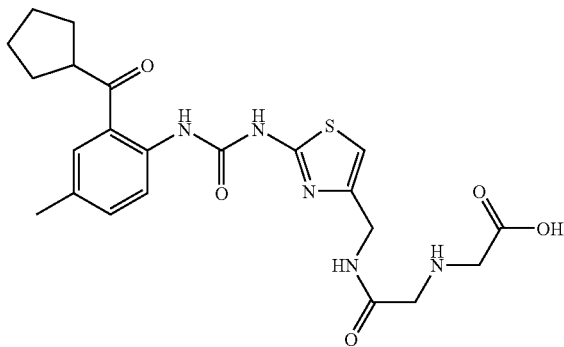

{[({2-[3-(2-Cyclopentanecarbonyl-4-methyl-phenyl)-ureido]-thiazol-4-ylmethyl}-carbamoyl)-methyl]-amino}-acetic acid (44 mg, 88%) was prepared from ({2-[3-(2-cyclopentanecarbonyl-4-methyl-phenyl)-ureido]-thiazol-4-ylmethyl}-methoxycarbonylmethylamino)-acetic acid methyl ester (50 mg, 0.1 mmol) following the general procedure J.

LC-MS (m/z): 474 (M+1)+; 1H NMR (400 MHz, CD3OD): δ 1.58 (m, 4H), 1.84 (m, 4H), 2.31 (s, 3H), 2.79 (d, 2H), 3.58 (d, 2H) 3.70 (m, 1H), 4.18 (s, 2H), 4.96 (br, 1H), 6.82 (s, 1H), 7.03 (br, 1H), 7.30 (d, 1H), 7.72 (s, 1H), 8.44 (d, 1H), 9.66 (br, 1H), 10.08 (br, 1H), and 11.46 (br, 1H).

Example 197

{[({2-[3-(2-Cyclopentanecarbonyl-4-methyl-phenyl)-ureido]-thiazol-4-ylmethyl}-carbamoyl)-methyl]-amino}-acetic acid methyl ester

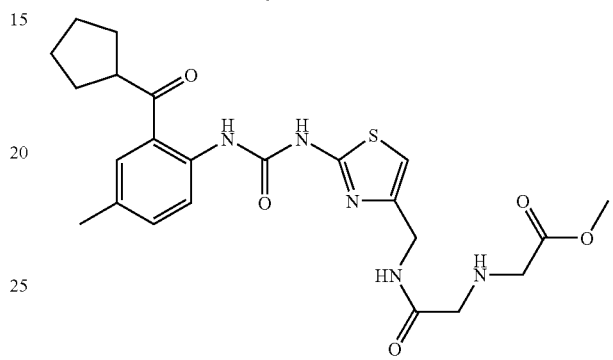

{[({2-[3-(2-Cyclopentanecarbonyl-4-methyl-phenyl)-ureido]-thiazol-4-ylmethyl}-carbamoyl)-methyl]-amino}-acetic acid methyl ester (44 mg, 88%) was prepared by treating 2-amino-N-{2-[3-(2-cyclopentanecarbonyl-4-methyl-phenyl)-ureido]-thiazol-4-ylmethyl}-acetamide (104 mg, 0.25 mmol) with methyl bromoacetate (0.023 mL, 0.25 mmol) in THF (5 mL) at 60° C. for 2 h followed by column purification [silica, DCM:ethyl acetate (80:20 to 20:80)].

LC-MS (m/z): 488 (M+1)+; 1H NMR (400 MHz, CDCl3): δ 1.64 (m, 4H), 1.82 (m, 4H), 2.38 (s, 3H), 2.66 (s, 2H), 2.78, (s, 2H), 3.18 (s, 2H), 3.52 (s, 3H), 3.72 (m, 1H), 6.76 (s, 1H), 7.06 (br, 1H), 7.28 (d, 1H), 7.66 (s, 1H), 8.38 (d, 1H), 8.86 (br, 1H), 9.74 (br, 1H), and 11.46 (br, 1H).

Example 198

3-({2-[3-(2-Cyclopentanecarbonyl-4-methyl-phenyl)-ureido]-thiazol-4-ylmethyl}-sulfamoyl)-propionic acid

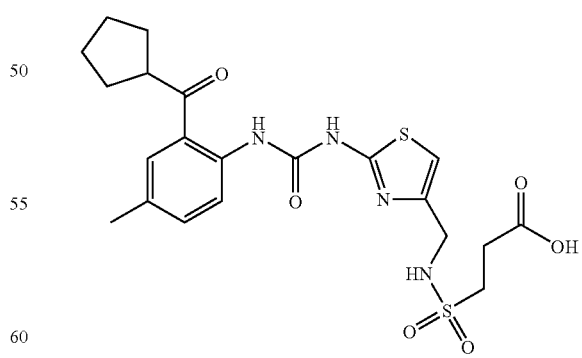

3-({2-[3-(2-Cyclopentanecarbonyl-4-methyl-phenyl)-ureido]-thiazol-4-ylmethyl}-sulfamoyl)-propionic acid (85 mg, 87%) was prepared from 3-({2-[3-(2-cyclopentanecarbonyl-4-methyl-phenyl)-ureido]-thiazol-4-ylmethyl}-sulfamoyl)-propionic acid metyl ester (101 mg, 0.20 mmol) following the general procedure J.

LC-MS (m/z): 495 (M+1)+; $^1$H NMR (400 MHz, CD3OD): δ 1.74 (m, 4H), 1.88 (m, 4H), 2.33 (s, 3H), 3.12 (t, 2H), 3.48 (t, 2H), 3.72 (p, 1H), 3.88 (d, 2H), 6.72 (s, 1H), 7.36 (d, 1H), 7.68 (s, 1H), 8.42 (d, 1H), 9.54 (br, 1H), 10.88 (br, 1H), 11.12 (br, 1H), and 11.54 (br, 1H).

Example 199

N-{2-[3-(2-Cyclopentanecarbonyl-4-methyl-phenyl)-ureido]-thiazol-4-ylmethyl}-2-methanesulfonyl-acetamide

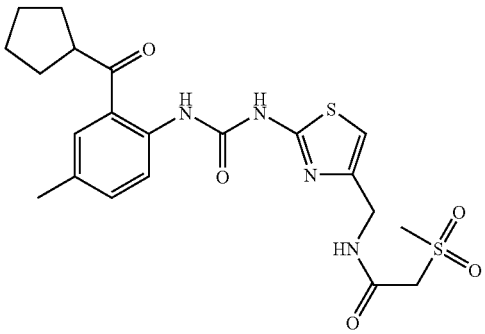

N-{2-[3-(2-Cyclopentanecarbonyl-4-methyl-phenyl)-ureido]-thiazol-4-ylmethyl}-2-methanesulfonyl-acetamide (103 mg, 84%) was prepared from 1-(4-aminomethyl-thiazol-2-yl)-3-(2-cyclopentanecarbonyl-4-methyl-phenyl)-urea (90 mg, 0.25 mmol) and methanesulfonyl acetic acid (55 mg, 0.4 mmol) following the general procedure T.

LC-MS (m/z): 479 (M+1)+; $^1$H NMR (400 MHz, CD3OD): δ 1.68 (m, 4H), 1.84 (m, 4H), 2.35 (s, 3H), 2.78 (s, 2H), 3.12 (s, 3H), 3.86 (m, 1H), 4.08 (d, 2H), 6.89 (s, 1H), 7.04 (br, 1H), 7.37 (d, 1H), 7.80 (s, 1H), 8.24 (d, 1H), 8.52 (br, 1H), and 11.36 (br, 1H).

Example 200

1-{2-[3-(2-Cyclopentanecarbonyl-4-methyl-phenyl)-ureido]-thiazol-4-ylmethyl}-piperidine-S-3-carboxylic acid ethyl ester

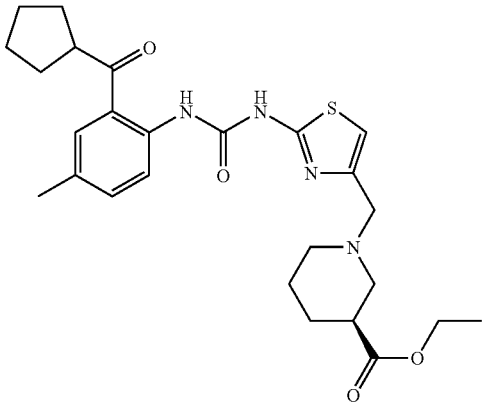

1-{2-[3-(2-Cyclopentanecarbonyl-4-methyl-phenyl)-ureido]-thiazol-4-ylmethyl}-piperidine-S-3-carboxylic acid ethyl ester (107 mg, 86%) was prepared from 2-[3-(2-1-(2-cyclopentanecarbonyl-4-methyl-phenyl)-3-(4-formyl-thiazol-2-yl)-urea (89 mg, 0.25 mmol) and piperidine-S-3-carboxylic acid ethyl ester (40 mg, 0.25 mmol) following the general procedure O.

LC-MS (m/z): 499 (M+1)+; $^1$H NMR (400 MHz, CDCl3): δ 1.22 (t, 3H), 1.63-1.70 (m, 6H), 1.89 (m, 4H), 2.22 (m, 1H), 2.35 (s, 3H), 2.60 (m, 2H), 2.84 (m, 2H), 3.00 (d, 2H), 3.55 (m, 2H), 3.72 (p, 1H), 4.10 (q, 2H), 6.67 (s, 1H), 7.33 (d, 1H), 7.68 (s, 1H), 8.40 (br, 1H), 10.50 (br, 1H), and 11.50 (br, 1H).

Example 201

1-{2-[3-(2-Cyclopentanecarbonyl-4-methyl-phenyl)-ureido]-thiazol-4-ylmethyl}-piperidine-S-3-carboxylic acid

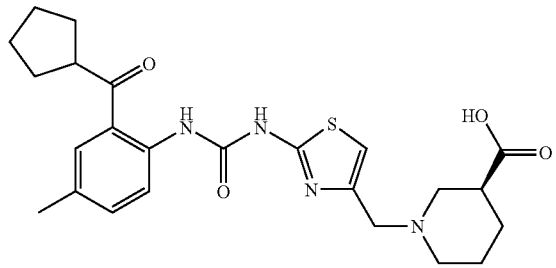

1-{2-[3-(2-Cyclopentanecarbonyl-4-methyl-phenyl)-ureido]-thiazol-4-ylmethyl}-piperidine-S-3-carboxylic acid (104 mg, 81%) was prepared from 1-{2-[3-(2-cyclopentanecarbonyl-4-methyl-phenyl)-ureido]-thiazol-4-ylmethyl}-piperidine-S-3-carboxylic acid ethyl ester (135 mg, 0.25 mmol) following the general procedure J.

LC-MS (m/z): 471 (M+1)+; $^1$H NMR (400 MHz, CDCl3): δ 1.58-1.64 (m, 4H), 1.84-1.96 (m, 6H), 2.16 (m, 1H), 2.28 (s, 3H), 2.80 (m, 1H), 3.05 (m, 1H), 3.34-3.49 (m, 2H), 3.66 (d, 1H), 3.93 (m, 1H), 4.34-4.50 (m, 2H), 4.70 (m, 1H), 6.83 (s, 1H), 7.36 (d, 1H), 7.60 (s, 1H), 8.25 (d, 1H), 9.00 (br, 1H), 10.20 (br, 1H), and 11.36 (br, 1H).

Example 202

({2-[3-(2-Cyclopentanecarbonyl-4-methyl-phenyl)-ureido]-thiazol-4-ylmethyl}-amino)-(tetrahydro-pyran-4-yl)-acetic acid methyl ester

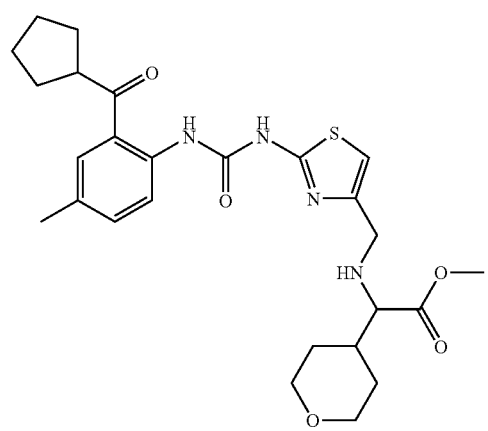

({2-[3-(2-Cyclopentanecarbonyl-4-methyl-phenyl)-ureido]-thiazol-4-ylmethyl}-amino)-(tetrahydro-pyran-4-yl)-acetic acid methyl ester (113 mg, 88%) was prepared from 2-[3-(2-1-(2-cyclopentanecarbonyl-4-methyl-phenyl)-3-(4-formyl-thiazol-2-yl)-urea (89 mg, 0.25 mmol) and amino-(tetrahydro-pyran-4-yl)-acetic acid methyl ester (44 mg, 0.25 mmol) following the general procedure O.

LC-MS (m/z): 515 (M+1)+; $^1$H NMR (400 MHz, CDCl3): δ 1.42 (m, 4H), 1.66-1.73 (m, 4H), 1.80-193 (m, 4H), 2.35 (s,

3H), 3.14 (d, 2H), 3.32 (t, 2H), 3.64 (t, 2H), 3.72 (p, 1H), 3.78 (d, 2H), 3.92 (s, 3H), 6.24 (br, 1H), 6.64 (s, 1H), 7.32 (d, 1H), 7.68 (s, 1H), 8.42 (br, 1H), 9.78 (br, 1H), and 11.50 (br, 1H).

Example 203

({2-[3-(2-Cyclopentanecarbonyl-4-methyl-phenyl)-ureido]-thiazol-4-ylmethyl}-amino)-(tetrahydro-pyran-4-yl)-acetic acid

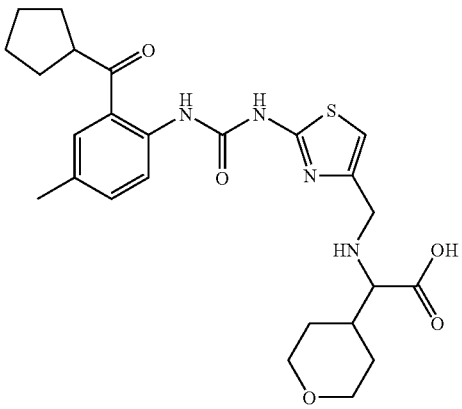

({2-[3-(2-Cyclopentanecarbonyl-4-methyl-phenyl)-ureido]-thiazol-4-ylmethyl}-amino)-(tetrahydro-pyran-4-yl)-acetic acid (87 mg, 87%) was prepared from ({2-[3-(2-cyclopentanecarbonyl-4-methyl-phenyl)-ureido]-thiazol-4-ylmethyl}-amino)-(tetrahydro-pyran-4-yl)-acetic acid methyl ester (128 mg, 0.25 mmol) following the general procedure J.

LC-MS (m/z): 501 (M+1)$^+$; $^1$H NMR (400 MHz, CDCl$_3$): δ 1.48 (m, 4H), 1.68-1.75 (m, 4H), 1.82-192 (m, 4H), 2.36 (s, 3H), 3.36 (d, 2H), 3.44 (t, 2H), 3.68 (t, 2H), 3.74 (p, 1H), 3.82 (d, 2H), 5.24 (br, 1H), 6.76 (s, 1H), 7.34 (d, 1H), 7.71 (s, 1H), 8.44 (d, 1H), 9.62 (br, 1H), 10.38 (br, 1H), and 11.20 (br, 1H).

Example 204

1-(2-Cyclopentanecarbonyl-4-methyl-phenyl)-3-{4-[(2-morpholin-4-yl-ethylamino)-methyl]-thiazol-2-yl}-urea

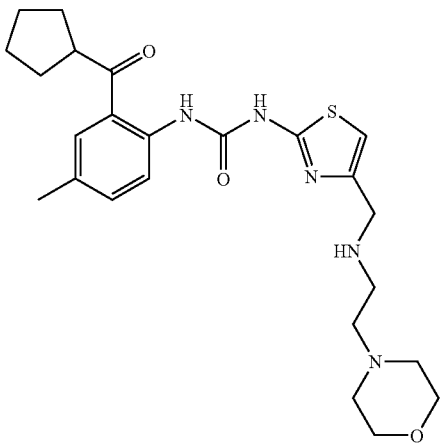

1-(2-Cyclopentanecarbonyl-4-methyl-phenyl)-3-{4-[(2-morpholin-4-yl-ethylamino)-methyl]-thiazol-2-yl}-urea (97 mg, 82%) was prepared from 2-[3-(2-1-(2-cyclopentanecarbonyl-4-methyl-phenyl)-3-(4-formyl-thiazol-2-yl)-urea (89 mg, 0.25 mmol) and 2-morpholin-4-yl-ethylamine (35 mg, 0.25 mmol) following the general procedure O.

LC-MS (m/z): 472 (M+1)$^+$; $^1$H NMR (400 MHz, CDCl$_3$): δ 1.66 (m, 4H), 1.88 (m, 4H), 2.33 (s, 3H), 2.38 (m, 2H), 2.50 (t, 2H), 2.80 (t, 2H), 3.59-3.64 (m, 6H), 3.70 p, 1H), 3.85 (m, 2H), 5.88 (br, 1H), 6.58 (s, 1H), 7.32 (d, 1H), 7.66 (s, 1H), 8.42 (d, 1H), 10.08 (br, 1H), and 11.28 (br, 1H).

Example 205

1-(2-Cyclopentanecarbonyl-4-methyl-phenyl)-3-(4-morpholin-4-ylmethyl-thiazol-2-yl)-urea

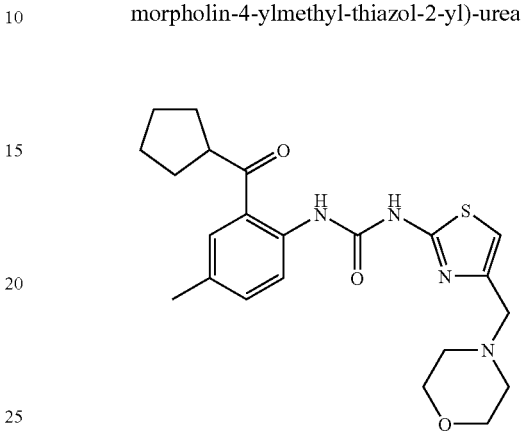

1-(2-Cyclopentanecarbonyl-4-methyl-phenyl)-3-(4-morpholin-4-ylmethyl-thiazol-2-yl)-urea (83 mg, 78%) was prepared from 2-[3-(2-1-(2-cyclopentanecarbonyl-4-methyl-phenyl)-3-(4-formyl-thiazol-2-yl)-urea (89 mg, 0.25 mmol) and (30 mg, 0.3 mmol) and morpholine (0.25 mL, 0.3 mmol) following the general procedure O.

LC-MS (m/z): 429 (M+1)$^+$; $^1$H NMR (400 MHz, CDCl$_3$): δ 1.62-1.80 (m, 4H), 1.80-1.94 (m, 4H), 2.35 (s, 3H), 2.50 (m, 4H), 3.53 (s, 2H), 3.70 (t, 4H), 3.75 (m, 1H), 6.70 (s, 1H), 7.34 (d, 1H), 7.69 (s, 1H), 8.40 (d, 1H), 9.75 (br, 1H), and 11.58 (br, 1H).

Example 206

1-(2-Cyclopentanecarbonyl-4-methyl-phenyl)-3-[4-(3-oxo-piperazin-1-ylmethyl)-thiazol-2-yl]-urea

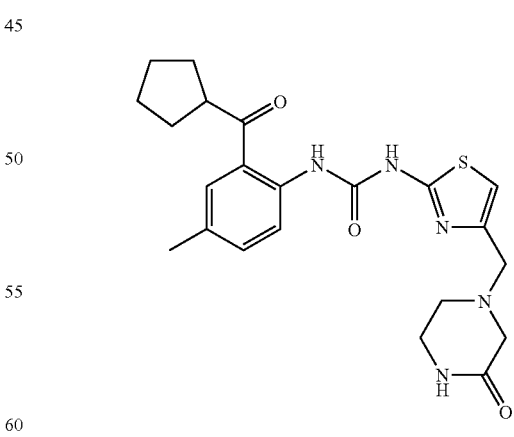

1-(2-Cyclopentanecarbonyl-4-methyl-phenyl)-3-[4-(3-oxo-piperazin-1-ylmethyl)-thiazol-2-yl]-urea (79 mg, 82%) was prepared from 2-[3-(2-1-(2-cyclopentanecarbonyl-4-methyl-phenyl)-3-(4-formyl-thiazol-2-yl)-urea (89 mg, 0.25 mmol) and piperazine-2-one (30 mg, 0.30 mmol) following the general procedure O.

LC-MS (m/z): 442 (M+1)+; 1H NMR (400 MHz, CDCl3): δ 1.60-1.74 (m, 4H), 1.80-1.94 (m, 4H), 2.35 (s, 3H), 2.67 (t, 2H), 3.30 (s, 2H), 3.38 (m, 2H), 3.58 (s, 2H), 3.73 (p, 1H), 6.66 (s, 1H), 7.32 (d, 1H), 7.67 (s, 1H), 7.78 (br, 1H), 8.38 (d, 1H), 10.44 (br, 1H), and 11.40 (br, 1H).

Example 207

(4-{2-[3-(2-Cyclopentanecarbonyl-4-methyl-phenyl)-ureido]-thiazol-4-ylmethyl}-piperazin-1-yl)-acetic acid ethyl ester

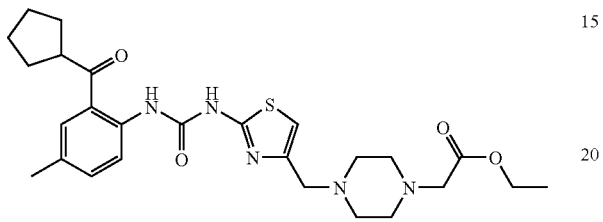

(4-{2-[3-(2-Cyclopentanecarbonyl-4-methyl-phenyl)-ureido]-thiazol-4-ylmethyl}-piperazin-1-yl)-acetic acid ethyl ester (79 mg, 82%) was prepared from 2-[3-(2-1-(2-cyclopentanecarbonyl-4-methyl-phenyl)-3-(4-formyl-thiazol-2-yl)-urea (89 mg, 0.25 mmol) and piperazin-1-yl-acetic acid ethyl ester (43 mg, 0.25 mmol) following the general procedure O.

LC-MS (m/z): 514 (M+1)+; 1H NMR (400 MHz, CDCl3): δ 1.28 (t, 3H), 1.46-1.62 (m, 4H), 1.66-1.86 (m, 4H), 2.35 (s, 3H), 3.28 (m, 2H), 3.42 (s, 2H), 3.40-3-64 (m, 4H), 3.83 (m, 1H), 3.92 (s, 2H), 4.12 (m, 2H), 4.48 (s, 2H), 6.84 (s, 1H), 7.29 (d, 1H), 7.67 (s, 1H), 8.28 (d, 1H), 11.14 (br, 1H), and 11.62 (br, 1H).

Example 208

(4-{2-[3-(2-Cyclopentanecarbonyl-4-methyl-phenyl)-ureido]-thiazol-4-ylmethyl}-piperazin-1-yl)-acetic acid

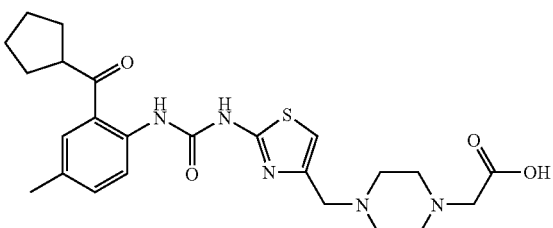

(4-{2-[3-(2-Cyclopentanecarbonyl-4-methyl-phenyl)-ureido]-thiazol-4-ylmethyl}-piperazin-1-yl)-acetic acid (40 mg, 83%) was prepared from (4-{2-[3-(2-cyclopentanecarbonyl-4-methyl-phenyl)-ureido]-thiazol-4-ylmethyl}-piperazin-1-yl)-acetic acid ethyl ester (52 mg, 0.10 mmol) following the general procedure J.

LC-MS (m/z): 486 (M+1)+; 1H NMR (400 MHz, CDCl3): δ 1.44-1.58 (m, 4H), 1.62-1.80 (m, 4H), 2.22 (s, 3H), 2.98 (s, 2H), 3.18 (m, 2H), 3.62 (p, 1H), 4.02-4.18 (m, 8H), 7.00 (s, 1H), 7.22 (d, 1H), 7.58 (s, 1H), 8.18 (d, 1H), 9.54 (br, 1H), 10.78 (br, 1H), and 11.44 (br, 1H).

Example 209

3-(4-{2-[3-(2-Cyclopentanecarbonyl-4-methyl-phenyl)-ureido]-thiazol-4-ylmethyl}-piperazin-1-yl)-propionic acid ethyl ester

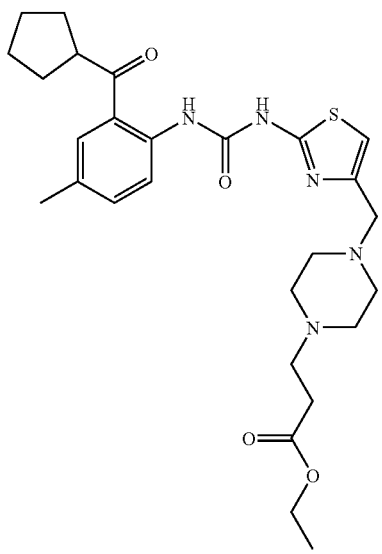

3-(4-{2-[3-(2-Cyclopentanecarbonyl-4-methyl-phenyl)-ureido]-thiazol-4-ylmethyl}-piperazin-1-yl)-propionic acid ethyl ester (118 mg, 89%) was prepared from 2-[3-(2-1-2-cyclopentanecarbonyl-4-methyl-phenyl)-3-(4-formyl-thiazol-2-yl)-urea (89 mg, 0.25 mmol) and 3-piperazin-1-yl-propionic acid ethyl ester (61 mg, 0.30 mmol) following the general procedure O.

LC-MS (m/z): 528 (M+1)+; 1H NMR (400 MHz, CDCl3): δ 1.24 (t, 3H), 1.44-1.64 (m, 4H), 1.64-1.80 (m, 4H), 2.36 (s, 3H), 3.22-3.38 (m, 6H), 3.40-3-64 (m, 4H), 3.83 (m, 1H), 3.96 (m, 2H), 4.08 (m, 2H), 4.58 (s, 2H), 6.97 (s, 1H), 7.14 (d, 1H), 7.64 (s, 1H), 8.16 (d, 1H), 11.04 (br, 1H), and 11.22 (br, 1H).

Example 210

3-(4-{2-[3-(2-Cyclopentanecarbonyl-4-methyl-phenyl)-ureido]-thiazol-4-ylmethyl}-piperazin-1-yl)-propionic acid

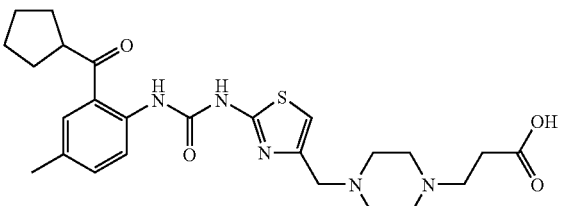

3-(4-{2-[3-(2-Cyclopentanecarbonyl-4-methyl-phenyl)-ureido]-thiazol-4-ylmethyl}-piperazin-1-yl)-propionic acid (38 mg, 76%) was prepared from 3-(4-{2-[3-(2-cyclopentanecarbonyl-4-methyl-phenyl)-ureido]-thiazol-4-ylmethyl}-piperazin-1-yl)-propionic acid ethyl ester (53 mg, 0.10 mmol) following the general procedure J.

LC-MS (m/z): 500 (M+1)+; 1H NMR (400 MHz, CDCl3): δ 1.42-1.60 (m, 4H), 1.64-1.78 (m, 4H), 2.26 (s, 3H), 3.38-3.44 (m, 6H), 3.48-3.66 (m, 4H), 3.77 (m, 1H), 4.02 (m, 2H), 4.64 (s, 2H), 6.88 (s, 1H), 7.30 (d, 1H), 7.73 (s, 1H), 8.28 (d, 1H), 9.88 (br, 1H), 10.38 (br, 1H), and 11.34 (br, 1H).

Example 211

(3-{2-[3-(2-Cyclopentanecarbonyl-4-methyl-phenyl)-ureido]-thiazol-4-ylmethyl}-ureido)-acetic acid

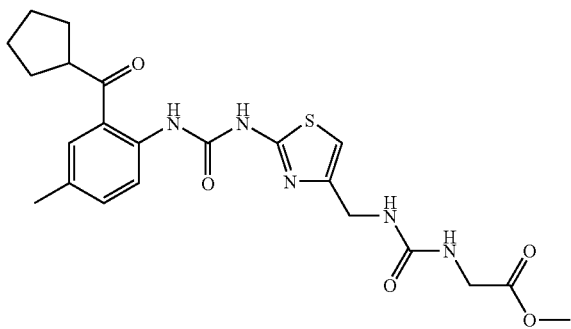

(3-{2-[3-(2-Cyclopentanecarbonyl-4-methyl-phenyl)-ureido]-thiazol-4-ylmethyl}-ureido)-acetic acid methyl ester (106 mg, 90%) was prepared from 2-[3-(2-cyclopentanecarbonyl-4-methyl-phenyl)-ureido]-thizol-4-yl acetic acid (97 mg, 0.25 mmol) and glycine methyl ester (48 mg, 0.5 mmol) following the general procedure M.

LC-MS (m/z): 460 (M+1)+; 1H NMR (400 MHz, CDCl3): δ 1.73 (m, 4H), 1.88 (m, 4H), 2.36 (s, 3H), 3.46 (s, 2H), 3.66 (s, 2H), 3.78 (p, 1H), 6.74 (s, 1H), 7.36 (d, 1H), 7.71 (s, 1H), 8.28 (d, 1H), 8.44 (br, 1H), 8.92 (br, 1H), 9.96 (br, 1H), and 11.68 (br, 1H).

Example 212

1-(2-Cyclopentanecarbonyl-4-methyl-phenyl)-3-[4-(2,5-dioxo-imidazolidin-1-ylmethyl)-thiazol-2-yl]-urea

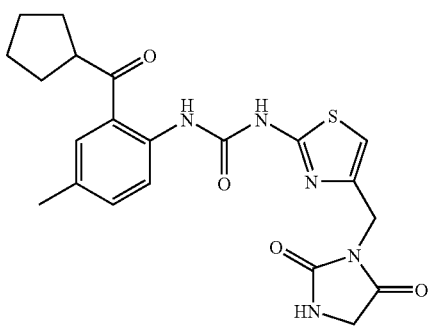

1-(2-Cyclopentanecarbonyl-4-methyl-phenyl)-3-[4-(2,5-dioxo-imidazolidin-1-ylmethyl)-thiazol-2-yl]-urea (78 mg, 69%) was prepared from 1-(4-aminomethyl-thiazol-2-yl)-3-(2-cyclopentanecarbonyl-4-methyl-phenyl)-urea (358 mg, 1.0 mmol) and t-Boc-glycine (90 mg, 0.80 mmol) following the general procedure U.

LC-MS (m/z): 442 (M+1)+; 1H NMR (400 MHz, CDCl3): δ 1.66 (m, 4H), 1.90 (m, 4H), 2.38 (s, 3H), 3.43 (s, 2H), 3.76 (p, 1H), 4.24 (s, 2H), 5.48 (br, 1H), 6.78 (s, 1H), 7.34 (d, 1H), 7.72 (s, 1H), 8.44 (d, 1H), 9.66 (br, 1H), and 11.64 (br, 1H).

Example 213

4-({2-[3-(2-Cyclopentanecarbonyl-4-methyl-phenyl)-ureido]-thiazol-4-ylmethyl}-sulfamoyl)-benzoic acid

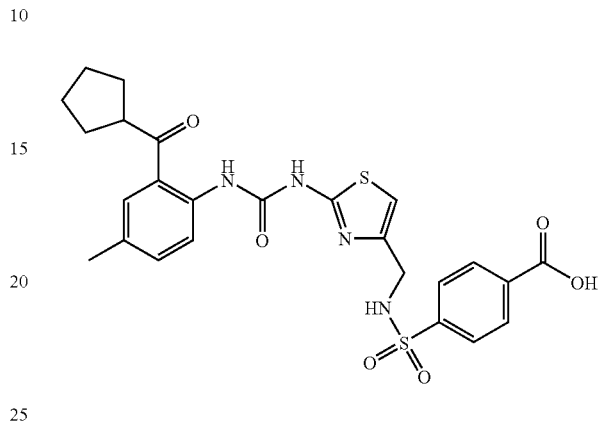

4-({2-[3-(2-Cyclopentanecarbonyl-4-methyl-phenyl)-ureido]-thiazol-4-ylmethyl}-sulfamoyl)-benzoic acid (78 mg, 58%) was prepared from 1-(4-aminomethyl-thiazol-2-yl)-3-(2-cyclopentanecarbonyl-4-methyl-phenyl)-urea (90 mg, 0.25 mmol) following the general procedure T.

LC-MS (m/z): 543 (M+1)+; 1H NMR (400 MHz, CD3OD): δ 1.73 (m, 4H), 1.88 (m, 4H), 2.33 (s, 3H), 3.68 (m, 2H), 3.74 (p, 1H), 5.88 (br, 1H), 6.82 (s, 1H), 7.36 (d, 1H), 7.48 (d, 2H), 7.68 (d, 2H), 7.74 (s, 1H), 8.48 (d, 1H), 9.76 (br, 1H), 10.38 (br, 1H), and 11.44 (br, 1H).

Example 214

3-({2-[3-(2-Cyclopentanecarbonyl-4-methyl-phenyl)-ureido]-thiazol-4-ylmethyl}-sulfamoyl)-propionic acid methyl ester

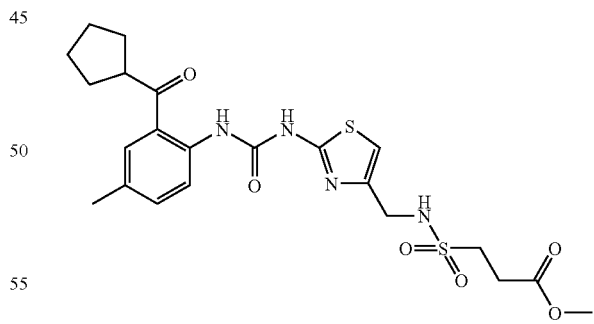

3-({2-[3-(2-Cyclopentanecarbonyl-4-methyl-phenyl)-ureido]-thiazol-4-ylmethyl}-sulfamoyl)-propionic acid metyl ester (116 mg, 91%) was prepared from 1-(4-aminomethyl-thiazol-2-yl)-3-(2-cyclopentanecarbonyl-4-methyl-phenyl)-urea (90 mg, 0.25 mmol) and 3-chlorosulfonyl-propionic acid methyl ester (47 mg, 0.25 mmol) following the general procedure T.

LC-MS (m/z): 509 (M+1)+; 1H NMR (400 MHz, CD3OD): δ 1.73 (m, 4H), 1.88 (m, 4H), 2.33 (s, 3H), 3.04 (t, 2H), 3.42

(t, 2H), 3.74 (p, 1H), 4.06 (d, 2H), 4.26 (s, 3H), 6.58 (s, 1H), 7.32 (d, 1H), 7.72 (s, 1H), 8.48 (d, 1H), 9.76 (br, 1H), 10.38 (br, 1H), and 11.52 (br, 1H).

Example 215

{2-[3-(2-Cyclopentanecarbonyl-5-methyl-phenyl)-ureido]-thiazol-4-yl}-acetic acid ethyl ester

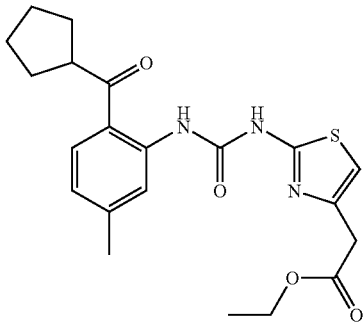

{2-[3-(2-Cyclopentanecarbonyl-5-methyl-phenyl)-ureido]-thiazol-4-yl}-acetic acid ethyl ester (154 mg, 80%) was prepared from 2-amino-4 methyl-phenyl-cyclopentyl-methanone (102 mg, 0.5 mmol) and ethyl-2-amino-4-thiazolyl acetate (112 mg, 0.5 mmol) following the general procedure D.

LC-MS (m/z): 416 (M+1)$^+$; $^1$H NMR (400 MHz, CDCl$_3$): δ 1.26 (t, 3H), 1.69 (m, 4H), 1.88 (m, 4H), 2.41 (s, 3H), 3.70 (s, 2H), 3.72 (m, 1H), 4.18 (m, 2H), 6.71 (s, 1H), 6.88 (d, 1H), 7.7.81 (d, 1H), 8.44 (s, 1H), 9.48 (br, 1H), 11.82 (br, 1H).

Example 216

{2-[3-(2-Cyclopentanecarbonyl-5-methyl-phenyl)-ureido]-thiazol-4-yl}-acetic acid

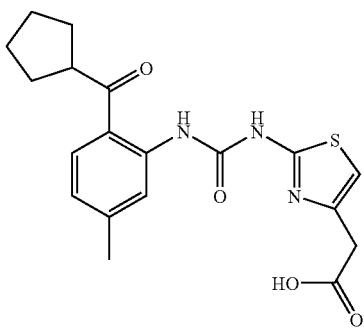

{2-[3-(2-Cyclopentanecarbonyl-5-methyl-phenyl)-ureido]-thiazol-4-yl}-acetic acid (175 mg, 90%) was prepared from {2-[3-2-cyclopentanecarbonyl-5-methyl-phenyl)-ureido]-thiazol-4-yl}-acetic acid ethyl ester (208 mg, 0.5 mmol) following the general procedure J.

LC-MS (m/z): 388 (M+1)$^+$; $^1$H NMR (400 MHz, DMSO-d$_6$): δ 1.74 (m, 4H), 1.87 (m, 4H), 2.35 (s, 3H), 3.56 (s 2H), 3.84 (m, 1H), 6.85 (s, 1H), 6.96 (d, 1H), 7.95 (d, 1H), 8.17 (s, 1H), 10.96 (br, 1H), 12.22 (br, 1H), 12.40 (br, 1H).

Example 217

{2-[3-(2-Cyclopentanecarbonyl-5-fluoro-phenyl)-ureido]-thiazol-4-yl}-acetic acid ethyl ester

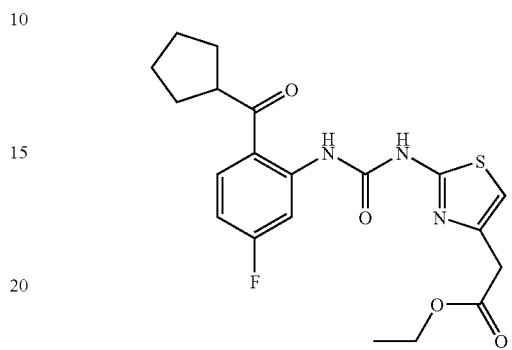

{2-[3-(2-Cyclopentanecarbonyl-4-fluorol-phenyl)-ureido]-thiazol-4-yl}-acetic acid ethyl ester (168 mg, 80%) was prepared from 2-amino-4-fluoro methyl-phenyl-cyclopentyl-methanone (103 mg, 0.5 mmol) and ethyl-2-amino-4-thiazolyl acetate(112 mg, 0.6 mmol) following the general procedure D.

LC-MS (m/z): 420 (M+1)$^+$; $^1$H NMR (400 MHz, CDCl$_3$): δ 1.26 (t, 3H), 1.69 (m, 4H), 1.88 (m, 4H), 3.67 (m, 1H), 3.72 (s, 2H), 4.18 (m, 2H), 6.68 (d, 1H), 6.75 (m, 1H), 7.93 (t, 1H), 8.44 (d, 1H), 10.20 (br, 1H), 11.90 (br, 1H).

Example 218

{2-[3-(2-Cyclopentanecarbonyl-5-fluoro-phenyl)-ureido]-thiazol-4-yl}-acetic acid

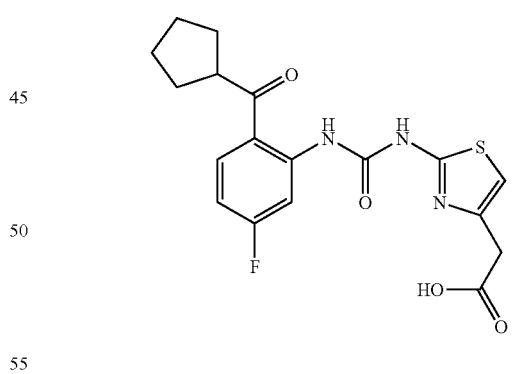

{2-[3-(2-Cyclopentanecarbonyl-5-methyl-phenyl)-ureido]-thiazol-4-yl}-acetic acid (180 mg, 92%) was prepared from {2-[3-(2-cyclopentanecarbonyl-5-methyl-phenyl)-ureido]-thiazol-4-yl}-acetic acid ethyl ester (209 mg, 0.5 mmol) following the general procedure J.

LC-MS (m/z): 392 (M+1)$^+$; $^1$H NMR (400 MHz, DMSO-d$_6$): δ 1.61 (m, 4H), 1.74 (m, 2H), 1.87 (m, 2H), 3.57 (s 2H), 3.84 (m, 1H), 6.88 (s, 1H), 6.98 (t, 1H), 8.21 (m, 2H), 11.23 (br, 1H), 12.20 (br, 1H).

Example 219

{2-[3-(4-Bromo-2-cyclopentanecarbonyl-phenyl)-ureido]-thiazol-4-yl}-acetic acid ethyl ester

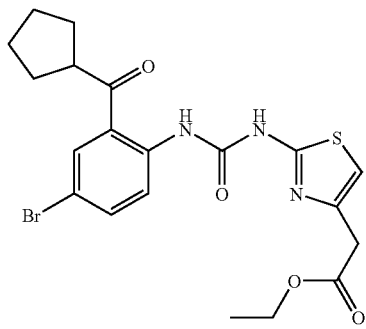

{2-[3-(4-Bromo-2-cyclopentanecarbonyl-phenyl)-ureido]-thiazol-4-yl}-acetic acid ethyl ester (192 mg, 80%) was prepared from 2-amino-5-bromo-phenyl-cyclopentyl-methanone (134 mg, 0.5 mmol) and ethyl-2-amino-4-thiazolyl acetate (112 mg, 0.6 mmol) following the general procedure D.

LC-MS (m/z): 481 (M+1)$^+$; $^1$H NMR (400 MHz, CDCl$_3$): δ 1.27 (t, 3H), 1.70 (m, 4H), 1.87 (m, 4H), 3.67 (m, 1H), 3.72 (s, 2H), 4.19 (m, 2H), 6.70 (s, 1H), 7.59 (dd, 1H), 7.99 (s, 1H), 8.53 (br, 1H), 9.59 (br, 1H), 11.56 (br, 1H).

Example 220

{2-[3-(4-Bromo-2-cyclopentanecarbonyl-phenyl)-ureido]-thiazol-4-yl}-acetic acid

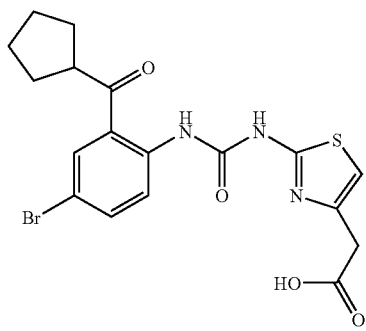

{2-[3-(4-Bromo-2-cyclopentanecarbonyl-phenyl)-ureido]-thiazol-4-yl}-acetic acid (204 mg, 90%) was prepared from {2-[3-(4-bromo-2-cyclopentanecarbonyl-phenyl)-ureido]-thiazol-4-yl}-acetic acid ethyl ester (240 mg, 0.5 mmol) following the general procedure J.

LC-MS (m/z): 453 (M+1)$^+$; $^1$H NMR (400 MHz, DMSO-d$_6$): δ 1.72 (m, 4H), 1.82 (m, 4H), 3.54 (s 2H), 3.78 (m, 1H), 6.86 (s, 1H), 7.72 (br, 1H), 8.10 (br, 1H), 8.22 (s, 1H), 10.65 (br, 1H), 11.70(br, 1H), 12.40 (br, 1H).

Example 221

{4-[3-(5-Chloro-thiazol-2-yl)-ureido]-3-cyclopentanecarbonyl-phenyl}-acetic acid ethyl ester

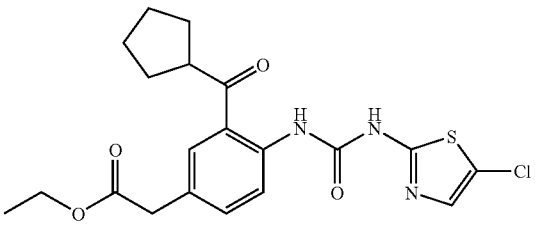

{4-[3-(5-Chloro-thiazol-2-yl)-ureido]-3-cyclopentanecarbonyl-phenyl}-acetic acid ethyl ester (157 mg, 72%) was prepared from ethyl (4-methylcarboxy)-2-cyclopentanoylaniline (138 mg, 0.5 mmol) and 5-chloro-thiazol-2-ylamine (81 mg, 0.6 mmol) following the general procedure D.

LC-MS (m/z): 436 (M+1)$^+$; $^1$H NMR (400 MHz, DMSO-d$_6$): δ 0.90 (t, 3H), 1.62 (m, 2H), 1.46 (m, 2H), 1.62 (m, 4H), 3.73 (s, 2H), 3.85 (m, 1H), 4.15 (q, 2H), 7.42 (s, 1H), 7.48 (d, 1H), 7.98 (s, 1H), 8.20 (d, 1H), 10.79 (br, 1H), 12.10 (br 1H).

Example 222

{4-[3-(5-Chloro-thiazol-2-yl)-ureido]-3-cyclopentanecarbonyl-phenyl}-acetic acid

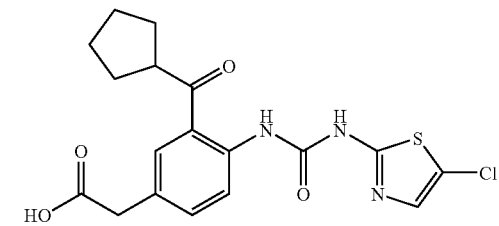

{4-[3-(5-Chloro-thiazol-2-yl)-ureido]-3-cyclopentanecarbonyl-phenyl}-acetic acid (180 mg, 88%) was prepared from {4-[3-(5-chloro-thiazol-2-yl)-ureido]-3-cyclopentanecarbonyl-phenyl}-acetic acid ethyl ester (218 mg, 0.5 mmol) following the general procedure J.

LC-MS (m/z): 408 (M+1)$^+$; $^1$H NMR (400 MHz, DMSO-d$_6$): δ 1.73 (m, 4H), 1.89 (m, 4H), 3.35 (s, 2H), 3.85 (m, 1H), 7.42 (s, 1H), 7.47 (d, 1H), 7.96 (s, 1H), 8.20 (d, 1H), 10.79 (s, 1H), 12.20 (br, 1H),

Example 223

2-{4-[3-(5-Chloro-thiazol-2-yl)-ureido]-3-cyclopentanecarbonyl-phenyl}-N-(2-methanesulfonyl-ethyl)-acetamide

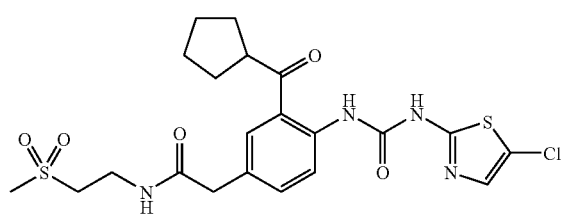

2-{4-[3-(5-Chloro-thiazol-2-yl)-ureido]-3-cyclopentanecarbonyl-phenyl}-N-(2-methanesulfonyl-ethyl)-acetamide (180 mg, 70%) was prepared from {4-[3-(5-chloro-thiazol-2-yl)-ureido]-3-cyclopentanecarbonyl-phenyl}-acetic acid (204 mg, 0.5 mmol) and 2-methanesulfonyl-ethylamine (62 mg, 0.5 mmol) following the general procedure K.

LC-MS (m/z): 514 (M+1)$^+$; $^1$H NMR (400 MHz, DMSO-d$_6$): δ 1.75 (m, 4H), 1.91 (m, 4H), 2.97 (s, 3H), 3.07 (q, 2H), 3.23 (t, 2H), 3.42 (s, 2H), 3.84 (m, 1H), 7.42 (s, 1H), 7.44 (d, 1H), 7.94 (s, 1H), 8.18 (d, 1H), 8.35 (t, 1H), 10.77 (s, 1H), 12.01 (br, 1H),

Example 224

[2-(3-{2-Cyclopentanecarbonyl-4-[(2-methanesulfonyl-ethylcarbamoyl)-methyl]-phenyl}-ureido)-thiazol-4-yl]-acetic acid ethyl ester

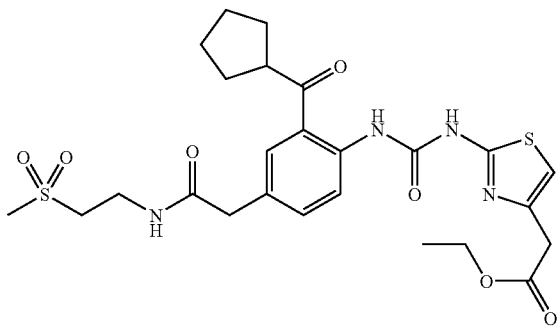

[2-(3-{2-Cyclopentanecarbonyl-4-[(2-methanesulfonyl-ethylcarbamoyl)-methyl]-phenyl}-ureido)-thiazol-4-yl]-acetic acid ethyl ester (174 mg, 65%) was prepared from 2-(4-amino-3-cyclopentanecarbonyl-phenyl)-N-(2-methanesulfonyl-ethyl)-acetamide (176 mg, 0.5 mmol) and (2-amino-thiazol-4-yl)-acetic acid ethyl ester (112 mg, 0.6 mmol) following the general procedure D.

LC-MS (m/z): 565 (M+1)$^+$; $^1$H NMR (400 MHz, CDCl$_3$): δ 1.28 (t, 3H), 1.65 (m, 4H), 1.79 (m, 2H), 1.88 (m, 2H), 3.01 (s, 3H), 3.31 (t, 2H), 3.53 (s, 2H), 3.68 (s, 2H), 3.83 (m, 1H), 4.20 (m, 3H), 7.42 (s, 1H), 7.44 (d, 1H), 7.94 (s, 1H), 8.18 (d, 1H), 8.35 (t, 1H), 10.77 (s, 1H), 12.01 (br, 1H),

Example 225

2-(3-{2-Cyclopentanecarbonyl-4-[2-methanesulfonyl-ethyl carbamoyl)-methyl]-phenyl}-ureido)-thiazol-4-yl-acetic acid

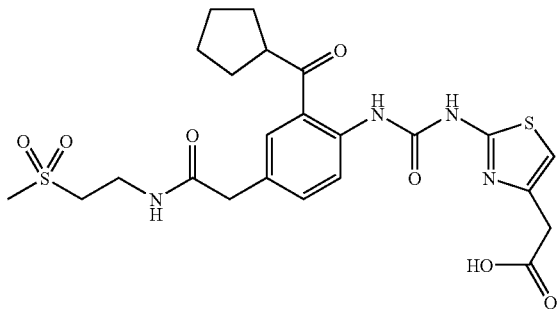

2-(3-{2-Cyclopentanecarbonyl-4-[2-methanesulfonyl-ethyl carbamoyl)-methyl]-phenyl}-ureido)-thiazol-4-yl-acetic acid (214 mg, 80%) was prepared from 2-(3-{2-cyclopentanecarbonyl-4-[2-methanesulfonyl-ethyl carbamoyl)-methyl]-phenyl}-ureido)-thiazol-4-yl-acetic acid ethyl ester (282 mg, 0.5 mmol) following the general procedure J.

LC-MS (m/z): 537 (M+1)$^+$; $^1$H NMR (400 MHz, CDCl$_3$): δ 1.65 (m, 4H), 1.79 (m, 2H), 1.88 (m, 2H), 2.97 (s, 3H), 3.22 (t, 2H), 3.45 (m, 2H), 3.47 (s, 2H), 3.56 (s, 2H), 3.82 (m, 1H), 6.84 (s, 1H), 7.42 (d, 1H), 7.92 (s, 1H), 8.18 (d, 1H), 8.33 (t, 1H), 10.70 (s, 1H), 11.84 (br, 1H),

Example 226

[3-Cyclopentanecarbonyl-4-(3-[1,3,4]thiadiazol-2-yl-ureido)-phenyl]-acetic acid ethyl ester

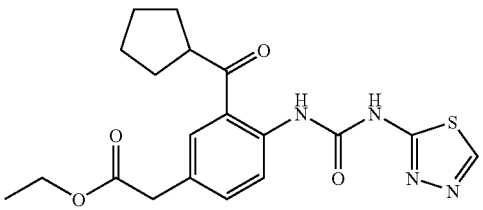

3-Cyclopentanecarbonyl-4-(3-[1,3,4]thiadiazol-2-yl-ureido)-phenyl]-acetic acid ethyl ester (147 mg, 73%) was prepared from (4-amino-3-cyclopentanecarbonyl-phenyl)-acetic acid ethyl ester (138 mg, 0.5 mmol) and [1,3,4]thiadiazol-2-ylamine (60 mg, 0.6 mmol) following the general procedure D.

LC-MS (m/z): 403 (M+1)$^+$; $^1$H NMR (400 MHz, CDCl$_3$): δ 1.27 (t, 6H), 1.67 (m, 4H), 1.91 (m, 4H), 3.64 (s, 2H), 3.77 (m, 1H), 4.17 (m, 4H), 7.46 (d, 1H), 7.89 (s, 2H), 8.47 (s, 1H), 8.77 (s, 1H), 10.40 (br, 1H), 11.89 (br, 1H).

Example 227

1-[2-Cyclopentanecarbonyl-4-(2-morpholin-4-yl-2-oxo-ethyl)-phenyl]-3-thiazol-2-yl-urea

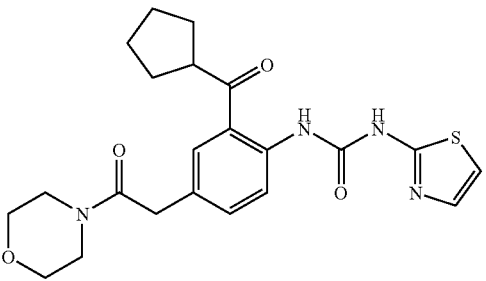

1-[2-Cyclopentanecarbonyl-4-(2-morpholin-4-yl-2-oxo-ethyl)-phenyl]-3-thiazol-2-yl-urea (151 mg, 68%) was prepared from [3-cyclopentanecarbonyl-4-(3-thiazol-2-yl-ureido) phenyl]-acetic acid (186 mg, 0.5 mmol) and morpholine (44 mg, 0.5 mmol) following the general procedure K.

LC-MS (m/z): 443 (M+1)$^+$; $^1$H NMR (400 MHz, CDCl$_3$/DMSO-d$_6$): δ 1.67 (m, 4H), 1.88 (m, 4H), 3.51 (t, 4H), 3.69 (t,

4H), 3.74 (m, 3H), 6.91 (d, 1H), 7.37 (dd, 1H), 7.64 (d, 1H), 7.84 (s, 1H), 8.52 (br, 2H), 11.32 (br, 1H).

Example 228

1-{2-Cyclopentanecarbonyl-4-[2-(4-methyl-piperazin-1-yl)-2-oxo-ethyl]-phenyl}-3-thiazol-2-yl-urea

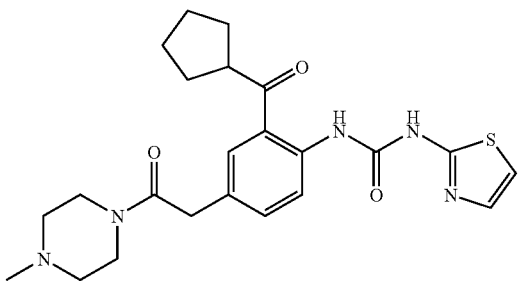

1-{2-Cyclopentanecarbonyl-4-[2-(4-methyl-piperazin-1-yl)-2-oxo-ethyl]-phenyl}-3-thiazol-2-yl-urea (137 mg, 60%) was prepared from [3-cyclopentanecarbonyl-4-(3-thiazol-2-yl-ureido)-phenyl]-acetic acid (186 mg, 0.5 mmol) and N-methyl piperazine (50 mg, 0.5 mmol) following the general procedure K.

LC-MS (m/z): 456 (M+1)$^+$; $^1$H NMR (400 MHz, CDCl$_3$/DMSO-d$_6$): δ 1.67 (m, 4H), 1.89 (m, 4H), 2.29 (s, 3H), 3.51 (t, 4H), 3.61 (s, 2H), 3.69 (m, 5H), 6.92 (d, 1H), 7.38 (d, 1H), 7.58 (s, 1H), 7.84 (s, 1H), 8.53 (d, 1H), 11.56 (br, 1H), 11.67 (br, 1H).

Example 229

{2-[3-Cyclopentanecarbonyl-4-(3-thiazol-2-yl-ureido)-phenyl]-acetylamino}-acetic acid

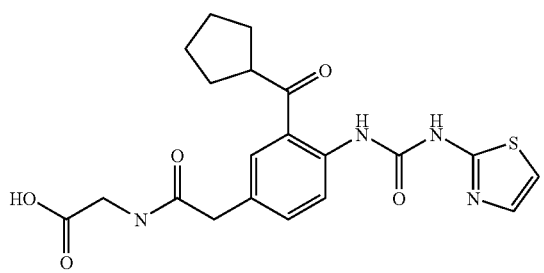

{2-[3-Cyclopentanecarbonyl-4-(3-thiazol-2-yl-ureido)-phenyl]-acetylamino}-acetic acid tert.butyl ester (158 mg, 65%) was prepared from [3-cyclopentanecarbonyl-4-(3-thiazol-2-yl-ureido)-phenyl]-acetic acid (186 mg, 0.5 mmol) and glycyne ter.butyl ester (60 mg, 0.5 mmol) following the general procedure K. The ester intermediate (122 mg, 0.25 mmol) upon hydrolysis with TFA furnished {2-[3-cyclopentanecarbonyl-4-(3-thiazol-2-yl-ureido)-phenyl]-acetylamino}-acetic acid (86 mg, 80%).

LC-MS (m/z): 431 (M+1)$^+$; $^1$H NMR (400 MHz, CDCl$_3$/DMSO-d$_6$): δ 1.67 (m, 4H), 1.94 (m, 4H), 3.69 (dd, 2H), 3.82 (m, 3H), 3.95 (t, 1H), 6.99 (m, 1H), 7.32 (dd, 1H), 7.39 (d, 1H), 7.75 (d, 1H), 8.45 (d, 1H), 12.16 (br, 1H).

Example 230

{2-[3-(2-Cyclopentanecarbonyl-4-methylcarbamoylmethyl-phenyl)-ureido]-thiazol-4-yl}-acetic acid

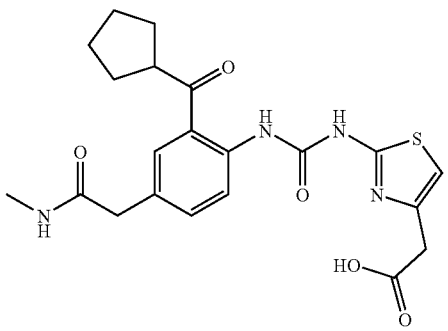

{2-[3-(2-Cyclopentanecarbonyl-4-methylcarbamoylmethyl-phenyl)-ureido]-thiazol-4-yl}-acetic acid (153 mg, 65%) was prepared from 2-(4-amino-3-cyclopentanecarbonyl-phenyl)-N-methyl-acetamide (130 mg, 0.5 mmol) and (2-amino-thiazol-4-yl)-acetic acid ethyl ester (112 mg, 0.6 mmol) following the general procedure D. The ester intermediate (236 mg, 0.5 mmol) upon hydrolysis following the general procedure J furnished {2-[3-(2-cyclopentanecarbonyl-4-methylcarbamoylmethyl-phenyl)-ureido]-thiazol-4-yl}-acetic acid (167 mg, 75%).

LC-MS (m/z): 445 (M+1)$^+$; $^1$H NMR (400 MHz, DMSO-d$_6$): δ 1.62 (m, 4H), 1.74 (m, 2H), 1.90 (m, 2H), 2.57 (d, 3H), 3.43 (s, 2H), 3.56 (s, 2H), 3.81 (m, 1H), 6.85 (d, 2H), 7.41 (d, 1H), 7.92 (s, 1H), 7.96 (d, 1H), 8.18 (d, 1H), 10.69 (s, 1H), 11.96 (br, 1H).

Example 231

{3-Cyclopentanecarbonyl-4-[3-(4-methylcarbamoylmethyl-thiazol-2-yl)-ureido]-phenyl}-acetic acid ethyl ester

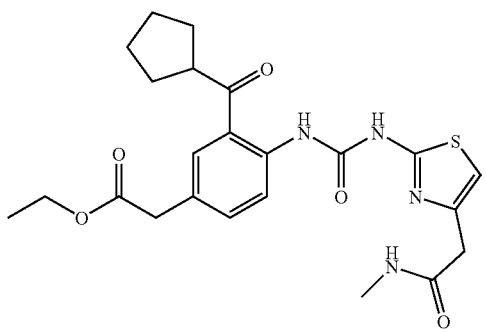

{3-Cyclopentanecarbonyl-4-[3-(4-methylcarbamoylmethyl-thiazol-2-yl)-ureido]-phenyl}-acetic acid ethyl ester (153 mg, 65%) was prepared from (4-amino-3-cyclopentanecarbonyl-phenyl)-acetic acid ethyl ester (138 mg, 0.5 mmol) and 2-(2-amino-thiazol-4-yl)-N-methyl-acetamide (103 mg, 0.6 mmol) following the general procedure D.

LC-MS (m/z): 473 (M+1)+; 1H NMR (400 MHz, CDCl3): δ 1.26 (t, 3H), 1.70 (m, 4H), 1.86 (m, 2H), 1.92 (m, 2H), 2.81 (d, 3H), 3.62 (s, 2H), 3.65 (s, 2H), 3.77 (m, 1H), 4.16 (q, 2H), 6.65 (s, 1H), 6.71 (br, 1H), 7.44 (dd, 1H), 7.88 (s, 1H), 8.52 (d, 1H), 9.39 (br, 1H), 11.71 (br, 1H).

Example 232

2-{3-Cyclopentanecarbonyl-4-[3-(4-methylcarbamoylmethyl-thiazol-2-yl)-ureido]-phenyl}-N-methylacetamide

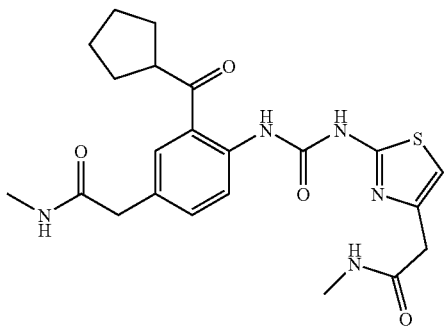

{3-Cyclopentanecarbonyl-4-[3-(4-methylcarbamoylmethyl-thiazol-2-yl)-ureido]-phenyl}-acetic acid (155 mg, 70%) was prepared from {3-cyclopentanecarbonyl-4-[3-(4-methylcarbamoylmethyl-thiazol-2-yl)-ureido]-phenyl}-acetic acid ethyl ester (236 mg, 0.5 mmol) following the general procedure J. The acid (222 mg, 0.5 mmol) was coupled with 1 N methyl amine following the general procedure K furnished 2-{3-cyclopentanecarbonyl-4-[3-(4-methylcarbamoylmethyl-thiazol-2-yl)-ureido]-phenyl}-N-methyl-acetamide (137 mg, 60%).

LC-MS (m/z): 458 (M+1)+; 1H NMR (400 MHz, CDCl3/DMSO-d6): δ 1.69 (m, 4H), 1.82 (m, 4H), 2.65 (d, 3H), 3.68 (d, 3H), 3.43 (s, 2H), 3.48 (s, 2H), 3.67 (m, 1H), 6.51 (d, 1H), 7.14 (br, 1H), 7.31 (m, 2H), 7.54 (d, 1H), 7.75 (dd, 1H), 8.31 (d, 1H), 11.13 (br, 1H).

Example 233

1-(2-Cyclopentanecarbonyl-4-methyl-phenyl)-3-{4-[2-(pyridin-2-yloxy)-ethyl]-thiazol-2-yl}-urea

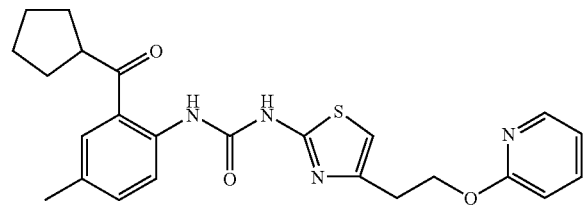

To a solution of {2-[3-(2-cyclopentanecarbonyl-4-methyl-phenyl)-ureido]-thiazol-4-yl}-acetic acid (0.38 g, 1.0 mmol) in THF (5 mL) at 0° C. was added 1.0 M solution of BH3-THF (3.0 mL, 3.0 mmol) dropwise. After stirring at 0° C. for 1 h, the excess BH3-THF complex was quenched with MeOH. The solution was concentrated under vacuum and purified on silica gel with 1:1 EtOAc/hexanes to obtain the alcohol as a white powder in 80% yield.

1-(2-Cyclopentanecarbonyl-4-methyl-phenyl)-3-{4-[2-(pyridin-2-yloxy)-ethyl]-thiazol-2-yl}-urea (30 mg, 50%) was prepared from 1-[2-(cyclopentanecarbonyl-4-methyl-phenyl]-3-[4-(2-hydroxy-ethyl)-thiazol-2-yl]-urea (0.05 g, 0.134 mmol), 2-hydroxypyridine (0.013 g, 0.143 mmol) following the general procedure P.

LC/MS (m/z): 451 (M+1)+; 1H NMR (400 MHz, CDCl3) d 1.67-1.72 (m, 4H), 1.89-1.85 (m, 4H), 2.36 (s, 3H), 3.13 (t, 2H), 3.64-3.80 (m, 1H), 4.60 (t, 2H), 6.60 (s, 1H), 6.72 (d, 1H), 6.86 (m, 1H), 7.34 (d, 1H), 7.56 (m, 1H), 7.70 (s, 1H), 8.15 (d, 1H), 8.45 (br, 1H), 11.85 (br, 1H).

Example 234

1-(2-Cyclopentanecarbonyl-4-methyl-phenyl)-3-{4-[2-(pyridin-4-yloxy)-ethyl]-thiazol-2-yl}-urea

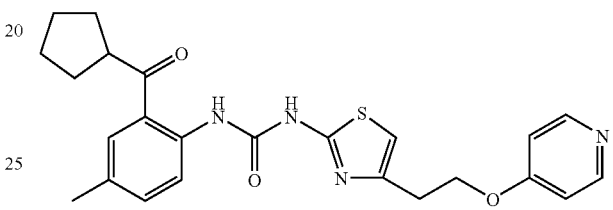

1-(2-Cyclopentanecarbonyl-4-methyl-phenyl)-3-{4-[2-(pyridin-4-yloxy)-ethyl]-thiazol-2-yl}-urea (50 mg, 42%) was prepared from 1-[2-(cyclopentanecarbonyl-4-methyl-phenyl]-3-[4-(2-hydroxy-ethyl)-thiazol-2-yl]-urea (0.10 g, 0.27 mmol) and 4-hydroxypyridine (0.05 g, 0.54 mmol) following the general procedure P.

LC/MS (m/z): 451 (M+1)+, 1H NMR (400 MHz, CDCl3) d 1.62-1.73 (m, 4H), 1.80-1985 (m, 4H), 2.37 (s, 3H), 2.85 (t, 2H), 3.87 (t, 2H), 3.75 (br, 1H), 6.52 (s, 1H), 7.46 (d, 2H) 7.48 (d, 2H), 7.52 (d, 1H), 7.70 (s, 1H), 8.44 (d, 1H).

Example 235

5-(2-{2-[3-(2-Cyclopentanecarbonyl-4-methyl-phenyl)-ureido]-thiazol-4-yl}ethoxy) nicotinic acid methyl ester

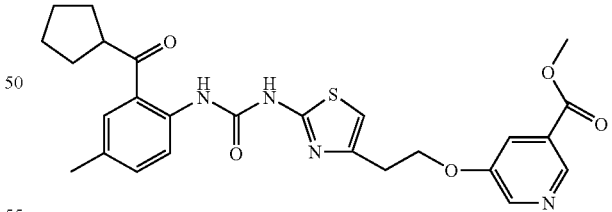

5-(2-{2-[3-(2-Cyclopentanecarbonyl-4-methyl-phenyl)-ureido]-thiazol-4-yl}ethoxy) nicotinic acid methyl ester (30 mg, 44%) was prepared from 1-[2-(cyclopentanecarbonyl-4-methyl-phenyl]-3-[4-(2-hydroxy-ethyl)-thiazol-2-yl]-urea (0.05 g, 0.134 mmol) and 5-hydroxynicotinic acid methyl ester (0.04 g, 0.27 mmol) following the general procedure P.

LC/MS (m/z): 509 (M+1)+; 1H NMR (400 MHz, CD3OD) d 1.65-1.74 (br, 4H), 1.83-1.89 (br, 4H), 2.35 (s, 3H), 3.15 (t, 2H), 3.74 (br, 1H), 3.92 (s, 3H), 4.42 (t, 2H), 6.75 (s, 1H), 7.72 (s, 1H), 7.85 (d, 1H), 8.27 (s, 1H), 8.42 (d, 1H), 8.57 (s, 1H), 8.67 (s, 1H),

Example 236

5-(2-{2-[3-(2-Cyclopentanecarbonyl 4-methyl-phenyl)-ureido]-thiazol-4-yl}ethoxy) nicotinic acid

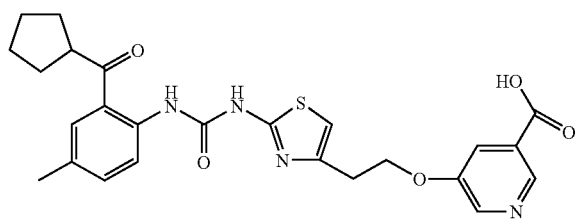

5-(2-{2-[3-(2-Cyclopentanecarbonyl-4-methyl-phenyl)-ureido]-thiazol-4-yl}ethoxy) nicotinic acid (23 mg, 95%) was prepared from 5-(2-{2-[3-(2-cyclopentanecarbonyl-4-methylphenyl)-ureido]-thiazol-4-yl}ethoxy) nicotinic acid methyl ester (0.025 g, 0.05 mmol) and 2.5M LiOH (20 ul) following the general procedure J.

LC/MS (m/z): 495 (M+1)$^+$; $^1$H NMR (400 MHz, CD$_3$OD) d 1.65-1.75 (br, 4H), 1.83-1.90 (br, 4H), 2.31 (s, 3H), 3.05 (t, 2H), 3.72-3.80 (m, 1H), 4.42 (t, 2H), 6.85 (s, 1H), 7.57 (s, 1H), 7.74 (d, 1H), 8.30 (s, 1H), 8.48 (d, 1H), 8.52 (s, 1H), 8.65 (s, 1H), 11.43 (br, 1H).

Example 237

4-(2-{2-[3-(2-Cyclopentanecarbonyl-4-methyl-phenyl)-ureido]-thiazol-4-yl}ethoxy) benzoic acid methyl ester

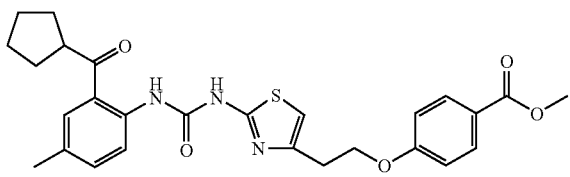

4-(2-{2-[3-(2-Cyclopentanecarbonyl-4-methyl-phenyl)-ureido]-thiazol-4-yl}ethoxy) benzoic acid methyl ester (50 mg, 37%) was prepared from 1-[2-(cyclopentanecarbonyl-4-methyl-phenyl]-3-[4-(2-hydroxy-ethyl)-thiazol-2-yl]-urea (0.10 g, 0.27 mmol) and 4-hydroxybenzoic acid methyl ester (0.08 g, 0.54 mmol) following the general procedure P.

LC/MS (m/z): 508 (M+1)$^+$; $^1$H NMR (400 MHz, CDCl$_3$) d 1.64-1.78 (m, 4H), 1.82-1.90 (m, 4H), 2.32 (s, 3H), 3.04 (t, 2H), 3.60-3.85 (m, 1H), 3.92 (s, 3H), 4.32 (t, 2H), 6.81 (s, 1H), 6.98 (d, 2H), 7.33 (d, 1H), 7.80 (s, 1H), 7.86 (d, 2H), 8.15 (br, 1H), 10.70 (br, 1H), 11.88 (br, 1H).

Example 238

4-(2-{2-[3-(2-Cyclopentanecarbonyl-4-methyl-phenyl)-ureido]-thiazol-4-yl}ethoxy) benzoic acid

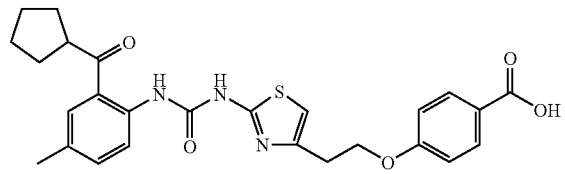

4-(2-{2-[3-(2-cyclopentanecarbonyl-4-methyl-phenyl)-ureido]-thiazol-4-yl}ethoxy) benzoic acid (19 mg, 96%) was prepared from 4-(2-{2-[3-(2-cyclopentanecarbonyl-4-methylphenyl)-ureido]-thiazol-4-yl}ethoxy) benzoic acid methyl ester (0.020 g, 0.04 mmol) and 2.5M LiOH (20 uL) following the general procedure J.

LC/MS (m/z): 494 (M+1)$^+$; $^1$H NMR (400 MHz, DMSO) d 1.65-1.78 (m, 4H), 1.80-1.92 (m, 4H), 2.32 (s, 3H), 3.04 (t, 2H), 3.60-3.85 (m, 1H), 4.34 (t, 2H), 6.82 (s, 1H), 7.01 (d, 2H), 7.36 (d, 2H), 7.81 (s, 1H), 7.86 (d, 2H), 8.13 (br, 1H), 8.88 (s, 1H), 10.66 (br, 1H).

Example 239

[4-(2-{2-[3-(2-Cyclopentanecarbonyl-4-methyl-phenyl)-ureido]-thiazol-4-yl}ethoxy)-phenyl] acetic acid methyl ester

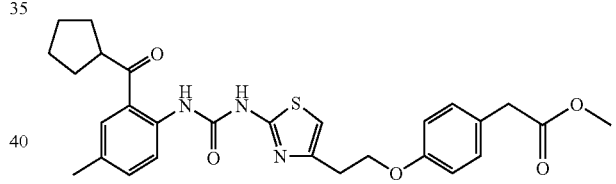

[4-(2-{2-[3-(2-Cyclopentanecarbonyl-4-methyl-phenyl)-ureido]-thiazol-4-yl}ethoxy)-phenyl] acetic acid methyl ester (56 mg, 40%) was prepared from 1-[2-(cyclopentanecarbonyl-4-methyl-phenyl]-3-[4-(2-hydroxy-ethyl)-thiazol-2-yl]-urea (0.10 g, 0.27 mmol) and 4-hydroxyphenylacetic acid methyl ester (0.09 g, 0.54 mmol) following the general procedure P.

LC/MS (M/Z): 522 (M+1)$^+$.

Example 240

[4-(2-{2-[3-(2-Cyclopentanecarbonyl-4-methyl-phenyl)-ureido]-thiazol-4-yl}ethoxy)-phenyl] acetic acid

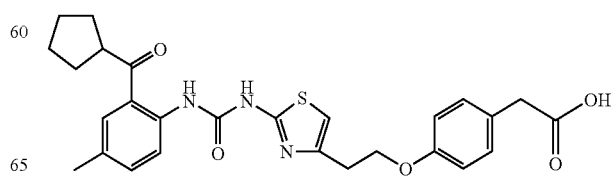

[4-(2-{2-[3-(2-Cyclopentanecarbonyl-4-methyl-phenyl)-ureido]-thiazol-4-yl}ethoxy)-phenyl] acetic acid (25 mg, 86%) was prepared from [4-(2-{2-[3-(2-Cyclopentanecarbonyl-4-methyl-phenyl)-ureido]-thiazol-4-yl}ethoxy)-phenyl] acetic acid methyl ester (0.03 g, 0.06 mmol) and 2.5M LiOH (20 uL) following the general procedure J.

LC/MS (m/z): 508 (M+1)+; $^1$H NMR (400 MHz, CDCl$_3$) d 1.65-1.76 (m, 4H), 1.83-1.95 (m, 4H), 2.36 (s, 3H), 3.10 (t, 2H), 3.70-3.82 (m, 1H), 4.24 (t, 2H), 4.96-5.02 (m, 2H), 6.50 (s, 1H), 6.88 (d, 2H), 7.20 (d, 2H), 7.30 (d, 1H), 7.68 (s, 1H), 8.45 (br, 1H), 11.45 (br, 1H).

Example 241

1-(2-Cyclopentanecarbonyl-4-methyl-phenyl)-3-[4-(2-morpholin-4-yl-ethyl)-thiazol-2-yl]-urea

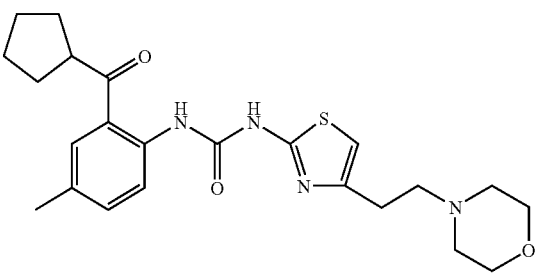

To 1-(2-cyclopentanecarbonyl-4-methyl-phenyl)-3-[4-(2-hydroxy-ethyl)-thiazol-2-yl]-urea (2.68 mmol) in CH$_2$Cl$_2$ (20 mL) at 0° C. was added Et$_3$N (1.64 mL, 11.70 mmol), dimethyl sulfoxide (10 mL) followed by sulfur trioxide-pyridine (1.46 g, 9.21 mmol). The reaction mixture was stirred for 1 h and then poured into water (30 mL), The mixture was extracted with CH$_2$Cl$_2$ and the organic layers was washed with 1.0 N ammonium chloride (2×20 mL), water (2×20 mL), brine (1×20 mL), dried (Na$_2$SO$_4$) and concentrated to give a solid. The solid was purified by column chromatography (silica, Hexanes/EtOAc, 20-50%) to obtain the aldehyde as a white solid in 50% yield.

1-(2-Cyclopentanecarbonyl-4-methyl-phenyl)-3-[4-(2-morpholin-4-yl-ethyl)-thiazol-2-yl]-urea (15 mg, 31%) was prepared from 1-(2-Cyclopentanecarbonyl-4-methyl-phenyl)-3-[4-(2-oxo-ethyl)-thiazol-2-yl]-urea (0.04 g, 0.11 mmol) and morpholine (0.009 g, 0.11 mmol) following the general procedure O.

LC/MS (m/z): 443 (M+1)+; $^1$H NMR (400 MHz, CDCl$_3$) δ 1.68-1.72 (m, 4H), 1.88-1.91 (m, 4H), 2.36 (s, 3H), 2.53 (br, 4H), 2.72 (t, 2H), 2.85 (t, 2H), 3.72-3.74 (m, 5H), 6.52 (s, 1H), 7.35 (d, 1H), 7.70 (s, 1H), 8.45 (br, 1H), 11.62 (br, 1H).

Example 242

1-(2-Cyclopentanecarbonyl-4-methyl-phenyl)-3-{4-[2-(2-morpholin-4-yl-ethylamino)-ethyl]-thiazol-2-yl}-urea

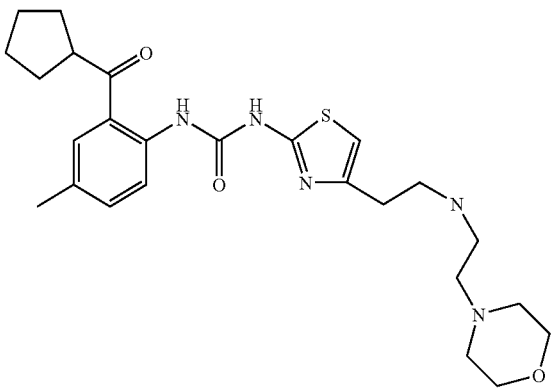

1-(2-Cyclopentanecarbonyl-4-methyl-phenyl)-3-{4-[2-(2-morpholin-4-yl-ethylamino)-ethyl]-thiazol-2-yl]-urea (23 mg, 44%) was prepared from (0.04 g, 0.11 mmol) and 4-ethylamino morpholine (0.014 g, 0.11 mmol) following the general procedure O.

LC/MS (m/z): 486 (M+1)+; $^1$H NMR (400 MHz, CDCl$_3$) δ 1.69-1.73 (m, 4H), 1.88-1.92 (m, 4H), 2.35 (s, 3H), 2.50 (t, 2H), 2.53 (br, 4H), 2.72 (t, 2H), 2.80 (t, 2H), 2.85 (t, 2H), 3.72-3.74 (m, 5H), 6.53 (s, 1H), 7.35 (d, 1H), 7.70 (s, 1H), 8.45 (br, 1H), 11.60 (br, 1H).

Example 243

1-(2-{2-[3-(2-Cyclopentanecarbonyl-4-methyl-phenyl)-ureido]-thiazol-4-yl}-ethyl)-piperidin-3-carboxylic acid ethyl ester

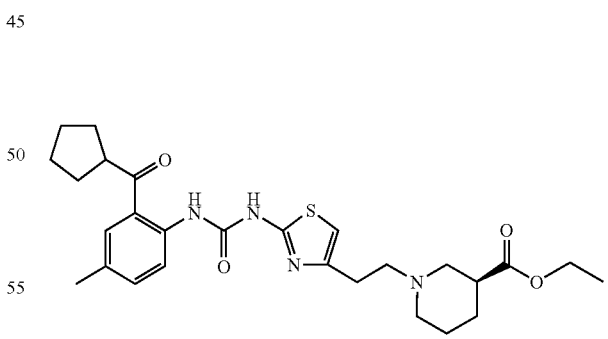

1-(2-{2-[3-(2-cyclopentanecarbonyl-4-methyl-phenyl)-ureido]-thiazol-4-yl}-ethyl)-piperidin-3-carboxylic acid ethyl ester (28 mg, 50%) was prepared from (0.04 g, 0.11 mmol) and (s)-(+)-nipecotic acid (0.017 g, 0.11 mmol) following the general procedure O.

LC/MS (m/z): 528 (M+1)+.

Example 244

1-(2-{2-[3-(2-Cyclopentanecarbonyl-4-methyl-phenyl)-ureido]-thiazol-4-yl}-ethyl)-piperidin-3-carboxylic acid

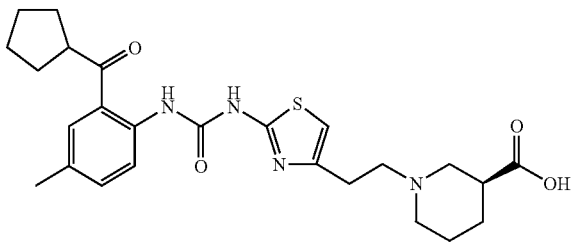

1-(2-{2-[3-(2-Cyclopentanecarbonyl-4-methyl-phenyl)-ureido]-thiazol-4-yl}-ethyl)-piperidin-3-carboxylic acid (18 mg, 95%) was prepared from 1-(2-{2-[3-(2-cyclopentanecarbonyl-4-methyl-phenyl)-ureido]-thiazol-4-yl}-ethyl)-piperidin-3-carboxylic acid ethyl ester (0.02 g, 0.04 mmol) and 2.5M LiOH (20 uL) following the general procedure J.

LC/MS (m/z): 513 (M+1)$^+$; $^1$H NMR (400 MHz, CDCl$_3$) δ 1.60-1.69 (m, 4H), 1.80-1.98 (m, 4H), 2.34 (s, 3H), 2.90-3.05 (m, 5H), 3.10-3.20 (m, 4H), 3.65-3.75 (m, 1H), 6.49 (s, 1H), 7.34 (d, 1H), 7.63 (s, 1H), 8.25 (d, 1H), 11.40 (br, 1H).

Example 245

1-(2-Cyclopentanecarbonyl-4-methyl-phenyl)-3-[4-(2-piperazin-1-yl-ethyl)-thiazol-2-yl]-urea

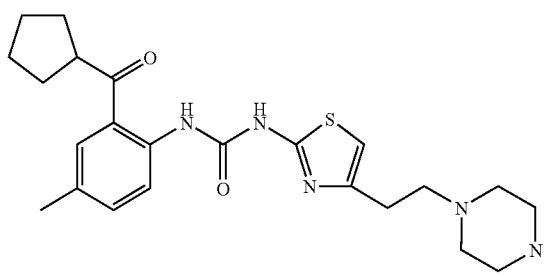

1-(2-Cyclopentanecarbonyl-4-methyl-phenyl)-3-[4-(2-piperazin-1-yl-ethyl)-thiazol-2-yl]-urea (35 mg, 70%) was prepared from methanesulfonic acid 2-{2-[3-(2-cyclopentanecarbonyl-4-methyl-phenyl)-ureido]-thiazol-4-yl}-ethyl ester (0.06 g, 0.13 mmol) and piperazine (0.50 g, 5.82 mmol) following the general procedure Z.

LC/MS (m/z): 442 (M+1)$^+$; $^1$H NMR (400 MHz, CDCl$_3$) δ 1.66-1.72 (m, 4H), 1.86-1.90 (m, 4H), 2.36 (s, 3H), 2.45-2.60 (br, 4H), 2.71 (t, 2H), 2.84 (t, 2H), 2.89-2.98 (m, 1H), 3.70-3.80 (m, 1H), 6.47 (s, 1H), 7.34 (d, 1H), 7.69 (s, 1H), 8.45 (br, 1H), 11.45 (br, 1H).

Example 246

1-(2-Cyclopentanecarbonyl-4-methyl-phenyl)-3-{4-[2-(4-methanesufonyl-piperazin-1-yl-ethyl]-thiazol-2-yl}-urea

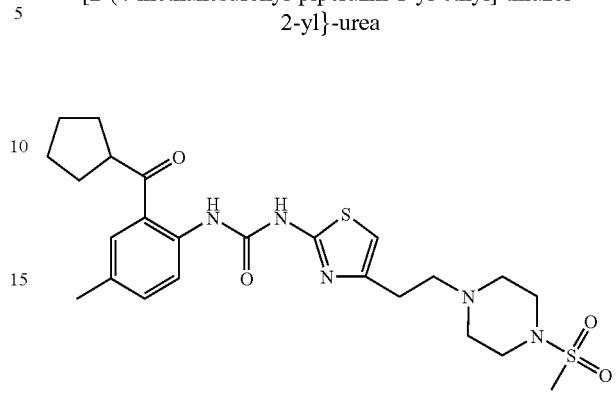

1-(2-Cyclopentanecarbonyl-4-methyl-phenyl)-3-{4-[2-(4-methanesufonyl-piperazin-1-yl-ethyl]-thiazol-2-yl}-urea (14 mg, 40%) was prepared from 1-(2-cyclopentanecarbonyl-4-methyl-phenyl)-3-[4-(2-piperazin-1-yl-ethyl)-thiazol-2-yl]-urea (0.03 g, 0.07 mmol) and sulfonyl chloride (0.008 g, 0.068 mmol) following the general procedure T.

LC/MS (m/z): 520 (M+1)$^+$; $^1$H NMR (400 MHz, CDCl$_3$) δ 1.65-1.75 (m, 4H), 1.85-1.95 (m, 4H), 2.37 (s, 3H), 2.60-2.64 (br, 4H), 2.76-2.95 (m, 4H), 2.78 (s, 3H), 3.25 (br, 4H), 3.70-3.80 (m, 1H), 6.50 (s, 1H), 7.35 (d, 1H), 7.70 (s, 1H), 8.45 (br, 1H), 11.65 (br, 1H).

Example 247

1-[4-(2-Amino-ethyl)-thiazol-2-yl]-3-(2-cyclopentanecarbonyl-4-methyl-phenyl)-urea

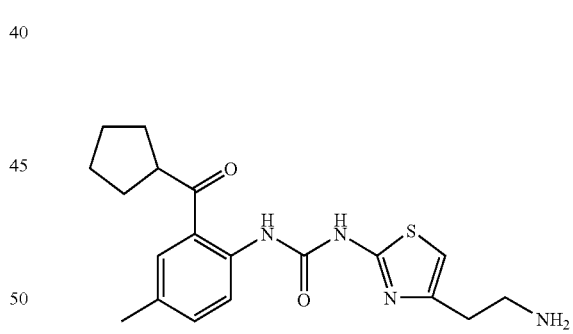

1-[4-2-Amino-ethyl)-thiazol-2-yl]-3-(2-cyclopentanecarbonyl-4-methyl-phenyl)-urea (0.15 g, 94%) was prepared from 1-[4-(2-azido-ethyl)-thiazol-2-yl]-3-(2-cyclopentanecarbonyl-4-methyl-phenyl)-urea (0.17 g, 0.43 mmol) following the general procedure T.

LC/MS (m/z): 373 (M+1)$^+$; $^1$H NMR (400 MHz, CDCl$_3$) δ 1.68-1.74 (m, 4H), 1.88-1.93 (m, 4H), 2.36 (s, 3H), 2.84 (t, 2H), 3.28 (t, 2H), 3.72-3.80 (m, 1H), 4.5 (br, 2H), 6.47 (s, 1H), 7.34 (d, 1H), 7.69 (s, 1H), 8.55 (d, 1H), 11.34 (br, 1H).

Example 248

3-(2-{-2-[3-(2-Cyclopentanecarbonyl-4-methyl-phenyl)-ureido]-thiazol-4-yl}-ethyl amino)-propionic acid

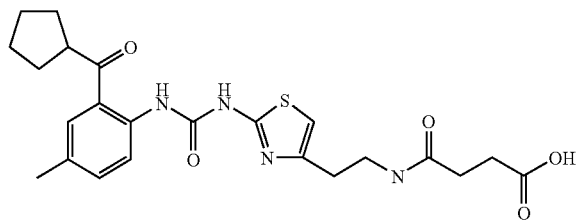

1-[4-(amino-ethyl)-thiazol-2-yl]-3-(2-cyclopentanecarbonyl-4-methyl-phenyl)-urea (0.03 g, 0.08 mmol) and succinic anhydride (0.02 g, 0.16 mmol) in 10 mL DCM were refluxed for 2 h. Reaction was concentrated and purified on silica gel using 5% MeOH/EtOAc to yield the pure product (20 mg, 53%).

LC/MS (m/z): 473 (M+1)+; 1H NMR (400 MHz, DMSO) δ 1.60-1.75 (m, 4H), 1.85-1.92 (m, 4H), 2.38 (s, 3H), 2.67 (t, 2H), 3.28-3.32 (m, 4H), 3.80-3.92 (br, 1H), 4.02 (t, 2H), 6.70 (s, 1H), 7.38 (d, 1H), 7.83 (s, 1H), 8.15 (d, 1H), 10.65 (br, 1H).

Example 249

(2-{-2-[3-(2-Cyclopentanecarbonyl-4-methyl-phenyl)-ureido]-thiazol-4-yl}-ethyl amino)-acetic acid methyl ester

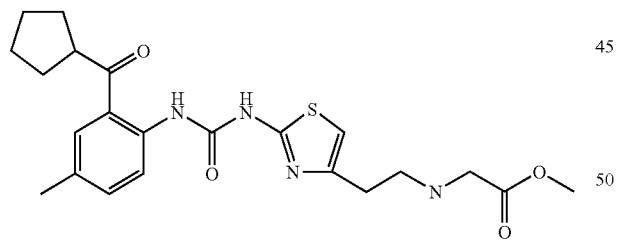

To 1-[4-(amino-ethyl)-thiazol-2-yl]-3-(2-cyclopentanecarbonyl-4-methyl-phenyl)-urea (0.03 g, 0.08 mmol) in 10 mL DCM was added methyl bromoacetate (0.01 g, 0.08 mmol) followed by Et3N (0.008 g, 0.08 mmol). After stirring at room temperature overnight, reation was concentrated and purified by flash chromatography on silica gel with 5% MeOH/EtOAc to obtain the product in 50% yield.

LC/MS (m/z): 445 (M+1)+

Example 250

(2-{-2-[3-(2-Cyclopentanecarbonyl-4-methyl-phenyl)-ureido]-thiazol-4-yl}-ethyl amino)-acetic acid

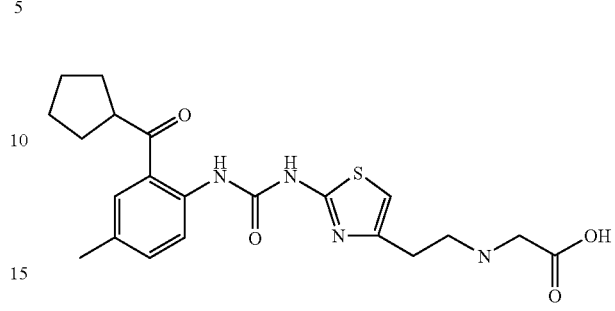

(2-{-2-[3-(2-cyclopentanecarbonyl-4-methyl-phenyl)-ureido]-thiazol-4-yl}-ethyl amino)-acetic acid (18 mg, 95%) was prepared from (2-{-2-[3-(2-cyclopentanecarbonyl-4-methyl-phenyl)-ureido]-thiazol-4-yl}-ethyl amino)-acetic acid ethyl ester (0.02 g, 0.05 mmol) and 2.5M LiOH (20 uL) following the general procedure J.

LC/MS (m/z): 431 (M+1)+; 1H NMR (400 MHz, CDCl3) δ 1.63-1.74 (m, 4H), 1.86-1.92 (m, 4H), 2.36 (s, 3H), 2.81 (t, 2H), 3.07 (t, 2H), 3.59 (s, 2H), 3.69-3.76 (m, 1H), 6.54 (s, 1H), 7.33 (d, 1H), 7.70 (s, 1H), 8.46 (br, 1H), 11.60 (br, 1H).

Example 251

N-(2-{-2-[3-(2-Cyclopentanecarbonyl-4-methyl-phenyl)-ureido]-thiazol-4-yl}-ethyl)-acetamide

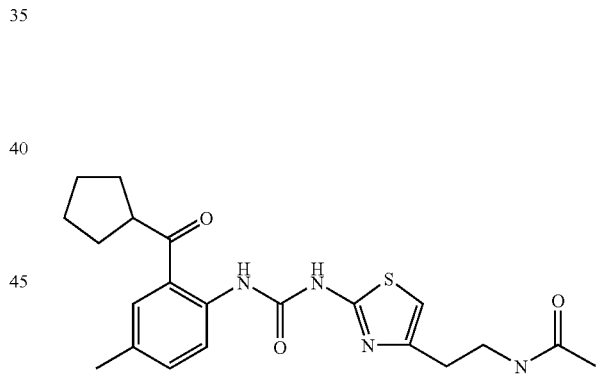

To 1-[4-(amino-ethyl)-thiazol-2-yl]-3-(2-cyclopentanecarbonyl-4-methyl-phenyl)-urea (0.05 g, 0.13 mmol) in 10 mL DCM at 0° C. was added acetyl chloride (0.02 g, 0.27 mmol) followed by pyridine (0.02 g, 0.21 mmol). After stirring for 3 h, reaction was concentrated and purified by flash chromatography on silica gel with 50% EtOAc/hexane to obtain the product in 64% yield.

LC/MS (m/z): 415 (M+1)+; 1H NMR (400 MHz, CDCl3) δ 1.65-1.75 (m, 4H), 1.84-1.90 (m, 4H), 1.97 (s, 3H), 2.37 (s, 3H), 2.84 (t, 2H), 3.58 (t, 2H), 3.70-3.80 (m, 1H), 6.54 (s, 1H), 7.34 (d, 1H), 7.70 (s, 1H), 8.45 (br, 1H), 11.65 (br, 1H).

Example 252

N-(2-{-2-[3-(2-Cyclopentanecarbonyl-4-methyl-phenyl)-ureido]-thiazol-4-yl}-ethyl)-methane-sulfonamide

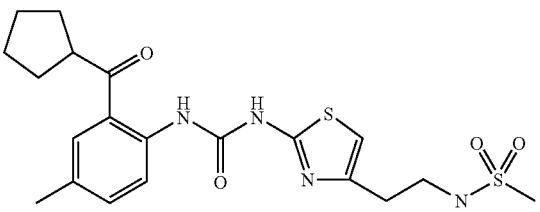

To 1-[4-(amino-ethyl)-thiazol-2-yl]-3-(2-cyclopentanecarbonyl-4-methyl-phenyl)-urea (0.05 g, 0.13 mmol) in 10 mL DCM at 0° C. was added methanesulfonyl chloride (0.02 g, 0.13 mmol) followed by pyridine (0.02 g, 0.21 mmol). The reaction was stirred at ambient temperature overnight, concentrated and purified by flash chromatography on silica gel with 20-50% EtOAc/hexane to obtain the product as white solid in 75% yield.

LC/MS (m/z): 451 (M+1)$^+$; $^1$H NMR (400 MHz, DMSO) δ 1.62-1.76 (m, 4H), 1.82-1.92 (m, 4H), 2.32 (s, 3H), 2.75 (t, 2H), 2.84 (s, 3H), 3.80-3.90 (m, 1H), 4.10 (t, 2H), 6.76 (s, 1H), 7.37 (d, 1H), 7.83 (s, 1H), 8.16 (d, 1H), 10.64 (br, 1H), 11.80 (br, 1H).

Example 253

N-(2-{2-[3-(2-Cyclopentanecarbonyl-4-methyl-phenyl)-ureido]-thiazol-4-yl}-ethyl)-2-dimethylamino acetamide

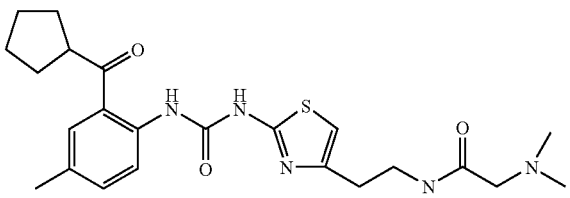

N-(2-{-2-[3-(2-Cyclopentanecarbonyl-4-methyl-phenyl)-ureido]-thiazol-4-yl}-ethyl)-2-dimethylamino acetamide (37 mg, 61%) was prepared from 1-[4-(amino-ethyl)-thiazol-2-yl]-3-(2-cyclopentanecarbonyl-4-methyl-phenyl)-urea (0.05 g, 0.13 mmol), dimethylamino acetic acid (0.02 g, 0.13 mmol) following the general procedure K.

LC/MS (m/z): 458 (M+1)$^+$; $^1$H NMR (400 MHz, CD$_3$OD) δ 1.63-1.70 (m, 4H), 1.80-1.95 (m, 4H), 2.36 (s, 3H), 2.70 (s, 6H), 2.85 (t, 2H), 3.60 (t, 2H), 3.62 (s, 2H), 3.86 (br, 1H), 6.65 (s, 1H), 7.38-7.28 (m, 2H), 7.65-7.74 (m, 1H), 7.80 (br, 1H), 8.20 (br, 1H),

Example 254

N-(2-{2-[3-(2-Cyclopentanecarbonyl-4-methyl-phenyl)-ureido]-thiazol-4-yl}-ethyl)-succinamic acid

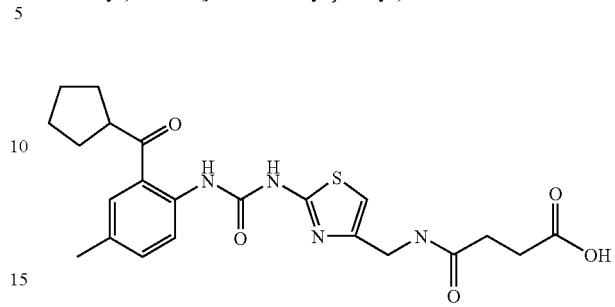

1-[4-(amino-methyl)-thiazol-2-yl]-3-(2-cyclopentanecarbonyl-4-methyl-phenyl)-urea (0.10 g, 0.28 mmol) and succinic anhydride (0.08 g, 0.78 mmol) in 10 mL DCM were refluxed for 2 h. Reaction was concentrated and purified on silica gel using 5% MeOH/EtOAc to yield the desired product (77 mg, 60%).

LC/MS (m/z): 459 (M+1)$^+$; $^1$H NMR (400 MHz, CD$_3$OD) δ 1.70-1.77 (m, 4H), 1.85-1.95 (m, 4H), 2.39 (s, 3H), 2.62-2.72 (m, 4H), 3.71 (s, 2H), 3.80-3.90 (m, 1H), 6.08 (s, 1H), 7.40-(d, 1H), 7.75 (s, 1H), 8.70 (d, 1H), 11.30 (s, 1H),

Example 255

3-{2-[3-(2-Cyclopentanecarbonyl-4-methyl-phenyl)-ureido]-thiazol-4-yl}-acrylic acid ethyl ester

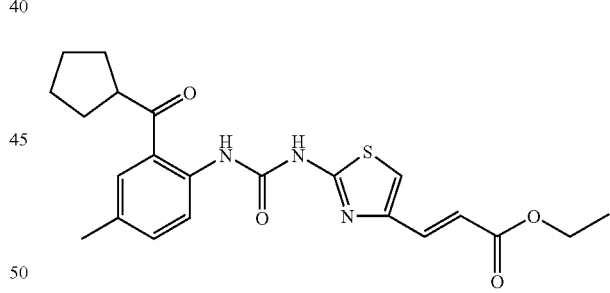

3-{2-[3-(2-Cyclopentanecarbonyl-4-methyl-phenyl)-ureido]-thiazol-4-yl}-acrylic acid ethyl ester (70 mg, 58%) was prepared from 1-(2-Cyclopentanecarbonyl-4-methyl-phenyl)-3-[4-(1-oxo-methyl)-thiazol-2-yl]-urea (0.10 g, 0.28 mmol) and (carbethoxymethylene)-triphenylphosphorane (0.12 g, 0.34 mmol) following the general procedure X.

LC/MS (m/z): 428 (M+1)$^+$; $^1$H NMR (400 MHz, CDCl$_3$) δ 1.29 (t, 3H), 1.67-1.75 (m, 4H), 1.80-1.95 (m, 4H), 2.37 (s, 3H), 3.70-3.80 (m, 1H), 4.19-4.22 (q, 2H), 6.56 (d, 1H), 7.07 (s, 1H), 7.36 (d, 1H), 7.50 (d, 1H), 7.72 (s, 1H), 8.45 (d, 1H),

Example 256

3-{2-[3-(2-Cyclopentanecarbonyl-4-methyl-phenyl)-ureido]-thiazol-4-yl}-propionic acid ethyl ester

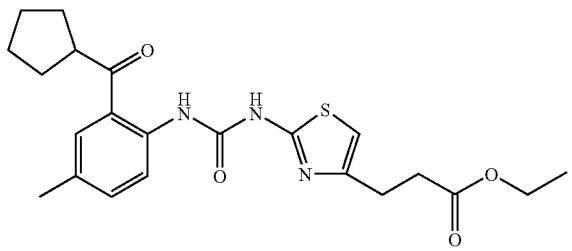

3-{2-[3-(2-Cyclopentanecarbonyl-4-methyl-phenyl)-ureido]-thiazol-4-yl}-propionic acid ethyl ester (48 mg, 96%) was prepared by hydrogenation of 3-{2-[3-(2-Cyclopentanecarbonyl-4-methyl-phenyl)-ureido]-thiazol-4-yl}-acrylic acid ethyl ester (0.05 g, 0.12 mmol) with Pd/C.

LC/MS (m/z): 430 (M+1)$^+$; $^1$H NMR (400 MHz, CDCl$_3$) δ 1.22 (t, 3H), 1.64-1.70 (m, 4H), 1.80-1.95 (m, 4H), 2.35 (s, 3H), 2.69 (t, 2H), 2.98 (t, 2H), 3.67-3.80 (m, 1H), 4.01-4.15 (q, 2H), 6.50 (s, 1H), 7.32 (d, 1H), 7.68 (s, 1H), 8.45 (br, 1H), 11.60 (br, 1H).

Example 257

3-{2-[3-(2-Cyclopentanecarbonyl-4-methyl-phenyl)-ureido]-thiazol-4-yl}-propionic acid

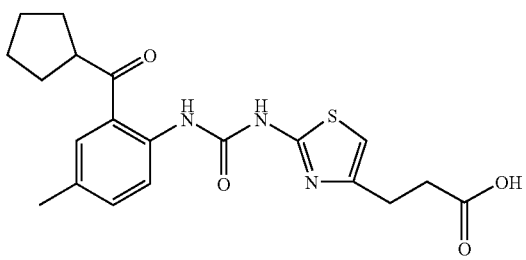

3-{2-[3-(2-Cyclopentanecarbonyl-4-methyl-phenyl)-ureido]-thiazol-4-yl}-propionic acid (15 mg, 88%) was prepared from 3-{2-[3-(2-Cyclopentanecarbonyl-4-methyl-phenyl)-ureido]-thiazol-4-yl}-propionic acid ethyl ester (0.03 g, 0.04 mmol) and 2.5M LiOH (20 μL) following the general procedure J.

LC/MS (m/z): 402 (M+1)$^+$; $^1$H NMR (400 MHz, CD$_3$OD) δ 1.70-1.80 (m, 4H), 1.82-1.95 (m, 4H), 2.34 (s, 3H), 2.58 (t, 2H), 2.80 (t, 2H), 3.82-3.94 (m, 1H), 6.69 (s, 1H), 7.38 (d, 1H), 7.85 (s, 1H), 8.19 (br, 1H), 10.65 (br, 1H).

Example 258

4-{2-[3-(2-Cyclopentanecarbonyl-4-methyl-phenyl)-ureido]-thiazol-4-yl}-but-2-enoic acid ethyl ester

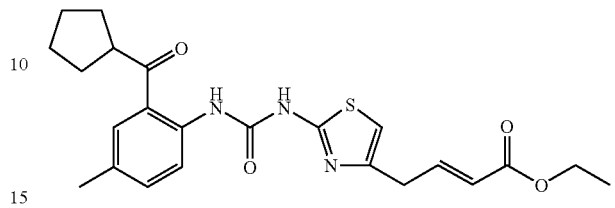

4-{2-[3-(2-Cyclopentanecarbonyl-4-methyl-phenyl)-ureido]-thiazol-4-yl}-but-2-enoic acid ethyl ester (50 mg, 42%) was prepared from 1-(2-Cyclopentanecarbonyl-4-methyl-phenyl)-3-[4-(2-oxo-ethyl)-thiazol-2-yl]-urea (0.10 g, 0.27 mmol) and (carbethoxymethylene)-triphenylphosphorane (0.09 g, 0.27 mmol) following the general procedure X.

LC/MS (m/z): 442 (M+1)$^+$; $^1$H NMR (400 MHz, CDCl$_3$) δ 1.28 (t, 3H), 1.67-1.73 (m, 4H), 2.37 (s, 3H), 3.56 (d, 1H), 3.70-3.80 (m, 1H), 4.15-4.21 (q, 2H), 5.88 (d, 1H), 6.55 (s, 1H), 7.37 (d, 1H), 7.65 (s, 1H), 8.43 (br, 1H), 11.65 (br, 1H).

Example 259

1-(2-Cyclopentanecarbonyl-4-methyl-phenyl)-3-[4-(1H-imidazol-2-ylsulfanylmethyl)-thiazol-2-yl]-urea

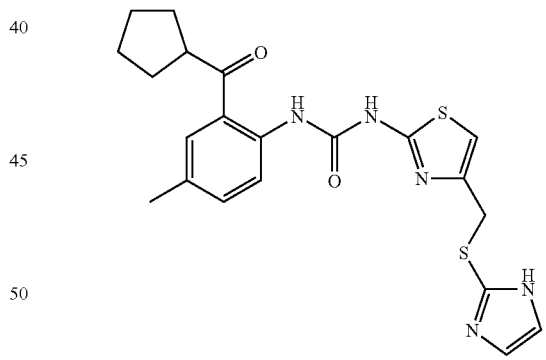

1-(2-Cyclopentanecarbonyl-4-methyl-phenyl)-3-[4-(1H-imidazol-2-ylsulfanylmethyl)-thiazol-2-yl]-urea (76 mg, 69%) was prepared from 1-(4-Chloromethyl-thiazol-2-yl)-3-(2-cyclopentanecarbonyl-4-methyl-phenyl)-urea (94 mg, 0.25 mmol) following the general procedure Q.

LC-MS (m/z): 442 (M+1)$^+$; $^1$H NMR (400 MHz, CDCl$_3$): δ 1.76 (m, 4H), 1.92 (m, 4H), 2.32 (s, 3H), 3.88 (p, 1H), 4.43 (s, 2H), 6.94 (s, 1H), 7.11 (d, 1H), 7.36 (d, 1H), 7.88 (d, 1H), 7.71 (s, 1H), 8.52 (d, 1H), 10.34 (br, 2H), and 11.42 (br, 1H).

Example 260

1-(2-Cyclopentanecarbonyl-4-methyl-phenyl)-3-[4-(1-methyl-1H-tetrazol-5-ylsulfanylmethyl)-thiazol-2-yl]-urea

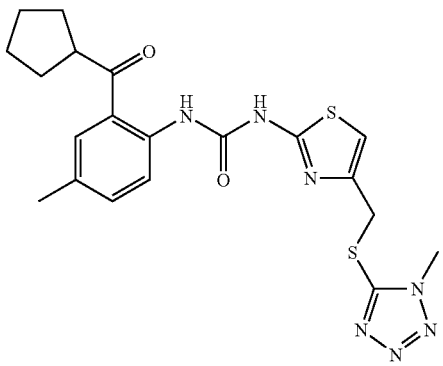

1-(2-Cyclopentanecarbonyl-4-methyl-phenyl)-3-[4-(1-methyl-1H-tetrazol-5-ylsulfanylmethyl)-thiazol-2-yl]-urea (93 mg, 79%) was prepared from 1-(4-chloromethyl-thiazol-2-yl)-3-(2-cyclopentanecarbonyl-4-methyl-phenyl)-urea (94 mg, 0.25 mmol) following the general procedure Q.

LC-MS (m/z): 458 (M+1)$^+$; $^1$H NMR (400 MHz, CDCl$_3$): δ 1.73 (m, 4H), 1.88 (m, 4H), 2.37 (s, 3H), 3.76 (p, 1H), 3.86 (s, 3H), 4.55 (s, 2H), 6.88 (s, 1H), 7.34 (d, 1H), 7.70 (s, 1H), 8.40 (d, 1H), 8.52 (br, 1H), and 11.78 (br, 1H).

Example 261

1-(2-Cyclopentanecarbonyl-4-methyl-phenyl)-3-[4-(9H-purin-6-ylsulfanylmethyl)-thiazol-2-yl]-urea

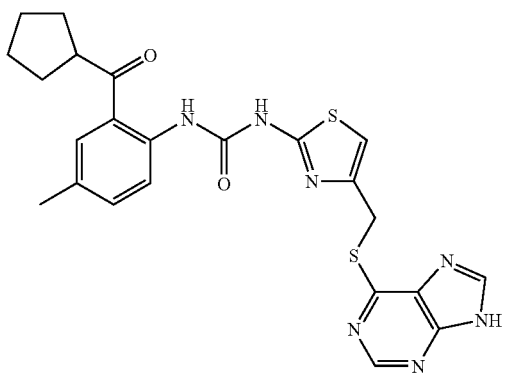

1-(2-Cyclopentanecarbonyl-4-methyl-phenyl)-3-[4-(9H-purin-6-ylsulfanylmethyl)-thiazol-2-yl]-urea (106 mg, 86%) was prepared from 1-(4-chloromethyl-thiazol-2-yl)-3-(2-cyclopentanecarbonyl-4-methyl-phenyl)-urea (94 mg, 0.25 mmol) following the general procedure Q.

LC-MS (m/z): 494 (M+1)$^+$; $^1$H NMR (400 MHz, CDCl$_3$): δ 1.66 (m, 4H), 1.84 (m, 4H), 2.21 (s, 3H), 3.72 (p, 1H), 4.29 (s, 2H), 4.63 (br, 1H), 6.78 (s, 1H), 7.11 (s, 1H), 7.28 (d, 1H), 7.75 (s, 1H), 8.13 (s, 1H), 8.42 (d, 1H), 9.24 (br, 1H), and 11.40 (br, 1H).

Example 262

1-(2-Cyclopentanecarbonyl-4-methyl-phenyl)-3-[4-(9H-purine-6-sulfonylmethyl)-thiazol-2-yl]-urea

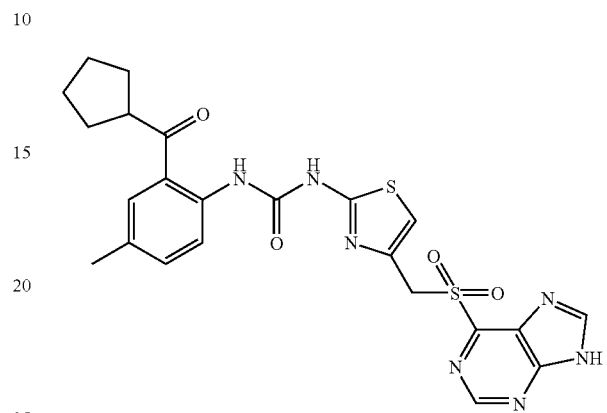

1-(2-Cyclopentanecarbonyl-4-methyl-phenyl)-3-[4-(9H-purine-6-sulfonylmethyl)-thiazol-2-yl]-urea (78 mg, 74%) was prepared from 1-(2-cyclopentanecarbonyl-4-methyl-phenyl)-3-[4-(9H-purin-6-ylsulfanylmethyl)-thiazol-2-yl]-urea (99 mg, 0.20 mmol) and following the general procedure R to give title compound.

LC-MS (m/z): 526 (M+1)$^+$; $^1$H NMR (400 MHz, CDCl$_3$): δ 1.58 (m, 4H), 1.66 (m, 2H), 1.74 (m, 2H), 2.32 (s, 3H), 3.74 (p, 1H), 4.58 (s, 2H), 6.71 (d, 1H), 7.06 (d, 1H), 7.16 (s, 1H), 7.42 (d, 1H), 7.72 (br, 1H), 8.18 (d, 1H), 8.98 (s, 1H), 9.88 (br, 1H), and 10.26 (br, 1H).

Example 263

1-(2-Cyclopentanecarbonyl-4-methyl-phenyl)-3-[4-(pyridin-4-ylsulfanylmethyl)-thiazol-2-yl]-urea

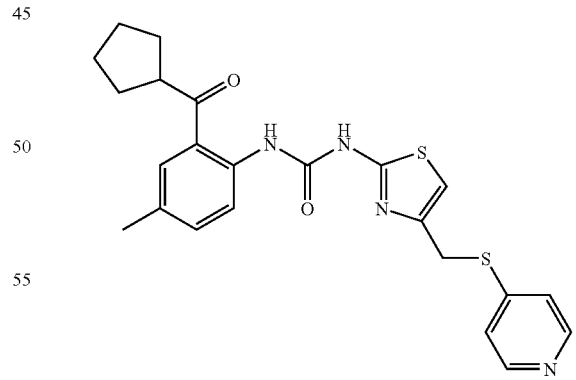

1-(2-Cyclopentanecarbonyl-4-methyl-phenyl)-3-[4-(pyridin-4-ylsulfanylmethyl)-thiazol-2-yl]-urea (79 mg, 70%) was prepared from 1-(4-chloromethyl-thiazol-2-yl)-3-(2-cyclopentanecarbonyl-4-methyl-phenyl)-urea (94 mg, 0.25 mmol) following the general procedure Q.

LC-MS (m/z): 453 (M+1)$^+$; $^1$H NMR (400 MHz, CDCl$_3$): δ 1.68 (m, 4H), 1.86 (m, 4H), 2.36 (s, 3H), 3.76 (p, 1H), 4.21

(s, 2H), 6.78 (s, 1H), 7.16-7.20 (dd, 2H), 7.34 (d, 1H), 7.70 (s, 1H), 8.13 (s, 1H), 8.38 (dd, 1H), 8.42 (d, 1H), 9.46 (br, 1H), and 11.70 (br, 1H).

Example 264

1-(2-Cyclopentanecarbonyl-4-methyl-phenyl)-3-[4-(pyridine-4-sulfonylmethyl)-thiazol-2-yl]-urea

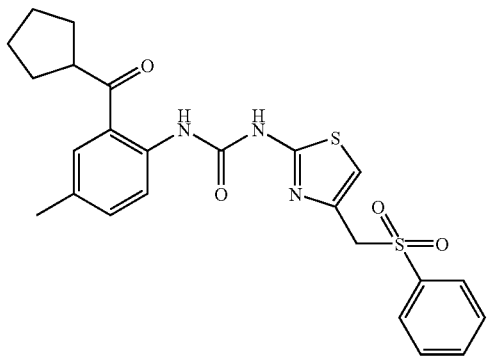

1-(2-Cyclopentanecarbonyl-4-methyl-phenyl)-3-[4-(pyridine-4-sulfonylmethyl)-thiazol-2-yl]-urea (73 mg, 75%) was prepared from 1-(2-cyclopentanecarbonyl-4-methyl-phenyl)-3-[4-(pyridin-4-ylsulfanylmethyl)-thiazol-2-yl]-urea (90 mg, 0.20 mmol) and following the general procedure R.

LC-MS (m/z): 485 (M+1)$^+$; $^1$H NMR (400 MHz, CDCl$_3$): δ 1.66 (m, 4H), 1.86 (m, 4H), 2.37 (s, 3H), 3.78 (p, 1H), 4.49 (s, 2H), 6.88 (s, 1H), 7.36 (d, 1H), 7.62 (dd, 2H), 7.72 (s, 1H), 8.42 (d, 1H), 8.86 (d, 2H), 9.40 (br, 1H), and 11.52 (br, 1H).

Example 265

(5-{2-[3-(2-Cyclopentanecarbonyl-4-methyl-phenyl)-ureido]-thiazol-4-ylmethylsulfanyl}-tetrazol-1-yl)-acetic acid

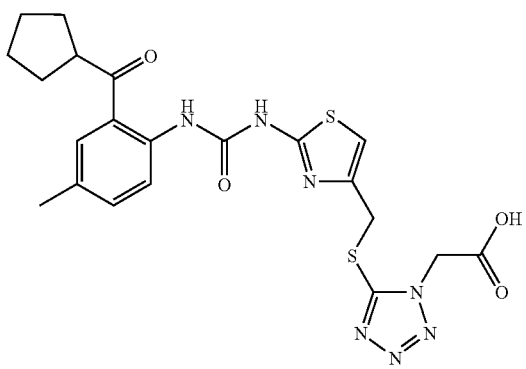

(5-{2-[3-(2-Cyclopentanecarbonyl-4-methyl-phenyl)-ureido]-thiazol-4-ylmethylsulfanyl}-tetrazol-1-yl)-acetic acid (100 mg, 80%) was prepared from 1-(4-chloromethyl-thiazol-2-yl)-3-(2-cyclopentanecarbonyl-4-methyl-phenyl)-urea (94 mg, 0.25 mmol) following the general procedure Q.

LC-MS (m/z): 501 (M+1)$^+$; $^1$H NMR (400 MHz, CDCl$_3$): δ 1.74 (m, 4H), 1.90 (m, 4H), 2.33 (s, 3H), 3.72 (p, 1H), 4.22 (s, 2H), 5.00 (s, 2H), 6.92 (s, 1H), 7.52 (d, 1H), 7.72 (s, 1H), 8.38 (d, 1H), 9.82 (br, 1H), 10.32 (br, 1H), and 11.70 (br, 1H).

Example 266

(5-{2-[3-(2-Cyclopentanecarbonyl-4-methyl-phenyl)-ureido]-thiazol-4-ylmethyl sulfanyl}-4-cyclopropyl-4H-[1,2,4]triazol-3-ylmethyl)-carbamic acid tert-butyl ester

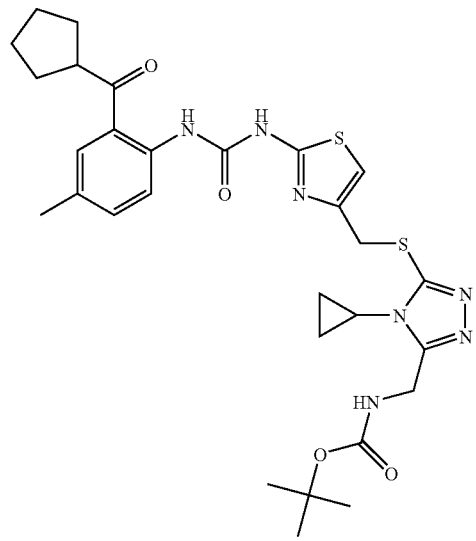

(5-{2-[3-(2-Cyclopentanecarbonyl-4-methyl-phenyl)-ureido]-thiazol-4-ylmethyl sulfanyl}-4-cyclopropyl-4H-[1,2,4]triazol-3-ylmethyl)-carbamic acid tert-butyl ester (136 mg, 89%) was prepared from 1-(4-chloromethyl-thiazol-2-yl)-3-(2-cyclopentanecarbonyl-4-methyl-phenyl)-urea (94 mg, 0.25 mmol) following the general procedure Q.

LC-MS (m/z): 612 (M+1)$^+$; $^1$H NMR (400 MHz, CDCl$_3$): δ 1.04 (m, 2H), 1.14 (m, 2H), 1.40 (s, 9H), 1.66 (m, 4H), 1.84 (m, 4H), 2.35 (s, 3H), 2.88 (p, 1H), 3.70 (p, 1H), 4.52 (s, 2H), 4.54 (s, 2H), 5.78 (br, 1H), 6.80 (s, 1H), 7.34 (d, 1H), 7.66 (s, 1H), 8.32 (d, 1H), 10.24 (br, 1H), and 11.36 (br, 1H).

Example 267

1-[4-(5-Aminomethyl-4-cyclopropyl-4H-[1,2,4]triazol-3-ylsulfanylmethyl)-thiazol-2-yl]-3-(2-cyclopentanecarbonyl-4-methyl-phenyl)-urea hydrochloride salt

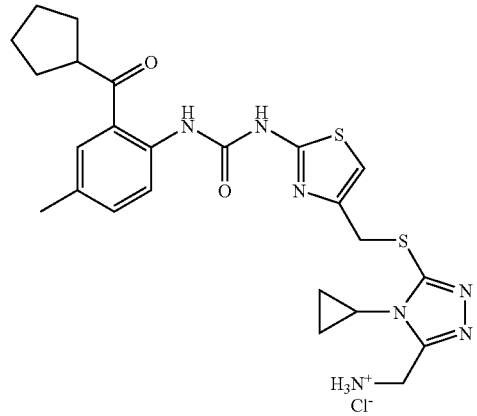

1-[4-(5-Aminomethyl-4-cyclopropyl-4H-[1,2,4]triazol-3-ylsulfanylmethyl)-thiazol-2-yl]-3-(2-cyclopentanecarbonyl-4-methyl-phenyl)-urea (51 mg, 99%) was prepared from (5-{2-[3-(2-Cyclopentanecarbonyl-4-methyl-phenyl)-ureido]-thiazol-4-ylmethyl sulfanyl}-4-cyclopropyl-4H-[1,2,4]

triazol-3-ylmethyl)-carbamic acid tert-butyl ester (61 mg, 0.10 mmol) and hydrochloric acid (4 mL, 4.0 M. in dioxane) following the general deprotection procedure.

LC-MS (m/z): 512 (M+1)+; 1H NMR (400 MHz, CDCl3): δ 1.24 (m, 2H), 1.38 (m, 2H), 1.72 (m, 4H), 1.94 (m, 4H), 2.38 (s, 3H), 2.92 (p, 1H), 3.65 (s, 2H), 3.77 (s, 2H), 4.08 (m, 1H), 5.24 (br, 2H), 6.90 (s, 1H), 7.52 (d, 1H), 7.72 (s, 1H), 8.42 (d, 1H), 10.24 (br, 1H), and 11.36 (br, 1H).

Example 268

2-{2-[3-(2-Cyclopentanecarbonyl-4-methyl-phenyl)-ureido]-thiazol-4-ylmethylsulfanyl}-1H-imidazole-4-carboxylic acid ethyl ester

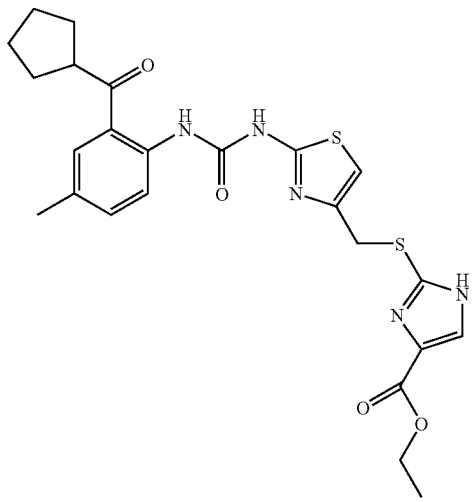

2-{2-[3-(2-Cyclopentanecarbonyl-4-methyl-phenyl)-ureido]-thiazol-4-ylmethylsulfanyl}-1H-imidazole-4-carboxylic acid ethyl ester (112 mg, 88%) was prepared from 1-(4-chloromethyl-thiazol-2-yl)-3-(2-cyclopentanecarbonyl-4-methyl-phenyl)-urea (94 mg, 0.25 mmol) following the general procedure Q.

LC-MS (m/z): 486 (M+1)+; 1H NMR (400 MHz, CDCl3): δ 1.36 (t, 3H), 1.74 (m, 4H), 1.90 (m, 4H), 2.36 (s, 3H), 3.78 (p, 1H), 4.08 (q, 2H), 4.34 (s, 2H), 6.84 (s, 1H), 7.34 (d, 1H), 7.72 (d, 1H), 7.88 (d, 1H), 8.18 (d, 1H), 8.38 (d, 1H), 10.24 (br, 1H), and 11.88 (br, 1H).

Example 269

2-{2-[3-(2-Cyclopentanecarbonyl-4-methyl-phenyl)-ureido]-thiazol-4-ylmethylsulfanyl}-1H-imidazole-4-carboxylic acid

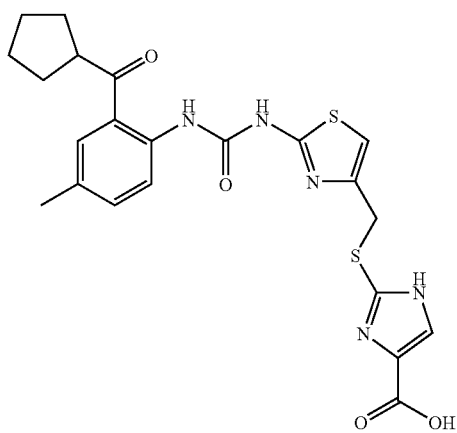

2-{2-[3-(2-Cyclopentanecarbonyl-4-methyl-phenyl)-ureido]-thiazol-4-ylmethylsulfanyl}-1H-imidazole-4-carboxylic acid (91 mg, 94%) was prepared from 2-{2-[3-(2-cyclopentanecarbonyl-4-methyl-phenyl)-ureido]-thiazol-4-ylmethylsulfanyl}-1H-imidazole-4-carboxylic acid ethyl ester (102 mg, 0.20 mmol) following the general procedure J.

LC-MS (m/z): 474 (M+1)+; 1H NMR (400 MHz, CDCl3): δ 1.74 (m, 4H), 1.92 (m, 4H), 2.34 (s, 3H), 3.87 (p, 1H), 4.37 (s, 2H), 6.89 (s, 1H), 7.39 (d, 1H), 7.68 (d, 1H), 7.84 (d, 1H), 8.15 (d, 1H), 8.26 (d, 1H), 9.28 (br, 1H), 10.66 (br, 1H), and 11.90 (br, 1H).

Example 270

2-{2-[3-(2-Cyclopentanecarbonyl-4-methyl-phenyl)-ureido]-thiazol-4-ylmethanesulfonyl}-1H-imidazole-4-carboxylic acid ethyl ester

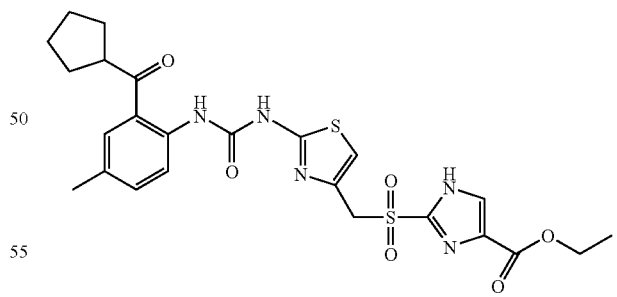

2-{2-[3-(2-Cyclopentanecarbonyl-4-methyl-phenyl)-ureido]-thiazol-4-ylmethanesulfonyl}-1H-imidazole-4-carboxylic acid ethyl ester (35 mg, 64%) was prepared from 2-{2-[3-(2-cyclopentanecarbonyl-4-methyl-phenyl)-ureido]-thiazol-4-ylmethylsulfanyl}-1H-imidazole-4-carboxylic acid ethyl ester (51 mg, 0.10 mmol) following the general procedure R.

LC-MS (m/z): 546 (M+1)+; 1H NMR (400 MHz, CDCl3): δ 1.42 (t, 3H), 1.63 (m, 4H), 1.76 (m, 2H), 1.88 (m, 2H), 2.34

(s, 3H), 3.88 (p, 1H), 4.12 (q, 2H), 4.82 (s, 2H), 6.94 (s, 1H), 7.38 (d, 1H), 7.55 (d, 1H), 7.72 (d, 1H), 7.91 (d, 1H), 6 (d, 1H), 9.78 (br, 1H), and 11.90 (br, 1H).

Example 271

2-{2-[3-(2-Cyclopentanecarbonyl-4-methyl-phenyl)-ureido]-thiazol-4-ylmethanesulfonyl}-1H-imidazole-4-carboxylic acid

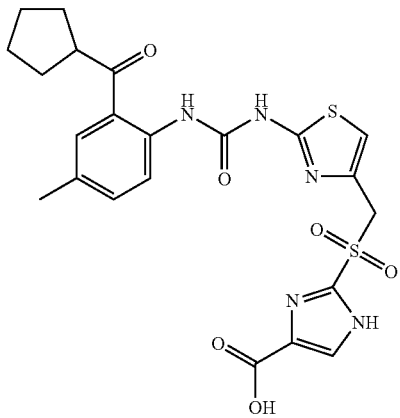

2-{2-[3-(2-Cyclopentanecarbonyl-4-methyl-phenyl)-ureido]-thiazol-4-ylmethanesulfonyl}-1H-imidazole-4-carboxylic acid (43 mg, 83%) was prepared from 2-{2-[3-(2-cyclopentanecarbonyl-4-methyl-phenyl)-ureido]-thiazol-4-ylmethanesulfonyl}-1H-imidazole-4-carboxylic acid ethyl ester (52 mg, 0.10 mmol) following the general procedure J.

LC-MS (m/z): 518 (M+1)$^+$; $^1$H NMR (400 MHz, DMSO-d$_6$): δ 1.63 (m, 4H), 1.74 (m, 2H), 1.86 (m, 2H), 2.34 (s, 3H), 3.85 (p, 1H), 4.82 (s, 2H), 6.92 (s, 1H), 7.38 (d, 1H), 7.54 (d, 1H), 7.72 (d, 1H), 7.90 (s, 1H), 7.96 (br, 1H), 8.22 (d, 1H), 10.58 (br, 1H), and 11.88 (br, 1H).

Example 272

4-Amino-2-{2-[3-(2-cyclopentanecarbonyl-4-methyl-phenyl)-ureido]-thiazol-4-ylmethylsulfanyl}-pyrimidine-5-carboxylic acid ethyl ester

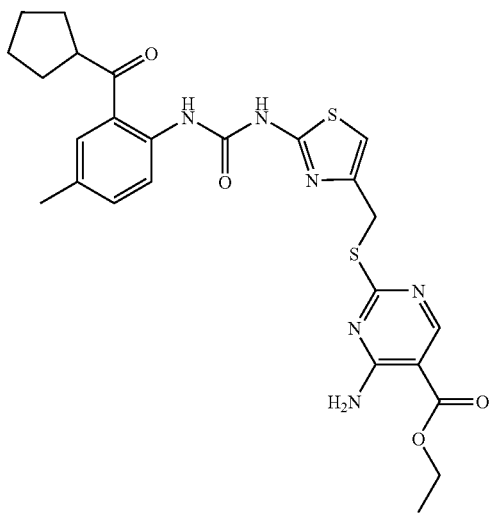

4-Amino-2-{2-[3-(2-cyclopentanecarbonyl-4-methyl-phenyl)-ureido]-thiazol-4-ylmethylsulfanyl}-pyrimidine-5-carboxylic acid ethyl ester (113 mg, 84%) was prepared from 1-(4-chloromethyl-thiazol-2-yl)-3-(2-cyclopentanecarbonyl-4-methyl-phenyl)-urea (94 mg, 0.25 mmol) following the general procedure Q.

LC-MS (m/z): 541 (M+1)$^+$; $^1$H NMR (400 MHz, CDCl$_3$): δ 1.34 (t, 3H), 1.72 (m, 4H), 1.88 (m, 4H), 2.34 (s, 3H), 3.62 (br, 2H), 3.74 (p, 1H), 4.10 (q, 2H), 4.36 (s, 2H), 6.90 (s, 1H), 7.36 (d, 1H), 7.74 (d, 1H), 8.18 (dd, 1H), 8.56 (s, 1H), 10.12 (br, 1H), and 11.78 (br, 1H).

Example 273

4-Amino-2-{2-[3-(2-cyclopentanecarbonyl-4-methyl-phenyl)-ureido]-thiazol-4-ylmethylsulfanyl}-pyrimidine-5-carboxylic acid

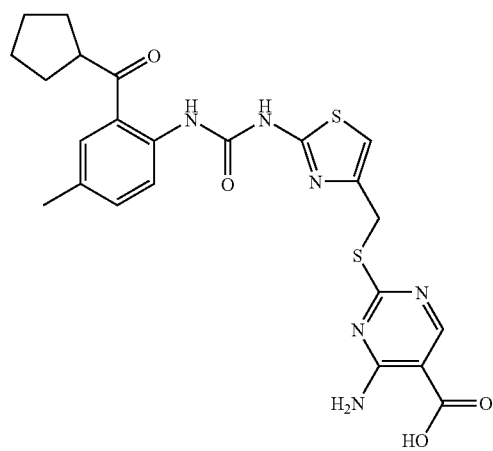

4-Amino-2-{2-[3-(2-cyclopentanecarbonyl-4-methyl-phenyl)-ureido]-thiazol-4-ylmethylsulfanyl}-pyrimidine-5-carboxylic acid (94 mg, 91%) was prepared from 4-amino-2-{2-[3-(2-cyclopentanecarbonyl-4-methyl-phenyl)-ureido]-thiazol-4-ylmethylsulfanyl}-pyrimidine-5-carboxylic acid ethyl ester (108 mg, 0.20 mmol) following the general procedure J.

LC-MS (m/z): 513 (M+1)$^+$; $^1$H NMR (400 MHz, DMSO-d$_6$): δ 1.72 (m, 4H), 1.88 (m, 4H), 2.34 (s, 3H), 3.66 (br, 2H), 3.86 (p, 1H), 4.36 (s, 2H), 7.07 (s, 1H), 7.32 (d, 1H), 7.72 (d, 1H), 8.20 (dd, 1H), 8.56 (s, 1H), 9.76 (br, 1H), 10.64 (br, 1H), and 11.74 (br, 1H).

Example 274

2-{2-[3-(2-Cyclopentanecarbonyl-4-methyl-phenyl)-ureido]-thiazol-4-ylmethylsulfanyl}-4-hydroxy-pyrimidine-5-carboxylic acid

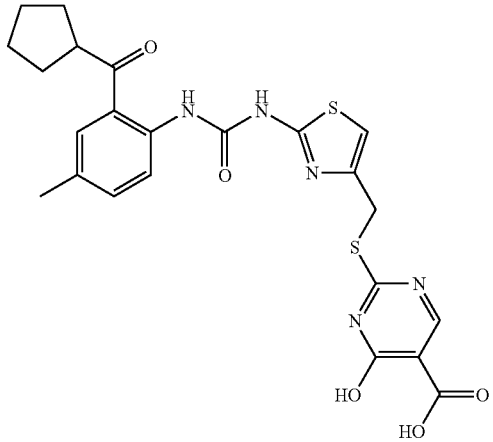

2-{2-[3-(2-Cyclopentanecarbonyl-4-methyl-phenyl)-ureido]-thiazol-4-ylmethylsulfanyl}-4-hydroxy-pyrimidine-5-carboxylic acid (104 mg, 81%) was prepared from 2-{2-[3-(2-cyclopentanecarbonyl-4-methyl-phenyl)-ureido]-thiazol-4-ylmethylsulfanyl}-4-hydroxy-pyrimidine-5-carboxylic acid ethyl ester (135 mg, 0.25 mmol) following the general procedure J.

LC-MS (m/z): 514 (M+1)$^+$; $^1$H NMR (400 MHz, CD$_3$OD): δ 1.74 (m, 4H), 1.90 (m, 4H), 2.36 (s, 3H), 3.84 (p, 1H), 4.28 (s, 2H), 6.98 (s, 1H), 7.36 (d, 1H), 7.70 (d, 1H), 8.36 (dd, 1H), 8.56 (s, 1H), 9.04 (br, 1H), 9.76 (br, 1H), 10.64 (br, 1H), and 11.74 (br, 1H).

Example 275

1-[4-(5-Amino-thiazol-2-ylsulfanylmethyl)-thiazol-2-yl]-3-(2-cyclopentanecarbonyl-4-methyl-phenyl)-urea

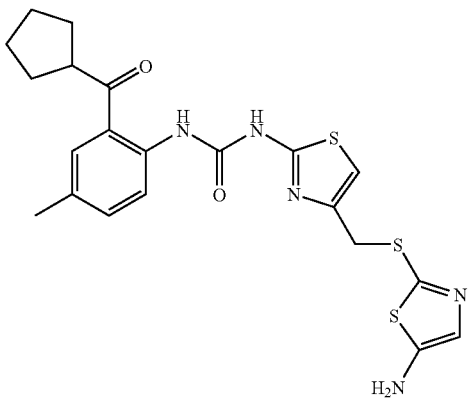

1-[4-(5-Amino-thiazol-2-ylsulfanylmethyl)-thiazol-2-yl]-3-(2-cyclopentanecarbonyl-4-methyl-phenyl)-urea (96 mg, 81%) was prepared from 1-(4-chloromethyl-thiazol-2-yl)-3-(2-cyclopentanecarbonyl-4-methyl-phenyl)-urea (94 mg, 0.25 mmol) following the general procedure Q.

LC-MS (m/z): 474 (M+1)$^+$; $^1$H NMR (400 MHz, CDCl$_3$): δ 1.68 (m, 4H), 1.84 (m, 4H), 2.37 (s, 3H), 3.72 (p, 1H), 4.34 (s, 2H), 5.18 (br, 2H), 6.58 (s, 1H), 7.16 (s, 1H), 7.36 (d, 1H), 7.64 (s, 1H), 8.26 (d, 1H), 10.56 (br, 1H), and 11.60 (br, 1H).

Example 276

{2-[3-(2-Cyclopentanecarbonyl-5-methanesulfonylamino-4-methyl-phenyl)-ureido]-thiazol-4-yl}acetic acid ethyl ester

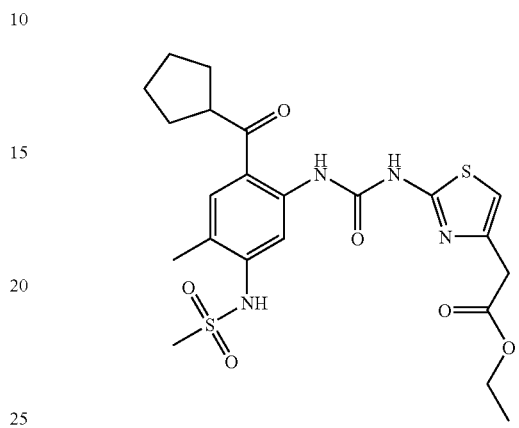

{2-[3-(2-Cyclopentanecarbonyl-5-methanesulfonylamino-4-methyl-phenyl)-ureido]-thiazol-4-yl}-acetic acid ethyl ester (102 mg, 80%) was prepared from N-(5-amino-4-cyclopentanecarbonyl-2-methyl-phenyl)-methanesulfonamide (198 mg, 0.5 mmol) and ethyl-2-amino-4-thiazolyl acetate (93 mg, 0.5 mmol) following the general procedure D.

LC-MS (m/z): 509 (M+1)$^+$; $^1$H NMR (400 MHz, CDCl$_3$): δ 1.27 (t, 3H), 1.70 (m, 4H), 1.88 (m, 4H), 2.29 (s, 3H), 3.30 (s, 2H), 3.68 (s, 3H), 4.19 (q, 2H), 4.24 (p, 1H), 6.48 (s, 1H), 6.72 (s, 1H), 7.74 (s, 1H), 8.64 (br, 1H), 9.62 (br, 1H), and 11.82 (br, 1H).

Example 277

{2-[3-(2-Cyclopentanecarbonyl-5-methanesulfonylamino-4-methyl-phenyl)-ureido]-thiazol-4-yl}-acetic acid

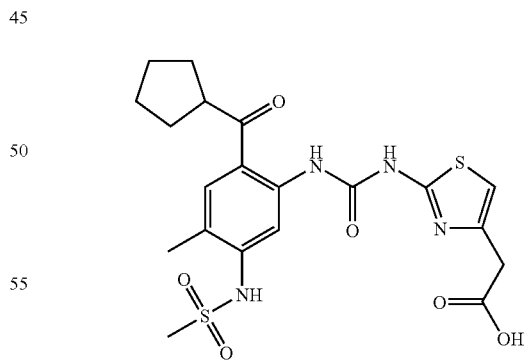

{2-[3-(2-Cyclopentanecarbonyl-5-methanesulfonylamino-4-methyl-phenyl)-ureido]-thiazol-4-yl}-acetic acid ethyl ester (116 mg, 97%) was prepared from {2-[3-(2-cyclopentanecarbonyl-5-methanesulfonylamino-4-methyl-phenyl)-ureido]-thiazol-4-yl}-acetic acid ethyl ester (127 mg, 0.25 mmol) following the general procedure J.

LC-MS (m/z): 481 (M+1)$^+$; $^1$H NMR (400 MHz, DMSO-d$_6$): δ 1.68 (m, 4H), 1.84 (m, 4H), 2.38 (s, 3H), 3.03 (s, 3H), 3.64 (s, 2H), 4.24 (p, 1H), 5.36 (br, 1H), 6.50 (s, 1H), 6.78 (s, 1H), 7.68 (s, 1H), 9.62 (br, 1H), 11.24 (br, 1H), and 12.54 (br, 1H).

Example 278

1-(2-Cyclopentanecarbonyl-4-methyl-phenyl)-3-{4-[2-(1H-imidazol-2-ylsulfanyl)-ethyl]-thiazol-2-yl}-urea

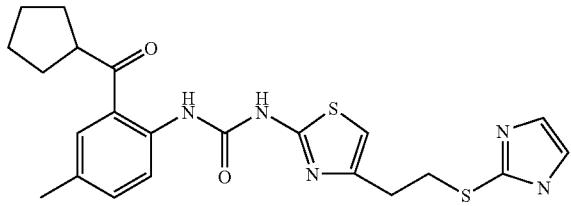

1-(2-Cyclopentanecarbonyl-4-methyl-phenyl)-3-{4-[2-(1H-imidazol-2-ylsulfanyl)-ethyl]-thiazol-2-yl}-urea (25 mg, 50%) was prepared from methanesulfonic acid 2-{2-[3-(2-cyclopentanecarbonyl-4-methyl-phenyl)-ureido]-thiazol-4-yl}-ethyl ester (0.05 g, 0.11 mmol) and 1H-imidazol-2-thiol (0.009 g, 0.11 mmol) following the general procedure Z.

LC/MS (m/z): 456 (M+1)$^+$; $^1$H NMR (400 MHz, CDCl$_3$) □ 1.63-1.68 (m, 4H), 1.83-1.88 (m, 4H), 2.35 (s, 3H), 2.87-2.93 (m, 2H), 3.25-3.28 (m, 2H), 3.60-3.75 (m, 1H), 6.74 (s, 1H), 6.85-7.10 (m, 2H), 7.33 (d, 1H), 7.65 (s, 1H), 8.4 (d, 1H), 11.35 (br, 1H).

Example 279

1-(2-Cyclopentanecarbonyl-4-methyl-phenyl)-3-{4-[2-(1-methyl-1H-imidazol-2-ylsulfanyl)-ethyl]-thiazol-2-yl}-urea

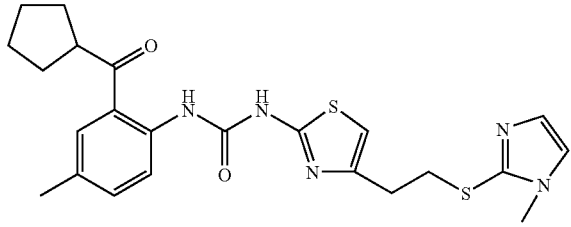

1-(2-Cyclopentanecarbonyl-4-methyl-phenyl)-3-{4-[2-(1-methyl-1H-imidazol-2-ylsulfanyl)-ethyl]-thiazol-2-yl}-urea (45 mg, 43%) was prepared from methanesulfonic acid 2-{2-[3-(2-cyclopentanecarbonyl-4-methyl-phenyl)-ureido]-thiazol-4-yl}-ethyl ester (0.10 g, 0.22 mmol) and 1-methyl-1H-immidazole-2-thiol (0.04 g, 0.33 mmol) following the general procedure Z.

LC/MS (m/z): 470 (M+1)$^+$; $^1$H NMR (400 MHz, CDCl$_3$) □ 1.73-1.76 (m, 4H), 1.90-1.93 (m, 4H), 2.36 (s, 3H), 3.04 (t, 2H), 3.35 (t, 2H), 3.63 (s, 3H), 3.65-3.80 (m, 1H), 6.51 (s, 1H), 6.71 (d, 2H), 7.33 (d, 1H), 7.68 (s, 1H), 8.40 (br, 1H), 11.43 (br, 1H).

Example 280

1-(2-Cyclopentanecarbonyl-4-methyl-phenyl)-3-{4-[2-(pyridin-2-ylsulfanyl)-ethyl]-thiazol-2-yl}-urea

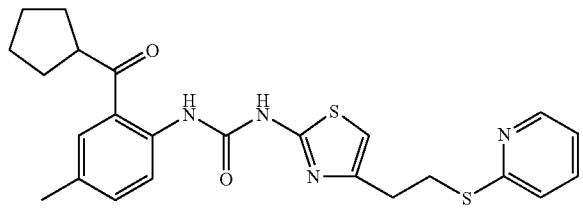

1-(2-cyclopentanecarbonyl-4-methyl-phenyl)-3-{4-[2-(pyridin-2-ylsulfanyl)-ethyl]-thiazol-2-yl}-urea (24 mg, 467%) was prepared from methanesulfonic acid 2-{2-[3-(2-cyclopentanecarbonyl-4-methyl-phenyl)-ureido]-thiazol-4-yl}-ethyl ester (0.05 g, 0.11 mmol) and 2-mercapto pyridine (0.012 g, 0.11 mmol) following the general procedure Z.

LC/MS (m/z): 467 (M+1)$^+$; $^1$H NMR (400 MHz, CDCl$_3$) □ 1.62-1.74 (m, 4H), 1.85-1.93 (m, 4H), 2.36 (s, 3H), 3.05 (t, 2H), 3.50 (t, 2H), 3.72-3.80 (m, 1H), 6.54 (s, 1H), 7.13-7.10 (m, 2H), 7.60-7.65 (m, 3H), 8.46-8.49 (m, 2H), 11.72 (br, 1H).

Example 281

1-(2-Cyclopentanecarbonyl-4-methyl-phenyl)-3-{4-[2-(pyridin-4-ylsulfanyl)-ethyl]-thiazol-2-yl}-urea

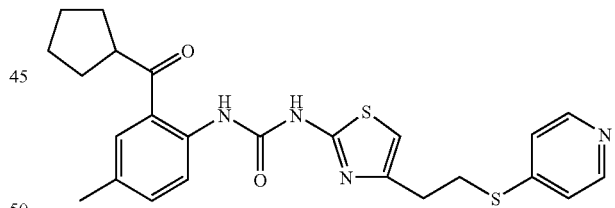

1-(2-Cyclopentanecarbonyl-4-methyl-phenyl)-3-{4-[2-(pyridin-4-ylsulfanyl)-ethyl]-thiazol-2-yl}-urea (74 mg, 60%) was prepared from methanesufonic acid 2-{2-[3-(2-cyclopentanecarbonyl-4-methyl-phenyl)-ureido]-thiazol-4-yl}-ethyl ester (0.12 g, 0.27 mmol) and 2-mercaptopyridine (0.04 g, 0.39 mmol) following the general procedure Z.

LC/MS (m/z): 467 (M+1)$^+$; $^1$H NMR (400 MHz, CDCl$_3$) δ 1.69-1.73 (m, 4H), 1.87-1.92 (m, 4H), 2.37 (s, 3H), 3.03 (t, 2H), 3.34 (t, 2H), 3.75-3.79 (m, 1H), 6.58 (s, 1H), 7.16 (d, 2H), 7.25 (d, 2H), 7.36 (d, 1H), 7.71 (s, 1H), 8.46 (d, 1H), 11.74 (s, 1H).

Example 282

3-{2-[3-(2-Acetyl-4-methyl-phenyl)-ureido]-thiazol-4-ylmethylsulfanyl}-propionic acid

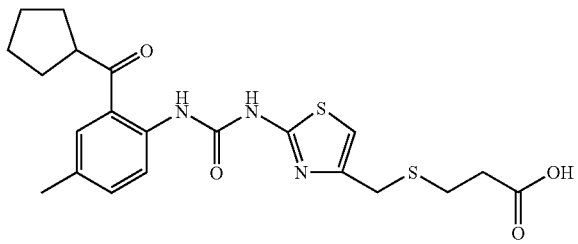

3-(2-Amino-thiazol-4-ylmethylsulfanyl)-propionic acid methyl ester (0.75 g, 60%) was prepared from 4-chloromethyl-thiazol-2-ylamine (1.00 g, 5.41 mmol) and 3-mercaptopropionic acid methyl ester (0.97 g, 8.11 mmol) according to procedure Z.

3-{2-[3-(2-Acetyl-4-methyl-phenyl)-ureido]-thiazol-4-ylmethylsulfanyl}-propionic acid methyl ester (0.28 g, 61%) was prepared from 3-(2-amino-thiazol-4-ylmethylsulfanyl)-propionic acid methyl ester (0.23g, 0.99 mmol) and (2-amino-5-methyl-phenyl)-cyclopentyl-methanone (0.24 g, 1.49 mmol) following the procedure D.

3-{2-[3-(2-Acetyl-4-methyl-phenyl)-ureido]-thiazol-4-ylmethylsulfanyl}-propionic acid (40 mg, 83%) was prepared from [4-(2-{2-[3-(2-cyclopentanecarbonyl-4-methyl-phenyl)-ureido]-thiazol-4-yl}ethoxy)-phenyl] acetic acid methyl ester (0.05 g, 0.11 mmol) and 2.5M LiOH (20 uL) following the general procedure J.

LC/MS (m/z): 448 (M+1)$^+$; $^1$H NMR (400 MHz, DMSO) ☐ 1.70-1.80 (m, 4H), 1.85-1.97 (m, 4H), 2.28 (s, 3H), 2.67 (t, 2H), 2.83 (t, 2H), 3.70 (s, 2H), 3.85-3.90 (m, 1H), 6.89 (s, 1H), 7.20 (d, 2H), 7.85 (s, 1H), 8.20 (d, 1H), 10.64 (br, 1H), 10.73 (br, 1H), 12.14 (br, 1H).

Example 283

1-(2-Cyclopentanecarbonyl-4-methyl-phenyl)-3-(5-methylsulfanyl-thiazol-2-yl)-urea

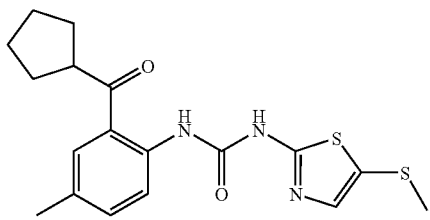

1-(2-Cyclopentanecarbonyl-4-methyl-phenyl)-3-(5-methylsulfanyl-thiazol-2-yl)-urea (94 mg, 25%) was prepared from 1-(5-bromo-thiazol-2-yl)-3-(2-cyclopentanecarbonyl-4-methyl-phenyl)-urea (408 mg, 1 mmol) and sodium methanethiolate (140 mg, 2 mmol) following the general procedure Q.

LC-MS (m/z): 376 (M+1)$^+$; $^1$H NMR (400 MHz, CDCl$_3$): δ 1.74 (m, 4H), 1.93 (m, 4H) 2.38 (s, 3H), 2.43 (s, 3H), 3.79 (m, 1H), 7.37 (d, 1H), 7.73 (s, 2H), 8.45 (d, 1H), 11.65 (br, 1H), 12.20 (br, 1H).

Example 284

{2-[3-(2-Cyclopentanecarbonyl-4-methyl-phenyl)-ureido]-thiazol-5-ylsulfanyl}-acetic acid methyl ester

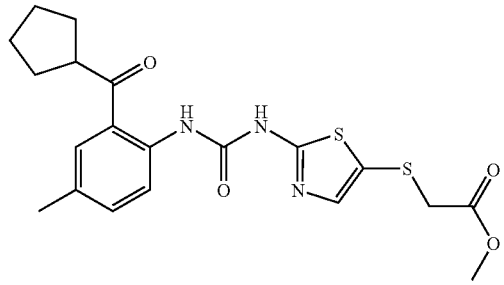

{2-[3-(2-Cyclopentanecarbonyl-4-methyl-phenyl)-ureido]-thiazol-5-ylsulfanyl}-acetic acid methyl ester (130 mg, 30%) was prepared from 1-(5-bromo-thiazol-2-yl)-3-(2-cyclopentanecarbonyl-4-methyl-phenyl)-urea (408 mg, 1 mmol), and mercapto-acetic acid methyl ester (212 mg, 2 mmol) following the general procedure Q.

LC-MS (m/z): 434 (M+1)$^+$; $^1$H NMR (400 MHz, CDCl$_3$): δ 1.71 (m, 4H), 1.91 (m, 4H), 2.38 (s, 3H), 3.47(s, 3H), 3.72 (s, 3H), 3.79 (m, 1H), 7.39 (d, 1H), 7.75 (d, 2H), 8.43 (d, 1H), 11.40 (br, 1H), 11.66 (br, 1H).

Example 285

{2-[3-(2-Cyclopentanecarbonyl-4-methyl-phenyl)-ureido]-thiazol-5-ylsulfanyl}-acetic acid

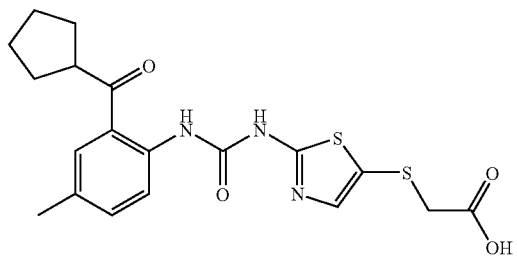

{2-[3-(2-Cyclopentanecarbonyl-4-methyl-phenyl)-ureido]-thiazol-5-ylsulfanyl}-acetic acid (161 mg, 75%) was prepared from {2-[3-2-cyclopentanecarbonyl-4-methyl-phenyl)-ureido]-thiazol-5-ylsulfanyl}-acetic acid methyl ester (229 mg, 0.5 mmol) following the general procedure J.

LC-MS (m/z): 420 (M+1)$^+$; $^1$H NMR (400 MHz, DMSO-d$_6$): δ 1.61 (m, 4H), 1.74 (m, 2H), 1.89 (m, 2H), 2.33 (s, 3H), 3.49(s, 3H), 3.88 (m, 1H), 7.41 (d, 2H), 7.92 (d, 1H) 8.33 (d, 1H), 10.80 (br, 1H), 10.98 (br, 1H) 12.12 (br, 1H).

Example 286

{2-[3-(2-Cyclopentanecarbonyl-4-methyl-phenyl)-ureido]-thiazole-5-sulfonyl}-acetic acid methyl ester

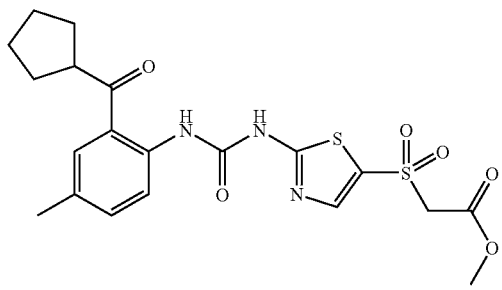

{2-[3-(2-Cyclopentanecarbonyl-4-methyl-phenyl)-ureido]-thiazole-5-sulfonyl}-acetic acid methyl ester (175 mg, 75%) was prepared from {2-[3-(2-cyclopentanecarbonyl-4-methylphenyl)-ureido]-thiazole-5-sulfanyl}-acetic acid methyl ester (217 mg, 0.5 mmol) by oxidation with m-cpba following the general procedure R.

LC-MS (m/z): 466 (M+1)$^+$; $^1$H NMR (400 MHz, CDCl$_3$): δ 1.71 (m, 4H), 1.91 (m, 4H), 2.38 (s, 3H), 3.78 (m, 4H), 4.24 (s, 2H), 7.41 (d, 1H), 7.77 (s, 1H), 8.30 (s, 1H), 8.42 (d, 1H), 11.89 (br, 1H).

Example 287

{2-[3-(2-Cyclopentanecarbonyl-4-methyl-phenyl)-ureido]-thiazole-5-sulfonyl}-acetic acid

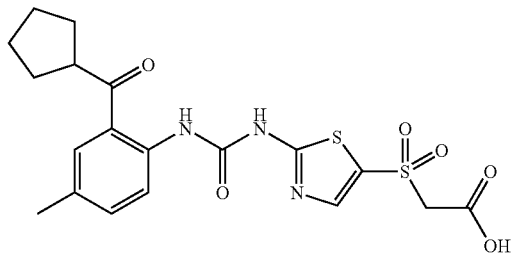

{2-[3-(2-Cyclopentanecarbonyl-4-methyl-phenyl)-ureido]-thiazol-5-ylsulfonyl}-acetic acid (158 mg, 70%) was prepared from {2-[3-(2-cyclopentanecarbonyl-4-methyl-phenyl)-ureido]-thiazol-5-ylsulfonyl}-acetic acid methyl ester (233 mg, 0.5 mmol) following the general procedure J.

LC-MS (m/z): 452 (M+1)$^+$; $^1$H NMR (400 MHz, acetone-d$_6$): δ 1.67 (m, 4H), 1.71 (m, 4H), 1.91 (m, 4H), 2.38 (s, 3H), 3.95 (m, 1H), 4.44 (s, 2H), 7.44 (d, 1H), 7.97 (s, 2H), 8.42 (d, 1H), 11.15 (br, 1H), 11.35 (br, 1H).

Example 288

3-{2-[3-(2-Cyclopentanecarbonyl-4-methyl-phenyl)-ureido]-thiazol-5-ylsulfanyl}-propionic acid methyl ester

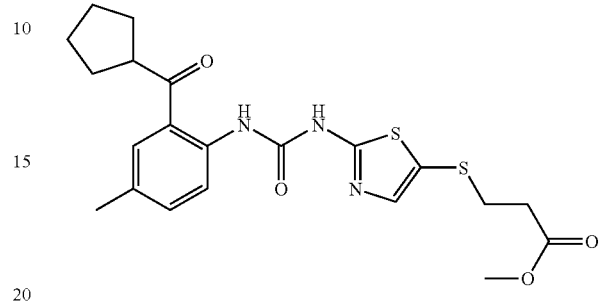

{2-[3-(2-Cyclopentanecarbonyl-4-methyl-phenyl)-ureido]-thiazol-5-ylsulfanyl}-propionic acid methyl ester (125 mg, 28%) was prepared from 1-(5-bromo-thiazol-2-yl)-3-(2-cyclopentanecarbonyl-4-methyl-phenyl)-urea (408 mg, 1 mmol), and mercapto-propionic acid methyl ester (240 mg, 2 mmol) following the general procedure Q.

LC-MS (m/z): 448 (M+1)$^+$; $^1$H NMR (400 MHz, CDCl$_3$): δ 1.71 (m, 4H), 1.91 (m, 4H), 2.38 (s, 3H), 2.65 (s, 2H), 3.51 (s, 2H), 3.66 (s, 3H), 3.78 (m, 1H), 6.90 (d, 1H), 7.38 (d, 1H), 7.73 (s, 1H), 8.42 (d, 1H) 11.62 (br, 1H), 11.65 (br, 1H).

Example 289

3-{2-[3-(2-Cyclopentanecarbonyl-4-methyl-phenyl)-ureido]-thiazol-5-ylsulfanyl}-propionic acid

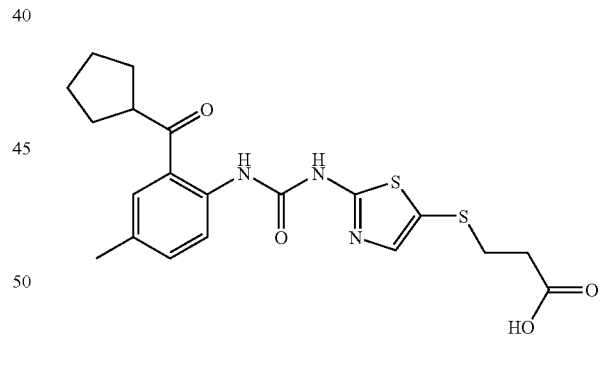

{2-[3-(2-Cyclopentanecarbonyl-4-methyl-phenyl)-ureido]-thiazol-5-ylsulfanyl}-propionic acid (138 mg, 72%) was prepared from {2-[3-(2-cyclopentanecarbonyl-4-methyl-phenyl)-ureido]-thiazol-5-ylsulfanyl}-propionic acid methyl ester (217 mg, 0.5 mmol) following the general procedure J.

LC-MS (m/z): 433 (M+1)$^+$; $^1$H NMR (400 MHz, CDCl$_3$): δ 1.67 (m, 4H), 1.89 (m, 4H), 2.36 (s, 3H), 2.51 (s, 2H), 3.59 (s, 2H), 3.78 (m, 1H), 6.90 (d, 1H), 7.41 (d, 1H), 7.93 (s, 1H), 8.45 (d, 1H), 9.56 (br, 1H), 11.16 (br, 1H), 11.25 (br, 1H).

Example 290

3-{2-[3-(2-Cyclopentanecarbonyl-4-methyl-phenyl)-ureido]-thiazole-5-sulfonyl}-propionic acid methyl ester

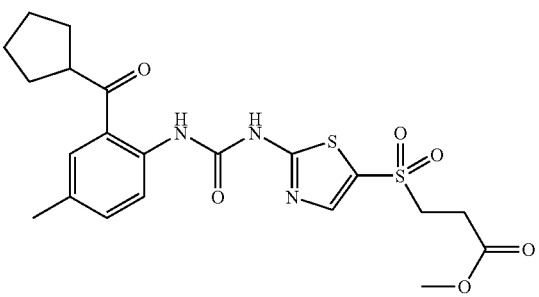

{2-[3-(2-Cyclopentanecarbonyl-4-methyl-phenyl)-ureido]-thiazole-5-sulfonyl}-propionic acid methyl ester (163 mg, 68%) was prepared from {2-[3-(2-cyclopentanecarbonyl-4-methylphenyl)-ureido]-thiazole-5-sulfanyl}-propionic acid methyl ester (224 mg, 0.5 mmol) by oxidation with m-cpba following the general procedure R.

LC-MS (m/z): 480 (M+1)$^+$; $^1$H NMR (400 MHz, CDCl$_3$): δ 1.71 (m, 6H), 1.91 (m, 2H), 2.40 (s, 3H), 2.85 (m, 2H), 3.56 (m, 2H), 3.67 (s, 3H), 3.81 (m, 1H), 7.41 (dd, 1H), 7.78 (s, 2H), 8.29 (s, 1H), 8.42 (d, 1H), 11.40 (br, 1H), 11.91 (br, 1H).

Example 291

3-{2-[3-(2-Cyclopentanecarbonyl-4-methyl-phenyl)-ureido]-thiazole-5-sulfonyl}-propionic acid

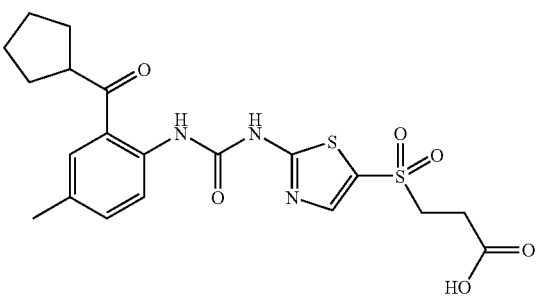

{2-[3-(2-Cyclopentanecarbonyl-4-methyl-phenyl)-ureido]-thiazol-5-ylsulfonyl}-propionic acid (168 mg, 72%) was prepared from {2-[3-(2-cyclopentanecarbonyl-4-methyl-phenyl)-ureido]-thiazol-5-ylsulfonyl}-propionic acid methyl ester (240 mg, 0.5 mmol) following the general procedure J.

LC-MS (m/z): 466 (M+1)$^+$; $^1$H NMR (400 MHz, CDCl$_3$): δ 1.71 (m, 4H), 1.91 (m, 4H), 2.38 (s, 3H), 2.89 (s, 2H), 3.63 (s, 2H), 3.81 (m, 1H), 7.39 (d, 1H), 7.75 (d, 2H), 8.43 (d, 1H), 11.40 (br, 1H), 11.66 (br, 1H).

Example 292

N-(2-{2-[3-(2-Cyclopentanecarbonyl-4-methyl-phenyl)-ureido]-thiazol-5-yl-sulfanyl}-ethyl)-acetamide

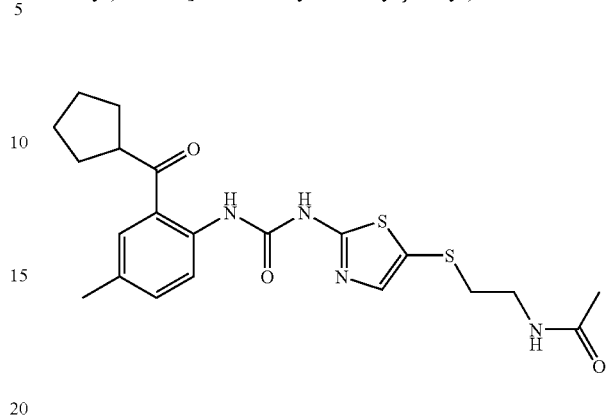

N-(2-{2-[3-(2-Cyclopentanecarbonyl-4-methyl-phenyl)-ureido]-thiazol-5-yl-sulfanyl}-ethyl)-acetamide (156 mg, 35%) was prepared from 1-(5-bromo-thiazol-2-yl)-3-(2-cyclopentanecarbonyl-4-methyl-phenyl)-urea (408 mg, 1 mmol), and N-(2-mercapto-ethyl)-acetamide (240 mg, 2 mmol) following the general procedure Q.

LC-MS (m/z): 447 (M+1)$^+$; $^1$H NMR (400 MHz, CDCl$_3$): δ 1.71 (m, 4H), 1.91 (m, 4H), 1.99 (s, 3H), 2.38 (s, 3H), 2.85 (t, 3H), 3.46 (q, 2H), 3.79 (m, 1H), 5.95 (br, 1H), 7.37 (d, 1H), 7.69 (d, 2H), 8.42 (d, 1H), 11.35 (br, 1H), 11.57 (br, 1H).

Example 293

N-(2-{2-[3-(2-Cyclopentanecarbonyl-4-methyl-phenyl)-ureido]-thiazol-5-yl-sulfonyl]-ethyl)-acetamide

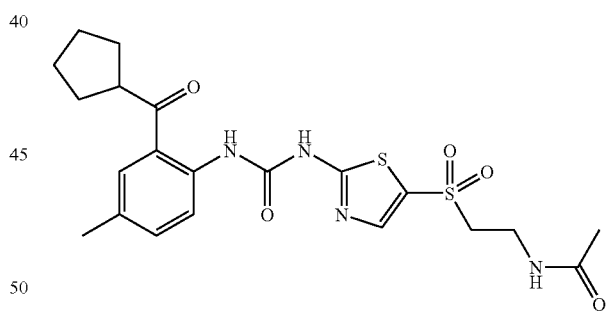

N-(2-{2-[3-(2-Cyclopentanecarbonyl-4-methyl-phenyl)-ureido]-thiazol-5-yl-sulfonyl]-ethyl)-acetamide (167 mg, 70%) was prepared from N-(2-{2-[3-(2-cyclopentanecarbonyl-4-methyl-phenyl)-ureido]-thiazol-5-yl-sulfanyl]}-ethyl)-acetamide (223 mg, 0.5 mmol) by oxidation with m-cpba following the general procedure R.

LC-MS (m/z): 479 (M+1)$^+$; $^1$H NMR (400 MHz, CDCl$_3$): δ 1.70 (m, 4H), 1.92 (m, 4H), 2.01 (s, 3H), 2.39 (s, 3H), 3.42 (m, 2H), 3.76 (m, 3H), 6.32 (m, 1H), 7.39 (d, 1H), 7.76 (s, 2H), 8.13 (s, 1H), 8.40 (d, 1H), 11.66 (br, 1H).

Example 294

2-Acetylamino-3-{2-[3-(2-cyclopentanecarbonyl-4-methyl-phenyl)-ureido]-thiazol-5-ylsulfanyl}-propionic acid methyl ester

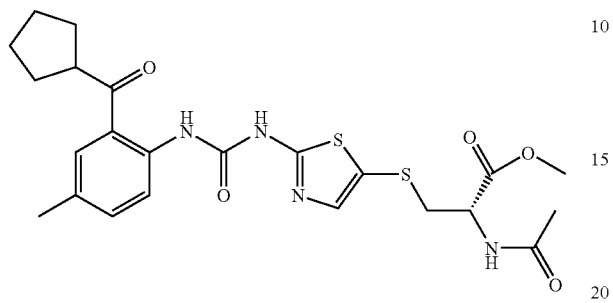

2-Acetylamino-3-2-[3-(2-cyclopentanecarbonyl-4-methyl-phenyl)-ureido]-thiazol-5-ylsulfanyl)propionic acid methyl ester (156 mg, 35%) was prepared from 1-(5-bromo-thiazol-2-yl)-3-(2-cyclo pentanecarbonyl-4-methyl-phenyl)-urea (408 mg, 1 mmol) and 2-acetylamino-3-mercapto-propionic acid methyl ester (354 mg, 2 mmol) following the general procedure Q.

LC-MS (m/z): 505 (M+1)+; 1H NMR (400 MHz, CDCl3): δ 1.71 (m, 6H), 1.91 (m, 2H), 2.03 (s, 3H), 2.38 (s, 3H), 3.24 (m, 2H), 3.66 (s, 3H), 3.79 (m, 1H), 4.84 (m, 1H), 6.42 (d, 1H), 7.39, d, 1H), 7.60 (s, 1H), 7.73 (s, 1H), 8.43 (d, 1H), 10.88 (br, 1H), 11.64 (br, 1H).

Example 295

2-Acetylamino-3-{2-[3-(2-cyclopentanecarbonyl-4-methyl-phenyl)-ureido]-thiazol-5-ylsulfanyl}-propionic acid

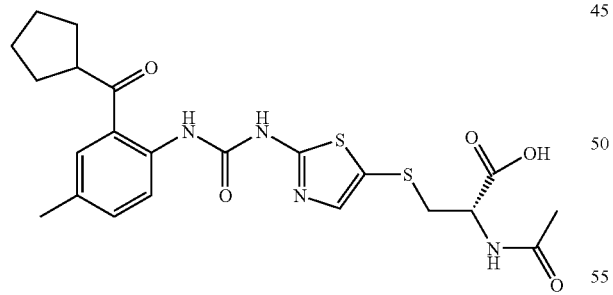

2-Acetylamino-3-{2-[3-(2-cyclopentanecarbonyl-4-methyl-phenyl)-ureido]-thiazol-5-ylsulfanyl}-propionic acid (187 mg, 76%) was prepared from 2-acetylamino-3-{2-[3-(2-cyclopentanecarbonyl-4-methyl-phenyl)-ureido]-thiazol-5-ylsulfanyl}-propionic acid methyl ester (245 mg, 0.5 mmol) following the general procedure J.

LC-MS (m/z): 491 (M+1)+; 1H NMR (400 MHz, Acetone-d6): δ 1.68 (m, 4H), 1.84 (m, 4H), 1.97 (s, 3H), 2.37 (s, 3H), 3.10 (m, 1H), 3.26 (m, 1H), 3.94 (m, 1H), 4.64 (m, 1H), 5.8 (br, 1H), 7.45 (d, 1H), 7.54 (d, 1H), 8.01 (s, 1H), 8.43 (d, 1H), 11.20 (br, 1H), 11.44 (br, 1H).

Example 296

2-tert-Butoxycarbonylamino-3-{2-[3-(2-cyclopentanecarbonyl-4-methyl-phenyl)-ureido]thiazol-5-ylsulfanyl}-propionic acid methyl ester

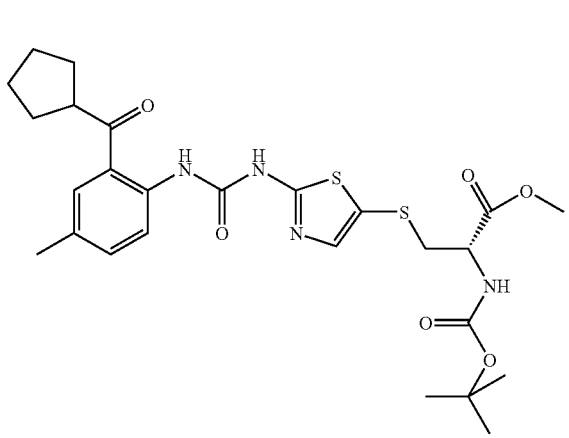

2-tert-Butoxycarbonylamino-3-{2-[3-(2-cyclopentanecarbonyl-4-methyl-phenyl)-ureido]thiazol-5-ylsulfanyl}-propionic acid methyl ester (196 mg, 35%) was prepared from 1-(5-bromo-thiazol-2-yl)-3-(2-cyclo pentanecarbonyl-4-methyl-phenyl)-urea (408 mg, 1 mmol) and 2-tert-butoxycarbonylamino-3-mercapto-propionic acid methyl ester (470 mg, 2 mmol) following the general procedure Q.

LC-MS (m/z): 563 (M+1)+; 1H NMR (400 MHz, CDCl3): δ 1.55 (s, 9H), 1.71 (m, 4H), 1.91 (m, 4H), 2.37 (s, 3H), 3.18 (m, 2H), 3.76 (m, 4H), 4.53 (m, 1H), 5.45 (m, 1H), 7.35 (d, 1H), 7.65 (s, 1H), 7.72 (s, 1H), 8.43 (d, 1H), 11.60 (br, 1H), 11.66 (br, 1H).

Example 297

(2-{2-[3-(2-Cyclopentanecarbonyl-4-methyl-phenyl)-ureido]-thiazol-5-ylsulfanyl}-ethyl)-carbamic acid tert-butyl ester

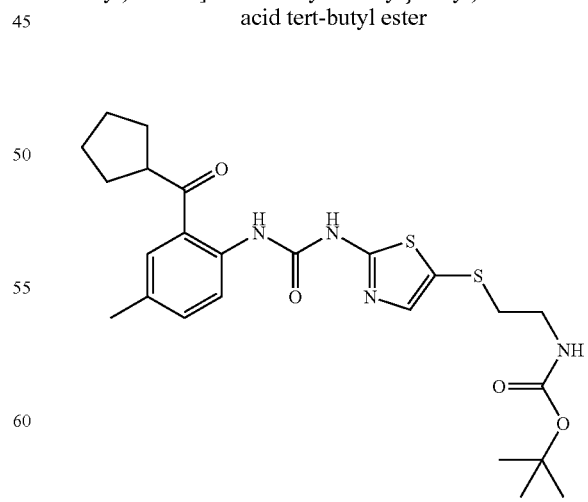

(2-{2-[3-(2-Cyclopentanecarbonyl-4-methyl-phenyl)-ureido]-thiazol-5-ylsulfanyl}-ethyl)-carbamic acid tert-butyl ester (202 mg, 40%) was prepared from 1-(5-bromo-thiazol- 2-yl)-3-(2-cyclo pentanecarbonyl-4-methyl-phenyl)-urea (408 mg, 1 mmol) and (2-mercapto-ethyl)-carbamic acid tert-butyl ester (354 mg, 2 mmol) following the general procedure Q.

LC-MS (m/z): 505 (M+1)+; $^1$H NMR (400 MHz, CDCl$_3$): δ 1.45(s, 9H), 1.71 (m, 4H), 1.92 (m, 4H), 2.38 (s, 3H), 2.83 (m, 2H), 3.32 (m, 2H), 3.78 (m, 1H), 4.95 (br, 1H), 7.36 (d, 1H), 7.73 (s, 2H), 8.43 (d, 1H), 11.48 (br, 1H), 11.62 (br, 1H).

Example 298

2-{2-[3-(2-Cyclopentanecarbonyl-4-methyl-phenyl)-ureido]-thiazol-5-ylsulfanyl}-ethyl-ammonium; chloride

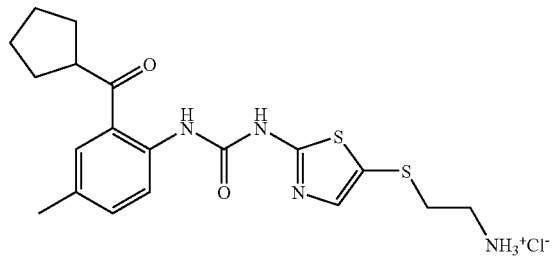

2-{2-[3-(2-Cyclopentanecarbonyl-4-methyl-phenyl)-ureido]-thiazol-5-ylsulfanyl}-ethyl-ammonium; chloride (183 mg, 90%) was prepared by reacting (2-{2-[3-(2-cyclopentanecarbonyl-4-methyl-phenyl)-ureido]-thiazol-5-ylsulfanyl}-ethyl)-carbamic acid tert-butyl ester (253 mg, 0.5 mmol) with 4 N HCl in dioxane LC-MS (m/z): 406 (M+1)+; $^1$H NMR (400 MHz, DMSO-d$_6$): δ 1.63 (m, 4H), 1.73 (m, 2H), 1.91 (m, 2H), 2.33 (s, 3H), 2.91 (m, 2H), 3.18 (m, 2H), 3.87 (m, 1H), 7.39 (d, 1H), 7.56 (s, 2H), 7.85 (s, 1H), 8.16 (d, 1H), 10.71 (br, 1H), 12.20 (br, 1H).

Example 299

(2-{2-[3-(2-Cyclopentanecarbonyl-4-methyl-phenyl)-ureido]-thiazole-5-sulfonyl}-ethyl) carbamic acid tert-butyl ester

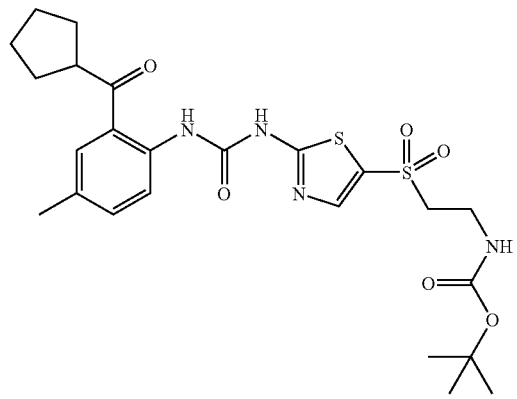

(2-{2-[3-(2-Cyclopentanecarbonyl-4-methyl-phenyl)-ureido]-thiazole-5-sulfonyl}-ethyl)-carbamic acid tert-butyl ester (195 mg, 73%) was prepared from (2-{2-[3-(2-cyclo pentanecarbonyl-4-methyl-phenyl)-ureido]-thiazole-5-sulfanyl}-ethyl) carbamic acid tert-butyl ester (252 mg, 0.5 mmol) by oxidation with m-cpba following the general procedure R.

LC-MS (m/z): 537 (M+1)+; $^1$H NMR (400 MHz, CDCl$_3$): δ 1.44 (s, 9H), 1.71 (m, 4H), 1.91 (m, 4H), 2.38 (s, 3H), 3.46 (t, 2H), 3.78 (m, 3H), 3.81 (m, 1H), 7.39 (d, 1H), 7.75 (d, 2H), 8.43 (d, 1H), 11.40 (br, 1H), 11.66 (br, 1H).

Example 300

2-{2-[3-(2-Cyclopentanecarbonyl-4-methyl-phenyl)-ureido]-thiazole-5-sulfonyl}-ethyl-ammonium; chloride

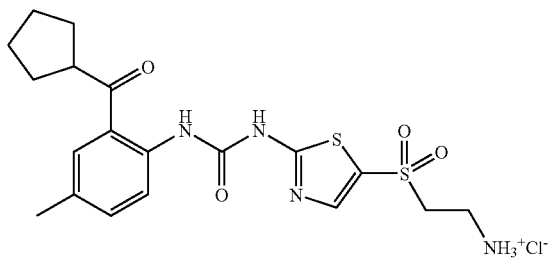

2-{2-[3-(2-Cyclopentanecarbonyl-4-methyl-phenyl)-ureido]-thiazol-5-ylsulfonyl}-ethyl-ammonium; chloride (185 mg, 85%) was prepared by reacting (2-{2-[3-(2-cyclopentanecarbonyl-4-methyl-phenyl)-ureido]-thiazol-5-ylsulfonyl}-ethyl)-carbamic acid tert-butyl ester (253 mg, 0,5 mmol) with 4 N HCl in dioxane LC-MS (m/z): 438 (M+1)+; $^1$H NMR (400 MHz, DMSO-d$_6$): δ 1.61(m, 4H), 1.72 (m, 2H), 1.88 (m, 2H), 2.34 (s, 3H), 3.01(br, 2H), 3.70 (t, 2H), 3.88 (m, 1H), 7.41 (d, 1H), 7.87 (s, 1H), 8.13 (d, 1H), 8.15 (br, 1H), 10.75 (br, 1H), 11.62 (br, 1H).

Example 301

1-(2-Cyclopentanecarbonyl-4-methyl-phenyl)-3-[5-(2-dimethylamino-ethylsulfanyl)-thiazol-2-yl]-urea

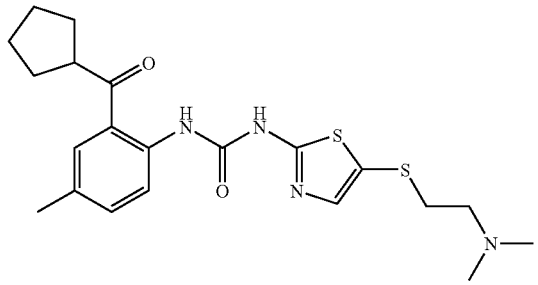

1-(2-Cyclopentanecarbonyl-4-methyl-phenyl)-3-[5-(2-dimethylamino-ethylsulfanyl)-thiazol-2-yl]-urea (130 mg, 30%) was prepared from 1-(5-bromo-thiazol-2-yl)-3-(2-cyclo pentanecarbonyl-4-methyl-phenyl)-urea (408 mg, 1 mmol) and 2-dimethylamino-ethanethiol (210 mg, 2 mmol) following the general procedure Q.

LC-MS (m/z): 433 (M+1)+; $^1$H NMR (400 MHz, CDCl$_3$): δ 1.71 (m, 4H), 1.92 (m, 4H), 2.24 (s, 6H), 2.38 (s, 3H), 2.55(m, 2H), 2.83 (m, 2H), 3.78 (m, 1H), 7.36 (d, 1H), 7.69 (s, 1H), 7.74(s, 1H), 8.44 (d, 1H), 11.65 (br, 1H).

Example 302

1-(2-Cyclopentanecarbonyl-4-methyl-phenyl)-3-[5-(2-hydroxy-ethylsulfanyl)-thiazol-2-yl]-urea

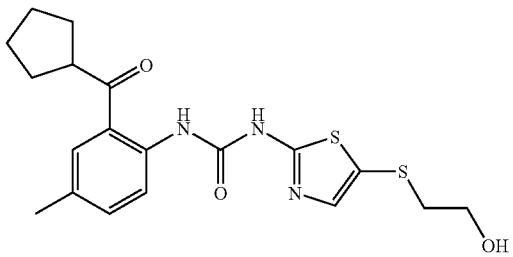

1-(2-Cyclopentanecarbonyl-4-methyl-phenyl)-3-[5-(2-hydroxy-ethylsulfanyl)-thiazol-2-yl]-urea (114 mg, 28%) was prepared from 1-(5-bromo-thiazol-2-yl)-3-(2-cyclo pentanecarbonyl-4-methyl-phenyl)-urea (408 mg, 1 mmol) and 2-hydroxy-ethanethiol (158 mg, 2 mmol) following the general procedure Q.

LC-MS (m/z): 406 (M+1)$^+$; $^1$H NMR (400 MHz, CDCl$_3$/acetone-d$_6$): δ 1.52 (m, 4H), 1.68 (m, 2H), 1.75 (m, 2H), 2.33 (s, 3H), 2.71 (t, 3H), 3.58 (m, 2H), 3.90 (m, 1H), 7.17 (d, 1H), 7.31 (s, 1H), 7.56 (s, 1H), 8.27 (d, 1H), 11.20 (br, 1H).

Example 303

1-(2-Cyclopentanecarbonyl-4-methyl-phenyl)-3-[5-(2-hydroxy-ethylsulfonyl)-thiazol-2-yl]-urea

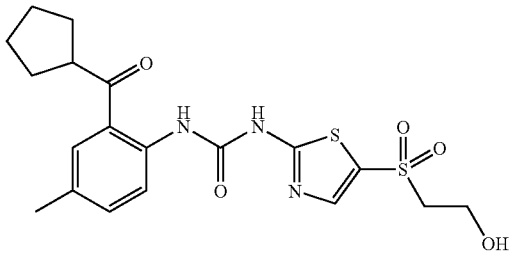

1-(2-Cyclopentanecarbonyl-4-methyl-phenyl)-3-[5-(2-hydroxy-ethylsulfonyl)-thiazol-2-yl]-urea (153, 70%) was prepared from 1-(2-cyclopentanecarbonyl-4-methyl-phenyl)-3-[5-(2-hydroxy-ethylsulfanyl)-thiazol-2-yl]-urea (204 mg, 0.5 mmol) by oxidation with m-cpba following the general procedure R.

LC-MS (m/z): 438 (M+1)$^+$; $^1$H NMR (400 MHz, CDCl$_3$/acetone-d$_6$): δ 1.66 (m, 4H), 1.89 (m, 4H), 2.37 (s, 3H), 3.48(m, 2H), 3.72 (m, 2H), 4.07 (m, 2H), 7.37 (d, 1H), 7.54 (d, 1H), 7.66 (d, 1H), 8.01 (d, 1H), 11.88 (br, 1H).

Example 304

1-(2-Cyclopentanecarbonyl-4-methyl-phenyl)-3-[5-(pyridin-2-ylsulfanyl)-thiazol-2-yl]-urea

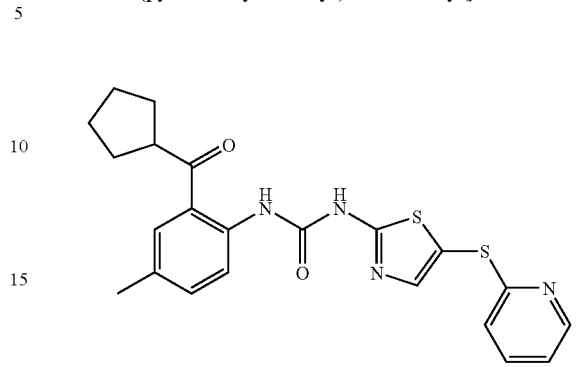

1-(2-Cyclopentanecarbonyl-4-methyl-phenyl)-3-[5-(pyridin-2-ylsulfanyl)-thiazol-2-yl]-urea (140 mg, 32%) was prepared from 1-(5-bromo-thiazol-2-yl)-3-(2-cyclo pentanecarbonyl-4-methyl-phenyl)-urea (408 mg, 1 mmol) and 2-mercaptopyridine (222 mg, 2 mmol) following the general procedure Q.

LC-MS (m/z): 439 (M+1)$^+$; $^1$H NMR (400 MHz, CDCl$_3$): δ 1.63 (m, 4H), 1.86 (m, 4H), 2.37 (s, 3H), 3.76 (m, 1H), 7.04 (m, 2H), 7.37 (d, 1H), 7.51 (m, 1H), 7.73 (s, 1H), 7.92 (s, 1H), 8.42 (d, 1H), 8.48 (d, 1H), 11.16 (br, 1H), 11.81 (br, 1H).

Example 305

1-(2-Cyclopentanecarbonyl-4-methyl-phenyl)-3-[5-(pyridine-2-sulfonyl)-thiazol-2-yl]-urea

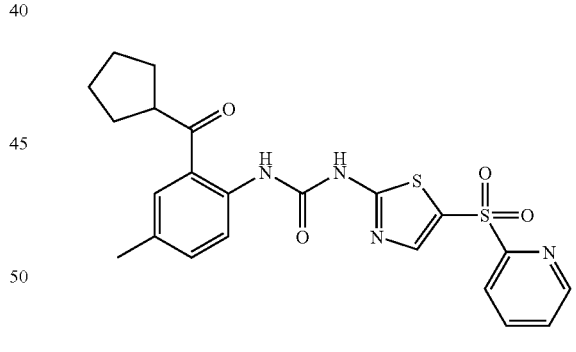

1-(2-Cyclopentanecarbonyl-4-methyl-phenyl)-3-[5-(pyridine-2-sulfonyl)-thiazol-2-yl]-urea (176 mg, 75%) was prepared from 1-(2-cyclopentanecarbonyl-4-methyl-phenyl)-3-[5-(pyridine-2-sulfanyl)-thiazol-2-yl]-urea (219 mg, 0.5 mmol) by oxidation with m-cpba following the general procedure R.

LC-MS (m/z): 471 (M+1)$^+$; $^1$H NMR (400 MHz, CDCl$_3$): δ 1.68 (m, 4H), 1.93 (m, 4H), 2.39 (s, 3H), 3.79 (m, 1H), 7.39 (d, 1H), 7.48 (m, 1H), 7.76 (s, 1H), 7.93 (dd, 1H), 8.15 (d, 1H), 8.33 (br, 1H), 8.42 (d, 1H), 8.70 (d, 1H), 10.8 (br, 1H), 11.93 (br, 1H).

Example 306

1-(2-Cyclopentanecarbonyl-4-methyl-phenyl)-3-[5-(pyrimidin-2-ylsulfanyl)-thiazol-2-yl]-urea

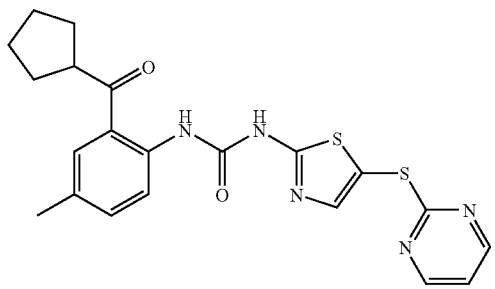

1-(2-Cyclopentanecarbonyl-4-methyl-phenyl)-3-[5-(pyrimidin-2-ylsulfanyl)-thiazol-2-yl]-urea (142 mg, 32%) was prepared from 1-(5-bromo-thiazol-2-yl)-3-(2-cyclo pentanecarbonyl-4-methyl-phenyl)-urea (408 mg, 1 mmol) and 2-mercaptopyrimidine (222 mg, 2 mmol) following the general procedure Q.

LC-MS (m/z): 440 (M+1)$^+$; $^1$H NMR (400 MHz, CDCl$_3$): δ 1.64 (m, 4H), 1.89 (m, 4H), 2.36 (s, 3H), 3.81 (m, 1H), 7.01 (t, 1H), 7.34 (d, 2H), 7.72 (s, 1H), 7.87 (s, 1H), 8.47 (d, 1H), 8.58 (d, 1H), 8.67 (d, 1H), 11.70 (br, 1H), 11.78 (br, 1H).

Example 307

1-(2-Cyclopentanecarbonyl-4-methyl-phenyl)-3-[5-(pyrimidin-2-ylsulfonyl)-thiazol-2-yl]-urea

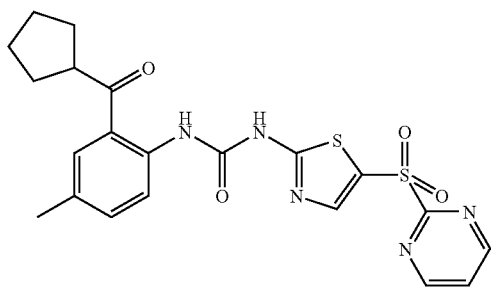

1-(2-Cyclopentanecarbonyl-4-methyl-phenyl)-3-[5-(pyrimidine-2-sulfonyl)-thiazol-2-yl]-urea (169 mg, 72%) was prepared from 1-(2-cyclopentanecarbonyl-4-methyl-phenyl)-3-[5-(pyrimidine-2-sulfanyl)-thiazol-2-yl]-urea (220 mg, 0.5 mmol) by oxidation with m-cpba following the general procedure R.

LC-MS (m/z): 472 (M+1)$^+$; $^1$H NMR (400 MHz, CDCl$_3$): δ 1.71 (m, 4H), 1.91 (m, 4H), 2.38 (s, 3H), 3.78 (m, 1H), 7.39 (d, 1H), 7.49 (t, 1H), 7.76 (s, 1H), 8.31 (s, 1H), 8.43 (d, 1H), 8.93 (d, 2H), 11.80 (br, 1H), 11.94 (br, 1H).

Example 308

1-(2-Cyclopentanecarbonyl-4-methyl-phenyl)-3-[5-(pyridin-4-ylsulfanyl)-thiazol-2-yl]-urea

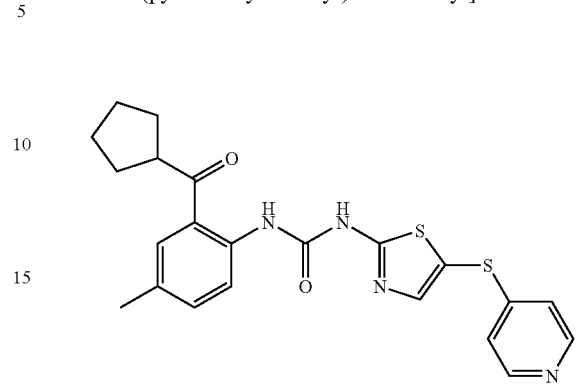

1-(2-Cyclopentanecarbonyl-4-methyl-phenyl)-3-[5-(pyridin-4-ylsulfanyl)-thiazol-2-yl]-urea (110 mg, 25%) was prepared from 1-(5-bromo-thiazol-2-yl)-3-(2-cyclo pentanecarbonyl-4-methyl-phenyl)-urea (408 mg, 1 mmol) and 4-mercaptopyridine (222 mg, 2 mmol) following the general procedure Q.

LC-MS (m/z): 439 (M+1)$^+$; $^1$H NMR (400 MHz, CDCl$_3$): δ 1.62 (m, 4H), 1.84 (m, 4H), 2.35 (s, 3H), 3.73 (m, 1H), 7.10 (d, 2H), 7.34 (d, 2H), 7.71 (s, 1H), 7.95 (s, 1H), 8.38 (d, 1H), 8.42 (d, 1H), 11.65 (br, 1H), 11.75 (br, 1H).

Example 309

1-(2-Cyclopentanecarbonyl-4-methyl-phenyl)-3-[5-(1-methyl-1H-imidazol-2-ylsulfanyl)-thiazol-2-yl]-urea

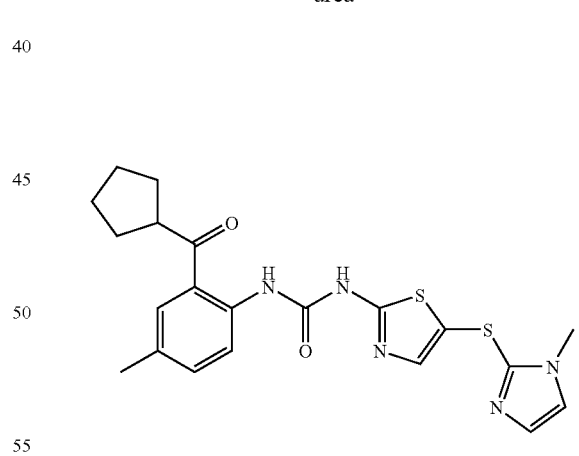

1-(2-Cyclopentanecarbonyl-4-methyl-phenyl)-3-[5-(1-methyl-1H-imidazol-2-ylsulfanyl)-thiazol-2-yl]-urea (141 mg, 32%) was prepared from 1-(5-bromo-thiazol-2-yl)-3-(2-cyclo pentanecarbonyl-4-methyl-phenyl)-urea (408 mg, 1 mmol) and 1-methyl-1H-imidazole-2-thiol (228 mg, 2 mmol) following the general procedure Q.

LC-MS (m/z): 442 (M+1)$^+$; $^1$H NMR (400 MHz, CDCl$_3$): δ 1.66 (m, 4H), 1.88 (m, 4H), 2.35 (s, 3H), 3.74 (m, 1H), 3.77 (s, 3H), 6.93 (s, 1H), 7.06 (s, 1H), 7.32 (d, 1H), 7.69 (s, 1H), 7.82 (s, 1H), 8.40 (d, 1H), 11.51 (br, 1H), 12.20 (br, 1H).

Example 310

1-(2-Cyclopentanecarbonyl-4-methyl-phenyl)-3-[5-(1H-imidazol-2-ylsulfanyl)-thiazol-2-yl]-urea

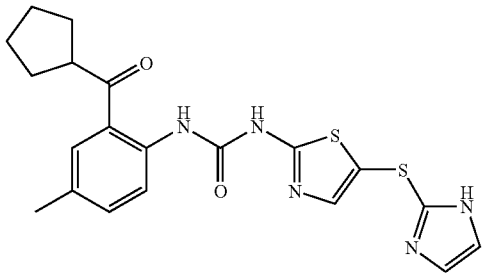

1-(2-Cyclopentanecarbonyl-4-methyl-phenyl)-3-[5-(1H-imidazol-2-ylsulfanyl)-thiazol-2-yl]-urea (149 mg, 35%) was prepared from 1-(5-bromo-thiazol-2-yl)-3-(2-cyclo pentanecarbonyl-4-methyl-phenyl)-urea (408 mg, 1 mmol) and 1H-imidazole-2-thiol (200 mg, 2 mmol) following the general procedure Q.

LC-MS (m/z): 428 (M+1)$^+$; $^1$H NMR (400 MHz, CDCl$_3$): δ 1.70 (m, 4H), 1.91 (m, 4H), 2.37 (s, 3H), 3.83 (m, 1H), 7.10 (s, 1H), 7.34 (d, 1H), 7.57 (s, 2H), 7.66 (s, 1H), 7.78 (s, 1H), 8.42 (d, 1H), 11.22 (br, 1H).

Example 311

1-(2-Cyclopentanecarbonyl-4-methyl-phenyl)-3-[5-(7H-purin-6-ylsulfanyl)-thiazol-2-yl]-urea

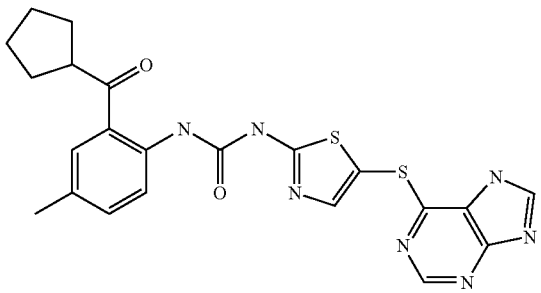

1-(2-Cyclopentanecarbonyl-4-methyl-phenyl)-3-[5-(7H-purin-6-ylsulfanyl)-thiazol-2-yl]-urea(124 mg, 28%) was prepared from 1-(5-bromo-thiazol-2-yl)-3-(2-cyclo pentanecarbonyl-4-methyl-phenyl)-urea (408 mg, 1 mmol) and 7H-purine-6-thiol (304 mg, 2 mmol) following the general procedure Q.

LC-MS (m/z): 480 (M+1)$^+$; $^1$H NMR (400 MHz, CDCl$_3$): δ 1.61 (m, 4H), 1.81 (m, 4H), 2.26 (s, 3H), 3.64 (m, 1H), 7.21 (d, 2H), 7.54 (d, 2H), 8.02 (s, 1H), 8.26 (d, 1H), 8.56 (s, 1H), 11.12 (br, 1H), 11.62 (br, 1H).

Example 312

2-{2-[3-(2-Cyclopentanecarbonyl-4-methyl-phenyl)-ureido]-thiazol-5-ylsulfanyl}-nicotinic acid methyl ester

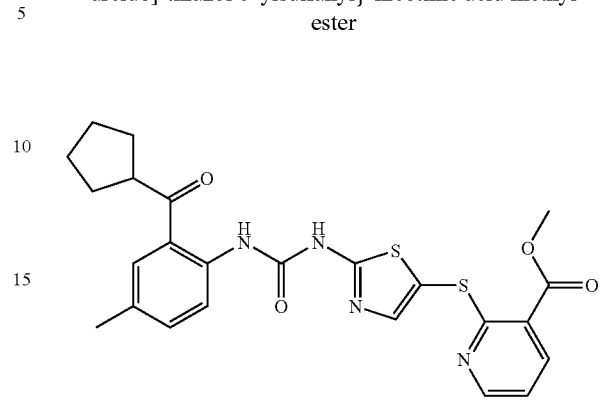

2-{2-[3-(2-Cyclopentanecarbonyl-4-methyl-phenyl)-ureido]-thiazol-5-ylsulfanyl}-nicotinic acid methyl ester (124 mg, 25%) was prepared from 1-(5-bromo-thiazol-2-yl)-3-(2-cyclo pentanecarbonyl-4-methyl-phenyl)-urea (408 mg, 1 mmol) and 2-mercapto-nicotinic acid methyl ester (340 mg, 2 mmol) following the general procedure Q.

LC-MS (m/z): 497 (M+1)$^+$; $^1$H NMR (400 MHz, CDCl$_3$): δ 1.64 (m, 4H), 1.85 (m, 4H), 2.36 (s, 3H), 3.74 (m, 1H), 3.98 (s, 3H), 7.08 (dd, 1H), 7.34 (d, 2H), 7.71 (s, 1H), 7.79 (s 1H), 8.22 (dd, 1H), 8.45 (d, 1H), 8.49 (dd, 1H), 11.45 (br, 1H), 11.75 (br, 1H).

Example 313

2-{2-[3-(2-Cyclopentanecarbonyl-4-methyl-phenyl)-ureido]-thiazol-5-ylsulfanyl}-nicotinic acid

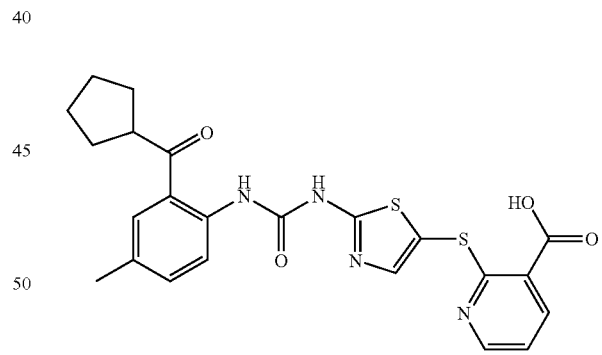

2-{2-[3-(2-Cyclopentanecarbonyl-4-methyl-phenyl)-ureido]-thiazol-5-ylsulfanyl}-nicotinic acid (186 mg, 75%) was prepared from 2-{2-[3-(2-cyclopentanecarbonyl-4-methyl-phenyl)-ureido]-thiazol-5-ylsulfanyl}-nicotinic acid methyl ester (248 mg, 0.5 mmol) following the general procedure J.

LC-MS (m/z): 483 (M+1)$^+$; $^1$H NMR (400 MHz, DMSO-d$_6$): δ 1.62 (m, 4H), 1.75 (m, 2H), 1.89 (m, 2H), 2.33 (s, 3H), 3.88 (m, 1H), 7.23 (dd, 1H), 7.39 (d, 1H), 7.47 (s, 1H), 7.86 (s, 1H), 8.19 (m, 2H), 8.24 (dd, 1H), 10.70 (br, 1H), 12.23 (br, 1H)

Example 314

2-{2-[3-(2-Cyclopentanecarbonyl-4-methyl-phenyl)-ureido]-thiazol-5-ylsulfonyl}-nicotinic acid methyl ester

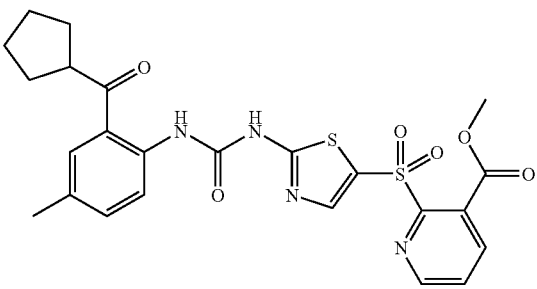

2-{2-[3-(2-Cyclopentanecarbonyl-4-methyl-phenyl)-ureido]-thiazol-5-ylsulfonyl}-nicotinic acid methyl ester (185 mg, 70%) was prepared from 2-{2-[3-(2-cyclopentanecarbonyl-4-methyl-phenyl)-ureido]-thiazol-5-ylsulfanyl}-nicotinic acid methyl ester (248 mg, 0.5 mmol) by oxidation with m-cpba following the general procedure R.

LC-MS (m/z): 529 (M+1)$^+$, $^1$H NMR (400 MHz, CDCl$_3$): δ 1.68 (m, 4H), 1.85 (m, 2H), 1.95 (m, 2H), 2.38 (s, 3H), 3.95 (m, 1H), 3.99 (s, 3H), 7.42 (d, 1H), 7.79 (dd, 2H), 7.97 (s, 1H), 8.14 (s, 1H), 8.15 (d, 1H), 8.82 (d, 1H), 8.79 (d, 1H), 11.35 (br, 1H), 11.68 (br, 1H).

Example 315

2-{2-[3-(2-Cyclopentanecarbonyl-4-methyl-phenyl)-ureido]-thiazol-5-ylsulfonyll}-nicotinic acid

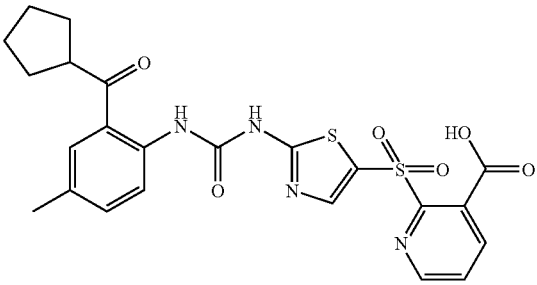

2-{2-[3-(2-Cyclopentanecarbonyl-4-methyl-phenyl)-ureido]-thiazol-5-ylsulfonyll}-nicotinic acid (200 mg, 78%) was prepared from 2-{2-[3-(2-cyclopentanecarbonyl-4-methylphenyl)-ureido]-thiazol-5-ylsulfonyll}-nicotinic acid methyl ester (264 mg, 0.5 mmol) following the general procedure J.

LC-MS (m/z): 515 (M+1)$^+$; $^1$H NMR (400 MHz, acetone-d$_6$): δ 1.67 (m, 4H), 1.84 (m, 2H), 1.95 (m, 2H), 2.38 (s, 3H), 3.95 (m, 1H), 7.44 (d, 1H), 7.76 (dd, 1H), 7.96 (s, 1H), 8.05 (s, 1H), 8.18 (d, 1H), 8.42 (d, 1H), 8.77 (d, 1H), 11.23 (br, 1H), 11.36 (br, 1H).

Example 316

6-{2-[3-(2-Cyclopentanecarbonyl-4-methyl-phenyl)-ureido]-thiazol-5-ylsulfanyl}-nicotinic acid methyl ester

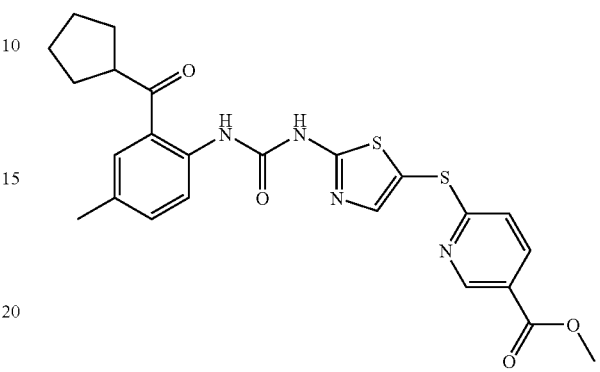

6-{2-[3-(2-Cyclopentanecarbonyl-4-methyl-phenyl)-ureido]-thiazol-5-ylsulfanyl}-nicotinic acid methyl ester (100 mg, 20%) was prepared from 1-(5-bromo-thiazol-2-yl)-3-(2-cyclo pentanecarbonyl-4-methyl-phenyl)-urea (408 mg, 1 mmol) and 6-mercapto-nicotinic acid methyl ester (340 mg, 2 mmol) following the general procedure Q.

LC-MS (m/z): 497 (M+1)$^+$; $^1$H NMR (400 MHz, CDCl$_3$): δ 1.64 (m, 4H), 1.85 (m, 4H), 2.33 (s, 3H), 3.79 (m, 1H), 3.99 (s, 3H), 7.10 (dd, 1H), 7.34 (dd, 1H), 7.71 (s, 1H), 7.79 (s 1H), 8.22 (dd, 1H), 8.45 (d, 1H), 8.50 (dd, 1H), 8.79 (s, 1H), 11.50 (br, 1H), 11.75 (br, 1H).

Example 317

6-{2-[3-(2-Cyclopentanecarbonyl-4-methyl-phenyl)-ureido]-thiazol-5-ylsulfanyl}-nicotinic acid

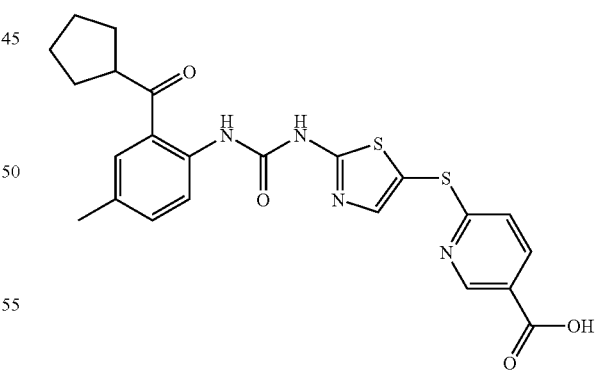

6-{2-[3-(2-Cyclopentanecarbonyl-4-methyl-phenyl)-ureido]-thiazol-5-ylsulfanyl}-nicotinic acid (169 mg, 70%) was prepared from 6-{2-[3-(2-cyclopentanecarbonyl-4-methylphenyl)-ureido]-thiazol-5-ylsulfanyl}-nicotinic acid methyl ester (248 mg, 0.5 mmol) following the general procedure J.

LC-MS (m/z): 483 (M+1)$^+$; $^1$H NMR (400 MHz, DMSO-d$_6$): δ 1.62 (m, 4H), 1.75 (m, 2H), 1.89 (m, 2H), 2.33 (s, 3H), 3.89 (m, 1H), 7.12 (d, 1H), 7.38 (d, 1H), 7.75 (s, 1H), 7.87 (s, 1H), 8.12 (dd, 2H), 8.24 (dd, 1H), 8.85 (s, 1H), 10.76 (br, 1H), 12.60 (br, 1H).

Example 318

6-{2-[3-(2-Cyclopentanecarbonyl-4-methyl-phenyl)-ureido]-thiazol-5-ylsulfonyl}-nicotinic acid methyl ester

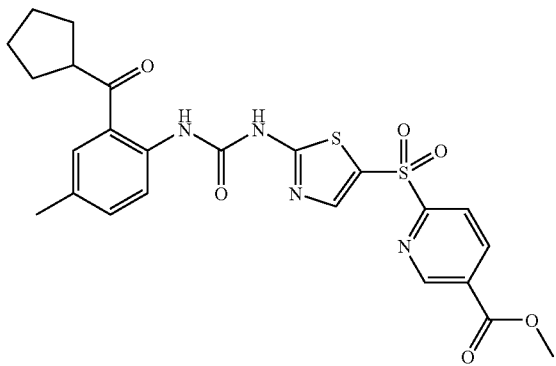

6-{2-[3-(2-Cyclopentanecarbonyl-4-methyl-phenyl)-ureido]-thiazol-5-ylsulfonyl}-nicotinic acid methyl ester (172 mg, 65%) was prepared from 6-{2-[3-(2-cyclopentanecarbonyl-4-methyl-phenyl)-ureido]-thiazol-5-ylsulfanyl}-nicotinic acid methyl ester (248 mg, 0.5 mmol) by oxidation with m-cpba following the general procedure R.

LC-MS (m/z): 529 (M+1)$^+$; $^1$H NMR (400 MHz, CDCl$_3$): δ 1.74 (m, 4H), 1.97 (m, 4H), 2.38 (s, 3H), 3.81 (m, 1H), 3.98 (s, 3H), 7.44 (t, 1H), 7.58 (d, 1H), 8.02 (dd, 1H), 8.11 (s, 1H), 8.23 (d, 1H), 8.52 (dd, 1H), 9.26 (d, 1H), 10.56 (br, 1H), 12.11 (br, 1H).

Example 319

3-{2-[3-(2-Cyclopentanecarbonyl-4-methyl-phenyl)-ureido]-thiazol-5-ylsulfanyl}-pyridine-2-carboxylic acid methyl ester

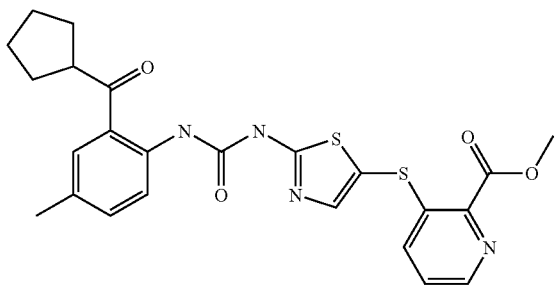

3-{2-[3-(2-Cyclopentanecarbonyl-4-methyl-phenyl)-ureido]-thiazol-5-ylsulfanyl}-pyridine-2-carboxylic acid methyl ester (149 mg, 30%) was prepared from 1-(5-bromo-thiazol-2-yl)-3-(2-cyclo pentanecarbonyl-4-methyl-phenyl)-urea (408 mg, 1 mmol) and 3-mercapto-pyridine-2-carboxylic acid methyl ester (340 mg, 2 mmol) following the general procedure Q.

LC-MS (m/z): 497 (M+1)$^+$; $^1$H NMR (400 MHz, CDCl$_3$): δ 1.59 (m, 4H), 1.80 (m, 2H), 1.91 (m, 2H), 2.37 (s, 3H), 3.73 (m, 1H), 4.01 (s, 3H), 7.29 (dd, 1H), 7.36 (d, 1H), 7.52 (dd, 1H), 7.72 (s, 1H), 7.97 (s, 1H), 8.11 (dd, 1H), 8.46 (m, 1H), 11.83 (br, 1H).

Example 320

3-{2-[3-(2-Cyclopentanecarbonyl-4-methyl-phenyl)-ureido]-thiazol-5-ylsulfanyl}-pyridine-2-carboxylic acid

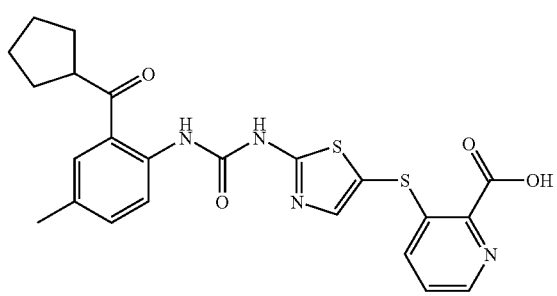

3-{2-[3-(2-Cyclopentanecarbonyl-4-methyl-phenyl)-ureido]-thiazol-5-ylsulfanyl}-pyridine-2-carboxylic acid (181 mg, 75%) was prepared from 3-{2-[3-(2-Cyclopentanecarbonyl-4-methyl-phenyl)-ureido]-thiazol-5-ylsulfanyl}-pyridine-2-carboxylic acid methyl ester (248 mg, 0.5 mmol) following the general procedure J.

LC-MS (m/z): 483 (M+1)$^+$; $^1$H NMR (400 MHz, DMSO-d$_6$): δ 1.62 (m, 4H), 1.75 (m, 2H), 1.91 (m, 2H), 2.32 (s, 3H), 3.88 (m, 1H), 7.38 (d, 2H), 7.51 (dd, 1H), 7.72 (s, 1H), 7.87 (s, 1H), 8.13 (d, 1H), 8.44 (d, 1H), 10.74 (br, 1H), 12.25 (br, 1H).

Example 321

2-{2-[3-(2-Cyclopentanecarbonyl-4-methyl-phenyl)-ureido]-thiazol-5-ylsulfanyl}-1H-imidazole-4-carboxylic acid ethyl ester

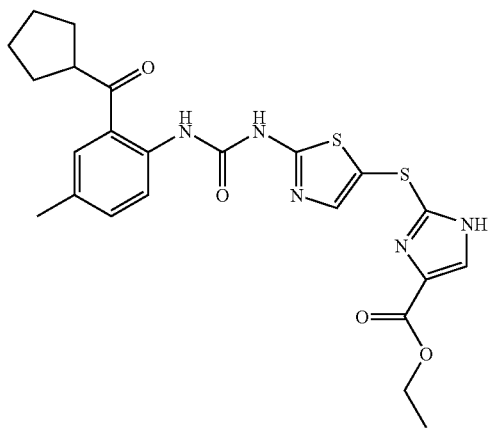

2-{2-[3-(2-Cyclopentanecarbonyl-4-methyl-phenyl)-ureido]-thiazol-5-ylsulfanyl}-1H-imidazole-4-carboxylic acid ethyl ester (190 mg, 38%) was prepared from 1-(5-bromo-thiazol-2-yl)-3-(2-cyclo pentanecarbonyl-4-methyl-phenyl)-urea (408 mg, 1 mmol) and 2-mercapto-1H-imidazole-4-carboxylic acid ethyl ester (340 mg, 2 mmol) following the general procedure Q.

LC-MS (m/z): 500 (M+1)+; 1H NMR (400 MHz, CDCl3): δ 1.27 (t, 3H), 1.62 (m, 4H), 1.72 (m, 2H), 1.89 (m, 2H), 2.34 (s, 3H), 3.87 (m, 1H), 4.16 (q, 2H), 6.60 (br, 1H), 7.39 (d, 1H), 7.70 (s, 1H), 7.82 (s, 2H), 8.15 (d, 1H), 10.22 (br, 1H), 11.90 (br, 1H).

Example 322

2-{2-[3-(2-Cyclopentanecarbonyl-4-methyl-phenyl)-ureido]-thiazol-5-ylsulfanyl}-1H-imidazole-4-carboxylic acid

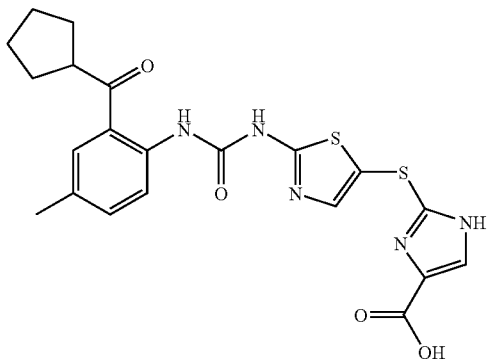

2-{2-[3-(2-Cyclopentanecarbonyl-4-methyl-phenyl)-ureido]-thiazol-5-ylsulfanyl}-1H-imidazole-4-carboxylic acid (167 mg, 71%) was prepared from 2-{2-[3-(2-cyclopentanecarbonyl-4-methyl-phenyl)-ureido]-thiazol-5-ylsulfanyl}-1H-imidazole-4-carboxylic acid ethyl ester (250 mg, 0.5 mmol) following the general procedure J.

LC-MS (m/z): 472 (M+1)+; 1H NMR (400 MHz, DMSO-d6): δ 1.61 (m, 4H), 1.73 (m, 2H), 1.89 (m, 2H), 2.33 (s, 3H), 3.87 (m, 1H), 6.53 (br, 1H), 7.37 (d, 1H), 7.64 (s, 1H), 7.83 (s, 2H), 8.14 (d, 1H), 10.70 (br, 1H), 12.20 (br, 1H).

Example 323

2-{2-[3-(2-Cyclopentanecarbonyl-4-methyl-phenyl)-ureido]-thiazol-5-ylsulfonyl}-1H-imidazole-4-carboxylic acid ethyl ester

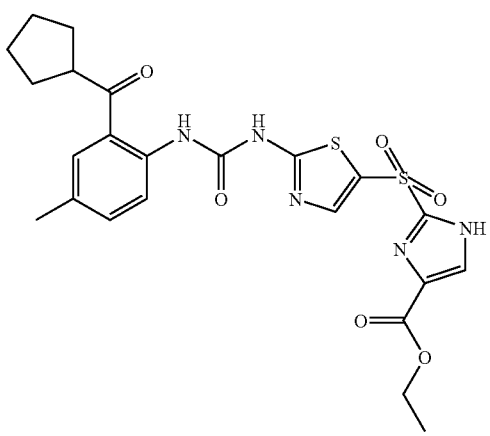

2-{2-[3-(2-Cyclopentanecarbonyl-4-methyl-phenyl)-ureido]-thiazol-5-ylsulfonyl}-1H-imidazole-4-carboxylic acid ethyl ester (181 mg, 68%) was prepared from 2-{2-[3-(2-cyclopentanecarbonyl-4-methyl-phenyl)-ureido]-thiazol-5-ylsulfonyl}-1H-imidazole-4-carboxylic acid ethyl ester (250 mg, 0.5 mmol) by oxidation with m-cpba following the general procedure R.

LC-MS (m/z): 532 (M+1)+; 1H NMR (400 MHz, CDCl3): δ 1.27 (t, 3H), 1.71 (m, 4H), 1.91 (m, 4H), 2.36 (s, 3H), 3.73 (m, 1H), 4.38 (q, 2H), 6.98 (s, 1H), 7.34 (d, 1H), 7.71 (s, 1H), 7.83 (s, 1H), 8.22 (br, 1H), 8.38 (d, 1H), 11.80 (br, 1H).

Example 324

2-{2-[3-(2-Cyclopentanecarbonyl-4-methyl-phenyl)-ureido]-thiazol-5-ylsulfonyl}-1H-imidazole-4-carboxylic acid

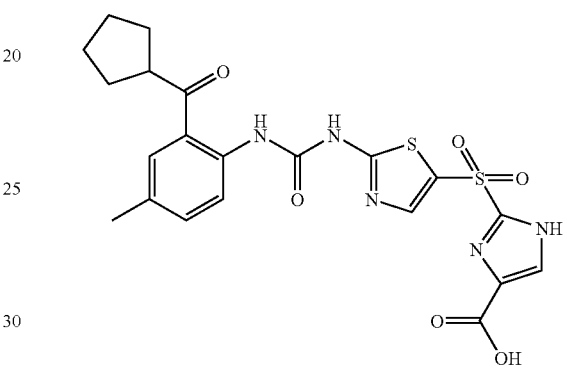

2-{2-[3-(2-Cyclopentanecarbonyl-4-methyl-phenyl)-ureido]-thiazol-5-ylsulfonyl}-1H-imidazole-4-carboxylic acid (171 mg, 68%) was prepared from 2-{2-[3-(2-cyclopentanecarbonyl-4-methyl-phenyl)-ureido]-thiazol-5-ylsulfonyl}-1H-imidazole-4-carboxylic acid ethyl ester (266 mg, 0.5 mmol) following the general procedure J.

LC-MS (m/z): 504 (M+1)+; 1H NMR (400 MHz, DMSO-d6): δ 1.61 (m, 4H), 1.75 (m, 2H), 1.89 (m, 2H), 2.33 (s, 3H), 3.88 (m, 1H), 7.41 (d, 1H), 7.53 (dd, 2H), 7.69 (dd, 1H), 7.88 (m, 1H), 8.01 (br, 1H), 8.14 (d, 1H), 10.86 (br, 1H).

Example 325

(3-Cyclopentanecarbonyl-4-{3-[5-(pyridin-2-ylsulfanyl)-thiazol-2-yl]-ureido}-phenyl)-acetic acid ethyl ester

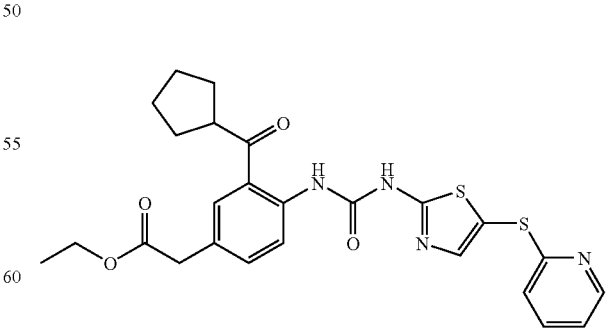

(3-Cyclopentanecarbonyl-4-{3-[5-(pyridin-2-ylsulfanyl)-thiazol-2-yl]-ureido}-phenyl)-acetic acid ethyl ester (153 mg, 30%) was prepared from {4-[3-(5-bromo-thiazol-2-yl)-ureido]-3-cyclopentanecarbonyl-phenyl}-acetic acid ethyl ester (480 mg, 1 mmol) and 2-mercaptopyridine (222 mg, 2 mmol) following the general procedure Q.

LC-MS (m/z): 511 (M+1)+; $^1$H NMR (400 MHz, CDCl$_3$): δ 1.26 (t, 3H), 1.61 (m, 4H), 1.85 (m, 4H), 3.62 (s, 2H), 3.76 (m, 1H), 4.16 (q, 2H), 7.01 (dd, 1H), 7.06 (d, 1H), 7.45 (d, 1H), 7.51 (d, 1H), 7.89 (s, 1H), 7.93 (s, 1H), 8.41 (dd, 1H), 8.55 (d, 1H), 11.70 (br, 1H), 11.89 (br, 1H).

Example 326

(3-Cyclopentanecarbonyl-4-{3-[5-(pyridin-2-ylsulfanyl)-thiazol-2-yl]-ureido}-phenyl)-acetic acid

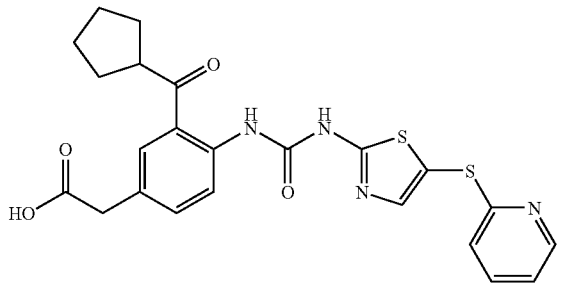

(3-Cyclopentanecarbonyl-4-{3-[5-(pyridin-2-ylsulfanyl)-thiazol-2-yl]-ureido}-phenyl)-acetic acid (173 mg, 72%) was prepared from (3-cyclopentanecarbonyl-4-{3-[5-(pyridin-2-ylsulfanyl)-thiazol-2-yl]-ureido}-phenyl)-acetic acid ethyl ester (255 mg, 0.5 mmol) following the general procedure J.

LC-MS (m/z): 483 (M+1)+; $^1$H NMR (400 MHz, Acetone d$_6$): δ 1.64 (m, 4H), 1.86 (m, 2H), 1.98 (m, 4H), 3.71 (s, 2H), 3.94 (m, 1H), 7.08 (d, 1H), 7.15 (dd, 1H), 7.53 (d, 1H), 7.61 (s, 1H), 7.68 (m, 1H), 8.11 (s, 1H), 8.39 (m, 1H), 8.52 (d, 1H), 11.30 (br, 1H), 11.35 (br, 1H).

Example 327

(3-Cyclopentanecarbonyl-4-{3-[5-(1H-imidazol-2-ylsulfanyl)-thiazol-2-yl]-ureido}-phenyl)acetic acid ethyl ester

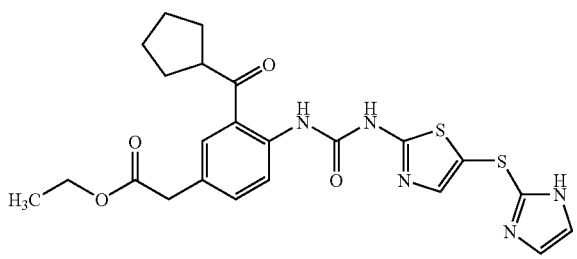

(3-Cyclopentanecarbonyl-4-{3-[5-(1H-imidazol-2-ylsulfanyl)-thiazol-2-yl]-ureido}-phenyl)acetic acid ethyl ester (120 mg, 24%) was prepared from {4-[3-(5-bromo-thiazol-2-yl)-ureido]-3-cyclopentanecarbonyl-phenyl}-acetic acid ethyl ester (480 mg, 1 mmol) and 1H-imidazole-2-thiol (200 mg, 2 mmol) following the general procedure Q.

LC-MS (m/z): 500 (M+1)+; $^1$H NMR (400 MHz, CDCl$_3$): δ 1.21 (t, 3H), 1.58 (m, 4H), 1.83 (m, 4H), 3.61 (m, 3H), 4.17 (q, 1H), 6.73 (s, 1H), 7.04 (m, 2H), 7.38 (d, 1H), 7.61 (br, 1H), 7.81 (s, 1H), 8.41 (d, 1H), 11.23 (br, 1H), 11.49 (br, 1H).

Example 328

(3-Cyclopentanecarbonyl-4-{3-[5-(1H-imidazol-2-ylsulfanyl)-thiazol-2-yl]-ureido}-phenyl)-acetic acid

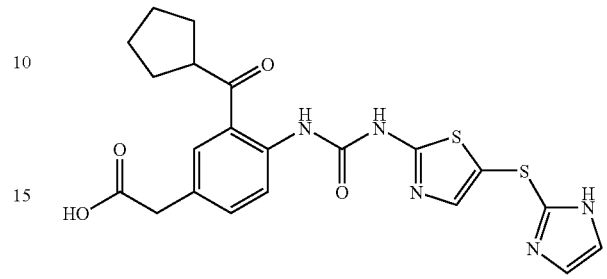

(3-Cyclopentanecarbonyl-4-{3-[5-(1H-imidazol-2-ylsulfanyl)-thiazol-2-yl]-ureido}-phenyl)-acetic acid (177 mg, 72%) was prepared from (3-cyclopentanecarbonyl-4-{3-[5-(1H-imidazol-2-ylsulfanyl)-thiazol-2-yl]-ureido}-phenyl)-acetic acid ethyl ester (250 mg, 0.5 mmol) following the general procedure J.

LC-MS (m/z): 472 (M+1)+; $^1$H NMR (400 MHz, acetone d$_6$): δ 1.61 (m, 4H), 1.91 (m, 4H), 3.58 (s, 2H), 3.72 (m, 1H), 6.77 (s, 1H), 7.04 (d, 1H), 7.33 m, 2H), 7.64 (br, 1H), 7.80 (s, 1H), 8.43 (d, 1H), 11.44 (br, 1H), 11.59 (br, 1H).

Example 329

1-(2-Cyclopentanecarbonyl-4-methyl-phenyl)-3-[5-(1-methyl-1H-tetrazol-5-ylsulfanyl)-thiazol-2-yl]-urea

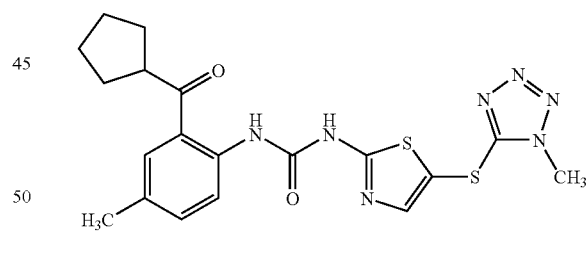

1-(2-Cyclopentanecarbonyl-4-methyl-phenyl)-3-[5-(1-methyl-1H-tetrazol-5-ylsulfanyl)-thiazol-2-yl]-urea (133 mg, 30%) was prepared from 1-(5-bromo-thiazol-2-yl)-3-(2-cyclopentanecarbonyl-4-methyl-phenyl)-urea (408 mg, 1 mmol) and 1-methyl-1H-tetrazole-5-thiol (202 mg, 2 mmol) following the general procedure Y LC-MS (m/z): 444 (M+1)+, $^1$H NMR (400 MHz, CDCl$_3$): δ 1.70 (m, 4H), 1.91 (m, 4H), 2.37 (s, 3H), 3.78 (m, 1H), 4.06 (s, 3H), 7.37 (d, 1H), 7.73 (s, 1H), 7.93 (s, 1H), 8.41 (d, 1H), 9.30 (br, 1H), 11.74 (br, 1H).

Example 330

(5-{2-[3-(2-Cyclopentanecarbonyl-4-methyl-phenyl)-ureido]-thiazol-5-ylsulfanyl}-tetrazol-1-yl)-acetic acid

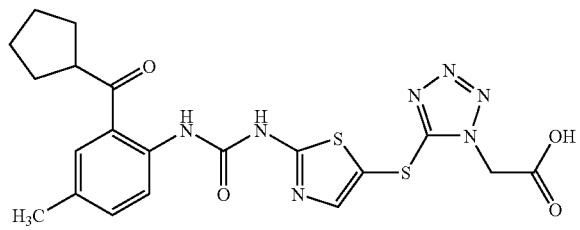

(5-{2-[3-(2-Cyclopentanecarbonyl-4-methyl-phenyl)-ureido]-thiazol-5-ylsulfanyl}-tetrazol-1-yl)-acetic acid (136 mg, 28%) was prepared from 1-(5-bromo-thiazol-2-yl)-3-(2-cyclo pentanecarbonyl-4-methyl-phenyl)-urea (408 mg, 1 mmol) and (5-mercapto-tetrazol-1-yl)-acetic acid (320 mg, 2 mmol) following the general procedure Y.

LC-MS (m/z): 488 (M+1)+, $^1$H NMR (400 MHz, DMSO-$d_6$): δ 1.70 (m, 4H), 1.91 (m, 4H), 2.34 (s, 3H), 3.89 (m, 1H), 5.48 (s, 2H), 7.42 (d, 1H), 7.81 (s, 1H), 7.88 (s, 1H), 8.17 (d, 1H), 10.76 (br, 1H), 12.25 (br, 2H).

Example 331

1-(2-Cyclopentanecarbonyl-4-methyl-phenyl)-3-{5-[1-(2-dimethylamino-ethyl)-1H-tetrazol-5-ylsulfanyl]-thiazol-2-yl}-urea

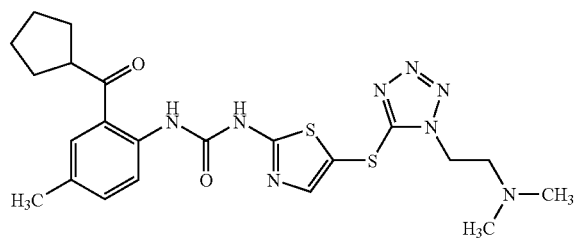

1-(2-Cyclopentanecarbonyl-4-methyl-phenyl)-3-{5-[1-(2-dimethylamino-ethyl)-1H-tetrazol-5-ylsulfanyl]-thiazol-2-yl}-urea (125 mg, 25%) was prepared from 1-(5-bromo-thiazol-2-yl)-3-(2-cyclopentanecarbonyl-4-methyl-phenyl)-urea (408 mg, 1 mmol) and 1-(2-dimethylamino-ethyl)-1H-tetrazole-5-thiol (346 mg, 2 mmol) following the general procedure Y LC-MS (m/z): 501 (M+1)+, $^1$H NMR (400 MHz, DMSO-$d_6$): δ 1.70 (m, 4H), 1.91 (m, 4H), 2.28 (s, 6H), 2.34 (s, 3H), 2.76 (t, 2H), 3.74 (m, 1H), 4.42 (t, 2H), 7.32 (d, 1H), 7.68 (s, 1H), 7.83 (s, 1H), 8.36 (d, 1H), 11.25 (br, 1H), 11.40 (br, 1H).

Example 332

1-(2-Cyclopentanecarbonyl-4-methyl-phenyl)-3-[5-(4H-[1,2,4]triazol-3-ylsulfanyl)-thiazol-2-yl]-urea

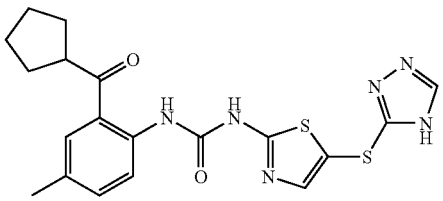

1-(2-Cyclopentanecarbonyl-4-methyl-phenyl)-3-[5-(4H-[1,2,4]triazol-3-ylsulfanyl)-thiazol-2-yl]-urea (129 mg, 30%) was prepared from 1-(5-bromo-thiazol-2-yl)-3-(2-cyclo pentanecarbonyl-4-methyl-phenyl)-urea (408 mg, 1 mmol) and 2H-[1,2,4]triazole-3-thiol (202 mg, 2 mmol) following the general procedure Y LC-MS (m/z): 429 (M+1)+, $^1$H NMR (400 MHz, DMSO-$d_6$): δ 1.63 (m, 4H), 1.70 (m, 2H), 1.91 (m, 2H), 2.34 (s, 3H), 3.89 (m, 1H), 7.41 (d, 1H), 7.63 (s, 1H), 7.87 (s, 1H), 8.17 (d, 1H), 10.72 (br, 1H), 12.18 (br, 1H).

Example 333

1-(2-Cyclopentanecarbonyl-4-methyl-phenyl)-3-[5-(4-methyl-4H-[1,2,4]triazol-3-ylsulfanyl)-thiazol-2-yl]-urea

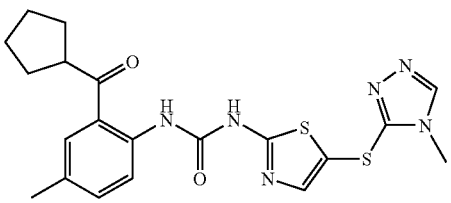

1-(2-Cyclopentanecarbonyl-4-methyl-phenyl)-3-[5-(4-methyl-4H-[1,2,4]triazol-3-ylsulfanyl)-thiazol-2-yl]-urea (125 mg, 25%) was prepared from 1-(5-bromo-thiazol-2-yl)-3-(2-cyclo pentanecarbonyl-4-methyl-phenyl)-urea (408 mg, 1 mmol) and 4-methyl-4H-[1,2,4]triazole-3-thiol (230 mg, 2 mmol) following the general procedure Y LC-MS (m/z): 443 (M+1)+, $^1$H NMR (400 MHz, DMSO-$d_6$): δ 1.63 (m, 4H), 1.75 (m, 2H), 1.91 (m, 1H), 2.34 (s, 3H), 3.70 (s, 3H), 3.89 (m, 1H), 7.41 (d, 1H), 7.73 (s, 1H), 7.87 (s, 1H), 8.16 (d, 1H), 8.62 (s, 1H), 10.72 (br, 1H), 12.15 (br, 1H).

Example 334

1-(2-Cyclopentanecarbonyl-4-methyl-phenyl)-3-[5-(4-methyl-4H-[1,2,4]triazole-3-sulfonyl)-thiazol-2-yl]-urea

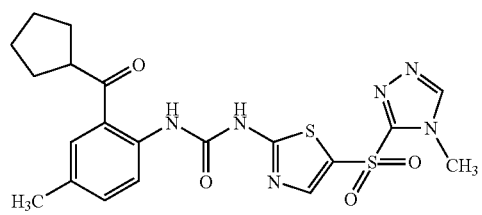

1-(2-Cyclopentanecarbonyl-4-methyl-phenyl)-3-[5-(4-methyl-4H-[1,2,4]triazole-3-sulfonyl)-thiazol-2-yl]-urea (171 mg, 72%) was prepared from 1-(2-cyclopentanecarbonyl-4-methyl-phenyl)-3-[5-(4-methyl-4H-[1,2,4]triazole-3-sulfanyl)-thiazol-2-yl]-urea (221 mg, 0.5 mmol) by oxidation with m-cpba following the general procedure R LC-MS (m/z): 475 (M+1)$^+$, $^1$H NMR (400 MHz, DMSO-d$_6$): δ 1.73 (m, 4H), 1.85 (m, 2H), 1.91 (m, 2H), 2.34 (s, 3H), 3.70 (s, 3H), 3.89 (m, 1H), 7.51 (d, 1H), 7.73 (s, 1H), 7.87 (s, 1H), 8.16 (d, 1H), 8.62 (s, 1H), 10.72 (br, 1H), 12.15 (br, 1H).

Example 335

(4-{2-[3-(2-Cyclopentanecarbonyl-4-methyl-phenyl)-ureido]-thiazol-5-yl sulfanyl}-phenyl)-acetic acid

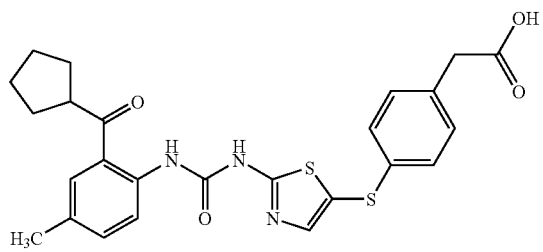

(4-{2-[3-(2-Cyclopentanecarbonyl-4-methyl-phenyl)-ureido]-thiazol-5-yl sulfanyl}-phenyl)-acetic acid (140 mg, 30%) was prepared from 1-(5-bromo-thiazol-2-yl)-3-(2-cyclopentanecarbonyl-4-methyl-phenyl)-urea (408 mg, 1 mmol) and (4-mercapto-phenyl)-acetic acid (336 mg, 2 mmol) following the general procedure Y.

(LC-MS (m/z): 496 (M+1)$^+$; $^1$H NMR (400 MHz, DMSO-d$_6$): δ 1.63 (m, 4H), 1.75 (m, 2H), 1.91 (m, 2H), 2.33 (s, 3H), 3.59 (s, 2H), 3.89 (m, 1H), 7.20 (m, 3H), 7.40 (d, 2H), 7.68 (s, 1H), 7.87 (s, 1H), 8.16 (d, 1H), 12.36 (br, 3H).

Example 336

1-(5-Acetyl-4-methyl-thiazol-2-yl)-3-(2-cyclopentanecarbonyl-4-methyl-phenyl)-urea

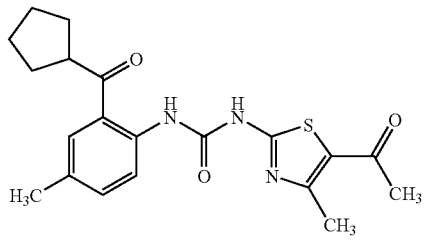

1-(5-Acetyl-4-methyl-thiazol-2-yl)-3-(2-cyclopentanecarbonyl-4-methyl-phenyl)-urea (116 mg, 60%) was prepared from (2-amino-5-methyl-phenyl)-cyclopentyl-methanone (102 mg, 0.5 mmol) and 1-(2-amino-4-methyl-thiazol-5-yl)-ethanone (94 mg, 0.6 mmol) following the general procedure D.

LC-MS (m/z): 386 (M+1)$^+$, $^1$H NMR (400 MHz, DMSO-d$_6$): δ 1.63 (m, 4H), 1.76 (m, 2H), 1.91 (m, 2H), 2.35 (s, 3H), 2.45 (s, 3H), 2.55 (s, 3H), 3.89 (m, 1H), 7.42 (d, 1H), 7.88 (s, 1H), 8.20 (s, 1H), 10:80 (br, 1H), 12.25 (br, 1H).

Example 337

1-(2-Cyclopentanecarbonyl-4-methyl-phenyl)-3-(5-nitro-thiazol-2-yl)-urea

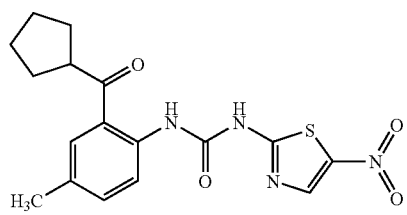

1-(2-Cyclopentanecarbonyl-4-methyl-phenyl)-3-(5-nitro-thiazol-2-yl)-urea (103 mg, 55%) was prepared from (2-amino-5-methyl-phenyl)-cyclopentyl-methanone (102 mg, 0.5 mmol) and 5-nitro-thiazol-2-ylamine (87 mg, 0.6 mmol) following the general procedure D.

LC-MS (m/z): 375 (M+1)$^+$, $^1$H NMR (400 MHz, DMSO-d$_6$): δ 1.64 (m, 4H), 1.76 (m, 2H), 1.91 (m, 2H), 2.36 (s, 3H), 3.91 (m, 1H), 7.44 (d, 1H), 7.91 (d, 1H), 8.21 (d, 1H), 8.58 (s, 1H), 10.97 (br, 1H), 12.25 (br, 1H).

Example 338

1-(4-tert-Butyl-thiazol-2-yl)-3-(2-cyclopentanecarbonyl-4-methyl-phenyl)-urea

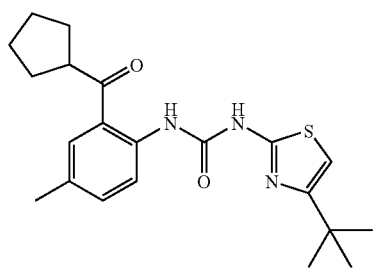

1-(4-tert-Butyl-thiazol-2-yl)-3-(2-cyclopentanecarbonyl-4-methyl-phenyl)-urea (127 mg, 66%) was prepared from (2-amino-5-methyl-phenyl)-cyclopentyl-methanone (102 mg, 0.5 mmol) and 4-tert-butyl-thiazol-2-ylamine (94 mg, 0.6 mmol) following the general procedure D.

LC-MS (m/z): 386 (M+1)$^+$, $^1$H NMR (400 MHz, DMSO-d$_6$): δ 1.24 (s, 9H), 1.62 (m, 4H), 1.76 (m, 2H), 1.91 (m, 2H), 2.32 (s, 3H), 3.87 (m, 1H), 6.63 (s, 1H), 7.37 (d, 1H), 7.83 (d, 1H), 8.13 (d, 1H), 10.53 (br, 1H), 11.82 (br, 1H).

Example 339

1-(2-Cyclopentanecarbonyl-4-methyl-phenyl)-3-pyridin-2-yl-urea

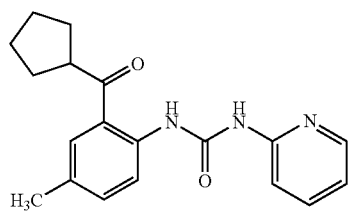

1-(2-Cyclopentanecarbonyl-4-methyl-phenyl)-3-pyridin-2-yl-urea (94 mg, 58%) was prepared from (2-amino-5-methyl-phenyl)-cyclopentyl-methanone (102 mg, 0.5 mmol) and 2-aminopyridine (57 mg, 0.6 mmol) following the general procedure D.

LC-MS (m/z): 324(M+1)$^+$, $^1$H NMR (400 MHz, DMSO-$d_6$): δ 1.63 (m, 4H), 1.76 (m, 2H), 1.91 (m, 2H), 2.35 (s, 3H), 3.90 (m, 1H), 6.03 (d, 1H), 7.42 (d, 1H), 7.80 (m, 4H), 8.21 (s, 1H), 10.77 (br, 1H), 12.24 (br, 1H).

Example 340

1-(2-Cyclopentanecarbonyl-4-methyl-phenyl)-3-(5-formyl-thiazol-2-yl)-urea

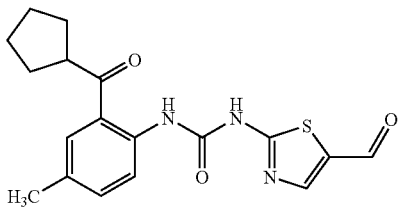

1-(2-Cyclopentanecarbonyl-4-methyl-phenyl)-3-(5-formyl-thiazol-2-yl)-urea (116 mg, 65%) was prepared from (2-amino-5-methyl-phenyl)-cyclopentyl-methanone (102 mg, 0.5 mmol) and 2-amino-thiazol-5-carbaldehyde (77 mg; 0.6 mmol) following the general procedure D.

LC-MS (m/z): 358 (M+1)$^+$; $^1$H NMR (400 MHz, DMSO-$d_6$): δ 1.65 (m, 4H), 1.76 (m, 2H), 1.90 (m, 2H), 2.35 (s, 3H), 3.89 (m 1H), 7.43 (d, 1H), 7.89 (d, 1H), 8.19 (d, 1H), 8.36 (s, 1H), 9.89 (s, 1H), 10.85 (br, 1H), 12.5 (br, 1H).

Example 341

1-(2-Cyclopentanecarbonyl-4-methyl-phenyl)-3-[5-(hydroxyimino-methyl)-thiazol-2-yl]-urea

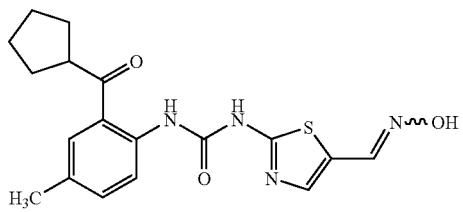

To a mixture of 2M aq NaHCO$_3$ (5 mL) and 1-(2-cyclopentanecarbonyl-4-methylphenyl)-3-(5-formyl-thiazol-2-yl)-urea (72 mg, 0.2 mmol) in THF (5 mL) was added hydroxylamine hydrochloride (200 mg) at room temperature with stirring. The resulting mixture was heated at 60° C. for 12 h. The reaction mixture was cooled and extracted with ethyl acetate. The organic layer was washed (brine), dried (Na$_2$SO$_4$) and concentrated to obtain 1-(2-cyclopentanecarbonyl-4-methyl-phenyl)-3-[5-(hydroxyimino-methyl)-thiazol-2-yl]-urea (56 mg, 76%) as a mixture of syn and anti-isomers.

LC-MS (m/z): 373 (M+1)$^+$.

Example 342

{2-[3-(2-Cyclopentanecarbonyl-4-methyl-phenyl)-ureido]-thiazol-5-ylmethyleneaminooxy}-acetic acid

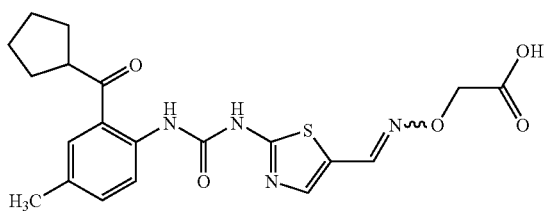

To a mixture of 2M aq NaHCO$_3$ (5 mL) and 1-(2-cyclopentanecarbonyl-4-methylphenyl)-3-(5-formyl-thiazol-2-yl)-urea (72 mg, 0.2 mmol) in THF (5 mL) was added hydroxylamine hydrochloride (200 mg) at room temperature with stirring. The resulting mixture was heated at 60° C. for 12 h. The reaction mixture was cooled, acidified to pH 6.5 (citric acid) and extracted with ethyl acetate. The organic layer was washed (brine), dried (Na$_2$SO$_4$) and concentrated to obtain {2-[3-(2-cyclopentanecarbonyl-4-methyl-phenyl)-ureido]-thiazol-5-ylmethyleneaminooxy}-acetic acid (56 mg, 76%) as a mixture of syn and anti-isomers.

LC-MS (m/z): 431 (M+1)$^+$.

Example 343

({2-[3-(2-Cyclopentanecarbonyl-4-methyl-phenyl)-ureido]-thiazol-5-ylmethyl}-amino)-acetic acid methyl ester

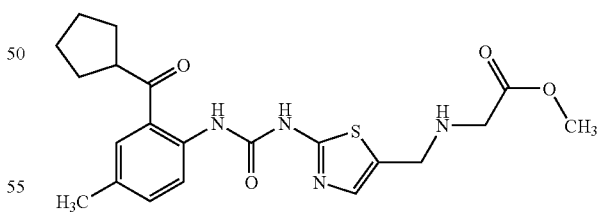

({2-[3-(2-Cyclopentanecarbonyl-4-methyl-phenyl)-ureido]-thiazol-5-ylmethyl}-amino)-acetic acid methyl ester (38 mg, 45%) was prepared from 1-(2-cyclopentanecarbonyl-4-methyl-phenyl)-3-(5-formyl-thiazol-2-yl)-urea (0.072 g, 0.2 mmol) and glycine methyl ester hydrochloride following the general procedure O.

LC-MS (m/z): 431 (M+1)$^+$; $^1$H NMR (400 MHz, DMSO-$d_6$): δ 1.64 (m, 4H), 1.76 (m, 2H), 1.91 (m, 2H), 2.33 (s, 3H), 3.33 (s, 2H), 3.35 (br, 1H), 3.63 (s, 3H), 3.83 (s, 2H), 3.91 (m,

1H), 7.14 (s, 1H), 7.38 (d, 1H), 7.83 (s, 1H), 8.17 (s, 1H), 10.63 (br, 1H), 11.56 (br, 1H).

Example 344

3-{2-[3-(2-Cyclopentanecarbonyl-4-methyl-phenyl)-ureido]-thiazol-5-yl}-acrylic acid ethyl ester

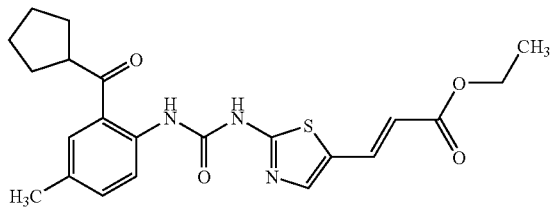

3-{2-[3-(2-Cyclopentanecarbonyl-4-methyl-phenyl)-ureido]-thiazol-5-yl}-acrylic acid ethyl ester (96 mg, 80%) was prepared from 1-(2-cyclopentanecarbonyl-4-methyl-phenyl)-3-(5-formyl-thiazol-2-yl)-urea (100 mg, 0.28 mmol) and (carbethoxymethylene)-triphenylphosphorane (0.12 g, 0.34 mmol) following the general procedure X LC-MS (m/z): 428 (M+1)$^+$, $^1$H NMR (400 MHz, CDCl$_3$): δ 1.33 (t, 3H), 1.69 (m, 4H), 1.92 (m, 4H), 2.38 (s, 3H), 3.78 (m, 1H), 4.24 (q, 2H), 6.10 (d, 1H), 7.25 (d, 1H), 7.38 (d, 1H), 7.46 (m, 2H), 7.99 (s, 1H), 8.46 (d, 1H), 10.40 (br, 1H), 11.72 (br, 1H).

Example 345

3-{2-[3-(2-Cyclopentanecarbonyl-4-methyl-phenyl)-ureido]-thiazol-5-yl}-propionic acid ethyl ester

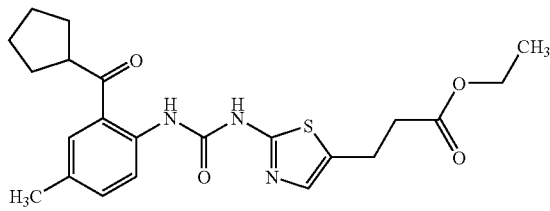

3-{2-[3-(2-Cyclopentanecarbonyl-4-methyl-phenyl)-ureido]-thiazol-5-yl}-propionic acid ethyl ester was prepared from 3-{2-[3-(2-cyclopentanecarbonyl-4-methyl-phenyl)-ureido]-thiazol-5-yl}-acrylic acid ethyl ester via hydrogenation under the conditions described in the general procedure C LC-MS (m/z): 430 (M+1)$^+$.

Example 346

1-[2-(2-Methoxy-benzoyl)-5-methyl-phenyl]-3-thiazol-2-yl-urea

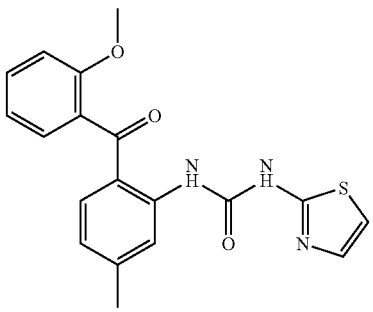

(2-Amino-4-methyl-phenyl)-(2-methoxy-phenyl)-methanone (723 g, 30%) was prepared from 2-amino-4-methyl-benzoic acid (1.51 g, 10 mmol) following the general procedure S. 1-[2-(2-methoxy-benzoyl)-5-methyl-phenyl]-3-thiazol-2-yl-urea (129 mg, 70%) was prepared from (2-amino-4-methyl-phenyl)-(2-methoxy-phenyl)-methanone (121 mg, 0.5 mmol) and 2-aminothiazole (0.060 g, 0.6 mmol) following the general procedure D.

LC-MS (m/z): 368 (M+1)$^+$; $^1$H NMR (400 MHz, CDCl$_3$): δ 2.42 (s, 3H), 3.75 (s, 3H), 6.78 (d, 1H), 6.91 (d, 1H), 6.98 (d, 1H), 7.04 (t, 1H), 7.26 (t, 1-H), 7.33 (d, 1H), 7.46 (m, 1H), 7.64 (d, 1H), 8.46 (s, 1H), 11.02 (br, 1H), 11.67 (br, 1H).

Example 347

1-[2-(2-Methoxy-benzoyl)-4-methyl-phenyl]-3-thiazol-2-yl-urea

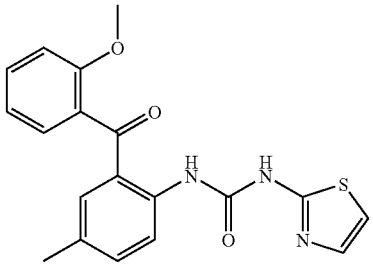

(2-Amino-5-methyl-phenyl)-(2-methoxy-phenyl)-methanone (843 g, 35%) was prepared from 2-amino-5-methyl-benzoic acid (1.51 g, 0.1 mol) following the general procedure S. 1-[2-(2-methoxy-benzoyl)-4-methyl-phenyl]-3-thiazol-2-yl-urea (132 mg, 72%) was prepared from (2-amino-5-methyl-phenyl)-(2-methoxy-phenyl)-methanone (121 mg, 0.5 mmol) and 2-aminothiazole (0.060 g, 0.6 mmol) following the general procedure D.

LC-MS (m/z): 368 (M+1)$^+$; $^1$H NMR (400 MHz, CDCl$_3$): δ 2.23 (s, 3H), 3.76 (s, 3H), 6.91 (d, 1H), 7.01 (d, 1H), 7.05 (t, 1H), 7.23 (bs, 1H), 7.29 (d, 1H), 7.36 (d, 1H), 7.48 (t, 1H), 7.59 (d, 1H), 8.48 (s, 1H), 10.56 (br, 1H), 11.45 (br, 1H).

Example 348

1-[5-Fluoro-2-(2-methoxy-benzoyl)-phenyl]-3-thiazol-2-yl-urea

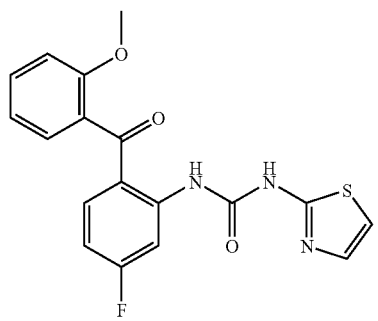

(2-Amino-4-fluoro-phenyl)-(2-methoxy-phenyl)-methanone (784 mg, 32%) was prepared from 2-amino-4-fluoro-benzoic acid (1.55 g, 0.1 mol) following the general procedure S. 1-[5-Fluoro-2-(2-methoxy-benzoyl)-phenyl]-3-thiazol-2-yl-urea (127 mg, 68%) was prepared from (2-amino-4-fluoro-phenyl)-(2-methoxy-phenyl)-methanone (123 mg, 0.5 mmol) and 2-aminothiazole (0.060 g, 0.6 mmol) following the general procedure D.

LC-MS (m/z): 372 (M+1)$^+$; $^1$H NMR (400 MHz, CDCl$_3$): δ 3.75 (s, 3H), 6.66 (m, 1H), 6.93 (d, 1H), 6.98 (t, 1H), 7.05 (t, 1H), 7.29 (d, 1H), 7.48 (m, 2H), 7.63 (d, 1H), 8.45 (dd, 1H), 11.18 (br, 1H), 11.84 (br, 1H).

Example 349

1-[5-Fluoro-2-(thiophene-2-carbonyl)-phenyl]-3-thiazol-2-yl-urea

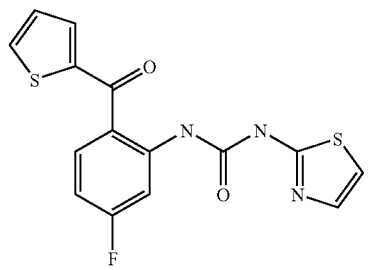

(2-Amino-4-fluoro-phenyl)-thiophen-2-yl-methanone was (618 g, 28%) was prepared from 2-amino-4-fluoro-benzoic acid (1.55 g, 10 mmol) following the general procedure S. N-[5-Fluoro-2-(thiophene-2-carbonyl)-phenyl]-N'-(thiazol-2-yl)urea (113 mg, 65%) was prepared from (2-amino-4-fluoro-phenyl)-thiophen-2-yl-methanone (110 mg, 0.5 mmol) and 2-aminothiazole (0.060 g, 0.6 mmol) following the general procedure D.

LC-MS (m/z): 348 (M+1)$^+$; $^1$H NMR (400 MHz, DMSO-d$_6$): δ 7.03 (m, 1H), 7.12 (d, 1H), 7.27 (t, 1H), 7.35 (d, 1H), 7.64 (d, 1H), 7.80 (dd, 1H), 8.07 (d, 1H), 8.14 (d, 1H), 9.63 (br, 1H), 11.60 (br, 1H).

Example 350

N-[2-(2-Methoxy-benzoyl)-5-methoxy-phenyl]-N'-(thiazol-2-yl)urea

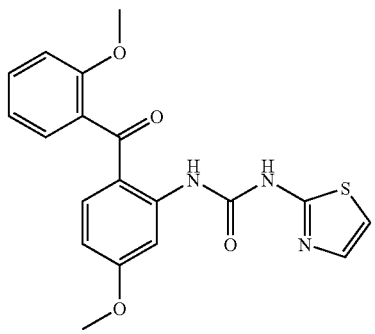

(2-Amino-4-methoxy-phenyl)-(2-methoxy-phenyl)-methanone (720 mg, 28%) was prepared from 2-amino-4-methoxy-benzoic acid (1.67 g, 0.1 mol) following the general procedure S. N-[2-(2-Methoxy-benzoyl)-5-methoxy-phenyl]-N'-(thiazol-2-yl)urea (131 mg, 68%) was prepared from (2-amino-4-methoxy-phenyl)-(2-methoxy-phenyl)-methanone (129 mg, 0.5 mmol) and 2-aminothiazole (0.060 g, 0.6 mmol) following the general procedure D.

LC-MS (m/z): 384 (M+1)$^+$; $^1$H NMR (400 MHz, CDCl$_3$): δ 3.77 (s, 3H), 3.93 (s, 3H), 6.91 (d, 1H), 6.98 (d, 1H), 7.04 (t, 1H), 7.23 (d, 1H), 7.25 (d, 1H), 7.36 (d, 1H), 7.45 (m, 1H), 7.54 (br, 1H), 8.27 (d, 1H), 10.20 (br, 1H), 12.10 (br, 1H).

Example 351

(2-{3-[2-(2-Methoxy-benzoyl)-5-methyl-phenyl]-ureido}-thiazol-4-yl)-acetic acid ethyl ester

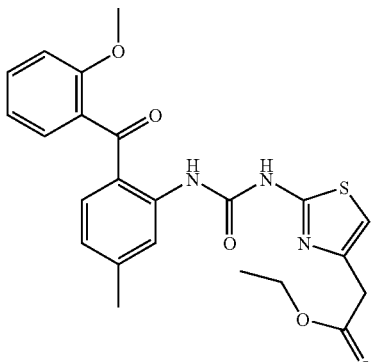

(2-{3-[2-(2-Methoxy-benzoyl)-5-methyl-phenyl]-ureido}-thiazol-4-yl)-acetic acid ethyl ester (163 mg, 72%) was prepared from (2-amino-4-methyl-phenyl)-(2-methoxy-phenyl)-methanone (121 mg, 0.5 mmol) and (2-amino-thiazol-4-yl)-acetic acid ethyl ester (111 mg, 0.6 mmol) following the general procedure D.

LC-MS (m/z): 454 (M+1)$^+$; $^1$H NMR (400 MHz, CDCl$_3$): δ 1.25 (t, 3H), 2.40 (s, 3H), 3.69 (s, 2H), 3.72 (s, 3H), 4.20 (q, 2H), 6.71 (s, 1H), 6.76 (d, 1H), 6.96 (d, 1H), 7.02 (t, 1H), 7.23 (d, 1H), 7.30 (d, 1H), 7.44 (t, 1H), 8.47 (s, 1H), 9.47 (br, 1H), 11.57 (br, 1H).

Example 352

(2-{3-[2-(2-Methoxy-benzoyl)-5-methyl-phenyl]-ureido}-thiazol-4-yl)-acetic acid

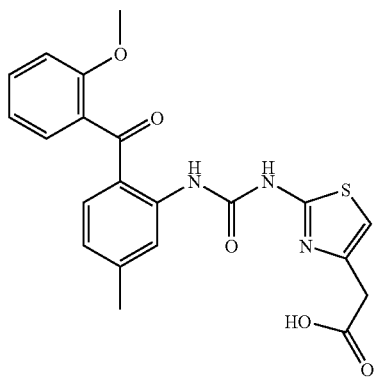

(2-{3-[2-(2-Methoxy-benzoyl)-5-methyl-phenyl]-ureido}-thiazol-4-yl)-acetic acid. (181 mg, 85%) was prepared from (2-{3-[2-(2-methoxy-benzoyl)-5-methyl-phenyl]-ureido}-thiazol-4-yl)-acetic acid ethyl ester (227 mg, 0.5 mmol) following the general procedure J.

LC-MS (m/z): 426 (M+1)$^+$; $^1$H NMR (400 MHz, DMSO-d$_6$): δ 2.36 (s, 3H), 3.57 (s, 2H), 3.68 (s, 3H), 6.86 (s, 1H), 7.07 (t, 1H), 7.22 (m, 2H), 7.31 (d, 1H), 7.50 (t, 2H), 8.26 (s, 1H), 10.92 (br, 1H), 12.20 (br, 1H).

Example 353

2-(2-{3-[2-(2-Methoxy-benzoyl)-5-methyl-phenyl]-ureido}-thiazol-4-yl)-N-methyl-acetamide

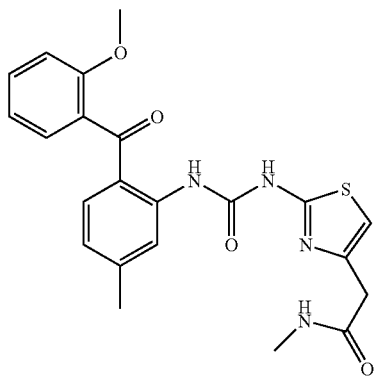

2-(2-{3-[2-(2-Methoxy-benzoyl)-5-methyl-phenyl]-ureido}-thiazol-4-yl)-N-methyl-acetamide (164 mg, 75%) was prepared from (2-{3-[2-(2-methoxy-benzoyl)-5-methyl-phenyl]-ureido}-thiazol-4-yl)-acetic acid (213 mg, 0.5 mmol) and 1 N solution of methylamine in THF (0.5 mL, 0.5 mmol) following the general procedure K.

LC-MS (m/z): 439 (M+1)$^+$; $^1$H NMR (400 MHz, CDCl$_3$): δ 2.41 (s, 3H), 2.74 (d, 3H), 3.62 (s, 2H), 3.73 (s, 3H), 6.66 (s, 1H), 6.79 (d, 1H), 6.97 (d, 1H), 7.03 (t, 1H), 7.24 (d, 1H), 7.32 (d, 1H), 7.46 (m, 1H), 8.45 (s, 1H), 11.60 (br, 1H), 11.82 (br, 1H).

Example 354

2-(2-{3-[2-(2-Methoxy-benzoyl)-5-methyl-phenyl]-ureido}-thiazol-4-yl)-N-(methoxy-ethyl)-acetamide

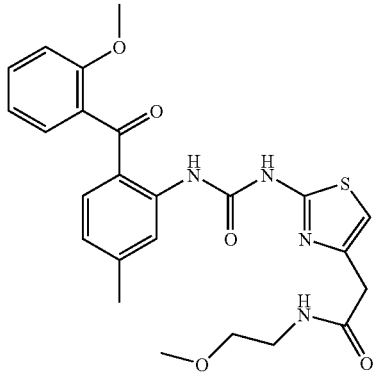

2-(2-{3-[2-(2-Methoxy-benzoyl)-5-methyl-phenyl]-ureido}-thiazol-4-yl)-N-(methoxy-ethyl)-acetamide (169 mg, 70%) was prepared from (2-{3-[2-(2-methoxy-benzoyl)-5-methyl-phenyl]-ureido}-thiazol-4-yl)-acetic acid (213 mg, 0.5 mmol) and 2-methoxyethylamine (38 mg, 0.5 mmol) following the general procedure K.

LC-MS (m/z): 483 (M+1)$^+$; $^1$H NMR (400 MHz, CDCl$_3$): δ 2.41 (s, 3H), 3.33 (s, 3H), 3.48 (m, 4H), 3.61 (s, 2H), 3.73 (s, 3H), 6.65 (s, 1H), 6.76 (d, 1H), 6.97 (d, 1H), 7.03 (t, 1H), 7.25 (d, 1H), 7.31 (d, 1H), 7.42 (bs, 1H), 7.46 (m, 1H), 8.48 (s, 1H), 10.02 (br, 1H), 11.62 (br, 1H).

Example 355

N-(2-Methanesulfonyl-ethyl)-2-(2-{3-[2-(2-methoxy-benzoyl)-5-methyl-phenyl]-ureido}-thiazol-4-yl)-acetamide

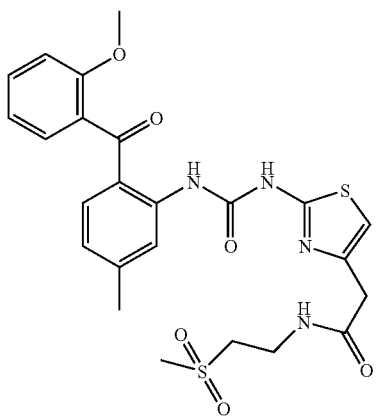

N-(2-Methanesulfonyl-ethyl)-2-(2-{3-[2-(2-methoxy-benzoyl)-5-methyl-phenyl]-ureido}-thiazol-4-yl)-acetamide (181 mg, 68%) was prepared from (2-{3-[2-(2-methoxy-benzoyl)-5-methyl-phenyl]-ureido}-thiazol-4-yl)-acetic acid (213 mg, 0.5 mmol) and 2-methanesulfonyl-ethylamine (61 mg, 0.5 mmol) following the general procedure K.

LC-MS (m/z): 531 (M+1)$^+$; $^1$H NMR (400 MHz, CDCl$_3$): δ 2.41 (s, 3H), 2.93 (s, 3H), 3.33 (t, 3H), 3.63 (s, 2H), 3.74 (s, 3H), 3.78 (m, 2H), 6.61 (s, 1H), 6.76 (d, 1H), 6.98 (d, 1H), 7.04 (t, 1H), 7.25 (d, 1H), 7.31 (d, 1H), 7.46 (m, 1H), 7.97 (t, 1H), 8.48 (s, 1H), 11.40 (br, 1H), 11.51 (br, 1H).

Example 356

(2-{3-[5-Fluoro-2-(2-Methoxy-benzoyl)-phenyl]-ureido}-thiazol-4-yl)-acetic acid ethyl ester

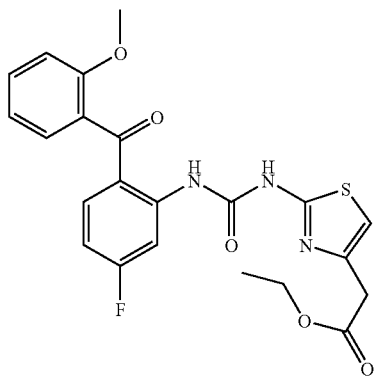

(2-{3-[5-Fluoro-2-(2-Methoxy-benzoyl)-phenyl]-ureido}-thiazol-4-yl)-acetic acid ethyl ester (164 mg, 72%) was prepared from (2-amino-4-fluoro-phenyl)-(2-methoxy-phenyl)-methanone (123 mg, 0.5 mmol) and (2-amino-thiazol-4-yl)-acetic acid ethyl ester (111 mg, 0.6 mmol) following the general procedure (D).

LC-MS (m/z): 458 (M+1)$^+$; $^1$H NMR (400 MHz, CDCl$_3$): δ 1.24 (t, 3H), 3.68 (s, 2H), 3.78 (s, 3H), 6.68 (s, 1H), 6.74 (d, 1H), 6.93 (d, 1H), 7.06 (t, 1H), 7.24 (m, 1H), 7.30 (d, 1H), 7.44 (t, 1H), 8.47 (s, 1H), 9.47 (br, 1H), 11.57 (br, 1H).

Example 357

(2-{3-[5-Fluoro-2-(2-methoxy-benzoyl)-phenyl]-ureido}-thiazol-4-yl)-acetic acid

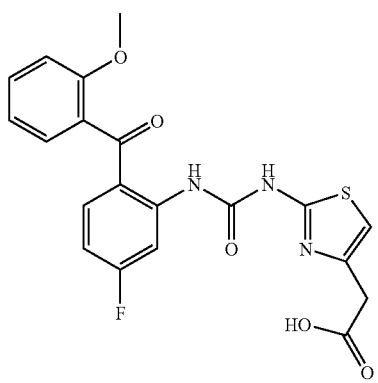

(2-{3-[5-Fluoro-2-(2-methoxy-benzoyl)-phenyl]-ureido}-thiazol-4-yl)-acetic acid (161 mg, 75%) was prepared from (2-{3-[5-fluoro-2-(2-methoxy-benzoyl)-phenyl]-ureido}-thiazol-4-yl)-acetic acid ethyl ester (229, 0.5 mmol) following the general procedure J.

LC-MS (m/z): 430 (M+1)$^+$; $^1$H NMR (400 MHz, DMSO-d$_6$): δ 3.57 (s, 2H), 3.69 (s, 3H), 6.89 (m, 2H), 7.08 (t, 1H), 7.18 (d, 1H), 7.33 (d, 1H), 7.40 (m, 1H), 7.54 (m, 1H), 8.28 (d, 1H), 11.12 (br, 1H), 12.32 (br, 1H).

Example 358

2-(2-{3-[5-Fluoro-2-(2-methoxy-benzoyl)-phenyl]-ureido}-thiazol-4-yl)-N-methyl-acetamide

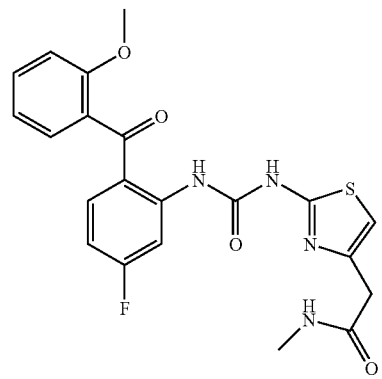

2-(2-{3-[5-fluoro-2-(2-methoxy-benzoyl)-phenyl]-ureido}-thiazol-4-yl)-N-methyl-acetamide (144 mg, 65%) was prepared from (2-{3-[5-fluoro-2-(2-methoxy-benzoyl)-phenyl]-ureido}-thiazol-4-yl)-acetic acid (215 mg, 0.5 mmol) and 1N solution of methyl amine in THF (0.5 mL, 0.5 mmol) following the general procedure K.

LC-MS (m/z): 443 (M+1)$^+$; $^1$H NMR (400 MHz, CDCl$_3$): δ 2.71 (d, 3H), 3.66 (s, 2H), 3.70 (s, s, 3H), 6.64 m, 2H), 6.85 (br, 1H), 7.36 (m, 2H), 6.95 (d, 1H), 7.02 (t, 1H), 7.24 (dd, 1H), 7.44 (m, 2H), 8.43 (dd, 1H), 10.72 (br, 1H), 11.84 (br, 1H).

Example 359

2-(2-{3-[5-Fluoro-2-(2-methoxy-benzoyl)-phenyl]-ureido}-thiazol-4-yl)-N-(2-methoxy-ethyl)-acetamide

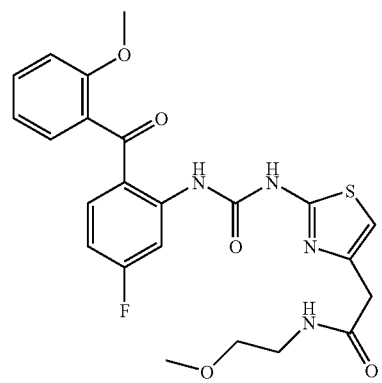

2-(2-{3-[5-Fluoro-2-(2-methoxy-benzoyl)-phenyl]-ureido}-thiazol-4-yl)-N-(2-methoxy-ethyl)-acetamide (158 mg, 65%) was prepared from (2-{3-[5-fluoro-2-(2-methoxy-benzoyl)-phenyl]-ureido}-thiazol-4-yl)-acetic acid (215 mg, 0.5 mmol) and 2-methoxyethylamine (38 mg, 0.5 mmol) following the general procedure K.

LC-MS (m/z): 487 (M+1)+; 1H NMR (400 MHz, CDCl3): δ 3.21 (s, 3H), 3.48 (m, 4H), 3.62 (s, 2H), 3.73 (s, 3H), 6.62-6.66 (m, 2H), 6.97 (d, 1H), 7.04 (t, 1H), 7.28 (d, 1H), 7.42 (br, 1H), 7.42-7.50 (m, 2H), 8.46 (dd, 1H), 10.20 (br, 1H), 11.28 (br, 1H),

Example 360

1-[2-(Hydroxyimino-phenyl-methyl)-phenyl]-3-thiazol-2-yl-urea

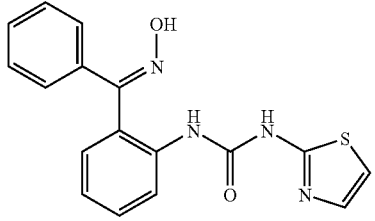

1-[2-(Hydroxyimino-phenyl-methyl)-phenyl]-3-thiazol-2-yl-urea (101 mg, 60%) was prepared from (2-Amino-phenyl)-phenyl-methanone oxime (106 mg, 0.5 mmol) and 2-amino thiazole (0.06 mg, 0.6 mmol) following the general procedure D.

LC-MS (m/z): 339 (M+1)+; 1H NMR (400 MHz, DMSO-d6): δ 7.2 (dd, 1H), 7.06 (d, 1H), 7.15 (m, 1H), 7.30 (d, 1H), 7.34-7.43 (m, 6H), 8.03 (d, 1H), 8.05 (br, 1H), 11.07 (br, 1H), 11.63 (br, 1H),

Example 361

1-[5-Chloro-2-(hydroxyimino-phenyl-methyl)-phenyl]-3-thiazol-2-yl-urea

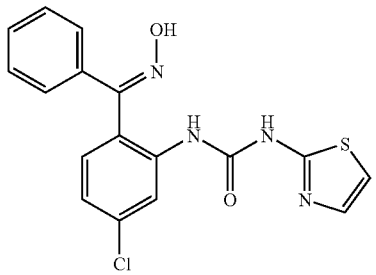

1-[5-Chloro-2-(hydroxyimino-phenyl-methyl)-phenyl]-3-thiazol-2-yl-urea (93 mg, 50%) was prepared from (2-Amino-4-chloro-phenyl)-phenyl-methanone oxime (123 mg, 0.5 mmol) and 2-amino thiazole (60 mgmg, 0.6 mmol) following the general procedure D.

LC-MS (m/z): 373 (M+1)+; 1H NMR (400 MHz, DMSO-d6): δ 7.04 (dd, 1H), 7.12 (d, 1H), 7.16 (m, 1H), 7.36 (d, 1H), 7.36-7.48 (m, 5H), 8.03 (d, 1H), 8.12 (br, 1H), 11.23 (br, 1H), 11.72 (br, 1H),

Example 362

1-(2-Benzoyl-5-methyl-phenyl)-3-thiazol-2-yl-urea

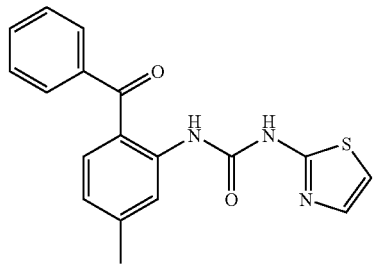

1-(2-Benzoyl-5-methyl-phenyl)-3-thiazol-2-yl-urea (60 mg, 65%) was prepared from (2-(2-amino-4-methyl-phenyl)-phenyl-methanone (55 mg, 0.25 mmol) following the general procedure D.

LC-MS (m/z): 338 (M+1)+; 1H NMR (400 MHz, CDCl3): δ 2.40 (s, 3H), 6.93 (s, 1H), 7.19 (t, 1H), 7.28 (s, 1H), 7.48 (t, 1H), 7.54-7.61 (m, 4H), 7.68 (dd, 1H), 8.54 (d, 1H), 10.64 (br, 1H), 11.22 (br, 1H).

Example 363

1-[4-Bromo-2-(2-fluoro-benzoyl)-phenyl]-3-thiazol-2-yl-urea

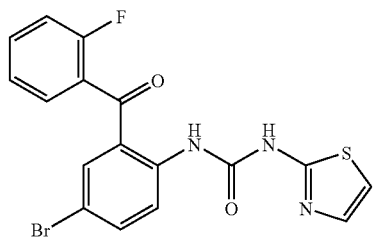

1-[4-Bromo-2-(2-fluoro-benzoyl)-phenyl]-3-thiazol-2-yl-urea (73 mg, 69%) was prepared from (2-amino-5-bromo-phenyl)-(2-fluoro-phenyl)-methanone (73 mg, 0.25 mmol) following the general procedure D.

LC-MS (m/z): 420 (M+1)+; 1H NMR (400 MHz, CDCl3): δ 6.93 (s, 1H), 7.19 (t, 1H), 7.28 (s, 1H), 7.48 (t, 1H), 7.54-7.61 (m, 3H), 7.68 (dd, 1H), 8.54 (d, 1H), 10.64 (br, 1H), 11.22 (br, 1H).

Example 364

1-[5-Chloro-2-2-fluoro-benzoyl)-phenyl]-3-thiazol-2-yl-urea

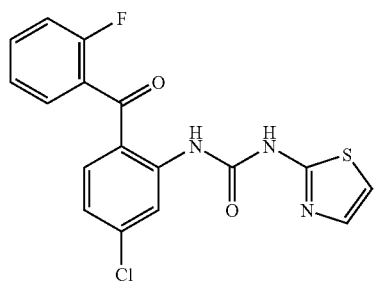

1-[5-Chloro-2-(2-fluoro-benzoyl)-phenyl]-3-thiazol-2-yl-urea (132 mg, 70%) was prepared from (2-amino-4-chlorophenyl)-(2-fluoro-phenyl)-methanone (125 mg, 0.5 mmol) and 2-aminothiazole (60 mg, 0.6 mmol) following the general procedure D.

LC-MS (m/z): 376 (M+1)$^+$; $^1$H NMR (400 MHz, DMSO-d$_6$): δ 6.76 (s, 1H), 6.89 (s, 1H), 7.16 (m, 1H), 7.25 (d, 1H), 7.48 (m, 4H), 8.58 (br, 1H), 10.88 (br, 1H).

Example 365

1-[4-Fluoro-2-(2-methylsulfanyl-phenoxy)-phenyl]-3-thiazol-2-yl-urea

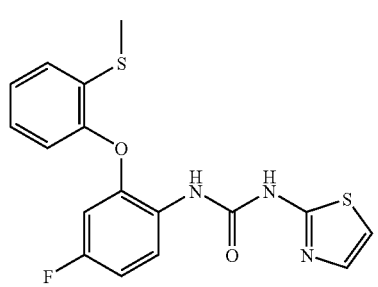

4-Fluoro-2-(2-methylsulfanylphenoxy)-1-nitrobenzene (1.06 g, 68%) was prepared from 2-hydroxythioanisole (0.77 g, 5.5 mmol) and 2,5-difluoro-1-nitro-benzene (0.80 g, 5.0 mmol) following the general procedure A. This was reduced to 4-fluoro-2-(2-methanesulfanyl-phenoxy)-phenylamine (0.52 g, 62%) following general procedure C. 1-[4-Fluoro-2-(2-methylsulfanyl-phenoxy)-phenyl]-3-thiazol-2-yl-urea (117 mg, 60%) was prepared from 4-fluoro-2-(2-methylsulfanylphenoxy)aniline (125 mg, 0.5 mmol) and 2-aminothiazole (60 mg, 0.6 mmol) following the general procedure D.

LC-MS (m/z): 376 (M+1)$^+$; $^1$H NMR (400 MHz, CDCl$_3$): δ 2.41 (s, 3H), 6.41 (dd, 1H), 6.56 (br, 1H), 6.76 (d, 1H), 6.94 (d, 1H), 7.15-7.34 (m, 4H), 8.26 (dd, 1H), 9.88 (br, 1H), 11.12 (br, 1H),

Example 366

2-[4-Fluoro-2-(3-thiazol-2-yl-ureido)-phenoxy]-6-methoxy-benzoic acid methyl ester

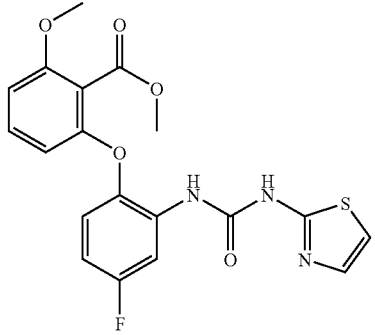

2-(4-Fluoro-2-nitro-phenoxy)-6-methoxy-benzoic acid methyl ester (0.94 g, 58%) was prepared from 2-hydroxy-6-methoxy-benzoic acid methyl ester (1.01 g, 5.5 mmol) and 2,5-difluoro-1-nitro-benzene (0.80 g, 5.0 mmol) following the general procedure A. This was reduced to 2-(2-amino-4-fluoro-phenoxy)-6-methoxy-benzoic acid methyl ester (0.51 g, 60%) following general procedure C. 2-[4-Fluoro-2-(3-thiazol-2-yl-ureido)-phenoxy]-6-methoxy-benzoic acid methyl ester (129 mg, 62%) was prepared from 2-(2-amino-4-fluoro-phenoxy)-6-methoxy-benzoic acid methyl ester (145 mg, 0.5 mmol) and 2-aminothiazole (60 mg, 0.6 mmol) following the general procedure D.

LC-MS (m/z): 418 (M+1)$^+$; $^1$H NMR (400 MHz, CDCl$_3$): δ 3.62 (s, 3H), 3.64 (s, 3H), 6.31 (s, 1H), 6.45 (dd, 1H), 6.55 (s, 1H), 7.05 (d, 1H), 7.22 (t, 1H), 7.33 (br, 1H), 7.45 (d, 1H), 78.02 (d, 1H), 8.63 (br, 1H), 11.74 (br, 1H).

Example 367

2-[4-Fluoro-2-(3-thiazol-2-yl-ureido)-phenoxy]-6-methoxy-N-methyl-benzamide

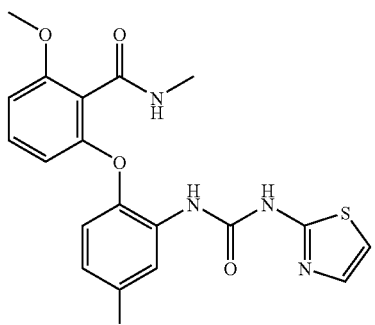

2-[4-Fluoro-2-(3-thiazol-2-yl-ureido)-phenoxy]-6-methoxy-N-methyl-benzamide (150 mg, 72%) was prepared from 2-[4-fluoro-2-(3-thiazol-2-yl-ureido)-phenoxy]-6-methoxy-benzoic acid (201 mg, 0.5 mmol) and 1N solution of methyl amine in THF (0.5 mL, 0.5 mmol) following the general procedure K.

LC-MS (m/z): 417 (M+1)$^+$; $^1$H NMR (400 MHz, DMSO-d$_6$): δ 3.42 (d, 3H), 3.67 (s, 3H), 6.51 (dd, 1H), 6.67 (m, 1H), 7.14 (m, 2H), 7.29 (m, 2H), 7.37 (d, 1H), 7.98 (dd, 1H), 8.11 (d, 1H), 9.13 (dd, 1H), 11.20 (br, 1H).

Example 368

1-[5-Fluoro-2-(2-methanesulfonyl-phenoxy)-phenyl]-3-thiazol-2-yl-urea

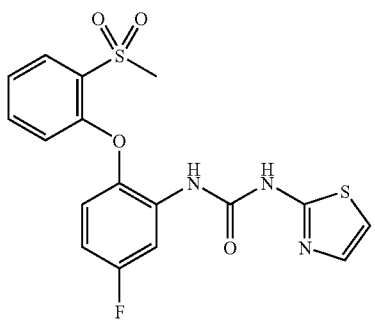

1-[5-Fluoro-2-(2-methanesulfonyl-phenoxy)-phenyl]-3-thiazol-2-yl-urea (153 mg, 75%) was prepared from 1-[5-fluoro-2-(2-methanesulfanyl-phenoxy)-phenyl]-3-thiazol-2-yl-urea (187 mg, 0.5 mmol) following the general procedure R.

LC-MS (m/z): 408 (M+1)$^+$; $^1$H NMR (400 MHz, CDCl$_3$): δ 3.44 (s, 3H), 6.80 (m, 1H), 6.84 (d, 1H), 7.03 (d, 1H), 7.27 (m, 2H), 7.33 (d, 1H), 7.56 (m, 1H), 8.05 (dd, 1H), 8.27 (dd, 1H), 9.13 (br, 1H), 11.12 (br, 1H).

Example 369

1-[2-(4,5-Dimethoxy-2-methyl-phenoxy)-phenyl]-3-thiazol-2-yl-urea

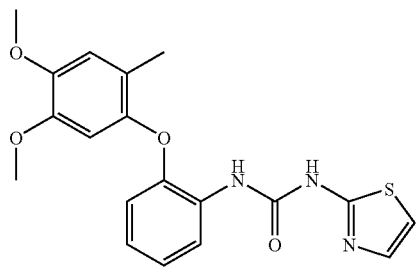

1-[2-(4,5-Dimethoxy-2-methyl-phenoxy)-phenyl]-3-thiazol-2-yl-urea (131 mg, 68%) was prepared from 2-(4,5-dimethoxy-2-methyl-phenoxy)-phenylamine (130 mg, 0.5 mmol) and 2-aminothiazole (60 mg, 0.6 mmol) following the general procedure D.

LC-MS (m/z): 386 (M+1)$^+$; $^1$H NMR (400 MHz, CDCl$_3$): δ 2.29 (s, 3H), 3.80 (s, 3H), 3.94 (s, 3H), 6.76 (s, 1H), 6.92 (d, 1H), 7.02 (t, 1H), 7.44 (d, 1H), 7.55 (t, 2H), 7.76 (d, 1H), 8.54 (d, 1H), 11.34 (br, 1H).

Example 370

3-[4-Fluoro-2-(3-thiazol-2-yl-ureido)-phenoxy]-benzoic acid methyl ester

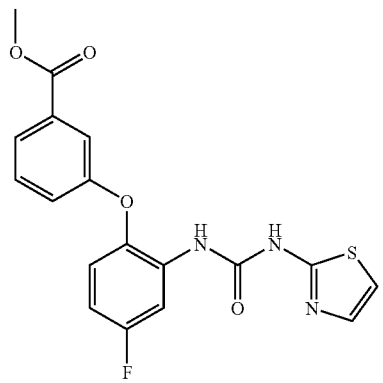

3-(4-Fluoro-2-nitro-phenoxy)-benzoic acid methyl ester (0.73 g, 50%) was prepared from 3-hydroxy-benzoic acid methyl ester (0.84 g, 5.5 mmol) and 2,5-difluoro-1-nitrobenzene (0.80 g, 5.0 mmol) following the general procedure A. This was reduced to 2-(2-amino-4-fluoro-phenoxy)-benzoic acid methyl ester (0.37 g, 58%) following general procedure C. 3-[4-Fluoro-2-(3-thiazol-2-yl-ureido)-phenoxy]-benzoic acid methyl ester (145 mg, 75%) was prepared from 3-(2-amino-4-fluoro-phenoxy)-benzoic acid methyl ester (130 mg, 0.5 mmol) and 2-aminothiazole (60 mg, 0.6 mmol) following the general procedure D.

LC-MS (m/z): 388 (M+1)$^+$; $^1$H NMR (400 MHz, CDCl$_3$): δ 3.87 (s, 3H), 6.78 (m, 1H), 6.89 (d, 1H), 7.12 (m, 1H), 7.18 (br, 1H), 7.34 (m, 1H), 7.41 (m, 1H), 7.60 (m, 1H), 7.72 (d, 1H), 8.22 (dd, 1H), 10.50 (br, 1H).

Example 371

3-[4-Fluoro-2-(3-thiazol-2-yl-ureido)-phenoxy]-benzoic acid

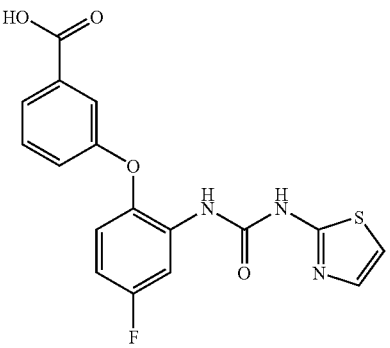

3-[4-Fluoro-2-(3-thiazol-2-yl-ureido)-phenoxy]-benzoic acid (150 mg, 80%) was prepared from 3-[4-fluoro-2-(3-thiazol-2-yl-ureido)-phenoxy]-benzoic acid methyl ester (194 mg, 0.5 mmol) following the general procedure J LC-MS (m/z): 374 (M+1)+; 1H NMR (400 MHz, CDCl3): δ 6.85 (m, 1H), 7.01 (dd, 1H), 7.13 (d, 1H), 7.26 (dd, 1H), 7.34 (d, 1H), 7.42 (m, 1H), 7.52 (t, 1H), 8.14 (dd, 1H), 9.47 (br, 1H), 11.28, br, 1H).

Example 372

2-[4-Fluoro-2-(3-thiazol-2-yl-ureido)-phenoxy]-benzoic acid methyl ester

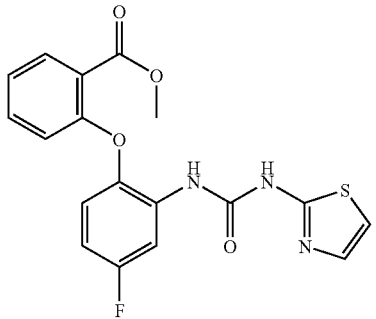

2-(4-Fluoro-2-nitro-phenoxy)-benzoic acid methyl ester (0.81 g, 55%) was prepared from 2-hydroxy-benzoic acid methyl ester (0.84 g, 5.5 mmol) and 2,5-difluoro-1-nitro-benzene (0.80 g, 5.0 mmol) following the general procedure A. This was reduced to 2-(2-amino-4-fluoro-phenoxy)-benzoic acid methyl ester (0.43 g, 60%) following general procedure C. 2-[4-Fluoro-2-(3-thiazol-2-yl-ureido)-phenoxy]-benzoic acid methyl ester (125 mg, 65%) was prepared from 2-(2-amino-4-fluoro-phenoxy)-benzoic acid methyl ester (130 mg, 0.5 mmol) and 2-aminothiazole (60 mg, 0.6 mmol) following the general procedure D.

LC-MS (m/z): 388 (M+1)+; 1H NMR (400 MHz, CDCl3): δ 3.84 (s, 3H), 6.73 (m, 1H), 6.85 (d, 1H), 7.14 (m, 1H), 7.13 (br, 1H), 7.31 (m, 1H), 7.41 (m, 1H), 7.54 (m, 1H), 7.71 (d, 1H), 8.22 (dd, 1H), 10.54 (br, 1H).

Example 373

2-[4-Fluoro-2-(3-thiazol-2-yl-ureido)-phenoxy]-N-methyl-benzamide

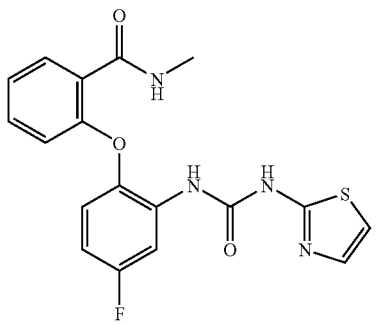

2-[4-Fluoro-2-(3-thiazol-2-yl-ureido)-phenoxy]-N-methyl-benzamide was prepared from 2-[4-fluoro-2-3-thiazol-2-yl-ureido)-phenoxy]-benzoic acid and 1N solution of methyl amine in THF (0.5 mL, 0.5 mmol) following the general procedure K.

LC-MS (m/z): 387 (M+1)+; 1H NMR (400 MHz, CDCl3): δ 3.53 (d, 3H), 6.73 (m, 1H), 5.86 (br, 1H), 6.88 (d, 1H), 7.16 (m, 1H), 7.18 (br, 1H), 7.35 (m, 1H), 7.41 (m, 1H), 7.60 (m, 1H), 7.76 (d, 1H), 8.23 (dd, 1H), 10.22 (br, 1H).

Example 374

N-{3-[4-Fluoro-2-(3-thiazol-2-yl-ureido)-phenoxy]-2-methoxy-phenyl}-methanesulfonamide

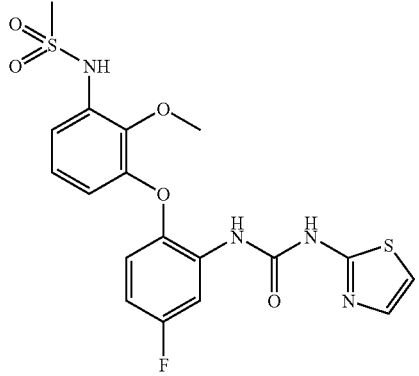

N-[3-(4-Fluoro-2-nitro-phenoxy)-2-methoxy-phenyl]-methanesulfonamide (0.86 g, 48%) was prepared from N-(3-hydroxy-2-methoxy-phenyl)-methanesulfonamide (1.2 g, 5.5 mmol) and 2,5-difluoro-1-nitro-benzene (0.80 g, 5.0 mmol) following the general procedure A. This was reduced to N-[3-(2-amino-4-fluoro-phenoxy)-2-methoxy-phenyl]-methanesulfonamide (0.51 g, 70%) following general procedure C. N-{3-[4-Fluoro-2-(3-thiazol-2-yl-ureido)-phenoxy]-2-methoxy-phenyl}-methanesulfonamide (144 mg, 64%) was prepared from N-[3-(2-amino-4-fluoro-phenoxy)-2-methoxy-phenyl]-methanesulfonamide (123 mg, 0.5 mmol) and 2-aminothiazole (60 mg, 0.6 mmol) following the general procedure D.

LC-MS (m/z): 453 (M+1)+; 1H NMR (400 MHz, CDCl3): δ 3.27 (s, 3H), 3.89 (s, 3H), 6.52 (d, 1H), 6.72 (m, 1H), 6.95 (d, 1H), 7.04 (m, 1H), 7.16 (m, 1H), 7.34 (d, 1H), 7.45 (dd, 1H), 7.63 (d, 1H), 8.21 (dd, 1H), 8.44 (br, 1H), 8.85 (br, 1H).

Example 375

N-[4-(2-Fluoro-6-methoxy-phenoxy)-3-(3-thiazol-2-yl-ureido)-phenyl]-acetamide

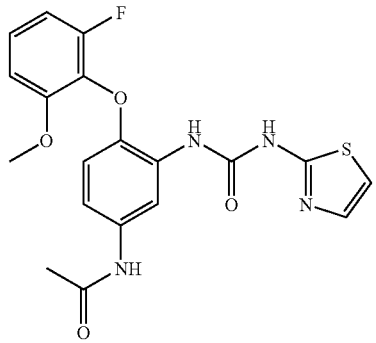

N-[4-(2-Fluoro-6-methoxy-phenoxy)-3-(3-thiazol-2-yl-ureido)-phenyl]-acetamide (81 mg, 78%) was prepared from N-[3-amino-4-(2-fluoro-6-methoxy-phenoxy)-phenyl]-acetamide (72 mg, 0.25 mmol) following the general procedure D.

LC-MS (m/z): 417 (M+1)⁺; ¹H NMR (400 MHz, DMSO-d₆): δ 1.78 (s, 3H), 3.43 (s, 3H), 6.32 (m, 1H), 6.44 (dd, 1H), 6.48 (d, 1H), 6.63 (t, 1H), 6.86 (dd, 1H), 6.97 (d, 1H), 7.13 (d, 1H), 7.88 (d, 1H), 8.90 (br, 1H), 9.32 (br, 1H), and 10.46 (br, 1H).

Example 376

N-[4-2-Fluoro-6-methoxy-phenoxy)-3-(3-thiazol-2-yl-ureido)-phenyl]-methanesulfonamide

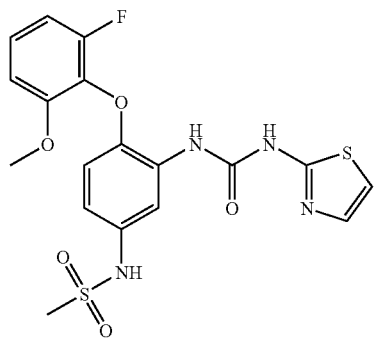

N-[4-(2-Fluoro-6-methoxy-phenoxy)-3-(3-thiazol-2-yl-ureido)-phenyl]methanesulfonamide (101 mg, 89%) was prepared from N-[3-amino-4-(2-fluoro-6-methoxy-phenoxy)-phenyl]-methanesulfonamide (81 mg, 0.25 mmol) following the general procedure L.

LC-MS (m/z): 453 (M+1)⁺; ¹H NMR (400 MHz, DMSO-d₆): δ 3.13 (s, 3H), 4.00 (s, 3H), 6.70 (d, 1H), 6.98 (dd, 1H), 7.14 (t, 1H), 7.21 (d, 1H), 7.38 (t, 1H), 7.46 (q, 1H), 7.55 (t, 1H), 8.14 (br, 1H), 8.38 (dd, 1H), 8.46 (d, 1H), and 10.86 (br, 1H).

Example 377

(2-{3-[2-(2-Fluoro-6-methoxy-phenoxy)-5-methane-sulfonylamino-phenyl]-ureido}-thiazol-4 yl)-acetic acid ethyl ester

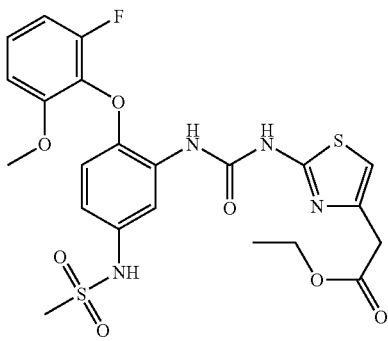

(2-{3-[2-(2-Fluoro-6-methoxy-phenoxy)-5-methane-sulfonylamino-phenyl]-ureido}-thiazol-4 yl)-acetic acid ethyl ester (118 mg, 87%) was prepared from N-[3-amino-4-(2-fluoro-6-methoxy-phenoxy)-phenyl]-methanesulfonamide (81 mg, 0.25 mmol) following the general procedure D.

LC-MS (m/z): 539 (M+1)⁺; ¹H NMR (400 MHz, DMSO-d₆): δ 1.24 (t, 2H), 3.03 (s, 3H), 3.74 (s, 2H), 3.80 (s, 3H), 4.21 (q, 3H), 6.59 (d, 1H), 6.68 (s, 1H), 6.78 (s, 1H), 6.83 (dd, 1H), 7.12-7.19 (m, 2H), 8.12 (d, 1H), 8.42 (s, 1H), 9.60 (br, 1H), and 11.84 (br, 1H).

Example 378

(2-{3-[2-(2-Fluoro-6-methoxy-phenoxy)-5-methane-sulfonylamino-phenyl]-ureido}-thiazol-4-yl)-acetic acid

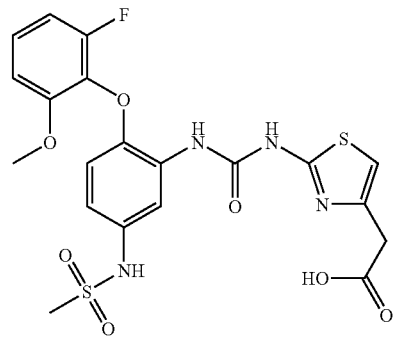

(2-{3-[2-(2-Fluoro-6-methoxy-phenoxy)-5-methane-sulfonylamino-phenyl]-ureido}-thiazol-4-yl)-acetic acid (85 mg, 83%) was prepared from (2-{3-[2-(2-fluoro-6-methoxy-phenoxy)-5-methanesulfonylamino-phenyl]-ureido}-thiazol-4 yl)-acetic acid ethyl ester (108 mg, 0.20 mmol) following the general procedure J.

LC-MS (m/z): 511 (M+1)⁺; ¹H NMR (400 MHz, CD₃OD): δ 3.12 (s, 3H), 3.54 (s, 2H), 3.81 (s, 3H), 6.54 (d, 1H), 6.64 (s, 1H), 6.84 (s, 1H), 6.92 (d, 1H), 7.11 (m, 1H), 7.16 (s, 1H), 7.44 (m, 1H), 8.46 (s, 1H), 9.40 (br, 1H), 10.83 (br, 1H), and 11.84 (br, 1H).

Example 379

N,N-[4-(2-Fluoro-6-methoxy-phenoxy)-3-(3-thiazol-2-yl-ureido)-phenyl]dimethanesulfonamide

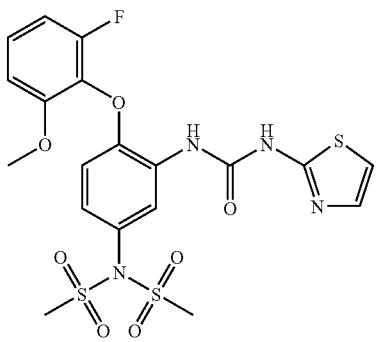

N,N-[4-(2-Fluoro-6-methoxy-phenoxy)-3-(3-thiazol-2-yl-ureido)-phenyl]dimethanesulfonamide (115 mg, 87%) was prepared from N-[3-amino-4-(2-fluoro-6-methoxy-phenoxy)-phenyl]-dimethanesulfonamide (101 mg, 0.25 mmol) following the general procedure D.

LC-MS (m/z): 531 (M+1)+; $^1$H NMR (400 MHz, DMSO-$d_6$): δ 3.22 (s, 3H), 3.24 (s, 3H), 4.11 (s, 3H), 6.78 (d, 1H), 6.89 (d, 1H), 7.11 (dd, 1H), 7.24 (d, 1H), 7.29 (m, 1H), 7.42 (t, 1H), 7.63 (m, 1H), 8.54 (d, 1H), 8.65 (dd, 1H), and 11.38 (br, 1H).

Example 380

N-[4-Isobutoxy-3-(3-thiazol-2-yl-ureido)-phenyl]-methanesulfonamide

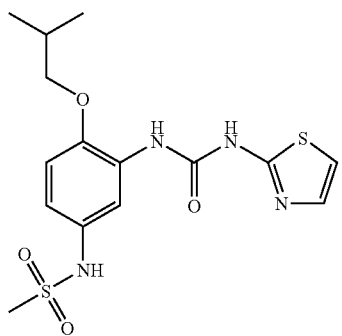

N-[4-Isobutoxy-3-(3-thiazol-2-yl-ureido)-phenyl]-methanesulfonamide (77 mg, 80%) was prepared from N-(3-amino-4-isobutoxy-phenyl)-methanesulfonamide (64 mg, 0.25 mmol) following the general procedure D.

LC-MS (m/z): 385 (M+1)+; $^1$H NMR (400 MHz, CDCl$_3$): δ 1.20 (d, 6H), 1.70 (m, 1H), 3.05 (d, 2H), 3.82 (s, 3H), 6.76 (dd, 1H), 6.86 (d, 1H), 6.94 (m, 1H), 7.36 (d, 1H), 7.42 (d, 1H), 8.42 (d, 1H), 9.56 (br, 1H), and 11.63 (br, 1H).

Example 381

1-[5-Amino-2-(2-fluoro-6-methoxy-phenoxy)-phenyl]-3-thiazol-2-yl-urea

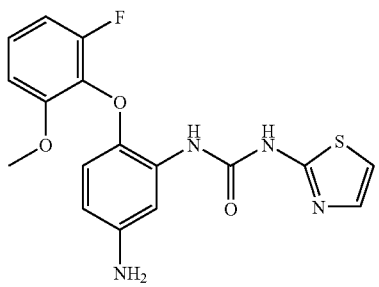

1-[5-Amino-2-(2-fluoro-6-methoxy-phenoxy)-phenyl]-3-thiazol-2-yl-urea (3.52 g, 94%) was prepared from 3-amino-4-(2-fluoro-6-methoxy-phenoxy)-phenyl]-carbamic acid tert-butyl ester (3.48 g, 10.0 mmol) following the general procedure D and the corresponding t-BOC protected product [4-(2-fluoro-6-methoxy-phenoxy)-3-(3-thiazol-2-yl-ureido)-phenyl]-carbamic acid tert-butyl ester was subjected to deprotection conditions with hydrochloric acid (40 ml, 4.0 M in dioxane).

LC-MS (m/z): 375 (M+1)+; $^1$H NMR (400 MHz, CD$_3$OD): δ 3.76 (s, 3H), 5.24 (br, 2H), 6.68 (d, 1H), 6.88 (q, 1H), 6.98 (d, 1H), 7.16 (m, 1H), 7.38 (dd, 1H), 7.63 (dd, 1H), 8.34 (dd, 1H), 8.44 (d, 1H), 8.86 (br, 1H), and 11.27 (br, 1H).

Example 382

Pyridine-2-carboxylic acid [4-(2-fluoro-6-methoxy-phenoxy)-3-(3-thiazol-2-yl-ureido)-phenyl]-amide

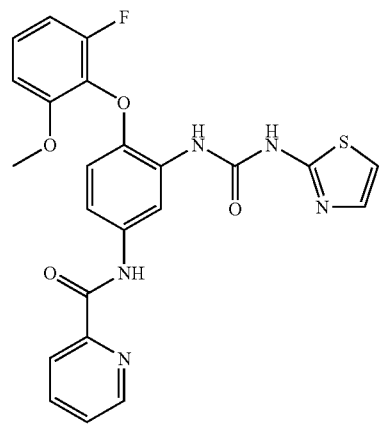

Pyridine-2-carboxylic acid [4-(2-fluoro-6-methoxy-phenoxy)-3-(3-thiazol-2-yl-ureido)-phenyl]-amide (98 mg, 82%) was prepared from 1-[5-amino-2-(2-fluoro-6-methoxy-phenoxy)-phenyl]-3-thiazol-2-yl-urea (94 mg, 0.25 mmol) following the general procedure K.

LC-MS (m/z): 480 (M+1)+; $^1$H NMR (400 MHz, CDCl$_3$): δ 3.74 (s, 3H), 6.64 (d, 1H), 6.74 (d, 1H), 6.78 (s, 1H), 6.82 (m, 1H), 7.16 (q, 1H), 7.46 (dd, 1H), 7.48 (d, 1H), 7.54 (t, 1H), 7.72 (br, 1H), 7.84 (dd, 1H), 7.88 (t, 1H), 8.24 (d, 1H), 8.38 (br, 1H), 8.62 (d, 1H), and 10.06 (br, 1H).

Example 383

N-[4-(2-Fluoro-6-methoxy-phenoxy)-3-(3-thiazol-2-yl-ureido)-phenyl]-isonicotinamide

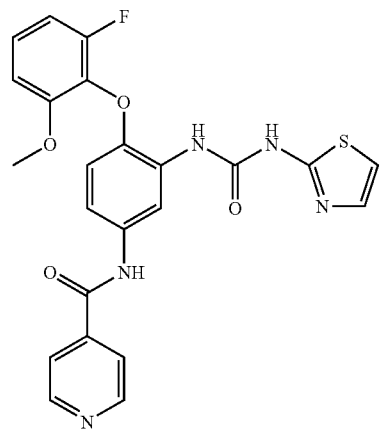

N-[4-(2-Fluoro-6-methoxy-phenoxy)-3-(3-thiazol-2-yl-ureido)-phenyl]-isonicotinamide (104 mg, 86%) was prepared from 1-[5-amino-2-(2-fluoro-6-methoxy-phenoxy)-phenyl]-3-thiazol-2-yl-urea (94 mg, 0.25 mmol) following the general procedure K.

LC-MS (m/z): 480 (M+1)+; 1H NMR (400 MHz, CD3OD): δ 3.58 (s, 3H), 6.32 (d, 1H), 6.62 (dd, 1H), 6.64 (d, 1H), 6.66 (d, 1H), 6.96 (m, 2H), 7.06 (d, 1H), 7.18 (dd, 1H), 7.60 (d, 2H), 8.12 (d, 1H), 8.40 (br, 1H), 8.48 (d, 1H), 9.62 (d, 1H), and 11.34 (br, 1H).

Example 384

5-Methyl-pyrazine-2-carboxylic acid [4-(2-fluoro-6-methoxy-phenoxy)-3-(3-thiazol-2-yl-ureido)-phenyl]-amide

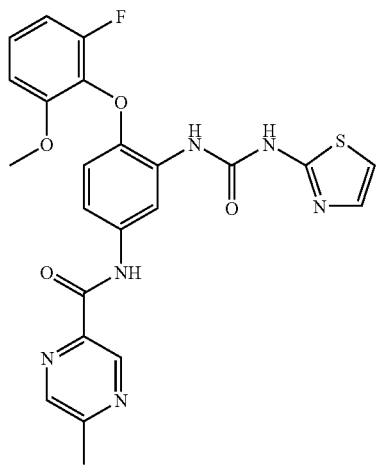

5-Methyl-pyrazine-2-carboxylic acid [4-(2-fluoro-6-methoxy-phenoxy)-3-(3-thiazol-2-yl-ureido)-phenyl]-amide (103 mg, 83%) was prepared from 1-[5-amino-2-(2-fluoro-6-methoxy-phenoxy)-phenyl]-3-thiazol-2-yl-urea (94 mg, 0.25 mmol) following the general procedure K.

LC-MS (m/z): 495 (M+1)+; 1H NMR (400 MHz, CDCl3): δ 2.68 (s, 3H), 3.63 (s, 3H), 6.52 (d, 1H), 6.61 (d, 1H), 6.66 (d, 2H), 7.06 (q, 1H), 7.36 (s, 1H), 7.78 (d, 1H), 8.20 (br, 1H), 8.43 (s, 1H), 8.76 (br, 1H), 9.32 (s, 1H), 9.62 (s, 1H), and 11.80 (br, 1H).

Example 385

2,2,2-Trifluoro-ethanesulfonic acid [4-(2-fluoro-6-methoxy-phenoxy)-3-(3-thiazol-2-yl-ureido)-phenyl]-amide

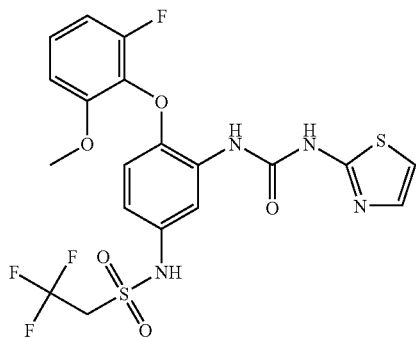

2,2,2-Trifluoro-ethanesulfonic acid [4-(2-fluoro-6-methoxy-phenoxy)-3-(3-thiazol-2-yl-ureido)-phenyl]-amide (105 mg, 81%) was prepared from 1-[5-amino-2-(2-fluoro-6-methoxy-phenoxy)-phenyl]-3-thiazol-2-yl-urea (94 mg, 0.25 mmol) following the general procedure L.

LC-MS (m/z): 521 (M+1)+; 1H NMR (400 MHz, CD3OD): δ 3.75 (s, 3H), 3.86 (q, 2H), 6.48 (d, 1H), 6.80 (m, 2H), 6.88 (d, 1H), 7.16 (q, 1H), 7.28 (d, 1H), 7.47 (s, 1H), 8.08 (d, 1H), 8.40 (br, 1H), 9.62 (d, 1H), and 11.34 (br, 1H).

Example 386

N-[4-(2-Fluoro-6-methoxy-phenoxy)-3-(3-thiazol-2-yl-ureido)-phenyl]-C-methanesulfonyl-methane-sulfonamide

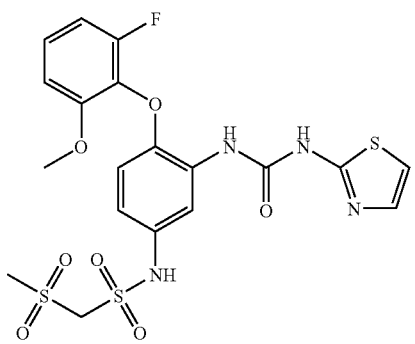

N-[4-(2-Fluoro-6-methoxy-phenoxy)-3-(3-thiazol-2-yl-ureido)-phenyl]-C-methanesulfonyl-methanesulfonamide (102 mg, 77%) was prepared from 1-[5-amino-2-(2-fluoro-6-methoxy-phenoxy)-phenyl]-3-thiazol-2-yl-urea (94 mg, 0.25 mmol) following the general procedure L.

LC-MS (m/z): 530 (M+1)+; 1H NMR (400 MHz, CD3OD): δ 3.01 (s, 3H), 3.27 (s, 2H), 3.82 (s, 3H), 6.56 (d, 1H), 6.85 (t, 1H), 6.94 (d, 1H), 7.21 (q, 1H), 7.34 (d, 1H), 7.46 (m, 1H), 7.96 (s, 1H), 8.22 (d, 1H), 8.40 (br, 1H), 9.62 (br, 1H), and 10.94 (br, 1H).

Example 387

1-Methyl-1H-imidazole-4-sulfonic acid [4-(2-fluoro-6-methoxy-phenoxy)-3-(3-thiazol-2-yl-ureido)-phenyl]-amide

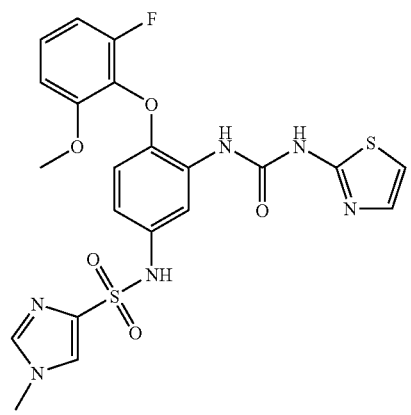

1-Methyl-1H-imidazole-4-sulfonic acid [4-(2-fluoro-6-methoxy-phenoxy)-3-(3-thiazol-2-yl-ureido)-phenyl]-amide (108 mg, 83%) was prepared from 1-[5-amino-2-(2-fluoro-6-methoxy-phenoxy)-phenyl]-3-thiazol-2-yl-urea (94 mg, 0.25 mmol) following the general procedure L.

LC-MS (m/z): 519 (M+1)+; 1H NMR (400 MHz, CD3OD): δ 3.00 (s, 3H), 3.78 (s, 3H), 6.46 (d, 1H), 6.74 (dd, 1H), 6.83 (d, 2H), 6.91 (d, 1H), 7.16-7.22 (m, 1H), 7.31 (d, 1H), 7.48 (m, 1H), 7.66 (s, 1H), 7.99 (d, 1H), 8.18 (d, 1H), 9.88 (br, 1H), and 11.24 (br, 1H).

Example 388

1,2-Dimethyl-1H-imidazole-4-sulfonic acid [4-(2-fluoro-6-methoxy-phenoxy)-3-(3-thiazol-2-yl-ureido)-phenyl]-amide

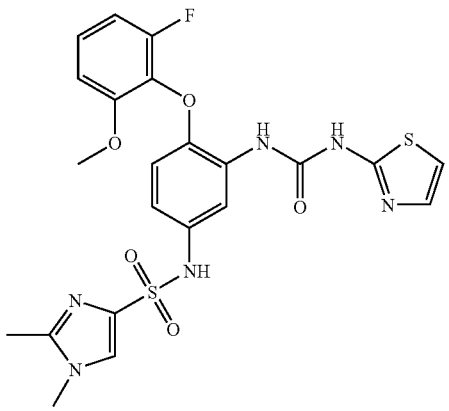

1,2-Dimethyl-1H-imidazole-4-sulfonic acid [4-(2-fluoro-6-methoxy-phenoxy)-3-(3-thiazol-2-yl-ureido)-phenyl]-amide (115 mg, 86%) was prepared from 1-[5-amino-2-(2-fluoro-6-methoxy-phenoxy)-phenyl]-3-thiazol-2-yl-urea (94 mg, 0.25 mmol) following the general procedure L.

LC-MS (m/z): 533 (M+1)+; 1H NMR (400 MHz, DMSO-d6): δ 2.74 (s, 3H), 3.20 (s, 3H), 3.99 (s, 3H), 6.79 (d, 1H), 7.09 (dd, 1H), 7.34 (t, 1H), 7.44 (d, 1H), 7.48 (d, 1H), 7.67 (q, 1H), 7.78 (d, 1H), 8.01 (s, 1H), 8.36 (s, 1H), 8.46 (d, 1H), 9.88 (br, 1H), and 11.24 (br, 1H).

Example 389

1-[2-(2-Fluoro-6-methoxy-phenoxy)-5-methylamino-phenyl]-3-thiazol-2-yl-urea

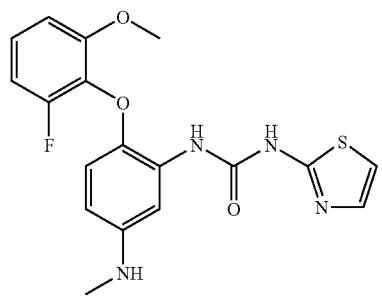

1-[2-(2-Fluoro-6-methoxy-phenoxy)-5-methylamino-phenyl]-3-thiazol-2-yl-urea (85 mg, 88%) was prepared from 1-[5-amino-2-(2-fluoro-6-methoxy-phenoxy)-phenyl]-3-thiazol-2-yl-urea (94 mg, 0.25 mmol) following the general procedure O.

LC-MS (m/z): 389 (M+1)+; 1H NMR (400 MHz, CDCl3): δ 3.66 (s, 3H), 4.09 (s, 3H), 5.62 (br, 1H), 6.82 (d, 1H), 6.99 (s, 1H), 7.16 (m, 1H), 7.40 (d, 1H), 7.45-7.53 (m, 1H), 7.58 (d, 1H), 7.64 (d, 1H), 8.76 (d, 1H), 9.38 (br, 1H), and 11.27 (br, 1H).

Example 390

1-[2-(2-Fluoro-6-methoxy-phenoxy)-5-(1-methyl-3-thiazol-2-yl-ureido)-phenyl]-3-thiazol-2-yl-urea

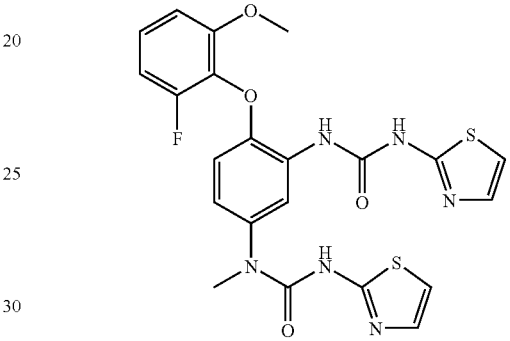

1-[2-(2-Fluoro-6-methoxy-phenoxy)-5-(1-methyl-3-thiazol-2-yl-ureido)-phenyl]-3-thiazol-2-yl-urea (86 mg, 67%) was prepared from 4-(2-fluoro-6-methoxy-phenoxy)-N'1'-methyl-benzene-1,3-diamine (64 mg, 0.25 mmol) following the general procedure D.

LC-MS (m/z): 515 (M+1)+; 1H NMR (400 MHz, CDCl3): δ 3.32 (s, 3H), 3.73 (s, 3H), 5.40 (br, 1H), 6.46 (d, 2H), 6.54 (d, 1H), 6.74 (d, 1H), 6.80 (d, 1H), 7.08 (d, 2H), 7.22 (d, 1H), 7.33 (br, 1H), 8.38 (d, 1H), 9.03 (br, 1H), and 11.27 (br, 1H).

Example 391

1-[5-Dimethylamino-2-(2-fluoro-6-methoxy-phenoxy)-phenyl]-3-thiazol-2-yl-urea

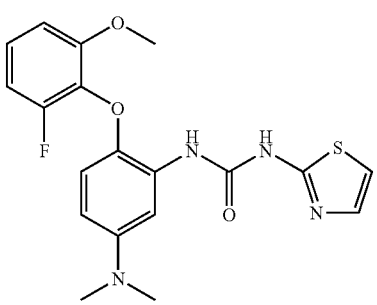

1-[5-Dimethylamino-2-(2-fluoro-6-methoxy-phenoxy)-phenyl]-3-thiazol-2-yl-urea (85 mg, 85%) was prepared from 1-[5-amino-2-(2-fluoro-6-methoxy-phenoxy)-phenyl]-3-thiazol-2-yl-urea (94 mg, 0.25 mmol) following the general procedure O.

LC-MS (m/z): 403 (M+1)+; 1H NMR (400 MHz, CDCl3): δ 2.93 (s, 6H), 3.66 (s, 3H), 6.38 (d, 1H), 6.49 (t, 1H), 6.62-6.74 (m, 2H), 7.07 (t, 1H), 7.39 (d, 1H), 7.84 (s, 1H), 8.00 (br, 1H), 8.42 (br, 1H), and 11.52 (br, 1H).

Example 392

1-{2-2-Fluoro-6-methoxy-phenoxy)-5-[(pyridin-3-ylmethyl)-amino]-phenyl}-3-thiazol-2-yl-urea

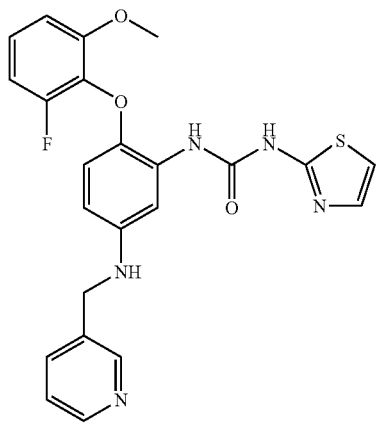

1-{2-(2-Fluoro-6-methoxy-phenoxy)-5-[(pyridin-3-ylmethyl)-amino]-phenyl}-3-thiazol-2-yl-urea (98 mg, 84%) was prepared from 1-[5-amino-2-(2-fluoro-6-methoxy-phenoxy)-phenyl]-3-thiazol-2-yl-urea (94 mg, 0.25 mmol) following the general procedure O.

LC-MS (m/z): 466 (M+1)+; 1H NMR (400 MHz, CD3OD): δ 3.16 (s, 2H), 3.62 (s, 3H), 6.42 (d, 1H), 6.68 (t, 1H), 6.78 (d, 1H), 6.88 (m, 1H), 7.05 (q, 1H), 7.21 (s, 1H), 7.41 (m, 1H), 7.52 (m, 1H), 7.81 (br, 1H), 8.00 (br, 1H), 8.16 (d, 1H), 8.42 (d, 1H), 8.56 (d, 1H), 8.70 (m, 1H), and 11.38 (br, 1H).

Example 393

1-[5-(Di-pyridin-2-yl-amino)-2-(2-fluoro-6-methoxy-phenoxy)-phenyl]-3-thiazol-2-yl-urea

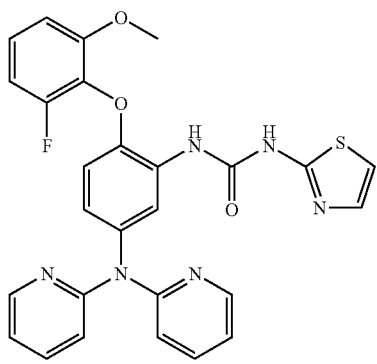

1-[5-(Di-pyridin-2-yl-amino)-2-(2-fluoro-6-methoxy-phenoxy)-phenyl]-3-thiazol-2-yl-urea (111 mg, 84%) was prepared from 1-[5-amino-2-(2-fluoro-6-methoxy-phenoxy)-phenyl]-3-thiazol-2-yl-urea (94 mg, 0.25 mmol) following the general procedure O.

LC-MS (m/z): 529 (M+1)+; 1H NMR (400 MHz, CD3OD): δ 3.67 (s, 3H), 6.42 (d, 1H), 6.46 (d, 1H), 6.50 (d, 2H), 6.72 (q, 2H), 6.87 (m, 4H), 7.02-7.10 (m, 2H), 7.42 (m, 1H), 7.54 (m, 1H), 8.14 (d, 2H), 9.70 (br, 1H), and 11.58 (br, 1H).

Example 394

Propane-1-sulfonic acid [4-(2-fluoro-6-methoxy-phenoxy)-3-(3-thiazol-2-yl-ureido)-phenyl]-amide

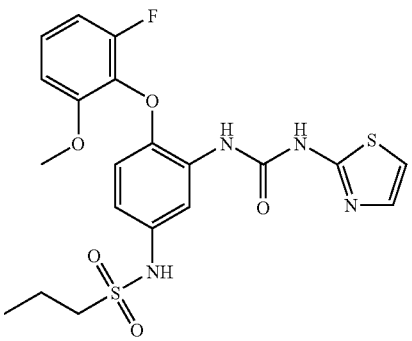

Propane-1-sulfonic acid [4-(2-fluoro-6-methoxy-phenoxy)-3-(3-thiazol-2-yl-ureido)-phenyl]-amide (100 mg, 83%) was prepared from 1-[5-amino-2-(2-fluoro-6-methoxy-phenoxy)-phenyl]-3-thiazol-2-yl-urea (94 mg, 0.25 mmol) following the general procedure L.

LC-MS (m/z): 481 (M+1)+; 1H NMR (400 MHz, Acetone-d6): δ 1.02 (t, 3H), 1.84 (m, 2H), 3.08 (t, 2H), 3.82 (s, 3H), 6.56 (d, 1H), 6.88 (d, 1H), 6.96-7.00 (m, 1H), 7.24 (q, 1H), 7.34 (dd, 1H), 7.88 (s, 1H), 7.99 (br, 1H), 8.32 (d, 1H), 8.48 (d, 1H), 8.64 (br, 1H), and 11.12 (br, 1H).

Example 395

N-[4-(2-Fluoro-6-methoxy-phenoxy)-3-(3-thiazol-2-yl-ureido)-phenyl]-C-phenyl methanesulfonamide

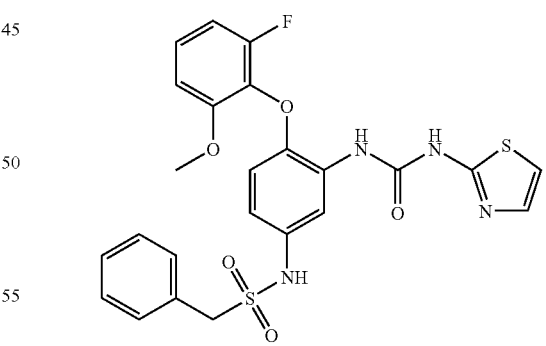

N-[4-(2-Fluoro-6-methoxy-phenoxy)-3-(3-thiazol-2-yl-ureido)-phenyl]-C-phenyl methanesulfonamide (104 mg, 79%) was prepared from 1-[5-amino-2-(2-fluoro-6-methoxy-phenoxy)-phenyl]-3-thiazol-2-yl-urea (94 mg, 0.25 mmol) following the general procedure L.

LC-MS (m/z): 529 (M+1)+; 1H NMR (400 MHz, CD3OD): δ 3.36 (s, 2H), 3.83 (s, 3H), 6.54 (d, 1H), 6.86 (m, 2H), 6.94 (m, 2H), 7.22 (q, 1H), 7.38 (m, 5H), 7.42 (d, 1H), 7.96 (br, 1H), 8.06 (d, 1H), 9.34 (br, 1H), and 11.24 (br, 1H).

Example 396

N-{4-[4-(2-Fluoro-6-methoxy-phenoxy)-3-(3-thiazol-2-yl-ureido)-phenylsulfamoyl]-phenyl}-acetamide

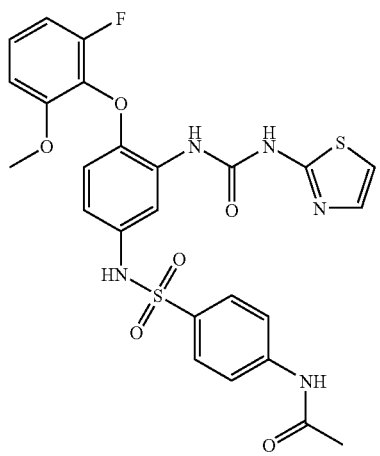

N-{4-[4-(2-Fluoro-6-methoxy-phenoxy)-3-(3-thiazol-2-yl-ureido)-phenylsulfamoyl]-phenyl}-acetamide (113 mg, 79%) was prepared from 1-[5-amino-2-(2-fluoro-6-methoxy-phenoxy)-phenyl]-3-thiazol-2-yl-urea (94 mg, 0.25 mmol) following the general procedure L.

LC-MS (m/z): 572 (M+1)$^+$; $^1$H NMR (400 MHz, CD$_3$OD): δ 3.02 (s, 3H), 3.85 (s, 3H), 6.48 (d, 1H), 6.86 (m, 2H), 6.98 (br, 1H), 7.03 (m, 2H), 7.41 (m, 3H), 7.76 (m, 3H), 8.23 (d, 1H), 9.06 (br, 1H), 9.54 (br, 1H), and 11.24 (br, 1H).

Example 397

1-{2-(2-Fluoro-6-methoxy-phenoxy)-5-[(5-methyl-3H-imidazol-4-ylmethyl)-amino]-phenyl}-3-thiazol-2-yl-urea

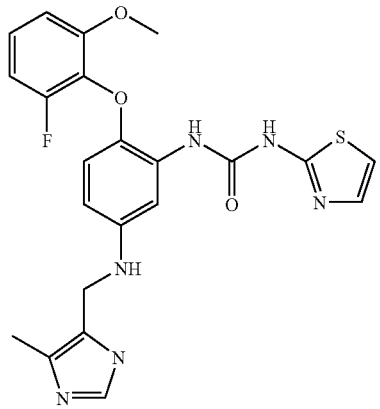

1-{2-(2-Fluoro-6-methoxy-phenoxy)-5-[(5-methyl-3H-imidazol-4-ylmethyl)-amino]-phenyl}-3-thiazol-2-yl-urea (98 mg, 84%) was prepared from 1-[5-amino-2-(2-fluoro-6-methoxy-phenoxy)-phenyl]-3-thiazol-2-yl-urea (94 mg, 0.25 mmol) following the general procedure O.

LC-MS (m/z): 469 (M+1)$^+$; $^1$H NMR (400 MHz, CD$_3$OD): δ 2.29 (s, 3H), 2.55 (s, 2H), 3.68 (s, 3H), 6.46 (d, 1H), 6.86 (m, 2H), 6.96 (br, 1H), 7.08 (d, 1H), 7.41 (m, 1H), 7.49 (m, 2H), 7.54 s, 1H), 7.64 (s, 1H), 7.72 (d, 1H), 9.46 (br, 1H), and 11.44 (br, 1H).

Example 398

4-Acetyl-N-[4-(2-fluoro-6-methoxy-phenoxy)-3-(3-thiazol-2-yl-ureido)-phenyl]-benzenesulfonamide

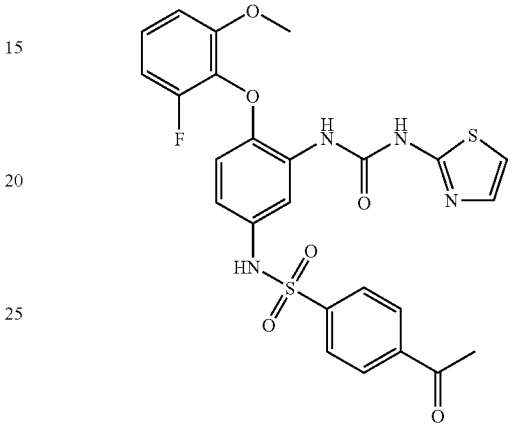

4-Acetyl-N-[4-(2-fluoro-6-methoxy-phenoxy)-3-(3-thiazol-2-yl-ureido)-phenyl]-benzenesulfonamide (98 mg, 84%) was prepared from 1-[5-amino-2-(2-fluoro-6-methoxy-phenoxy)-phenyl]-3-thiazol-2-yl-urea (94 mg, 0.25 mmol) following the general procedure L.

LC-MS (m/z): 557 (M+1)$^+$; $^1$H NMR (400 MHz, CD$_3$OD): δ 2.61 (s, 3H), 3.78 (s, 3H), 6.48 (d, 1H), 6.88 (m, 2H), 7.06 (m, 2H), 7.08 (d, 1H), 7.22 (br, 1H), 7.36 (d, 1H), 7.82 (m, 1H), 7.92 (d, 2H), 7.98 (t, 1H), 8.12 (d, 1H), 8.24 (br, 1H), and 11.88 (br, 1H).

Example 399

4-Cyano-N-[4-(2-fluoro-6-methoxy-phenoxy)-3-(3-thiazol-2-yl-ureido)-phenyl] benzenesulfonamide

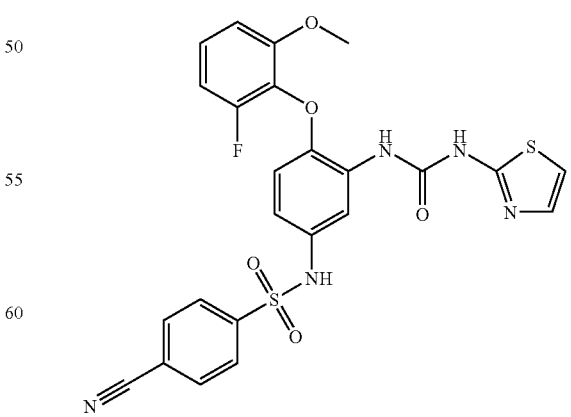

4-Cyano-N-[4-(2-fluoro-6-methoxy-phenoxy)-3-(3-thiazol-2-yl-ureido)-phenyl] benzenesulfonamide (115 mg, 85%) was prepared from 1-[5-amino-2-(2-fluoro-6-methoxy-phenoxy)-phenyl]-3-thiazol-2-yl-urea (94 mg, 0.25 mmol) following the general procedure L.

LC-MS (m/z): 540 (M+1)+; 1H NMR (400 MHz, CDCl3): δ 3.76 (s, 3H), 6.52 (d, 1H), 6.80 (m, 1H), 6.88 (d, 1H), 7.08 (d, 2H), 7.12-7.18 (m, 1H), 7.30 (d, 1H), 7.38 (d, 1H), 7.54 (d, 1H), 7.71 (t, 1H), 7.91 (q, 1H), 8.01 (s, 1H), 8.08 (br, 1H), 8.22 (d, 1H), and 11.22 (br, 1H).

Example 400

N-[4-(2-Fluoro-6-methoxy-phenoxy)-3-(3-thiazol-2-yl-ureido)-phenyl]-4-isopropyl-benzenesulfonamide

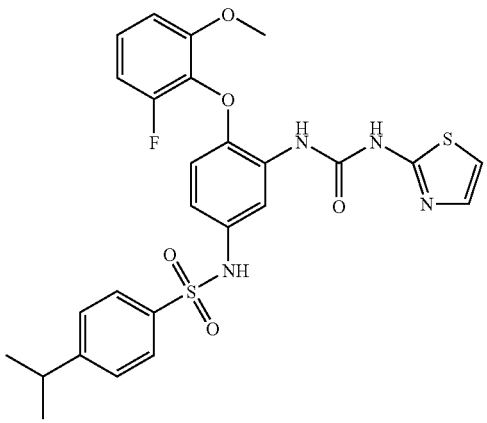

N-[4-(2-Fluoro-6-methoxy-phenoxy)-3-(3-thiazol-2-yl-ureido)-phenyl]-4-isopropyl-benzenesulfonamide (103 mg, 74%) was prepared from 1-[5-amino-2-(2-fluoro-6-methoxy-phenoxy)-phenyl]-3-thiazol-2-yl-urea (94 mg, 0.25 mmol) following the general procedure L.

LC-MS (m/z): 557 (M+1)+; 1H NMR (400 MHz, CDCl3): δ 1.22 (d, 6H), 1.56 (m, 1H), 3.74 (s, 3H), 6.54 (d, 1H), 6.78 (m, 2H), 6.84 (d, 1H), 6.98 (m, 1H), 7.06 (d, 1H), 7.12-7.18 (m, 2H), 7.22 (d, 1H), 7.34 (d, 1H), 7.72 (d, 1H), 8.00 (br, 1H), 8.22 (d, 1H), 8.58 (br, 1H), and 10.74 (br, 1H).

Example 401

N-{5-[4-(2-Fluoro-6-methoxy-phenoxy)-3-(3-thiazol-2-yl-ureido)-phenylsulfamoyl]-4-methyl-thiazol-2-yl}-acetamide

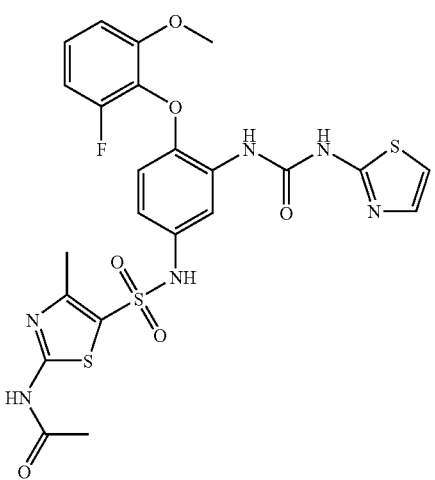

N-{5-[4-(2-Fluoro-6-methoxy-phenoxy)-3-(3-thiazol-2-yl-ureido)-phenylsulfamoyl]-4-methyl-thiazol-2-yl}-acetamide (121 mg, 82%) was prepared from 1-[5-amino-2-(2-fluoro-6-methoxy-phenoxy)-phenyl]-3-thiazol-2-yl-urea (94 mg, 0.25 mmol) following the general procedure L.

LC-MS (m/z): 593 (M+1)+; 1H NMR (400 MHz, CD3OD): δ 2.32 (s, 3H), 3.00 (s, 3H), 3.77 (s, 3H), 4.04 (br, 1H), 6.48 (d, 1H), 6.84 (d, 1H), 6.88 (dd, 1H), 6.96 (d, 1H), 7.16-7.22 (m, 1H), 7.32 (d, 1H), 7.36 (d, 1H), 7.92 (d, 1H), 7.98 (br, 1H), 8.84 (br, 1H), and 10.74 (br, 1H).

Example 402

5-Bromo-6-chloro-pyridine-3-sulfonic acid [4-(2-fluoro-6-methoxy-phenoxy)-3-(3-thiazol-2-yl-ureido)-phenyl]-amide

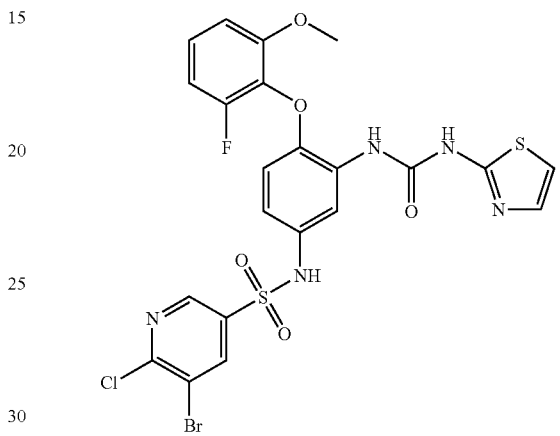

5-Bromo-6-chloro-pyridine-3-sulfonic acid [4-(2-fluoro-6-methoxy-phenoxy)-3-(3-thiazol-2-yl-ureido)-phenyl]-amide (120 mg, 76%) was prepared from 1-[5-amino-2-(2-fluoro-6-methoxy-phenoxy)-phenyl]-3-thiazol-2-yl-urea (94 mg, 0.25 mmol) following the general procedure L.

LC-MS (m/z): 629 (M+1)+; 1H NMR (400 MHz, CDCl3): δ 3.78 (s, 3H), 6.56 (d, 1H), 6.88 (d, 1H), 6.78 (m, 1H), 6.88 (dd, 1H), 7.14 (d, 1H), 7.22 (d, 1H), 7.36 (d, 1H), 8.02 (d, 1H), 8.12 (br, 1H), 8.33 (d, 1H), 8.73 (d, 1H), 9.78 (br, 1H), and 10.74 (br, 1H).

Example 403

3,5-Dimethyl-isoxazole-4-sulfonic acid [4-(2-fluoro-6-methoxy-phenoxy)-3-(3-thiazol-2-yl-ureido)-phenyl]-amide

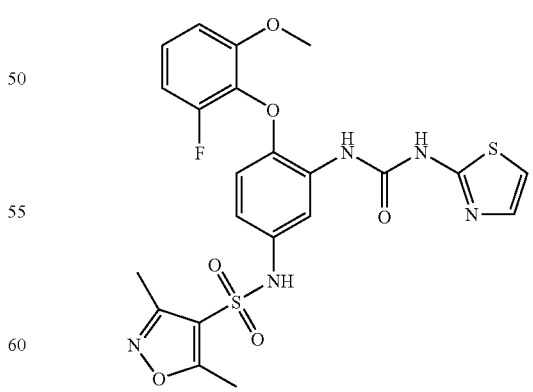

3,5-Dimethyl-isoxazole-4-sulfonic acid [4-(2-fluoro-6-methoxy-phenoxy)-3-(3-thiazol-2-yl-ureido)-phenyl]-amide (98 mg, 73%) was prepared from 1-[5-amino-2-(2-fluoro-6-methoxy-phenoxy)-phenyl]-3-thiazol-2-yl-urea (94 mg, 0.25 mmol) following the general procedure L.

LC-MS (m/z): 534 (M+1)+; 1H NMR (400 MHz, CDCl3): δ 2.88 (s, 3H), 3.00 (s, 3H), 3.75 (s, 3H), 5.21 (br, 1H), 6.54 (d, 1H), 6.80-6.88 (m, 1H), 6.96 (m, 1H), 7.10-7.20 (m, 1H), 7.38 (d, 1H), 7.52 (d, 1H), 7.72 (br, 1H), 8.01 (d, 1H), 8.22 (d, 1H), and 10.74 (br, 1H).

Example 404

5-Chloro-1,3-dimethyl-1H-pyrazole-4-sulfonic acid [4-(2-fluoro-6-methoxy-phenoxy)-3-(3-thiazol-2-yl-ureido)-phenyl]-amide

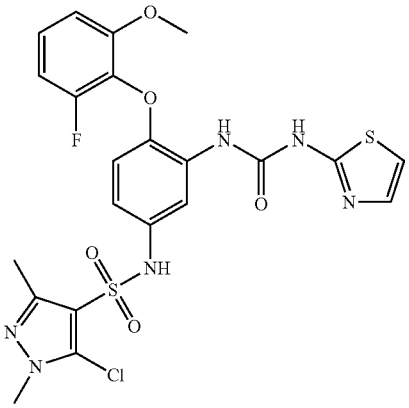

5-Chloro-1,3-dimethyl-1H-pyrazole-4-sulfonic acid [4-(2-fluoro-6-methoxy-phenoxy)-3-(3-thiazol-2-yl-ureido)-phenyl]-amide (111 mg, 79%) was prepared from 1-[5-amino-2-(2-fluoro-6-methoxy-phenoxy)-phenyl]-3-thiazol-2-yl-urea (94 mg, 0.25 mmol) following the general procedure L.

LC-MS (m/z): 568 (M+1)+; 1H NMR (400 MHz, CDCl3): δ 2.32 (s, 3H), 2.63 (s, 3H), 3.74 (s, 3H), 6.48 (d, 1H), 6.76-6.84 (m, 1H), 6.94 (d, 1H), 7.06-7.18 (m, 1H), 7.22 (d, 1H), 7.38 (d, 1H), 7.52 (d, 1H), 7.94 (d, 1H), 8.08 (d, 1H), 8.20 (br, 1H), and 11.16 (br, 1H).

Example 405

6-Morpholin-4-yl-pyridine-3-sulfonic acid [4-(2-fluoro-6-methoxy-phenoxy)-3-(3-thiazol-2-yl-ureido)-phenyl]-amide

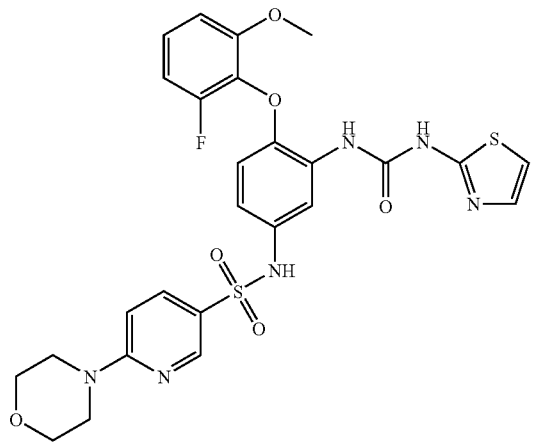

6-Morpholin-4-yl-pyridine-3-sulfonic acid [4-(2-fluoro-6-methoxy-phenoxy)-3-(3-thiazol-2-yl-ureido)-phenyl]-amide (115 mg, 76%) was prepared from 1-[5-amino-2-(2-fluoro-6-methoxy-phenoxy)-phenyl]-3-thiazol-2-yl-urea (94 mg, 0.25 mmol) following the general procedure L.

LC-MS (m/z): 601 (M+1)+; 1H NMR (400 MHz, CD3OD): δ 2.15 (m, 4H), 3.60 (t, 2H), 3.70 (t, 2H), 3.76 (s, 3H), 6.42 (d, 1H), 6.78 (d, 2H), 6.84 (d, 1H), 6.96 (d, 1H), 7.04 (m, 2H), 7.20 (m, 1H), 7.34 (d, 1H), 7.79 (d, 1H), 8.02 (d, 1H), 8.39 (d, 1H), 8.52 (br, 1H), and 11.28 (br, 1H).

Example 406

6-Oxazol-5-yl-pyridine-3-sulfonic acid [4-(2-fluoro-6-methoxy-phenoxy)-3-(3-thiazol-2-yl-ureido)-phenyl]-amide

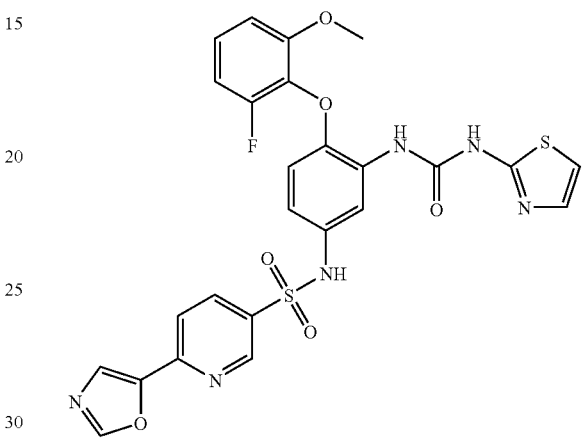

6-Oxazol-5-yl-pyridine-3-sulfonic acid [4-(2-fluoro-6-methoxy-phenoxy)-3-(3-thiazol-2-yl-ureido)-phenyl]-amide (96 mg, 66%) was prepared from 1-[5-amino-2-(2-fluoro-6-methoxy-phenoxy)-phenyl]-3-thiazol-2-yl-urea (94 mg, 0.25 mmol) following the general procedure L.

LC-MS (m/z): 583 (M+1)+; 1H NMR (400 MHz, CD3OD): δ 3.77 (s, 3H), 6.46 (d, 1H), 6.78-6.86 (m, 2H), 6.94 (d, 1H), 6.92-6.99 (m, 2H), 7.20 (q, 1H), 7.33 (dd, 1H), 7.55 (d, 1H), 7.80 (d, 1H), 7.86-7.92 (m, 2H), 8.05 (d, 1H), 8.18 (d, 1H), 9.88 (br, 1H), and 11.16 (br, 1H).

Example 407

2-(2-{3-[2-(2-Fluoro-6-methoxy-phenoxy)-5-methanesulfonylamino-phenyl]-ureido}-thiazol-4-yl)-N-methyl-acetamide

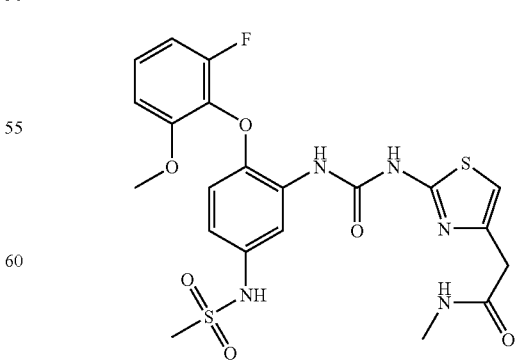

(2-{3-[2-(2-Fluoro-6-methoxy-phenoxy)-5-methanesulfonylamino-phenyl]-ureido}-thiazol-4-yl)-N-methyl-acetamide (47 mg, 87.9%) was prepared from (2-{3-[2-(2-fluoro-6-methoxy-phenoxy)-5-methanesulfonylamino-phenyl]-ureido}-thiazol-4-yl)-acetic acid (51 mg, 0.10 mmol) following the general procedure K.

LC-MS (m/z): 524 (M+1)+; $^1$H NMR (400 MHz, CD$_3$OD): δ 2.93 (s, 3H), 3.48 (d, 3H), 3.56 (s, 2H), 4.02 (s, 3H), 4.82 (br, 1H), 6.76 (d, 1H), 7.04 (s, 1H), 7.09 (dd, 1H), 7.16 (t, 1H), 7.22 (d, 1H), 7.52 (q, 1H), 8.12 (br, 1H), 8.44 (d, 1H), 9.88 (br, 1H) and 11.84 (br, 1H).

Example 408

[4-(2-Fluoro-6-methoxy-phenoxy)-3-(3-thiazol-2-yl-ureido)-phenyl]-carbamic acid tert-butyl ester

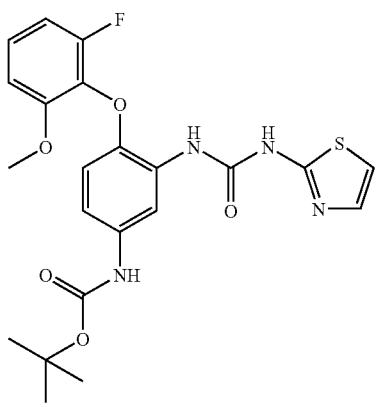

[4-(2-Fluoro-6-methoxy-phenoxy)-3-(3-thiazol-2-yl-ureido)-phenyl]-carbamic acid tert-butyl ester (4.56 g, 96.2%) was prepared from 3-amino-4-(2-fluoro-6-methoxy-phenoxy)-phenyl]-carbamic acid tert-butyl ester (3.48 g, 10.0 mmol) following the general procedure D.

LC-MS (m/z): 475 (M+1)+; $^1$H NMR (400 MHz, CD$_3$OD): δ 1.74 (s, 9H), 3.74 (s, 3H), 6.64 (d, 1H), 6.92 (dd, 1H), 7.02 (d, 1H), 7.14 (m, 1H), 7.34 (dd, 1H), 7.68 (dd, 1H), 7.88 (br, 1H), 8.32 (dd, 1H), 8.46 (d, 1H), 9.26 (br, 1H), 11.62 (br, 1H).

Example 409

1-(4-Methyl-2-propoxy-phenyl)-3-thiazol-2-yl-urea

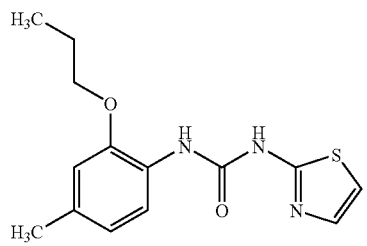

3-Propoxy-4-nitrotoluene (0.79 g, 80%) was prepared from 1-propanol and 3-fluoro-4-nitrotoluene (0.77 g, 5.0 mmol) following the general procedure G. This was reduced to 4-methyl-2-propoxyaniline (0.54 g, 82%) following general procedure C. 1-(4-Methyl-2-propoxy-phenyl)-3-thiazol-2-yl-urea (220 mg, 75%) was prepared from 4-methyl-2-propoxyaniline (165 mg, 1.0 mmol) and 2-aminothiazole (100 mg, 1.0 mmol) following the general procedure D.

LC-MS (m/z): 292 (M+1)+; $^1$H NMR (400 MHz, DMSO-d$_6$): δ 1.03 (t, 3H), 1.80 (m, 2H), 2.25 (s, 3H), 3.98 (t, 2H), 6.70 (dd, 1H), 6.83 (d, 1H), 7.10 (d, 1H), 7.37 (d, 1H), 7.98 (d, 1H), 8.50 (br, 1H), 11.27 (br, 1H).

Example 410

1-(2-Butoxy-4-methyl-phenyl)-3-thiazol-2-yl-urea

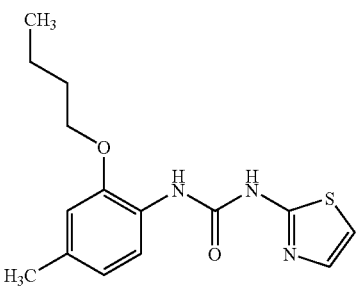

3-(1-Butoxy)-4-nitrotoluene (0.78 g, 75%) was prepared from 1-butanol and 3-fluoro-4-nitrotoluene (0.77 g, 5.0 mmol) following the general procedure G. This was reduced to 4-methyl-2-(1-butoxy)aniline (0.47 g, 70%) following general procedure C. 1-(2-Butoxy-4-methyl-phenyl)-3-thiazol-2-yl-urea (210 mg, 70%) was prepared from 4-methyl-2-(1-butoxy)aniline (179 mg, 1.0 mmol) and 2-aminothiazole (100 mg, 1.0 mmol) following the general procedure D.

LC-MS (m/z): 306 (M+1)+; $^1$H NMR (400 MHz, DMSO-d$_6$): δ 0.95 (t, 3H), 1.52 (m, 2H), 1.78 (m, 2H), 2.25 (s, 3H), 4.04 (t, 2H), 6.71 (dd, 1H), 6.86 (d, 1H), 7.11 (d, 1H), 7.36 (d, 1H), 7.96 (d, 1H), 8.50 (br, 1H), 11.26 (br, 1H).

Example 411

1-[4-Methyl-2-(3-methyl-butoxy)-phenyl]-3-thiazol-2-yl-urea

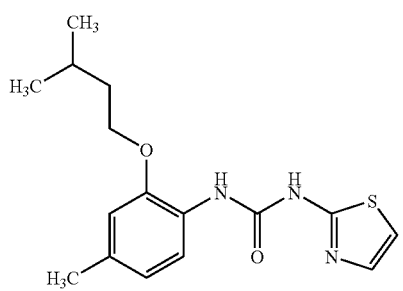

3-(3-Methyl-butoxy)-4-nitrotoluene (0.89 g, 80%) was prepared from 3-methylbutanol and 3-fluoro-4-nitrotoluene (0.77 g, 5.0 mmol) following the general procedure G. This was reduced to 4-methyl-2-(3-methylbutoxy)aniline (0.55 g, 72%) following general procedure C. 1-[4-Methyl-2-3-methyl-butoxy)-phenyl]-3-thiazol-2-yl-urea (240 mg, 76%) was prepared from 4-methyl-2-(3-methyl-butoxy)aniline (193 mg, 1.0 mmol) and 2-aminothiazole (100 mg, 1.0 mmol) following the general procedure D.

LC-MS (m/z): 320 (M+1)+; $^1$H NMR (400 MHz, DMSO-d$_6$): δ 0.94 (d, 6H), 1.71 (m, 2H), 1.85 (m, 1H), 2.26 (s, 3H), 4.04 (t, 2H), 6.70 (d, 1H), 6.87 (s, 1H), 7.11 (d, 1H), 7.36 (d, 1H), 7.96 (d, 1H), 8.50 (br, 1H), 11.26 (br, 1H).

Example 412

1-(2-Allyloxy-4-methyl-phenyl)-3-thiazol-2-yl-urea

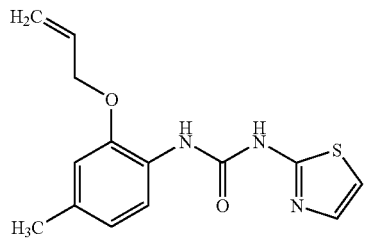

3-Allyloxy-4-nitrotoluene (0.67 g, 70%) was prepared from allyl alcohol and 3-fluoro-4-nitrotoluene (0.77 g, 5.0 mmol) following the general procedure G. This was reduced to 4-methyl-2-(allyloxy)aniline (0.40 g, 70%) following general procedure B. 1-(2-Allyloxy-4-methyl-phenyl)-3-thiazol-2-yl-urea (196 mg, 68%) was prepared from 4-methyl-2-(2-methylpropoxy)aniline (163 mg, 1.0 mmol) and 2-aminothiazole (100 mg, 1.0 mmol) following the general procedure D.

LC-MS (m/z): 290 (M+1)$^+$; $^1$H NMR (400 MHz, DMSO-$d_6$): δ 2.25 (s, 3H), 4.64 (d, 2H), 5.30 (m, 1H), 5.49 (m, 1H), 6.09 (m, 1H), 6.74 (dd, 1H), 6.87 (s, 1H), 7.10 (d, 1H), 7.36 (dd, 1H), 7.97 (d, 1H), 8.60 (br, 1H), 11.15 (br, 1H).

Example 413

1-[4-Methyl-2-(2-methyl-allyloxy)-phenyl]-3-thiazol-2-yl-urea

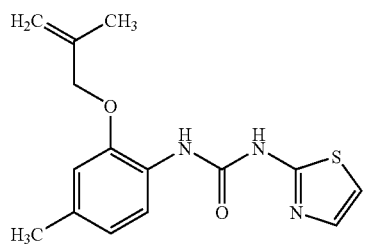

3-(2-Methyl-allyloxy)-4-nitrotoluene (0.78 g, 75%) was prepared from methallyl alcohol and 3-fluoro-4-nitrotoluene (0.77 g, 5.0 mmol) following the general procedure G. This was reduced to 4-methyl-2-2-methyl-allyloxy)aniline (0.47 g, 70%) following general procedure B. 1-[4-Methyl-2-(2-methyl-allyloxy)-phenyl]-3-thiazol-2-yl-urea (210 mg, 70%) was prepared from 4-methyl-2-(2-methyl-allyloxy)aniline (179 mg, 1.0 mmol) and 2-aminothiazole (100 mg, 1.0 mmol) following the general procedure D.

LC-MS (m/z): 304 (M+1)$^+$; $^1$H NMR (400 MHz, DMSO-$d_6$): δ 1.83 (s, 3H), 2.25 (s, 3H), 4.54 (s, 2H), 5.00 (s, 1H), 5.15 (s, 1H), 6.72 (d, 1H), 6.86 (s, 1H), 7.10 (d, 1H), 7.36 (d, 1H), 7.97 (d, 1H), 8.60 (br, 1H), 11.21 (br, 1H).

Example 414

1-[4-Methyl-2-(3-methyl-but-2-enyloxy)-phenyl]-3-thiazol-2-yl-urea

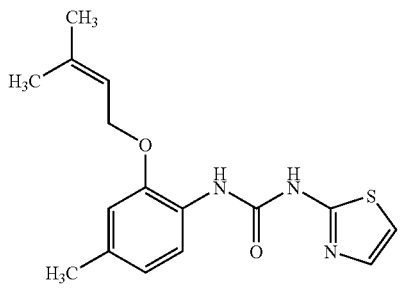

3-(3-methyl-but-2-enyloxy)-4-nitrotoluene (0.8 g, 72%) was prepared from 3-methylbut-2-en-1-ol and 3-fluoro-4-nitrotoluene (0.77 g, 5.0 mmol) following the general procedure G. This was reduced to 4-methyl-2-(3-methyl-but-2-enyloxy)aniline (0.43 g, 62%) following general procedure B. 1-[4-Methyl-2-(3-methyl-but-2-enyloxy)-phenyl]-3-thiazol-2-yl-urea (206 mg, 65%) was prepared from 4-methyl-2-(3-methyl-but-2-enyloxy)aniline (191 mg, 1.0 mmol) and 2-aminothiazole (100 mg, 1.0 mmol) following the general procedure D.

LC-MS (m/z): 318 (M+1)$^+$; $^1$H NMR (400 MHz, DMSO-$d_6$): δ 1.75 (d, 6H), 2.25 (s, 3H), 4.60 (d, 2H), 5.26 (t, 1H), 6.71 (d, 1H), 6.89 (s, 1H), 7.09 (d, 1H), 7.35 (d, 1H), 7.96 (dd, 1H), 8.56 (br, 1H), 11.17 (br, 1H).

Example 415

1-(2-Isopropoxy-4-methyl-phenyl)-3-thiazol-2-yl-urea

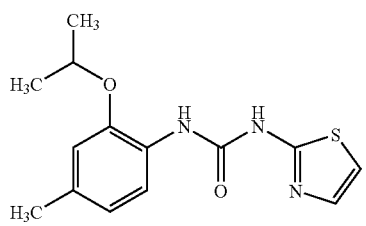

3-(2-Isopropoxy)-4-nitrotoluene (0.72 g, 74%) was prepared from 2-propanol and 3-fluoro-4-nitrotoluene (0.77 g, 5.0 mmol) following the general procedure G. This was reduced to 2-isopropoxy-4-methyl-aniline (0.42 g, 70%) following general procedure C. 1-(2-Isopropoxy-4-methyl-phenyl)-3-thiazol-2-yl-urea (180 mg, 62%) was prepared from 2-isopropoxy-4-methyl-aniline (165 mg, 1.0 mmol) and 2-aminothiazole (100 mg, 1.0 mmol) following the general procedure D.

LC-MS (m/z): 292 (M+1)$^+$; $^1$H NMR (400 MHz, DMSO-$d_6$): δ 1.32 (d, 6H), 2.24 (s, 3H), 4.63 (m, 1H), 6.70 (dd, 1H), 6.88 (d, 1H), 7.10 (d, 1H), 7.37 (d, 1H), 7.97 (d, 1H), 8.60 (br, 1H), 11.27 (br, 1H).

Example 416

1-(2-Cyclopentyloxy-4-methyl-phenyl)-3-thiazol-2-yl-urea

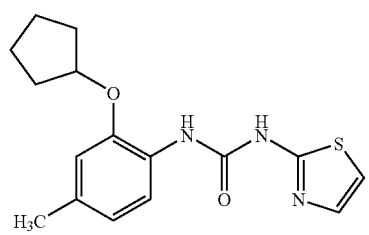

3-Cyclopentyloxy-4-nitrotoluene (0.68 g, 62%) was prepared from cyclopentanol and 3-fluoro-4-nitrotoluene (0.77 g, 5.0 mmol) following the general procedure G. This was reduced to 2-cyclopentyloxy-4-methyl-aniline (0.43 g, 70%) following general procedure C. 1-(2-Cyclopentyloxy-4-methyl-phenyl)-3-thiazol-2-yl-urea (220 mg, 70%) was prepared from 2-cyclopentyloxy-4-methyl-aniline (191 mg, 1.0 mmol) and 2-aminothiazole (100 mg, 1.0 mmol) following the general procedure D.

LC-MS (m/z): 318 (M+1)$^+$; $^1$H NMR (400 MHz, DMSO-$d_6$): δ 1.60 (m, 2H), 1.80 (m, 4H), 1.93 (m, 2H), 2.25 (s, 3H), 4.86 (m, 1H), 6.68 (dd, 1H), 6.81 (d, 1H), 7.10 (d, 1H), 7.37 (d, 1H), 7.97 (d, 1H), 8.40 (br, 1H), 11.31 (br, 1H).

Example 417

1-(2-Cyclopropylmethoxy-4-methyl-phenyl)-3-thiazol-2-yl-urea

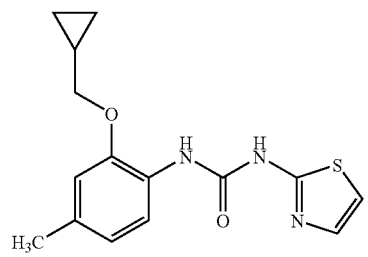

3-Cyclopropylmethoxy-4-nitrotoluene (0.77 g, 75%) was prepared from cyclopropylmethanol and 3-fluoro-4-nitrotoluene (0.77 g, 5.0 mmol) following the general procedure G. This was reduced to 2-cyclopropylmethoxy-4-methyl-aniline (0.47 g, 71%) following general procedure C. 1-(2-Cyclopropylmethoxy-4-methyl-phenyl)-3-thiazol-2-yl-urea (218 mg, 72%) was prepared from 2-cyclopropylmethoxy-4-methyl-aniline (177 mg, 1.0 mmol) and 2-aminothiazole (100 mg, 1.0 mmol) following the general procedure D.

LC-MS (m/z): 304 (M+1)$^+$; $^1$H NMR (400 MHz, DMSO-$d_6$): δ 0.37 (m, 2H), 0.59 (m, 2H), 1.29 (m, 1H), 2.24 (s, 3H), 3.88 (d, 2H), 6.71 (d, 1H), 6.84 (d, 1H), 7.10 (d, 1H), 7.37 (d, 1H), 7.96 (d, 1H), 8.60 (br, 1H), 11.25 (br, 1H).

Example 418

1-[4-Methyl-2-(tetrahydro-pyran-2-ylmethoxy)-phenyl]-3-thiazol-2-yl-urea

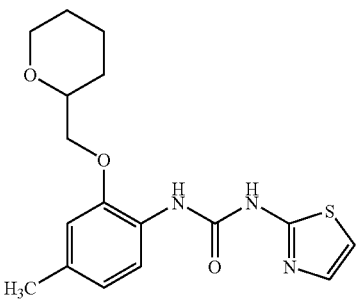

4-Nitro-3-(tetrahydro-pyran-2-ylmethoxy)-toluene (0.80 g, 64%) was prepared from tetrahydropyran-2-ylmethanol and 3-fluoro-4-nitrotoluene (0.77 g, 5.0 mmol) following the general procedure G. This was reduced to 4-methyl-2-(tetrahydro-pyran-2-ylmethoxy)-aniline (0.50 g, 71%) following general procedure C. 1-[4-Methyl-2-(tetrahydro-pyran-2-ylmethoxy)-phenyl]-3-thiazol-2-yl-urea (246 mg, 71%) was prepared from 4-methyl-2-(tetrahydro-pyran-2-ylmethoxy)-aniline (221 mg, 1.0 mmol) and 2-aminothiazole (100 mg, 1.0 mmol) following the general procedure D.

LC-MS (m/z): 348 (M+1)$^+$; $^1$H NMR (400 MHz, DMSO-$d_6$): δ 1.34 (m, 1H), 1.50 (m, 2H), 1.55 (m, 1H), 1.75 (d, 1H), 1.83 (m, 1H), 2.25 (s, 3H), 3.43 (m, 1H), 3.90 (m, 2H), 4.01 (m, 1H), 6.72 (d, 1H), 6.86 (d, 1H), 7.10 (d, 1H), 7.37 (d, 1H), 7.96 (d, 1H), 8.50 (br, 1H), 11.28 (br, 1H).

Example 419

1-[4-Methyl-2-(tetrahydro-furan-2-ylmethoxy)-phenyl]-3-thiazol-2-yl-urea

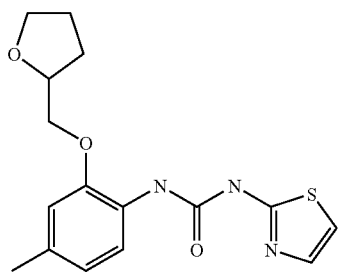

4-Nitro-3-(tetrahydro-furan-2-ylmethoxy)-toluene (0.88 g, 75%) was prepared from tetrahydro-furan-2-ylmethanol and 3-fluoro-4-nitrotoluene (0.77 g, 5.0 mmol) following the general procedure G. This was reduced to 4-methyl-2-(tetrahydro-furan-2-ylmethoxy)-aniline (0.50 g, 65%) following general procedure C. 1-[4-Methyl-2-(tetrahydro-furan-2-ylmethoxy)-phenyl]-3-thiazol-2-yl-urea (236 mg, 71%) was prepared from 4-methyl-2-(tetrahydro-furan-2-ylmethoxy)-aniline (207 mg, 1.0 mmol) and 2-aminothiazole (100 mg, 1.0 mmol) following the general procedure D.

LC-MS (m/z): 334 (M+1)$^+$.

Example 420

1-(2-Cyclopentylmethoxy-4-methyl-phenyl)-3-thiazol-2-yl-urea

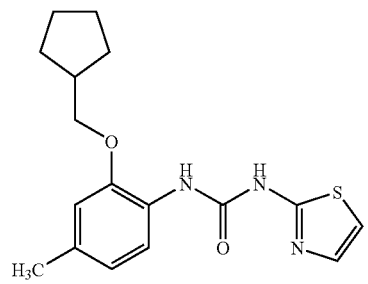

3-Cyclopentylmethoxy-4-nitrotoluene (0.82 g, 70%) was prepared from cyclopentylmethanol and 3-fluoro-4-nitrotoluene (0.77 g, 5.0 mmol) following the general procedure G. This was reduced to 2-cyclopentylmethoxy-4-methyl-aniline (0.58 g, 81%) following general procedure C. 1-(2-Cyclopentylmethoxy-4-methyl-phenyl)-3-thiazol-2-yl-urea (225 mg, 68%) was prepared from 2-cyclopentylmethoxy-4-methyl-aniline (205 mg, 1.0 mmol) and 2-aminothiazole (100 mg, 1.0 mmol) following the general procedure D.

LC-MS (m/z): 332 (M+1)$^+$;

Example 421

{2-[3-(2-Cyclopropylmethoxy-4-methyl-phenyl)-ureido]-thiazol-4-yl}-acetic acid

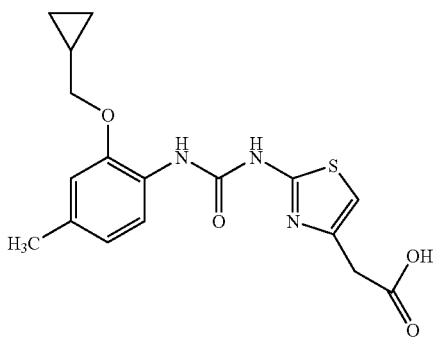

{2-[3-(2-Cyclopropylmethoxy-4-methyl-phenyl)-ureido]-thiazol-4-yl}-acetic acid ethyl ester (253 mg, 65%) was prepared from 2-cyclopropylmethoxy-4-methyl-aniline (177 mg, 1.0 mmol) and (2-amino-thiazol-4-yl)-acetic acid ethyl ester (186 mg, 1.0 mmol) following the general procedure D.

LC-MS (m/z): 390 (M+1)$^+$, $^1$H NMR (400 MHz, DMSO-d$_6$): δ 0.36 (m, 2H), 0.59 (m, 2H), 1.18 (t, 3H), 1.28 (m, 1H), 2.24 (s, 3H), 3.64 (s, 2H), 3.88 (d, 2H), 4.08 (q, 2H), 6.71 (dd, 1H), 6.83 (d, 1H), 6.86 (d, 1H), 7.94 (d, 1H), 8.40 (br, 1H), 11.36 (br, 1H).

{2-[3-(2-Cyclopropylmethoxy-4-methyl-phenyl)-ureido]-thiazol-4-yl}-acetic acid (165 mg, 92%) was prepared from {2-[3-(2-cyclopropylmethoxy-4-methyl-phenyl)-ureido]-thiazol-4-yl}-acetic acid ethyl ester (195 mg, 0.5 mmol) following the general procedure J.

LC-MS (m/z): 362 (M+1)$^+$.

Example 422

{2-[3-(2-Cyclopentyloxy-4-methyl-phenyl)-ureido]-thiazol-4-yl}-acetic acid

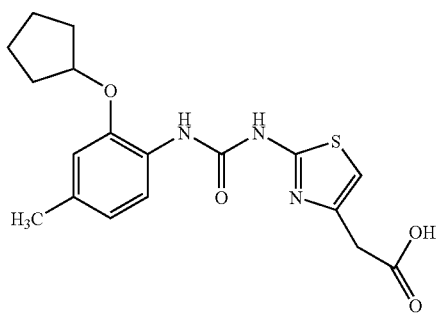

{2-[3-(2-Cyclopentyloxy-4-methyl-phenyl)-ureido]-thiazol-4-yl}-acetic acid ethyl ester (250 mg, 62%) was prepared from 2-cyclopentyloxy-4-methyl-aniline (191 mg, 1.0 mmol) and (2-amino-thiazol-4-yl)-acetic acid ethyl ester (186 mg, 1.0 mmol) following the general procedure D. {2-[3-(2-Cyclopentyloxy-4-methyl-phenyl)-ureido]-thiazol-4-yl}-acetic acid (170 mg, 91%) was prepared from {2-[3-(2-cyclopropylmethoxy-4-methyl-phenyl)-ureido]-thiazol-4-yl}-acetic acid ethyl ester (200 mg, 0.5 mmol) following the general procedure J.

LC-MS (m/z): 376 (M+1)$^+$.

Example 423

1-(2-Isobutoxy-4-methanesulfonylmethyl-phenyl)-3-thiazol-2-yl-urea

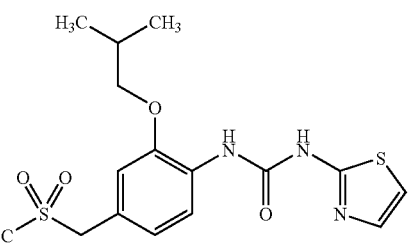

2-Isobutoxy-4-methanesulfonylmethyl-1-nitro-benzene (0.93 g, 65%) was prepared from 2-methylpropanol and 2-fluoro-4-methanesulfonylmethyl-1-nitro-benzene (1.16 g, 5.0 mmol) following the general procedure G. This was reduced to 2-isobutoxy-4-methanesulfonylmethyl-aniline (0.46 g, 56%) following general procedure B. 1-(2-Isobutoxy-4-methanesulfonylmethyl-phenyl)-3-thiazol-2-yl-urea (250 mg, 65%) was prepared from 2-isobutoxy-4-methanesulfonylmethyl-aniline (257 mg, 1.0 mmol) and 2-aminothiazole (100 mg, 1.0 mmol) following the general procedure D.

LC-MS (m/z): 384 (M+1)$^+$; $^1$H NMR (400 MHz, DMSO-d$_6$): δ 1.06 (d, 6H), 2.14 (m, 1H), 2.88 (s, 3H), 3.11 (s, 2H), 4.39 (d, 2H), 6.19 (s, 1H), 6.89 (d, 1H), 7.14 (s, 1H), 7.39 (d, 1H), 8.13 (d, 1H), 8.50 (br, 1H), 11.24 (br, 1H).

Example 424

(2-{2-[3-(2-Isobutoxy-4-methyl-phenyl)-ureido]-thiazol-4-yl}-acetylamino)-acetic acid

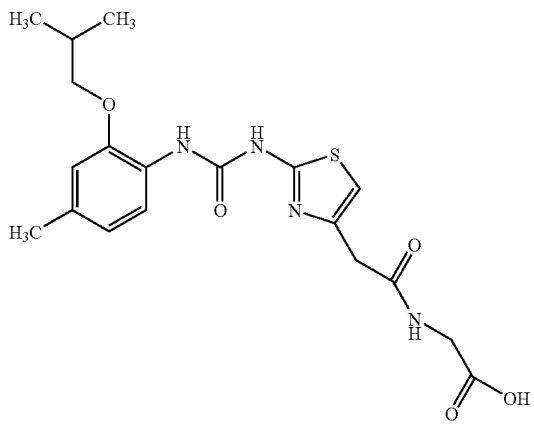

(2-{2-[3-(2-Isobutoxy-4-methyl-phenyl)-ureido]-thiazol-4-yl}-acetylamino)-acetic acid (90 mg, 86%) was prepared from (2-{2-[3-(2-isobutoxy-4-methyl-phenyl)-ureido]-thiazol-4-yl}-acetylamino)-acetic acid methyl ester (108 mg, 0.25 mmol) following the general procedure J. (2-{2-[3-(2-Isobutoxy-4-methyl-phenyl)-ureido]-thiazol-4-yl}-acetylamino)-acetic acid methyl ester (150 mg, 70%) was in turn prepared from {2-[3-(2-isobutoxy-4-methyl-phenyl)-ureido]-thiazol-4-yl}-acetic acid (181 mg, 0.5 mmol) and glycine methyl ester hydrochloride following the general procedure K.

LC-MS (m/z): 421 (M+1)$^+$.

Example 425

1-(5-Formyl-2-isobutoxy-phenyl)-3-thiazol-2-yl-urea

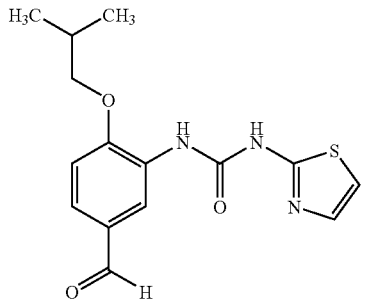

4-(2-Methylpropoxy)-3-nitrobenzaldehyde (0.83 g, 75%) was prepared from 2-methyl-propanol (0.46 ml, 5.0 mmol) and 4-fluoro-3-nitrobenzaldehyde (0.77 g, 5.0 mmol) following the general procedure G. This was reduced to 5-formyl-2-(2-methylpropoxy)-aniline (0.49 g, 68%) following general procedure B. 1-(5-Formyl-2-isobutoxy-phenyl)-3-thiazol-2-yl-urea (208 mg, 65%) was prepared from 5-formyl-2-(2-methylpropoxy)aniline (193 mg, 1.0 mmol) and 2-aminothiazole (100 mg, 1.0 mmol) following the general procedure D.

LC-MS (m/z): 320 (M+1)$^+$; $^1$H NMR (400 MHz, DMSO-d$_6$): δ 1.06 (d, 6H), 2.16 (m, 1H), 3.96 (d, 2H), 7.16 (d, 1H), 7.25 (d, 1H), 7.40 (dd, 1H), 7.61 (d, 1H), 8.69 (s, 1H), 9.86 (s, 1H), 10.75 (br, 1H), 11.51 (br, 1H).

Example 426

2-{2-[3-(2-Isobutoxy-4-methyl-phenyl)-ureido]-thiazol-4-yl}-N-(2-methoxy-ethyl)-acetamide

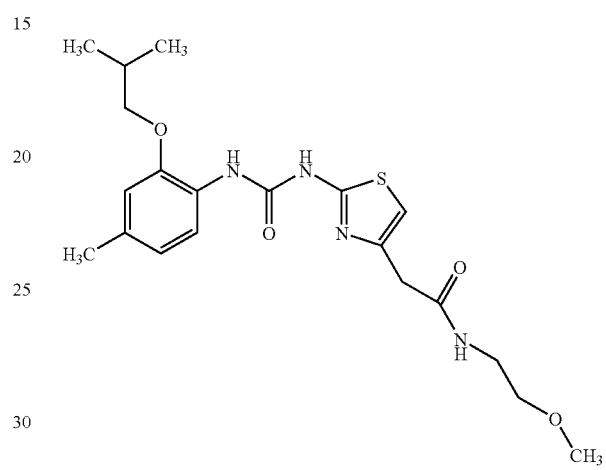

2-{2-[3-(2-Isobutoxy-4-methyl-phenyl)-ureido]-thiazol-4-yl}-N-(2-methoxy-ethyl)-acetamide (130 mg, 62%) was prepared from {2-[3-(2-isobutoxy-4-methyl-phenyl)-ureido]-thiazol-4-yl}-acetic acid (181 mg, 0.5 mmol) and 2-methoxyethylamine following the general procedure K.

LC-MS (m/z): 421 (M+1)$^+$.

Example 427

1-(5-Fluoro-2-isobutoxy-4-methyl-phenyl)-3-thiazol-2-yl-urea

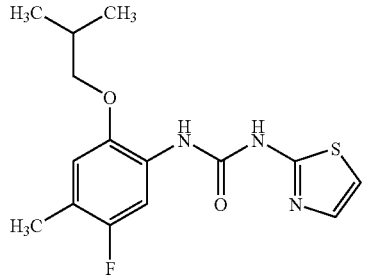

2-Fluoro-5-(2-methylpropoxy)-4-nitrotoluene (0.73 g, 65%) was prepared from 2-methylpropanol (0.46 ml, 5.0 mmol) and 2,5-difluoro-4-nitrotoluene (0.86 g, 5.0 mmol) following the general procedure G. This was reduced to 5-fluoro-4-methyl-2-(2-methylpropoxy)-aniline (0.45 g, 70%) following general procedure C. 1-(5-Fluoro-2-isobutoxy-4-methyl-phenyl)-3-thiazol-2-yl-urea (205 mg, 64%) was prepared from 5-fluoro-4-methyl-2-(2-methylpropoxy)- aniline (197 mg, 1.0 mmol) and 2-aminothiazole (100 mg, 1.0 mmol) following the general procedure D.

LC-MS (m/z): 324 (M+1)+; $^1$H NMR (400 MHz, DMSO-$d_6$): δ 1.03 (d, 6H), 2.16 (m, 1H), 2.17 (s, 3H), 3.80 (d, 2H), 6.92 (d, 1H), 7.14 (d, 1H), 7.38 (d, 1H), 7.93 (d, 1H), 8.50 (br, 1H), 11.44 (br, 1H).

Example 428

1-(5-Fluoro-2-isobutoxy-phenyl)-3-thiazol-2-yl-urea

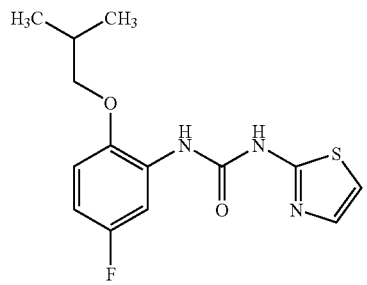

5-Fluoro-2-(2-methylpropoxy)-4-nitrobenzene (0.83 g, 78%) was prepared from 2-methylpropanol (0.46 ml, 5.0 mmol) and 2,5-difluoro-4-nitrobenzene (0.80 g, 5.0 mmol) following the general procedure G. This was reduced to 5-fluoro-2-(2-methylpropoxy)-aniline (0.58 g, 81%) following general procedure C. 1-(5-Fluoro-2-isobutoxy-phenyl)-3-thiazol-2-yl-urea (220 mg, 72%) was prepared from 5-fluoro-2-(2-methylpropoxy)-aniline (183 mg, 1.0 mmol) and 2-aminothiazole (100 mg, 1.0 mmol) following the general procedure D.

LC-MS (m/z): 310 (M+1)+; $^1$H NMR (400 MHz, DMSO-$d_6$): δ 1.03 (d, 6H), 2.11 (m, 1H), 3.80 (d, 2H), 6.79 (m, 1H), 6.99 (m, 1H), 7.15 (d, 1H), 7.39 (d, 1H), 8.01 (dd, 1H), 8.60 (br, 1H), 11.52 (br, 1H).

Example 429

1-(2-Isobutylsulfanyl-4-methyl-phenyl)-3-thiazol-2-yl-urea

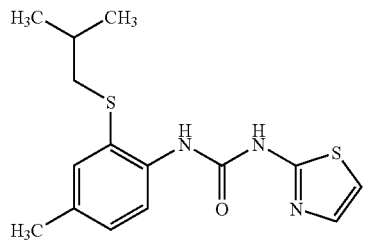

3-(Isobutylsulfanyl)-4-nitrotoluene (0.75 g, 67%) was prepared from 2-methyl-propanethiol and 3-fluoro-4-nitrotoluene (0.77 g, 5.0 mmol) following the general procedure A. This was reduced to 2-isobutylsulfanyl-4-methyl-aniline (0.46 g, 63%) following general procedure B. 1-(2-Isobutylsulfanyl-4-methyl-phenyl)-3-thiazol-2-yl-urea (218 mg, 68%) was prepared from 2-isobutylsulfanyl-4-methyl-aniline (195 mg, 1.0 mmol) and 2-aminothiazole (100 mg, 1.0 mmol) following the general procedure D.

LC-MS (m/z): 318 (M+1)+, $^1$H NMR (400 MHz, DMSO-$d_6$): δ 0.85 (m, 6H), 1.40 (m, 1H), 2.26 (s, 3H), 2.80 (m, 2H), 7.11 (s, 1H), 7.29 (s, 1H), 7.38 (d, 1H), 7.89 (d, 1H), 8.65 (br, 1H), 11.28 (br, 1H).

Example 430

{2-[3-(2-Isobutylsulfanyl-4-methyl-phenyl)-ureido]-thiazol-4-yl}-acetic acid ethyl ester

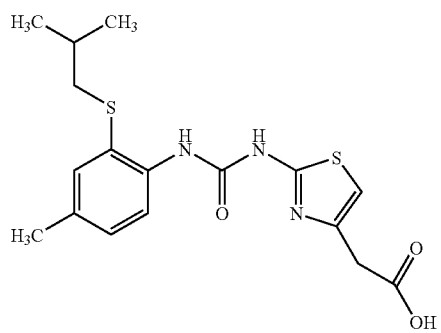

{2-[3-(2-Isobutylsulfanyl-4-methyl-phenyl)-ureido]-thiazol-4-yl}-acetic acid ethyl ester (276 mg, 68%) was prepared from 2-isobutylsulfanyl-4-methyl-aniline (195 mg, 1.0 mmol) and ethyl 2-amino-4-thiazolylacetate (186 mg, 1.0 mmol) following the general procedure D. Hydrolysis of this ester following general procedure J gave {2-[3-(2-isobutylsulfanyl-4-methyl-phenyl)-ureido]-thiazol-4-yl}-acetic acid (230 mg, 90%).

LC-MS (m/z): 380 (M+1)+, $^1$H NMR (400 MHz, DMSO-$d_6$): δ 0.85 (m, 6H), 1.49 (m, 1H), 2.26 (s, 3H), 2.83 (m, 2H), 3.56 (s, 2H), 6.85 (s, 1H), 7.09 (d, 1H), 7.29 (d, 1H), 7.89 (d, 1H), 8.65 (br, 1H), 11.28 (br, 2H).

Example 431

1-(2-Cyclopentanesulfinyl-4-methyl-phenyl)-3-thiazol-2-yl-urea

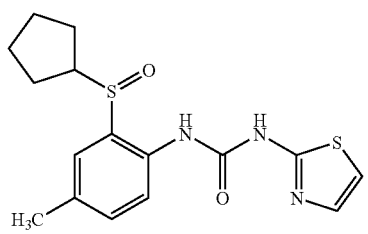

3-Cyclopentanesulfanyl-4-nitrotoluene (0.47 g, 2.0 mmol) was oxidized to 3-cyclopentanesulfinyl-4-nitrotoluene (0.46 g, 91%) following general procedure R (using one equivalent of m-CPBA). 3-Cyclopentanesulfinyl-4-nitrotoluene was reduced to 2-cyclopentanesulfinyl-4-methyl-aniline (0.33 g, 81%) following general procedure C. 1-(2-Cyclopentanesulfinyl-4-methyl-phenyl)-3-thiazol-2-yl-urea (225 mg, 65%) was prepared from 2-cyclopentanesulfinyl-4-methyl-aniline (223 mg, 1.0 mmol) and 2-aminothiazole (100 mg, 1.0 mmol) following the general procedure D.

LC-MS (m/z): 350 (M+1)+; $^1$H NMR (400 MHz, DMSO-$d_6$): δ 1.58 (m, 6H), 1.78 (m, 1H), 1.94 (m, 1H), 2.34 (s, 3H), 3.43 (m, 1H), 7.11 (d, 1H), 7.33 (dd, 1H), 7.36 (dd, 1H), 7.43 (s, 1H), 7.80 (d, 1H), 8.93 (br, 1H), 11.25 (br, 1H).

Example 432

1-(2-Cyclopentanesulfonyl-4-methyl-phenyl)-3-thiazol-2-yl-urea

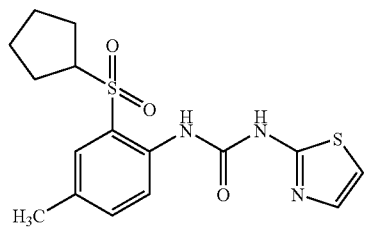

3-Cyclopentanesulfanyl-4-nitrotoluene (0.83 g, 70%) was prepared from cyclopentyl mercaptan and 3-fluoro-4-nitrotoluene (0.77 g, 5.0 mmol) following the general procedure A. This was oxidized to 3-cyclopentanesulfonyl-4-nitrotoluene (0.84 g, 90%) following general procedure R. 3-Cyclopentanesulfonyl-4-nitrotoluene was reduced to 2-cyclopentanesulfonyl-4-methyl-aniline (0.53 g, 70%) following general procedure C. 1-(2-Cyclopentanesulfonyl-4-methyl-phenyl)-3-thiazol-2-yl-urea (225 mg, 62%) was prepared from 2-cyclopentanesulfonyl-4-methyl-aniline (239 mg, 1.0 mmol) and 2-aminothiazole (100 mg, 1.0 mmol) following the general procedure D.

LC-MS (m/z): 366 (M+1)+; $^1$H NMR (400 MHz, DMSO-$d_6$): δ 1.58 (m, 2H), 1.78 (m, 2H), 1.86 (m, 2H), 2.04 (m, 2H), 2.38 (s, 3H), 3.54 (m, 1H), 6.94 (d, 1H), 7.43 (dd, 1H), 7.61 (d, 1H), 7.67 (d, 1H), 8.18 (d, 1H), 9.20 (br, 1H), 11.25 (br, 1H).

Example 433

{2-[3-(2-Cyclopentanesulfonyl-4-methyl-phenyl)-ureido]-thiazol-4-yl}-acetic acid ethyl ester

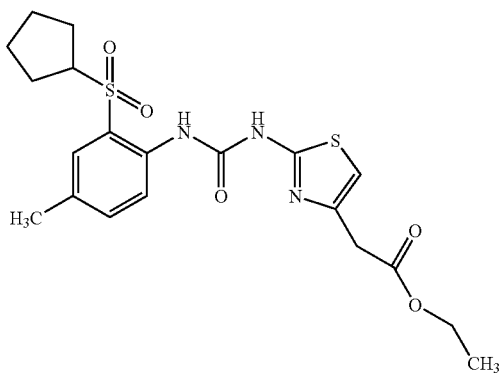

{2-[3-(2-Cyclopentanesulfonyl-4-methyl-phenyl)-ureido]-thiazol-4-yl}-acetic acid ethyl ester (305 mg, 68%) was prepared from 2-cyclopentanesulfonyl-4-methyl-aniline (239 mg, 1.0 mmol) and ethyl 2-amino-4-thiazolylacetate (186 mg, 1.0 mmol) following the general procedure D.

LC-MS (m/z): 452 (M+1)+, $^1$H NMR (400 MHz, DMSO-$d_6$): δ 1.19 (t, 3H); 1.58 (m, 4H), 1.84 (m, 4H), 2.35 (s, 3H), 3.65 (s, 2H), 3.77 (m, 1H), 4.08 (q, 2H), 6.91 (s, 1H), 7.52 (d, 1H), 7.63 (s, 1H), 8.00 (d, 1H), 8.91 (br, 1H), 11.89 (br, 1H).

Example 434

{2-[3-(2-Cyclopentanesulfonyl-4-methyl-phenyl)-ureido]-thiazol-4-yl}-acetic acid

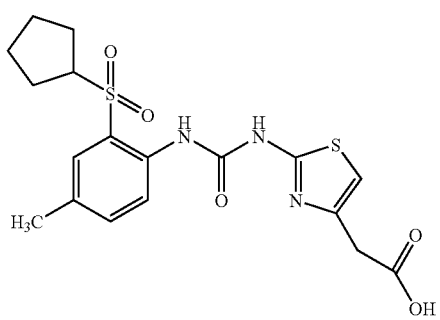

Following the general procedure J, {2-[3-(2-cyclopentanesulfonyl-4-methyl-phenyl)-ureido]-thiazol-4-yl}-acetic acid ethyl ester (225 mg, 0.5 mmol) was hydrolyzed to afford {2-[3-(4-methyl-2-[2-methylpropoxy]phenyl)-ureido]-thiazol-4-yl}-acetic acid (193 mg, 92%).

LC-MS (m/z): 424 (M+1)+, $^1$H NMR (400 MHz, DMSO-$d_6$): δ 1.60 (m, 4H), 1.84 (m, 4H), 2.36 (s, 3H), 3.57 (s, 2H), 3.77 (m, 1H), 6.87 (s, 1H), 7.52 (d, 1H), 7.63 (s, 1H), 8.01 (d, 1H), 8.95 (br, 1H), 12.32 (br, 2H).

Example 435

2-{2-[3-(2-Cyclopentanesulfonyl-4-methyl-phenyl)-ureido]-thiazol-4-yl}-N-methyl-acetamide

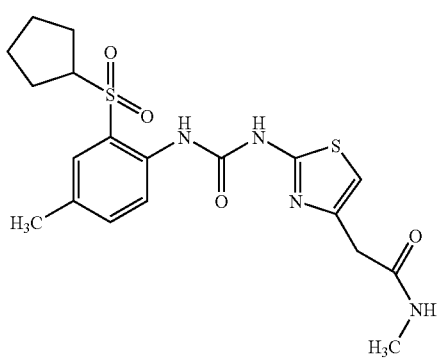

2-{2-[3-(2-Cyclopentanesulfonyl-4-methyl-phenyl)-ureido]-thiazol-4-yl}-N-methyl-acetamide (30 mg, 68%) was prepared from {2-[3-(4-methyl-2-[2-methylpropoxy]phenyl)-ureido]-thiazol-4-yl}-acetic acid (42 mg, 0.1 mmol) and methylamine following the general procedure K.

LC-MS (m/z): 437 (M+1)+.

Example 436

2-{2-[3-(2-Cyclopentanesulfonyl-4-methyl-phenyl)-ureido]-thiazol-4-yl}-N-(2-methoxy-ethyl)-acetamide

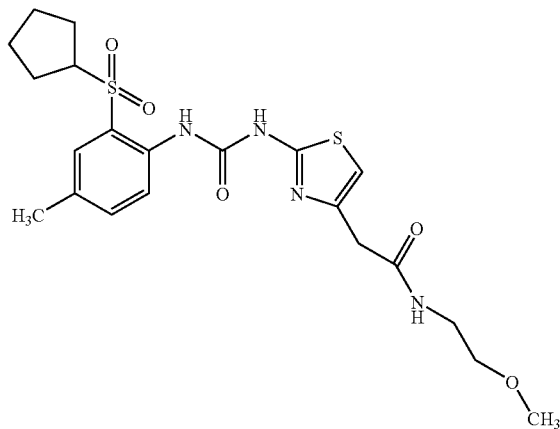

2-{2-[3-(2-Cyclopentanesulfonyl-4-methyl-phenyl)-ureido]-thiazol-4-yl}-N-methyl-acetamide (30 mg, 68%) was prepared from {2-[3-(4-methyl-2-[2-methylpropoxy]phenyl)-ureido]-thiazol-4-yl}-acetic acid (42 mg, 0.1 mmol) and 2-methoxyethylamine following the general procedure K.

LC-MS (m/z): 480 (M+1)$^+$, $^1$H NMR (400 MHz, DMSO-$d_6$): δ 1.60 (m, 4H), 1.84 (m, 4H), 2.36 (s, 3H), 3.21 (m, 4H), 3.24 (s, 3H), 3.43 (s, 2H), 3.76 (m, 1H), 6.81 (s, 1H), 7.52 (d, 1H), 7.63 (s, 1H), 8.05 (br, 2H), 8.95 (br, 1H), 11.85 (br, 1H).

Example 437

1-(2-Cyclopentylamino-4-methyl-phenyl)-3-thiazol-2-yl-urea

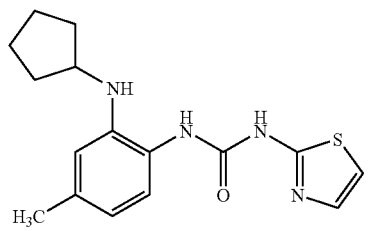

2-Cyclopentylamino-4-methyl-aniline (0.64 g, 68%) was prepared from cyclopentylamine (1.0 ml, 10.0 mmol) and 3-fluoro-4-nitrotoluene (0.77 g, 5.0 mmol) following the general procedure W. 1-(2-Cyclopentylamino-4-methyl-phenyl)-3-thiazol-2-yl-urea (195 mg, 62%) was prepared from 2-cyclopentylamino-4-methyl-aniline (190 mg, 1.0 mmol) and 2-aminothiazole (100 mg, 1.0 mmol) following the general procedure D.

LC-MS (m/z): 317 (M+1)$^+$, $^1$H NMR (400 MHz, CDCl$_3$): δ 1.46 (m, 2H), 1.59 (m, 2H), 1.68 (m, 2H), 2.01(m, 2H), 2.32 (s, 3H), 3.78 (m, 1H), 6.51 (d, 1H), 6.56 (s, 1H), 6.88 (d, 1H), 7.07 (br, 1H), 7.31 (d, 1H), 9.30 (br, 1H), 10.72 (br, 1H).

Example 438

1-(2-Isobutylamino-4-methyl-phenyl)-3-thiazol-2-yl-urea

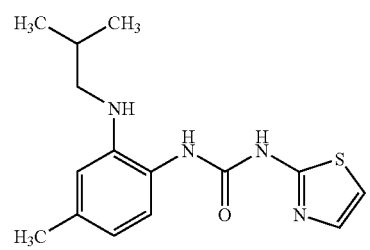

2-Isobutylamino-4-methyl-aniline (0.61 g, 69%) was prepared from isobutylamine (0.73 g, 10.0 mmol) and 3-fluoro-4-nitrotoluene (0.77 g, 5.0 mmol) following the general procedure W. 1-(2-Isobutylamino-4-methyl-phenyl)-3-thiazol-2-yl-urea (196 mg, 65%) was prepared from 2-Isobutylamino-4-methyl-aniline (178 mg, 1.0 mmol) and 2-aminothiazole (100 mg, 1.0 mmol) following the general procedure D.

LC-MS (m/z): 305 (M+1)$^+$, $^1$H NMR (400 MHz, CDCl$_3$): δ 0.95 (d, 6H), 1.88 (m, 1H), 2.31 (s, 3H), 2.92 (d, 2H), 4.15 (br, 1H), 6.51 (m, 2H), 6.87 (d, 1H), 7.08 (m, 1H), 7.31 (d, 1H), 9.30 (br, 1H), 10.72 (br, 1H).

Example 439

1-[4-Methyl-2-(methyl-propyl-amino)-phenyl]-3-thiazol-2-yl-urea

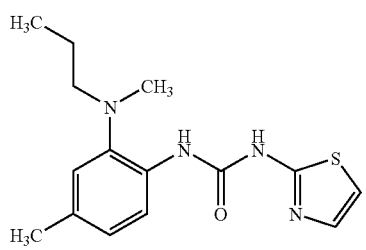

4-Methyl-2-(methyl-propyl-amino)-aniline (0.56 g, 63%) was prepared from N-methyl-propylamine (0.73 g, 10.0 mmol) and 3-fluoro-4-nitrotoluene (0.77 g, 5.0 mmol) following the general procedure W. 1-[4-Methyl-2-(methyl-propyl-amino)-phenyl]-3-thiazol-2-yl-urea (215 mg, 71%) was prepared from 4-methyl-2-(methyl-propyl-amino)-aniline (178 mg, 1.0 mmol) and 2-aminothiazole (100 mg, 1.0 mmol) following the general procedure D.

LC-MS (m/z): 305 (M+1)$^+$, $^1$H NMR (400 MHz, DMSO-$d_6$): δ 0.85 (t, 3H), 1.40 (m, 2H), 2.24 (s, 3H), 2.54 (s, 3H), 2.79 (t, 2H), 6.87 (dd, 1H), 7.02 (d, 1H), 7.09 (d, 1H), 7.37 (d, 1H), 7.99 (d, 1H), 8.80 (br, 1H), 11.36 (br, 1H).

Example 440

1-[2-(Butyl-methyl-amino)-4-methyl-phenyl]-3-thiazol-2-yl-urea

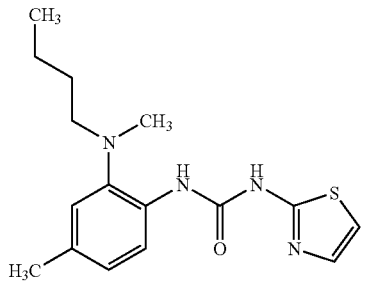

4-Methyl-2-(butyl-methyl-amino)-aniline (0.62 g, 65%) was prepared from N-methyl-butylamine (0.87 g, 10.0 mmol) and 3-fluoro-4-nitrotoluene (0.77 g, 5.0 mmol) following the general procedure W. 1-[2-(Butyl-methyl-amino)-4-methyl-phenyl]-3-thiazol-2-yl-urea (220 mg, 69%) was prepared from 4-methyl-2-(butyl-methyl-amino)-aniline (192 mg, 1.0 mmol) and 2-aminothiazole (100 mg, 1.0 mmol) following the general procedure D.

LC-MS (m/z): 319 (M+1)$^+$, $^1$H NMR (400 MHz, DMSO-$d_6$): δ 0.82 (t, 3H), 1.27 (m, 2H), 1.38 (m, 2H), 2.24 (s, 3H), 2.54 (s, 3H), 2.82 (t, 2H), 6.87 (d, 1H), 7.02 (s, 1H), 7.09 (d, 1H), 7.37 (d, 1H), 7.97 (d, 1H), 8.80 (br, 1H), 1-1.37 (br, 1H).

Example 441

1-(2-Diethylamino-4-methyl-phenyl)-3-thiazol-2-yl-urea

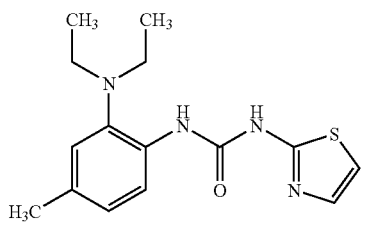

2-(Diethyl-amino)-4-methyl-aniline (0.63 g, 71%) was prepared from diethylamine (0.73 g, 10.0 mmol) and 3-fluoro-4-nitrotoluene (0.77 g, 5.0 mmol) following the general procedure W. 1-(2-Diethylamino-4-methyl-phenyl)-3-thiazol-2-yl-urea (188 mg, 62%) was prepared from 2-(diethyl-amino)-4-methyl-aniline (178 mg, 1.0 mmol) and 2-aminothiazole (100 mg, 1.0 mmol) following the general procedure D.

LC-MS (m/z): 305 (M+1)$^+$, $^1$H NMR (400 MHz, DMSO-$d_6$): δ 0.89 (t, 6H), 2.24 (s, 3H), 2.90 (q, 4H), 6.92 (dd, 1H), 7.04 (d, 1H), 7.09 (d, 1H), 7.37 (d, 1H), 8.04 (d, 1H), 9.00 (br, 1H), 11.44 (br, 1H).

Example 442

1-[2-(Cyclopropylmethyl-propyl-amino)-4-methyl-phenyl]-3-thiazol-2-yl-urea

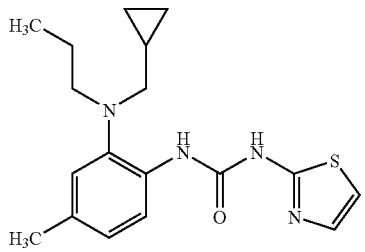

2-(Cyclopropylmethyl-propyl-amino)-4-methyl-aniline (0.68 g, 63%) was prepared from N-propyl-cyclopropanemethylamine (1.13 g, 10.0 mmol) and 3-fluoro-4-nitrotoluene (0.77 g, 5.0 mmol) following the general procedure W. 1-[4-Methyl-2-(methyl-propyl-amino)-phenyl]-3-thiazol-2-yl-urea (210 mg, 61%) was prepared from 4-methyl-2-(methyl-propyl-amino)-aniline (218 mg, 1.0 mmol) and 2-aminothiazole (100 mg, 1.0 mmol) following the general procedure D.

LC-MS (m/z): 345 (M+1)$^+$, $^1$H NMR (400 MHz, DMSO-$d_6$): δ -0.24 (m, 2H), 0.30 (m, 2H), 0.80 (m, 4H), 1.32 (m, 2H), 2.24 (s, 3H), 2.69 (d, 2H), 2.91 (t, 2H), 6.90 (dd, 1H), 7.07 (m, 2H), 7.37 (d, 1H), 8.01 (m, 1H), 9.00 (br, 1H), 11.51 (br, 1H).

Example 443

1-[2-(Isobutyl-methyl-amino)-4-methyl-phenyl]-3-thiazol-2-yl-urea

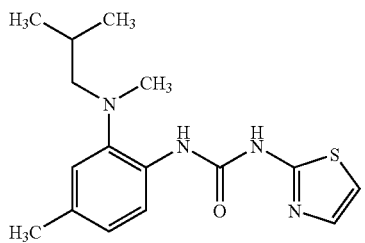

2-(Isobutyl-methyl-amino)-4-methyl-aniline (0.62 g, 65%) was prepared from N-isobutyl-methylamine (0.87 g, 10.0 mmol) and 3-fluoro-4-nitrotoluene (0.77 g, 5.0 mmol) following the general procedure W. 1-[2-(Isobutyl-methyl-amino)-4-methyl-phenyl]-3-thiazol-2-yl-urea (216 mg, 68%) was prepared from 2-(isobutyl-methyl-amino)-4-methyl-aniline (192 mg, 1.0 mmol) and 2-aminothiazole (100 mg, 1.0 mmol) following the general procedure D.

LC-MS (m/z): 319 (M+1)$^+$, $^1$H NMR (400 MHz, CDCl$_3$): δ 0.86 (d, 6H), 1.68 (m, 1H), 2.31 (s, 3H), 2.58 (s, 3H), 2.66 (d, 2H), 6.88 (d, 1H), 6.96 (m, 2H), 7.44 (d, 1H), 8.12 (d, 1H), 9.20 (br, 1H), 11.36 (br, 1H).

Example 444

(2-{3-[2-(Isobutyl-methyl-amino)-4-methyl-phenyl]-ureido}-thiazol-4-yl)-acetic acid ethyl ester

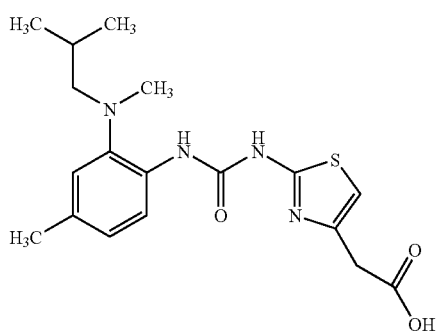

(2-{3-[2-(Isobutyl-methyl-amino)-4-methyl-phenyl]-ureido}-thiazol-4-yl)-acetic acid ethyl ester (290 mg, 72%) was prepared from 2-(isobutyl-methyl-amino)-4-methyl-aniline (192 mg, 1.0 mmol) and ethyl 2-amino-4-thiazolylacetate (186 mg, 1.0 mmol) following the general procedure D. Hydrolysis of this ester following the general procedure J gave (2-{3-[2-(isobutyl-methyl-amino)-4-methyl-phenyl]-ureido}-thiazol-4-yl)-acetic acid (250 mg, 92%).

LC-MS (m/z): 377 (M+1)$^+$, $^1$H NMR (400 MHz, DMSO-d$_6$): δ 0.85 (d, 6H), 1.60 (m, 1H), 2.21 (s, 3H), 2.66 (m, 5H), 3.53 (s, 2H), 6.81 (s, 1H), 6.85 (d, 1H), 6.99 (s, 1H), 7.95 (d, 1H), 8.60 (br, 1H), 11.55 (br, 1H), 12.35 (br, 1H).

Example 445

2-(2-{3-[2-(Isobutyl-methyl-amino)-4-methyl-phenyl]-ureido}-thiazol-4-yl)-N-methyl-acetamide

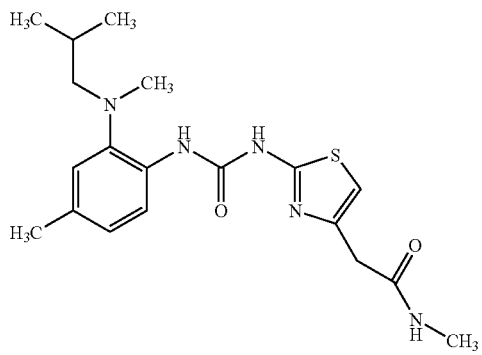

2-(2-{3-[2-(Isobutyl-methyl-amino)-4-methyl-phenyl]-ureido}-thiazol-4-yl)-N-methyl-acetamide (63 mg, 65%) was prepared from (2-{3-[2-(isobutyl-methyl-amino)-4-methyl-phenyl]-ureido}-thiazol-4-yl)-acetic acid (95 mg, 0.25 mmol) and methylamine following the general procedure K.

LC-MS (m/z): 390 (M+1)$^+$, $^1$H NMR (400 MHz, CDCl$_3$): δ 0.85 (d, 6H), 1.67 (m, 1H), 2.29 (s, 3H), 2.63 (s, 3H), 2.75 (s, 2H), 2.80 (s, 3H), 3.62 (s, 2H), 6.50 (br, 1H), 6.62 (s, 1H), 6.93 (m, 2H), 8.04 (d, 1H), 8.68 (br, 1H), 10.00 (br, 1H).

Example 446

2-(2-{3-[2-(Isobutyl-methyl-amino)-4-methyl-phenyl]-ureido}-thiazol-4-yl)-N-(2-methoxy-ethyl)-acetamide

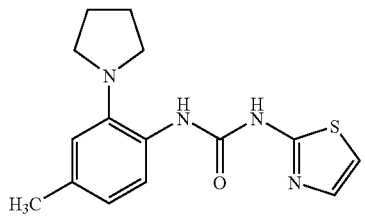

2-(2-{3-[2-(Isobutyl-methyl-amino)-4-methyl-phenyl]-ureido}-thiazol-4-yl)-N-(2-methoxy-ethyl)-acetamide (78 mg, 72%) was prepared from (2-{3-[2-(isobutyl-methyl-amino)-4-methyl-phenyl]-ureido}-thiazol-4-yl)-acetic acid (95 mg, 0.25 mmol) and 2-methoxymethylamine following the general procedure K.

LC-MS (m/z): 434 (M+1)$^+$.

Example 447

1-(4-Methyl-2-pyrrolidin-1-yl-phenyl)-3-thiazol-2-yl-urea

4-Methyl-2-(pyrrolidin-1-yl)aniline (0.57 g, 65%) was prepared from pyrrolidine (0.71 g, 10.0 mmol) and 3-fluoro-4-nitrotoluene (0.77 g, 5.0 mmol) following the general procedure W. 1-(4-Methyl-2-pyrrolidin-1-yl-phenyl)-3-thiazol-2-yl-urea (217 mg, 72%) was prepared from 4-methyl-2-(pyrrolidin-1-yl)aniline (176 mg, 1.0 mmol) and 2-aminothiazole (100 mg, 1.0 mmol) following the general procedure D.

LC-MS (m/z): 303 (M+1)+, 1H NMR (400 MHz, DMSO-d6): δ 1.89 (m, 4H), 2.23 (s, 3H), 3.02 (m, 4H), 6.75 (dd, 1H), 6.88 (d, 1H), 7.09 (d, 1H), 7.36 (dd, 1H), 7.70 (d, 1H), 8.40 (br, 1H), 11.07 (br, 1H).

Example 448

1-[2-(2,3-Dihydro-indol-1-yl)-5-fluoro-phenyl]-3-thiazol-2-yl-urea

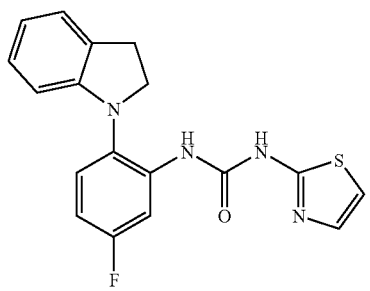

2-(2,3-Dihydro-indol-1-yl)-5-fluoro-aniline (0.59 g, 52%) was prepared from indoline (0.6 g, 5.0 mmol) and 2,5-difluoro-nitrobenzene (0.80 g, 5.0 mmol) following the general procedure W. 1-[2-(2,3-Dihydro-indol-1-yl)-5-fluoro-phenyl]-3-thiazol-2-yl-urea (198 mg, 56%) was prepared from 2-(2,3-dihydro-indol-1-yl)-5-fluoro-aniline (228 mg, 1.0 mmol) and 2-aminothiazole (100 mg, 1.0 mmol) following the general procedure D.

LC-MS (m/z): 355 (M+1)+, 1H NMR (400 MHz, DMSO-d6): δ 3.16 (t, 2H), 3.70 (br, 2H), 6.10 (d, 1H), 6.73 (m, 1H), 6.94 (m, 2H), 7.14 (d, 1H), 7.22 (d, 1H), 7.34 (m, 2H), 8.13 (dd, 1H), 9.01 (br, 1H), 11.32 (br, 1H).

Example 449

1-(4-Methyl-2-piperidin-1-yl-phenyl)-3-thiazol-2-yl-urea

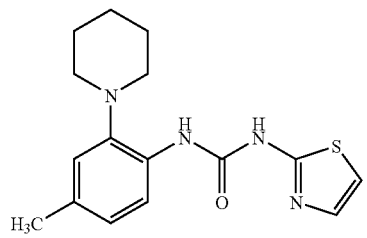

4-Methyl-2-(piperidin-1-yl)-aniline (0.63 g, 67%) was prepared from piperidine (0.85 g, 10.0 mmol) and 3-fluoro-4-nitrotoluene (0.77 g, 5.0 mmol) following the general procedure W. 1-(4-Methyl-2-piperidin-1-yl-phenyl)-3-thiazol-2-yl-urea (214 mg, 68%) was prepared from 4-methyl-2-(piperidin-1-yl)-aniline (190 mg, 1.0 mmol) and 2-aminothiazole (100 mg, 1.0 mmol) following the general procedure D.

LC-MS (m/z): 317 (M+1)+, 1H NMR (400 MHz, CDCl3): δ 1.49 (m, 2H), 1.69 (m, 4H), 2.30 (s, 3H), 2.82 (t, 4H), 6.92 (m, 3H), 7.47 (d, 1H), 7.96 (d, 1H), 8.90 (br, 1H), 11.36 (br, 1H).

Example 450

{2-[3-(4-Methyl-2-piperidin-1-yl-phenyl)-ureido]-thiazol-4-yl}-acetic acid

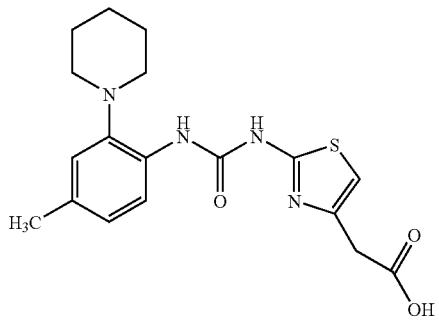

{2-[3-(4-Methyl-2-piperidin-1-yl-phenyl)-ureido]-thiazol-4-yl}-acetic acid ethyl ester (285 mg, 71%) was prepared from 4-methyl-2-(piperidin-1-yl)-aniline (190 mg, 1.0 mmol) and ethyl 2-amino-4-thiazolylacetate (186 mg, 1.0 mmol) following the general procedure D. Hydrolysis of this ester following general procedure J gave {2-[3-(4-methyl-2-piperidin-1-yl-phenyl)-ureido]-thiazol-4-yl}-acetic acid (238 mg, 90%).

LC-MS (m/z): 375 (M+1)+; 1H NMR (400 MHz, DMSO-d6): δ 1.53 (br, 2H), 1.75 (m, 4H), 2.23 (s, 3H), 2.70 (m, 4H), 3.55 (s, 2H), 6.83 (s, 1H), 6.87 (d, 1H), 6.99 (s, 1H), 7.92 (d, 1H), 8.40 (br, 1H), 11.28 (br, 1H), 12.42 (br, 1H).

Example 451

1-[2-(2-Fluoro-6-methoxy-phenoxy)-4-methyl-phenyl]-3-thiazol-2-yl-urea

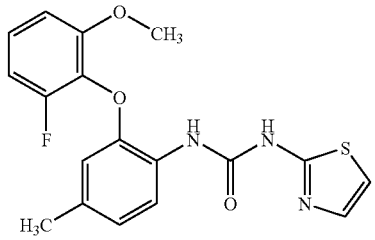

3-2-fluoro-6-methoxyphenoxy)-nitrotoluene (0.9 g, 65%) was prepared from 2-fluoro-6-methoxyphenol (0.78 g, 5.5 mmol) and 3-fluoro-4-nitrotoluene (0.77 g, 5.0 mmol) following the general procedure A. This compound was reduced to 4-fluoro-2-(2-fluoro-6-methoxyphenoxy)aniline (0.58 g, 72%) following the general procedure C. 1-[2-(2-Fluoro-6-methoxy-phenoxy)-4-methyl-phenyl]-3-thiazol-2-yl-urea (122 mg, 65%) was prepared from 2-(2-fluoro-6-methoxy-phenoxy)-4-methyl-aniline (124 mg, 0.5 mmol) and 2-aminothiazole (60 mg, 0.6 mmol) following the general procedure D.

LCMS (m/z): 374 (M+2)+; 1H NMR (400 MHz, DMSO-d6): δ 2.13 (s, 3H), 3.79 (s, 3H), 6.30 (s, 1H), 6.83 (d, 1H), 7.07 (m, 3H), 7.34 (m, 2H), 8.06 (d, 1H), 8.97 (br, 1H), 10.93 (s, 1H).

Example 452

1-[2-(2-Fluoro-6-methoxy-phenoxy)-4-(4-methyl-piperazin-1-ylmethyl)-phenyl]-3-thiazol-2-yl-urea

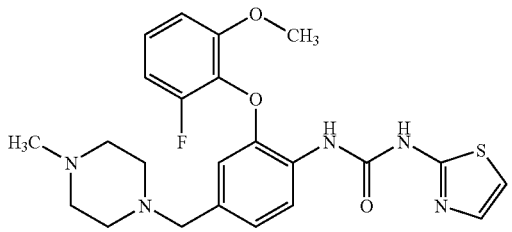

3-(2-fluoro-6-methoxyphenoxy)-nitrotoluene (0.28 g, 1.0 mmol) was heated with N-bromosuccinimide (200 mg, 1.1 mmol) and dibenzoyl peroxide (10 mg) in CCl4 (10 mL) at 90° C. for 3 hr. The reaction mixture was cooled, filtered and the filtrate was concentrated. To the residue was added N-methylpiperizine (110 mg, 1.1 mmol) in THF (5 mL) and the mixture was heated at 60° C. for 4 hr. The volatiles were removed under reduced pressure. The residue was dissolved in ethyl acetate and washed (brine), dried (Na2SO4) and concentrated. The resulting nitrobenzene was reduced to 2-(2-fluoro-6-methoxy-phenoxy)-4-(4-methyl-piperazin-1-ylmethyl)-aniline (224 mg, 65%) following the general procedure C. 1-[2-(2-Fluoro-6-methoxy-phenoxy)-4-(4-methyl-piperazin-1-ylmethyl)-phenyl]-3-thiazol-2-yl-urea (130 mg, 55%) was prepared from 2-(2-fluoro-6-methoxy-phenoxy)-4-(4-methyl-piperazin-1-ylmethyl)-aniline (172 mg, 0.5 mmol) and 2-aminothiazole (60 mg, 0.6 mmol) following the general procedure D.

LCMS (m/z): 472 (M+2)+; 1H NMR (400 MHz, DMSO-d6): δ 2.12 (s, 3H), 2.24 (br, 8H), 3.28 (s, 2H), 3.77 (s, 3H), 6.46 (s, 1H), 6.89 (d, 1H), 7.07 (m, 3H), 7.34 (m, 2H), 8.11 (d, 1H), 9.02 (br, 1H), 10.96 (s, 1H).

Example 453

(2-{3-[2-(2-Fluoro-6-methoxy-phenoxy)-4-methyl-phenyl]-ureido}-thiazol-4-yl)-acetic acid

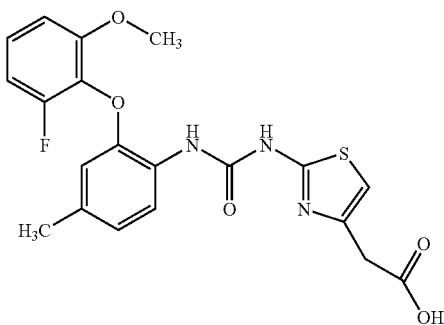

(2-{3-[2-(2-Fluoro-6-methoxy-phenoxy)-4-methyl-phenyl]-ureido}-thiazol-4-yl)-acetic acid ethyl ester (330 mg, 72%) was prepared from 2-(2-fluoro-6-methoxyphenoxy)-aniline (247 mg, 1.0 mmol) and ethyl 2-amino-4-thiazolylacetate (186 mg, 1.0 mmol) following the general procedure D. Hydrolysis of this ester following general procedure J gave (2-{3-[2-(2-fluoro-6-methoxy-phenoxy)-4-methyl-phenyl]-ureido}-thiazol-4-yl)acetic acid (283 mg, 91%).

LCMS (m/z): 432 (M+2)+; 1H NMR (400 MHz, DMSO-d6): δ 2.13 (s, 3H), 3.55 (s, 2H), 3.79 (s, 3H), 6.30 (s, 1H), 6.83 (d, 1H), 6.88 (s, 1H), 7.03 (m, 2H), 7.34 (m, 1H), 8.04 (d, 1H), 9.05 (br, 1H), 11.02 (br, 2H).

Example 454

1-[2-(2-Fluoro-6-methoxy-phenoxy)-5-formyl-phenyl]-3-thiazol-2-yl-urea

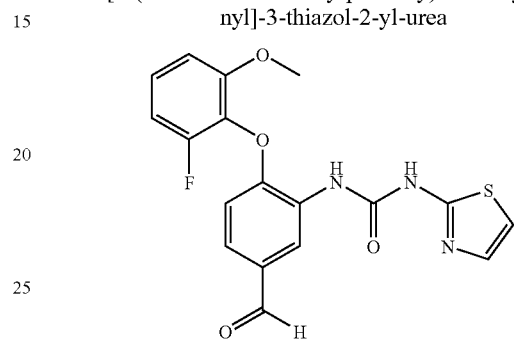

4-(2-Fluoro-6-methoxy-phenoxy)-3-nitrobenzaldehyde (1.0 g, 70%) was prepared from 2-fluoro-6-methoxyphenol (0.78 g, 5.5 mmol) and 4-fluoro-3-nitrobenzaldehyde (0.84 g, 5.0 mmol) following the general procedure A. This was reduced to 5-formyl-2-(2-fluoro-6-methoxy-phenoxy)-aniline (0.57 g, 62%) following general procedure B. 1-[2-(2-Fluoro-6-methoxy-phenoxy)-5-formyl-phenyl]-3-thiazol-2-yl-urea (265 mg, 69%) was prepared from 5-formyl-2-(2-fluoro-6-methoxy-phenoxy)-aniline (261 mg, 1.0 mmol) and 2-aminothiazole (100 mg, 1.0 mmol) following the general procedure D.

LC-MS (m/z): 388 (M+1)+, 1H NMR (400 MHz, DMSO-d6): δ 3.80 (s, 3H), 6.71 (d, 1H), 7.14 (m, 3H), 7.39 (m, 2H), 7.52 (dd, 1H), 8.78 (d, 1H), 9.31 (br, 1H), 9.90 (s, 1H), 11.04 (s, 1H).

Example 455

1-[2-(2-Fluoro-6-methoxy-phenoxy)-5-morpholin-4-ylmethyl-phenyl]-3-thiazol-2-yl-urea

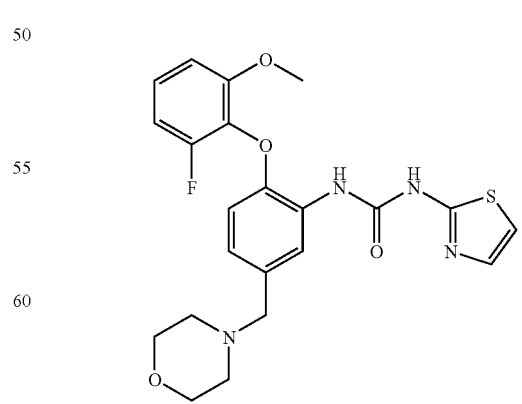

1-[2-(2-Fluoro-6-methoxy-phenoxy)-5-morpholin-4-ylmethyl-phenyl]-3-thiazol-2-yl-urea (35 mg, 78%) was prepared from 1-[2-2-fluoro-6-methoxy-phenoxy)-5-formyl-phenyl]-3-thiazol-2-yl-urea (39 mg, 0.1 mmol) and morpholine following the general procedure O.

LC-MS (m/z): 459 (M+1)+, $^1$H NMR (400 MHz, DMSO-d$_6$): δ 2.24 (s, 4H), 3.30 (s, 2H), 3.48 (s, 4H), 3.77 (s, 3H), 6.48 (s, 1H), 6.93 (d, 1H), 7.10 (m, 3H), 7.37 (m, 2H), 8.12 (d, 1H), 9.04 (br, 1H), 10.96 (br, 1H).

Example 456

1-[2-(2-Fluoro-6-methoxy-phenoxy)-5-methane-sulfonylmethyl-phenyl]-3-thiazol-2-yl-urea

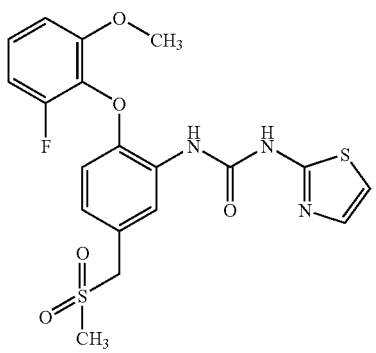

4-(2-Fluoro-6-methoxyphenoxy)-3-nitrotoluene (0.28 g, 1.0 mmol) was heated with N-bromosuccinimide (200 mg, 1.1 mmol) and dibenzoyl peroxide (10 mg) in CCl$_4$ (10 mL) at 90° C. for 3 hr. The reaction mixture was cooled, filtered and the filtrate was concentrated. To this residue was added sodium methanesulfinate (110 mg, 1.1 mmol) in THF (5 mL) and the mixture was heated at 60° C. for 4 hr. The volatiles were removed under reduced pressure. The residue was dissolved in ethyl acetate and was washed (brine), dried (Na$_2$SO$_4$) and concentrated. The resulting nitrobenzene was reduced to 2-(2-fluoro-6-methoxy-phenoxy)-5-methane-sulfonylmethyl-aniline (210 mg, 65%) following the general procedure B. 1-[2-(2-Fluoro-6-methoxy-phenoxy)-5-methanesulfonylmethyl-phenyl]-3-thiazol-2-yl-urea (138 mg, 61%) was prepared from 2-(2-fluoro-6-methoxy-phenoxy)-5-methanesulfonylmethyl-aniline (162 mg, 0.5 mmol) and 2-aminothiazole (60 mg, 0.6 mmol) following the general procedure D.

LCMS (m/z): 452 (M+1)+; $^1$H NMR (400 MHz, DMSO-d$_6$): δ 2.93 (s, 3H), 3.35 (s, 2H), 3.80 (s, 3H), 6.52 (d, 1H), 6.93 (d, 1H), 7.07 (m, 3H), 7.35 (m, 2H), 8.31 (s, 1H), 9.22 (br, 1H), 11.02 (s, 1H).

Example 457

{5-Chloro-2-[3-(2-cyclopentanecarbonyl-4-methyl-phenyl)-ureido]-thiazol-4-yl}-acetic acid ethyl ester

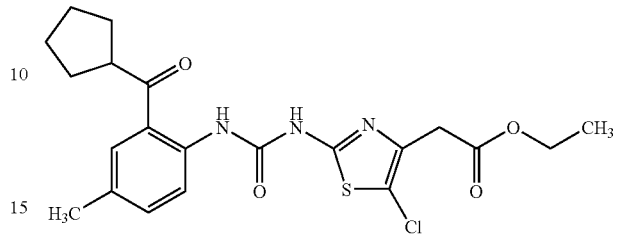

To a solution of {2-[3-(2-cyclopentanecarbonyl-4-methyl-phenyl)-ureido]-thiazol-4-yl}-acetic acid ethyl ester (0.05 g, 0.12 mmol) in 2 ml of acetonitrile was added N-chlorosuccinimide (0.018 g, 0.13 mmol). The reaction mixture was stirred under nitrogen in a pressure bottle excluded from light for 1.5 hour at 80° C. The mixture was diluted with 15 ml of DCM, washed (1N HCl, saturated NaHCO$_3$, water), dried (MgSO$_4$) and concentrated under reduced pressure. The crude product was purified by preparative HPLC to afford the title compound (0.08 g, 15%).

HPLC-MS (Method A): m/z=450, 452 (M+1)+; R$_t$=5.55 min.

$^1$H NMR (300 MHz, CDCl$_3$): δ 1.29 (t, J=7.2 Hz, 3H), 1.71 (m, 4H), 1.90 (m, 4H), 2.37 (s, 3H), 3.70 (s, 2H), 3.75 (m, 1H), 4.24 (q, J=7.2 Hz, 2H), 7.35 (d, J=7.9 Hz, 1H), 7.70 (s, 1H), 8.42 (d, J=8.3 Hz, 1H) and 11.59 (s, 1H)

Example 458

{5-Bromo-2-[3-(2-cyclopentanecarbonyl-4-methyl-phenyl)-ureido]-thiazol-4-yl}-acetic acid ethyl ester

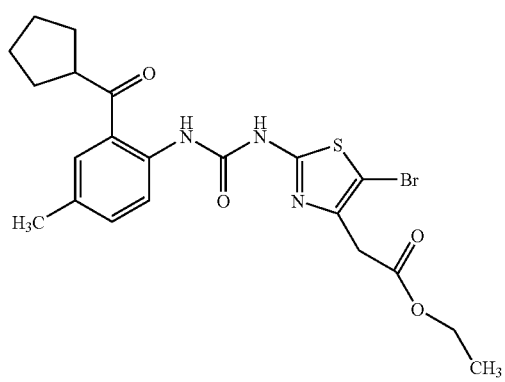

To a solution of {2-[3-(2-cyclopentanecarbonyl-4-methyl-phenyl)-ureido]-thiazol-4-yl}-acetic acid ethyl ester (0.05 g, 0.12 mmol) in 2 ml of acetonitrile was added N-bromosuccinimide (0.024 g, 0.13 mmol). The reaction mixture was stirred under nitrogen in a pressure bottle excluded from light overnight at 25° C. The mixture was diluted with 15 ml of DCM, washed (1N HCl, saturated NaHCO$_3$, water), dried (MgSO$_4$) and concentrated under reduced pressure. The crude product was purified by preparative HPLC to afford the title compound (0.013 g, 21%).

HPLC-MS (Method A): m/z=494, 496 (M+1)⁺; $R_t$=5.45 min.

¹H NMR (300 MHz, CDCl₃): δ 1.29 (t, J=7.2 Hz, 3H), 1.71 (m, 4H), 1.92 (m, 4H), 2.38 (s, 3H), 3.73 (s, 2H), 3.77 (m, 1H), 4.23 (q, J=7.2 Hz, 2H), 7.36 (dd, J=1.3, 8.5 Hz, 1H), 7.73 (s, 1H), 8.37 (d, J=8.3 Hz, 1H) and 11.81 (s, 1H).

Example 459

{5-Chloro-2-[3-(2-cyclopentanecarbonyl-4-methyl-phenyl)-ureido]-thiazol-4-yl}-acetic acid

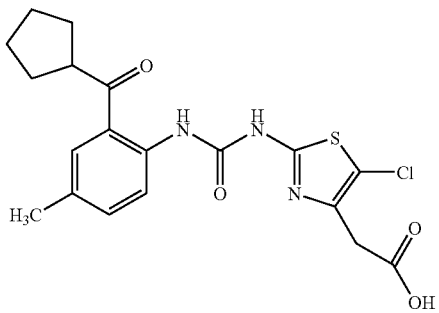

To a suspension of {2-[3-(2-cyclopentanecarbonyl-4-methyl-phenyl)-ureido]-thiazol-4-yl}-acetic acid (0.50 g, 1.29 mmol) in 20 ml of acetonitrile was added N-chlorosuccinimide (0.19 g, 1.42 mmol). The reaction mixture was stirred under nitrogen, in a pressure bottle excluded from light, for 2 h at 80° C. The mixture was concentrated under reduced pressure, dissolved in DMSO and purified by preparative HPLC to afford the title compound (0.128 g, 24%).

HPLC-MS (Method A): m/z=422, 424 (M+1)⁺; $R_t$=5.84 min.

¹H NMR (300 MHz, DMSO-d₆): δ 1.64 (m, 4H), 1.77 (m, 2H), 1.90 (m, 2H), 1.90 (m, 2H), 2.34 (s, 3H), 3.56 (s, 2H), 3.88 (m, 1H), 7.40 (dd, J=1.5, 8.7 Hz, 1H), 7.86 (d, J=1.1 Hz, 1H), 8.15 (d, J=8.3 Hz, 1H) and 10.69 (s, 1H)

Example 460

{5-Bromo-2-[3-(2-cyclopentanecarbonyl-4-methyl-phenyl)-ureido]-thiazol-4-yl}-acetic acid

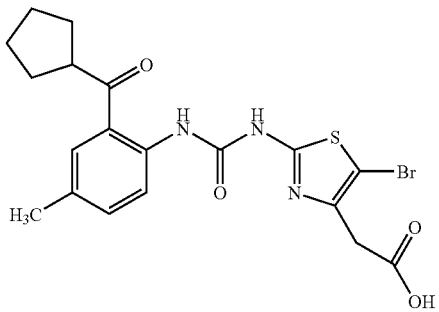

To a suspension of {2-[3-(2-cyclopentanecarbonyl-4-methyl-phenyl)-ureido]-thiazol-4-yl}-acetic acid ethyl ester (0.20 g, 0.52 mmol) in 10 ml of acetic acid was added N-bromosuccinimide (0.10 g, 0.57 mmol). The reaction mixture was stirred under nitrogen in a pressure bottle excluded from light overnight at 25° C. The mixture was concentrated under reduced pressure, dissolved in DMSO and purified by preparative HPLC to afford the title compound (0.137 g, 57%).

HPLC-MS (Method A): m/z=466, 468 (M+1)⁺; $R_t$=4.59 min.

¹H NMR (300 MHz, DMSO-d₆): δ 1.64 (M, 4H), 1.76 (m, 2H), 1.89 (m, 2H), 2.34 (s, 3H), 3.55 (s, 2H), 3.88 (m, 1H), 7.40 (d, J=8.3 Hz, 1H), 7.87 (s, 1H), 8.15 (d, J=8.7 Hz, 1H), 10.71 (s, 1H) and 12.15 (s, 1H)

Example 461

Bromo-{2-[3-(2-cyclopentanecarbonyl-4-methyl-phenyl)-ureido]-thiazol-4-yl}-acetic acid ethyl ester

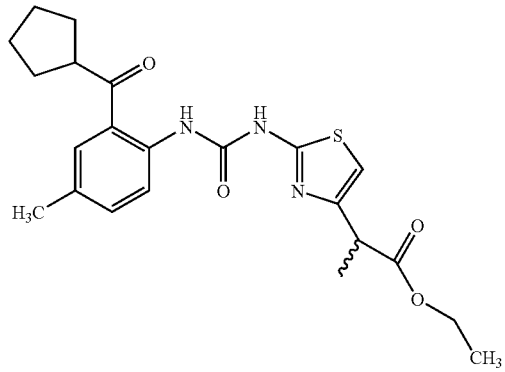

To a solution of {2-[3-(2-cyclopentanecarbonyl-4-methyl-phenyl)-ureido]-thiazol-4-yl}-acetic acid ethyl ester (0.05 g, 0.12 mmol) in 2 ml of acetonitrile was added N-bromosuccinimide (0.024 g, 0.13 mmol). The reaction mixture was stirred under nitrogen in a pressure bottle excluded from light overnight at 25° C. The mixture was diluted with 15 ml of DCM, washed (1N HCl, saturated NaHCO₃, water), dried (MgSO₄) and concentrated under reduced pressure. The crude product was purified by preparative HPLC to afford the title compound (0.010 g, 17%).

HPLC-MS (Method A): m/z=494, 496 (M+1)⁺; $R_t$=5.19 min.

¹H NMR (300 MHz, CDCl₃): δ 1.33 (t, J=7.2 Hz, 3H), 1.71 (m, 4H), 1.92 (m, 4H), 2.37 (s, 3H), 3.76 (m, 1H), 4.30 (dq, J=2.3, 7.2 Hz, 2H), 5.45 (s, 1H), 7.17 (s, 1H), 7.36 (d, J=8.7 Hz, 1H), 7.73 (s, 1H), 8.40 (d, J=8.7 Hz, 1H) and 11.83 (s, 1H)

Example 462

General Procedure D

{2-[3-(2-Cyclopentanecarbonyl-phenyl)-ureido]-thiazol-4-yl}-acetic acid ethyl ester

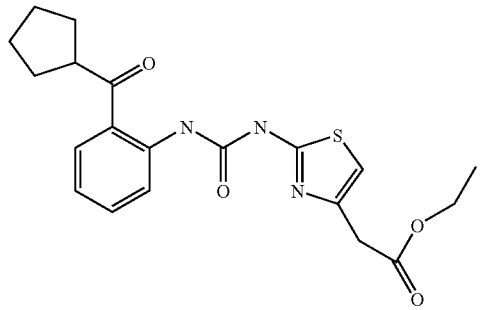

To a stirred solution of phenyl-carbamic acid tert-butyl ester (1.2 g, 6.2 mmol) in Et₂O (12 mL) under a nitrogen atmosphere was added dropwise a 1.7 M solution of t-BuLi in pentan (8.4 mL, 14.3 mmol) over a 10-min period at −20° C. The mixture was stirred at −10° C. for 2.5 h and then cyclopentanecarboxylic acid methoxy-methyl-amide (1.07 g, 6.8 mmol) was added over 5 min. The mixture was allowed to warm to room temperature and stirred for further 1 h before it was quenched with aqueous NH$_4$Cl. The organic phase was isolated and the aqueous phase was extracted with CH$_2$Cl$_2$, and the combined organic phases were dried and concentrated in vacuo. The crude material was dissolved CH$_2$Cl$_2$ (18 mL) and TFA (6 mL) and stirred at room temperature for 2 h. The reaction mixture was evaporated in vacuo, and added aqueous NaHCO3 to pH 7 and extracted with CH$_2$Cl$_2$. The combined organic phases were dried and concentrated in vacuo to give 1.03 g (68%) of (2-amino-phenyl)-cyclopentyl-methanone as an oil.

The title compound (41 mg, 16%) was prepared from 2-amino-phenyl-cyclopentyl-methanone (120 mg, 0.63 mmol) and ethyl-2-amino-4-thiazolyl acetate (118 mg, 0.63 mmol) following the general procedure D.

$^1$H NMR (400 MHz; CDCl$_3$): δ 1.28 (t, 3H), 1.66-1.77 (m, 4H), 1.84-1.96 (m, 4H), 3.70 (s, 2H), 3.74 (br t, 1H), 4.20 (q, 2H), 6.72 (s, 1H), 7.10 (t, 1H), 7.53 (t, 1H), 7.92 (d, 1H), 8.57 (br s, 1H), 11.78 (s, 1H); HPLC-MS: m/z=424.0 (M+23); R$_t$=4.45 min.

Example 463

General Procedure J

{2-[3-(2-Cyclopentanecarbonyl-phenyl)-ureido]-thiazol-4-yl}-acetic acid

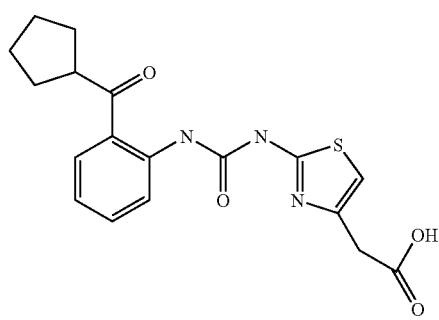

The title compound (9 mg, 27%) was prepared from {2-[3-(2-cyclopentanecarbonyl-phenyl)-ureido]-thiazol-4-yl}-acetic acid ethyl ester (208 mg, 0.5 mmol) following the general procedure J.

$^1$H NMR (400 MHz; Acetone d$_6$): δ 1.85-2.11 (m, 8H), 3.71 (s, 2H), 3.94 (br t, 1H), 6.86 (s, 1H), 7.18 (t, 1H), 7.79 (t, 1H), 8.09 (d, 1H), 8.56 (d, 1H), 11.36 (s, 1H); HPLC-MS: m/z=396.1 (M+23); R$_t$=3.87 min.

Example 464

General Procedure AA

{2-[3-(2-Cyclopentanecarbonyl-4-methoxy-phenyl)-ureido]-thiazol-4-yl}-acetic acid ethyl ester

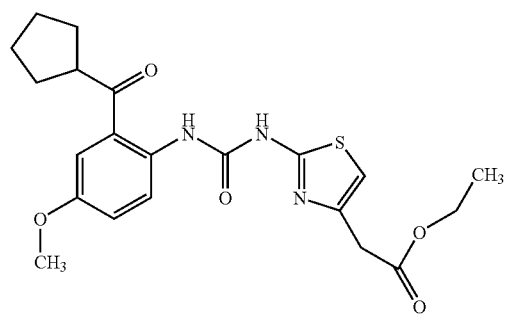

To a stirred solution of (4-methoxy-phenyl)-carbamic acid tert-butyl ester (2.0 g, 9.0 mmol) in Et$_2$O (20 mL) under a nitrogen atmosphere was added dropwise a 1.7 M solution of t-BuLi in pentan (12.1 mL, 20.6 mmol) over a 10-min period at −20° C. The mixture was stirred at −15° C. for 1.5 h and then cyclopentanecarboxylic acid methoxy-methyl-amide (1.55 g, 9.9 mmol) was added over 5 min. The mixture was allowed to warm to room temperature and stirred for further 1 h before it was quenched with aqueous NH$_4$Cl. The organic phase was isolated and the aqueous phase was extracted with CH$_2$Cl$_2$, and the combined organic phases were dried and concentrated in vacuo. The crude material was dissolved CH$_2$Cl$_2$ (18 mL) and TFA (6 mL) and stirred at room temperature for 2 h. The reaction mixture was evaporated in vacuo, and added aqueous NaHCO3 to pH 7 and extracted with CH$_2$Cl$_2$, dried and concentrated to give a crude product which was purified by flash chromatography (Quad flash 25, EtOAc-heptane 1:20->1:4). This gave 0.65 g (31%) of (2-amino-5-methoxy-phenyl)-cyclopentyl-methanone as an oil.

The title compound (158 mg, 80%) was prepared from (2-amino-5-methoxy-phenyl)-cyclopentyl-methanone (100 mg, 0.46 mmol) and ethyl-2-amino-4-thiazolyl acetate (85 mg, 0.46 mmol) following the general procedure AA.

$^1$H NMR (400 MHz; CDCl$_3$): δ 1.28 (t, 3H), 1.66-1.74 (m, 4H), 1.86-1.96 (m, 4H), 3.68 (br t, 1H), 3.70 (s, 2H), 3.84 (s, 3H), 4.20 (q, 2H), 6.71 (s, 1H), 7.10 (dd, 1H), 7.42 (d, 1H), 8.45 (br s, 1H), 9.13 (br s, 1H), 11.31 (br s, 1H); HPLC-MS: m/z=454.1 (M+23); R$_t$=5.48 min.

Example 465

General Procedure J

{2-[3-(2-Cyclopentanecarbonyl-4-methoxy-phenyl)-ureido]-thiazol-4-yl}-acetic acid

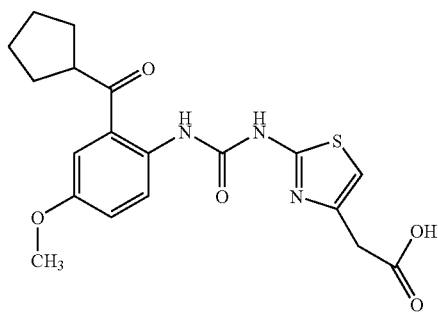

The title compound (92 mg, 86%) was prepared from {2-[3-(2-cyclopentanecarbonyl-4-methoxy-phenyl)-ureido]-thiazol-4-yl}-acetic acid ethyl ester (112 mg, 0.26 mmol) following the general procedure J.

$^1$H NMR (400 MHz; DMSO d$_6$): δ 1.58-1.65 (m, 4H), 1.70-1.92 (m, 4H), 3.57 (s, 2H), 3.82 (s, 3H), 3.88 (br p, 1H), 6.84 (s, 1H), 7.19 (dd, 1H), 7.44 (s, 1H), 8.08 (d, 1H), 10.22 (s, 1H), 12.05 (br s, 2H); HPLC-MS: m/z=426.1 (M+23); R$_t$=4.49 min.

Example 466

General Procedure AA

{2-[3-(2-Cyclopropanecarbonyl-4-methyl-phenyl)-ureido]-thiazol-4-yl}-acetic acid ethyl ester

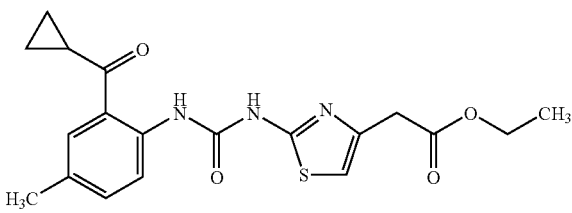

To a stirred solution of p-tolyl-carbamic acid tert-butyl ester (1.0 g, 4.8 mmol) in Et$_2$O (10 mL) under a nitrogen atmosphere was added dropwise a 1.7 M solution of t-BuLi in pentan (6.5 mL, 11.1 mmol) over a 10-min period at −20° C. The mixture was stirred at −10° C. for 2.5 h and then cyclopropanecarboxylic acid methoxy-methyl-amide (0.92 g, 6.3 mmol) was added over 5 min. The mixture was allowed to warm to room temperature and stirred for further 1 h before it was quenched with aqueous NH$_4$Cl. The organic phase was isolated and the aqueous phase was extracted with CH$_2$Cl$_2$, and the combined organic phases were dried and concentrated in vacuo. The crude material was dissolved CH$_2$Cl$_2$ (15 mL) and TFA (15 mL) and stirred at room temperature for 3 h. The reaction mixture was evaporated in vacuo, and added aqueous NaHCO3 to pH 7 and extracted with CH$_2$Cl$_2$. The combined organic phases were dried and concentrated in vacuo to give 0.80 g crude (2-amino-5-methyl-phenyl)-cyclopropyl-methanone as a yellow oil.

The title compound (190 mg, 43%) was prepared from crude (2-amino-5-methyl-phenyl)-cyclopropyl-methanone (200 mg, 1.14 mmol) and ethyl-2-amino-4-thiazolyl acetate (212 mg, 1.14 mmol) following the general procedure AA.

$^1$H NMR (400 MHz; CDCl$_3$): δ 1.04-1.10 (m, 2H), 1.24-1.30 (m, 5H), 2.39 (s, 3H), 2.62-2.72 (m, 1H), 3.73 (s, 2H), 4.20 (q, 2H), 6.78 (s, 1H), 7.37 (dd, 1H), 7.89 (d, 1H), 8.37 (d, 1H), 9.42 (br s, 2H), 11.50 (s, 1H); HPLC-MS: m/z=410.0 (M+23); R$_t$=4.11 min.

Example 467

General Procedure J

{2-[3-(2-Cyclopropanecarbonyl-4-methyl-phenyl)-ureido]-thiazol-4-yl}-acetic acid

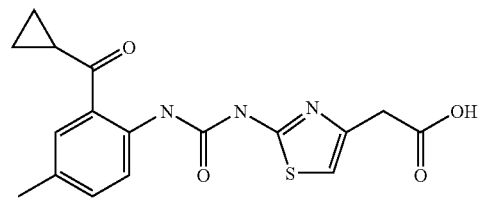

The title compound (111 mg, 99%) was prepared from {2-[3-(2-cyclopentanecarbonyl-phenyl)-ureido]-thiazol-4-yl}-acetic acid ethyl ester (120 mg, 0.31 mmol) following the general procedure J.

$^1$H NMR (400 MHz; DMSO d$_6$): δ 1.04 (br s, 4H), 2.38 (s, 3H), 2.76 (br s, 1H), 3.58 (s, 2H), 6.86 (s, 1H), 6.92 (d, 1H), 8.02 (s, 1H), 8.14 (d, 1H), 10.46 (s, 1H), 12.05 (br s, 2H); HPLC-MS: m/z=382.0 (M+23); R$_t$=3.38 min.

Example 468

General Procedure AA

{2-[3-(2-Cyclobutanecarbonyl-4-methyl-phenyl)-ureido]-thiazol-4-yl}-acetic acid ethyl ester

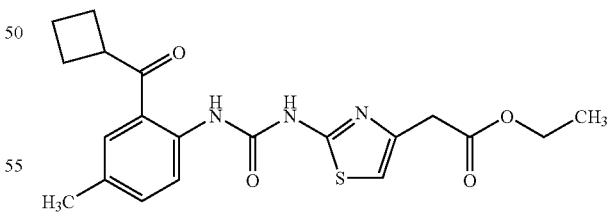

Crude (2-amino-5-methyl-phenyl)-cyclobutyl-methanone (80%, oil) was prepared in a similar fashion as described for (2-amino-5-methyl-phenyl)-cyclopropyl-methanone using cyclobutanecarboxylic acid methoxy-methyl-amide instead of cyclopropanecarboxylic acid methoxy-methyl-amide.

The title compound (210 mg, 49%) was prepared from crude (2-amino-5-methyl-phenyl)-cyclobutyl-methanone (200 mg, 1.06 mmol) and ethyl-2-amino-4-thiazolyl acetate (197 mg, 1.06 mmol) following the general procedure AA.

$^1$H NMR (400 MHz; CDCl$_3$): δ 1.30 (t, 3H), 1.83-2.50 (m, 6H), 2.36 (s, 3H), 3.76 (s, 2H), 4.05 (p, 1H), 4.22 (q, 2H), 6.80 (s, 1H), 7.35 (d, 1H), 7.52 (s, 1H), 8.41 (br d, 1H), 11.9 (br s, 1H); HPLC-MS: m/z=424.1 (M+23); R$_t$=4.48 min.

Example 469

General Procedure J

{2-[3-(2-Cyclobutanecarbonyl-4-methyl-phenyl)-ureido]-thiazol-4-yl}-acetic acid

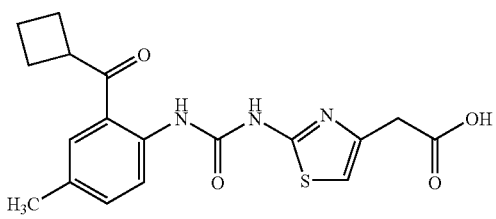

The title compound (112 mg, 73%) was prepared from {2-[3-(2-cyclobutanecarbonyl-4-methyl-phenyl)-ureido]-thiazol-4-yl}-acetic acid ethyl ester (165 mg, 0.41 mmol) following the general procedure J.

$^1$H NMR (400 MHz; DMSO d$_6$): δ 1.70-2.30 (m, 6H), 2.32 (s, 3H), 3.56 (s, 2H), 4.19 (br t, 1H), 6.86 (s, 1H), 7.39 (d, 1H), 7.63 (s, 1H), 8.22 (d, 1H), 10.81 (s, 1H), 12.15 (br s, 2H); HPLC-MS: m/z=396.1 (M+23); R$_t$=3.75 min.

Example 470

General Procedure AA

{2-[3-(2-Cyclohexanecarbonyl-4-methyl-phenyl)-ureido]-thiazol-4-yl}-acetic acid ethyl ester

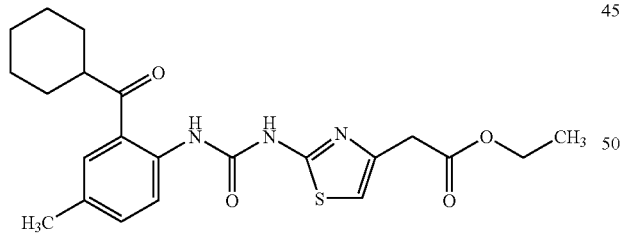

Crude (2-amino-5-methyl-phenyl)-cyclohexyl-methanone (75%, oil) was prepared in a similar fashion as described for (2-amino-5-methyl-phenyl)-cyclopropyl-methanone using cyclohexanecarboxylic acid methoxy-methyl-amide instead of cyclopropanecarboxylic acid methoxy-methyl-amide.

The title compound (188 mg, 48%) was prepared from crude (2-amino-5-methyl-phenyl)-cyclohexyl-methanone (200 mg, 0.92 mmol) and ethyl-2-amino-4-thiazolyl acetate (171 mg, 1.06 mmol) following the general procedure AA.

$^1$H NMR (400 MHz; CDCl$_3$): δ 1.30 (t, 3H), 1.37-1.59 (m, 5H), 1.71-1.91 (m, 5H), 2.37 (s, 3H), 3.30 (br s, 1H), 3.73 (s, 2H), 4.22 (q, 2H), 6.78 (s, 1H), 7.34 (d, 1H), 7.68 (s, 1H), 8.39 (br d, 1H), 11.78 (br s, 1H); HPLC-MS: m/z=452.2 (M+23); R$_t$=4.92 min.

Example 471

General Procedure J

{2-[3-(2-Cyclohexanecarbonyl-4-methyl-phenyl)-ureido]-thiazol-4-yl}-acetic acid

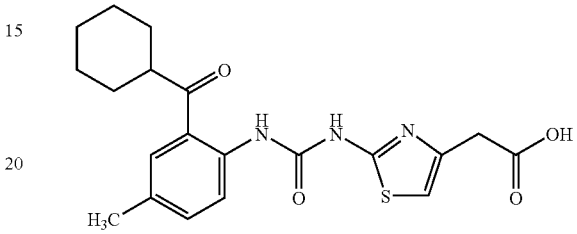

The title compound (100 mg, 89%) was prepared from {2-[3-(2-cyclohexanecarbonyl-4-methyl-phenyl)-ureido]-thiazol-4-yl}-acetic acid ethyl ester (112 mg, 0.28 mmol) following the general procedure J.

$^1$H NMR (400 MHz; DMSO d$_6$): δ 1.13-1.45 (m, 5H), 1.62-1.83 (m, 5H), 2.34 (s, 3H), 3.42 (br s, 1H), 3.57 (s, 2H); 6.83 (s, 1H), 7.39 (d, 1H), 7.81 (s, 1H), 8.15 (d, 1H), 10.50 (s, 1H), 12.07 (br s, 2H); HPLC-MS: m/z=402.0 (M+1); R$_t$=4.18 min.

Example 472

{2-[(2-Cyclopentanecarbonyl-4-methyl-phenylaminooxalyl)-amino]-thiazol-4-yl}-acetic acid ethyl ester

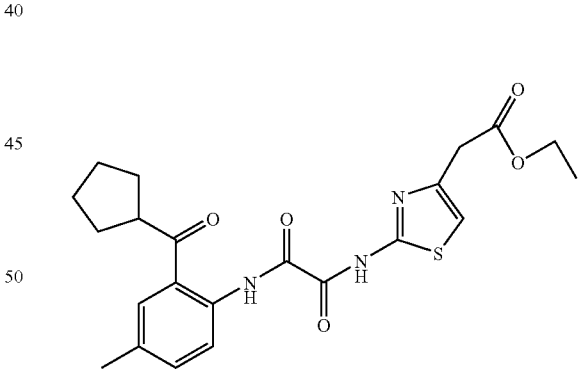

To a solution of ethyl-2-aminothiazole-4-acetate (2 g) in dichloromethane (80 mL) at ice bath temperature was added ethyl oxalyl chloride (1.2 mL) and the reaction stirred 1 h. The reaction mixture was washed with water, and the organic phase concentrated to give N-(4-ethoxycarbonylmethyl-thiazol-2-yl)-oxalamic acid ethyl ester (1.2 g).

To N-(4-ethoxycarbonylmethyl-thiazol-2-yl)-oxalamic acid ethyl ester (1 g) was added THF (5 mL) and 2 N lithium hydroxide (4 mL). A white precipitated formed and after 1 h the reaction mixture was acidified to pH5 and the white precipitate recovered by filtration, and triturated with a 1:1 mixture of ether and ethyl acetate to remove unreacted starting material. The solid residue was dried in a vacuum oven to give N-(4-ethoxycarbonylmethyl-thiazol-2-yl)-oxalamic acid (300 mg).

N-(4-ethoxycarbonylmethyl-thiazol-2-yl)-oxalamic acid (80 mg) was dissolved in DMF (5 mL) and (2-amino-5-methyl-phenyl)-cyclopentyl-methanone was added followed by PyBOP. The reaction was stirred for 24 h and water was added. The aqueous phase was extracted with ether/ethyl acetate and the organic phase dried, concentrated and purified by flash chromatography to give the title compound (15 mg).

$^1$H NMR (CDCl$_3$): 1.25 (3H, t), 1.6-2.1 (8H, m), 2.45 (3H, s), 3.65-3.75 (1H, m), 3.7 (1H, s), 4.2 (4H, q), 6.9 (1H), 7.4 (1H, dd), 7.8 (1H, s), 8.65 (1H, d), 10.5 (1H, bs), 13.3 (1H, s).

Example 473

{2-[(2-Cyclopentanecarbonyl-4-methyl-phenylaminooxalyl)-amino]-thiazol-4-yl}-acetic acid

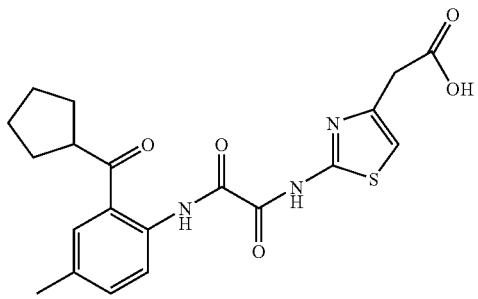

To {2-[(2-cyclopentanecarbonyl-4-methyl-phenylaminooxalyl)-amino]-thiazol-4-yl}-acetic acid ethyl ester (15 mg) in methanol (2 mL) was added 1N sodium hydroxide (1N) and the mixture was stirred 3 h at room temperature. The mixture was acidified with 1N HCl, concentrated under reduced pressure and purified by HPLC to give the title compound (4 mg).

LCMS (m/z): 416 (M+1)

$^1$H NMR (CDCl$_3$+MeOD): 1.6-2.1 (8H, m), 2.45 (3H, s), 3.7 (1H, s), 3.70-3.85 (1H, m), 6.9 (1H), 7.4 (1H, dd), 7.8 (1H, s), 8.65 (1H, d), 13.3 (1H, s).

Example 474

[2-[3-(2-Cyclopentanecarbonyl-4-methyl-phenyl)-ureido]-5-(pyridin-2-ylsulfanyl)-thiazol-4-yl]-acetic acid ethyl ester

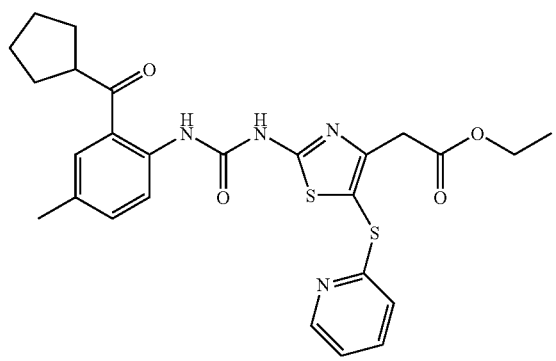

To a solution of {5-chloro-2-[3-(2-cyclopentanecarbonyl-4-methyl-phenyl)-ureido]-thiazol-4-yl}-acetic acid ethyl ester (0.1 g, 0.22 mmol) in DMF (4 mL) was added sodium hydrogen carbonate (0.075 g, 0.89 mmol) and 2-puridylthiole (0,027 g, 0.24 mmol). The reaction mixture was stirred under nitrogen in a pressure bottle excluded from light for 2.0 hour at 80° C. The crude product was purified by flash chromatography (isopropanole/heptane 1:4) and recrystallized (dichloromethane/heptane) to afford the title compound (0.02 g).

$^1$H NMR (300 MHz, CDCl$_3$): δ 1.20 (t, 3H), 1.60-1.82 (m, 4H), 1.82-2.02 (m, 4H), 2.38 (s, 3H), 3.68-3.80 (m, 1H), 3.85 (s, 2H), 4.12 (q, 2H), 7.00 (t, 2H), 7.35 (d, 1H), 7.50 (t, 1H), 7.73 (s, 1H), 8.40 (m, 2H), 11.80 (s, 1H).

Example 475

General Procedure (AA)

{2-[3-(2-Cyclopentanecarbonyl-4-trifluoromethyl-phenyl)-ureido]-thiazol-4-yl}-acetic acid ethyl ester

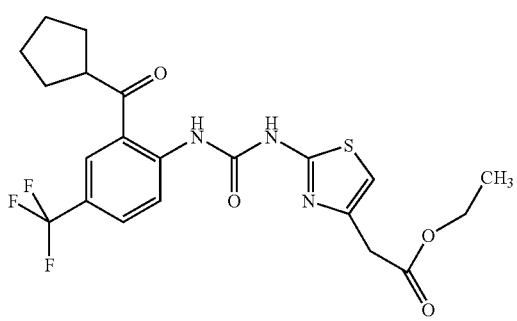

To a stirred solution of (4-trifluoromethyl-phenyl)-carbamic acid tert-butyl ester (15 mmol) in Et$_2$O (40 mL) under a nitrogen atmosphere was added dropwise a 1.7 M solution of t-BuLi in pentan (38 mmol) over a 10-min period at −20° C. The mixture was stirred at −15° C. for 1.5 h and then cyclopentanecarboxylic acid methoxy-methyl-amide (20 mmol) was added over 5 min. The mixture was allowed to warm to room temperature and stirred for further 1 h before it was quenched with aqueous NH$_4$Cl. The organic phase was isolated and the aqueous phase was extracted with CH$_2$Cl$_2$, and the combined organic phases were dried and concentrated in vacuo. The crude material was dissolved in CH$_2$Cl$_2$ (25 mL) and TFA (25 mL) and stirred at room temperature for 2 h. The reaction mixture was evaporated in vacuo, and added aqueous NaHCO3 to pH 7 and extracted with CH$_2$Cl$_2$, dried and concentrated to give a crude product which was purified by flash chromatography (Quad flash 40, EtOAc-Heptane 0:1->1:3). This gave 70% of (2-amino-5-trifluoromethyl-phenyl)-cyclopentyl-methanone as an oil.

The title compound (15%) was prepared from (2-amino-5-trifluoromethyl-phenyl)-cyclopentyl-methanone and ethyl-2-amino-4-thiazolyl acetate following the general procedure AA.

$^1$H NMR (400 MHz; CDCl$_3$): δ 1.28 (t, 3H), 1.64-1.99 (m, 8H), 3.70 (br t, 1H), 3.74 (s, 2H), 4.20 (q, 2H), 6.74 (s, 1H), 7.73 (d, 1H), 8.13 (s, 1H), 8.74 (br s, 1H), 9.53 (br s, 1H), 11.82 (br s, 1H); HPLC-MS: m/z=492.1 (M+23); R$_t$=5.02 min.

Example 476

General Procedure J

{2-[3-(2-Cyclopentanecarbonyl-4-trifluoromethyl-phenyl)-ureido]-thiazol-4-yl}-acetic acid

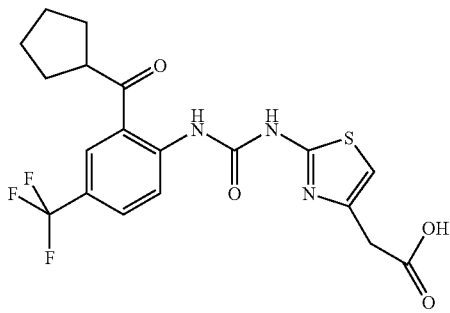

The title compound (13 mg, 33%) was prepared from {2-[3-(2-cyclopentanecarbonyl-4-trifluoromethyl-phenyl)-ureido]-thiazol-4-yl}-acetic acid ethyl ester (42 mg, 0.09 mmol) following the general procedure J.

$^1$H NMR (400 MHz; DMSO d$_6$): δ 1.65-1.95 (m, 8H), 3.60 (s, 2H), 3.99 (br s, 1H), 6.94 (s, 1H), 7.90 (d, 1H), 8.25 (br s, 1H), 8.54 (br s, 1H), 10.94 (br s, 1H), 12.25 (br s, 2H); HPLC-MS: m/z=426.1 (M+23); R$_t$=4.49 min.

Example 477

General Procedure (AA)

{2-[3-(4-Chloro-2-cyclopentanecarbonyl-phenyl)-ureido]-thiazol-4-yl}-acetic acid ethyl ester

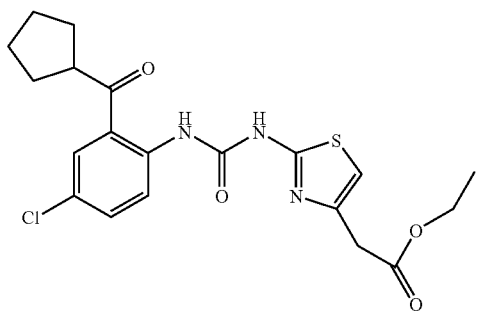

To a stirred solution of (4-chloro-phenyl)-carbamic acid tert-butyl ester (35 mmol) in Et$_2$O (80 mL) under a nitrogen atmosphere was added dropwise a 1.7 M solution of t-BuLi in pentan (88 mmol) over a 10-min period at −20° C. The mixture was stirred at 0° C. for 1.5 h and then cyclopentanecarboxylic acid methoxy-methyl-amide (45 mmol) was added over 5 min. The mixture was allowed to warm to room temperature and stirred for further 1 h before it was quenched with aqueous NH$_4$Cl. The organic phase was isolated and the aqueous phase was extracted with CH$_2$Cl$_2$, and the combined organic phases were dried and concentrated in vacuo. The crude material was dissolved in CH$_2$Cl$_2$ (50 mL) and TFA (50 mL) and stirred at room temperature for 1 h. The reaction mixture was evaporated in vacuo, and added aqueous NaHCO3 to pH 7 and extracted with CH$_2$Cl$_2$, dried and concentrated to give a crude product which was purified by flash chromatography (Quad flash 65, EtOAc-Heptane 0:1->1:3). This gave 75% of (2-amino-5-chloro-phenyl)-cyclopentyl-methanone as an oil.

The title compound (30%) was prepared from (2-amino-5-chloro-phenyl)-cyclopentyl-methanone and ethyl-2-amino-4-thiazolyl acetate following the general procedure AA.

$^1$H NMR (400 MHz; CDCl$_3$): δ 1.28 (t, 3H), 1.62-1.99 (m, 8H), 3.3.67 (br t, 1H), 3.73 (s, 2H), 4.20 (q, 2H), 6.72 (s, 1H), 7.46 (dd, 1H), 7.84 (d, 1H), 8.56 (br s, 1H), 9.50 (br s, 1H), 11.58 (br s, 1H); HPLC-MS: m/z=458.0 (M+23); R$_t$=4.86 min.

Example 478

General Procedure J

{2-[3-(4-Chloro-2-cyclopentanecarbonyl-phenyl)-ureido]-thiazol-4-yl}-acetic acid

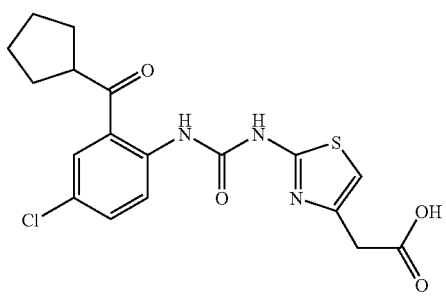

The title compound (39 mg, 85%) was prepared from {2-[3-(4-chloro-2-cyclopentanecarbonyl-phenyl)-ureido]-thiazol-4-yl}-acetic acid ethyl ester (49 mg, 0.11 mmol) following the general procedure J.

$^1$H NMR (400 MHz; DMSO d$_6$): δ 1.67-1.92 (m, 8H), 3.59 (s, 2H), 3.89 (br s, 1H), 6.88 (s, 1H), 7.63 (d, 1H), 8.04 (br s, 1H), 8.32 (br s, 1H), 10.64 (s, 1H), 12.20 (br s, 2H); HPLC-MS: m/z=430.0 (M+23); R$_t$=4.11 min.

Example 479

General Procedure (AA)

{2-[3-(2-Cyclopentanecarbonyl-4-fluoro-phenyl)-ureido]-thiazol-4-yl}-acetic acid ethyl ester

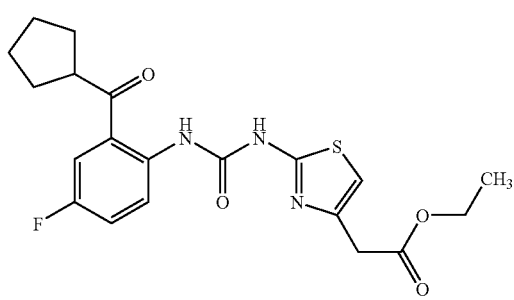

To a stirred solution of (4-fluoro-phenyl)-carbamic acid tert-butyl ester (9.5 mmol) in Et$_2$O (20 mL) under a nitrogen atmosphere was added dropwise a 1.7 M solution of t-BuLi in pentan (22 mmol) over a 10-min period at −30° C. The mixture was stirred at −20° C. for 1.5 h and then cyclopentanecarboxylic acid methoxy-methyl-amide (10.5 mmol) was added over 5 min. The mixture was allowed to warm to room temperature and stirred for further 1 h before it was quenched with aqueous NH$_4$Cl. The organic phase was isolated and the aqueous phase was extracted with CH$_2$Cl$_2$, and the combined organic phases were dried and concentrated in vacuo. The crude material was dissolved in CH$_2$Cl$_2$ (25 mL) and TFA (25 mL) and stirred at room temperature for 2 h. The reaction mixture was evaporated in vacuo, and added aqueous NaHCO3 to pH 7 and extracted with CH$_2$Cl$_2$, dried and concentrated to give a crude product which was purified by flash chromatography (Quad flash 40, EtOAc-Heptane 0:1->1:3). This gave 60% of (2-amino-5-fluoro-phenyl)-cyclopentyl-methanone as an oil.

The title compound (26%) was prepared from (2-amino-5-fluoro-phenyl)-cyclopentyl-methanone and ethyl-2-amino-4-thiazolyl acetate following the general procedure M.

$^1$H NMR (400 MHz; CDCl$_3$): δ 1.28 (t, 3H), 1.63-1.97 (m, 8H), 3.64 (br t, 1H), 3.73 (s, 2H), 4.20 (q, 2H), 6.72 (s, 1H), 7.22-7.29 (m, 1H), 7.58 (dd, 1H), 8.55 (br s, 1H), 9.40 (br s, 1H), 11.45 (br s, 1H); HPLC-MS: m/z=442.0 (M+23); R$_t$=4.49 min.

Example 480

General Procedure J

{2-[3-(2-Cyclopentanecarbonyl-4-fluoro-phenyl)-ureido]-thiazol-4-yl}-acetic acid

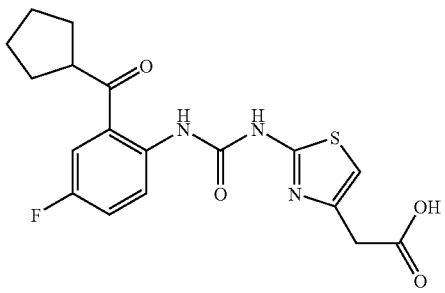

The title compound (75 mg, 87%) was prepared from {2-[3-(2-cyclopentanecarbonyl-4-fluoro-phenyl)-ureido]-thiazol-4-yl}-acetic acid ethyl ester (92 mg, 0.22 mmol) following the general procedure J.

$^1$H NMR (400 MHz; DMSO d$_6$): δ 1.65-1.94 (m, 8H), 3.57 (s, 2H), 3.84 (br s, 1H), 6.88 (s, 1H), 7.45 (t, 1H), 7.85 (br s, 1H), 8.25 (br s, 1H), 10.48 (s, 1H), 12.10 (br s, 2H); HPLC-MS: m/z=414.1 (M+23); R$_t$=3.74 min.

Using the methods disclosed herein the following compounds may also be made:
1-(5-Chloro-thiazol-2-yl)-3-(2-cyclopentanecarbonyl-4-methyl-phenyl)-urea
1-(5-Chloro-thiazol-2-yl)-3-(2-cyclopentanecarbonyl-phenyl)-urea
1-(4-Chloro-2-cyclopentanecarbonyl-phenyl)-3-(5-chloro-thiazol-2-yl)-urea
1-(5-Chloro-thiazol-2-yl)-3-(2-cyclopentanecarbonyl-4-fluoro-phenyl)-urea
1-(5-Chloro-thiazol-2-yl)-3-(2-cyclopentanecarbonyl-4-trifluoromethyl-phenyl)-urea
1-(5-Chloro-thiazol-2-yl)-3-(2-cyclopentanecarbonyl-4-methoxy-phenyl)-urea
1-(5-Chloro-thiazol-2-yl)-3-(2-cyclopentanecarbonyl-4-dimethylamino-phenyl)-urea
1-(5-Chloro-thiazol-2-yl)-3-(2-cyclopentanecarbonyl-4-morpholin-4-yl-phenyl)-urea
1-(5-Chloro-thiazol-2-yl)-3-(3-cyclopentanecarbonyl-pyridin-4-yl)-urea
1-(5-Chloro-thiazol-2-yl)-3-(4-cyclopentanecarbonyl-pyridin-3-yl)-urea
1-(5-Chloro-thiazol-2-yl)-3-(3-cyclopentanecarbonyl-pyridin-2-yl)-urea
1-(5-Bromo-thiazol-2-yl)-3-(2-cyclopentanecarbonyl-4-methyl-phenyl)-urea
1-(5-Bromo-thiazol-2-yl)-3-(2-cyclopentanecarbonyl-phenyl)-urea
1-(5-Bromo-thiazol-2-yl)-3-(4-chloro-2-cyclopentanecarbonyl-phenyl)-urea
1-(5-Bromo-thiazol-2-yl)-3-(2-cyclopentanecarbonyl-4-fluoro-phenyl)-urea
1-(5-Bromo-thiazol-2-yl)-3-(2-cyclopentanecarbonyl-4-trifluoromethyl-phenyl)-urea
1-(5-Bromo-thiazol-2-yl)-3-(2-cyclopentanecarbonyl-4-methoxy-phenyl)-urea
1-(5-Bromo-thiazol-2-yl)-3-(2-cyclopentanecarbonyl-4-dimethylamino-phenyl)-urea
1-(5-Bromo-thiazol-2-yl)-3-(2-cyclopentanecarbonyl-4-morpholin-4-yl-phenyl)-urea
1-(5-Bromo-thiazol-2-yl)-3-(3-cyclopentanecarbonyl-pyridin-4-yl)-urea
1-(5-Bromo-thiazol-2-yl)-3-(4-cyclopentanecarbonyl-pyridin-3-yl)-urea
1-(5-Bromo-thiazol-2-yl)-3-(3-cyclopentanecarbonyl-pyridin-2-yl)-urea
1-(2-Cyclopentanecarbonyl-4-methyl-phenyl)-3-(5-methylsulfanyl-thiazol-2-yl)-urea
1-(2-Cyclopentanecarbonyl-phenyl)-3-(5-methylsulfanyl-thiazol-2-yl)-urea
1-(4-Chloro-2-cyclopentanecarbonyl-phenyl)-3-(5-methylsulfanyl-thiazol-2-yl)-urea
1-(2-Cyclopentanecarbonyl-4-fluoro-phenyl)-3-(5-methylsulfanyl-thiazol-2-yl)-urea
1-(2-Cyclopentanecarbonyl-4-trifluoromethyl-phenyl)-3-(5-methylsulfanyl-thiazol-2-yl)-urea
1-(2-Cyclopentanecarbonyl-4-methoxy-phenyl)-3-(5-methylsulfanyl-thiazol-2-yl)-urea
1-(2-Cyclopentanecarbonyl-4-dimethylamino-phenyl)-3-(5-methylsulfanyl-thiazol-2-yl)-urea
1-(2-Cyclopentanecarbonyl-4-morpholin-4-yl-phenyl)-3-(5-methylsulfanyl-thiazol-2-yl)-urea
1-(3-Cyclopentanecarbonyl-pyridin-4-yl)-3-(5-methylsulfanyl-thiazol-2-yl)-urea
1-(4-Cyclopentanecarbonyl-pyridin-3-yl)-3-(5-methylsulfanyl-thiazol-2-yl)-urea
1-(3-Cyclopentanecarbonyl-pyridin-2-yl)-3-(5-methylsulfanyl-thiazol-2-yl)-urea
1-(2-Cyclopentanecarbonyl-4-methyl-phenyl)-3-(5-methanesulfonyl-thiazol-2-yl)-urea
1-(2-Cyclopentanecarbonyl-phenyl)-3-(5-methanesulfonyl-thiazol-2-yl)-urea
1-(4-Chloro-2-cyclopentanecarbonyl-phenyl)-3-(5-methanesulfonyl-thiazol-2-yl)-urea 1-(2-Cyclopentanecarbonyl-4-fluoro-phenyl)-3-(5-methanesufonyl-thiazol-2-yl)-urea
1-(2-Cyclopentanecarbonyl-4-trifluoromethyl-phenyl)-3-(5-methanesulfonyl-thiazol-2-yl)-urea
1-(2-Cyclopentanecarbonyl-4-methoxy-phenyl)-3-(5-methanesufonyl-thiazol-2-yl)-urea
1-(2-Cyclopentanecarbonyl-4-dimethylamino-phenyl)-3-(5-methanesulfonyl-thiazol-2-yl)-urea
1-(2-Cyclopentanecarbonyl-4-morpholin-4-yl-phenyl)-3-(5-methanesulfonyl-thiazol-2-yl)-urea
1-(3-Cyclopentanecarbonyl-pyridin-4-yl)-3-(5-methanesulfonyl-thiazol-2-yl)-urea
1-(4-Cyclopentanecarbonyl-pyridin-3-yl)-3-(5-methanesulfonyl-thiazol-2-yl)-urea
1-(3-Cyclopentanecarbonyl-pyridin-2-yl)-3-(5-methanesulfonyl-thiazol-2-yl)-urea
1-(2-Cyclopentanecarbonyl-4-methyl-phenyl)-3-[5-(pyridin-2-ylsulfanyl)-thiazol-2-yl]-urea
1-(2-Cyclopentanecarbonyl-phenyl)-3-[5-(pyridin-2-ylsulfanyl)-thiazol-2-yl]-urea
1-(4-Chloro-2-cyclopentanecarbonyl-phenyl)-3-[5-(pyridin-2-ylsulfanyl)-thiazol-2-yl]-urea
1-(2-Cyclopentanecarbonyl-4-fluoro-phenyl)-3-[5-(pyridin-2-ylsulfanyl)-thiazol-2-yl]-urea
1-(2-Cyclopentanecarbonyl-4-trifluoromethyl-phenyl)-3-[5-(pyridin-2-ylsulfanyl)-thiazol-2-yl]-urea
1-(2-Cyclopentanecarbonyl-4-methoxy-phenyl)-3-[5-(pyridin-2-ylsulfanyl)-thiazol-2-yl]-urea
1-(2-Cyclopentanecarbonyl-4-dimethylamino-phenyl)-3-[5-(pyridin-2-ylsulfanyl)-thiazol-2-yl]-urea
1-(2-Cyclopentanecarbonyl-4-morpholin-4-yl-phenyl)-3-[5-(pyridin-2-ylsulfanyl)-thiazol-2-yl]-urea
1-(3-Cyclopentanecarbonyl-pyridin-4-yl)-3-[5-(pyridin-2-ylsulfanyl)-thiazol-2-yl]-urea
1-(4-Cyclopentanecarbonyl-pyridin-3-yl)-3-[5-(pyridin-2-ylsulfanyl)-thiazol-2-yl]-urea
1-(3-Cyclopentanecarbonyl-pyridin-2-yl)-3-[5-pyridin-2-ylsulfanyl)-thiazol-2-yl]-urea
1-(2-Cyclopentanecarbonyl-4-methyl-phenyl)-3-[5-(pyridine-2-sulfonyl)-thiazol-2-yl]-urea
1-(2-Cyclopentanecarbonyl-phenyl)-3-[5-(pyridine-2-sulfonyl)-thiazol-2-yl]-urea
1-(4-Chloro-2-cyclopentanecarbonyl-phenyl)-3-[5-pyridine-2-sulfonyl)-thiazol-2-yl]-urea
1-(2-Cyclopentanecarbonyl-4-fluoro-phenyl)-3-[5-(pyridine-2-sulfonyl)-thiazol-2-yl]-urea
1-(2-Cyclopentanecarbonyl-4-trifluoromethyl-phenyl)-3-[5-(pyridine-2-sulfonyl)-thiazol-2-yl]-urea
1-(2-Cyclopentanecarbonyl-4-methoxy-phenyl)-3-[5-(pyridine-2-sulfonyl)-thiazol-2-yl]-urea
1-(2-Cyclopentanecarbonyl-4-dimethylamino-phenyl)-3-[5-(pyridine-2-sulfonyl)-thiazol-2-yl]-urea
1-(2-Cyclopentanecarbonyl-4-morpholin-4-yl-phenyl)-3-[5-(pyridine-2-sulfonyl)-thiazol-2-yl]-urea
1-(3-Cyclopentanecarbonyl-pyridin-4-yl)-3-[5-(pyridine-2-sulfonyl)-thiazol-2-yl]-urea
1-(4-Cyclopentanecarbonyl-pyridin-3-yl)-3-[5-(pyridine-2-sulfonyl)-thiazol-2-yl]-urea
1-(3-Cyclopentanecarbonyl-pyridin-2-yl)-3-[5-(pyridine-2-sulfonyl)-thiazol-2-yl]-urea
1-(2-Cyclopentanecarbonyl-4-methyl-phenyl)-3-[5-(1H-imidazol-2-ylsulfanyl)-thiazol-2-yl]-urea
1-(2-Cyclopentanecarbonyl-phenyl)-3-[5-(1H-imidazol-2-ylsulfanyl)-thiazol-2-yl]-urea
1-(4-Chloro-2-cyclopentanecarbonyl-phenyl)-3-[5-(1H-imidazol-2-ylsulfanyl)-thiazol-2-yl]-urea
1-(2-Cyclopentanecarbonyl-4-fluoro-phenyl)-3-[5-(1H-imidazol-2-ylsulfanyl)-thiazol-2-yl]-urea
1-(2-Cyclopentanecarbonyl-4-trifluoromethyl-phenyl)-3-[5-(1H-imidazol-2-ylsulfanyl)-thiazol-2-yl]-urea
1-(2-Cyclopentanecarbonyl-4-methoxy-phenyl)-3-[5-(1H-imidazol-2-ylsulfanyl)-thiazol-2-yl]-urea
1-(2-Cyclopentanecarbonyl-4-dimethylamino-phenyl)-3-[5-(1H-imidazol-2-ylsulfanyl)-thiazol-2-yl]-urea
1-(2-Cyclopentanecarbonyl-4-morpholin-4-yl-phenyl)-3-[5-(1H-imidazol-2-ylsulfanyl)-thiazol-2-yl]-urea
1-(3-Cyclopentanecarbonyl-pyridin-4-yl)-3-[5-(1H-imidazol-2-ylsulfanyl)-thiazol-2-yl]-urea
1-(4-Cyclopentanecarbonyl-pyridin-3-yl)-3-[5-(1H-imidazol-2-ylsulfanyl)-thiazol-2-yl]-urea
1-(3-Cyclopentanecarbonyl-pyridin-2-yl)-3-[5-(1H-imidazol-2-ylsulfanyl)-thiazol-2-yl]-urea
1-(2-Cyclopentanecarbonyl-4-methyl-phenyl)-3-[5-(1H-imidazole-2-sulfonyl)-thiazol-2-yl]-urea
1-(2-Cyclopentanecarbonyl-phenyl)-3-[5-(1H-imidazole-2-sulfonyl)-thiazol-2-yl]-urea
1-(4-Chloro-2-cyclopentanecarbonyl-phenyl)-3-[5-(1H-imidazole-2-sulfonyl)-thiazol-2-yl]-urea
1-(2-Cyclopentanecarbonyl-4-fluoro-phenyl)-3-[5-(1H-imidazole-2-sulfonyl)-thiazol-2-yl]-urea
1-(2-Cyclopentanecarbonyl-4-trifluoromethyl-phenyl)-3-[5-(1H-imidazole-2-sulfonyl)-thiazol-2-yl]-urea
1-(2-Cyclopentanecarbonyl-4-methoxy-phenyl)-3-[5-(1H-imidazole-2-sulfonyl)-thiazol-2-yl]-urea
1-(2-Cyclopentanecarbonyl-4-dimethylamino-phenyl)-3-[5-(1H-imidazole-2-sulfonyl)-thiazol-2-yl]-urea
1-(2-Cyclopentanecarbonyl-4-morpholin-4-yl-phenyl)-3-[5-(1H-imidazole-2-sulfonyl)-thiazol-2-yl]-urea
1-(3-Cyclopentanecarbonyl-pyridin-4-yl)-3-[5-(1H-imidazole-2-sulfonyl)-thiazol-2-yl]-urea
1-(4-Cyclopentanecarbonyl-pyridin-3-yl)-3-[5-(1H-imidazole-2-sulfonyl)-thiazol-2-yl]-urea
1-(3-Cyclopentanecarbonyl-pyridin-2-yl)-3-[5-(1H-imidazole-2-sulfonyl)-thiazol-2-yl]-urea
1-(2-Cyclopentanecarbonyl-4-methyl-phenyl)-3-[5-(1-methyl-1H-tetrazol-5-ylsulfanyl)-thiazol-2-yl]-urea
1-(2-Cyclopentanecarbonyl-phenyl)-3-[5-(1-methyl-1H-tetrazol-5-ylsulfanyl)-thiazol-2-yl]-urea
1-(4-Chloro-2-cyclopentanecarbonyl-phenyl)-3-[5-(1-methyl-1H-tetrazol-5-ylsulfanyl)-thiazol-2-yl]-urea
1-(2-Cyclopentanecarbonyl-4-fluoro-phenyl)-3-[5-(1-methyl-1H-tetrazol-5-ylsulfanyl)-thiazol-2-yl]-urea
1-(2-Cyclopentanecarbonyl-4-trifluoromethyl-phenyl)-3-[5-(1-methyl-1H-tetrazol-5-ylsulfanyl)-thiazol-2-yl]-urea
1-(2-Cyclopentanecarbonyl-4-methoxy-phenyl)-3-[5-(1-methyl-1H-tetrazol-5-ylsulfanyl)-thiazol-2-yl]-urea
1-(2-Cyclopentanecarbonyl-4-dimethylamino-phenyl)-3-[5-(1-methyl-1H-tetrazol-5-ylsulfanyl)-thiazol-2-yl]-urea
1-(2-Cyclopentanecarbonyl-4-morpholin-4-yl-phenyl)-3-[5-(1-methyl-1H-tetrazol-5-ylsulfanyl)-thiazol-2-yl]-urea
1-(3-Cyclopentanecarbonyl-pyridin-4-yl)-3-[5-(1-methyl-1H-tetrazol-5-ylsulfanyl)-thiazol-2-yl]-urea
1-(4-Cyclopentanecarbonyl-pyridin-3-yl)-3-[5-(1-methyl-1H-tetrazol-5-ylsulfanyl)-thiazol-2-yl]-urea
1-(3-Cyclopentanecarbonyl-pyridin-2-yl)-3-[5-(1-methyl-1H-tetrazol-5-ylsulfanyl)-thiazol-2-yl]-urea
1-(2-Cyclopentanecarbonyl-4-methyl-phenyl)-3-[5-(1-methyl-1H-tetrazole-5-sulfonyl)-thiazol-2-yl]-urea
1-(2-Cyclopentanecarbonyl-phenyl)-3-[5-(1-methyl-1H-tetrazole-5-sulfonyl)-thiazol-2-yl]-urea
1-(4-Chloro-2-cyclopentanecarbonyl-phenyl)-3-[5-(1-methyl-1H-tetrazole-5-sulfonyl)-thiazol-2-yl]-urea 1-(2-Cyclopentanecarbonyl-4-fluoro-phenyl)-3-[5-(1-methyl-1H-tetrazole-5-sulfonyl)-thiazol-2-yl]-urea
1-(2-Cyclopentanecarbonyl-4-trifluoromethyl-phenyl)-3-[5-(1-methyl-1H-tetrazole-5-sulfonyl)-thiazol-2-yl]-urea
1-(2-Cyclopentanecarbonyl-4-methoxy-phenyl)-3-[5-(1-methyl-1H-tetrazole-5-sulfonyl)-thiazol-2-yl]-urea
1-(2-Cyclopentanecarbonyl-4-dimethylamino-phenyl)-3-[5-(1-methyl-1H-tetrazole-5-sulfonyl)-thiazol-2-yl]-urea
1-(2-Cyclopentanecarbonyl-4-morpholin-4-yl-phenyl)-3-[5-(1-methyl-1H-tetrazole-5-sulfonyl)-thiazol-2-yl]-urea
1-(3-Cyclopentanecarbonyl-pyridin-4-yl)-3-[5-(1-methyl-1H-tetrazole-5-sulfonyl)-thiazol-2-yl]-urea
1-(4-Cyclopentanecarbonyl-pyridin-3-yl)-3-[5-(1-methyl-1H-tetrazole-5-sulfonyl)-thiazol-2-yl]-urea
1-(3-Cyclopentanecarbonyl-pyridin-2-yl)-3-[5-(1-methyl-1H-tetrazole-5-sulfonyl)-thiazol-2-yl]-urea
1-(2-Cyclopentanecarbonyl-4-methyl-phenyl)-3-[5-(1H-tetrazole-5-sulfonyl)-thiazol-2-yl]-urea
1-(2-Cyclopentanecarbonyl-phenyl)-3-[5-(1H-tetrazole-5-sulfonyl)-thiazol-2-yl]-urea
1-(4-Chloro-2-cyclopentanecarbonyl-phenyl)-3-[5-(1H-tetrazole-5-sulfonyl)-thiazol-2-yl]-urea
1-(2-Cyclopentanecarbonyl-4-fluoro-phenyl)-3-[5-(1H-tetrazole-5-sulfonyl)-thiazol-2-yl]-urea
1-(2-Cyclopentanecarbonyl-4-trifluoromethyl-phenyl)-3-[5-(1H-tetrazole-5-sulfonyl)-thiazol-2-yl]-urea
1-(2-Cyclopentanecarbonyl-4-methoxy-phenyl)-3-[5-(1H-tetrazole-5-sulfonyl)-thiazol-2-yl]-urea
1-(2-Cyclopentanecarbonyl-4-dimethylamino-phenyl)-3-[5-(1H-tetrazole-5-sulfonyl)-thiazol-2-yl]-urea
1-(2-Cyclopentanecarbonyl-4-morpholin-4-yl-phenyl)-3-[5-(1H-tetrazole-5-sulfonyl)-thiazol-2-yl]-urea
1-(3-Cyclopentanecarbonyl-pyridin-4-yl)-3-[5-(1H-tetrazole-5-sulfonyl)-thiazol-2-yl]-urea
1-(4-Cyclopentanecarbonyl-pyridin-3-yl)-3-[5-(1H-tetrazole-5-sulfonyl)-thiazol-2-yl]-urea
1-(3-Cyclopentanecarbonyl-pyridin-2-yl)-3-[5-(1H-tetrazole-5-sulfonyl)-thiazol-2-yl]-urea
5-Chloro-2-[3-(2-cyclopentanecarbonyl-4-methyl-phenyl)-ureido]-thiazole-4-carboxylic acid
5-Chloro-2-[3-(2-cyclopentanecarbonyl-phenyl)-ureido]-thiazole-4-carboxylic acid
5-Chloro-2-[3-(4-chloro-2-cyclopentanecarbonyl-phenyl)-ureido]-thiazole-4-carboxylic acid
5-Chloro-2-[3-(2-cyclopentanecarbonyl-4-fluoro-phenyl)-ureido]-thiazole-4-carboxylic acid
5-Chloro-2-[3-(2-cyclopentanecarbonyl-4-trifluoromethyl-phenyl)-ureido]-thiazole-4-carboxylic acid
5-Chloro-2-[3-(2-cyclopentanecarbonyl-4-methoxy-phenyl)-ureido]-thiazole-4-carboxylic acid
5-Chloro-2-[3-(2-cyclopentanecarbonyl-4-dimethylamino-phenyl)-ureido]-thiazole-4-carboxylic acid
5-Chloro-2-[3-(2-cyclopentanecarbonyl-4-morpholin-4-yl-phenyl)-ureido]-thiazole-4-carboxylic acid
5-Chloro-2-[3-(3-cyclopentanecarbonyl-pyridin-4-yl)-ureido]-thiazole-4-carboxylic acid
5-Chloro-2-[3-(4-cyclopentanecarbonyl-pyridin-3-yl)-ureido]-thiazole-4-carboxylic acid
5-Chloro-2-[3-(3-cyclopentanecarbonyl-pyridin-2-yl)-ureido]-thiazole-4-carboxylic acid
5-Bromo-2-[3-(2-cyclopentanecarbonyl-4-methyl-phenyl)-ureido]-thiazole-4-carboxylic acid
5-Bromo-2-[3-(2-cyclopentanecarbonyl-phenyl)-ureido]-thiazole-4-carboxylic acid
5-Bromo-2-[3-(4-chloro-2-cyclopentanecarbonyl-phenyl)-ureido]-thiazole-4-carboxylic acid
5-Bromo-2-[3-(2-cyclopentanecarbonyl-4-fluoro-phenyl)-ureido]-thiazole-4-carboxylic acid
5-Bromo-2-[3-(2-cyclopentanecarbonyl-4-trifluoromethyl-phenyl)-ureido]-thiazole-4-carboxylic acid
5-Bromo-2-[3-(2-cyclopentanecarbonyl-4-methoxy-phenyl)-ureido]-thiazole-4-carboxylic acid
5-Bromo-2-[3-(2-cyclopentanecarbonyl-4-dimethylamino-phenyl)-ureido]-thiazole-4-carboxylic acid
5-Bromo-2-[3-(2-cyclopentanecarbonyl-4-morpholin-4-yl-phenyl)-ureido]-thiazole-4-carboxylic acid
5-Bromo-2-[3-(3-cyclopentanecarbonyl-pyridin-4-yl)-ureido]-thiazole-4-carboxylic acid
5-Bromo-2-[3-(4-cyclopentanecarbonyl-pyridin-3-yl)-ureido]-thiazole-4-carboxylic acid
5-Bromo-2-[3-(3-cyclopentanecarbonyl-pyridin-2-yl)-ureido]-thiazole-4-carboxylic acid
2-[3-(2-Cyclopentanecarbonyl-4-methyl-phenyl)-ureido]-5-methylsulfanyl-thiazole-4-carboxylic acid
2-[3-(2-Cyclopentanecarbonyl-phenyl)-ureido]-5-methylsulfanyl-thiazole-4-carboxylic acid
2-[3-(4-Chloro-2-cyclopentanecarbonyl-phenyl)-ureido]-5-methylsulfanyl-thiazole-4-carboxylic acid
2-[3-(2-Cyclopentanecarbonyl-4-fluoro-phenyl)-ureido]-5-methylsulfanyl-thiazole-4-carboxylic acid
2-[3-(2-Cyclopentanecarbonyl-4-trifluoromethyl-phenyl)-ureido]-5-methylsulfanyl-thiazole-4-carboxylic acid
2-[3-(2-Cyclopentanecarbonyl-4-methoxy-phenyl)-ureido]-5-methylsulfanyl-thiazole-4-carboxylic acid
2-[3-(2-Cyclopentanecarbonyl-4-dimethylamino-phenyl)-ureido]-5-methylsulfanyl-thiazole-4-carboxylic acid
2-[3-(2-Cyclopentanecarbonyl-4-morpholin-4-yl-phenyl)-ureido]-5-methylsulfanyl-thiazole-4-carboxylic acid
2-[3-(3-Cyclopentanecarbonyl-pyridin-4-yl)-ureido]-5-methylsulfanyl-thiazole-4-carboxylic acid
2-[3-(4-Cyclopentanecarbonyl-pyridin-3-yl)-ureido]-5-methylsulfanyl-thiazole-4-carboxylic acid
2-[3-(3-Cyclopentanecarbonyl-pyridin-2-yl)-ureido]-5-methylsulfanyl-thiazole-4-carboxylic acid
2-[3-(2-Cyclopentanecarbonyl-4-methyl-phenyl)-ureido]-5-methanesulfonyl-thiazole-4-carboxylic acid
2-[3-(2-Cyclopentanecarbonyl-phenyl)-ureido]-5-methanesulfonyl-thiazole-4-carboxylic acid
2-[3-(4-Chloro-2-cyclopentanecarbonyl-phenyl)-ureido]-5-methanesulfonyl-thiazole-4-carboxylic acid
2-[3-(2-Cyclopentanecarbonyl-4-fluoro-phenyl)-ureido]-5-methanesulfonyl-thiazole-4-carboxylic acid
2-[3-(2-Cyclopentanecarbonyl-4-trifluoromethyl-phenyl)-ureido]-5-methanesufonyl-thiazole-4-carboxylic acid
2-[3-(2-Cyclopentanecarbonyl-4-methoxy-phenyl)-ureido]-5-methanesulfonyl-thiazole-4-carboxylic acid
2-[3-(2-Cyclopentanecarbonyl-4-dimethylamino-phenyl)-ureido]-5-methanesulfonyl-thiazole-4-carboxylic acid
2-[3-(2-Cyclopentanecarbonyl-4-morpholin-4-yl-phenyl)-ureido]-5-methanesulfonyl-thiazole-4-carboxylic acid
2-[3-(3-Cyclopentanecarbonyl-pyridin-4-yl)-ureido]-5-methanesulfonyl-thiazole-4-carboxylic acid
2-[3-(4-Cyclopentanecarbonyl-pyridin-3-yl)-ureido]-5-methanesulfonyl-thiazole-4-carboxylic acid
2-[3-(3-Cyclopentanecarbonyl-pyridin-2-yl)-ureido]-5-methanesulfonyl-thiazole-4-carboxylic acid
2-[3-(2-Cyclopentanecarbonyl-4-methyl-phenyl)-ureido]-5-(pyridin-2-ylsulfanyl)-thiazole-4-carboxylic acid
2-[3-(2-Cyclopentanecarbonyl-phenyl)-ureido]-5-(pyridin-2-ylsulfanyl)-thiazole-4-carboxylic acid
2-[3-(4-Chloro-2-cyclopentanecarbonyl-phenyl)-ureido]-5-(pyridin-2-ylsulfanyl)-thiazole-4-carboxylic acid 2-[3-(2-Cyclopentanecarbonyl-4-fluoro-phenyl)-ureido]-5-(pyridin-2-ylsulfanyl)-thiazole-4-carboxylic acid 2-[3-(2-Cyclopentanecarbonyl-4-trifluoromethyl-phenyl)-ureido]-5-(pyridin-2-ylsulfanyl)-thiazole-4-carboxylic acid 2-[3-(2-Cyclopentanecarbonyl-4-methoxy-phenyl)-ureido]-5-(pyridin-2-ylsulfanyl)-thiazole-4-carboxylic acid 2-[3-(2-Cyclopentanecarbonyl-4-dimethylamino-phenyl)-ureido]-5-(pyridin-2-ylsulfanyl)-thiazole-4-carboxylic acid 2-[3-(2-Cyclopentanecarbonyl-4-morpholin-4-yl-phenyl)-ureido]-5-(pyridin-2-ylsulfanyl)-thiazole-4-carboxylic acid 2-[3-(3-Cyclopentanecarbonyl-pyridin-4-yl)-ureido]-5-pyridin-2-ylsulfanyl)-thiazole-4-carboxylic acid 2-[3-(4-Cyclopentanecarbonyl-pyridin-3-yl)-ureido]-5-(pyridin-2-ylsulfanyl)-thiazole-4-carboxylic acid 2-[3-(3-Cyclopentanecarbonyl-pyridin-2-yl)-ureido]-5-(pyridin-2-ylsulfanyl)-thiazole-4-carboxylic acid 2-[3-(2-Cyclopentanecarbonyl-4-methyl-phenyl)-ureido]-5-(pyridine-2-sulfonyl)-thiazole-4-carboxylic acid 2-[3-(2-Cyclopentanecarbonyl-phenyl)-ureido]-5-(pyridine-2-sulfonyl)-thiazole-4-carboxylic acid 2-[3-(4-Chloro-2-cyclopentanecarbonyl-phenyl)-ureido]-5-(pyridine-2-sulfonyl)-thiazole-4-carboxylic acid 2-[3-(2-Cyclopentanecarbonyl-4-fluoro-phenyl)-ureido]-5-(pyridine-2-sulfonyl)-thiazole-4-carboxylic acid 2-[3-(2-Cyclopentanecarbonyl-4-trifluoromethyl-phenyl)-ureido]-5-(pyridine-2-sulfonyl)-thiazole-4-carboxylic acid 2-[3-(2-Cyclopentanecarbonyl-4-methoxy-phenyl)-ureido]-5-(pyridine-2-sulfonyl)-thiazole-4-carboxylic acid 2-[3-(2-Cyclopentanecarbonyl-4-dimethylamino-phenyl)-ureido]-5-(pyridine-2-sulfonyl)-thiazole-4-carboxylic acid 2-[3-(2-Cyclopentanecarbonyl-4-morpholin-4-yl-phenyl)-ureido]-5-pyridine-2-sulfonyl)-thiazole-4-carboxylic acid 2-[3-(3-Cyclopentanecarbonyl-pyridin-4-yl)-ureido]-5-(pyridine-2-sulfonyl)-thiazole-4-carboxylic acid 2-[3-(4-Cyclopentanecarbonyl-pyridin-3-yl)-ureido]-5-pyridine-2-sulfonyl)-thiazole-4-carboxylic acid 2-[3-(3-Cyclopentanecarbonyl-pyridin-2-yl)-ureido]-5-(pyridine-2-sulfonyl)-thiazole-4-carboxylic acid 2-[3-(2-Cyclopentanecarbonyl-4-methyl-phenyl)-ureido]-5-(1H-imidazol-2-ylsulfanyl)-thiazole-4-carboxylic acid 2-[3-(2-Cyclopentanecarbonyl-phenyl)-ureido]-5-(1H-imidazol-2-ylsulfanyl)-thiazole-4-carboxylic acid 2-[3-(4-Chloro-2-cyclopentanecarbonyl-phenyl)-ureido]-5-(1H-imidazol-2-ylsulfanyl)-thiazole-4-carboxylic acid 2-[3-(2-Cyclopentanecarbonyl-4-fluoro-phenyl)-ureido]-5-(1H-imidazol-2-ylsulfanyl)-thiazole-4-carboxylic acid 2-[3-(2-Cyclopentanecarbonyl-4-trifluoromethyl-phenyl)-ureido]-5-(1H-imidazol-2-ylsulfanyl)-thiazole-4-carboxylic acid 2-[3-(2-Cyclopentanecarbonyl-4-methoxy-phenyl)-ureido]-5-(1H-imidazol-2-ylsulfanyl)-thiazole-4-carboxylic acid 2-[3-(2-Cyclopentanecarbonyl-4-dimethylamino-phenyl)-ureido]-5-(1H-imidazol-2-ylsulfanyl)-thiazole-4-carboxylic acid 2-[3-(2-Cyclopentanecarbonyl-4-morpholin-4-yl-phenyl)-ureido]-5-(1H-imidazol-2-ylsulfanyl)-thiazole-4-carboxylic acid 2-[3-(3-Cyclopentanecarbonyl-pyridin-4-yl)-ureido]-5-(1H-imidazol-2-ylsulfanyl)-thiazole-4-carboxylic acid 2-[3-(4-Cyclopentanecarbonyl-pyridin-3-yl)-ureido]-5-(1H-imidazol-2-ylsulfanyl)-thiazole-4-carboxylic acid 2-[3-(3-Cyclopentanecarbonyl-pyridin-2-yl)-ureido]-5-(1H-imidazol-2-ylsulfanyl)-thiazole-4-carboxylic acid 2-[3-(2-Cyclopentanecarbonyl-4-methyl-phenyl)-ureido]-5-(1H-imidazole-2-sulfonyl)-thiazole-4-carboxylic acid 2-[3-(2-Cyclopentanecarbonyl-phenyl)-ureido]-5-(1H-imidazole-2-sulfonyl)-thiazole-4-carboxylic acid 2-[3-(4-Chloro-2-cyclopentanecarbonyl-phenyl)-ureido]-5-(1H-imidazole-2-sulfonyl)-thiazole-4-carboxylic acid 2-[3-(2-Cyclopentanecarbonyl-4-fluoro-phenyl)-ureido]-5-(1H-imidazole-2-sulfonyl)-thiazole-4-carboxylic acid 2-[3-(2-Cyclopentanecarbonyl-4-trifluoromethyl-phenyl)-ureido]-5-(1H-imidazole-2-sulfonyl)-thiazole-4-carboxylic acid 2-[3-(2-Cyclopentanecarbonyl-4-methoxy-phenyl)-ureido]-5-(1H-imidazole-2-sulfonyl)-thiazole-4-carboxylic acid 2-[3-(2-Cyclopentanecarbonyl-4-dimethylamino-phenyl)-ureido]-5-(1H-imidazole-2-sulfonyl)-thiazole-4-carboxylic acid 2-[3-(2-Cyclopentanecarbonyl-4-morpholin-4-yl-phenyl)-ureido]-5-(1H-imidazole-2-sulfonyl)-thiazole-4-carboxylic acid 2-[3-(3-Cyclopentanecarbonyl-pyridin-4-yl)-ureido]-5-(1H-imidazole-2-sulfonyl)-thiazole-4-carboxylic acid 2-[3-(4-Cyclopentanecarbonyl-pyridin-3-yl)-ureido]-5-(1H-imidazole-2-sulfonyl)-thiazole-4-carboxylic acid 2-[3-(3-Cyclopentanecarbonyl-pyridin-2-yl)-ureido]-5-(1H-imidazole-2-sulfonyl)-thiazole-4-carboxylic acid 2-[3-(2-Cyclopentanecarbonyl-4-methyl-phenyl)-ureido]-5-(1-methyl-1H-tetrazol-5-ylsulfanyl)-thiazole-4-carboxylic acid 2-[3-(2-Cyclopentanecarbonyl-phenyl)-ureido]-5-(1-methyl-1H-tetrazol-5-ylsulfanyl)-thiazole-4-carboxylic acid 2-[3-(4-Chloro-2-cyclopentanecarbonyl-phenyl)-ureido]-5-(1-methyl-1H-tetrazol-5-ylsulfanyl)-thiazole-4-carboxylic acid 2-[3-(2-Cyclopentanecarbonyl-4-fluoro-phenyl)-ureido]-5-(1-methyl-1H-tetrazol-5-ylsulfanyl)-thiazole-4-carboxylic acid 2-[3-(2-Cyclopentanecarbonyl-4-trifluoromethyl-phenyl)-ureido]-5-(1-methyl-1H-tetrazol-5-ylsulfanyl)-thiazole-4-carboxylic acid 2-[3-(2-Cyclopentanecarbonyl-4-methoxy-phenyl)-ureido]-5-(1-methyl-1H-tetrazol-5-ylsulfanyl)-thiazole-4-carboxylic acid 2-[3-(2-Cyclopentanecarbonyl-4-dimethylamino-phenyl)-ureido]-5-(1-methyl-1H-tetrazol-5-ylsulfanyl)-thiazole-4-carboxylic acid 2-[3-(2-Cyclopentanecarbonyl-4-morpholin-4-yl-phenyl)-ureido]-5-(1-methyl-1H-tetrazol-5-ylsulfanyl)-thiazole-4-carboxylic acid 2-[3-(3-Cyclopentanecarbonyl-pyridin-4-yl)-ureido]-5-(1-methyl-1H-tetrazol-5-ylsulfanyl)-thiazole-4-carboxylic acid 2-[3-(4-Cyclopentanecarbonyl-pyridin-3-yl)-ureido]-5-(1-methyl-1H-tetrazol-5-ylsulfanyl)-thiazole-4-carboxylic acid 2-[3-(3-Cyclopentanecarbonyl-pyridin-2-yl)-ureido]-5-(1-methyl-1H-tetrazol-5-ylsulfanyl)-thiazole-4-carboxylic acid 2-[3-(2-Cyclopentanecarbonyl-4-methyl-phenyl)-ureido]-5-(1-methyl-1H-tetrazole-5-sulfonyl)-thiazole-4-carboxylic acid 2-[3-(2-Cyclopentanecarbonyl-phenyl)-ureido]-5-(1-methyl-1H-tetrazole-5-sulfonyl)-thiazole-4-carboxylic acid 2-[3-(4-Chloro-2-cyclopentanecarbonyl-phenyl)-ureido]-5-(1-methyl-1H-tetrazole-5-sulfonyl)-thiazole-4-carboxylic acid 2-[3-(2-Cyclopentanecarbonyl-4-fluoro-phenyl)-ureido]-5-(1-methyl-1H-tetrazole-5-sulfonyl)-thiazole-4-carboxylic acid
2-[3-(2-Cyclopentanecarbonyl-4-trifluoromethyl-phenyl)-ureido]-5-(1-methyl-1H-tetrazole-5-sulfonyl)-thiazole-4-carboxylic acid
2-[3-(2-Cyclopentanecarbonyl-4-methoxy-phenyl)-ureido]-5-(1-methyl-1H-tetrazole-5-sulfonyl)-thiazole-4-carboxylic acid
2-[3-(2-Cyclopentanecarbonyl-4-dimethylamino-phenyl)-ureido]-5-(1-methyl-1H-tetrazole-5-sulfonyl)-thiazole-4-carboxylic acid
2-[3-(2-Cyclopentanecarbonyl-4-morpholin-4-yl-phenyl)-ureido]-5-(1-methyl-1H-tetrazole-5-sulfonyl)-thiazole-4-carboxylic acid
2-[3-(3-Cyclopentanecarbonyl-pyridin-4-yl)-ureido]-5-(1-methyl-1H-tetrazole-5-sulfonyl)-thiazole-4-carboxylic acid
2-[3-(4-Cyclopentanecarbonyl-pyridin-3-yl)-ureido]-5-(1-methyl-1H-tetrazole-5-sulfonyl)-thiazole-4-carboxylic acid
2-[3-(3-Cyclopentanecarbonyl-pyridin-2-yl)-ureido]-5-(1-methyl-1H-tetrazole-5-sulfonyl)-thiazole-4-carboxylic acid
2-[3-(2-Cyclopentanecarbonyl-4-methyl-phenyl)-ureido]-5-(1H-tetrazole-5-sulfonyl)-thiazole-4-carboxylic acid
2-[3-(2-Cyclopentanecarbonyl-phenyl)-ureido]-5-(1H-tetrazole-5-sulfonyl)-thiazole-4-carboxylic acid
2-[3-(4-Chloro-2-cyclopentanecarbonyl-phenyl)-ureido]-5-(1H-tetrazole-5-sulfonyl)-thiazole-4-carboxylic acid
2-[3-(2-Cyclopentanecarbonyl-4-fluoro-phenyl)-ureido]-5-(1H-tetrazole-5-sulfonyl)-thiazole-4-carboxylic acid
2-[3-(2-Cyclopentanecarbonyl-4-trifluoromethyl-phenyl)-ureido]-5-(1H-tetrazole-5-sulfonyl)-thiazole-4-carboxylic acid
2-[3-(2-Cyclopentanecarbonyl-4-methoxy-phenyl)-ureido]-5-(1H-tetrazole-5-sulfonyl)-thiazole-4-carboxylic acid
2-[3-(2-Cyclopentanecarbonyl-4-dimethylamino-phenyl)-ureido]-5-(1H-tetrazole-5-sulfonyl)-thiazole-4-carboxylic acid
2-[3-(2-Cyclopentanecarbonyl-4-morpholin-4-yl-phenyl)-ureido]-5-(1H-tetrazole-5-sulfonyl)-thiazole-4-carboxylic acid
2-[3-(3-Cyclopentanecarbonyl-pyridin-4-yl)-ureido]-5-(1H-tetrazole-5-sulfonyl)-thiazole-4-carboxylic acid
2-[3-(4-Cyclopentanecarbonyl-pyridin-3-yl)-ureido]-5-(1H-tetrazole-5-sulfonyl)-thiazole-4-carboxylic acid
2-[3-(3-Cyclopentanecarbonyl-pyridin-2-yl)-ureido]-5-(1H-tetrazole-5-sulfonyl)-thiazole-4-carboxylic acid
{5-Chloro-2-[3-(2-cyclopentanecarbonyl-4-methyl-phenyl)-ureido]-thiazol-4-yl}-acetic acid
{5-Chloro-2-[3-(2-cyclopentanecarbonyl-phenyl)-ureido]-thiazol-4-yl}-acetic acid
{5-Chloro-2-[3-(4-chloro-2-cyclopentanecarbonyl-phenyl)-ureido]-thiazol-4-yl}-acetic acid
{5-Chloro-2-[3-(2-cyclopentanecarbonyl-4-fluoro-phenyl)-ureido]-thiazol-4-yl}-acetic acid
{5-Chloro-2-[3-(2-cyclopentanecarbonyl-4-trifluoromethyl-phenyl)-ureido]-thiazol-4-yl}-acetic acid
{5-Chloro-2-[3-(2-cyclopentanecarbonyl-4-methoxy-phenyl)-ureido]-thiazol-4-yl}-acetic acid
{5-Chloro-2-[3-(2-cyclopentanecarbonyl-4-dimethylamino-phenyl)-ureido]-thiazol-4-yl}-acetic acid
{5-Chloro-2-[3-(2-cyclopentanecarbonyl-4-morpholin-4-yl-phenyl)-ureido]-thiazol-4-yl}-acetic acid
{5-Chloro-2-[3-(3-cyclopentanecarbonyl-pyridin-4-yl)-ureido]-thiazol-4-yl}-acetic acid
{5-Chloro-2-[3-(4-cyclopentanecarbonyl-pyridin-3-yl)-ureido]-thiazol-4-yl}-acetic acid
{5-Chloro-2-[3-(3-cyclopentanecarbonyl-pyridin-2-yl)-ureido]-thiazol-4-yl}-acetic acid
{5-Bromo-2-[3-(2-cyclopentanecarbonyl-4-methyl-phenyl)-ureido]-thiazol-4-yl}-acetic acid
{5-Bromo-2-[3-(2-cyclopentanecarbonyl-phenyl)-ureido]-thiazol-4-yl}-acetic acid
{5-Bromo-2-[3-(4-chloro-2-cyclopentanecarbonyl-phenyl)-ureido]-thiazol-4-yl}-acetic acid
{5-Bromo-2-[3-(2-cyclopentanecarbonyl-4-fluoro-phenyl)-ureido]-thiazol-4-yl}-acetic acid
{5-Bromo-2-[3-(2-cyclopentanecarbonyl-4-trifluoromethyl-phenyl)-ureido]-thiazol-4-yl}-acetic acid
{5-Bromo-2-[3-(2-cyclopentanecarbonyl-4-methoxy-phenyl)-ureido]-thiazol-4-yl}-acetic acid
{5-Bromo-2-[3-(2-cyclopentanecarbonyl-4-dimethylamino-phenyl)-ureido]-thiazol-4-yl}-acetic acid
{5-Bromo-2-[3-(2-cyclopentanecarbonyl-4-morpholin-4-yl-phenyl)-ureido]-thiazol-4-yl}-acetic acid
{5-Bromo-2-[3-(3-cyclopentanecarbonyl-pyridin-4-yl)-ureido]-thiazol-4-yl}-acetic acid
{5-Bromo-2-[3-(4-cyclopentanecarbonyl-pyridin-3-yl)-ureido]-thiazol-4-yl}-acetic acid
{5-Bromo-2-[3-(3-cyclopentanecarbonyl-pyridin-2-yl)-ureido]-thiazol-4-yl}-acetic acid
{2-[3-(2-Cyclopentanecarbonyl-4-methyl-phenyl)-ureido]-5-methylsulfanyl-thiazol-4-yl}-acetic acid
{2-[3-(2-Cyclopentanecarbonyl-phenyl)-ureido]-5-methylsulfanyl-thiazol-4-yl}-acetic acid
{2-[3-(4-Chloro-2-cyclopentanecarbonyl-phenyl)-ureido]-5-methylsulfanyl-thiazol-4-yl}-acetic acid
{2-[3-(2-Cyclopentanecarbonyl-4-fluoro-phenyl)-ureido]-5-methylsulfanyl-thiazol-4-yl}-acetic acid
{2-[3-(2-Cyclopentanecarbonyl-4-trifluoromethyl-phenyl)-ureido]-5-methylsulfanyl-thiazol-4-yl}-acetic acid
{2-[3-(2-Cyclopentanecarbonyl-4-methoxy-phenyl)-ureido]-5-methylsulfanyl-thiazol-4-yl}-acetic acid
{2-[3-(2-Cyclopentanecarbonyl-4-dimethylamino-phenyl)-ureido]-5-methylsulfanyl-thiazol-4-yl}-acetic acid
{2-[3-(2-Cyclopentanecarbonyl-4-morpholin-4-yl-phenyl)-ureido]-5-methylsulfanyl-thiazol-4-yl}-acetic acid
{2-[3-(3-Cyclopentanecarbonyl-pyridin-4-yl)-ureido]-5-methylsulfanyl-thiazol-4-yl}-acetic acid
{2-[3-(4-Cyclopentanecarbonyl-pyridin-3-yl)-ureido]-5-methylsulfanyl-thiazol-4-yl}-acetic acid
{2-[3-(3-Cyclopentanecarbonyl-pyridin-2-yl)-ureido]-5-methylsulfanyl-thiazol-4-yl}-acetic acid
{2-[3-(2-Cyclopentanecarbonyl-4-methyl-phenyl)-ureido]-5-methanesulfonyl-thiazol-4-yl}-acetic acid
{2-[3-(2-Cyclopentanecarbonyl-phenyl)-ureido]-5-methanesulfonyl-thiazol-4-yl}-acetic acid
{2-[3-(4-Chloro-2-cyclopentanecarbonyl-phenyl)-ureido]-5-methanesulfonyl-thiazol-4-yl}-acetic acid
{2-[3-(2-Cyclopentanecarbonyl-4-fluoro-phenyl)-ureido]-5-methanesulfonyl-thiazol-4-yl}-acetic acid
{2-[3-(2-Cyclopentanecarbonyl-4-trifluoromethyl-phenyl)-ureido]-5-methanesulfonyl-thiazol-4-yl}-acetic acid
{2-[3-(2-Cyclopentanecarbonyl-4-methoxy-phenyl)-ureido]-5-methanesulfonyl-thiazol-4-yl}-acetic acid
{2-[3-(2-Cyclopentanecarbonyl-4-dimethylamino-phenyl)-ureido]-5-methanesulfonyl-thiazol-4-yl}-acetic acid
{2-[3-(2-Cyclopentanecarbonyl-4-morpholin-4-yl-phenyl)-ureido]-5-methanesulfonyl-thiazol-4-yl}-acetic acid
{2-[3-(3-Cyclopentanecarbonyl-pyridin-4-yl)-ureido]-5-methanesulfonyl-thiazol-4-yl}-acetic acid {2-[3-(4-Cyclopentanecarbonyl-pyridin-3-yl)-ureido]-5-methanesulfonyl-thiazol-4-yl}-acetic acid {2-[3-(3-Cyclopentanecarbonyl-pyridin-2-yl)-ureido]-5-methanesulfonyl-thiazol-4-yl}-acetic acid

[2-[3-(2-Cyclopentanecarbonyl-4-methyl-phenyl)-ureido]-5-(pyridin-2-ylsulfanyl)-thiazol-4-yl]-acetic acid

[2-[3-(2-Cyclopentanecarbonyl-phenyl)-ureido]-5-(pyridin-2-ylsulfanyl)-thiazol-4-yl]-acetic acid

[2-[3-(4-Chloro-2-cyclopentanecarbonyl-phenyl)-ureido]-5-(pyridin-2-ylsulfanyl)-thiazol-4-yl]-acetic acid

[2-[3-(2-Cyclopentanecarbonyl-4-fluoro-phenyl)-ureido]-5-(pyridin-2-ylsulfanyl)-thiazol-4-yl]-acetic acid

[2-[3-(2-Cyclopentanecarbonyl-4-trifluoromethyl-phenyl)-ureido]-5-(pyridin-2-ylsulfanyl)-thiazol-4-yl]-acetic acid

[2-[3-(2-Cyclopentanecarbonyl-4-methoxy-phenyl)-ureido]-5-(pyridin-2-ylsulfanyl)-thiazol-4-yl]-acetic acid

[2-[3-(2-Cyclopentanecarbonyl-4-dimethylamino-phenyl)-ureido]-5-pyridin-2-ylsulfanyl)-thiazol-4-yl]-acetic acid

[2-[3-(2-Cyclopentanecarbonyl-4-morpholin-4-yl-phenyl)-ureido]-5-(pyridin-2-ylsulfanyl)-thiazol-4-yl]-acetic acid

[2-[3-(3-Cyclopentanecarbonyl-pyridin-4-yl)-ureido]-5-(pyridin-2-ylsulfanyl)-thiazol-4-yl]-acetic acid

[2-[3-(4-Cyclopentanecarbonyl-pyridin-3-yl)-ureido]-5-(pyridin-2-ylsulfanyl)-thiazol-4-yl]-acetic acid

[2-[3-(3-Cyclopentanecarbonyl-pyridin-2-yl)-ureido]-5-(pyridin-2-ylsulfanyl)-thiazol-4-yl]-acetic acid

[2-[3-(2-Cyclopentanecarbonyl-4-methyl-phenyl)-ureido]-5-(pyridine-2-sulfonyl)-thiazol-4-yl]-acetic acid

[2-[3-(2-Cyclopentanecarbonyl-phenyl)-ureido]-5-(pyridine-2-sulfonyl)-thiazol-4-yl]-acetic acid

[2-[3-(4-Chloro-2-cyclopentanecarbonyl-phenyl)-ureido]-5-(pyridine-2-sulfonyl)-thiazol-4-yl]-acetic acid

[2-[3-(2-Cyclopentanecarbonyl-4-fluoro-phenyl)-ureido]-5-(pyridine-2-sulfonyl)-thiazol-4-yl]-acetic acid

[2-[3-(2-Cyclopentanecarbonyl-4-trifluoromethyl-phenyl)-ureido]-5-(pyridine-2-sulfonyl)-thiazol-4-yl]-acetic acid

[2-[3-(2-Cyclopentanecarbonyl-4-methoxy-phenyl)-ureido]-5-(pyridine-2-sulfonyl)-thiazol-4-yl]-acetic acid

[2-[3-(2-Cyclopentanecarbonyl-4-dimethylamino-phenyl)-ureido]-5-(pyridine-2-sulfonyl)-thiazol-4-yl]-acetic acid

[2-[3-(2-Cyclopentanecarbonyl-4-morpholin-4-yl-phenyl)-ureido]-5-(pyridine-2-sulfonyl)-thiazol-4-yl]-acetic acid

[2-[3-(3-Cyclopentanecarbonyl-pyridin-4-yl)-ureido]-5-(pyridine-2-sulfonyl)-thiazol-4-yl]-acetic acid

[2-[3-(4-Cyclopentanecarbonyl-pyridin-3-yl)-ureido]-5-(pyridine-2-sulfonyl)-thiazol-4-yl]-acetic acid

[2-[3-(3-Cyclopentanecarbonyl-pyridin-2-yl)-ureido]-5-(pyridine-2-sulfonyl)-thiazol-4-yl]-acetic acid

[2-[3-(2-Cyclopentanecarbonyl-4-methyl-phenyl)-ureido]-5-(1H-imidazol-2-ylsulfanyl)-thiazol-4-yl]-acetic acid

[2-[3-(2-Cyclopentanecarbonyl-phenyl)-ureido]-5-(1H-imidazol-2-ylsulfanyl)-thiazol-4-yl]-acetic acid

[2-[3-(4-Chloro-2-cyclopentanecarbonyl-phenyl)-ureido]-5-(1H-imidazol-2-ylsulfanyl)-thiazol-4-yl]-acetic acid

[2-[3-(2-Cyclopentanecarbonyl-4-fluoro-phenyl)-ureido]-5-(1H-imidazol-2-ylsulfanyl)-thiazol-4-yl]-acetic acid

[2-[3-(2-Cyclopentanecarbonyl-4-trifluoromethyl-phenyl)-ureido]-5-(1H-imidazol-2-ylsulfanyl)-thiazol-4-yl]-acetic acid

[2-[3-(2-Cyclopentanecarbonyl-4-methoxy-phenyl)-ureido]-5-(1H-imidazol-2-ylsulfanyl)-thiazol-4-yl]-acetic acid

[2-[3-(2-Cyclopentanecarbonyl-4-dimethylamino-phenyl)-ureido]-5-(1H-imidazol-2-ylsulfanyl)-thiazol-4-yl]-acetic acid

[2-[3-(2-Cyclopentanecarbonyl-4-morpholin-4-yl-phenyl)-ureido]-5-(1H-imidazol-2-ylsulfanyl)-thiazol-4-yl]-acetic acid

[2-[3-(3-Cyclopentanecarbonyl-pyridin-4-yl)-ureido]-5-(1H-imidazol-2-ylsulfanyl)-thiazol-4-yl]-acetic acid

[2-[3-(4-Cyclopentanecarbonyl-pyridin-3-yl)-ureido]-5-(1H-imidazol-2-ylsulfanyl)-thiazol-4-yl]-acetic acid

[2-[3-(3-Cyclopentanecarbonyl-pyridin-2-yl)-ureido]-5-(1H-imidazol-2-ylsulfanyl)-thiazol-4-yl]-acetic acid

[2-[3-(2-Cyclopentanecarbonyl-4-methyl-phenyl)-ureido]-5-(1H-imidazole-2-sulfonyl)-thiazol-4-yl]-acetic acid

[2-[3-(2-Cyclopentanecarbonyl-phenyl)-ureido]-5-(1H-imidazole-2-sulfonyl)-thiazol-4-yl]-acetic acid

[2-[3-(4-Chloro-2-cyclopentanecarbonyl-phenyl)-ureido]-5-(1H-imidazole-2-sulfonyl)-thiazol-4-yl]-acetic acid

[2-[3-2-Cyclopentanecarbonyl-4-fluoro-phenyl)-ureido]-5-(1H-imidazole-2-sulfonyl)-thiazol-4-yl]-acetic acid

[2-[3-(2-Cyclopentanecarbonyl-4-trifluoromethyl-phenyl)-ureido]-5-(1H-imidazole-2-sulfonyl)-thiazol-4-yl]-acetic acid

[2-[3-(2-Cyclopentanecarbonyl-4-methoxy-phenyl)-ureido]-5-(1H-imidazole-2-sulfonyl)-thiazol-4-yl]-acetic acid

[2-[3-(2-Cyclopentanecarbonyl-4-dimethylamino-phenyl)-ureido]-5-(1H-imidazole-2-sulfonyl)-thiazol-4-yl]-acetic acid

[2-[3-(2-Cyclopentanecarbonyl-4-morpholin-4-yl-phenyl)-ureido]-5-(1H-imidazole-2-sulfonyl)-thiazol-4-yl]-acetic acid

[2-[3-(3-Cyclopentanecarbonyl-pyridin-4-yl)-ureido]-5-(1H-imidazole-2-sulfonyl)-thiazol-4-yl]-acetic acid

[2-[3-(4-Cyclopentanecarbonyl-pyridin-3-yl)-ureido]-5-(1H-imidazole-2-sulfonyl)-thiazol-4-yl]-acetic acid

[2-[3-(3-Cyclopentanecarbonyl-pyridin-2-yl)-ureido]-5-(1H-imidazole-2-sulfonyl)-thiazol-4-yl]-acetic acid

[2-[3-(2-Cyclopentanecarbonyl-4-methyl-phenyl)-ureido]-5-(1-methyl-1H-tetrazol-5-ylsulfanyl)-thiazol-4-yl]-acetic acid

[2-[3-(2-Cyclopentanecarbonyl-phenyl)-ureido]-5-(1-methyl-1H-tetrazol-5-ylsulfanyl)-thiazol-4-yl]-acetic acid

[2-[3-(4-Chloro-2-cyclopentanecarbonyl-phenyl)-ureido]-5-(1-methyl-1H-tetrazol-5-ylsulfanyl)-thiazol-4-yl]-acetic acid

[2-[3-(2-Cyclopentanecarbonyl-4-fluoro-phenyl)-ureido]-5-(1-methyl-1H-tetrazol-5-ylsulfanyl)-thiazol-4-yl]-acetic acid

[2-[3-(2-Cyclopentanecarbonyl-4-trifluoromethyl-phenyl)-ureido]-5-(1-methyl-1H-tetrazol-5-ylsulfanyl)-thiazol-4-yl]-acetic acid

[2-[3-(2-Cyclopentanecarbonyl-4-methoxy-phenyl)-ureido]-5-(1-methyl-1H-tetrazol-5-ylsulfanyl)-thiazol-4-yl]-acetic acid

[2-[3-(2-Cyclopentanecarbonyl-4-dimethylamino-phenyl)-ureido]-5-(1-methyl-1H-tetrazol-5-ylsulfanyl)-thiazol-4-yl]-acetic acid

[2-[3-(2-Cyclopentanecarbonyl-4-morpholin-4-yl-phenyl)-ureido]-5-(1-methyl-1H-tetrazol-5-ylsulfanyl)-thiazol-4-yl]-acetic acid

[2-[3-(3-Cyclopentanecarbonyl-pyridin-4-yl)-ureido]-5-(1-methyl-1H-tetrazol-5-ylsulfanyl)-thiazol-4-yl]-acetic acid

[2-[3-(4-Cyclopentanecarbonyl-pyridin-3-yl)-ureido]-5-(1-methyl-1H-tetrazol-5-ylsulfanyl)-thiazol-4-yl]-acetic acid

[2-[3-(3-Cyclopentanecarbonyl-pyridin-2-yl)-ureido]-5-(1-methyl-1H-tetrazol-5-ylsulfanyl)-thiazol-4-yl]-acetic acid

[2-[3-(2-Cyclopentanecarbonyl-4-methyl-phenyl)-ureido]-5-(1-methyl-1H-tetrazole-5-sulfonyl)-thiazol-4-yl]-acetic acid

[2-[3-(2-Cyclopentanecarbonyl-phenyl)-ureido]-5-(1-methyl-1H-tetrazole-5-sulfonyl)-thiazol-4-yl]-acetic acid
[2-[3-(4-Chloro-2-cyclopentanecarbonyl-phenyl)-ureido]-5-(1-methyl-1H-tetrazole-5-sulfonyl)-thiazol-4-yl]-acetic acid
[2-[3-(2-Cyclopentanecarbonyl-4-fluoro-phenyl)-ureido]-5-(1-methyl-1H-tetrazole-5-sulfonyl)-thiazol-4-yl]-acetic acid
[2-[3-(2-Cyclopentanecarbonyl-4-trifluoromethyl-phenyl)-ureido]-5-(1-methyl-1H-tetrazole-5-sulfonyl)-thiazol-4-yl]-acetic acid
[2-[3-(2-Cyclopentanecarbonyl-4-methoxy-phenyl)-ureido]-5-(1-methyl-1H-tetrazole-5-sulfonyl)-thiazol-4-yl]-acetic acid
[2-[3-(2-Cyclopentanecarbonyl-4-dimethylamino-phenyl)-ureido]-5-(1-methyl-1H-tetrazole-5-sulfonyl)-thiazol-4-yl]-acetic acid
[2-[3-(2-Cyclopentanecarbonyl-4-morpholin-4-yl-phenyl)-ureido]-5-(1-methyl-1H-tetrazole-5-sulfonyl)-thiazol-4-yl]-acetic acid
[2-[3-(3-Cyclopentanecarbonyl-pyridin-4-yl)-ureido]-5-(1-methyl-1H-tetrazole-5-sulfonyl)-thiazol-4-yl]-acetic acid
[2-[3-(4-Cyclopentanecarbonyl-pyridin-3-yl)-ureido]-5-(1-methyl-1H-tetrazole-5-sulfonyl)-thiazol-4-yl]-acetic acid
[2-[3-(3-Cyclopentanecarbonyl-pyridin-2-yl)-ureido]-5-(1-methyl-1H-tetrazole-5-sulfonyl)-thiazol-4-yl]-acetic acid
[2-[3-(2-Cyclopentanecarbonyl-4-methyl-phenyl)-ureido]-5-(1H-tetrazole-5-sulfonyl)-thiazol-4-yl]-acetic acid
[2-[3-(2-Cyclopentanecarbonyl-phenyl)-ureido]-5-(1H-tetrazole-5-sulfonyl)-thiazol-4-yl]-acetic acid
[2-[3-(4-Chloro-2-cyclopentanecarbonyl-phenyl)-ureido]-5-(1H-tetrazole-5-sulfonyl)-thiazol-4-yl]-acetic acid
[2-[3-(2-Cyclopentanecarbonyl-4-fluoro-phenyl)-ureido]-5-(1H-tetrazole-5-sulfonyl)-thiazol-4-yl]-acetic acid
[2-[3-(2-Cyclopentanecarbonyl-4-trifluoromethyl-phenyl)-ureido]-5-(1H-tetrazole-5-sulfonyl)-thiazol-4-yl]-acetic acid
[2-[3-(2-Cyclopentanecarbonyl-4-methoxy-phenyl)-ureido]-5-(1H-tetrazole-5-sulfonyl)-thiazol-4-yl]-acetic acid
[2-[3-(2-Cyclopentanecarbonyl-4-dimethylamino-phenyl)-ureido]-5-(1H-tetrazole-5-sulfonyl)-thiazol-4-yl]-acetic acid
[2-[3-(2-Cyclopentanecarbonyl-4-morpholin-4-yl-phenyl)-ureido]-5-(1H-tetrazole-5-sulfonyl)-thiazol-4-yl]-acetic acid
[2-[3-(3-Cyclopentanecarbonyl-pyridin-4-yl)-ureido]-5-(1H-tetrazole-5-sulfonyl)-thiazol-4-yl]-acetic acid
[2-[3-(4-Cyclopentanecarbonyl-pyridin-3-yl)-ureido]-5-(1H-tetrazole-5-sulfonyl)-thiazol-4-yl]-acetic acid
[2-[3-(3-Cyclopentanecarbonyl-pyridin-2-yl)-ureido]-5-(1H-tetrazole-5-sulfonyl)-thiazol-4-yl]-acetic acid
1-(5-Chloro-4-phenylsulfanylmethyl-thiazol-2-yl)-3-(2-cyclopentanecarbonyl-4-methyl-phenyl)-urea
1-(5-Chloro-4-phenylsulfanylmethyl-thiazol-2-yl)-3-(2-cyclopentanecarbonyl-phenyl)-urea
1-(4-Chloro-2-cyclopentanecarbonyl-phenyl)-3-(5-chloro-4-phenylsulfanylmethyl-thiazol-2-yl)-urea
1-(5-Chloro-4-phenylsulfanylmethyl-thiazol-2-yl)-3-(2-cyclopentanecarbonyl-4-fluoro-phenyl)-urea
1-(5-Chloro-4-phenylsulfanylmethyl-thiazol-2-yl)-3-(2-cyclopentanecarbonyl-4-trifluoromethyl-phenyl)-urea
1-(5-Chloro-4-phenylsulfanylmethyl-thiazol-2-yl)-3-(2-cyclopentanecarbonyl-4-methoxy-phenyl)-urea
1-(5-Chloro-4-phenylsulfanylmethyl-thiazol-2-yl)-3-(2-cyclopentanecarbonyl-4-dimethylamino-phenyl)-urea
1-(5-Chloro-4-phenylsulfanylmethyl-thiazol-2-yl)-3-(2-cyclopentanecarbonyl-4-morpholin-4-yl-phenyl)-urea
1-(5-Chloro-4-phenylsulfanylmethyl-thiazol-2-yl)-3-(3-cyclopentanecarbonyl-pyridin-4-yl)urea
1-(5-Chloro-4-phenylsulfanylmethyl-thiazol-2-yl)-3-(4-cyclopentanecarbonyl-pyridin-3-yl)-urea
1-(5-Chloro-4-phenylsulfanylmethyl-thiazol-2-yl)-3-(3-cyclopentanecarbonyl-pyridin-2-yl)-urea
1-(5-Bromo-4-phenylsulfanylmethyl-thiazol-2-yl)-3-(2-cyclopentanecarbonyl-4-methyl-phenyl)-urea
1-(5-Bromo-4-phenylsulfanylmethyl-thiazol-2-yl)-3-(2-cyclopentanecarbonyl-phenyl)-urea
1-(5-Bromo-4-phenylsulfanylmethyl-thiazol-2-yl)-3-(4-chloro-2-cyclopentanecarbonyl-phenyl)-urea
1-(5-Bromo-4-phenylsulfanylmethyl-thiazol-2-yl)-3-(2-cyclopentanecarbonyl-4-fluoro-phenyl)-urea
1-(5-Bromo-4-phenylsulfanylmethyl-thiazol-2-yl)-3-(2-cyclopentanecarbonyl-4-trifluoromethyl-phenyl)-urea
1-(5-Bromo-4-phenylsulfanylmethyl-thiazol-2-yl)-3-(2-cyclopentanecarbonyl-4-methoxy-phenyl)-urea
1-(5-Bromo-4-phenylsulfanylmethyl-thiazol-2-yl)-3-(2-cyclopentanecarbonyl-4-dimethylamino-phenyl)-urea
1-(5-Bromo-4-phenylsulfanylmethyl-thiazol-2-yl)-3-(2-cyclopentanecarbonyl-4-morpholin-4-yl-phenyl)-urea
1-(5-Bromo-4-phenylsulfanylmethyl-thiazol-2-yl)-3-(3-cyclopentanecarbonyl-pyridin-4-yl)-urea
1-(5-Bromo-4-phenylsulfanylmethyl-thiazol-2-yl)-3-(4-cyclopentanecarbonyl-pyridin-3-yl)-urea
1-(5-Bromo-4-phenylsulfanylmethyl-thiazol-2-yl)-3-(3-cyclopentanecarbonyl-pyridin-2-yl)-urea
1-(2-Cyclopentanecarbonyl-4-methyl-phenyl)-3-(5-methylsulfanyl-4-phenylsulfanylmethyl-thiazol-2-yl)-urea
1-(2-Cyclopentanecarbonyl-phenyl)-3-(5-methylsulfanyl-4-phenylsulfanylmethyl-thiazol-2-yl)-urea
1-(4-Chloro-2-cyclopentanecarbonyl-phenyl)-3-(5-methylsulfanyl-4-phenylsulfanylmethyl-thiazol-2-yl)-urea
1-(2-Cyclopentanecarbonyl-4-fluoro-phenyl)-3-(5-methylsulfanyl-4-phenylsulfanylmethyl-thiazol-2-yl)-urea
1-(2-Cyclopentanecarbonyl-4-trifluoromethyl-phenyl)-3-(5-methylsulfanyl-4-phenylsulfanylmethyl-thiazol-2-yl)-urea
1-(2-Cyclopentanecarbonyl-4-methoxy-phenyl)-3-(5-methylsulfanyl-4-phenylsulfanylmethyl-thiazol-2-yl)-urea
1-(2-Cyclopentanecarbonyl-4-dimethylamino-phenyl)-3-(5-methylsulfanyl-4-phenylsulfanylmethyl-thiazol-2-yl)-urea
1-(2-Cyclopentanecarbonyl-4-morpholin-4-yl-phenyl)-3-(5-methylsulfanyl-4-phenylsulfanylmethyl-thiazol-2-yl)-urea
1-(3-Cyclopentanecarbonyl-pyridin-4-yl)-3-(5-methylsulfanyl-4-phenylsulfanylmethyl-thiazol-2-yl)-urea
1-(4-Cyclopentanecarbonyl-pyridin-3-yl)-3-(5-methylsulfanyl-4-phenylsulfanylmethyl-thiazol-2-yl)-urea
1-(3-Cyclopentanecarbonyl-pyridin-2-yl)-3-(5-methylsulfanyl-4-phenylsulfanylmethyl-thiazol-2-yl)-urea
1-(2-Cyclopentanecarbonyl-4-methyl-phenyl)-3-(5-methanesulfonyl-4-phenylsulfanylmethyl-thiazol-2-yl)-urea
1-(2-Cyclopentanecarbonyl-phenyl)-3-(5-methanesulfonyl-4-phenylsulfanylmethyl-thiazol-2-yl)-urea
1-(4-Chloro-2-cyclopentanecarbonyl-phenyl)-3-(5-methanesulfonyl-4-phenylsulfanylmethyl-thiazol-2-yl)-urea
1-(2-Cyclopentanecarbonyl-4-fluoro-phenyl)-3-(5-methanesulfonyl-4-phenylsulfanylmethyl-thiazol-2-yl)-urea
1-(2-Cyclopentanecarbonyl-4-trifluoromethyl-phenyl)-3-(5-methanesulfonyl-4-phenylsulfanylmethyl-thiazol-2-yl)-urea
1-(2-Cyclopentanecarbonyl-4-methoxy-phenyl)-3-(5-methanesufonyl-4-phenylsulfanylmethyl-thiazol-2-yl)-urea 1-(2-Cyclopentanecarbonyl-4-dimethylamino-phenyl)-3-(5-methanesufonyl-4-phenylsulfanylmethyl-thiazol-2-yl)-urea
1-(2-Cyclopentanecarbonyl-4-morpholin-4-yl-phenyl)-3-(5-methanesulfonyl-4-phenylsulfanylmethyl-thiazol-2-yl)-urea
1-(3-Cyclopentanecarbonyl-pyridin-4-yl)-3-(5-methanesulfonyl-4-phenylsulfanylmethyl-thiazol-2-yl)-urea
1-(4-Cyclopentanecarbonyl-pyridin-3-yl)-3-(5-methanesulfonyl-4-phenylsulfanylmethyl-thiazol-2-yl)-urea
1-(3-Cyclopentanecarbonyl-pyridin-2-yl)-3-(5-methanesufonyl-4-phenylsulfanylmethyl-thiazol-2-yl)-urea
1-(2-Cyclopentanecarbonyl-4-methyl-phenyl)-3-[4-phenylsulfanylmethyl-5-(pyridin-2-ylsulfanyl)-thiazol-2-yl]-urea
1-(2-Cyclopentanecarbonyl-phenyl)-3-[4-phenylsulfanylmethyl-5-(pyridin-2-ylsulfanyl)-thiazol-2-yl]-urea
1-(4-Chloro-2-cyclopentanecarbonyl-phenyl)-3-[4-phenylsulfanylmethyl-5-(pyridin-2-ylsulfanyl)-thiazol-2-yl]-urea
1-(2-Cyclopentanecarbonyl-4-fluoro-phenyl)-3-[4-phenylsulfanylmethyl-5-(pyridin-2-ylsulfanyl)-thiazol-2-yl]-urea
1-(2-Cyclopentanecarbonyl-4-trifluoromethyl-phenyl)-3-[4-phenylsulfanylmethyl-5-(pyridin-2-ylsulfanyl)-thiazol-2-yl]-urea
1-(2-Cyclopentanecarbonyl-4-methoxy-phenyl)-3-[4-phenylsulfanylmethyl-5-(pyridin-2-ylsulfanyl)-thiazol-2-yl]-urea
1-(2-Cyclopentanecarbonyl-4-dimethylamino-phenyl)-3-[4-phenylsulfanylmethyl-5-(pyridin-2-ylsulfanyl)-thiazol-2-yl]-urea
1-(2-Cyclopentanecarbonyl-4-morpholin-4-yl-phenyl)-3-[4-phenylsulfanylmethyl-5-(pyridin-2-ylsulfanyl)-thiazol-2-yl]-urea
1-(3-Cyclopentanecarbonyl-pyridin-4-yl)-3-[4-phenylsulfanylmethyl-5-(pyridin-2-ylsulfanyl)-thiazol-2-yl]-urea
1-(4-Cyclopentanecarbonyl-pyridin-3-yl)-3-[4-phenylsulfanylmethyl-5-(pyridin-2-ylsulfanyl)-thiazol-2-yl]-urea
1-(3-Cyclopentanecarbonyl-pyridin-2-yl)-3-[4-phenylsulfanylmethyl-5-(pyridin-2-ylsulfanyl)-thiazol-2-yl]-urea
1-(2-Cyclopentanecarbonyl-4-methyl-phenyl)-3-[4-phenylsulfanylmethyl-5-(pyridine-2-sulfonyl)-thiazol-2-yl]-urea
1-(2-Cyclopentanecarbonyl-phenyl)-3-[4-phenylsulfanylmethyl-5-(pyridine-2-sulfonyl)-thiazol-2-yl]-urea
1-(4-Chloro-2-cyclopentanecarbonyl-phenyl)-3-[4-phenylsulfanylmethyl-5-(pyridine-2-sulfonyl)-thiazol-2-yl]-urea
1-(2-Cyclopentanecarbonyl-4-fluoro-phenyl)-3-[4-phenylsulfanylmethyl-5-(pyridine-2-sulfonyl)-thiazol-2-yl]-urea
1-(2-Cyclopentanecarbonyl-4-trifluoromethyl-phenyl)-3-[4-phenylsulfanylmethyl-5-(pyridine-2-sulfonyl)-thiazol-2-yl]-urea
1-(2-Cyclopentanecarbonyl-4-methoxy-phenyl)-3-[4-phenylsulfanylmethyl-5-(pyridine-2-sulfonyl)-thiazol-2-yl]-urea
1-(2-Cyclopentanecarbonyl-4-dimethylamino-phenyl)-3-[4-phenylsulfanylmethyl-5-(pyridine-2-sulfonyl)-thiazol-2-yl]-urea
1-(2-Cyclopentanecarbonyl-4-morpholin-4-yl-phenyl)-3-[4-phenylsulfanylmethyl-5-(pyridine-2-sulfonyl)-thiazol-2-yl]-urea
1-(3-Cyclopentanecarbonyl-pyridin-4-yl)-3-[4-phenylsulfanylmethyl-5-(pyridine-2-sulfonyl)-thiazol-2-yl]-urea
1-(4-Cyclopentanecarbonyl-pyridin-3-yl)-3-[4-phenylsulfanylmethyl-5-(pyridine-2-sulfonyl)-thiazol-2-yl]-urea
1-(3-Cyclopentanecarbonyl-pyridin-2-yl)-3-[4-phenylsulfanylmethyl-5-(pyridine-2-sulfonyl)-thiazol-2-yl]-urea
1-(2-Cyclopentanecarbonyl-4-methyl-phenyl)-3-[5-(1H-imidazol-2-ylsulfanyl)-4-phenylsulfanylmethyl-thiazol-2-yl]-urea
1-(2-Cyclopentanecarbonyl-phenyl)-3-[5-(1H-imidazol-2-ylsulfanyl)-4-phenylsulfanylmethyl-thiazol-2-yl]-urea
1-(4-Chloro-2-cyclopentanecarbonyl-phenyl)-3-[5-(1H-imidazol-2-ylsulfanyl)-4-phenylsulfanylmethyl-thiazol-2-yl]-urea
1-(2-Cyclopentanecarbonyl-4-fluoro-phenyl)-3-[5-(1H-imidazol-2-ylsulfanyl)-4-phenylsulfanylmethyl-thiazol-2-yl]-urea
1-(2-Cyclopentanecarbonyl-4-trifluoromethyl-phenyl)-3-[5-(1H-imidazol-2-ylsulfanyl)-4-phenylsulfanylmethyl-thiazol-2-yl]-urea
1-(2-Cyclopentanecarbonyl-4-methoxy-phenyl)-3-[5-(1H-imidazol-2-ylsulfanyl)-4-phenylsulfanylmethyl-thiazol-2-yl]-urea
1-(2-Cyclopentanecarbonyl-4-dimethylamino-phenyl)-3-[5-(1H-imidazol-2-ylsulfanyl)-4-phenylsulfanylmethyl-thiazol-2-yl]-urea
1-(2-Cyclopentanecarbonyl-4-morpholin-4-yl-phenyl)-3-[5-(1H-imidazol-2-ylsulfanyl)-4-phenylsulfanylmethyl-thiazol-2-yl]-urea
1-(3-Cyclopentanecarbonyl-pyridin-4-yl)-3-[5-(1H-imidazol-2-ylsulfanyl)-4-phenylsulfanylmethyl-thiazol-2-yl]-urea
1-(4-Cyclopentanecarbonyl-pyridin-3-yl)-3-[5-(1H-imidazol-2-ylsulfanyl)-4-phenylsulfanylmethyl-thiazol-2-yl]-urea
1-(3-Cyclopentanecarbonyl-pyridin-2-yl)-3-[5-(1H-imidazol-2-ylsulfanyl)-4-phenylsulfanylmethyl-thiazol-2-yl]-urea
1-(2-Cyclopentanecarbonyl-4-methyl-phenyl)-3-[5-(1H-imidazole-2-sulfonyl)-4-phenylsulfanylmethyl-thiazol-2-yl]-urea
1-(2-Cyclopentanecarbonyl-phenyl)-3-[5-(1H-imidazole-2-sulfonyl)-4-phenylsulfanylmethyl-thiazol-2-yl]-urea
1-(4-Chloro-2-cyclopentanecarbonyl-phenyl)-3-[5-(1H-imidazole-2-sulfonyl)-4-phenylsulfanylmethyl-thiazol-2-yl]-urea
1-(2-Cyclopentanecarbonyl-4-fluoro-phenyl)-3-[5-(1H-imidazole-2-sulfonyl)-4-phenylsulfanylmethyl-thiazol-2-yl]-urea
1-(2-Cyclopentanecarbonyl-4-trifluoromethyl-phenyl)-3-[5-(1H-imidazole-2-sulfonyl)-4-phenylsulfanylmethyl-thiazol-2-yl]-urea
1-(2-Cyclopentanecarbonyl-4-methoxy-phenyl)-3-[5-(1H-imidazole-2-sulfonyl)-4-phenylsulfanylmethyl-thiazol-2-yl]-urea
1-(2-Cyclopentanecarbonyl-4-dimethylamino-phenyl)-3-[5-(1H-imidazole-2-sulfonyl)-4-phenylsulfanylmethyl-thiazol-2-yl]-urea
1-(2-Cyclopentanecarbonyl-4-morpholin-4-yl-phenyl)-3-[5-(1H-imidazole-2-sulfonyl)-4-phenylsulfanylmethyl-thiazol-2-yl]-urea
1-(3-Cyclopentanecarbonyl-pyridin-4-yl)-3-[5-(1H-imidazole-2-sulfonyl)-4-phenylsulfanylmethyl-thiazol-2-yl]-urea
1-(4-Cyclopentanecarbonyl-pyridin-3-yl)-3-[5-(1H-imidazole-2-sulfonyl)-4-phenylsulfanylmethyl-thiazol-2-yl]-urea
1-(3-Cyclopentanecarbonyl-pyridin-2-yl)-3-[5-(1H-imidazole-2-sulfonyl)-4-phenylsulfanylmethyl-thiazol-2-yl]-urea
1-(2-Cyclopentanecarbonyl-4-methyl-phenyl)-3-[5-(1-methyl-1H-tetrazol-5-ylsulfanyl)-4-phenylsulfanylmethyl-thiazol-2-yl]-urea 1-(2-Cyclopentanecarbonyl-phenyl)-3-[5-(1-methyl-1H-tetrazol-5-ylsulfanyl)-4-phenylsulfanylmethyl-thiazol-2-yl]-urea 1-(4-Chloro-2-cyclopentanecarbonyl-phenyl)-3-[5-(1-methyl-1H-tetrazol-5-ylsulfanyl)-4-phenylsulfanylmethyl-thiazol-2-yl]-urea 1-(2-Cyclopentanecarbonyl-4-fluoro-phenyl)-3-[5-(1-methyl-1H-tetrazol-5-ylsulfanyl)-4-phenylsulfanylmethyl-thiazol-2-yl]-urea 1-(2-Cyclopentanecarbonyl-4-trifluoromethyl-phenyl)-3-[5-(1-methyl-1H-tetrazol-5-ylsulfanyl)-4-phenylsulfanylmethyl-thiazol-2-yl]-urea 1-(2-Cyclopentanecarbonyl-4-methoxy-phenyl)-3-[5-(1-methyl-1H-tetrazol-5-ylsulfanyl)-4-phenylsulfanylmethyl-thiazol-2-yl]-urea 1-(2-Cyclopentanecarbonyl-4-dimethylamino-phenyl)-3-[5-(1-methyl-1H-tetrazol-5-ylsulfanyl)-4-phenylsulfanylmethyl-thiazol-2-yl]-urea 1-(2-Cyclopentanecarbonyl-4-morpholin-4-yl-phenyl)-3-[5-(1-methyl-1H-tetrazol-5-ylsulfanyl)-4-phenylsulfanylmethyl-thiazol-2-yl]-urea 1-(3-Cyclopentanecarbonyl-pyridin-4-yl)-3-[5-(1-methyl-1H-tetrazol-5-ylsulfanyl)-4-phenylsulfanylmethyl-thiazol-2-yl]-urea 1-(4-Cyclopentanecarbonyl-pyridin-3-yl)-3-[5-(1-methyl-1H-tetrazol-5-ylsulfanyl)-4-phenylsulfanylmethyl-thiazol-2-yl]-urea 1-(3-Cyclopentanecarbonyl-pyridin-2-yl)-3-[5-(1-methyl-1H-tetrazol-5-ylsulfanyl)-4-phenylsulfanylmethyl-thiazol-2-yl]-urea 1-(2-Cyclopentanecarbonyl-4-methyl-phenyl)-3-[5-(1-methyl-1H-tetrazole-5-sulfonyl)-4-phenylsulfanylmethyl-thiazol-2-yl]-urea 1-(2-Cyclopentanecarbonyl-phenyl)-3-[5-(1-methyl-1H-tetrazole-5-sulfonyl)-4-phenylsulfanylmethyl-thiazol-2-yl]-urea 1-(4-Chloro-2-cyclopentanecarbonyl-phenyl)-3-[5-(1-methyl-1H-tetrazole-5-sulfonyl)-4-phenylsulfanylmethyl-thiazol-2-yl]-urea 1-(2-Cyclopentanecarbonyl-4-fluoro-phenyl)-3-[5-(1-methyl-1H-tetrazole-5-sulfonyl)-4-phenylsulfanylmethyl-thiazol-2-yl]-urea 1-(2-Cyclopentanecarbonyl-4-trifluoromethyl-phenyl)-3-[5-(1-methyl-1H-tetrazole-5-sulfonyl)-4-phenylsulfanylmethyl-thiazol-2-yl]-urea 1-(2-Cyclopentanecarbonyl-4-methoxy-phenyl)-3-[5-(1-methyl-1H-tetrazole-5-sulfonyl)-4-phenylsulfanylmethyl-thiazol-2-yl]-urea 1-(2-Cyclopentanecarbonyl-4-dimethylamino-phenyl)-3-[5-(1-methyl-1H-tetrazole-5-sulfonyl)-4-phenylsulfanylmethyl-thiazol-2-yl]-urea 1-(2-Cyclopentanecarbonyl-4-morpholin-4-yl-phenyl)-3-[5-(1-methyl-1H-tetrazole-5-sulfonyl)-4-phenylsulfanylmethyl-thiazol-2-yl]-urea 1-(3-Cyclopentanecarbonyl-pyridin-4-yl)-3-[5-(1-methyl-1H-tetrazole-5-sulfonyl)-4-phenylsulfanylmethyl-thiazol-2-yl]-urea 1-(4-Cyclopentanecarbonyl-pyridin-3-yl)-3-[5-(1-methyl-1H-tetrazole-5-sulfonyl)-4-phenylsulfanylmethyl-thiazol-2-yl]-urea 1-(3-Cyclopentanecarbonyl-pyridin-2-yl)-3-[5-(1-methyl-1H-tetrazole-5-sulfonyl)-4-phenylsulfanylmethyl-thiazol-2-yl]-urea 1-(2-Cyclopentanecarbonyl-4-methyl-phenyl)-3-[4-phenylsulfanylmethyl-5-(1H-tetrazole-5-sulfonyl)-thiazol-2-yl]-urea 1-(2-Cyclopentanecarbonyl-phenyl)-3-[4-phenylsulfanylmethyl-5-(1H-tetrazole-5-sulfonyl)-thiazol-2-yl]-urea 1-(4-Chloro-2-cyclopentanecarbonyl-phenyl)-3-[4-phenylsulfanylmethyl-5-(1H-tetrazole-5-sulfonyl)-thiazol-2-yl]-urea 1-(2-Cyclopentanecarbonyl-4-fluoro-phenyl)-3-[4-phenylsulfanylmethyl-5-(1H-tetrazole-5-sulfonyl)-thiazol-2-yl]-urea 1-(2-Cyclopentanecarbonyl-4-trifluoromethyl-phenyl)-3-[4-phenylsulfanylmethyl-5-(1H-tetrazole-5-sulfonyl)-thiazol-2-yl]-urea 1-(2-Cyclopentanecarbonyl-4-methoxy-phenyl)-3-[4-phenylsulfanylmethyl-5-(1H-tetrazole-5-sulfonyl)-thiazol-2-yl]-urea 1-(2-Cyclopentanecarbonyl-4-dimethylamino-phenyl)-3-[4-phenylsulfanylmethyl-5-(1H-tetrazole-5-sulfonyl)-thiazol-2-yl]-urea 1-(2-Cyclopentanecarbonyl-4-morpholin-4-yl-phenyl)-3-[4-phenylsulfanylmethyl-5-(H-tetrazole-5-sulfonyl)-thiazol-2-yl]-urea 1-(3-Cyclopentanecarbonyl-pyridin-4-yl)-3-[4-phenylsulfanylmethyl-5-(1H-tetrazole-5-sulfonyl)-thiazol-2-yl]-urea 1-(4-Cyclopentanecarbonyl-pyridin-3-yl)-3-[4-phenylsulfanylmethyl-5-(1H-tetrazole-5-sulfonyl)-thiazol-2-yl]-urea 1-(3-Cyclopentanecarbonyl-pyridin-2-yl)-3-[4-phenylsulfanylmethyl-5-(1H-tetrazole-5-sulfonyl)-thiazol-2-yl]-urea N-{5-Chloro-2-[3-(2-cyclopentanecarbonyl-4-methyl-phenyl)-ureido]-thiazol-4-ylmethyl}-methanesulfonamide N-{5-Chloro-2-[3-(2-cyclopentanecarbonyl-phenyl)-ureido]-thiazol-4-ylmethyl}-methanesulfonamide N-{5-Chloro-2-[3-(4-chloro-2-cyclopentanecarbonyl-phenyl)-ureido]-thiazol-4-ylmethyl}-methanesulfonamide N-{5-Chloro-2-[3-(2-cyclopentanecarbonyl-4-fluoro-phenyl)-ureido]-thiazol-4-ylmethyl}-methanesulfonamide N-{5-Chloro-2-[3-(2-cyclopentanecarbonyl-4-trifluoromethyl-phenyl)-ureido]-thiazol-4-ylmethyl}-methanesulfonamide N-{5-Chloro-2-[3-(2-cyclopentanecarbonyl-4-methoxy-phenyl)-ureido]-thiazol-4-ylmethyl}-methanesulfonamide N-{5-Chloro-2-[3-(2-cyclopentanecarbonyl-4-dimethylamino-phenyl)-ureido]-thiazol-4-ylmethyl}-methanesulfonamide N-{5-Chloro-2-[3-(2-cyclopentanecarbonyl-4-morpholin-4-yl-phenyl)-ureido]-thiazol-4-ylmethyl}-methanesulfonamide N-{5-Chloro-2-[3-(3-cyclopentanecarbonyl-pyridin-4-yl)-ureido]-thiazol-4-ylmethyl}-methanesulfonamide N-{5-Chloro-2-[3-(4-cyclopentanecarbonyl-pyridin-3-yl)-ureido]-thiazol-4-ylmethyl}-methanesulfonamide N-{5-Chloro-2-[3-(3-cyclopentanecarbonyl-pyridin-2-yl)-ureido]-thiazol-4-ylmethyl}-methanesulfonamide N-{5-Bromo-2-[3-(2-cyclopentanecarbonyl-4-methyl-phenyl)-ureido]-thiazol-4-ylmethyl}-methanesulfonamide N-{5-Bromo-2-[3-(2-cyclopentanecarbonyl-phenyl)-ureido]-thiazol-4-ylmethyl}-methanesulfonamide N-{5-Bromo-2-[3-(4-chloro-2-cyclopentanecarbonyl-phenyl)-ureido]-thiazol-4-ylmethyl}-methanesulfonamide N-{5-Bromo-2-[3-(2-cyclopentanecarbonyl-4-fluoro-phenyl)-ureido]-thiazol-4-ylmethyl}-methanesulfonamide N-{5-Bromo-2-[3-(2-cyclopentanecarbonyl-4-trifluoromethyl-phenyl)-ureido]-thiazol-4-ylmethyl}-methanesulfonamide N-{5-Bromo-2-[3-(2-cyclopentanecarbonyl-4-methoxy-phenyl)-ureido]-thiazol-4-ylmethyl}-methanesulfonamide N-{5-Bromo-2-[3-(2-cyclopentanecarbonyl-4-dimethylamino-phenyl)-ureido]-thiazol-4-ylmethyl}-methanesulfonamide N-{5-Bromo-2-[3-(2-cyclopentanecarbonyl-4-morpholin-4-yl-phenyl)-ureido]-thiazol-4-ylmethyl}-methanesulfonamide N-{5-Bromo-2-[3-(3-cyclopentanecarbonyl-pyridin-4-yl)-ureido]-thiazol-4-ylmethyl}-methanesulfonamide N-{5-Bromo-2-[3-(4-cyclopentanecarbonyl-pyridin-3-yl)-ureido]-thiazol-4-ylmethyl}-methanesulfonamide N-{5-Bromo-2-[3-(3-cyclopentanecarbonyl-pyridin-2-yl)-ureido]-thiazol-4-ylmethyl}-methanesulfonamide N-{2-[3-(2-Cyclopentanecarbonyl-4-methyl-phenyl)-ureido]-5-methylsulfanyl-thiazol-4-ylmethyl}-methanesulfonamide N-{2-[3-(2-Cyclopentanecarbonyl-phenyl)-ureido]-5-methylsulfanyl-thiazol-4-ylmethyl}-methanesulfonamide N-{2-[3-(4-Chloro-2-cyclopentanecarbonyl-phenyl)-ureido]-5-methylsulfanyl-thiazol-4-ylmethyl}-methanesulfonamide N-{2-[3-(2-Cyclopentanecarbonyl-4-fluoro-phenyl)-ureido]-5-methylsulfanyl-thiazol-4-ylmethyl}-methanesulfonamide N-{2-[3-(2-Cyclopentanecarbonyl-4-trifluoromethyl-phenyl)-ureido]-5-methylsulfanyl-thiazol-4-ylmethyl}-methanesulfonamide N-{2-[3-(2-Cyclopentanecarbonyl-4-methoxy-phenyl)-ureido]-5-methylsulfanyl-thiazol-4-ylmethyl}-methanesulfonamide N-{2-[3-(2-Cyclopentanecarbonyl-4-dimethylamino-phenyl)-ureido]-5-methylsulfanyl-thiazol-4-ylmethyl}-methanesulfonamide N-{2-[3-(2-Cyclopentanecarbonyl-4-morpholin-4-yl-phenyl)-ureido]-5-methylsulfanyl-thiazol-4-ylmethyl}-methanesulfonamide N-{2-[3-(3-Cyclopentanecarbonyl-pyridin-4-yl)-ureido]-5-methylsulfanyl-thiazol-4-ylmethyl}-methanesulfonamide N-{2-[3-(4-Cyclopentanecarbonyl-pyridin-3-yl)-ureido]-5-methylsulfanyl-thiazol-4-ylmethyl}-methanesulfonamide N-{2-[3-(3-Cyclopentanecarbonyl-pyridin-2-yl)-ureido]-5-methylsulfanyl-thiazol-4-ylmethyl}-methanesulfonamide N-{2-[3-(2-Cyclopentanecarbonyl-4-methyl-phenyl)-ureido]-5-methanesulfonyl-thiazol-4-ylmethyl}-methanesulfonamide N-{2-[3-(2-Cyclopentanecarbonyl-phenyl)-ureido]-5-methanesulfonyl-thiazol-4-ylmethyl}-methanesulfonamide N-{2-[3-(4-Chloro-2-cyclopentanecarbonyl-phenyl)-ureido]-5-methanesulfonyl-thiazol-4-ylmethyl}-methanesulfonamide N-{2-[3-(2-Cyclopentanecarbonyl-4-fluoro-phenyl)-ureido]-5-methanesulfonyl-thiazol-4-ylmethyl}-methanesulfonamide N-{2-[3-(2-Cyclopentanecarbonyl-4-trifluoromethyl-phenyl)-ureido]-5-methanesulfonyl-thiazol-4-ylmethyl}-methanesulfonamide N-{2-[3-(2-Cyclopentanecarbonyl-4-methoxy-phenyl)-ureido]-5-methanesulfonyl-thiazol-4-ylmethyl}-methanesulfonamide N-{2-[3-(2-Cyclopentanecarbonyl-4-dimethylamino-phenyl)-ureido]-5-methanesulfonyl-thiazol-4-ylmethyl}-methanesulfonamide N-{2-[3-2-Cyclopentanecarbonyl-4-morpholin-4-yl-phenyl)-ureido]-5-methanesulfonyl-thiazol-4-ylmethyl}-methanesulfonamide N-{2-[3-(3-Cyclopentanecarbonyl-pyridin-4-yl)-ureido]-5-methanesulfonyl-thiazol-4-ylmethyl}-methanesulfonamide N-{2-[3-4-Cyclopentanecarbonyl-pyridin-3-yl)-ureido]-5-methanesulfonyl-thiazol-4-ylmethyl}-methanesulfonamide N-{2-[3-(3-Cyclopentanecarbonyl-pyridin-2-yl)-ureido]-5-methanesulfonyl-thiazol-4-ylmethyl}-methanesulfonamide N-[2-[3-(2-Cyclopentanecarbonyl-4-methyl-phenyl)-ureido]-5-(pyridin-2-ylsulfanyl)-thiazol-4-ylmethyl]-methanesulfonamide N-[2-[3-(2-Cyclopentanecarbonyl-phenyl)-ureido]-5-(pyridin-2-ylsulfanyl)-thiazol-4-ylmethyl]-methanesulfonamide N-[2-[3-(4-Chloro-2-cyclopentanecarbonyl-phenyl)-ureido]-5-(pyridin-2-ylsulfanyl)-thiazol-4-ylmethyl]-methanesulfonamide N-[2-[3-(2-Cyclopentanecarbonyl-4-fluoro-phenyl)-ureido]-5-(pyridin-2-ylsulfanyl)-thiazol-4-ylmethyl]-methanesulfonamide N-[2-[3-(2-Cyclopentanecarbonyl-4-trifluoromethyl-phenyl)-ureido]-5-(pyridin-2-ylsulfanyl)-thiazol-4-ylmethyl]-methanesulfonamide N-[2-[3-(2-Cyclopentanecarbonyl-4-methoxy-phenyl)-ureido]-5-(pyridin-2-ylsulfanyl)-thiazol-4-ylmethyl]-methanesulfonamide N-[2-[3-(2-Cyclopentanecarbonyl-4-dimethylamino-phenyl)-ureido]-5-(pyridin-2-ylsulfanyl)-thiazol-4-ylmethyl]-methanesulfonamide N-[2-[3-(2-Cyclopentanecarbonyl-4-morpholin-4-yl-phenyl)-ureido]-5-(pyridin-2-ylsulfanyl)-thiazol-4-ylmethyl]-methanesulfonamide N-[2-[3-(3-Cyclopentanecarbonyl-pyridin-4-yl)-ureido]-5-(pyridin-2-ylsulfanyl)-thiazol-4-ylmethyl]-methanesulfonamide N-[2-[3-(4-Cyclopentanecarbonyl-pyridin-3-yl)-ureido]-5-(pyridin-2-ylsulfanyl)-thiazol-4-ylmethyl]-methanesulfonamide N-[2-[3-(3-Cyclopentanecarbonyl-pyridin-2-yl)-ureido]-5-(pyridin-2-ylsulfanyl)-thiazol-4-ylmethyl]-methanesulfonamide N-[2-[3-(2-Cyclopentanecarbonyl-4-methyl-phenyl)-ureido]-5-(pyridine-2-sulfonyl)-thiazol-4-ylmethyl]-methanesulfonamide N-[2-[3-(2-Cyclopentanecarbonyl-phenyl)-ureido]-5-(pyridine-2-sulfonyl)-thiazol-4-ylmethyl]-methanesulfonamide N-[2-[3-(4-Chloro-2-cyclopentanecarbonyl-phenyl)-ureido]-5-(pyridine-2-sulfonyl)-thiazol-4-ylmethyl]-methanesulfonamide N-[2-[3-(2-Cyclopentanecarbonyl-4-fluoro-phenyl)-ureido]-5-pyridine-2-sulfonyl)-thiazol-4-ylmethyl]-methanesulfonamide N-[2-[3-(2-Cyclopentanecarbonyl-4-trifluoromethyl-phenyl)-ureido]-5-(pyridine-2-sulfonyl)-thiazol-4-ylmethyl]-methanesulfonamide N-[2-[3-(2-Cyclopentanecarbonyl-4-methoxy-phenyl)-ureido]-5-(pyridine-2-sulfonyl)-thiazol-4-ylmethyl]-methanesulfonamide N-[2-[3-(2-Cyclopentanecarbonyl-4-dimethylamino-phenyl)-ureido]-5-(pyridine-2-sulfonyl)-thiazol-4-ylmethyl]-methanesulfonamide N-[2-[3-(2-Cyclopentanecarbonyl-4-morpholin-4-yl-phenyl)-ureido]-5-(pyridine-2-sulfonyl)-thiazol-4-ylmethyl]-methanesulfonamide N-[2-[3-(3-Cyclopentanecarbonyl-pyridin-4-yl)-ureido]-5-(pyridine-2-sulfonyl)-thiazol-4-ylmethyl]-methanesulfonamide N-[2-[3-(4-Cyclopentanecarbonyl-pyridin-3-yl)-ureido]-5-(pyridine-2-sulfonyl)-thiazol-4-ylmethyl]-methanesulfonamide N-[2-[3-(3-Cyclopentanecarbonyl-pyridin-2-yl)-ureido]-5-(pyridine-2-sulfonyl)-thiazol-4-ylmethyl]-methanesulfonamide N-[2-[3-(2-Cyclopentanecarbonyl-4-methyl-phenyl)-ureido]-5-(1H-imidazol-2-ylsulfanyl)-thiazol-4-ylmethyl]-methanesulfonamide N-[2-[3-(2-Cyclopentanecarbonyl-phenyl)-ureido]-5-(1H-imidazol-2-ylsulfanyl)-thiazol-4-ylmethyl]-methanesulfonamide N-[2-[3-(4-Chloro-2-cyclopentanecarbonyl-phenyl)-ureido]-5-(1H-imidazol-2-ylsulfanyl)-thiazol-4-ylmethyl]-methanesulfonamide N-[2-[3-(2-Cyclopentanecarbonyl-4-fluoro-phenyl)-ureido]-5-(1H-imidazol-2-ylsulfanyl)-thiazol-4-ylmethyl]-methanesulfonamide N-[2-[3-(2-Cyclopentanecarbonyl-4-trifluoromethyl-phenyl)-ureido]-5-(1H-imidazol-2-ylsulfanyl)-thiazol-4-ylmethyl]-methanesulfonamide N-[2-[3-(2-Cyclopentanecarbonyl-4-methoxy-phenyl)-ureido]-5-(1H-imidazol-2-ylsulfanyl)-thiazol-4-ylmethyl]-methanesulfonamide N-[2-[3-(2-Cyclopentanecarbonyl-4-dimethylamino-phenyl)-ureido]-5-(1H-imidazol-2-ylsulfanyl)-thiazol-4-ylmethyl]-methanesulfonamide N-[2-[3-(2-Cyclopentanecarbonyl-4-morpholin-4-yl-phenyl)-ureido]-5-(1H-imidazol-2-ylsulfanyl)-thiazol-4-ylmethyl]-methanesulfonamide N-[2-[3-(3-Cyclopentanecarbonyl-pyridin-4-yl)-ureido]-5-1H-imidazol-2-ylsulfanyl)-thiazol-4-ylmethyl]-methanesulfonamide N-[2-[3-4-Cyclopentanecarbonyl-pyridin-3-yl)-ureido]-5-(1H-imidazol-2-ylsulfanyl)-thiazol-4-ylmethyl]-methanesulfonamide N-[2-[3-(3-Cyclopentanecarbonyl-pyridin-2-yl)-ureido]-5-(1H-imidazol-2-ylsulfanyl)-thiazol-4-ylmethyl]-methanesulfonamide N-[2-[3-(2-Cyclopentanecarbonyl-4-methyl-phenyl)-ureido]-5-(1H-imidazole-2-sulfonyl)-thiazol-4-ylmethyl]-methanesulfonamide N-[2-[3-(2-Cyclopentanecarbonyl-phenyl)-ureido]-5-(1H-imidazole-2-sulfonyl)-thiazol-4-ylmethyl]-methanesulfonamide N-[2-[3-4-Chloro-2-cyclopentanecarbonyl-phenyl)-ureido]-5-(1H-imidazole-2-sulfonyl)-thiazol-4-ylmethyl]-methanesulfonamide N-[2-[3-(2-Cyclopentanecarbonyl-4-fluoro-phenyl)-ureido]-5-(1H-imidazole-2-sulfonyl)-thiazol-4-ylmethyl]-methanesulfonamide N-[2-[3-(2-Cyclopentanecarbonyl-4-trifluoromethyl-phenyl)-ureido]-5-(1H-imidazole-2-sulfonyl)-thiazol-4-ylmethyl]-methanesulfonamide N-[2-[3-(2-Cyclopentanecarbonyl-4-methoxy-phenyl)-ureido]-5-(1H-imidazole-2-sulfonyl)-thiazol-4-ylmethyl]-methanesulfonamide N-[2-[3-(2-Cyclopentanecarbonyl-4-dimethylamino-phenyl)-ureido]-5-(1H-imidazole-2-sulfonyl)-thiazol-4-ylmethyl]-methanesulfonamide N-[2-[3-(2-Cyclopentanecarbonyl-4-morpholin-4-yl-phenyl)-ureido]-5-(1H-imidazole-2-sulfonyl)-thiazol-4-ylmethyl]-methanesulfonamide N-[2-[3-(3-Cyclopentanecarbonyl-pyridin-4-yl)-ureido]-5-(1H-imidazole-2-sulfonyl)-thiazol-4-ylmethyl]-methanesulfonamide N-[2-[3-(4-Cyclopentanecarbonyl-pyridin-3-yl)-ureido]-5-(1H-imidazole-2-sulfonyl)thiazol-4-ylmethyl]-methanesulfonamide N-[2-[3-(3-Cyclopentanecarbonyl-pyridin-2-yl)-ureido]-5-(1H-imidazole-2-sulfonyl)-thiazol-4-ylmethyl]-methanesulfonamide N-[2-[3-(2-Cyclopentanecarbonyl-4-methyl-phenyl)-ureido]-5-(1-methyl-1H-tetrazol-5-ylsulfanyl)-thiazol-4-ylmethyl]-methanesulfonamide N-[2-[3-(2-Cyclopentanecarbonyl-phenyl)-ureido]-5-(1-methyl-1H-tetrazol-5-ylsulfanyl)-thiazol-4-ylmethyl]-methanesulfonamide N-[2-[3-(4-Chloro-2-cyclopentanecarbonyl-phenyl)-ureido]-5-(1-methyl-1H-tetrazol-5-ylsulfanyl)-thiazol-4-ylmethyl]-methanesulfonamide N-[2-[3-2-Cyclopentanecarbonyl-4-fluoro-phenyl)-ureido]-5-(1-methyl-1H-tetrazol-5-ylsulfanyl)-thiazol-4-ylmethyl]-methanesulfonamide N-[2-[3-(2-Cyclopentanecarbonyl-4-trifluoromethyl-phenyl)-ureido]-5-(1-methyl-1H-tetrazol-5-ylsulfanyl)-thiazol-4-ylmethyl]-methanesulfonamide N-[2-[3-2-Cyclopentanecarbonyl-4-methoxy-phenyl)-ureido]-5-(1-methyl-1H-tetrazol-5-ylsulfanyl)-thiazol-4-ylmethyl]-methanesulfonamide N-[2-[3-(2-Cyclopentanecarbonyl-4-dimethylamino-phenyl)-ureido]-5-(1-methyl-1H-tetrazol-5-ylsulfanyl)-thiazol-4-ylmethyl]-methanesulfonamide N-[2-[3-(2-Cyclopentanecarbonyl-4-morpholin-4-yl-phenyl)-ureido]-5-(1-methyl-1H-tetrazol-5-ylsulfanyl)-thiazol-4-ylmethyl]-methanesulfonamide N-[2-[3-(3-Cyclopentanecarbonyl-pyridin-4-yl)-ureido]-5-(1-methyl-1H-tetrazol-5-ylsulfanyl)-thiazol-4-ylmethyl]-methanesulfonamide N-[2-[3-(4-Cyclopentanecarbonyl-pyridin-3-yl)-ureido]-5-(1-methyl-1H-tetrazol-5-ylsulfanyl)-thiazol-4-ylmethyl]-methanesulfonamide N-[2-[3-(3-Cyclopentanecarbonyl-pyridin-2-yl)-ureido]-5-(1-methyl-1H-tetrazol-5-ylsulfanyl)-thiazol-4-ylmethyl]-methanesulfonamide N-[2-[3-(2-Cyclopentanecarbonyl-4-methyl-phenyl)-ureido]-5-(1-methyl-1H-tetrazole-5-sulfonyl)-thiazol-4-ylmethyl]-methanesulfonamide N-[2-[3-(2-Cyclopentanecarbonyl-phenyl)-ureido]-5-(1-methyl-1H-tetrazole-5-sulfonyl)-thiazol-4-ylmethyl]-methanesulfonamide N-[2-[3-(4-Chloro-2-cyclopentanecarbonyl-phenyl)-ureido]-5-(1-methyl-1H-tetrazole-5-sulfonyl)-thiazol-4-ylmethyl]-methanesulfonamide N-[2-[3-(2-Cyclopentanecarbonyl-4-fluoro-phenyl)-ureido]-5-(1-methyl-1H-tetrazole-5-sulfonyl)-thiazol-4-ylmethyl]-methanesulfonamide N-[2-[3-(2-Cyclopentanecarbonyl-4-trifluoromethyl-phenyl)-ureido]-5-(1-methyl-1H-tetrazole-5-sulfonyl)-thiazol-4-ylmethyl]-methanesulfonamide N-[2-[3-(2-Cyclopentanecarbonyl-4-methoxy-phenyl)-ureido]-5-(1-methyl-1H-tetrazole-5-sulfonyl)-thiazol-4-ylmethyl]-methanesulfonamide N-[2-[3-(2-Cyclopentanecarbonyl-4-dimethylamino-phenyl)-ureido]-5-(1-methyl-1H-tetrazole-5-sulfonyl)-thiazol-4-ylmethyl]-methanesulfonamide N-[2-[3-(2-Cyclopentanecarbonyl-4-morpholin-4-yl-phenyl)-ureido]-5-(1-methyl-1H-tetrazole-5-sulfonyl)-thiazol-4-ylmethyl]-methanesulfonamide N-[2-[3-(3-Cyclopentanecarbonyl-pyridin-4-yl)-ureido]-5-(1-methyl-1H-tetrazole-5-sulfonyl)-thiazol-4-ylmethyl]-methanesulfonamide N-[2-[3-4-Cyclopentanecarbonyl-pyridin-3-yl)-ureido]-5-(1-methyl-1H-tetrazole-5-sulfonyl)-thiazol-4-ylmethyl]-methanesulfonamide N-[2-[3-(3-Cyclopentanecarbonyl-pyridin-2-yl)-ureido]-5-(1-methyl-1H-tetrazole-5-sulfonyl)-thiazol-4-ylmethyl]-methanesulfonamide N-[2-[3-2-Cyclopentanecarbonyl-4-methyl-phenyl)-ureido]-5-(1H-tetrazole-5-sulfonyl)-thiazol-4-ylmethyl]-methanesulfonamide N-[2-[3-(2-Cyclopentanecarbonyl-phenyl)-ureido]-5-(1H-tetrazole-5-sulfonyl)-thiazol-4-ylmethyl]-methanesulfonamide N-[2-[3-(4-Chloro-2-cyclopentanecarbonyl-phenyl)-ureido]-5-(1H-tetrazole-5-sulfonyl)-thiazol-4-ylmethyl]-methanesulfonamide N-[2-[3-(2-Cyclopentanecarbonyl-4-fluoro-phenyl)-ureido]-5-(1H-tetrazole-5-sulfonyl)-thiazol-4-ylmethyl]-methanesulfonamide N-[2-[3-(2-Cyclopentanecarbonyl-4-trifluoromethyl-phenyl)-ureido]-5-(1H-tetrazole-5-sulfonyl)-thiazol-4-ylmethyl]-methanesulfonamide N-[2-[3-(2-Cyclopentanecarbonyl-4-methoxy-phenyl)-ureido]-5-(1H-tetrazole-5-sulfonyl)-thiazol-4-ylmethyl]-methanesulfonamide N-[2-[3-(2-Cyclopentanecarbonyl-4-dimethylamino-phenyl)-ureido]-5-(1H-tetrazole-5-sulfonyl)-thiazol-4-ylmethyl]-methanesulfonamide N-[2-[3-(2-Cyclopentanecarbonyl-4-morpholin-4-yl-phenyl)-ureido]-5-(1H-tetrazole-5-sulfonyl)-thiazol-4-ylmethyl]-methanesulfonamide N-[2-[3-(3-Cyclopentanecarbonyl-pyridin-4-yl)-ureido]-5-(1H-tetrazole-5-sulfonyl)-thiazol-4-ylmethyl]-methanesulfonamide N-[2-[3-(4-Cyclopentanecarbonyl-pyridin-3-yl)-ureido]-5-(1H-tetrazole-5-sulfonyl)-thiazol-4-ylmethyl]-methanesulfonamide N-[2-[3-(3-Cyclopentanecarbonyl-pyridin-2-yl)-ureido]-5-(1H-tetrazole-5-sulfonyl)-thiazol-4-ylmethyl]-methanesulfonamide N-(2-cyclopentanecarbonyl-phenyl)-N'-thiazol-2-yl-oxalamide N-(5-bromo-thiazol-2-yl)-N'-(2-cyclopentanecarbonyl-phenyl)-oxalamide N-(5-chloro-thiazol-2-yl)-N'-(2-cyclopentanecarbonyl-phenyl)-oxalamide 4; N-(2-cyclopentanecarbonyl-phenyl)-N'-(5-methylsulfanyl-thiazol-2-yl)-oxalamide N-(2-cyclopentanecarbonyl-phenyl)-N'-(5-methanesulfonyl-thiazol-2-yl)-oxalamide N-(2-cyclopentanecarbonyl-phenyl)-N'-[5-(pyridin-2-ylsulfanyl)-thiazol-2-yl]-oxalamide N-(2-cyclopentanecarbonyl-phenyl)-N'-[5-(1H-imidazol-2-ylsulfanyl)-thiazol-2-yl]-oxalamide {5-bromo-2-[(2-cyclopentanecarbonyl-phenylaminooxalyl)-amino]-thiazol-4-yl}-acetic acid {5-chloro-2-[(2-cyclopentanecarbonyl-phenylaminooxalyl)-amino]-thiazol-4-yl}acetic acid {2-[(2-cyclopentanecarbonyl-phenylaminooxalyl)-amino]-5-methylsulfanyl-thiazol-4-yl}-acetic acid {2-[(2-cyclopentanecarbonyl-phenylaminooxalyl)-amino]-5-methanesulfonyl-thiazol-4-yl}-acetic acid

[2-[(2-cyclopentanecarbonyl-phenylaminooxalyl)-amino]-5-(pyridin-2-ylsulfanyl)-thiazol-4-yl]-acetic acid

[2-[(2-cyclopentanecarbonyl-phenylaminooxalyl)-amino]-5-(1H-imidazol-2-ylsulfanyl)-thiazol-4-yl]-acetic acid N-(2-cyclopentanecarbonyl-phenyl)-N'-[4-(methanesulfonylamino-methyl)-thiazol-2-yl]-oxalamide N-[5-bromo-4-(methanesulfonylamino-methyl)-thiazol-2-yl]-N'-(2-cyclopentanecarbonyl-phenyl)-oxalamide N-[5-chloro-4-(methanesulfonylamino-methyl)-thiazol-2-yl]-N'-(2-cyclopentanecarbonyl-phenyl)-oxalamide N-(2-cyclopentanecarbonyl-phenyl)-N'-[4-(methanesulfonylamino-methyl)-5-methylsulfanyl-thiazol-2-yl]-oxalamide N-(2-cyclopentanecarbonyl-phenyl)-N'-[5-methanesulfonyl-4-(methanesulfonylamino-methyl)-thiazol-2-yl]-oxalamide N-(2-cyclopentanecarbonyl-phenyl)-N'-[4-(methanesulfonylamino-methyl)-5-(pyridin-2-ylsulfanyl)-thiazol-2-yl]-oxalamide N-(2-cyclopentanecarbonyl-phenyl)-N'-[5-(1H-imidazol-2-ylsulfanyl)-4-(methanesulfonylamino-methyl)-thiazol-2-yl]-oxalamide N-(2-cyclopentanecarbonyl-phenyl)-N'-thiazol-2-yl-malonamide N-(5-bromo-thiazol-2-yl)-N'-(2-cyclopentanecarbonyl-phenyl)-malonamide N-(5-chloro-thiazol-2-yl)-N'-(2-cyclopentanecarbonyl-phenyl)-malonamide N-(2-cyclopentanecarbonyl-phenyl)-N'-(5-methylsulfanyl-thiazol-2-yl)-malonamide N-(2-cyclopentanecarbonyl-phenyl)-N'-(5-methanesulfonyl-thiazol-2-yl)-malonamide N-(2-cyclopentanecarbonyl-phenyl)-N'-[5-(pyridin-2-ylsulfanyl)-thiazol-2-yl]-malonamide N-(2-cyclopentanecarbonyl-phenyl)-N'-[5-(1H-imidazol-2-ylsulfanyl)-thiazol-2-yl]-malonamide {2-[2-(2-cyclopentanecarbonyl-phenylcarbamoyl)-acetylamino]-thiazol-4-yl}-acetic acid {5-bromo-2-[2-(2-cyclopentanecarbonyl-phenylcarbamoyl)-acetylamino]-thiazol-4-yl}-acetic acid {5-chloro-2-[2-(2-cyclopentanecarbonyl-phenylcarbamoyl)-acetylamino]-thiazol-4-yl)acetic acid {2-[2-(2-cyclopentanecarbonyl-phenylcarbamoyl)-acetylamino]-5-methylsulfanyl-thiazol-4-yl}-acetic acid {2-[2-(2-cyclopentanecarbonyl-phenylcarbamoyl)-acetylamino]-5-methanesulfonyl-thiazol-4-yl}-acetic acid

[2-[2-(2-cyclopentanecarbonyl-phenylcarbamoyl)-acetylamino]-5-(pyridin-2-ylsulfanyl)-thiazol-4-yl]-acetic acid

[2-[2-(2-cyclopentanecarbonyl-phenylcarbamoyl)-acetylamino]-5-(1H-imidazol-2-ylsulfanyl)-thiazol-4-yl]-acetic acid N-(2-cyclopentanecarbonyl-phenyl)-N'-[4-(methanesulfonylamino-methyl)-thiazol-2-yl]-malonamide N-[5-bromo-4-(methanesulfonylamino-methyl)-thiazol-2-yl]-N'-(2-cyclopentanecarbonyl-phenyl)-malonamide N-[5-chloro-4-(methanesulfonylamino-methyl)-thiazol-2-yl]-N'-(2-cyclopentanecarbonyl-phenyl)-malonamide N-(2-cyclopentanecarbonyl-phenyl)-N'-[4-(methanesulfonylamino-methyl)-5-methylsulfanyl-thiazol-2-yl]-malonamide N-(2-cyclopentanecarbonyl-phenyl)-N'-[5-methanesulfonyl-4-(methanesulfonylamino-methyl)-thiazol-2-yl]-malonamide N-(2-cyclopentanecarbonyl-phenyl)-N'-[4-(methanesulfonylamino-methyl)-5-(pyridin-2-ylsulfanyl)-thiazol-2-yl]-malonamide N-(2-cyclopentanecarbonyl-phenyl)-N'-[5-(1H-imidazol-2-ylsulfanyl)-4-(methanesulfonylamino-methyl)-thiazol-2-yl]-malonamide N-(2-isobutoxy-phenyl)-N'-thiazol-2-yl-oxalamide N-(5-bromo-thiazol-2-yl)-N'-(2-isobutoxy-phenyl)-oxalamide N-(5-chloro-thiazol-2-yl)-N'-(2-isobutoxy-phenyl)-oxalamide
N-(2-isobutoxy-phenyl)-N'-(5-methylsulfanyl-thiazol-2-yl)-oxalamide
N-(2-isobutoxy-phenyl)-N'-(5-methanesulfonyl-thiazol-2-yl)-oxalamide
N-(2-isobutoxy-phenyl)-N'-[5-(pyridin-2-ylsulfanyl)-thiazol-2-yl]-oxalamide
N-[5-(1H-imidazol-2-ylsulfanyl)-thiazol-2-yl]-N'-(2-isobutoxy-phenyl)-oxalamide
{2-[(2-isobutoxy-phenylaminooxalyl)-amino]-thiazol-4-yl}-acetic acid
{5-bromo-2-[(2-isobutoxy-phenylaminooxalyl)-amino]-thiazol-4-yl}-acetic acid
{5-chloro-2-[(2-isobutoxy-phenylaminooxalyl)-amino]-thiazol-4-yl}-acetic acid
{2-[(2-isobutoxy-phenylaminooxalyl)-amino]-5-methylsulfanyl-thiazol-4-yl}-acetic acid
{2-[(2-isobutoxy-phenylaminooxalyl)-amino]-5-methanesulfonyl-thiazol-4-yl}-acetic acid
[2-[(2-isobutoxy-phenylaminooxalyl)-amino]-5-(pyridin-2-ylsulfanyl)-thiazol-4-yl]-acetic acid
{5-(1H-imidazol-2-ylsulfanyl)-2-[(2-isobutoxy-phenylaminooxalyl)-amino]-thiazol-4-yl}-acetic acid
N-(2-isobutoxy-phenyl)-N'-[4-(methanesulfonylamino-methyl)-thiazol-2-yl]-oxalamide
N-[5-bromo-4-(methanesulfonylamino-methyl)-thiazol-2-yl]-N'-(2-isobutoxy-phenyl)-oxalamide
N-[5-chloro-4-(methanesulfonylamino-methyl)-thiazol-2-yl]-N'-(2-isobutoxy-phenyl)-oxalamide
N-(2-isobutoxy-phenyl)-N'-[4-(methanesulfonylamino-methyl)-5-methylsulfanyl-thiazol-2-yl]-oxalamide
N-(2-isobutoxy-phenyl)-N'-[5-methanesulfonyl-4-(methanesulfonylamino-methyl)-thiazol-2-yl]-oxalamide
N-(2-isobutoxy-phenyl)-N'-[4-(methanesulfonylamino-methyl)-5-(pyridin-2-ylsulfanyl)-thiazol-2-yl]-oxalamide
N-[5-(1H-imidazol-2-ylsulfanyl)-4-(methanesulfonylamino-methyl)-thiazol-2-yl]-N'-(2-isobutoxy-phenyl)-oxalamide
N-(2-isobutoxy-phenyl)-N'-thiazol-2-yl-malonamide
N-(5-bromo-thiazol-2-yl)-N'-(2-isobutoxy-phenyl)-malonamide
N-(5-chloro-thiazol-2-yl)-N'-(2-isobutoxy-phenyl)-malonamide
N-(2-isobutoxy-phenyl)-N'-(5-methylsulfanyl-thiazol-2-yl)-malonamide
N-(2-isobutoxy-phenyl)-N'-(5-methanesulfonyl-thiazol-2-yl)-malonamide
N-(2-isobutoxy-phenyl)-N'-[5-(pyridin-2-ylsulfanyl)-thiazol-2-yl]-malonamide
N-[5-(1H-imidazol-2-ylsulfanyl)-thiazol-2-yl]-N'-(2-isobutoxy-phenyl)-malonamide
{2-[2-(2-isobutoxy-phenylcarbamoyl)-acetylamino]-thiazol-4-yl}-acetic acid
{5-bromo-2-[2-(2-isobutoxy-phenylcarbamoyl)-acetylamino]-thiazol-4-yl}-acetic acid
{5-chloro-2-[2-(2-isobutoxy-phenylcarbamoyl)-acetylamino]-thiazol-4-yl}-acetic acid
{2-[2-(2-isobutoxy-phenylcarbamoyl)-acetylamino]-5-methylsulfanyl-thiazol-4-yl}-acetic acid
{2-[2-(2-isobutoxy-phenylcarbamoyl)-acetylamino]-5-methanesulfonyl-thiazol-4-yl}-acetic acid
[2-[2-(2-isobutoxy-phenylcarbamoyl)-acetylamino]-5-(pyridin-2-ylsulfanyl)-thiazol-4-yl]-acetic acid
{5-(1H-imidazol-2-ylsulfanyl)-2-[2-(2-isobutoxy-phenylcarbamoyl)-acetylamino]-thiazol-4-yl}-acetic acid
N-(2-isobutoxy-phenyl)-N'-[4-(methanesulfonylamino-methyl)-thiazol-2-yl]-malonamide
N-[5-bromo-4-(methanesulfonylamino-methyl)-thiazol-2-yl]-N'-(2-isobutoxy-phenyl)-malonamide
N-[5-chloro-4-(methanesulfonylamino-methyl)-thiazol-2-yl]-N'-(2-isobutoxy-phenyl)-malonamide
N-(2-isobutoxy-phenyl)-N'-[4-(methanesulfonylamino-methyl)-5-methylsulfanyl-thiazol-2-yl]-malonamide
N-(2-isobutoxy-phenyl)-N'-[5-methanesulfonyl-4-(methanesulfonylamino-methyl)-thiazol-2-yl]-malonamide
N-(2-isobutoxy-phenyl)-N'-[4-(methanesulfonylamino-methyl)-5-(pyridin-2-ylsulfanyl)-thiazol-2-yl]-malonamide
N-[5-(1H-imidazol-2-ylsulfanyl)-4-(methanesulfonylamino-methyl)-thiazol-2-yl]-N'-(2-isobutoxy-phenyl)-malonamide
N-[2-(2-methoxy-phenoxy)-phenyl]-N'-thiazol-2-yl-oxalamide
N-(5-bromo-thiazol-2-yl)-N'-[2-(2-methoxy-phenoxy)-phenyl]-oxalamide
N-(5-chloro-thiazol-2-yl)-N'-[2-(2-methoxy-phenoxy)-phenyl]-oxalamide
N-[2-(2-methoxy-phenoxy)-phenyl]-N'-(5-methylsulfanyl-thiazol-2-yl)-oxalamide
N-(5-methanesulfonyl-thiazol-2-yl)-N'-[2-(2-methoxy-phenoxy)-phenyl]-oxalamide
N-[2-(2-methoxy-phenoxy)-phenyl]-N'-[5-(pyridin-2-ylsulfanyl)-thiazol-2-yl]-oxalamide
N-[5-(1H-imidazol-2-ylsulfanyl)-thiazol-2-yl]-N'-[2-(2-methoxy-phenoxy)-phenyl]-oxalamide
(2-{[2-(2-methoxy-phenoxy)-phenylaminooxalyl]-amino}-thiazol-4-yl)-acetic acid
(5-bromo-2-{[2-(2-methoxy-phenoxy)-phenylaminooxalyl]-amino}-thiazol-4-yl)-acetic acid
(5-chloro-2-[2-(2-methoxy-phenoxy)-phenylaminooxalyl]-amino}-thiazol-4-yl)-acetic acid
(2-{[2-(2-methoxy-phenoxy)-phenylaminooxalyl]-amino}-5-methylsulfanyl-thiazol-4-yl)-acetic acid
(5-methanesulfonyl-2-{[2-(2-methoxy-phenoxy)-phenylaminooxalyl]-amino}-thiazol-4-yl)-acetic acid
[2-{[2-(2-methoxy-phenoxy)-phenylaminooxalyl]-amino}-5-(pyridin-2-ylsulfanyl)-thiazol-4-yl]-acetic acid
(5-(1H-imidazol-2-ylsulfanyl)-2-{[2-(2-methoxy-phenoxy)-phenylaminooxalyl]-amino}thiazol-4-yl)-acetic acid
N-[4-(methanesulfonylamino-methyl)-thiazol-2-yl]-N'-[2-(2-methoxy-phenoxy)-phenyl]-oxalamide
N-[5-bromo-4-(methanesulfonylamino-methyl)-thiazol-2-yl]-N'-[2-(2-methoxy-phenoxy)-phenyl]-oxalamide
N-[5-chloro-4-(methanesulfonylamino-methyl)-thiazol-2-yl]-N'-[2-(2-methoxy-phenoxy)-phenyl]-oxalamide
N-[4-(methanesulfonylamino-methyl)-5-methylsulfanyl-thiazol-2-yl]-N'-[2-(2-methoxy-phenoxy)-phenyl]-oxalamide
N-[5-methanesulfonyl-4-(methanesulfonylamino-methyl)-thiazol-2-yl]-N'-[2-(2-methoxy-phenoxy)-phenyl]-oxalamide
N-[4-(methanesulfonylamino-methyl)-5-(pyridin-2-ylsulfanyl)-thiazol-2-yl]-N'-[2-(2-methoxy-phenoxy)-phenyl]-oxalamide
N-[5-(1H-imidazol-2-ylsulfanyl)-4-(methanesulfonylamino-methyl)-thiazol-2-yl]-N'-[2-(2-methoxy-phenoxy)-phenyl]-oxalamide
N-[2-(2-methoxy-phenoxy)-phenyl]-N'-thiazol-2-yl-malonamide
N-(5-bromo-thiazol-2-yl)-N'-[2-(2-methoxy-phenoxy)-phenyl]-malonamide
N-(5-chloro-thiazol-2-yl)-N'-[2-(2-methoxy-phenoxy)-phenyl]-malonamide N-[2-(2-methoxy-phenoxy)-phenyl]-N'-(5-methylsulfanyl-thiazol-2-yl)-malonamide
N-(5-methanesulfonyl-thiazol-2-yl)-N'-[2-(2-methoxy-phenoxy)-phenyl]-malonamide
N-[2-(2-methoxy-phenoxy)-phenyl]-N'-[5-(pyridin-2-ylsulfanyl)-thiazol-2-yl]-malonamide
N-[5-(1H-imidazol-2-ylsulfanyl)-thiazol-2-yl]-N'-[2-(2-methoxy-phenoxy)-phenyl]-malonamide
(2-{2-[2-(2-methoxy-phenoxy)-phenylcarbamoyl]-acetylamino}thiazol-4-yl)-acetic acid
(5-bromo-2-{2-[2-(2-methoxy-phenoxy)-phenylcarbamoyl]-acetylamino}-thiazol-4-yl)-acetic acid
(5-chloro-2-{2-[2-(2-methoxy-phenoxy)-phenylcarbamoyl]-acetylamino}-thiazol-4-yl)-acetic acid
(2-{2-[2-(2-methoxy-phenoxy)-phenylcarbamoyl]-acetylamino}-5-methylsulfanyl-thiazol-4-yl)-acetic acid
(5-methanesulfonyl-2-{2-[2-(2-methoxy-phenoxy)-phenylcarbamoyl]-acetylamino}-thiazol-4-yl)-acetic acid
[2-{2-[2-(2-methoxy-phenoxy)-phenylcarbamoyl]-acetylamino}-5-(pyridin-2-ylsulfanyl)-thiazol-4-yl]-acetic acid
(5-(1H-imidazol-2-ylsulfanyl)-2-{2-[2-(2-methoxy-phenoxy)-phenylcarbamoyl]-acetylamino}-thiazol-4-yl)-acetic acid
N-[4-(methanesulfonylamino-methyl)-thiazol-2-yl]-N'-[2-(2-methoxy-phenoxy)-phenyl]-malonamide
N-[5-bromo-4-(methanesulfonylamino-methyl)-thiazol-2-yl]-N'-[2-(2-methoxy-phenoxy)-phenyl]-malonamide
N-[5-chloro-4-(methanesulfonylamino-methyl)-thiazol-2-yl]-N'-[2-(2-methoxy-phenoxy)-phenyl]-malonamide
N-[4-methanesulfonylamino-methyl)-5-methylsulfanyl-thiazol-2-yl]-N'-[2-(2-methoxy-phenoxy)-phenyl]-malonamide
N-[5-methanesulfonyl-4-(methanesulfonylamino-methyl)-thiazol-2-yl]-N'-[2-(2-methoxy-phenoxy)-phenyl]-malonamide
N-[4-(methanesulfonylamino-methyl)-5-(pyridin-2-ylsulfanyl)-thiazol-2-yl]-N'-[2-(2-methoxy-phenoxy)-phenyl]-malonamide
N-[5-(1H-imidazol-2-ylsulfanyl)-4-(methanesulfonylamino-methyl)-thiazol-2-yl]-N'-[2-(2-methoxy-phenoxy)-phenyl]-malonamide
N-(2-cyclopentanecarbonyl-4-methyl-phenyl)-N'-thiazol-2-yl-oxalamide
N-(5-bromo-thiazol-2-yl)-N'-(2-cyclopentanecarbonyl-4-methyl-phenyl)-oxalamide
N-(5-chloro-thiazol-2-yl)-N'-(2-cyclopentanecarbonyl-4-methyl-phenyl)-oxalamide
N-(2-cyclopentanecarbonyl-4-methyl-phenyl)-N'-(5-methylsulfanyl-thiazol-2-yl)-oxalamide
N-(2-cyclopentanecarbonyl-4-methyl-phenyl)-N'-(5-methanesulfonyl-thiazol-2-yl)-oxalamide
N-(2-cyclopentanecarbonyl-4-methyl-phenyl)-N'-[5-(pyridin-2-ylsulfanyl)-thiazol-2-yl]-oxalamide
N-(2-cyclopentanecarbonyl-4-methyl-phenyl)-N'-[5-(1H-imidazol-2-ylsulfanyl)-thiazol-2-yl]-oxalamide
{2-[(2-cyclopentanecarbonyl-4-methyl-phenylaminooxalyl)-amino]-thiazol-4-yl}-acetic acid
{5-bromo-2-[(2-cyclopentanecarbonyl-4-methyl-phenylaminooxalyl)-amino]-thiazol-4-yl}-acetic acid
{5-chloro-2-[(2-cyclopentanecarbonyl-4-methyl-phenylaminooxalyl)-amino]-thiazol-4-yl}-acetic acid
{2-[(2-cyclopentanecarbonyl-4-methyl-phenylaminooxalyl)-amino]-5-methylsulfanyl-thiazol-4-yl}-acetic acid
{2-[(2-cyclopentanecarbonyl-4-methyl-phenylaminooxalyl)-amino]-5-methanesulfonyl-thiazol-4-yl}-acetic acid
[2-[(2-cyclopentanecarbonyl-4-methyl-phenylaminooxalyl)-amino]-5-(pyridin-2-ylsulfanyl)-thiazol-4-yl]-acetic acid
[2-[(2-cyclopentanecarbonyl-4-methyl-phenylaminooxalyl)-amino]-5-(1H-imidazol-2-ylsulfanyl)-thiazol-4-yl]-acetic acid
N-(2-cyclopentanecarbonyl-4-methyl-phenyl)-N'-[4-(methanesulfonylamino-methyl)-thiazol-2-yl]-oxalamide
N-[5-bromo-4-(methanesulfonylamino-methyl)-thiazol-2-yl]-N'-(2-cyclopentanecarbonyl-4-methyl-phenyl)-oxalamide
N-[5-chloro-4-(methanesulfonylamino-methyl)-thiazol-2-yl]-N'-(2-cyclopentanecarbonyl-4-methyl-phenyl)-oxalamide
N-(2-cyclopentanecarbonyl-4-methyl-phenyl)-N'-[4-(methanesulfonylamino-methyl)-5-methylsulfanyl-thiazol-2-yl]-oxalamide
N-(2-cyclopentanecarbonyl-4-methyl-phenyl)-N'-[5-methanesulfonyl-4-(methanesulfonylamino-methyl)-thiazol-2-yl]-oxalamide
N-(2-cyclopentanecarbonyl-4-methyl-phenyl)-N'-[4-(methanesulfonylamino-methyl)-5-(pyridin-2-ylsulfanyl)-thiazol-2-yl]-oxalamide
N-(2-cyclopentanecarbonyl-4-methyl-phenyl)-N'-[5-(1H-imidazol-2-ylsulfanyl)-4-(methanesulfonylamino-methyl)-thiazol-2-yl]-oxalamide
N-(2-cyclopentanecarbonyl-4-methyl-phenyl)-N'-thiazol-2-yl-malonamide
N-(5-bromo-thiazol-2-yl)-N'-(2-cyclopentanecarbonyl-4-methyl-phenyl)-malonamide
N-(5-chloro-thiazol-2-yl)-N'-(2-cyclopentanecarbonyl-4-methyl-phenyl)-malonamide
N-(2-cyclopentanecarbonyl-4-methyl-phenyl)-N'-(5-methylsulfanyl-thiazol-2-yl)-malonamide
N-(2-cyclopentanecarbonyl-4-methyl-phenyl)-N'-(5-methanesufonyl-thiazol-2-yl)-malonamide
N-(2-cyclopentanecarbonyl-4-methyl-phenyl)-N'-[5-(pyridin-2-ylsulfanyl)-thiazol-2-yl]-malonamide
N-(2-cyclopentanecarbonyl-4-methyl-phenyl)-N'-[5-(1H-imidazol-2-ylsulfanyl)-thiazol-2-yl]-malonamide
{2-[2-(2-cyclopentanecarbonyl-4-methyl-phenylcarbamoyl)-acetylamino]-thiazol-4-yl}-acetic acid
{5-bromo-2-[2-(2-cyclopentanecarbonyl-4-methyl-phenylcarbamoyl)-acetylamino]-thiazol-4-yl}-acetic acid
{5-chloro-2-[2-(2-cyclopentanecarbonyl-4-methyl-phenylcarbamoyl)-acetylamino]-thiazol-4-yl}-acetic acid
{2-[2-(2-cyclopentanecarbonyl-4-methyl-phenylcarbamoyl)-acetylamino]-5-methylsulfanyl-thiazol-4-yl}-acetic acid
{2-[2-(2-cyclopentanecarbonyl-4-methyl-phenylcarbamoyl)-acetylamino]-5-methanesulfonyl-thiazol-4-yl}-acetic acid
[2-[2-(2-cyclopentanecarbonyl-4-methyl-phenylcarbamoyl)-acetylamino]-5-(pyridin-2-ylsulfanyl)-thiazol-4-yl]-acetic acid
[2-[2-(2-cyclopentanecarbonyl-4-methyl-phenylcarbamoyl)-acetylamino]-5-(1H-imidazol-2-ylsulfanyl)-thiazol-4-yl]-acetic acid
N-(2-cyclopentanecarbonyl-4-methyl-phenyl)-N'-[4-(methanesulfonylamino-methyl)-thiazol-2-yl]-malonamide
N-[5-bromo-4-(methanesulfonylamino-methyl)-thiazol-2-yl]-N'-(2-cyclopentanecarbonyl-4-methyl-phenyl)-malonamide
N-[5-chloro-4-(methanesulfonylamino-methyl)-thiazol-2-yl]-N'-(2-cyclopentanecarbonyl-4-methyl-phenyl)-malonamide 165;165;N-(2-cyclopentanecarbonyl-4-methyl-phenyl)-N'-[4-(methanesulfonylamino-methyl)-5-methylsulfanyl-thiazol-2-yl]-malonamide
N-(2-cyclopentanecarbonyl-4-methyl-phenyl)-N'-[5-methanesulfonyl-4-(methanesulfonylamino-methyl)-thiazol-2-yl]-malonamide
N-(2-cyclopentanecarbonyl-4-methyl-phenyl)-N'-[4-(methanesulfonylamino-methyl)-5-(pyridin-2-ylsulfanyl)-thiazol-2-yl]-malonamide
N-(2-cyclopentanecarbonyl-4-methyl-phenyl)-N'-[5-(1H-imidazol-2-ylsulfanyl)-4-(methanesulfonylamino-methyl)-thiazol-2-yl]-malonamide
N-(2-isobutoxy-4-methyl-phenyl)-N'-thiazol-2-yl-oxalamide
N-(5-bromo-thiazol-2-yl)-N'-(2-isobutoxy-4-methyl-phenyl)-oxalamide
N-(5-chloro-thiazol-2-yl)-N'-(2-isobutoxy-4-methyl-phenyl)-oxalamide
N-(2-isobutoxy-4-methyl-phenyl)-N'-(5-methylsulfanyl-thiazol-2-yl)-oxalamide
N-(2-isobutoxy-4-methyl-phenyl)-N'-(5-methanesulfonyl-thiazol-2-yl)-oxalamide
N-(2-isobutoxy-4-methyl-phenyl)-N'-[5-(pyridin-2-ylsulfanyl)-thiazol-2-yl]-oxalamide
N-[5-(1H-imidazol-2-ylsulfanyl)-thiazol-2-yl]-N'-(2-isobutoxy-4-methyl-phenyl)-oxalamide
2-[(2-isobutoxy-4-methyl-phenylaminooxalyl)-amino]-thiazol-4-yl}-acetic acid
5-bromo-2-[(2-isobutoxy-4-methyl-phenylaminooxalyl)-amino]-thiazol-4-yl}-acetic acid
5-chloro-2-[(2-isobutoxy-4-methyl-phenylaminooxalyl)-amino]-thiazol-4-yl}-acetic acid
{2-[(2-isobutoxy-4-methyl-phenylaminooxalyl)-amino]-5-methylsulfanyl-thiazol-4-yl}-acetic acid
{2-[(2-isobutoxy-4-methyl-phenylaminooxalyl)-amino]-5-methanesulfonyl-thiazol-4-yl}acetic acid
[2-[(2-isobutoxy-4-methyl-phenylaminooxalyl)-amino]-5-(pyridin-2-ylsulfanyl)-thiazol-4-yl]-acetic acid
{5-(1H-imidazol-2-ylsulfanyl)-2-[(2-isobutoxy-4-methyl-phenylaminooxalyl)-amino]-thiazol-4-yl}-acetic acid
N-(2-isobutoxy-4-methyl-phenyl)-N'-[4-(methanesulfonylamino-methyl)-thiazol-2-yl]-oxalamide
N-[5-bromo-4-(methanesulfonylamino-methyl)-thiazol-2-yl]-N'-(2-isobutoxy-4-methyl-phenyl)-oxalamide
N-[5-chloro-4-methanesulfonylamino-methyl)-thiazol-2-yl]-N'-(2-isobutoxy-4-methyl-phenyl)-oxalamide
N-(2-isobutoxy-4-methyl-phenyl)-N'-[4-(methanesulfonylamino-methyl)-5-methylsulfanyl-thiazol-2-yl]-oxalamide
N-(2-isobutoxy-4-methyl-phenyl)-N'-[5-methanesulfonyl-4-(methanesulfonylamino-methyl)-thiazol-2-yl]-oxalamide
N-(2-isobutoxy-4-methyl-phenyl)-N'-[4-(methanesulfonylamino-methyl)-5-(pyridin-2-ylsulfanyl)-thiazol-2-yl]-oxalamide
N-[5-(1H-imidazol-2-ylsulfanyl)-4-(methanesulfonylamino-methyl)-thiazol-2-yl]-N'-(2-isobutoxy-4-methyl-phenyl)-oxalamide
N-(2-isobutoxy-4-methyl-phenyl)-N'-thiazol-2-yl-malonamide
N-(5-bromo-thiazol-2-yl)-N'-(2-isobutoxy-4-methyl-phenyl)-malonamide
N-(5-chloro-thiazol-2-yl)-N'-(2-isobutoxy-4-methyl-phenyl)-malonamide
N-(2-isobutoxy-4-methyl-phenyl)-N'-(5-methylsulfanyl-thiazol-2-yl)-malonamide
N-(2-isobutoxy-4-methyl-phenyl)-N'-(5-methanesulfonyl-thiazol-2-yl)-malonamide
N-(2-isobutoxy-4-methyl-phenyl)-N'-[5-(pyridin-2-ylsulfanyl)-thiazol-2-yl]-malonamide
N-[5-(1H-imidazol-2-ylsulfanyl)-thiazol-2-yl]-N'-(2-isobutoxy-4-methyl-phenyl)-malonamide
{2-[2-(2-isobutoxy-4-methyl-phenylcarbamoyl)-acetylamino]-thiazol-4-yl}-acetic acid
{5-bromo-2-[2-(2-isobutoxy-4-methyl-phenylcarbamoyl)-acetylamino]-thiazol-4-yl}-acetic acid
{5-chloro-2-[2-(2-isobutoxy-4-methyl-phenylcarbamoyl)-acetylamino]-thiazol-4-yl}-acetic acid
{2-[2-(2-isobutoxy-4-methyl-phenylcarbamoyl)-acetylamino]-5-methylsulfanyl-thiazol-4-yl}-acetic acid
{2-[2-(2-isobutoxy-4-methyl-phenylcarbamoyl)-acetylamino]-5-methanesulfonyl-thiazol-4-yl}-acetic acid
[2-[2-(2-isobutoxy-4-methyl-phenylcarbamoyl)-acetylamino]-5-(pyridin-2-ylsulfanyl)-thiazol-4-yl]-acetic acid
{5-(1H-imidazol-2-ylsulfanyl)-2-[2-(2-isobutoxy-4-methyl-phenylcarbamoyl)-acetylamino]-thiazol-4-yl}-acetic acid
N-(2-isobutoxy-4-methyl-phenyl)-N'-[4-(methanesulfonylamino-methyl)-thiazol-2-yl]-malonamide
N-[5-bromo-4-(methanesulfonylamino-methyl)-thiazol-2-yl]-N'-(2-isobutoxy-4-methyl-phenyl)-malonamide
N-[5-chloro-4-(methanesulfonylamino-methyl)-thiazol-2-yl]-N'-(2-isobutoxy-4-methyl-phenyl)-malonamide
N-(2-isobutoxy-4-methyl-phenyl)-N'-[4-(methanesulfonylamino-methyl)-5-methylsulfanyl-thiazol-2-yl]-malonamide
N-(2-isobutoxy-4-methyl-phenyl)-N'-[5-methanesulfonyl-4-(methanesulfonylamino-methyl)-thiazol-2-yl]-malonamide
N-(2-isobutoxy-4-methyl-phenyl)-N'-[4-(methanesulfonylamino-methyl)-5-(pyridin-2-ylsulfanyl)-thiazol-2-yl]-malonamide
N-[5-(1H-imidazol-2-ylsulfanyl)-4-(methanesulfonylamino-methyl)-thiazol-2-yl]-N'-(2-isobutoxy-4-methyl-phenyl)-malonamide
N-[2-(2-methoxy-phenoxy)-4-methyl-phenyl]-N'-thiazol-2-yl-oxalamide
N-(5-bromo-thiazol-2-yl)-N'-[2-(2-methoxy-phenoxy)-4-methyl-phenyl]-oxalamide
N-(5-chloro-thiazol-2-yl)-N'-[2-(2-methoxy-phenoxy)-4-methyl-phenyl]-oxalamide
N-[N-(5-methanesulfonyl-thiazol-N-[N-[5-(1H-imidazol-((5-bromo-(5-chloro-((5-methanesulfonyl-[(5(1H-imidazol-N-[4-(methanesulfonylamino-methyl)-thiazol-N-[5-bromo-4-(methanesulfonylamino-methyl)-thiazol-N-[5-chloro-4-(methanesulfonylamino-methyl)-thiazol-N-[4-(methanesulfonylamino-methyl)-5-methylsulfanyl-thiazol-N-[5-methanesulfonyl-4-(methanesulfonylamino-methyl)-thiazol-N-[4-(methanesulfonylamino-methyl)-5-(pyridin-N-[5-(1H-imidazol-N-[N-(5-bromo-thiazol-N-(5-chloro-thiazol-N-[N-(5-methanesulfonyl-thiazol-N-[N-[5-(1H-imidazol-((5-bromo-5-chloro-((5-methanesulfonyl-[(5-(1H-imidazol-N-[4-(methanesulfonylamino-methyl)-thiazol-N-[5-bromo-4-(methanesulfonylamino-methyl)-thiazol-N-[5-chloro-4-(methanesulfonylamino-methyl)-thiazol-N-[4-(methanesulfonylamino-methyl)-5-methylsulfanyl-thiazol-N-[5-methanesulfonyl-4-(methanesulfonylamino-methyl)-thiazol-N-[4-(methanesulfonylamino-methyl)-5-(pyridin-N-[5-(1H-imidazol-N-(N-(5-bromo-thiazol-N-(5-chloro-thiazol-N-(N-(5-methanesulfonyl-thiazol-N-(N-(N-({{5-bromo-{5-chloro-{{[[N-(N-[5-bromo-4-(methanesulfonylamino-methyl)-thiazol-N-[5-chloro-4-(methanesulfonylamino-methyl)-thiazol-N-(N-(N-(N-(N-(N-(5-bromo-thiazol-N-(5- chloro-thiazol-N-(N-(N-(N-({{5-bromo-5-chloro-{{[[N-(N-[5-bromo-4-(methanesulfonylamino-methyl)-thiazol-N-[5-chloro-4-(methanesulfonylamino-methyl)-thiazol-N-(N-(N-(N-(4-fluoro-N-(5-bromo-thiazol-N-(5-chloro-thiazol-N-(4-fluoro-N-(4-fluoro-2-isobutoxy-phenyl)-N'-(5-methanesulfonyl-thiazol-2-yl)-oxalamide N-(4-fluoro-2-isobutoxy-phenyl)-N'-[5-(pyridin-2-ylsulfanyl)-thiazol-2-yl]-oxalamide N-(4-fluoro-2-isobutoxy-phenyl)-N'-[5-(1H-imidazol-2-ylsulfanyl)-thiazol-2-yl]-oxalamide {2-[(4-fluoro-2-isobutoxy-phenylaminooxalyl)-amino]-thiazol-4-yl}-acetic acid {5-bromo-2-[(4-fluoro-2-isobutoxy-phenylaminooxalyl)-amino]-thiazol-4-yl}-acetic acid {5-chloro-2-[(4-fluoro-2-isobutoxy-phenylaminooxalyl)-amino]-thiazol-4-yl}-acetic acid {2-[(4-fluoro-2-isobutoxy-phenylaminooxalyl)-amino]-5-methylsulfanyl-thiazol-4-yl}-acetic acid {2-[(4-fluoro-2-isobutoxy-phenylaminooxalyl)-amino]-5-methanesulfonyl-thiazol-4-yl}-acetic acid

[2-[(4-fluoro-2-isobutoxy-phenylaminooxalyl)-amino]-5-(pyridin-2-ylsulfanyl)-thiazol-4-yl]-acetic acid

[2-[(4-fluoro-2-isobutoxy-phenylaminooxalyl)-amino]-5-(1H-imidazol-2-ylsulfanyl)-thiazol-4-yl]-acetic acid N-(4-fluoro-2-isobutoxy-phenyl)-N'-[4-(methanesulfonylamino-methyl)-thiazol-2-yl]-oxalamide N-[5-bromo-4-(methanesulfonylamino-methyl)-thiazol-2-yl]-N'-(4-fluoro-2-isobutoxy-phenyl)-oxalamide N-[5-chloro-4-(methanesulfonylamino-methyl)-thiazol-2-yl]-N'-(4-fluoro-2-isobutoxy-phenyl)-oxalamide N-(4-fluoro-2-isobutoxy-phenyl)-N'-[4-(methanesulfonylamino-methyl)-5-methylsulfanyl-thiazol-2-yl]-oxalamide N-(4-fluoro-2-isobutoxy-phenyl)-N'-[5-methanesulfonyl-4-(methanesulfonylamino-methyl)-thiazol-2-yl]-oxalamide N-(4-fluoro-2-isobutoxy-phenyl)-N'-[4-(methanesulfonylamino-methyl)-5-(pyridin-2-ylsulfanyl)-thiazol-2-yl]-oxalamide N-(4-fluoro-2-isobutoxy-phenyl)-N'-[5-(1H-imidazol-2-ylsulfanyl)-4-(methanesulfonylamino-methyl)-thiazol-2-yl]-oxalamide N-(4-fluoro-2-isobutoxy-phenyl)-N'-thiazol-2-yl-malonamide N-(5-bromo-thiazol-2-yl)-N'-(4-fluoro-2-isobutoxy-phenyl)-malonamide N-(5-chloro-thiazol-2-yl)-N'-(4-fluoro-2-isobutoxy-phenyl)-malonamide N-(4-fluoro-2-isobutoxy-phenyl)-N'-(5-methylsulfanyl-thiazol-2-yl)-malonamide N-(4-fluoro-2-isobutoxy-phenyl)-N'-(5-methanesulfonyl-thiazol-2-yl)-malonamide N-(4-fluoro-2-isobutoxy-phenyl)-N'-[5-(pyridin-2-ylsulfanyl)-thiazol-2-yl]-malonamide N-(4-fluoro-2-isobutoxy-phenyl)-N'-[5-(1H-imidazol-2-ylsulfanyl)-thiazol-2-yl]-malonamide {2-[2-(4-fluoro-2-isobutoxy-phenylcarbamoyl)-acetylamino]-thiazol-4-yl}-acetic acid {5-bromo-2-[2-(4-fluoro-2-isobutoxy-phenylcarbamoyl)-acetylamino]-thiazol-4-yl}-acetic acid {5-chloro-2-[2-(4-fluoro-2-isobutoxy-phenylcarbamoyl)-acetylamino]-thiazol-4-yl)acetic acid {2-[2-(4-fluoro-2-isobutoxy-phenylcarbamoyl)-acetylamino]-5-methylsulfanyl-thiazol-4-yl}-acetic acid {2-[2-(4-fluoro-2-isobutoxy-phenylcarbamoyl)-acetylamino]-5-methanesulfonyl-thiazol-4-yl}-acetic acid

[2-[2-(4-fluoro-2-isobutoxy-phenylcarbamoyl)-acetylamino]-5-(pyridin-2-ylsulfanyl)-thiazol-4-yl]-acetic acid

[2-[2-(4-fluoro-2-isobutoxy-phenylcarbamoyl)-acetylamino]-5-(1H-imidazol-2-ylsulfanyl)-thiazol-4-yl]-acetic acid N-(4-fluoro-2-isobutoxy-phenyl)-N'-[4-(methanesulfonylamino-methyl)-thiazol-2-yl]-malonamide N-[5-bromo-4-(methanesulfonylamino-methyl)-thiazol-2-yl]-N'-(4-fluoro-2-isobutoxy-phenyl)-malonamide N-[5-chloro-4-(methanesulfonylamino-methyl)-thiazol-2-yl]-N'-(4-fluoro-2-isobutoxy-phenyl)-malonamide N-(4-fluoro-2-isobutoxy-phenyl)-N'-[4-(methanesulfonylamino-methyl)-5-methylsulfanyl-thiazol-2-yl]-malonamide N-(4-fluoro-2-isobutoxy-phenyl)-N'-[5-methanesulfonyl-4-(methanesulfonylamino-methyl)-thiazol-2-yl]-malonamide N-(4-fluoro-2-isobutoxy-phenyl)-N'-[4-(methanesulfonylamino-methyl)-5-(pyridin-2-ylsulfanyl)-thiazol-2-yl]-malonamide N-(4-fluoro-2-isobutoxy-phenyl)-N'-[5-(1H-imidazol-2-ylsulfanyl)-4-(methanesulfonylamino-methyl)-thiazol-2-yl]-malonamide N-[4-fluoro-2-(2-methoxy-phenoxy)-phenyl]-N'-thiazol-2-yl-oxalamide N-(5-bromo-thiazol-2-yl)-N'-[4-fluoro-2-(2-methoxy-phenoxy)-phenyl]-oxalamide N-(5-chloro-thiazol-2-yl)-N'-[4-fluoro-2-(2-methoxy-phenoxy)-phenyl]-oxalamide N-[4-fluoro-2-(2-methoxy-phenoxy)-phenyl]-N'-(5-methylsulfanyl-thiazol-2-yl)-oxalamide N-[4-fluoro-2-(2-methoxy-phenoxy)-phenyl]-N'-(5-methanesulfonyl-thiazol-2-yl)-oxalamide N-[4-fluoro-2-(2-methoxy-phenoxy)-phenyl]-N'-[5-(pyridin-2-ylsulfanyl)-thiazol-2-yl]-oxalamide N-[4-fluoro-2-(2-methoxy-phenoxy)-phenyl]-N'-[5-(1H-imidazol-2-ylsulfanyl)-thiazol-2-yl]-oxalamide (2-{[4-fluoro-2-(2-methoxy-phenoxy)-phenylaminooxalyl]-amino}-thiazol-4-yl)-acetic acid (5-bromo-2-{[4-fluoro-2-(2-methoxy-phenoxy)-phenylaminooxalyl]-amino}thiazol-4-yl)-acetic acid (5-chloro-2-[4-fluoro-2-(2-methoxy-phenoxy)-phenylaminooxalyl]-amino)thiazol-4-yl)-acetic acid (2-{[4-fluoro-2-(2-methoxy-phenoxy)-phenylaminooxalyl]-amino}-5-methylsulfanyl-thiazol-4-yl)-acetic acid (2-{[4-fluoro-2-(2-methoxy-phenoxy)-phenylaminooxalyl]-amino}-5-methanesulfonyl-thiazol-4-yl)-acetic acid

[2-[4-fluoro-2-(2-methoxy-phenoxy)-phenylaminooxalyl]-amino}-5-(pyridin-2-ylsulfanyl)-thiazol-4-yl]-acetic acid

[2-{[4-fluoro-2-(2-methoxy-phenoxy)-phenylaminooxalyl]-amino}-5-(1H-imidazol-2-ylsulfanyl)-thiazol-4-yl]-acetic acid N-[4-fluoro-2-(2-methoxy-phenoxy)-phenyl]-N'-[4-(methanesulfonylamino-methyl)-thiazol-2-yl]-oxalamide N-[5-bromo-4-(methanesulfonylamino-methyl)-thiazol-2-yl]-N'-[4-fluoro-2-(2-methoxy-phenoxy)-phenyl]-oxalamide N-[5-chloro-4-(methanesulfonylamino-methyl)-thiazol-2-yl]-N'-[4-fluoro-2-(2-methoxy-phenoxy)-phenyl]-oxalamide N-[4-fluoro-2-(2-methoxy-phenoxy)-phenyl]-N'-[4-(methanesulfonylamino-methyl)-5-methylsulfanyl-thiazol-2-yl]-oxalamide N-[4-fluoro-2-(2-methoxy-phenoxy)-phenyl]-N'-[5-methanesulfonyl-4-(methanesulfonylamino-methyl)-thiazol-2-yl]-oxalamide N-[4-fluoro-2-(2-methoxy-phenoxy)-phenyl]-N'-[4-(methanesulfonylamino-methyl)-5-(pyridin-2-ylsulfanyl)-thiazol-2-yl]-oxalamide N-[4-fluoro-2-(2-methoxy-phenoxy)-phenyl]-N'-[5-(1H-imidazol-2-ylsulfanyl)-4-(methanesulfonylamino-methyl)-thiazol-2-yl]-oxalamide
N-[4-fluoro-2-(2-methoxy-phenoxy)-phenyl]-N'-thiazol-2-yl-malonamide
N-(5-bromo-thiazol-2-yl)-N'-[4-fluoro-2-(2-methoxy-phenoxy)-phenyl]-malonamide
N-(5-chloro-thiazol-2-yl)-N'-[4-fluoro-2-(2-methoxy-phenoxy)-phenyl]-malonamide
N-[4-fluoro-2-(2-methoxy-phenoxy)-phenyl]-N'-(5-methylsulfanyl-thiazol-2-yl)-malonamide
N-[4-fluoro-2-(2-methoxy-phenoxy)-phenyl]-N'-(5-methanesulfonyl-thiazol-2-yl)-malonamide
N-[4-fluoro-2-(2-methoxy-phenoxy)-phenyl]-N'-[5-(pyridin-2-ylsulfanyl)-thiazol-2-yl]-malonamide
N-[4-fluoro-2-(2-methoxy-phenoxy)-phenyl]-N'-[5-(1H-imidazol-2-ylsulfanyl)-thiazol-2-yl]-malonamide
(2-{2-[4-fluoro-2-(2-methoxy-phenoxy)-phenylcarbamoyl]-acetylamino}-thiazol-4-yl)-acetic acid
(5-bromo-2-{2-[4-fluoro-2-(2-methoxy-phenoxy)-phenylcarbamoyl]-acetylamino}-thiazol-4-yl)-acetic acid
(5-chloro-2-{2-[4-fluoro-2-(2-methoxy-phenoxy)-phenylcarbamoyl]-acetylamino}-thiazol-4-yl)-acetic acid
(2-{2-[4-fluoro-2-(2-methoxy-phenoxy)-phenylcarbamoyl]-acetylamino}-5-methylsulfanyl-thiazol-4-yl)-acetic acid
(2-{2-[4-fluoro-2-(2-methoxy-phenoxy)-phenylcarbamoyl]-acetylamino}-5-methanesulfonyl-thiazol-4-yl)-acetic acid
[2-{2-[4-fluoro-2-(2-methoxy-phenoxy)-phenylcarbamoyl]-acetylamino}-5-(pyridin-2-ylsulfanyl)-thiazol-4-yl]-acetic acid
[2-{2-[4-fluoro-2-(2-methoxy-phenoxy)-phenylcarbamoyl]-acetylamino}-5-(1H-imidazol-2-ylsulfanyl)-thiazol-4-yl]-acetic acid
N-[4-fluoro-2-(2-methoxy-phenoxy)-phenyl]-N'-[4-(methanesulfonylamino-methyl)-thiazol-2-yl]-malonamide
N-[5-bromo-4-(methanesulfonylamino-methyl)-thiazol-2-yl]-N'-[4-fluoro-2-(2-methoxy-phenoxy)-phenyl]-malonamide
N-[5-chloro-4-(methanesulfonylamino-methyl)-thiazol-2-yl]-N'-[4-fluoro-2-(2-methoxy-phenoxy)-phenyl]-malonamide
N-[4-fluoro-2-(2-methoxy-phenoxy)-phenyl]-N'-[4-(methanesulfonylamino-methyl)-5-methylsulfanyl-thiazol-2-yl]-malonamide
N-[4-fluoro-2-(2-methoxy-phenoxy)-phenyl]-N'-[5-methanesulfonyl-4-(methanesulfonylamino-methyl)-thiazol-2-yl]-malonamide
N-[4-fluoro-2-(2-methoxy-phenoxy)-phenyl]-N'-[4-(methanesulfonylamino-methyl)-5-(pyridin-2-ylsulfanyl)-thiazol-2-yl]-malonamide
N-[4-fluoro-2-(2-methoxy-phenoxy)-phenyl]-N'-[5-(1H-imidazol-2-ylsulfanyl)-4-(methanesulfonylamino-methyl)-thiazol-2-yl]-malonamide
N-(2-cyclopentanecarbonyl-4-methoxy-phenyl)-N'-thiazol-2-yl-oxalamide
N-(5-bromo-thiazol-2-yl)-N'-(2-cyclopentanecarbonyl-4-methoxy-phenyl)-oxalamide
N-(5-chloro-thiazol-2-yl)-N'-(2-cyclopentanecarbonyl-4-methoxy-phenyl)-oxalamide
N-(2-cyclopentanecarbonyl-4-methoxy-phenyl)-N'-(5-methylsulfanyl-thiazol-2-yl)-oxalamide
N-(2-cyclopentanecarbonyl-4-methoxy-phenyl)-N'-(5-methanesulfonyl-thiazol-2-yl)-oxalamide
N-(2-cyclopentanecarbonyl-4-methoxy-phenyl)-N'-[5-(pyridin-2-ylsulfanyl)-thiazol-2-yl]-oxalamide
N-(2-cyclopentanecarbonyl-4-methoxy-phenyl)-N'-[5-(1H-imidazol-2-ylsulfanyl)-thiazol-2-yl]-oxalamide
{2-[(2-cyclopentanecarbonyl-4-methoxy-phenylaminooxalyl)-amino]-thiazol-4-yl}-acetic acid
{5-bromo-2-[(2-cyclopentanecarbonyl-4-methoxy-phenylaminooxalyl)-amino]-thiazol-4-yl}-acetic acid
{5-chloro-2-[(2-cyclopentanecarbonyl-4-methoxy-phenylaminooxalyl)-amino]-thiazol-4-yl}-acetic acid
{2-[(2-cyclopentanecarbonyl-4-methoxy-phenylaminooxalyl)-amino]-5-methylsulfanyl-thiazol-4-yl}-acetic acid
{2-[(2-cyclopentanecarbonyl-4-methoxy-phenylaminooxalyl)-amino]-5-methanesulfonyl-thiazol-4-yl}-acetic acid
[2-[(2-cyclopentanecarbonyl-4-methoxy-phenylaminooxalyl)-amino]-5-(pyridin-2-ylsulfanyl)-thiazol-4-yl]-acetic acid
[2-[(2-cyclopentanecarbonyl-4-methoxy-phenylaminooxalyl)-amino]-5-(1H-imidazol-2-ylsulfanyl)-thiazol-4-yl]-acetic acid
N-(2-cyclopentanecarbonyl-4-methoxy-phenyl)-N'-[4-(methanesulfonylamino-methyl)-thiazol-2-yl]-oxalamide
N-[5-bromo-4-(methanesulfonylamino-methyl)-thiazol-2-yl]-N'-(2-cyclopentanecarbonyl-4-methoxy-phenyl)-oxalamide
N-[5-chloro-4-(methanesulfonylamino-methyl)-thiazol-2-yl]-N'-(2-cyclopentanecarbonyl-4-methoxy-phenyl)-oxalamide
N-(2-cyclopentanecarbonyl-4-methoxy-phenyl)-N'-[4-(methanesulfonylamino-methyl)-5-methylsulfanyl-thiazol-2-yl]-oxalamide
N-(2-cyclopentanecarbonyl-4-methoxy-phenyl)-N'-[5-methanesulfonyl-4-(methanesulfonylamino-methyl)-thiazol-2-yl]-oxalamide
N-(2-cyclopentanecarbonyl-4-methoxy-phenyl)-N'-[N-(2-cyclopentanecarbonyl-N-(N-[N-[4-(methanesulfonylamino-methyl)-N-[4-(methanesulfonylamino-methyl)-N-[5-(1H-imidazol-2-ylsulfanyl)-4-(methanesulfonylamino-methyl)-thiazol-2-yl]-N'-[4-methoxy-2-(2-methoxy-phenoxy)-phenyl]-malonamide
1-(2-Cyclopentanecarbonyl-4-methyl-phenyl)-3-(5-morpholin-4-ylmethyl-thiazol-2-yl)-urea
1-(2-Cyclopentanecarbonyl-4-methyl-phenyl)-3-(5-dimethylaminomethyl-thiazol-2-yl)-urea
1-(2-Cyclopentanecarbonyl-4-methyl-phenyl)-3-(5-piperazin-1-ylmethyl-thiazol-2-yl)-urea
1-(2-Cyclopentanecarbonyl-4-methyl-phenyl)-3-[5-(4-methyl-piperazin-1-ylmethyl)-thiazol-2-yl]-urea
1-[5-(4-Acetyl-piperazin-1-ylmethyl)-thiazol-2-yl]-3-(2-cyclopentanecarbonyl-4-methyl-phenyl)-urea
1-(2-Cyclopentanecarbonyl-4-methyl-phenyl)-3-[5-(4-methanesulfonyl-piperazin-1-ylmethyl)-thiazol-2-yl]-urea
(4-{2-[3-(2-Cyclopentanecarbonyl-4-methyl-phenyl)-ureido]-thiazol-5-ylmethyl}-piperazin-1-yl)-acetic acid
2-{2-[3-(2-Cyclopentanecarbonyl-4-methyl-phenyl)-ureido]-thiazol-5-ylmethylsulfanyl}-1H-imidazole-4-carboxylic acid
1-(2-Cyclopentanecarbonyl-4-methyl-phenyl)-3-[5-(1H-imidazol-2-ylsulfanylmethyl)-thiazol-2-yl]-urea
1-(2-Cyclopentanecarbonyl-4-methyl-phenyl)-3-[5-(1-methyl-1H-imidazol-2-ylsulfanylmethyl)-thiazol-2-yl]-urea
1-(2-Cyclopentanecarbonyl-4-methyl-phenyl)-3-[5-(4-methyl-4H-[1,2,4]triazol-3-ylsulfanylmethyl)-thiazol-2-yl]-urea
1-(2-Cyclopentanecarbonyl-4-methyl-phenyl)-3-[5-(4H-[1,2,4]triazol-3-ylsulfanylmethyl)-thiazol-2-yl]-urea
1-(2-Cyclopentanecarbonyl-4-methyl-phenyl)-3-[5-(1-methyl-1H-tetrazol-5-ylsulfanylmethyl)-thiazol-2-yl]-urea (5-{2-[3-(2-Cyclopentanecarbonyl-4-methyl-phenyl)-ureido]-thiazol-5-ylmethylsulfanyl}-tetrazol-1-yl)-acetic acid
1-(2-Cyclopentanecarbonyl-4-methyl-phenyl)-3-{5-[1-(2-dimethylamino-ethyl)-1H-tetrazol-5-ylsulfanylmethyl]-thiazol-2-yl}-urea
(5-{2-[3-(2-Cyclopentanecarbonyl-4-methyl-phenyl)-ureido]-thiazol-5-ylmethanesulfonyl}-tetrazol-1-yl)-acetic acid
1-(2-Cyclopentanecarbonyl-4-methyl-phenyl)-3-{5-[1-(2-dimethylamino-ethyl)-1H-tetrazole-5-sulfonylmethyl]-thiazol-2-yl}-urea
1-(2-Cyclopentanecarbonyl-4-methyl-phenyl)-3-[5-(1-methyl-1H-tetrazole-5-sulfonylmethyl)-thiazol-2-yl]-urea
1-(2-Cyclopentanecarbonyl-4-methyl-phenyl)-3-[5-(4H-[1,2,4]triazole-3-sulfonylmethyl)-thiazol-2-yl]-urea
1-(2-Cyclopentanecarbonyl-4-methyl-phenyl)-3-[5-(4-methyl-4H-[1,2,4]triazole-3-sulfonylmethyl)-thiazol-2-yl]-urea
1-(2-Cyclopentanecarbonyl-4-methyl-phenyl)-3-[5-(1-methyl-1H-imidazole-2-sulfonylmethyl)-thiazol-2-yl]-urea
1-(2-Cyclopentanecarbonyl-4-methyl-phenyl)-3-[5-(1H-imidazole-2-sulfonylmethyl)-thiazol-2-yl]-urea
1-(2-Cyclopentanecarbonyl-4-methyl-phenyl)-3-[5-(pyridine-2-sulfonylmethyl)-thiazol-2-yl]-urea
1-(2-Cyclopentanecarbonyl-4-methyl-phenyl)-3-[5-(pyridin-2-ylsulfanylmethyl)-thiazol-2-yl]-urea
1-(2-Cyclopentanecarbonyl-4-methyl-phenyl)-3-[5-(pyridin-3-ylsulfanylmethyl)-thiazol-2-yl]-30 urea
1-(2-Cyclopentanecarbonyl-4-methyl-phenyl)-3-[5-(pyridine-3-sulfonylmethyl)-thiazol-2-yl]-urea
1-(2-Cyclopentanecarbonyl-4-methyl-phenyl)-3-[5-(pyridin-4-ylsulfanylmethyl)-thiazol-2-yl]-urea
1-(2-Cyclopentanecarbonyl-4-methyl-phenyl)-3-[5-(pyridine-4-sulfonylmethyl)-thiazol-2-yl]-urea
1-(2-Cyclopentanecarbonyl-4-methyl-phenyl)-3-[5-(pyridin-4-yloxymethyl)-thiazol-2-yl]-urea
1-(2-Cyclopentanecarbonyl-4-methyl-phenyl)-3-[5-(pyridin-3-yloxymethyl)-thiazol-2-yl]-urea
1-(2-Cyclopentanecarbonyl-4-methyl-phenyl)-3-[5-(pyridin-2-yloxymethyl)-thiazol-2-yl]-urea
(4-{2-[3-(2-Cyclopentanecarbonyl-4-methyl-phenyl)-ureido]-thiazol-5-ylmethoxy}-phenyl)-acetic acid
(4-{2-[3-(2-Cyclopentanecarbonyl-4-methyl-phenyl)-ureido]-thiazol-5-ylmethylsulfanyl}-phenyl)-acetic acid
(4-{2-[3-(2-Cyclopentanecarbonyl-4-methyl-phenyl)-ureido]-thiazol-5-ylmethanesulfonyl}-phenyl)-acetic acid
3-(4-{2-[3-(2-Cyclopentanecarbonyl-4-methyl-phenyl)-ureido]-thiazol-5-ylmethoxy}-phenyl)-propionic acid
3-(4-{2-[3-(2-Cyclopentanecarbonyl-4-methyl-phenyl)-ureido]-thiazol-5-ylmethylsulfanyl}-phenyl)-propionic acid
3-(4-{2-[3-(2-Cyclopentanecarbonyl-4-methyl-phenyl)-ureido]-thiazol-5-ylmethanesulfonyl}-phenyl)-propionic acid
4-{2-[3-(2-Cyclopentanecarbonyl-4-methyl-phenyl)-ureido]-thiazol-5-ylmethylsulfanyl}-benzoic acid
4-{2-[3-(2-Cyclopentanecarbonyl-4-methyl-phenyl)-ureido]-thiazol-5-ylmethanesulfonyl}-benzoic acid
4-{2-[3-(2-Cyclopentanecarbonyl-4-methyl-phenyl)-ureido]-thiazol-5-ylmethoxy}-benzoic acid
N-{2-[3-(2-Cyclopentanecarbonyl-4-methyl-phenyl)-ureido]-thiazol-5-ylmethyl}-acetamide
N-{2-[3-(2-Cyclopentanecarbonyl-4-methyl-phenyl)-ureido]-thiazol-5-ylmethyl}-methanesulfonamide
1-(2-Cyclopentanecarbonyl-4-methyl-phenyl)-3-[5-(pyridin-2-ylaminomethyl)-thiazol-2-yl]-urea
2-{2-[3-(2-Cyclopentanecarbonyl-4-methyl-phenyl)-ureido]-thiazol-5-ylmethanesulfonyl}-1H-imidazole-4-carboxylic acid
2-(2-{2-[3-(2-Cyclopentanecarbonyl-4-methyl-phenyl)-ureido]-thiazol-5-yl}-ethyl)-1H-imidazole-4-carboxylic acid
2-(2-{2-[3-(2-Cyclopentanecarbonyl-4-methyl-phenyl)-ureido]-thiazol-5-yl}-ethyl)-oxazole-4-carboxylic acid
2-(2-{2-[3-(2-Cyclopentanecarbonyl-4-methyl-phenyl)-ureido]-thiazol-5-yl}-ethyl)-1-methyl-1H-imidazole-4-carboxylic acid
2-[3-(2-Cyclopentanecarbonyl-4-methyl-phenyl)-ureido]-thiazole-5-carboxylic acid
2-[3-(2-Cyclopentanecarbonyl-4-methyl-phenyl)-ureido]-thiazole-5-carboxylic acid amide
2-[3-(2-Cyclopentanecarbonyl-4-methyl-phenyl)-ureido]-thiazole-5-carboxylic acid methylamide
({2-[3-(2-Cyclopentanecarbonyl-4-methyl-phenyl)-ureido]-thiazole-5-carbonyl}-amino)-acetic acid
({2-[3-(2-Cyclopentanecarbonyl-4-methyl-phenyl)-ureido]-thiazole-5-carbonyl}-methanesulfonyl-amino)-acetic acid
N-{2-[3-(2-Cyclopentanecarbonyl-4-methyl-phenyl)-ureido]-thiazole-5-carbonyl}-methanesulfonamide
{2-[3-(2-Cyclopentanecarbonyl-4-methyl-phenyl)-ureido]-thiazol-5-yl}-acetic acid
2-{2-[3-(2-Cyclopentanecarbonyl-4-methyl-phenyl)-ureido]-thiazol-5-yl}-acetamide
2-{2-[3-(2-Cyclopentanecarbonyl-4-methyl-phenyl)-ureido]-thiazol-5-yl}-N-methyl-acetamide
(2-{2-[3-(2-Cyclopentanecarbonyl-4-methyl-phenyl)-ureido]-thiazol-5-yl}-acetylamino)-acetic acid
N-(2-{2-[3-(2-Cyclopentanecarbonyl-4-methyl-phenyl)-ureido]-thiazol-5-yl}-acetyl)-methanesulfonamide
N-(2-{2-[3-(2-Cyclopentanecarbonyl-4-methyl-phenyl)-ureido]-thiazol-5-yl}-ethyl)-methanesulfonamide
N-(2-{2-[3-(2-Cyclopentanecarbonyl-4-methyl-phenyl)-ureido]-thiazol-5-yl}-ethyl)-acetamide
1-(2-Cyclopentanecarbonyl-4-methyl-phenyl)-3-(5-guanidinomethyl-thiazol-2-yl)-urea
1-(2-Cyclopentanecarbonyl-4-methyl-phenyl)-3-(5-ureidomethyl-thiazol-2-yl)-urea
1-(2-Cyclopentanecarbonyl-4-methyl-phenyl)-3-{5-[3-(2-dimethylamino-ethyl)-ureidomethyl]-thiazol-2-yl}-urea
{2-[3-(2-Cyclopentanecarbonyl-4-methyl-phenyl)-ureido]-thiazol-5-ylmethyl}-carbamic acid 2-dimethylamino-ethyl ester
{2-[3-(2-Cyclopentanecarbonyl-4-methyl-phenyl)-ureido]-thiazol-5-ylmethyl}-carbamic acid methyl ester
(2-{2-[3-(2-Cyclopentanecarbonyl-4-methyl-phenyl)-ureido]-thiazol-5-yl}-ethyl)-carbamic acid methyl ester
1-(2-Cyclopentanecarbonyl-4-methyl-phenyl)-3-[5-(2-guanidino-ethyl)-thiazol-2-yl]-urea
1-(2-Cyclopentanecarbonyl-4-methyl-phenyl)-3-[5-(2-ureido-ethyl)-thiazol-2-yl]-urea
[3-(2-{2-[3-(2-Cyclopentanecarbonyl-4-methyl-phenyl)-ureido]-thiazol-5-yl}-ethyl)-ureido]-acetic acid
1-(2-Cyclopentanecarbonyl-4-methyl-phenyl)-3-(5-{2-[3-(2-dimethylamino-ethyl)-ureido]-ethyl}-thiazol-2-yl)-urea
(2-{2-[3-(2-Cyclopentanecarbonyl-4-methyl-phenyl)-ureido]-thiazol-5-yl}-ethyl)-carbamic acid 2-dimethylamino-ethyl ester
1-(2-Cyclopentanecarbonyl-4-methyl-phenyl)-3-{5-[2-(1H-imidazol-2-ylsulfanyl)-ethyl]-thiazol-2-yl}-urea
1-(2-Cyclopentanecarbonyl-4-methyl-phenyl)-3-{5-[2-(1H-imidazole-2-sulfonyl)-ethyl]-thiazol-2-yl}-urea 1-(2-Cyclopentanecarbonyl-4-methyl-phenyl)-3-{5-[2-(1-methyl-1H-imidazol-2-ylsulfanyl)-ethyl]-thiazol-2-yl}-urea
1-(2-Cyclopentanecarbonyl-4-methyl-phenyl)-3-{5-[2-(1-methyl-1H-imidazole-2-sulfonyl)-ethyl]-thiazol-2-yl}-urea
2-(2-{2-[3-(2-Cyclopentanecarbonyl-4-methyl-phenyl)-ureido]-thiazol-5-yl}-ethylsulfanyl)-1H-imidazole-4-carboxylic acid
6-{2-[3-(2-Cyclopentanecarbonyl-4-methyl-phenyl)-ureido]-thiazol-5-ylmethylsulfanyl}-nicotinic acid
6-{2-[3-(2-Cyclopentanecarbonyl-4-methyl-phenyl)-ureido]-thiazol-5-ylmethanesulfonyl}-nicotinic acid
2-(2-{2-[3-(2-Cyclopentanecarbonyl-4-methyl-phenyl)-ureido]-thiazol-5-yl}-ethylsulfanyl)-1-methyl-1H-imidazole-4-carboxylic acid
[4-(2-{2-[3-(2-Cyclopentanecarbonyl-4-methyl-phenyl)-ureido]-thiazol-5-yl}-ethylsulfanyl)-phenyl]-acetic acid
[4-(2-{2-[3-(2-Cyclopentanecarbonyl-4-methyl-phenyl)-ureido]-thiazol-5-yl}-ethanesulfonyl)-phenyl]-acetic acid
1-(2-Cyclopentanecarbonyl-4-methyl-phenyl)-3-{5-[2-(pyridin-2-ylsulfanyl)-ethyl]-thiazol-2-yl}-urea
1-(2-Cyclopentanecarbonyl-4-methyl-phenyl)-3-{5-[2-(pyridine-2-sulfonyl)-ethyl]-thiazol-2-yl}-urea
6-(2-{2-[3-(2-Cyclopentanecarbonyl-4-methyl-phenyl)-ureido]-thiazol-5-yl}-ethylsulfanyl)-nicotinic acid
6-(2-{2-[3-(2-Cyclopentanecarbonyl-4-methyl-phenyl)-ureido]-thiazol-5-yl}-ethanesulfonyl)-nicotinic acid
1-(2-Cyclopentanecarbonyl-4-methyl-phenyl)-3-(5-[1,2,4]oxadiazol-5-ylmethyl-thiazol-2-yl)-urea
1-(2-Cyclopentanecarbonyl-4-methyl-phenyl)-3-[5-(2-[1,2,4]oxadiazol-5-yl-ethyl)-thiazol-2-yl]-urea
4-{2-[3-(2-Cyclopentanecarbonyl-4-methyl-phenyl)-ureido]-thiazol-5-yl}-butyric acid
1-(2-Isobutoxy-4-methyl-phenyl)-3-(5-piperidin-1-ylmethyl-thiazol-2-yl)-urea
1-(2-Isobutoxy-4-methyl-phenyl)-3-(5-morpholin-4-ylmethyl-thiazol-2-yl)-urea
1-(5-Dimethylaminomethyl-thiazol-2-yl)-3-(2-isobutoxy-4-methyl-phenyl)-urea
1-(2-Isobutoxy-4-methyl-phenyl)-3-(5-piperazin-1-ylmethyl-thiazol-2-yl)-urea
1-(2-Isobutoxy-4-methyl-phenyl)-3-[5-(4-methyl-piperazin-1-ylmethyl)-thiazol-2-yl]-urea
1-[5-(4-Acetyl-piperazin-1-ylmethyl)-thiazol-2-yl]-3-(2-isobutoxy-4-methyl-phenyl)-urea
1-(2-Isobutoxy-4-methyl-phenyl)-3-[5-(4-methanesulfonyl-piperazin-1-ylmethyl)-thiazol-2-yl]-urea
(4-{2-[3-(2-Isobutoxy-4-methyl-phenyl)-ureido]-thiazol-5-ylmethyl}-piperazin-1-yl)-acetic acid
2-{2-[3-(2-Isobutoxy-4-methyl-phenyl)-ureido]-thiazol-5-ylmethylsulfanyl}-1H-imidazole-4-carboxylic acid
1-[5-(1H-Imidazol-2-ylsulfanylmethyl)-thiazol-2-yl]-3-(2-isobutoxy-4-methyl-phenyl)-urea
1-(2-Isobutoxy-4-methyl-phenyl)-3-[5-(1-methyl-1H-imidazol-2-ylsulfanylmethyl)-thiazol-2-yl]-urea
1-(2-Isobutoxy-4-methyl-phenyl)-3-[5-(4-methyl-4H-[1,2,4]triazol-3-ylsulfanylmethyl)-thiazol-2-yl]-urea
1-(2-Isobutoxy-4-methyl-phenyl)-3-[5-(4H-[1,2,4]triazol-3-ylsulfanylmethyl)-thiazol-2-yl]-urea
1-(2-Isobutoxy-4-methyl-phenyl)-3-[5-(1-methyl-1H-tetrazol-5-ylsulfanylmethyl)-thiazol-2-yl]-urea
(5-{2-[3-(2-Isobutoxy-4-methyl-phenyl)-ureido]-thiazol-5-ylmethylsulfanyl}-tetrazol-1-yl)-acetic acid
1-{5-[1-(2-Dimethylamino-ethyl)-1H-tetrazol-5-ylsulfanylmethyl]-thiazol-2-yl}-3-(2-isobutoxy-4-methyl-phenyl)-urea
(5-{2-[3-(2-Isobutoxy-4-methyl-phenyl)-ureido]-thiazol-5-ylmethanesulfonyl}-tetrazol-1-yl)-acetic acid
1-{5-[1-(2-Dimethylamino-ethyl)-1H-tetrazole-5-sulfonylmethyl]-thiazol-2-yl}-3-(2-isobutoxy-4-methyl-phenyl)-urea
1-(2-Isobutoxy-4-methyl-phenyl)-3-[5-(1-methyl-1H-tetrazole-5-sulfonylmethyl)-thiazol-2-yl]-urea
1-(2-Isobutoxy-4-methyl-phenyl)-3-[5-(4H-[1,2,4]triazole-3-sulfonylmethyl)-thiazol-2-yl]-urea
1-(2-Isobutoxy-4-methyl-phenyl)-3-[5-(4-methyl-4H-[1,2,4]triazole-3-sulfonylmethyl)-thiazol-2-yl]-urea
1-(2-Isobutoxy-4-methyl-phenyl)-3-[5-(1-methyl-1H-imidazole-2-sulfonylmethyl)-thiazol-2-yl]-urea
1-[5-(1H-Imidazole-2-sulfonylmethyl)-thiazol-2-yl]-3-(2-isobutoxy-4-methyl-phenyl)-urea
1-(2-Isobutoxy-4-methyl-phenyl)-3-[5-(pyridine-2-sulfonylmethyl)-thiazol-2-yl]-urea
1-(2-Isobutoxy-4-methyl-phenyl)-3-[5-(pyridin-2-ylsulfanylmethyl)-thiazol-2-yl]-urea
1-(2-Isobutoxy-4-methyl-phenyl)-3-[5-(pyridin-3-ylsulfanylmethyl)-thiazol-2-yl]-urea
1-(2-Isobutoxy-4-methyl-phenyl)-3-[5-(pyridine-3-sulfonylmethyl)-thiazol-2-yl]-urea
1-(2-Isobutoxy-4-methyl-phenyl)-3-[5-(pyridin-4-ylsulfanylmethyl)-thiazol-2-yl]-urea
1-(2-Isobutoxy-4-methyl-phenyl)-3-[5-(pyridine-4-sulfonylmethyl)-thiazol-2-yl]-urea
1-(2-Isobutoxy-4-methyl-phenyl)-3-[5-(pyridin-4-yloxymethyl)-thiazol-2-yl]-urea
1-(2-Isobutoxy-4-methyl-phenyl)-3-[5-(pyridin-3-yloxymethyl)-thiazol-2-yl]-urea
1-(2-Isobutoxy-4-methyl-phenyl)-3-[5-(pyridin-2-yloxymethyl)-thiazol-2-yl]-urea
(4-{2-[3-(2-Isobutoxy-4-methyl-phenyl)-ureido]-thiazol-5-ylmethoxy}-phenyl)-acetic acid
(4-{2-[3-(2-Isobutoxy-4-methyl-phenyl)-ureido]-thiazol-5-ylmethylsulfanyl}-phenyl)-acetic acid
(4-{2-[3-(2-Isobutoxy-4-methyl-phenyl)-ureido]-thiazol-5-ylmethanesulfonyl}-phenyl)-acetic acid
3-(4-{2-[3-(2-Isobutoxy-4-methyl-phenyl)-ureido]-thiazol-5-ylmethoxy}-phenyl)-propionic acid
3-(4-{2-[3-(2-Isobutoxy-4-methyl-phenyl)-ureido]-thiazol-5-ylmethylsulfanyl}-phenyl)-propionic acid
3-(4-{2-[3-(2-Isobutoxy-4-methyl-phenyl)-ureido]-thiazol-5-ylmethanesulfonyl}-phenyl)-propionic acid
4-{2-[3-(2-Isobutoxy-4-methyl-phenyl)-ureido]-thiazol-5-ylmethylsulfanyl}-benzoic acid
4-{2-[3-(2-Isobutoxy-4-methyl-phenyl)-ureido]-thiazol-5-ylmethanesulfonyl}-benzoic acid
4-{2-[3-(2-Isobutoxy-4-methyl-phenyl)-ureido]-thiazol-5-ylmethoxy}-benzoic acid
N-{2-[3-(2-isobutoxy-4-methyl-phenyl)-ureido]-thiazol-5-ylmethyl}-acetamide
N-{2-[3-(2-Isobutoxy-4-methyl-phenyl)-ureido]-thiazol-5-ylmethyl}-methanesulfonamide
1-(2-Isobutoxy-4-methyl-phenyl)-3-[5-(pyridin-2-ylaminomethyl)-thiazol-2-yl]-urea
2-{2-[3-(2-Isobutoxy-4-methyl-phenyl)-ureido]-thiazol-5-ylmethanesulfonyl}-1H-imidazole-4-carboxylic acid
2-(2-{2-[3-(2-Isobutoxy-4-methyl-phenyl)-ureido]-thiazol-5-yl}-ethyl)-1H-imidazole-4-carboxylic acid
2-(2-{2-[3-(2-isobutoxy-4-methyl-phenyl)-ureido]-thiazol-5-yl}-ethyl)-oxazole-4-carboxylic acid
2-(2-{2-[3-(2-Isobutoxy-4-methyl-phenyl)-ureido]-thiazol-5-yl}-ethyl)-1-methyl-1H-imidazole-4-carboxylic acid
2-[3-(2-Isobutoxy-4-methyl-phenyl)-ureido]-thiazole-5-carboxylic acid 2-[3-(2-Isobutoxy-4-methyl-phenyl)-ureido]-thiazole-5-carboxylic acid amide
2-[3-(2-Isobutoxy-4-methyl-phenyl)-ureido]-thiazole-5-carboxylic acid methylamide
({2-[3-(2-Isobutoxy-4-methyl-phenyl)-ureido]-thiazole-5-carbonyl}-amino)-acetic acid
({2-[3-(2-Isobutoxy-4-methyl-phenyl)-ureido]-thiazole-5-carbonyl}-methanesulfonyl-amino)-acetic acid
N-{2-[3-(2-Isobutoxy-4-methyl-phenyl)-ureido]-thiazole-5-carbonyl}-methanesulfonamide
{2-[3-(2-Isobutoxy-4-methyl-phenyl)-ureido]-thiazol-5-yl}-acetic acid
2-{2-[3-(2-Isobutoxy-4-methyl-phenyl)-ureido]-thiazol-5-yl}-acetamide
2-{2-[3-(2-Isobutoxy-4-methyl-phenyl)-ureido]-thiazol-5-yl}-N-methyl-acetamide
(2-{2-[3-(2-Isobutoxy-4-methyl-phenyl)-ureido]-thiazol-5-yl}-acetylamino)-acetic acid
N-(2-{2-[3-(2-Isobutoxy-4-methyl-phenyl)-ureido]-thiazol-5-yl}-acetyl)-methanesulfonamide
N-(2-{2-[3-(2-Isobutoxy-4-methyl-phenyl)-ureido]-thiazol-5-yl}-ethyl)-methanesulfonamide
N-(2-{2-[3-(2-Isobutoxy-4-methyl-phenyl)-ureido]-thiazol-5-yl}-ethyl)-acetamide
1-(5-Guanidinomethyl-thiazol-2-yl)-3-(2-isobutoxy-4-methyl-phenyl)-urea
1-(2-Isobutoxy-4-methyl-phenyl)-3-(5-ureidomethyl-thiazol-2-yl)-urea
1-{5-[3-(2-Dimethylamino-ethyl)-ureidomethyl]-thiazol-2-yl}-3-(2-isobutoxy-4-methyl-phenyl)-urea
{2-[3-(2-Isobutoxy-4-methyl-phenyl)-ureido]-thiazol-5-ylmethyl}-carbamic acid 2-dimethylamino-ethyl ester
{2-[3-(2-Isobutoxy-4-methyl-phenyl)-ureido]-thiazol-5-ylmethyl}-carbamic acid methyl ester
(2-{2-[3-(2-isobutoxy-4-methyl-phenyl)-ureido]-thiazol-5-yl}-ethyl)-carbamic acid methyl ester
1-[5-(2-Guanidino-ethyl)-thiazol-2-yl]-3-(2-isobutoxy-4-methyl-phenyl)-urea
1-(2-Isobutoxy-4-methyl-phenyl)-3-[5-(2-ureido-ethyl)-thiazol-2-yl]-urea
[3-(2-{2-[3-(2-Isobutoxy-4-methyl-phenyl)-ureido]-thiazol-5-yl}-ethyl)-ureido]-acetic acid
1-(5-{2-[3-(2-Dimethylamino-ethyl)-ureido]-ethyl}-thiazol-2-yl)-3-(2-isobutoxy-4-methyl-phenyl)-urea
(2-{2-[3-(2-isobutoxy-4-methyl-phenyl)-ureido]-thiazol-5-yl}-ethyl)-carbamic acid 2-dimethylamino-ethyl ester
1-{5-[2-(1H-Imidazol-2-ylsulfanyl)-ethyl]-thiazol-2-yl}-3-(2-isobutoxy-4-methyl-phenyl)-urea
1-{5-[2-(1H-Imidazole-2-sulfonyl)-ethyl]-thiazol-2-yl}-3-(2-isobutoxy-4-methyl-phenyl)-urea
1-(2-Isobutoxy-4-methyl-phenyl)-3-{5-[2-(1-methyl-1H-imidazol-2-ylsulfanyl)-ethyl]-thiazol-2-yl}-urea
1-(2-Isobutoxy-4-methyl-phenyl)-3-{5-[2-(1-methyl-1H-imidazole-2-sulfonyl)-ethyl]-thiazol-2-yl}-urea
2-(2-{2-[3-(2-Isobutoxy-4-methyl-phenyl)-ureido]-thiazol-5-yl}-ethylsulfanyl)-1H-imidazole-4-carboxylic acid
6-{2-[3-(2-Isobutoxy-4-methyl-phenyl)-ureido]-thiazol-5-ylmethylsulfanyl}-nicotinic acid
6-{2-[3-(2-Isobutoxy-4-methyl-phenyl)-ureido]-thiazol-5-ylmethanesulfonyl}-nicotinic acid
2-(2-{2-[3-(2-Isobutoxy-4-methyl-phenyl)-ureido]-thiazol-5-yl}-ethylsulfanyl)-1-methyl-1H-imidazole-4-carboxylic acid
[4-(2-{2-[3-(2-Isobutoxy-4-methyl-phenyl)-ureido]-thiazol-5-yl}-ethylsulfanyl)-phenyl]-acetic acid
[4-(2-{2-[3-(2-Isobutoxy-4-methyl-phenyl)-ureido]-thiazol-5-yl}-ethanesulfonyl)-phenyl]-acetic acid
1-(2-Isobutoxy-4-methyl-phenyl)-3-{5-[2-(pyridin-2-ylsulfanyl)-ethyl]-thiazol-2-yl}-urea
1-(2-Isobutoxy-4-methyl-phenyl)-3-{5-[2-(pyridine-2-sulfonyl)-ethyl]-thiazol-2-yl}-urea
6-(2-{2-[3-(2-Isobutoxy-4-methyl-phenyl)-ureido]-thiazol-5-yl}-ethylsulfanyl)-nicotinic acid
6-(2-{2-[3-(2-Isobutoxy-4-methyl-phenyl)-ureido]-thiazol-5-yl}-ethanesulfonyl)-nicotinic acid
1-(2-Isobutoxy-4-methyl-phenyl)-3-(5-[1,2,4]oxadiazol-5-ylmethyl-thiazol-2-yl)-urea
1-(2-Isobutoxy-4-methyl-phenyl)-3-[5-(2-[1,2,4]oxadiazol-5-yl-ethyl)-thiazol-2-yl]-urea
4-{2-[3-(2-Isobutoxy-4-methyl-phenyl)-ureido]-thiazol-5-yl}-butyric acid
1-[5-(1H-Imidazol-2-ylsulfanyl)-thiazol-2-yl]-3-(2-isobutoxy-4-methyl-phenyl)-urea
1-(2-Isobutoxy-4-methyl-phenyl)-3-[5-(1-methyl-1H-imidazol-2-ylsulfanyl)-thiazol-2-yl]-urea
2-{2-[3-(2-Isobutoxy-4-methyl-phenyl)-ureido]-thiazol-5-ylsulfanyl}-1-methyl-1H-imidazole-4-carboxylic acid
2-{2-[3-(2-Isobutoxy-4-methyl-phenyl)-ureido]-thiazole-5-sulfonyl}-1-methyl-1H-imidazole-4-carboxylic acid
2-{2-[3-(2-Isobutoxy-4-methyl-phenyl)-ureido]-thiazole-5-sulfonyl}-1H-imidazole-4-carboxylic acid
1-[5-(1H-Imidazole-2-sulfonyl)-thiazol-2-yl]-3-(2-isobutoxy-4-methyl-phenyl)-urea
1-(2-Isobutoxy-4-methyl-phenyl)-3-[5-(pyridine-2-sulfonyl)-thiazol-2-yl]-urea
1-(2-Isobutoxy-4-methyl-phenyl)-3-[5-(pyridine-3-sulfonyl)-thiazol-2-yl]-urea
1-(2-Isobutoxy-4-methyl-phenyl)-3-[5-(pyridine-4-sulfonyl)-thiazol-2-yl]-urea
1-(2-Isobutoxy-4-methyl-phenyl)-3-[5-(pyridin-4-ylsulfanyl)-thiazol-2-yl]-urea
1-(2-Isobutoxy-4-methyl-phenyl)-3-[5-(pyridin-3-ylsulfanyl)-thiazol-2-yl]-urea
1-(2-Isobutoxy-4-methyl-phenyl)-3-[5-(pyridin-2-ylsulfanyl)-thiazol-2-yl]-urea
6-{2-[3-(2-Isobutoxy-4-methyl-phenyl)-ureido]-thiazol-5-ylsulfanyl}-nicotinic acid
6-{2-[3-(2-Isobutoxy-4-methyl-phenyl)-ureido]-thiazole-5-sulfonyl}-nicotinic acid
1-(2-Isobutoxy-4-methyl-phenyl)-3-(5-methanesulfonyl-thiazol-2-yl)-urea
3-{2-[3-(2-Isobutoxy-4-methyl-phenyl)-ureido]-thiazole-5-sulfonyl}-propionic acid
3-{2-[3-(2-Isobutoxy-4-methyl-phenyl)-ureido]-thiazol-5-ylsulfanyl}-propionic acid
1-(5-Bromo-thiazol-2-yl)-3-(2-isobutoxy-4-methyl-phenyl)-urea
{5-Chloro-2-[3-(2-isobutoxy-4-methyl-phenyl)-ureido]-thiazol-4-yl}-acetic acid
{5-Bromo-2-[3-(2-isobutoxy-4-methyl-phenyl)-ureido]-thiazol-4-yl}-acetic acid
1-[2-(2-Methoxy-benzoyl)-4-methyl-phenyl]-3-(5-piperidin-1-ylmethyl-thiazol-2-yl)-urea
1-[2-(2-Methoxy-benzoyl)-4-methyl-phenyl]-3-(5-morpholin-4-ylmethyl-thiazol-2-yl)-urea
1-(5-Dimethylaminomethyl-thiazol-2-yl)-3-[2-(2-methoxy-benzoyl)-4-methyl-phenyl]-urea
1-[2-(2-Methoxy-benzoyl)-4-methyl-phenyl]-3-(5-piperazin-1-ylmethyl-thiazol-2-yl)-urea
1-[2-(2-Methoxy-benzoyl)-4-methyl-phenyl]-3-[5-(4-methyl-piperazin-1-ylmethyl)-thiazol-2-yl]-urea
1-[5-(4-Acetyl-piperazin-1-ylmethyl)-thiazol-2-yl]-3-[2-(2-methoxy-benzoyl)-4-methyl-phenyl]-urea 1-[5-(4-Methanesulfonyl-piperazin-1-ylmethyl)-thiazol-2-yl]-3-[2-(2-methoxy-benzoyl)-4-methyl-phenyl]-urea
[4-(2-{3-[2-(2-Methoxy-benzoyl)-4-methyl-phenyl]-ureido}-thiazol-5-ylmethyl)-piperazin-1-yl]-acetic acid
2-(2-{3-[2-(2-Methoxy-benzoyl)-4-methyl-phenyl]-ureido}-thiazol-5-ylmethylsulfanyl)-1H-imidazole-4-carboxylic acid
1-[5-(1H-Imidazol-2-ylsulfanylmethyl)-thiazol-2-yl]-3-[2-(2-methoxy-benzoyl)-4-methyl-phenyl]-urea
1-[2-(2-Methoxy-benzoyl)-4-methyl-phenyl]-3-[5-(1-methyl-1H-imidazol-2-ylsulfanylmethyl)-thiazol-2-yl]-urea
1-[2-(2-Methoxy-benzoyl)-4-methyl-phenyl]-3-[5-(4-methyl-4H-[1,2,4]triazol-3-ylsulfanylmethyl)-thiazol-2-yl]-urea
1-[2-(2-Methoxy-benzoyl)-4-methyl-phenyl]-3-[5-(4H-[1,2,4]triazol-3-ylsulfanylmethyl)-thiazol-2-yl]-urea
1-[2-(2-Methoxy-benzoyl)-4-methyl-phenyl]-3-[5-(1-methyl-1H-tetrazol-5-ylsulfanylmethyl)-thiazol-2-yl]-urea
[5-(2-{3-[2-(2-Methoxy-benzoyl)-4-methyl-phenyl]-ureido}thiazol-5-ylmethylsulfanyl)-tetrazol-1-yl]-acetic acid
1-{5-[1-(2-Dimethylamino-ethyl)-1H-tetrazol-5-ylsulfanylmethyl]-thiazol-2-yl}-3-[2-(2-methoxy-benzoyl)-4-methyl-phenyl]-urea
[5-(2-{3-[2-(2-Methoxy-benzoyl)-4-methyl-phenyl]-ureido}-thiazol-5-ylmethanesulfonyl)-tetrazol-1-yl]-acetic acid
1-{5-[1-(2-Dimethylamino-ethyl)-1H-tetrazole-5-sulfonylmethyl]-thiazol-2-yl}-3-[2-(2-methoxy-benzoyl)-4-methyl-phenyl]-urea
1-[2-(2-Methoxy-benzoyl)-4-methyl-phenyl]-3-[5-(1-methyl-1H-tetrazole-5-sulfonylmethyl)-thiazol-2-yl]-urea
1-[2-(2-Methoxy-benzoyl)-4-methyl-phenyl]-3-[5-(4H-[1,2,4]triazole-3-sulfonylmethyl)-thiazol-2-yl]-urea
1-[2-(2-Methoxy-benzoyl)-4-methyl-phenyl]-3-[5-(4-methyl-4H-[1,2,4]triazole-3-sulfonylmethyl)-thiazol-2-yl]-urea
1-[2-(2-Methoxy-benzoyl)-4-methyl-phenyl]-3-[5-(1-methyl-1H-imidazole-2-sulfonylmethyl)-thiazol-2-yl]-urea
1-[5-(1H-Imidazole-2-sulfonylmethyl)-thiazol-2-yl]-3-[2-(2-methoxy-benzoyl)-4-methyl-phenyl]-urea
1-[2-(2-Methoxy-benzoyl)-4-methyl-phenyl]-3-[5-(pyridine-2-sulfonylmethyl)-thiazol-2-yl]-urea
1-[2-(2-Methoxy-benzoyl)-4-methyl-phenyl]-3-[5-(pyridin-2-ylsulfanylmethyl)-thiazol-2-yl]-urea
1-[2-(2-Methoxy-benzoyl)-4-methyl-phenyl]-3-[5-(pyridin-3-ylsulfanylmethyl)-thiazol-2-yl]-urea
1-[2-(2-Methoxy-benzoyl)-4-methyl-phenyl]-3-[5-(pyridine-3-sulfonylmethyl)-thiazol-2-yl]-urea
1-[2-(2-Methoxy-benzoyl)-4-methyl-phenyl]-3-[5-(pyridin-4-ylsulfanylmethyl)-thiazol-2-yl]-urea
1-[2-(2-Methoxy-benzoyl)-4-methyl-phenyl]-3-[5-(pyridine-4-sulfonylmethyl)-thiazol-2-yl]-urea
1-[2-(2-Methoxy-benzoyl)-4-methyl-phenyl]-3-[5-(pyridin-4-yloxymethyl)-thiazol-2-yl]-urea
1-[2-(2-Methoxy-benzoyl)-4-methyl-phenyl]-3-[5-(pyridin-3-yloxymethyl)-thiazol-2-yl]-urea
1-[2-(2-Methoxy-benzoyl)-4-methyl-phenyl]-3-[5-(pyridin-2-yloxymethyl)-thiazol-2-yl]-urea
[4-(2-{3-[2-(2-Methoxy-benzoyl)-4-methyl-phenyl]-ureido}-thiazol-5-ylmethoxy)-phenyl]-acetic acid
[4-(2-{3-[2-(2-Methoxy-benzoyl)-4-methyl-phenyl]-ureido}-thiazol-5-ylmethylsulfanyl)-phenyl]-acetic acid
[4-(2-{3-[2-(2-Methoxy-benzoyl)-4-methyl-phenyl]-ureido}-thiazol-5-ylmethanesulfonyl)-phenyl]-acetic acid
3-[4-(2-{3-[2-(2-Methoxy-benzoyl)-4-methyl-phenyl]-ureido}-thiazol-5-ylmethoxy)-phenyl]-propionic acid
3-[4-(2-{3-[2-(2-Methoxy-benzoyl)-4-methyl-phenyl]-ureido}-thiazol-5-ylmethylsulfanyl)-phenyl]-propionic acid
3-[4-(2-{3-[2-(2-Methoxy-benzoyl)-4-methyl-phenyl]-ureido}-thiazol-5-ylmethanesulfonyl)-phenyl]-propionic acid
4-(2-{3-[2-(2-Methoxy-benzoyl)-4-methyl-phenyl]-ureido}-thiazol-5-ylmethylsulfanyl)-benzoic acid
4-(2-{3-[2-(2-Methoxy-benzoyl)-4-methyl-phenyl]-ureido}-thiazol-5-ylmethanesulfonyl)-benzoic acid
4-(2-{3-[2-(2-Methoxy-benzoyl)-4-methyl-phenyl]-ureido}-thiazol-5-ylmethoxy)-benzoic acid
N-(2-{3-[2-(2-Methoxy-benzoyl)-4-methyl-phenyl]-ureido}-thiazol-5-ylmethyl)-acetamide
N-(2-{3-[2-(2-Methoxy-benzoyl)-4-methyl-phenyl]-ureido}-thiazol-5-ylmethyl)-methanesulfonamide
1-[2-(2-Methoxy-benzoyl)-4-methyl-phenyl]-3-[5-(pyridin-2-ylaminomethyl)-thiazol-2-yl]-urea
2-(2-{3-[2-(2-Methoxy-benzoyl)-4-methyl-phenyl]-ureido}-thiazol-5-ylmethanesulfonyl)-1H-imidazole-4-carboxylic acid
2-[2-(2-{3-[2-(2-Methoxy-benzoyl)-4-methyl-phenyl]-ureido}-thiazol-5-yl)-ethyl]-1H-imidazole-4-carboxylic acid
2-[2-(2-{3-[2-(2-Methoxy-benzoyl)-4-methyl-phenyl]-ureido}-thiazol-5-yl)-ethyl]-oxazole-4-carboxylic acid
2-[2-(2-{3-[2-(2-Methoxy-benzoyl)-4-methyl-phenyl]-ureido}-thiazol-5-yl)-ethyl]-1-methyl-1H-imidazole-4-carboxylic acid
2-{3-[2-(2-Methoxy-benzoyl)-4-methyl-phenyl]-ureido}-thiazole-5-carboxylic acid
2-{3-[2-(2-Methoxy-benzoyl)-4-methyl-phenyl]-ureido}-thiazole-5-carboxylic acid amide
2-{3-[2-(2-Methoxy-benzoyl)-4-methyl-phenyl]-ureido}-thiazole-5-carboxylic acid methylamide
[(2-{3-[2-(2-Methoxy-benzoyl)-4-methyl-phenyl]-ureido}-thiazole-5-carbonyl)-amino]-acetic acid
[Methanesulfonyl-(2-{3-[2-(2-methoxy-benzoyl)-4-methyl-phenyl]-ureido}-thiazole-5-carbonyl)-amino]-acetic acid
N-(2-{3-[2-(2-Methoxy-benzoyl)-4-methyl-phenyl]-ureido}-thiazole-5-carbonyl)-methanesulfonamide
(2-{3-[2-(2-Methoxy-benzoyl)-4-methyl-phenyl]-ureido}-thiazol-5-yl)-acetic acid
2-(2-{3-[2-(2-Methoxy-benzoyl)-4-methyl-phenyl]-ureido}-thiazol-5-yl)-acetamide
2-(2-{3-[2-(2-Methoxy-benzoyl)-4-methyl-phenyl]-ureido}-thiazol-5-yl)-N-methyl-acetamide
[2-(2-{3-[2-(2-Methoxy-benzoyl)-4-methyl-phenyl]-ureido}-thiazol-5-yl)-acetylamino]-acetic acid
N-[2-(2-{3-[2-(2-Methoxy-benzoyl)-4-methyl-phenyl]-ureido}-thiazol-5-yl)-acetyl]-methanesulfonamide
N-[2-(2-{3-[2-(2-Methoxy-benzoyl)-4-methyl-phenyl]-ureido}-thiazol-5-yl)-ethyl]-methanesulfonamide
N-[2-(2-{3-[2-(2-Methoxy-benzoyl)-4-methyl-phenyl]-ureido}-thiazol-5-yl)-ethyl]-acetamide
1-(5-Guanidinomethyl-thiazol-2-yl)-3-[2-(2-methoxy-benzoyl)-4-methyl-phenyl]-urea
1-[2-(2-Methoxy-benzoyl)-4-methyl-phenyl]-3-(5-ureidomethyl-thiazol-2-yl)-urea
1-{5-[3-(2-Dimethylamino-ethyl)-ureidomethyl]-thiazol-2-yl}-3-[2-(2-methoxy-benzoyl)-4-methyl-phenyl]-urea
(2-{3-[2-(2-Methoxy-benzoyl)-4-methyl-phenyl]-ureido}-thiazol-5-ylmethyl)-carbamic acid 2-dimethylamino-ethyl ester
(2-{3-[2-(2-Methoxy-benzoyl)-4-methyl-phenyl]-ureido}-thiazol-5-ylmethyl)-carbamic acid methyl ester
[2-(2-{3-[2-(2-Methoxy-benzoyl)-4-methyl-phenyl]-ureido}-thiazol-5-yl)-ethyl]-carbamic acid methyl ester 1-[5-(2-Guanidino-ethyl)-thiazol-2-yl]-3-[2-(2-methoxy-benzoyl)-4-methyl-phenyl]-urea
1-[2-(2-Methoxy-benzoyl)-4-methyl-phenyl]-3-[5-(2-ureido-ethyl)-thiazol-2-yl]-urea
{3-[2-(2-{3-[2-(2-Methoxy-benzoyl)-4-methyl-phenyl]-ureido}-thiazol-5-yl)-ethyl]-ureido}-acetic acid
1-(5-{2-[3-(2-Dimethylamino-ethyl)-ureido]-ethyl}-thiazol-2-yl)-3-[2-(2-methoxy-benzoyl)-4-methyl-phenyl]-urea
[2-(2-{3-[2-(2-Methoxy-benzoyl)-4-methyl-phenyl]-ureido}-thiazol-5-yl)-ethyl]-carbamic acid 2-dimethylamino-ethyl ester
1-{5-[2-(1H-Imidazol-2-ylsulfanyl)-ethyl]-thiazol-2-yl}-3-[2-(2-methoxy-benzoyl)-4-methyl-phenyl]-urea
1-{5-[2-(1H-Imidazole-2-sulfonyl)-ethyl]-thiazol-2-yl}-3-[2-(2-methoxy-benzoyl)-4-methyl-phenyl]-urea
1-[2-(2-Methoxy-benzoyl)-4-methyl-phenyl]-3-{5-[2-(1-methyl-1H-imidazol-2-ylsulfanyl)-ethyl]-thiazol-2-yl}-urea
1-[2-(2-Methoxy-benzoyl)-4-methyl-phenyl]-3-{5-[2-(1-methyl-1H-imidazole-2-sulfonyl)-ethyl]-thiazol-2-yl}-urea
2-[2-(2-{3-[2-(2-Methoxy-benzoyl)-4-methyl-phenyl]-ureido}-thiazol-5-yl)-ethylsulfanyl]-1H-imidazole-4-carboxylic acid
6-(2-{3-[2-(2-Methoxy-benzoyl)-4-methyl-phenyl]-ureido}-thiazol-5-ylmethylsulfanyl)-nicotinic acid
6-(2-{3-[2-(2-Methoxy-benzoyl)-4-methyl-phenyl]-ureido}-thiazol-5-ylmethanesulfonyl)-nicotinic acid
2-[2-(2-{3-[2-(2-Methoxy-benzoyl)-4-methyl-phenyl]-ureido}-thiazol-5-yl)-ethylsulfanyl]-1-methyl-1H-imidazole-4-carboxylic acid
{4-[2-(2-{3-[2-(2-Methoxy-benzoyl)-4-methyl-phenyl]-ureido}-thiazol-5-yl)-ethylsulfanyl]-phenyl}-acetic acid
{4-[2-(2-{3-[2-(2-Methoxy-benzoyl)-4-methyl-phenyl]-ureido}-thiazol-5-yl)-ethanesulfonyl]-phenyl}-acetic acid
1-[2-(2-Methoxy-benzoyl)-4-methyl-phenyl]-3-{5-[2-(pyridin-2-ylsulfanyl)-ethyl]-thiazol-2-yl}-urea
1-[2-(2-Methoxy-benzoyl)-4-methyl-phenyl]-3-{5-[2-(pyridine-2-sulfonyl)-ethyl]-thiazol-2-yl}-urea
6-[2-(2-{3-[2-(2-Methoxy-benzoyl)-4-methyl-phenyl]-ureido}-thiazol-5-yl)-ethylsulfanyl]-nicotinic acid
6-[2-(2-{3-[2-(2-Methoxy-benzoyl)-4-methyl-phenyl]-ureido}-thiazol-5-yl)-ethanesulfonyl]-nicotinic acid
1-[2-(2-Methoxy-benzoyl)-4-methyl-phenyl]-3-(5-[1,2,4]oxadiazol-5-ylmethyl-thiazol-2-yl)-urea
1-[2-(2-Methoxy-benzoyl)-4-methyl-phenyl]-3-[5-(2-[1,2,4]oxadiazol-5-yl-ethyl)-thiazol-2-yl]-urea
4-(2-{3-[2-(2-Methoxy-benzoyl)-4-methyl-phenyl]-ureido}-thiazol-5-yl)-butyric acid
1-[5-(1H-Imidazol-2-ylsulfanyl)-thiazol-2-yl]-3-[2-(2-methoxy-benzoyl)-4-methyl-phenyl]-urea
1-[2-(2-Methoxy-benzoyl)-4-methyl-phenyl]-3-[5-(1-methyl-1H-imidazol-2-ylsulfanyl)-thiazol-2-yl]-urea
2-(2-{3-[2-(2-Methoxy-benzoyl)-4-methyl-phenyl]-ureido}-thiazol-5-ylsulfanyl)-1-methyl-1H-imidazole-4-carboxylic acid
2-(2-{3-[2-(2-Methoxy-benzoyl)-4-methyl-phenyl]-ureido}-thiazole-5-sulfonyl)-1-methyl-1H-imidazole-4-carboxylic acid
2-(2-{3-[2-(2-Methoxy-benzoyl)-4-methyl-phenyl]-ureido}-thiazole-5-sulfonyl)-1H-imidazole-4-carboxylic acid
1-[5-(1H-Imidazole-2-sulfonyl)-thiazol-2-yl]-3-[2-(2-methoxy-benzoyl)-4-methyl-phenyl]-urea
1-[2-(2-Methoxy-benzoyl)-4-methyl-phenyl]-3-[5-(pyridine-2-sulfonyl)-thiazol-2-yl]-urea
1-[2-(2-Methoxy-benzoyl)-4-methyl-phenyl]-3-[5-(pyridine-3-sulfonyl)-thiazol-2-yl]-urea
1-[2-(2-Methoxy-benzoyl)-4-methyl-phenyl]-3-[5-(pyridine-4-sulfonyl)-thiazol-2-yl]-urea
1-[2-(2-Methoxy-benzoyl)-4-methyl-phenyl]-3-[5-(pyridin-4-ylsulfanyl)-thiazol-2-yl]-urea
1-[2-(2-Methoxy-benzoyl)-4-methyl-phenyl]-3-[5-(pyridin-3-ylsulfanyl)-thiazol-2-yl]-urea
1-[2-(2-Methoxy-benzoyl)-4-methyl-phenyl]-3-[5-(pyridin-2-ylsulfanyl)-thiazol-2-yl]-urea
6-(2-{3-[2-(2-Methoxy-benzoyl)-4-methyl-phenyl]-ureido}-thiazol-5-ylsulfanyl)-nicotinic acid
6-(2-{3-[2-(2-Methoxy-benzoyl)-4-methyl-phenyl]-ureido}-thiazole-5-sulfonyl)-nicotinic acid
1-(5-Methanesulfonyl-thiazol-2-yl)-3-[2-(2-methoxy-benzoyl)-4-methyl-phenyl]-urea
3-(2-{3-[2-(2-Methoxy-benzoyl)-4-methyl-phenyl]-ureido}-thiazole-5-sulfonyl)-propionic acid
3-(2-{3-[2-(2-Methoxy-benzoyl)-4-methyl-phenyl]-ureido}-thiazol-5-ylsulfanyl)-propionic acid
1-(5-Bromo-thiazol-2-yl)-3-[2-(2-methoxy-benzoyl)-4-methyl-phenyl]-urea
(5-Chloro-2-{3-[2-(2-methoxy-benzoyl)-4-methyl-phenyl]-ureido}-thiazol-4-yl)-acetic acid
(5-Bromo-2-{3-[2-(2-methoxy-benzoyl)-4-methyl-phenyl]-ureido}-thiazol-4-yl)-acetic acid
1-(5-Chloro-thiazol-2-yl)-3-[2-(2-methoxy-benzoyl)-4-methyl-phenyl]-urea
1-(5-Chloro-thiazol-2-yl)-3-(2-isobutoxy-4-methyl-phenyl)-urea
1-(4-Methyl-2-piperidin-1-yl-phenyl)-3-(5-piperidin-1-ylmethyl-thiazol-2-yl)-urea
1-(4-Methyl-2-piperidin-1-yl-phenyl)-3-(5-morpholin-4-ylmethyl-thiazol-2-yl)-urea
1-(5-Dimethylaminomethyl-thiazol-2-yl)-3-(4-methyl-2-piperidin-1-yl-phenyl)-urea
1-(4-Methyl-2-piperidin-1-yl-phenyl)-3-(5-piperazin-1-ylmethyl-thiazol-2-yl)-urea
1-[5-(4-Methyl-piperazin-1-ylmethyl)-thiazol-2-yl]-3-(4-methyl-2-piperidin-1-yl-phenyl)-urea
1-[5-(4-Acetyl-piperazin-1-ylmethyl)-thiazol-2-yl]-3-(4-methyl-2-piperidin-1-yl-phenyl)-urea
1-[5-(4-Methanesulfonyl-piperazin-1-ylmethyl)-thiazol-2-yl]-3-(4-methyl-2-piperidin-1-yl-phenyl)-urea
(4-{2-[3-(4-Methyl-2-piperidin-1-yl-phenyl)-ureido]-thiazol-5-ylmethyl}-piperazin-1-yl)-acetic acid
2-{2-[3-(4-Methyl-2-piperidin-1-yl-phenyl)-ureido]-thiazol-5-ylmethylsulfanyl}-1H-imidazole-4-carboxylic acid
1-[5-(1H-Imidazol-2-ylsulfanylmethyl)-thiazol-2-yl]-3-(4-methyl-2-piperidin-1-yl-phenyl)-urea
1-[5-(1-Methyl-1H-imidazol-2-ylsulfanylmethyl)-thiazol-2-yl]-3-(4-methyl-2-piperidin-1-yl-phenyl)-urea
1-(4-Methyl-2-piperidin-1-yl-phenyl)-3-[5-(4-methyl-4H-[1,2,4]triazol-3-ylsulfanylmethyl)-thiazol-2-yl]-urea
1-(4-Methyl-2-piperidin-1-yl-phenyl)-3-[5-(4H-[1,2,4]triazol-3-ylsulfanylmethyl)-thiazol-2-yl]-urea
1-(4-Methyl-2-piperidin-1-yl-phenyl)-3-[5-(1-methyl-1H-tetrazol-5-ylsulfanylmethyl)-thiazol-2-yl]-urea
(5-{2-[3-(4-Methyl-2-piperidin-1-yl-phenyl)-ureido]-thiazol-5-ylmethylsulfanyl}-tetrazol-1-yl)-acetic acid
1-{5-[1-(2-Dimethylamino-ethyl)-1H-tetrazol-5-ylsulfanylmethyl]-thiazol-2-yl}-3-(4-methyl-2-piperidin-1-yl-phenyl)-urea
(5-{2-[3-(4-Methyl-2-piperidin-1-yl-phenyl)-ureido]-thiazol-5-ylmethanesulfonyl}-tetrazol-1-yl)-acetic acid 1-{5-[1-(2-Dimethylamino-ethyl)-1H-tetrazole-5-sulfonyl-methyl]-thiazol-2-yl}-3-(4-methyl-2-piperidin-1-yl-phenyl)-urea
1-(4-Methyl-2-piperidin-1-yl-phenyl)-3-[5-(1-methyl-1H-tetrazole-5-sulfonylmethyl)-thiazol-2-yl]-urea
1-(4-Methyl-2-piperidin-1-yl-phenyl)-3-[5-(4H-[1,2,4]triazole-3-sulfonylmethyl)-thiazol-2-yl]-urea
1-(4-Methyl-2-piperidin-1-yl-phenyl)-3-[5-(4-methyl-4H-[1,2,4]triazole-3-sulfonylmethyl)-thiazol-2-yl]-urea
1-[5-(1-Methyl-1H-imidazole-2-sulfonylmethyl)-thiazol-2-yl]-3-(4-methyl-2-piperidin-1-yl-phenyl)-urea
1-[5-(1H-Imidazole-2-sulfonylmethyl)-thiazol-2-yl]-3-(4-methyl-2-piperidin-1-yl-phenyl)-urea
1-(4-Methyl-2-piperidin-1-yl-phenyl)-3-[5-(pyridine-2-sulfonylmethyl)-thiazol-2-yl]-urea
1-(4-Methyl-2-piperidin-1-yl-phenyl)-3-[5-(pyridin-2-ylsulfanylmethyl)-thiazol-2-yl]-urea
1-(4-Methyl-2-piperidin-1-yl-phenyl)-3-[5-(pyridin-3-ylsulfanylmethyl)-thiazol-2-yl]-urea
1-(4-Methyl-2-piperidin-1-yl-phenyl)-3-[5-(pyridine-3-sulfonylmethyl)-thiazol-2-yl]-urea
1-(4-Methyl-2-piperidin-1-yl-phenyl)-3-[5-(pyridin-4-ylsulfanylmethyl)-thiazol-2-yl]-urea
1-(4-Methyl-2-piperidin-1-yl-phenyl)-3-[5-(pyridine-4-sulfonylmethyl)-thiazol-2-yl]-urea
1-(4-Methyl-2-piperidin-1-yl-phenyl)-3-[5-(pyridin-4-yloxymethyl)-thiazol-2-yl]-urea
1-(4-Methyl-2-piperidin-1-yl-phenyl)-3-[5-(pyridin-3-yloxymethyl)-thiazol-2-yl]-urea
1-(4-Methyl-2-piperidin-1-yl-phenyl)-3-[5-(pyridin-2-yloxymethyl)-thiazol-2-yl]-urea
(4-{2-[3-(4-Methyl-2-piperidin-1-yl-phenyl)-ureido]-thiazol-5-ylmethoxy}-phenyl)-acetic acid
(4-{2-[3-(4-Methyl-2-piperidin-1-yl-phenyl)-ureido]-thiazol-5-ylmethylsulfanyl}-phenyl)-acetic acid
(4-{2-[3-(4-Methyl-2-piperidin-1-yl-phenyl)-ureido]-thiazol-5-ylmethanesulfonyl}-phenyl)-acetic acid
3-(4-{2-[3-(4-Methyl-2-piperidin-1-yl-phenyl)-ureido]-thiazol-5-ylmethoxy}-phenyl)-propionic acid
3-(4-{2-[3-(4-Methyl-2-piperidin-1-yl-phenyl)-ureido]-thiazol-5-ylmethylsulfanyl}-phenyl)-propionic acid
3-(4-{2-[3-(4-Methyl-2-piperidin-1-yl-phenyl)-ureido]-thiazol-5-ylmethanesulfonyl}-phenyl)-propionic acid
4-{2-[3-(4-Methyl-2-piperidin-1-yl-phenyl)-ureido]-thiazol-5-ylmethylsulfanyl}-benzoic acid
4-{2-[3-(4-Methyl-2-piperidin-1-yl-phenyl)-ureido]-thiazol-5-ylmethanesulfonyl}-benzoic acid
4-{2-[3-(4-Methyl-2-piperidin-1-yl-phenyl)-ureido]-thiazol-5-ylmethoxy}-benzoic acid
N-{2-[3-(4-Methyl-2-piperidin-1-yl-phenyl)-ureido]-thiazol-5-ylmethyl}-acetamide
N-{2-[3-(4-Methyl-2-piperidin-1-yl-phenyl)-ureido]-thiazol-5-ylmethyl}-methanesulfonamide
1-(4-Methyl-2-piperidin-1-yl-phenyl)-3-[5-(pyridin-2-ylaminomethyl)-thiazol-2-yl]-urea
2-{2-[3-(4-Methyl-2-piperidin-1-yl-phenyl)-ureido]-thiazol-5-ylmethanesulfonyl}-1H-imidazole-4-carboxylic acid
2-(2-{2-[3-(4-Methyl-2-piperidin-1-yl-phenyl)-ureido]-thiazol-5-yl}-ethyl)-1H-imidazole-4-carboxylic acid
2-(2-{2-[3-(4-Methyl-2-piperidin-1-yl-phenyl)-ureido]-thiazol-5-yl}-ethyl)-oxazole-4-carboxylic acid
1-Methyl-2-(2-{2-[3-(4-methyl-2-piperidin-1-yl-phenyl)-ureido]-thiazol-5-yl}-ethyl)-1H-imidazole-4-carboxylic acid
2-[3-(4-Methyl-2-piperidin-1-yl-phenyl)-ureido]-thiazole-5-carboxylic acid
2-[3-(4-Methyl-2-piperidin-1-yl-phenyl)-ureido]-thiazole-5-carboxylic acid amide
2-[3-(4-Methyl-2-piperidin-1-yl-phenyl)-ureido]-thiazole-5-carboxylic acid methylamide
({2-[3-(4-Methyl-2-piperidin-1-yl-phenyl)-ureido]-thiazole-5-carbonyl}-amino)-acetic acid
(Methanesulfonyl-{2-[3-(4-methyl-2-piperidin-1-yl-phenyl)-ureido]-thiazole-5-carbonyl}-amino)acetic acid
N-{2-[3-(4-Methyl-2-piperidin-1-yl-phenyl)-ureido]-thiazole-5-carbonyl}-methanesulfonamide
{2-[3-(4-Methyl-2-piperidin-1-yl-phenyl)-ureido]-thiazol-5-yl}-acetic acid
2-{2-[3-(4-Methyl-2-piperidin-1-yl-phenyl)-ureido]-thiazol-5-yl}-acetamide
N-Methyl-2-{2-[3-(4-methyl-2-piperidin-1-yl-phenyl)-ureido]-thiazol-5-yl}-acetamide
(2-{2-[3-(4-Methyl-2-piperidin-1-yl-phenyl)-ureido]-thiazol-5-yl}-acetylamino)-acetic acid
N-(2-{2-[3-(4-Methyl-2-piperidin-1-yl-phenyl)-ureido]-thiazol-5-yl}-acetyl)-methanesulfonamide
N-(2-{2-[3-(4-Methyl-2-piperidin-1-yl-phenyl)-ureido]-thiazol-5-yl}-ethyl)-methanesulfonamide
N-(2-{2-[3-(4-Methyl-2-piperidin-1-yl-phenyl)-ureido]-thiazol-5-yl}-ethyl)-acetamide
1-(5-Guanidinomethyl-thiazol-2-yl)-3-(4-methyl-2-piperidin-1-yl-phenyl)-urea
1-(4-Methyl-2-piperidin-1-yl-phenyl)-3-(5-ureidomethyl-thiazol-2-yl)-urea
1-{5-[3-(2-Dimethylamino-ethyl)-ureidomethyl]-thiazol-2-yl}-3-(4-methyl-2-piperidin-1-yl-phenyl)-urea
{2-[3-(4-Methyl-2-piperidin-1-yl-phenyl)-ureido]-thiazol-5-ylmethyl}-carbamic acid 2-dimethylamino-ethyl ester
{2-[3-(4-Methyl-2-piperidin-1-yl-phenyl)-ureido]-thiazol-5-ylmethyl}-carbamic acid methyl ester
(2-{2-[3-(4-Methyl-2-piperidin-1-yl-phenyl)-ureido]-thiazol-5-yl}-ethyl)-carbamic acid methyl ester
1-[5-(2-Guanidino-ethyl)-thiazol-2-yl]-3-(4-methyl-2-piperidin-1-yl-phenyl)-urea
1-(4-Methyl-2-piperidin-1-yl-phenyl)-3-[5-(2-ureido-ethyl)-thiazol-2-yl]-urea
[3-(2-{2-[3-(4-Methyl-2-piperidin-1-yl-phenyl)-ureido]-thiazol-5-yl}-ethyl)-ureido]-acetic acid
1-(5-{2-[3-(2-Dimethylamino-ethyl)-ureido]-ethyl}-thiazol-2-yl)-3-(4-methyl-2-piperidin-1-yl-phenyl)-urea
(2-{2-[3-(4-Methyl-2-piperidin-1-yl-phenyl)-ureido]-thiazol-5-yl}-ethyl)-carbamic acid 2-dimethylamino-ethyl ester
1-{5-[2-(1H-Imidazol-2-ylsulfanyl)-ethyl]-thiazol-2-yl}-3-(4-methyl-2-piperidin-1-yl-phenyl)-urea
1-{5-[2-(1H-Imidazole-2-sulfonyl)-ethyl]-thiazol-2-yl}-3-(4-methyl-2-piperidin-1-yl-phenyl)-urea
1-{5-[2-(1-Methyl-1H-imidazol-2-ylsulfanyl)-ethyl]-thiazol-2-yl}-3-(4-methyl-2-piperidin-1-yl-phenyl)-urea
1-{5-[2-(1-Methyl-1H-imidazole-2-sulfonyl)-ethyl]-thiazol-2-yl}-3-(4-methyl-2-piperidin-1-yl-phenyl)-urea
2-(2-{2-[3-(4-Methyl-2-piperidin-1-yl-phenyl)-ureido]-thiazol-5-yl}-ethylsulfanyl)-1H-imidazole-4-carboxylic acid
6-{2-[3-(4-Methyl-2-piperidin-1-yl-phenyl)-ureido]-thiazol-5-ylmethylsulfanyl}-nicotinic acid
6-{2-[3-(4-Methyl-2-piperidin-1-yl-phenyl)-ureido]-thiazol-5-ylmethanesulfonyl}-nicotinic acid
1-Methyl-2-(2-{2-[3-(4-methyl-2-piperidin-1-yl-phenyl)-ureido]-thiazol-5-yl}-ethylsulfanyl)-1H-imidazole-4-carboxylic acid
[4-(2-{2-[3-(4-Methyl-2-piperidin-1-yl-phenyl)-ureido]-thiazol-5-yl}-ethylsulfanyl)-phenyl]-acetic acid

[4-(2-{2-[3-(4-Methyl-2-piperidin-1-yl-phenyl)-ureido]-thiazol-5-yl}-ethanesulfonyl)-phenyl]-acetic acid
1-(4-Methyl-2-piperidin-1-yl-phenyl)-3-{5-[2-(pyridin-2-ylsulfanyl)-ethyl]-thiazol-2-yl}-urea
1-(4-Methyl-2-piperidin-1-yl-phenyl)-3-{5-[2-(pyridine-2-sulfonyl)-ethyl]-thiazol-2-yl}-urea
6-(2-{2-[3-(4-Methyl-2-piperidin-1-yl-phenyl)-ureido]-thiazol-5-yl}-ethylsulfanyl)-nicotinic acid
6-(2-{2-[3-(4-Methyl-2-piperidin-1-yl-phenyl)-ureido]-thiazol-5-yl}-ethanesulfonyl)-nicotinic acid
1-(4-Methyl-2-piperidin-1-yl-phenyl)-3-(5-[1,2,4]oxadiazol-5-ylmethyl-thiazol-2-yl)-urea
1-(4-Methyl-2-piperidin-1-yl-phenyl)-3-[5-(2-[1,2,4]oxadiazol-5-yl-ethyl)-thiazol-2-yl]-urea
4-{2-[3-(4-Methyl-2-piperidin-1-yl-phenyl)-ureido]-thiazol-5-yl}-butyric acid
1-[5-(1H-Imidazol-2-ylsulfanyl)-thiazol-2-yl]-3-(4-methyl-2-piperidin-1-yl-phenyl)-urea
1-[5-(1-Methyl-1H-imidazol-2-ylsulfanyl)-thiazol-2-yl]-3-(4-methyl-2-piperidin-1-yl-phenyl)-urea
1-Methyl-2-{2-[3-(4-methyl-2-piperidin-1-yl-phenyl)-ureido]-thiazol-5-ylsulfanyl}-1H-imidazole-4-carboxylic acid
1-Methyl-2-{2-[3-(4-methyl-2-piperidin-1-yl-phenyl)-ureido]-thiazole-5-sulfonyl}-1H-imidazole-4-carboxylic acid
2-{2-[3-(4-Methyl-2-piperidin-1-yl-phenyl)-ureido]-thiazole-5-sulfonyl}-1H-imidazole-4-carboxylic acid
1-[5-(1H-Imidazole-2-sulfonyl)-thiazol-2-yl]-3-(4-methyl-2-piperidin-1-yl-phenyl)-urea
1-(4-Methyl-2-piperidin-1-yl-phenyl)-3-[5-(pyridine-2-sulfonyl)-thiazol-2-yl]-urea
1-(4-Methyl-2-piperidin-1-yl-phenyl)-3-[5-(pyridine-3-sulfonyl)-thiazol-2-yl]-urea
1-(4-Methyl-2-piperidin-1-yl-phenyl)-3-[5-(pyridine-4-sulfonyl)-thiazol-2-yl]-urea
1-(4-Methyl-2-piperidin-1-yl-phenyl)-3-[5-(pyridin-4-ylsulfanyl)-thiazol-2-yl]-urea
1-(4-Methyl-2-piperidin-1-yl-phenyl)-3-[5-(pyridin-3-ylsulfanyl)-thiazol-2-yl]-urea
1-(4-Methyl-2-piperidin-1-yl-phenyl)-3-[5-(pyridin-2-ylsulfanyl)-thiazol-2-yl]-urea
6-{2-[3-(4-Methyl-2-piperidin-1-yl-phenyl)-ureido]-thiazol-5-ylsulfanyl}-nicotinic acid
6-{2-[3-(4-Methyl-2-piperidin-1-yl-phenyl)-ureido]-thiazole-5-sulfonyl}-nicotinic acid
1-(5-Methanesulfonyl-thiazol-2-yl)-3-(4-methyl-2-piperidin-1-yl-phenyl)-urea
3-{2-[3-(4-Methyl-2-piperidin-1-yl-phenyl)-ureido]-thiazole-5-sulfonyl}-propionic acid
3-{2-[3-(4-Methyl-2-piperidin-1-yl-phenyl)-ureido]-thiazol-5-ylsulfanyl}-propionic acid
1-(5-Bromo-thiazol-2-yl)-3-(4-methyl-2-piperidin-1-yl-phenyl)-urea
{5-Chloro-2-[3-(4-methyl-2-piperidin-1-yl-phenyl)-ureido]-thiazol-4-yl}-acetic acid
{5-Bromo-2-[3-(4-methyl-2-piperidin-1-yl-phenyl)-ureido]-thiazol-4-yl}-acetic acid
N-{2-[3-(4-Methyl-2-piperidin-1-yl-phenyl)-ureido]-thiazol-4-ylmethyl}-methanesulfonamide
N-(2-{2-[3-(4-Methyl-2-piperidin-1-yl-phenyl)-ureido]-thiazol-4-yl}-acetyl)-methanesulfonamide
1-(4-Dimethylaminomethyl-thiazol-2-yl)-3-(4-methyl-2-piperidin-1-yl-phenyl)-urea
1-(4-Methyl-2-piperidin-1-yl-phenyl)-3-(4-piperazin-1-ylmethyl-thiazol-2-yl)-urea
1-[4-(4-Methanesulfonyl-piperazin-1-ylmethyl)-thiazol-2-yl]-3-(4-methyl-2-piperidin-1-yl-phenyl)-urea
1-(4-Methyl-2-piperidin-1-yl-phenyl)-3-(4-morpholin-4-ylmethyl-thiazol-2-yl)-urea
2-[3-(4-Methyl-2-piperidin-1-yl-phenyl)-ureido]-thiazole-4-carboxylic acid methylamide
1-(4-Methyl-2-piperidin-1-yl-phenyl)-3-[4-(morpholine-4-carbonyl)-thiazol-2-yl]-urea
{2-[3-(4-Methyl-2-piperidin-1-yl-phenyl)-ureido]-thiazol-4-ylmethyl}-carbamic acid methyl ester
1-(4-Methyl-2-piperidin-1-yl-phenyl)-3-(4-ureidomethyl-thiazol-2-yl)-urea
{2-[3-(4-Methyl-2-piperidin-1-yl-phenyl)-ureido]-thiazol-4-ylmethyl}-carbamic acid 2-dimethylamino-ethyl ester
1-(4-Guanidinomethyl-thiazol-2-yl)-3-(4-methyl-2-piperidin-1-yl-phenyl)-urea
(3-{2-[3-(4-Methyl-2-piperidin-1-yl-phenyl)-ureido]-thiazol-4-ylmethyl}-ureido)-acetic acid
1-{4-[3-(2-Dimethylamino-ethyl)-ureidomethyl]-thiazol-2-yl}-3-(4-methyl-2-piperidin-1-yl-phenyl)-urea
N-{2-[3-(2-Isobutoxy-4-methyl-phenyl)-ureido]-thiazol-4-ylmethyl}-methanesulfonamide
N-(2-{2-[3-(2-Isobutoxy-4-methyl-phenyl)-ureido]-thiazol-4-yl}-acetyl)-methanesulfonamide
1-(4-Dimethylaminomethyl-thiazol-2-yl)-3-(2-isobutoxy-4-methyl-phenyl)-urea
1-(2-Isobutoxy-4-methyl-phenyl)-3-(4-piperazin-1-ylmethyl-thiazol-2-yl)-urea
1-(2-Isobutoxy-4-methyl-phenyl)-3-[4-(4-methanesulfonyl-piperazin-1-ylmethyl)-thiazol-2-yl]-urea
1-(2-Isobutoxy-4-methyl-phenyl)-3-(4-morpholin-4-ylmethyl-thiazol-2-yl)-urea
2-[3-(2-Isobutoxy-4-methyl-phenyl)-ureido]-thiazole-4-carboxylic acid methylamide
1-(2-Isobutoxy-4-methyl-phenyl)-3-[4-(morpholine-4-carbonyl)-thiazol-2-yl]-urea
{2-[3-(2-Isobutoxy-4-methyl-phenyl)-ureido]-thiazol-4-ylmethyl}-carbamic acid methyl ester
1-(2-Isobutoxy-4-methyl-phenyl)-3-(4-ureidomethyl-thiazol-2-yl)-urea
{2-[3-(2-Isobutoxy-4-methyl-phenyl)-ureido]-thiazol-4-ylmethyl}-carbamic acid 2-dimethylamino-ethyl ester
1-(4-Guanidinomethyl-thiazol-2-yl)-3-(2-isobutoxy-4-methyl-phenyl)-urea
(3-{2-[3-(2-Isobutoxy-4-methyl-phenyl)-ureido]-thiazol-4-ylmethyl}-ureido)-acetic acid
1-{4-[3-(2-Dimethylamino-ethyl)-ureidomethyl]-thiazol-2-yl}-3-(2-isobutoxy-4-methyl-phenyl)-urea
N-(2-{3-[2-(2-Methoxy-benzoyl)-4-methyl-phenyl]-ureido}-thiazol-4-ylmethyl)-methanesulfonamide
N-[2-(2-{3-[2-(2-Methoxy-benzoyl)-4-methyl-phenyl]-ureido}-thiazol-4-yl)-acetyl]-methanesulfonamide
1-(4-Dimethylaminomethyl-thiazol-2-yl)-3-[2-(2-methoxy-benzoyl)-4-methyl-phenyl]-urea
1-[2-(2-Methoxy-benzoyl)-4-methyl-phenyl]-3-(4-piperazin-1-ylmethyl-thiazol-2-yl)-urea
1-[4-(4-Methanesulfonyl-piperazin-1-ylmethyl)-thiazol-2-yl]-3-[2-(2-methoxy-benzoyl)-4-methyl-phenyl]-urea
1-[2-(2-Methoxy-benzoyl)-4-methyl-phenyl]-3-(4-morpholin-4-ylmethyl-thiazol-2-yl)-urea
2-(3-[2-(2-Methoxy-benzoyl)-4-methyl-phenyl]-ureido)thiazole-4-carboxylic acid methylamide
1-[2-(2-Methoxy-benzoyl)-4-methyl-phenyl]-3-[4-(morpholine-4-carbonyl)-thiazol-2-yl]-urea
(2-{3-[2-(2-Methoxy-benzoyl)-4-methyl-phenyl]-ureido}-thiazol-4-ylmethyl)-carbamic acid methyl ester 1-[2-(2-Methoxy-benzoyl)-4-methyl-phenyl]-3-(4-ureidomethyl-thiazol-2-yl)-urea
(2-{3-[2-(2-Methoxy-benzoyl)-4-methyl-phenyl]-ureido}-thiazol-4-ylmethyl)-carbamic acid 2-dimethylamino-ethyl ester
1-(4-Guanidinomethyl-thiazol-2-yl)-3-[2-(2-methoxy-benzoyl)-4-methyl-phenyl]-urea
[3-(2-{3-[2-(2-Methoxy-benzoyl)-4-methyl-phenyl]-ureido}-thiazol-4-ylmethyl)-ureido]-acetic acid
1-{4-[3-(2-Dimethylamino-ethyl)-ureidomethyl]-thiazol-2-yl}-3-[2-(2-methoxy-benzoyl)-4-methyl-phenyl]-urea
2-({2-[3-(2-Cyclopentanecarbonyl-4-methyl-phenyl)-ureido]-thiazole-5-carbonyl}-amino)-1H-imidazole-4-carboxylic acid
2-({2-[3-(2-Cyclopentanecarbonyl-4-methyl-phenyl)-ureido]-thiazole-5-carbonyl}-amino)-oxazole-4-carboxylic acid
2-({2-[3-(2-Cyclopentanecarbonyl-4-methyl-phenyl)-ureido]-thiazole-5-carbonyl}-amino)-1-methyl-1H-imidazole-4-carboxylic acid
2-({2-[3-(2-Cyclopentanecarbonyl-4-methyl-phenyl)-ureido]-thiazol-5-ylmethyl}-amino)-1H-imidazole-4-carboxylic acid
2-({2-[3-(2-Cyclopentanecarbonyl-4-methyl-phenyl)-ureido]-thiazol-5-ylmethyl}-amino)-oxazole-4-carboxylic acid
2-({2-[3-(2-Cyclopentanecarbonyl-4-methyl-phenyl)-ureido]-thiazol-5-ylmethyl}-amino)-1-methyl-1H-imidazole-4-carboxylic acid
6-({2-[3-(2-Cyclopentanecarbonyl-4-methyl-phenyl)-ureido]-thiazole-5-carbonyl}-amino)-nicotinic acid
2-({2-[3-(2-Cyclopentanecarbonyl-4-methyl-phenyl)-ureido]-thiazole-5-carbonyl}-amino)-pyrimidine-5-carboxylic acid
5-({2-[3-(2-Cyclopentanecarbonyl-4-methyl-phenyl)-ureido]-thiazole-5-carbonyl}-amino)-1-methyl-1H-pyrazole-3-carboxylic acid
2-(2-{2-[3-(2-Cyclopentanecarbonyl-4-methyl-phenyl)-ureido]-thiazol-5-yl}-ethyl)-5-methyl-1H-imidazole-4-carboxylic acid
2-(2-{2-[3-(2-Cyclopentanecarbonyl-4-methyl-phenyl)-ureido]-thiazol-5-yl}-ethyl)-5-trifluoromethyl-1H-imidazole-4-carboxylic acid
1-{5-[2-(1H-Benzoimidazol-2-yl)-ethyl]-thiazol-2-yl}-3-(2-cyclopentanecarbonyl-4-methyl-phenyl)-urea
1-(2-Cyclopentanecarbonyl-4-methyl-phenyl)-3-{5-[2-(1H-imidazo[4,5-#b!]pyridin-2-yl)-ethyl]-thiazol-2-yl}-urea
2-{2-[3-(2-Cyclopentanecarbonyl-4-methyl-phenyl)-ureido]-thiazol-5-ylmethyl}-1H-imidazole-4-carboxylic acid
2-{2-[3-(2-Cyclopentanecarbonyl-4-methyl-phenyl)-ureido]-thiazol-5-ylmethyl}-1-1H-imidazole-4-carboxylic acid
2-{2-[3-(2-Cyclopentanecarbonyl-4-methyl-phenyl)-ureido]-thiazol-5-ylmethyl}-oxazole-4-carboxylic acid
1-[5-(1H-Benzoimidazol-2-ylmethyl)-thiazol-2-yl]-3-(2-cyclopentanecarbonyl-4-methyl-phenyl)-urea
1-(2-Cyclopentanecarbonyl-4-methyl-phenyl)-3-[5-(1H-imidazo[4,5-#b!]pyridin-2-ylmethyl)-thiazol-2-yl]-urea
1-(5-Benzooxazol-2-ylmethyl-thiazol-2-yl)-3-(2-cyclopentanecarbonyl-4-methyl-phenyl)-urea
1-(2-Cyclopentanecarbonyl-4-methyl-phenyl)-3-(5-oxazolo[4,5-#b!]pyridin-2-ylmethyl-thiazol-2-yl)-urea
2-(2-{2-[3-(2-Cyclopentanecarbonyl-4-methyl-phenyl)-ureido]-thiazol-5-yl}-ethyl)-5-trifluoromethyl-oxazole-4-carboxylic acid
2-(2-{2-[3-(2-Cyclopentanecarbonyl-4-methyl-phenyl)-ureido]-thiazol-5-yl}-ethyl)-5-methyl-oxazole-4-carboxylic acid
1-(2-Cyclopentanecarbonyl-4-methyl-phenyl)-3-{5-[2-(4H-[1,2,4]triazol-3-yl)-ethyl]-thiazol-2-yl}-urea
1-(2-Cyclopentanecarbonyl-4-methyl-phenyl)-3-{5-[2-(4-methyl-4H-[1,2,4]triazol-3-yl)-ethyl]-thiazol-2-yl}-urea
[3-(2-{2-[3-(2-Cyclopentanecarbonyl-4-methyl-phenyl)-ureido]-thiazol-5-yl}-ethyl)-[1,2,4]triazol-4-yl]-acetic acid
[5-(2-{2-[3-(2-Cyclopentanecarbonyl-4-methyl-phenyl)-ureido]-thiazol-5-yl}-ethyl)-tetrazol-1-yl]-acetic acid
1-(2-Cyclopentanecarbonyl-4-methyl-phenyl)-3-{5-[2-(1-methyl-1H-tetrazol-5-yl)-ethyl]-thiazol-2-yl}-urea
1-(2-Cyclopentanecarbonyl-4-methyl-phenyl)-3-{5-[2-(1H-tetrazol-5-yl)-ethyl]-thiazol-2-yl}-urea
1-(2-Cyclopentanecarbonyl-4-methyl-phenyl)-3-[5-(2-[1,3,4]thiadiazol-2-yl-ethyl)-thiazol-2-yl]-urea
2-[3-(2-Cyclopentanecarbonyl-4-methyl-phenyl)-ureido]-thiazole-5-carboxylic acid [1,3,4]thiadiazol-2-ylamide
1-(2-Cyclopentanecarbonyl-4-methyl-phenyl)-3-[5-([1,3,4]thiadiazol-2-ylaminomethyl)-thiazol-2-yl]-urea
[2-(2-{2-[3-(2-Cyclopentanecarbonyl-4-methyl-phenyl)-ureido]-thiazol-5-yl}-ethyl)-imidazol-1-yl]-acetic acid
2-[(2-{3-[2-(2-Methoxy-benzoyl)-4-methyl-phenyl]-ureido}-thiazole-5-carbonyl)-amino]-1H-imidazole-4-carboxylic acid
2-[(2-{3-[2-(2-Methoxy-benzoyl)-4-methyl-phenyl]-ureido}-thiazole-5-carbonyl)-amino]-oxazole-4-carboxylic acid
2-[(2-{3-[2-(2-Methoxy-benzoyl)-4-methyl-phenyl]-ureido}-thiazole-5-carbonyl)-amino]-1-methyl-1H-imidazole-4-carboxylic acid
2-[(2-{3-[2-(2-Methoxy-benzoyl)-4-methyl-phenyl]-ureido}-thiazol-5-ylmethyl)-amino]-1H-imidazole-4-carboxylic acid
2-[(2-{3-[2-(2-Methoxy-benzoyl)-4-methyl-phenyl]-ureido}-thiazol-5-ylmethyl)-amino]-oxazole-4-carboxylic acid
2-[(2-{3-[2-(2-Methoxy-benzoyl)-4-methyl-phenyl]-ureido}-thiazol-5-ylmethyl)-amino]-1-methyl-1H-imidazole-4-carboxylic acid
6-[(2-{3-[2-(2-Methoxy-benzoyl)-4-methyl-phenyl]-ureido}-thiazole-5-carbonyl)-amino]-nicotinic acid
2-[(2-{3-[2-(2-Methoxy-benzoyl)-4-methyl-phenyl]-ureido}-thiazole-5-carbonyl)-amino]-pyrimidine-5-carboxylic acid
5-[(2-{3-[2-(2-Methoxy-benzoyl)-4-methyl-phenyl]-ureido}-thiazole-5-carbonyl)-amino]-methyl-1H-pyrazole-3-carboxylic acid
2-[2-(2-{3-[2-(2-Methoxy-benzoyl)-4-methyl-phenyl]-ureido}-thiazol-5-yl)-ethyl]-5-methyl-1H-imidazole-4-carboxylic acid
2-[2-(2-{3-[2-(2-Methoxy-benzoyl)-4-methyl-phenyl]-ureido}-thiazol-5-yl)-ethyl]-5-trifluoromethyl-1H-imidazole-4-carboxylic acid
1-{5-[2-(1H-Benzoimidazol-2-yl)-ethyl]-thiazol-2-yl}-3-[2-(2-methoxy-benzoyl)-4-methyl-phenyl]-urea
1-{5-[2-(1H-Imidazo[4,5-#b!]pyridin-2-yl)-ethyl]-thiazol-2-yl}-3-[2-(2-methoxy-benzoyl)-4-methyl-phenyl]-urea
2-(2-{3-[2-(2-Methoxy-benzoyl)-4-methyl-phenyl]-ureido}-thiazol-5-ylmethyl)-1H-imidazole-4-carboxylic acid
2-(2-{3-[2-(2-Methoxy-benzoyl)-4-methyl-phenyl]-ureido}-thiazol-5-ylmethyl)-1H-imidazole-4-carboxylic acid
2-(2-{3-[2-(2-Methoxy-benzoyl)-4-methyl-phenyl]-ureido}-thiazol-5-ylmethyl)-oxazole-4-carboxylic acid 1-[5-(1H-Benzoimidazol-2-ylmethyl)-thiazol-2-yl]-3-[2-(2-methoxy-benzoyl)-4-methyl-phenyl]-urea 1-[5-(1H-Imidazo[4,5-#b!]pyridin-2-ylmethyl)-thiazol-2-yl]-3-[2-(2-methoxy-benzoyl)-4-methyl-phenyl]-urea 1-(5-Benzooxazol-2-ylmethyl-thiazol-2-yl)-3-[2-(2-methoxy-benzoyl)-4-methyl-phenyl-urea 1-[2-(2-Methoxy-benzoyl)-4-methyl-phenyl]-3-(5-oxazolo[4,5-#b!]pyridin-2-ylmethyl-thiazol-2-yl)-urea 2-[2-(2-{3-[2-(2-Methoxy-benzoyl)-4-methyl-phenyl]-ureido}-thiazol-5-yl)-ethyl-5-trifluoromethyl-oxazole-4-carboxylic acid 2-[2-(2-{3-[2-(2-Methoxy-benzoyl)-4-methyl-phenyl]-ureido}-thiazol-5-yl)-ethyl]-5-methyl-oxazole-4-carboxylic acid 1-[2-(2-Methoxy-benzoyl)-4-methyl-phenyl]-3-{5-[2-(4H-[1,2,4]triazol-3-yl)-ethyl]-thiazol-2-yl}-urea 1-[2-(2-Methoxy-benzoyl)-4-methyl-phenyl]-3-{5-[2-(4-methyl-4H-[1,2,4]triazol-3-yl)-ethyl]-thiazol-2-yl}-urea {3-[2-(2-{3-[2-(2-Methoxy-benzoyl)-4-methyl-phenyl]-ureido}-thiazol-5-yl)-ethyl]-[1,2,4]triazol-4-yl}-acetic acid {5-[2-(2-{3-[2-(2-Methoxy-benzoyl)-4-methyl-phenyl]-ureido}-thiazol-5-yl)-ethyl]-tetrazol-1-yl}-acetic acid 1-[2-(2-Methoxy-benzoyl)-4-methyl-phenyl]-3-{5-[2-(1-methyl-1H-tetrazol-5-yl)-ethyl]-thiazol-2-yl}-urea 1-[2-(2-Methoxy-benzoyl)-4-methyl-phenyl]-3-{5-[2-(1H-tetrazol-5-yl)-ethyl]-thiazol-2-yl}-urea 1-[2-(2-Methoxy-benzoyl)-4-methyl-phenyl]-3-[5-(2-[1,3,4]thiadiazol-2-yl-ethyl)-thiazol-2-yl]-urea 2-{3-[2-(2-Methoxy-benzoyl)-4-methyl-phenyl]-ureido}-thiazole-5-carboxylic acid [1,3,4]thiadiazol-2-ylamide 1-[2-(2-Methoxy-benzoyl)-4-methyl-phenyl]-3-[5-([1,3,4]thiadiazol-2-ylaminomethyl)-thiazol-2-yl]-urea {2-[2-(2-{3-[2-(2-Methoxy-benzoyl)-4-methyl-phenyl]-ureido}-thiazol-5-yl)-ethyl]-imidazol-1-yl}-acetic acid 2-({2-[3-(2-isobutoxy-4-methyl-phenyl)-ureido]-thiazole-5-carbonyl}-amino)-1H-imidazole-4-carboxylic acid 2-({2-[3-(2-Isobutoxy-4-methyl-phenyl)-ureido]-thiazole-5-carbonyl}-amino)-oxazole-4-carboxylic acid 2-({2-[3-(2-Isobutoxy-4-methyl-phenyl)-ureido]-thiazole-5-carbonyl}-amino)-1-methyl-1H-imidazole-4-carboxylic acid 2-({2-[3-(2-Isobutoxy-4-methyl-phenyl)-ureido]-thiazol-5-ylmethyl}-amino)-1H-imidazole-4-carboxylic acid 2-({2-[3-(2-Isobutoxy-4-methyl-phenyl)-ureido]-thiazol-5-ylmethyl}-amino)-oxazole-4-carboxylic acid 2-({2-Isobutoxy-4-methyl-phenyl)-ureido]-thiazol-5-ylmethyl}-amino)-1-methyl-1H-imidazole-4-carboxylic acid 6-({2-[3-(2-Isobutoxy-4-methyl-phenyl)-ureido]-thiazole-5-carbonyl}-amino)-nicotinic acid 2-({2-[3-(2-Isobutoxy-4-methyl-phenyl)-ureido]-thiazole-5-carbonyl}-amino)-pyrimidine-5-carboxylic acid 5-({2-[3-(2-Isobutoxy-4-methyl-phenyl)-ureido]-thiazole-5-carbonyl}-amino)-1-methyl-1H-pyrazole-3-carboxylic acid 2-(2-{2-[3-(2-Isobutoxy-4-methyl-phenyl)-ureido]-thiazol-5-yl}-ethyl)-5-methyl-1H-imidazole-4-carboxylic acid 2-(2-{2-[3-(2-Isobutoxy-4-methyl-phenyl)-ureido]-thiazol-5-yl}-ethyl)-5-trifluoromethyl-1H-imidazole-4-carboxylic acid 1-{5-[2-(1H-Benzoimidazol-2-yl)-ethyl]-thiazol-2-yl}-3-(2-isobutoxy-4-methyl-phenyl)-urea 1-{5-[2-(1H-Imidazo[4,5-#b!]pyridin-2-yl)-ethyl]-thiazol-2-yl}-3-(2-isobutoxy-4-methyl-phenyl)-urea 2-{2-[3-(2-Isobutoxy-4-methyl-phenyl)-ureido]-thiazol-5-ylmethyl}-1H-imidazole-4-carboxylic acid 2-{2-[3-(2-Isobutoxy-4-methyl-phenyl)-ureido]-thiazol-5-ylmethyl}-1-methyl-1H-imidazole-4-carboxylic acid 2-{2-[3-(2-Isobutoxy-4-methyl-phenyl)-ureido]-thiazol-5-ylmethyl}-oxazole-4-carboxylic acid 1-[5-(1H-Benzoimidazol-2-ylmethyl)-thiazol-2-yl]-3-(2-isobutoxy-4-methyl-phenyl)-urea 1-[5-(1H-Imidazo[4,5-#b!]pyridin-2-ylmethyl)-thiazol-2-yl]-3-(2-isobutoxy-4-methyl-phenyl)-urea 1-(5-Benzooxazol-2-ylmethyl-thiazol-2-yl)-3-(2-isobutoxy-4-methyl-phenyl)-urea 1-(2-Isobutoxy-4-methyl-phenyl)-3-(5-oxazolo[4,5-#b!]pyridin-2-ylmethyl-thiazol-2-yl)-urea 2-(2-{2-[3-(2-Isobutoxy-4-methyl-phenyl)-ureido]-thiazol-5-yl}-ethyl)-5-trifluoromethyl-oxazole-4-carboxylic acid 2-(2-{2-[3-(2-isobutoxy-4-methyl-phenyl)-ureido]-thiazol-5-yl}-ethyl)-5-methyl-oxazole-4-carboxylic acid 1-(2-Isobutoxy-4-methyl-phenyl)-3-{5-[2-(4H-[1,2,4]triazol-3-yl)-ethyl]-thiazol-2-yl}-urea 1-(2-Isobutoxy-4-methyl-phenyl)-3-{5-[2-(4-methyl-4H-[1,2,4]triazol-3-yl)-ethyl]-thiazol-2-yl}-urea

[3-(2-{2-[3-(2-Isobutoxy-4-methyl-phenyl)-ureido]-thiazol-5-yl}-ethyl)-[1,2,4]triazol-4-yl]-acetic acid

[5-(2-{2-[3-(2-Isobutoxy-4-methyl-phenyl)-ureido]-thiazol-5-yl}-ethyl)-tetrazol-1-yl]-acetic acid 1-(2-Isobutoxy-4-methyl-phenyl)-3-{5-[2-(1-methyl-1H-tetrazol-5-yl)-ethyl]-thiazol-2-yl}-urea 1-(2-Isobutoxy-4-methyl-phenyl)-3-{5-[2-(1H-tetrazol-5-yl)-ethyl]-thiazol-2-yl}-urea 1-(2-Isobutoxy-4-methyl-phenyl)-3-[5-(2-[1,3,4]thiadiazol-2-yl-ethyl)-thiazol-2-yl]-urea 2-[3-(2-Isobutoxy-4-methyl-phenyl)-ureido]-thiazole-5-carboxylic acid [1,3,4]thiadiazol-2-ylamide 1-(2-Isobutoxy-4-methyl-phenyl)-3-[5-([1,3,4]thiadiazol-2-ylaminomethyl)-thiazol-2-yl]-urea

[2-(2-{2-[3-(2-Isobutoxy-4-methyl-phenyl)-ureido]-thiazol-5-yl}-ethyl)-imidazol-1-yl]-acetic acid 2-({2-[3-(4-Methyl-2-piperidin-1-yl-phenyl)-ureido]-thiazole-5-carbonyl}-amino)-1H-imidazole-4-carboxylic acid 2-({2-[3-(4-Methyl-2-piperidin-1-yl-phenyl)-ureido]-thiazole-5-carbonyl}-amino)-oxazole-4-carboxylic acid 1-Methyl-2-({2-[3-(4-methyl-2-piperidin-1-yl-phenyl)-ureido]-thiazole-5-carbonyl}-amino)-1H-imidazole-4-carboxylic acid 2-({2-[3-(4-Methyl-2-piperidin-1-yl-phenyl)-ureido]-thiazol-5-ylmethyl}-amino)-1H-imidazole-4-carboxylic acid 2-({2-[3-(4-Methyl-2-piperidin-1-yl-phenyl)-ureido]-thiazol-5-ylmethyl}-amino)-oxazole-4-carboxylic acid 1-Methyl-2-({2-[3-(4-methyl-2-piperidin-1-yl-phenyl)-ureido]-thiazol-5-ylmethyl}-amino)-1H-imidazole-4-carboxylic acid 6-({2-[3-(4-Methyl-2-piperidin-1-yl-phenyl)-ureido]-thiazole-5-carbonyl}-amino)-nicotinic acid 2-({2-[3-(4-Methyl-2-piperidin-1-yl-phenyl)-ureido]-thiazole-5-carbonyl}-amino)-pyrimidine-5-carboxylic acid 1-Methyl-5-({2-[3-(4-methyl-2-piperidin-1-yl-phenyl)-ureido]-thiazole-5-carbonyl}-amino)-1H-pyrazole-3-carboxylic acid 5-Methyl-2-(2-{2-[3-(4-methyl-2-piperidin-1-yl-phenyl)-ureido]-thiazol-5-yl}-ethyl)-1H-imidazole-4-carboxylic acid 2-(2-{2-[3-(4-Methyl-2-piperidin-1-yl-phenyl)-ureido]-thiazol-5-yl}-ethyl)-5-trifluoromethyl-1H-imidazole-4-carboxylic acid 1-{5-[2-(1H-Benzoimidazol-2-yl)-ethyl]-thiazol-2-yl}-3-(4-methyl-2-piperidin-1-yl-phenyl)-urea 1-{5-[2-(1H-Imidazo[4,5-#b!]pyridin-2-yl)-ethyl]-thiazol-2-yl}-3-(4-methyl-2-piperidin-1-yl-phenyl)-urea 2-{2-[3-(4-Methyl-2-piperidin-1-yl-phenyl)-ureido]-thiazol-5-ylmethyl}-1H-imidazole-4-carboxylic acid 1-Methyl-2-{2-[3-(4-methyl-2-piperidin-1-yl-phenyl)-ureido]-thiazol-5-ylmethyl}-1H-imidazole-4-carboxylic acid
2-{2-[3-(4-Methyl-2-piperidin-1-yl-phenyl)-ureido]-thiazol-5-ylmethyl}-oxazole-4-carboxylic acid
1-[5-(1H-Benzoimidazol-2-ylmethyl)-thiazol-2-yl]-3-(4-methyl-2-piperidin-1-yl-phenyl)-urea
1-[5-(1H-Imidazo[4,5-#b!]pyridin-2-ylmethyl)-thiazol-2-yl]-3-(4-methyl-2-piperidin-1-yl-phenyl)-urea
1-(5-Benzooxazol-2-ylmethyl-thiazol-2-yl)-3-(4-methyl-2-piperidin-1-yl-phenyl)-urea
1-(4-Methyl-2-piperidin-1-yl-phenyl)-3-(5-oxazolo[4,5-#b!]pyridin-2-ylmethyl-thiazol-2-yl)-urea
2-(2-{2-[3-(4-Methyl-2-piperidin-1-yl-phenyl)-ureido]-thiazol-5-yl}-ethyl)-5-trifluoromethyl-oxazole-4-carboxylic acid
5-Methyl-2-(2-{2-[3-(4-methyl-2-piperidin-1-yl-phenyl)-ureido]-thiazol-5-yl}-ethyl)-oxazole-4-carboxylic acid
1-(4-Methyl-2-piperidin-1-yl-phenyl)-3-{5-[2-(4H-[1,2,4]triazol-3-yl)-ethyl]-thiazol-2-yl}-urea
1-(4-Methyl-2-piperidin-1-yl-phenyl)-3-{5-[2-(4-methyl-4H-[1,2,4]triazol-3-yl)-ethyl]-thiazol-2-yl}-urea
[3-(2-{2-[3-(4-Methyl-2-piperidin-1-yl-phenyl)-ureido]-thiazol-5-yl}-ethyl)-[1,2,4]triazol-4-yl]-acetic acid
[5-(2-{2-[3-(4-Methyl-2-piperidin-1-yl-phenyl)-ureido]-thiazol-5-yl}-ethyl)-tetrazol-1-yl]-acetic acid
1-(4-Methyl-2-piperidin-1-yl-phenyl)-3-{5-[2-(1-methyl-1H-tetrazol-5-yl)-ethyl]-thiazol-2-yl}-urea
1-(4-Methyl-2-piperidin-1-yl-phenyl)-3-{5-[2-(1H-tetrazol-5-yl)-ethyl]-thiazol-2-yl}-urea
1-(4-Methyl-2-piperidin-1-yl-phenyl)-3-[5-(2-[1,3,4]thiadiazol-2-yl-ethyl)-thiazol-2-yl]-urea
2-[3-(4-Methyl-2-piperidin-1-yl-phenyl)-ureido]-thiazole-5-carboxylic acid [1,3,4]thiadiazol-2-ylamide
1-(4-Methyl-2-piperidin-1-yl-phenyl)-3-[5-([1,3,4]thiadiazol-2-ylaminomethyl)-thiazol-2-yl]-urea
1-(2-Cyclopentanecarbonyl-phenyl)-3-[1,2,4]thiadiazol-5-yl-urea
{5-[3-(2-Cyclopentanecarbonyl-phenyl)-ureido]-[1,2,4]thiadiazol-3-yl}-acetic acid
N-{5-[3-(2-Cyclopentanecarbonyl-phenyl)-ureido]-[1,2,4]thiadiazol-3-ylmethyl}-methanesulfonamide
1-(2-Cyclopentanecarbonyl-phenyl)-3-(3-methoxy-[1,2,4]thiadiazol-5-yl)-urea
1-(2-Cyclopentanecarbonyl-phenyl)-3-(3-ethyl-[1,2,4]thiadiazol-5-yl)-urea
1-(2-Cyclopentanecarbonyl-phenyl)-3-(3-methyl-[1,2,4]thiadiazol-5-yl)-urea
1-(2-Cyclopentanecarbonyl-phenyl)-3-(3-isopropyl-[1,2,4]thiadiazol-5-yl)-urea
1-(2-Cyclopentanecarbonyl-phenyl)-3-(3-phenyl-[1,2,4]thiadiazol-5-yl)-urea
1-(2-Isobutoxy-phenyl)-3-[1,2,4]thiadiazol-5-yl-urea
{5-[3-(2-Isobutoxy-phenyl)-ureido]-[1,2,4]thiadiazol-3-yl}-acetic acid
N-{5-[3-(2-Isobutoxy-phenyl)-ureido]-[1,2,4]thiadiazol-3-ylmethyl}-methanesulfonamide
1-(2-Isobutoxy-phenyl)-3-(3-methoxy-[1,2,4]thiadiazol-5-yl)-urea
1-(3-Ethyl-[1,2,4]thiadiazol-5-yl)-3-(2-isobutoxy-phenyl)-urea
1-(2-Isobutoxy-phenyl)-3-(3-methyl-[1,2,4]thiadiazol-5-yl)-urea
1-(2-Isobutoxy-phenyl)-3-(3-isopropyl-[1,2,4]thiadiazol-5-yl)-urea
1-(2-Isobutoxy-phenyl)-3-(3-phenyl-[1,2,4]thiadiazol-5-yl)-urea
1-[2-(2-Methoxy-benzoyl)-phenyl]-3-[1,2,4]thiadiazol-5-yl-urea
(5-{3-[2-(2-Methoxy-benzoyl)-phenyl]-ureido}-[1,2,4]thiadiazol-3-yl)-acetic acid
N-(5-{3-[2-(2-Methoxy-benzoyl)-phenyl]-ureido}-[1,2,4]thiadiazol-3-ylmethyl)-methanesulfonamide
1-[2-(2-Methoxy-benzoyl)-phenyl]-3-(3-methoxy-1,2,4]thiadiazol-5-yl)-urea
1-(3-Ethyl-[1,2,4]thiadiazol-5-yl)-3-[2-(2-methoxy-benzoyl)-phenyl]-urea
1-[2-(2-Methoxy-benzoyl)-phenyl]-3-(3-methyl-[1,2,4]thiadiazol-5-yl)-urea
1-(3-Isopropyl-[1,2,4]thiadiazol-5-yl)-3-[2-(2-methoxy-benzoyl)-phenyl]-urea
1-[2-(2-Methoxy-benzoyl)-phenyl]-3-(3-phenyl-[1,2,4]thiadiazol-5-yl)-urea
1-(2-Piperidin-1-yl-phenyl)-3-[1,2,4]thiadiazol-5-yl-urea
{5-[3-(2-Piperidin-1-yl-phenyl)-ureido]-[1,2,4]thiadiazol-3-yl}-acetic acid
N-{5-[3-(2-Piperidin-1-yl-phenyl)-ureido]-[1,2,4]thiadiazol-3-ylmethyl}-methanesulfonamide
1-(3-Methoxy-[1,2,4]thiadiazol-5-yl)-3-(2-piperidin-1-yl-phenyl)-urea
1-(3-Ethyl-[1,2,4]thiadiazol-5-yl)-3-(2-piperidin-1-yl-phenyl)-urea
1-(3-Methyl-[1,2,4]thiadiazol-5-yl)-3-(2-piperidin-1-yl-phenyl)-urea
1-(3-Isopropyl-[1,2,4]thiadiazol-5-yl)-3-(2-piperidin-1-yl-phenyl)-urea
1-(3-Phenyl-1,2,4]thiadiazol-5-yl)-3-(2-piperidin-1-yl-phenyl)-urea
1-(2-Cyclopentanecarbonyl-4-methyl-phenyl)-3-[1,2,4]thiadiazol-5-yl-urea
{5-[3-(2-Cyclopentanecarbonyl-4-methyl-phenyl)-ureido]-[1,2,4]thiadiazol-3-yl}-acetic acid
N-{5-[3-(2-Cyclopentanecarbonyl-4-methyl-phenyl)-ureido]-[1,2,4]thiadiazol-3-ylmethyl}-methanesulfonamide
1-(2-Cyclopentanecarbonyl-4-methyl-phenyl)-3-(3-methoxy-[1,2,4]thiadiazol-5-yl)-urea
1-(2-Cyclopentanecarbonyl-4-methyl-phenyl)-3-(3-ethyl-[1,2,4]thiadiazol-5-yl)-urea
1-(2-Cyclopentanecarbonyl-4-methyl-phenyl)-3-(3-methyl-[1,2,4]thiadiazol-5-yl)-urea
1-(2-Cyclopentanecarbonyl-4-methyl-phenyl)-3-(3-isopropyl-1,2,4]thiadiazol-5-yl)-urea
1-(2-Cyclopentanecarbonyl-4-methyl-phenyl)-3-(3-phenyl-[1,2,4]thiadiazol-5-yl)-urea
1-(2-Isobutoxy-4-methyl-phenyl)-3-[1,2,4]thiadiazol-5-yl-urea
{5-[3-(2-Isobutoxy-4-methyl-phenyl)-ureido]-[1,2,4]thiadiazol-3-yl}-acetic acid
N-{5-[3-(2-Isobutoxy-4-methyl-phenyl)-ureido]-[1,2,4]thiadiazol-3-ylmethyl}-methanesulfonamide
1-(2-Isobutoxy-4-methyl-phenyl)-3-(3-methoxy-[1,2,4]thiadiazol-5-yl)-urea
1-(3-Ethyl-[1,2,4]thiadiazol-5-yl)-3-(2-isobutoxy-4-methyl-phenyl)-urea
1-(2-Isobutoxy-4-methyl-phenyl)-3-(3-methyl-[1,2,4]thiadiazol-5-yl)-urea
1-(2-Isobutoxy-4-methyl-phenyl)-3-(3-isopropyl-[1,2,4]thiadiazol-5-yl)-urea
1-(2-Isobutoxy-4-methyl-phenyl)-3-(3-phenyl-[1,2,4]thiadiazol-5-yl)-urea
1-[2-(2-Methoxy-benzoyl)-4-methyl-phenyl]-3-[1,2,4]thiadiazol-5-yl-urea
(5-{3-[2-(2-Methoxy-benzoyl)-4-methyl-phenyl]-ureido}-[1,2,4]thiadiazol-3-yl)-acetic acid N-(5-{3-[2-(2-Methoxy-benzoyl)-4-methyl-phenyl]-ureido}-[1,2,4]thiadiazol-3-ylmethyl)-methanesulfonamide
1-[2-(2-Methoxy-benzoyl)-4-methyl-phenyl]-3-(3-methoxy-[1,2,4]thiadiazol-5-yl)-urea
1-(3-Ethyl-[1,2,4]thiadiazol-5-yl)-3-[2-(2-methoxy-benzoyl)-4-methyl-phenyl]-urea
1-[2-(2-Methoxy-benzoyl)-4-methyl-phenyl]-3-(3-methyl-[1,2,4]thiadiazol-5-yl)-urea
1-(3-Isopropyl-[1,2,4]thiadiazol-5-yl)-3-[2-(2-methoxy-benzoyl)-4-methyl-phenyl]-urea
1-[2-(2-Methoxy-benzoyl)-4-methyl-phenyl]-3-(3-phenyl-[1,2,4]thiadiazol-5-yl)-urea
1-(4-Methyl-2-piperidin-1-yl-phenyl)-3-[1,2,4]thiadiazol-5-yl-urea
{5-[3-(4-Methyl-2-piperidin-1-yl-phenyl)-ureido]-[1,2,4]thiadiazol-3-yl}-acetic acid
N-{5-[3-(4-Methyl-2-piperidin-1-yl-phenyl)-ureido]-[1,2,4]thiadiazol-3-ylmethyl}-methanesulfonamide
1-(3-Methoxy-[1,2,4]thiadiazol-5-yl)-3-(4-methyl-2-piperidin-1-yl-phenyl)-urea
1-(3-Ethyl-[1,2,4]thiadiazol-5-yl)-3-(4-methyl-2-piperidin-1-yl-phenyl)-urea
1-(4-Methyl-2-piperidin-1-yl-phenyl)-3-(3-methyl-[1,2,4]thiadiazol-5-yl)-urea
1-(3-Isopropyl-[1,2,4]thiadiazol-5-yl)-3-(4-methyl-2-piperidin-1-yl-phenyl)-urea
1-(4-Methyl-2-piperidin-1-yl-phenyl)-3-(3-phenyl-[1,2,4]thiadiazol-5-yl)-urea
1-(2-Cyclopentanecarbonyl-4-fluoro-phenyl)-3-[1,2,4]thiadiazol-5-yl-urea
{5-[3-(2-Cyclopentanecarbonyl-4-fluoro-phenyl)-ureido]-[1,2,4]thiadiazol-3-yl}-acetic acid
N-{5-[3-(2-Cyclopentanecarbonyl-4-fluoro-phenyl)-ureido]-[1,2,4]thiadiazol-3-ylmethyl}-methanesulfonamide
1-(2-Cyclopentanecarbonyl-4-fluoro-phenyl)-3-(3-methoxy-[1,2,4]thiadiazol-5-yl)-urea
1-(2-Cyclopentanecarbonyl-4-fluoro-phenyl)-3-(3-ethyl-[1,2,4]thiadiazol-5-yl)-urea
1-(2-Cyclopentanecarbonyl-4-fluoro-phenyl)-3-(3-methyl-[1,2,4]thiadiazol-5-yl)-urea
1-(2-Cyclopentanecarbonyl-4-fluoro-phenyl)-3-(3-isopropyl-[1,2,4]thiadiazol-5-yl)-urea
1-(2-Cyclopentanecarbonyl-4-fluoro-phenyl)-3-(3-phenyl-[1,2,4]thiadiazol-5-yl)-urea
1-(4-Fluoro-2-isobutoxy-phenyl)-3-[1,2,4]thiadiazol-5-yl-urea
{5-[3-(4-Fluoro-2-isobutoxy-phenyl)-ureido]-[1,2,4]thiadiazol-3-yl}-acetic acid
N-{5-[3-(4-Fluoro-2-isobutoxy-phenyl)-ureido]-[1,2,4]thiadiazol-3-ylmethyl}-methanesulfonamide
1-(4-Fluoro-2-isobutoxy-phenyl)-3-(3-methoxy-[1,2,4]thiadiazol-5-yl)-urea
1-(3-Ethyl-[1,2,4]thiadiazol-5-yl)-3-(4-fluoro-2-isobutoxy-phenyl)-urea
1-(4-Fluoro-2-isobutoxy-phenyl)-3-(3-methyl-[1,2,4]thiadiazol-5-yl)-urea
1-(4-Fluoro-2-isobutoxy-phenyl)-3-(3-isopropyl-[1,2,4]thiadiazol-5-yl)-urea
1-(4-Fluoro-2-isobutoxy-phenyl)-3-(3-phenyl-[1,2,4]thiadiazol-5-yl)-urea
1-[4-Fluoro-2-(2-methoxy-benzoyl)-phenyl]-3-[1,2,4]thiadiazol-5-yl-urea
(5-{3-[4-Fluoro-2-(2-methoxy-benzoyl)-phenyl]-ureido}-[1,2,4]thiadiazol-3-yl)-acetic acid
N-(5-{3-[4-Fluoro-2-(2-methoxy-benzoyl)-phenyl]-ureido}-[1,2,4]thiadiazol-3-ylmethyl)-methanesulfonamide
1-[4-Fluoro-2-(2-methoxy-benzoyl)-phenyl]-3-(3-methoxy-[1,2,4]thiadiazol-5-yl)-urea
1-(3-Ethyl-[1,2,4]thiadiazol-5-yl)-3-[4-fluoro-2-(2-methoxy-benzoyl)-phenyl]-urea
1-[4-Fluoro-2-(2-methoxy-benzoyl)-phenyl]-3-(3-methyl-[1,2,4]thiadiazol-5-yl)-urea
1-[4-Fluoro-2-(2-methoxy-benzoyl)-phenyl]-3-(3-isopropyl-[1,2,4]thiadiazol-5-yl)-urea
1-[4-Fluoro-2-(2-methoxy-benzoyl)-phenyl]-3-(3-phenyl-[1,2,4]thiadiazol-5-yl)-urea
1-(4-Fluoro-2-piperidin-1-yl-phenyl)-3-[1,2,4]thiadiazol-5-yl-urea
{5-[3-(4-Fluoro-2-piperidin-1-yl-phenyl)-ureido]-[1,2,4]thiadiazol-3-yl}-acetic acid
N-{5-[3-(4-Fluoro-2-piperidin-1-yl-phenyl)-ureido]-[1,2,4]thiadiazol-3-ylmethyl}-methanesulfonamide
1-(4-Fluoro-2-piperidin-1-yl-phenyl)-3-(3-methoxy-[1,2,4]thiadiazol-5-yl)-urea
1-(3-Ethyl-[1,2,4]thiadiazol-5-yl)-3-(4-fluoro-2-piperidin-1-yl-phenyl)-urea
1-(4-Fluoro-2-piperidin-1-yl-phenyl)-3-(3-methyl-[1,2,4]thiadiazol-5-yl)-urea
1-(4-Fluoro-2-piperidin-1-yl-phenyl)-3-(3-isopropyl-[1,2,4]thiadiazol-5-yl)-urea
1-(4-Fluoro-2-piperidin-1-yl-phenyl)-3-(3-phenyl-[1,2,4]thiadiazol-5-yl)-urea
1-(2-Cyclopentanecarbonyl-4-morpholin-4-yl-phenyl)-3-[1,2,4]thiadiazol-5-yl-urea
{5-[3-(2-Cyclopentanecarbonyl-4-morpholin-4-yl-phenyl)-ureido]-[1,2,4]thiadiazol-3-yl}-acetic acid
N-{5-[3-(2-Cyclopentanecarbonyl-4-morpholin-4-yl-phenyl)-ureido]-[1,2,4]thiadiazol-3-ylmethyl}-methanesulfonamide
1-(2-Cyclopentanecarbonyl-4-morpholin-4-yl-phenyl)-3-(3-methoxy-[1,2,4]thiadiazol-5-yl)-urea
1-(2-Cyclopentanecarbonyl-4-morpholin-4-yl-phenyl)-3-(3-ethyl-[1,2,4]thiadiazol-5-yl)-urea
1-(2-Cyclopentanecarbonyl-4-morpholin-4-yl-phenyl)-3-(3-methyl-[1,2,4]thiadiazol-5-yl)-urea
1-(2-Cyclopentanecarbonyl-4-morpholin-4-yl-phenyl)-3-(3-isopropyl-[1,2,4]thiadiazol-5-yl)-urea
1-(2-Cyclopentanecarbonyl-4-morpholin-4-yl-phenyl)-3-(3-phenyl-[1,2,4]thiadiazol-5-yl)-urea
1-(2-Isobutoxy-4-morpholin-4-yl-phenyl)-3-[1,2,4]thiadiazol-5-yl-urea
{5-[3-(2-Isobutoxy-4-morpholin-4-yl-phenyl)-ureido]-[1,2,4]thiadiazol-3-yl}-acetic acid
N-{5-[3-(2-Isobutoxy-4-morpholin-4-yl-phenyl)-ureido]-[1,2,4]thiadiazol-3-ylmethyl}-methanesulfonamide
1-(2-Isobutoxy-4-morpholin-4-yl-phenyl)-3-(3-methoxy-[1,2,4]thiadiazol-5-yl)-urea
1-(3-Ethyl-[1,2,4]thiadiazol-5-yl)-3-(2-isobutoxy-4-morpholin-4-yl-phenyl)-urea
1-(2-Isobutoxy-4-morpholin-4-yl-phenyl)-3-(3-methyl-[1,2,4]thiadiazol-5-yl)-urea
1-(2-Isobutoxy-4-morpholin-4-yl-phenyl)-3-(3-isopropyl-[1,2,4]thiadiazol-5-yl)-urea
1-(2-Isobutoxy-4-morpholin-4-yl-phenyl)-3-(3-phenyl-[1,2,4]thiadiazol-5-yl)-urea
1-[2-(2-Methoxy-benzoyl)-4-morpholin-4-yl-phenyl]-3-[1,2,4]thiadiazol-5-yl-urea
(5-{3-[2-(2-Methoxy-benzoyl)-4-morpholin-4-yl-phenyl]-ureido}-[1,2,4]thiadiazol-3-yl)-acetic acid
N-(5-{3-[2-(2-Methoxy-benzoyl)-4-morpholin-4-yl-phenyl]-ureido}-[1,2,4]thiadiazol-3-ylmethyl)-methanesulfonamide 1-[2-(2-Methoxy-benzoyl)-4-morpholin-4-yl-phenyl]-3-(3-methoxy-[1,2,4]thiadiazol-5-yl)-urea 1-(3-Ethyl-[1,2,4]thiadiazol-5-yl)-3-[2-(2-methoxy-benzoyl)-4-morpholin-4-yl-phenyl]-urea 1-[2-(2-Methoxy-benzoyl)-4-morpholin-4-yl-phenyl]-3-(3-methyl-[1,2,4]thiadiazol-5-yl)-urea 1-(3-Isopropyl-[1,2,4]thiadiazol-5-yl)-3-[2-(2-methoxy-benzoyl)-4-morpholin-4-yl-phenyl]-urea 1-[2-(2-Methoxy-benzoyl)-4-morpholin-4-yl-phenyl]-3-(3-phenyl-[1,2,4]thiadiazol-5-yl)-urea 1-(4-Morpholin-4-yl-2-piperidin-1-yl-phenyl)-3-[1,2,4]thiadiazol-5-yl-urea {5-[3-(4-Morpholin-4-yl-2-piperidin-1-yl-phenyl)-ureido]-[1,2,4]thiadiazol-3-yl}-acetic acid N-{5-[3-(4-Morpholin-4-yl-2-piperidin-1-yl-phenyl)-ureido]-[1,2,4]thiadiazol-3-ylmethyl}-methanesulfonamide 1-(3-Methoxy-[1,2,4]thiadiazol-5-yl)-3-(4-morpholin-4-yl-2-piperidin-1-yl-phenyl)-urea 1-(3-Ethyl-[1,2,4]thiadiazol-5-yl)-3-(4-morpholin-4-yl-2-piperidin-1-yl-phenyl)-urea 1-(3-Methyl-[1,2,4]thiadiazol-5-yl)-3-(4-morpholin-4-yl-2-piperidin-1-yl-phenyl)-urea 1-(3-Isopropyl-[1,2,4]thiadiazol-5-yl)-3-(4-morpholin-4-yl-2-piperidin-1-yl-phenyl)-urea 1-(4-Morpholin-4-yl-2-piperidin-1-yl-phenyl)-3-(3-phenyl-[1,2,4]thiadiazol-5-yl)-urea 4-{2-[3-(2-Cyclopentanecarbonyl-4-methyl-phenyl)-ureido]-thiazol-4-yl}-2-methyl-butyric acid 2-[3-(2-Cyclopentanecarbonyl-4-methyl-phenyl)-ureido]-4,5,6,7-terahydro-benzothiazole-7-carboxylic acid Biological Assay Glucokinase Activity Assay (I)

Glucokinase activity is assayed spectrometrically coupled to glucose 6-phosphate dehydrogenase to determine compound activation of glucokinase. The final assay contains 50 mM Hepes, pH 7.1, 50 mM KCl, 5 mM $MgCl_2$, 2 mM dithiothreitol, 0.6 mM NADP, 1 mM ATP, 0.195 µM G-6-P dehydrogenase (from Roche, 127 671), 15 nM recombinant human glucokinase. The glucokinase is human liver glucokinase N-terminally truncated with an N-terminal His-tag ((His)$_8$-VEQILA ... Q466) and is expressed in E. coli as a soluble protein with enzymatic activity comparable to liver extracted GK.

The purification of His-tagged human glucokinase (hGK) was performed as follows: The cell pellet from 50 ml E. coli culture was resuspended in 5 ml extraction buffer A (25 mM HEPES, pH 8.0, 1 mM $MgCl_2$, 150 mM NaCl, 2 mM mercaptoethanol) with addition of 0.25 mg/ml lysozyme and 50 µg/ml sodium azide. After 5 minutes at room temperature 5 ml of extraction buffer B (1.5 M NaCl, 100 mM $CaCl_2$, 100 mM $MgCl_2$, 0.02 mg/ml DNase 1, protease inhibitor tablet (Complete® 1697498): 1 tablet pr. 20 ml buffer) was added. The extract was then centrifugated at 15.000 g for 30 minutes. The resulting supernatant was loaded on a 1 ml Metal Chelate Affinity Chromatography (MCAC) Column charged with $Ni^{2+}$. The column is washed with 2 volumes buffer A containing 20 mM imidazole and the bound his-tagged hGK is subsequently eluted using a 20 minute gradient of 20 to 500 mM imididazol in buffer A. Fractions are examined using SDS-gel-electrophoresis, and fractions containing hGK (MW: 52 KDa) are pooled. Finally a gelfiltration step is used for final polishing and buffer exchange. hGK containing fractions are loaded onto a Superdex 75 (16/60) gelfiltration column and eluted with Buffer B (25 mM HEPES, pH 8.0, 1 mM $MgCl_2$, 150 mM NaCl, 1 mM Dithiothreitol). The purified hGK is examined by SDS-gel electrophoresis and MALDI mass spectrometry and finally 20% glycerol is added before freezing. The yield from 50 ml E. coli culture is generally approximately 2-3 mg hGK with a purity>90%.

The compound to be tested is added into the well in final 2.5% DMSO concentration in an amount sufficient to give a desired concentration of compound, for instance 1, 5, 10, 25 or 50 µM. The reaction starts after glucose is added to a final concentration of 2, 5, 10 or 15 mM. The assay uses a 96-well UV plate and the final assay volume used is 200 µl/well. The plate is incubated at 25° C. for 5 min and kinetics is measured at 340 nm in SpectraMax every 30 seconds for 5 minutes. Results for each compound are expressed as the fold activation of the glucokinase activity compared to the activation of the glucokinase enzyme in an assay without compound after having been subtracted from a "blank", which is without glucokinase enzyme and without compound. The compounds in each of the Examples exhibits activation of glucokinase in this assay. A compound, which at a concentration of at or below 30 µM gives 1.5-fold higher glucokinase activity than the result from the assay without compound, is deemed to be an activator of glucokinase.

The glucose sensitivity of the compounds are measured at a compound concentration of 10 µM and at glucose concentrations of 5 and 15 mM.

While the invention has been described and illustrated with reference to certain preferred embodiments thereof, those skilled in the art will appreciate that various changes, modifications and substitutions can be made therein without departing from the spirit and scope of the present invention. For example, effective dosages other than the preferred dosages as set forth herein may be applicable as a consequence of variations in the responsiveness of the mammal being treated for glucokinase-deficiency mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

Glucokinase Activity Assay (II)

Determination of Glycogen Deposition in Isolated Rat Hepatocytes:

Hepatocytes are isolated from rats fed ad libitum by a two-step perfusion technique. Cell viability, assessed by trypan blue exclusion, is consistently greater than 80%. Cells are plated onto collagen-coated 96-well plates in basal medium (Medium 199 (5.5 mM glucose) supplemented with 0.1 µM dexamethasone, 100 units/ml penicillin, 100 mg/ml streptomycin, 2 mM L-glutamine and 1 nM insulin) with 4% FCS at a cell density of 30,000 cells/well. The medium is replaced with basal medium 1 hour after initial plating in order to remove dead cells. Medium is changed after 24 hours to basal medium supplemented with 9.5 mM glucose and 10 nM insulin to induce glycogen synthesis, and experiments are performed the next day. The hepatocytes are washed twice with prewarmed (37° C.) buffer A (117.6 mM NaCl, 5.4 mM KCl, 0.82 mM $Mg_2SO_4$, 1.5 mM $KH_2PO_4$, 20 mM HEPES, 9 mM $NaHCO_3$, 0.1% w/v HSA, and 2.25 mM $CaCl_2$, pH 7.4 at 37° C.) and incubated in 100 µl buffer A containing 15 mM glucose and increasing concentrations of the test compound, such as for instance 1, 5, 10, 25, 50 or 100 µM, for 180 minutes. Glycogen content is measured using standard procedures (Agius, L. et al, Biochem J. 266, 91-102 (1990). A compound, which when used in this assay gives an significant increase in glycogen content compared to the result from the assay without compound, is deemed to have activity in this assay.

Glucokinase Activity Assay (III)

Stimulation of Insulin Secretion by Glucokinase Activators in INS-1 E Cells

The glucose responsive β-cell line INS-1 E is cultivated as described by Asfari M et al., Endocrinology, 130, 167-178 (1992). The cells are then seeded into 96 well cell culture plates and grown to a density of approximately 5×10$^4$ per well. Stimulation of glucose dependent insulin secretion is tested by incubation for 2 hours in Krebs Ringer Hepes buffer at glucose concentrations from 2.5 to 15 mM with or without addition of glucokinase activating compounds in concentrations of for instance 1, 5, 10, 25, 50 or 100 μM, and the supernatants collected for measurements of insulin concentrations by ELISA (n=4). A compound, which when used in this assay gives an significant increase in insulin secretion in response to glucose compared to the result from the assay without compound, is deemed to have activity in this assay.

What is claimed is:

1. A compound of Formula (Ib)

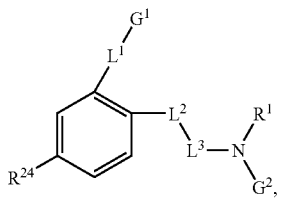

Formula (Ib)

wherein
R$^{24}$ is selected from the group consisting of F, Cl, Br, and —CH$_3$;
L$^1$ is —C(O)—;
G$^1$ is selected from the group consisting of methyl, ethyl, propyl, butyl, isopropyl, isobutyl, cyclopentyl, cyclohexyl, tetrahydrofuranyl, tetrahydropyranyl, piperidyl, and hexahydroazepinyl; L$^2$ is —N—(R$^{20}$)—; R$^{20}$ is H;
L$^3$ is —C(O)—;
R$^1$ is hydrogen;
G$^2$ is

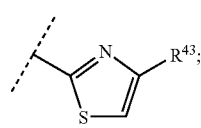

R$^{43}$ is —C$_{1-6}$-alkylene-C(O)OR$^{54}$;
R$^{54}$ is hydrogen, methyl, ethyl, propyl, butyl, isopropyl, isobutyl, sec-butyl, tert-butyl, 3-pentyl, 2-pentyl, or 3-methyl-butyl;
or a pharmaceutically acceptable salt or solvate thereof.

2. The compound, pharmaceutically acceptable salt or solvate thereof of claim 1, wherein G$^1$ is cyclopentyl.

3. The compound, pharmaceutically acceptable salt or solvate thereof of claim 1, wherein R$^{24}$ is methyl.

4. The compound, pharmaceutically acceptable salt or solvate thereof of claim 2, wherein R$^{24}$ is methyl.

5. The compound, pharmaceutically acceptable salt or solvate thereof of claim 1, wherein R$^{54}$ is hydrogen.

6. The compound, pharmaceutically acceptable salt or solvate thereof of claim 2, wherein R$^{54}$ is hydrogen.

7. The compound, pharmaceutically acceptable salt or solvate thereof of claim 3, wherein R$^{54}$ is hydrogen.

8. The compound, pharmaceutically acceptable salt or solvate thereof of claim 4, wherein R$^{54}$ is hydrogen.

9. The compound, pharmaceutically acceptable salt or solvate thereof of claim 1, wherein R$^{43}$ is —CH$_2$—C(O)OR$^{54}$.

10. The compound of claim 1, wherein the compound is selected from the group consisting of:
{2-[3-(2-Cyclopentanecarbonyl-4-methyl-phenyl)-ureido]-thiazol-4-yl}-acetic acid ethyl ester;
{2-[3-(2-Cyclopentanecarbonyl-4-methyl-phenyl)-ureido]-thiazol-4-yl} acetic acid;
2-[3-(2-Cyclopentanecarbonyl-4-methylphenyl)-ureido]-thiazole-4-carboxylic acid ethyl ester;
2-[3-(2-Cyclopentanecarbonyl-4-methylphenyl)-ureido]-thiazole-4-carboxylic acid;
{2-[3-(4-Methyl-2-[2-methylpropoxy] phenyl)-ureido]-thiazol-4-yl}-acetic acid;
{2-[3-(4-Bromo-2-cyclopentanecarbonyl-phenyl)-ureido]-thiazol-4-yl}-acetic acid ethyl ester;
{2-[3-(4-Bromo-2-cyclopentanecarbonyl-phenyl)-ureido]-thiazol-4-yl}-acetic acid;
3- {2-[3-(2-Cyclopentanecarbonyl-4-methyl-phenyl)-ureido]-thiazol-4-yl}-propionic acid ethyl ester;
3- {2-[3-(2-Cyclopentanecarbonyl-4-methyl-phenyl)-ureido]-thiazol-4-yl}-propionic acid;
{2-[3-(2-Cyclohexanecarbonyl-4-methyl-phenyl)-ureido]-thiazol-4-yl}-acetic acid ethyl ester;
{2-[3-(2-Cyclohexanecarbonyl-4-methyl-phenyl)-ureido]-thiazol-4-yl}-acetic;
{2-[3-(4-Chloro-2-cyclopentanecarbonyl-phenyl)-ureido]-thiazol-4-yl}-acetic acid ethyl ester;
{2-[3-(4-Chloro-2-cyclopentanecarbonyl-phenyl)-ureido]-thiazol-4-yl}-acetic acid;
{2-[3-(2-Cyclopentanecarbonyl-4-fluoro-phenyl)-ureido]-thiazol-4-yl}-acetic acid ethyl ester; and
{2-[3-(2-Cyclopentanecarbonyl-4-fluoro-phenyl)-ureido]-thiazol-4-yl}-acetic acid or a pharmaceutically acceptable salt or solvate thereof.

11. The compound {2-[3-(2-cyclopentanecarbonyl-4-methyl-phenyl)-ureido]-thiazol-4-yl} acetic acid or a pharmaceutically acceptable salt or solvate thereof.

12. A pharmaceutical composition comprising the compound of Formula (Ib)

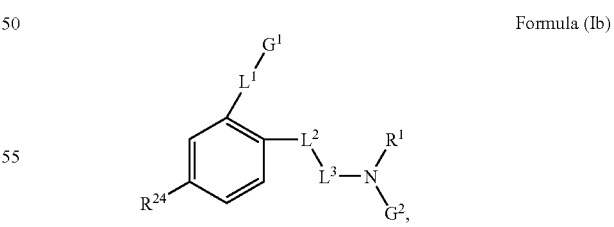

Formula (Ib)

wherein
R$^{24}$ is selected from the group consisting of F, Cl, Br, and —CH$_3$;
L$^1$ is —C(O)—;
G$^1$ is selected from the group consisting of methyl, ethyl, propyl, butyl, isopropyl, isobutyl, cyclopentyl, cyclohexyl, tetrahydrofiaranyl, tetrahydropyranyl, piperidyl, and hexahydroazepinyl; L$^2$ is —N—(R$^{20}$)—; R$^{20}$ is H;

$L^3$ is —C(O)—;
$R^1$ is hydrogen;
$G^2$ is

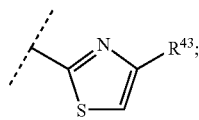

$R^{43}$ is —$C_{1-6}$-alkylene-C(O)O$R^{54}$;
$R^{54}$ is hydrogen, methyl, ethyl, propyl, butyl, isopropyl, isobutyl, sec-butyl, tert-butyl, 3-pentyl, 2-pentyl, or 3-methyl-butyl;
or a pharmaceutically acceptable salt or solvate thereof, and a pharmaceutically acceptable carrier, diluent, excipient, or mixture thereof.

13. The pharmaceutical composition of claim 12, wherein $G^1$ is cyclopentyl.

14. The pharmaceutical composition of claim 12, wherein $R^{24}$ is methyl.

15. The pharmaceutical composition of claim 13, wherein $R^{24}$ is methyl.

16. The pharmaceutical composition of claim 12, wherein $R^{54}$ is hydrogen.

17. The pharmaceutical composition of claim 13, wherein $R^{54}$ is hydrogen.

18. The pharmaceutical composition of claim 14, wherein $R^{54}$ is hydrogen.

19. The pharmaceutical composition of claim 15, wherein $R^{54}$ is hydrogen.

20. The pharmaceutical composition of claim 12, wherein $R^{43}$ is —$CH_2$—C(O)O$R^{54}$.

21. The pharmaceutical composition of claim 12, wherein the compound is selected from the group consisting of {2-[3-(2-Cyclopentanecarbonyl-4-methyl-phenyl)-ureido]-thiazol-4-yl}-acetic acid ethyl ester;
{2-[3-(2-Cyclopentanecarbonyl-4-methyl-phenyl)-ureido]-thiazol-4-yl} acetic acid;
2-[3-(2-Cyclopentanecarbonyl-4-methylphenyl)-ureido]-thiazole-4-carboxylic acid ethyl ester;
$^2$-[3-(2-Cyclopentanecarbonyl-4-methylphenyl)-ureido]-thiazole-4-carboxylic acid;
{2-[3-(4-Methyl-2-[$^2$-methylpropoxy] phenyl)-ureido]-thiazol-4-yl}-acetic acid;
{2-[3-($^4$-Bromo-2-cyclopentanecarbonyl-phenyl)-ureido]-thiazol-4-yl}-acetic acid ethyl ester;
{2-[3-(4-Bromo-2-cyclopentanecarbonyl-phenyl)-ureido]-thiazol-4-yl}-acetic acid;
3-{2-[3-(2-Cyclopentanecarbonyl-4-methyl-phenyl)-ureido]-thiazol-4-yl}-propionic acid ethyl ester;
3-{2-[3-(2-Cyclopentanecarbonyl-4-methyl-phenyl)-ureido]-thiazol-4-yl}-propionic acid;
{2-[3-(2-Cyclohexanecarbonyl-4-methyl-phenyl)-ureido]-thiazol-4-yl}-acetic acid ethyl ester;
{2-[3-(2-Cyclohexanecarbonyl-4-methyl-phenyl)-ureido]-thiazol-4-yl}-acetic;
{2-[3-(4-Chloro-2-cyclopentanecarbonyl-phenyl)-ureido]-thiazol-4-yl}-acetic acid ethyl ester;
{2-[3-(4-Chloro-2-cyclopentanecarbonyl-phenyl)-ureido]-thiazol-4-yl}-acetic acid;
{2-[3-(2-Cyclopentanecarbonyl-4-fluoro-phenyl)-ureido]-thiazol-4-yl}-acetic acid ethyl ester; and
{2-[3-(2-Cyclopentanecarbonyl-4-fluoro-phenyl)-ureido]-thiazol-4-yl}-acetic acid, or a pharmaceutically acceptable salt or solvate thereof.

22. A pharmaceutical composition comprising the compound {2-[3-(2-cyclopentanecarbonyl-4-methyl-phenyl)-ureido]-thiazol-4-yl} acetic acid or a pharmaceutically acceptable salt or solvate thereof and a pharmaceutically acceptable carrier, diluent, excipient, or mixture thereof.

* * * * *